US008993295B2

(12) United States Patent
Seed et al.

(10) Patent No.: US 8,993,295 B2

(45) **Date of Patent: *Mar. 31, 2015**

(54) METHODS, COMPOSITIONS, AND KITS FOR THE SELECTIVE ACTIVATION OF PROTOXINS THROUGH COMBINATORIAL TARGETING

(75) Inventors: Brian Seed, Boston, MA (US); Jia Liu Wolfe, Winchester, MA (US); Glen S. Cho, Brookline, MA (US); Chia-Iun Tsai, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 1188 days.

This patent is subject to a terminal disclaimer.

(21) Appl. No.: 12/374,616

(22) PCT Filed: Jul. 20, 2007

(86) PCT No.: PCT/US2007/016475

§ 371 (c)(1), (2), (4) Date: Nov. 9, 2009

(87) PCT Pub. No.: WO2008/011157

PCT Pub. Date: Jan. 24, 2008

(65) Prior Publication Data

US 2010/0055761 A1 Mar. 4, 2010

Related U.S. Application Data

(60) Provisional application No. 60/832,022, filed on Jul. 20, 2006.

(51) Int. Cl.

| | |
|---|---|
| ***C12N 9/96*** | (2006.01) |
| ***C07K 16/28*** | (2006.01) |
| ***A61K 47/48*** | (2006.01) |
| ***B82Y 5/00*** | (2011.01) |
| ***C07K 14/195*** | (2006.01) |
| ***C07K 14/28*** | (2006.01) |
| ***C07K 14/34*** | (2006.01) |
| ***C12N 9/16*** | (2006.01) |
| *A61K 38/00* | (2006.01) |

(52) U.S. Cl.

CPC ....... *C07K 16/2803* (2013.01); *A61K 47/48561* (2013.01); *A61K 47/48715* (2013.01); *A61K 47/48761* (2013.01); *B82Y 5/00* (2013.01); *C07K 14/195* (2013.01); *C07K 14/28* (2013.01); *C07K 14/34* (2013.01); *C12N 9/16* (2013.01); *A61K 38/00* (2013.01); *C07K 2319/55* (2013.01)

USPC ........................................................ 435/188

(58) Field of Classification Search

USPC ........................................................ 435/188

See application file for complete search history.

(56) References Cited

U.S. PATENT DOCUMENTS

| | | | | |
|---|---|---|---|---|
| 4,975,278 | A | 12/1990 | Senter | |
| 5,156,840 | A | 10/1992 | Goers | |
| 6,258,360 | B1 | 7/2001 | Von Borstel | |
| 2002/0142359 | A1 | 10/2002 | Copley | |
| 2003/0054000 | A1 | 3/2003 | Dowdy | |
| 2004/0048784 | A1 | 3/2004 | Keener et al. | |
| 2009/0016988 | A1 * | 1/2009 | Buckley | 424/85.2 |
| 2010/0256070 | A1 * | 10/2010 | Seed et al. | 514/19.3 |

FOREIGN PATENT DOCUMENTS

| | | | |
|---|---|---|---|
| WO | WO 98/20135 | A2 | 5/1998 |
| WO | WO 01/14570 | A1 | 3/2001 |
| WO | WO 2004/094478 | A2 | 11/2004 |

OTHER PUBLICATIONS

Chiron et al. (JBC 272(50):31707-31711 (1997)).*

Nygren et al., "Overview of the clinical efficacy of investigational anticancer drugs" *Journal of Internal Medicine.* 253:46-75 (2003).

Stenter et al., "Activation of prodrugs by antibody-enzyme conjugates: a new approach to cancer therapy," *The FASEB Journal* 4:188-193 (1990).

Holliger et al., "Engineered antibody fragments and the rise of single domains," *Nature Biotechnology.* 23: 1126-1136 (2005).

Hudson et al., "Engineered antibodies" *Nature Medicine.* 9(1):129-134 (2003).

Xu et al. "Strategies for Enzyme/Prodrug Cancer Therapy," *Clinical Cancer Research.* 7:3314-3324 (2001).

Chang et al., "CD13 (aminopeptidase N) can associate with tumor-associated antigen L6 and enhance the motility of human lung cancer cells." *Int. J. Cancer.*116:234-252 (2005).

Melton et al., "The use of prodrugs in targeted anticancer therapies," *S.T.P. Pharma Sciences.* 9:13-33 (1999).

Cortez-Retamozo et al., "Efficient Cancer Therapy with a Nanobody-Based Conjugate," *Cancer Research.* 64:2853-2857 (2004).

Rita Mulherkar., "Gene Therapy for Cancer," *Current Science.* 81(5):555-560 (2001).

De Groot et al. "Anticancer Prodrugs for Application in Monotherapy: Targeting Hypoxia, Tumor-Associated Enzymes, and Receptors," *Current Medicinal Chemistry.* 8:1093-1122 (2001).

Frankel et al. "Peptide Toxins Directed at the Matrix Dissolution Systems of Cancer Cells." *Protein and Peptide Letters*( Bentham Science Publishers Ltd.) 9 (1):1-14 (2002).

(Continued)

*Primary Examiner* — Lynn Bristol

(74) *Attorney, Agent, or Firm* — Clark & Elbing LLP

(57) ABSTRACT

The present invention provides methods and compositions for treating various diseases through selective killing of targeted cells using a combinatorial targeting approach. The invention features protoxin fusion proteins containing a cell targeting moiety and, a modifiable activation moiety which is activated by an activation moiety not naturally operably found in, on, or in the vicinity of a target cell. These methods also include the combinatorial use of two or more therapeutic agents, at minimum comprising a protoxin and a protoxin activator, to target and destroy a specific cell population.

17 Claims, 28 Drawing Sheets

(56) References Cited

OTHER PUBLICATIONS

Tait et al., "Prourokinase-annexin V Chimeras: Construction, expression, and characterization of recombinant proteins," *J Biol. Chem.* 270:21594-21599, 1995.

Wels et al., "Construction, bacterial expression and characterization of a bifunctional single-chain antibody-phosphatase fusion protein targeted to the human erbB-2 receptor," *Biotechnology* (N.Y.) 10:1128-1132, 1992.

Supplementary European Search Report for European Application No. EP 07810652, issued May 7, 2012.

* cited by examiner

A
B
PE domains
% identities/positives
Domain I (1-252) 31/48
Domain II (253-404) 30/46
Domain III (405-613) 39/54
Overall 33/49
C
VCE
PEA
DT A
CD5
CD19
B
buffer
GrB-anti-CD19
1.2
0.8
0.4
0
PBMNC
CD5+ Raji
C
relative [3H] uptake
1.2
0.8
0.4
0.0
-11
-10
-9
-8
-7
Log [anti-CD5-VCE GrB] M
PBMNC
PBMNC +GrB-anti-CD19
CD5+ Raji
CD5+ Raji +GrB-anti-CD19

A

Enzymatically active GrB-(YSA)$_2$

Enterokinase activatable Pro-GrB-(YSA)$_2$ (DDDDK-GrB-(YSA)$_2$)

(SEQ ID NO:27) NSSYKDDDDK

Furin activatable Pro-GrB-(YSA)$_2$ (RSRR-GrB-(YSA)$_2$)

(SEQ ID NO:28) NSSYKDDDDKRSRR

B

C

SEQUENCE LISTING

```
<160> NUMBER OF SEQ ID NOS: 127

<210> SEQ ID NO 1
<211> LENGTH: 4
<212> TYPE: PRT
<213> ORGANISM: Artificial Sequence
<220> FEATURE:
<223> OTHER INFORMATION: synthetic construct

<400> SEQUENCE: 1

Leu Leu Gln Gly
1


<210> SEQ ID NO 2
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa = any amino acid

<400> SEQUENCE: 2

Leu Pro Xaa Thr Gly
1               5


<210> SEQ ID NO 3
<211> LENGTH: 5
<212> TYPE: PRT
<213> ORGANISM: Artificial Sequence
<220> FEATURE:
<223> OTHER INFORMATION: synthetic construct

<400> SEQUENCE: 3

Asn Pro Gln Thr Asn
1               5


<210> SEQ ID NO 4
<211> LENGTH: 6
<212> TYPE: PRT
<213> ORGANISM: Artificial Sequence
<220> FEATURE:
<223> OTHER INFORMATION: synthetic construct

<400> SEQUENCE: 4

Arg Val Arg Arg Ser Val
1               5


<210> SEQ ID NO 5
<211> LENGTH: 6
<212> TYPE: PRT
<213> ORGANISM: Artificial Sequence
<220> FEATURE:
<223> OTHER INFORMATION: synthetic construct

<400> SEQUENCE: 5
```

Arg Gln Pro Arg Gly Trp
1 5

<210> SEQ ID NO 6
<211> LENGTH: 6
<212> TYPE: PRT
<213> ORGANISM: Artificial Sequence
<220> FEATURE:
<223> OTHER INFORMATION: synthetic construct

<400> SEQUENCE: 6

Arg Lys Pro Lys Asp Leu
1 5

<210> SEQ ID NO 7
<211> LENGTH: 6
<212> TYPE: PRT
<213> ORGANISM: Artificial Sequence
<220> FEATURE:
<223> OTHER INFORMATION: synthetic construct

<400> SEQUENCE: 7

Lys Val Arg Arg Ala Arg
1 5

<210> SEQ ID NO 8
<211> LENGTH: 4
<212> TYPE: PRT
<213> ORGANISM: Artificial Sequence
<220> FEATURE:
<223> OTHER INFORMATION: synthetic construct

<400> SEQUENCE: 8

Leu Leu Gln Gly
1

<210> SEQ ID NO 9
<211> LENGTH: 4
<212> TYPE: PRT
<213> ORGANISM: Artificial Sequence
<220> FEATURE:
<223> OTHER INFORMATION: synthetic construct

<400> SEQUENCE: 9

Ile Glu Pro Asp
1

<210> SEQ ID NO 10
<211> LENGTH: 4
<212> TYPE: PRT
<213> ORGANISM: Artificial Sequence
<220> FEATURE:
<223> OTHER INFORMATION: synthetic construct

<400> SEQUENCE: 10

Asp Pro Pro Ile
1

<210> SEQ ID NO 11
<211> LENGTH: 4
<212> TYPE: PRT
<213> ORGANISM: Artificial Sequence
<220> FEATURE:
<223> OTHER INFORMATION: synthetic construct

<400> SEQUENCE: 11

Lys Val Pro Leu

1

<210> SEQ ID NO 12
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Ser or Gly

<400> SEQUENCE: 12

Glu Xaa Xaa Tyr Xaa Gln Xaa
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic construct

<400> SEQUENCE: 13

Ile Glu Pro Asp Ser Gly
1               5

<210> SEQ ID NO 14
<211> LENGTH: 6
<212> TYPE: PRT
<213> ORGANISM: Artificial Sequence
<220> FEATURE:
<223> OTHER INFORMATION: synthetic construct

<400> SEQUENCE: 14

Ala Leu Phe Gln Gly Pro
1               5

<210> SEQ ID NO 15
<211> LENGTH: 4
<212> TYPE: PRT
<213> ORGANISM: Artificial Sequence
<220> FEATURE:
<223> OTHER INFORMATION: synthetic construct

<400> SEQUENCE: 15

Lys Asp Glu Leu
1

<210> SEQ ID NO 16
<211> LENGTH: 612
<212> TYPE: PRT
<213> ORGANISM: Pseudomonas aeruginosa

<400> SEQUENCE: 16

Glu Glu Ala Phe Asp Leu Trp Asn Glu Cys Ala Lys Ala Cys Val Leu
1               5                   10                  15

Asp Leu Lys Asp Gly Val Arg Ser Ser Arg Met Ser Val Asp Pro Ala
            20                  25                  30

-continued

```
Ile Ala Asp Thr Asn Gly Gln Gly Val Leu His Tyr Ser Met Val Leu
        35                  40                  45

Glu Gly Gly Asn Asp Ala Leu Lys Leu Ala Ile Asp Asn Ala Leu Ser
    50                  55                  60

Ile Thr Ser Asp Gly Leu Thr Ile Arg Leu Glu Gly Gly Val Glu Pro
65                  70                  75                  80

Asn Lys Pro Val Arg Tyr Ser Tyr Thr Arg Gln Ala Arg Gly Ser Trp
                85                  90                  95

Ser Leu Asn Trp Leu Val Pro Ile Gly His Glu Lys Pro Ser Asn Ile
            100                 105                 110

Lys Val Phe Ile His Glu Leu Asn Ala Gly Asn Gln Leu Ser His Met
        115                 120                 125

Ser Pro Ile Tyr Thr Ile Glu Met Gly Asp Glu Leu Leu Ala Lys Leu
    130                 135                 140

Ala Arg Asp Ala Thr Phe Phe Val Arg Ala His Glu Ser Asn Glu Met
145                 150                 155                 160

Gln Pro Thr Leu Ala Ile Ser His Ala Gly Val Ser Val Val Met Ala
                165                 170                 175

Gln Thr Gln Pro Arg Arg Glu Lys Arg Trp Ser Glu Trp Ala Ser Gly
            180                 185                 190

Lys Val Leu Cys Leu Leu Asp Pro Leu Asp Gly Val Tyr Asn Tyr Leu
        195                 200                 205

Ala Gln Gln Arg Cys Asn Leu Asp Asp Thr Trp Glu Gly Lys Ile Tyr
    210                 215                 220

Arg Val Leu Ala Gly Asn Pro Ala Lys His Asp Leu Asp Ile Lys Pro
225                 230                 235                 240

Thr Val Ile Ser His Arg Leu His Phe Pro Glu Gly Gly Ser Leu Ala
                245                 250                 255

Ala Leu Thr Ala His Gln Ala Cys His Leu Pro Leu Glu Thr Phe Thr
            260                 265                 270

Arg His Arg Gln Pro Arg Gly Trp Glu Gln Leu Glu Gln Cys Gly Tyr
        275                 280                 285

Pro Val Gln Arg Leu Val Ala Leu Tyr Leu Ala Ala Arg Leu Ser Trp
    290                 295                 300

Asn Gln Val Asp Gln Val Ile Arg Asn Ala Leu Ala Ser Pro Gly Ser
305                 310                 315                 320

Gly Gly Asp Leu Gly Glu Ala Ile Arg Glu Gln Pro Glu Gln Ala Arg
                325                 330                 335

Leu Ala Leu Thr Leu Ala Ala Ala Glu Ser Glu Arg Phe Val Arg Gln
            340                 345                 350

Gly Thr Gly Asn Asp Glu Ala Gly Ala Ala Asn Ala Asp Val Val Ser
        355                 360                 365

Leu Thr Cys Pro Val Ala Ala Gly Glu Cys Ala Gly Pro Ala Asp Ser
    370                 375                 380

Gly Asp Ala Leu Leu Glu Arg Asn Tyr Pro Thr Gly Ala Glu Phe Leu
385                 390                 395                 400

Gly Asp Gly Gly Asp Val Ser Phe Ser Thr Arg Gly Thr Gln Asn Trp
                405                 410                 415

Thr Val Glu Arg Leu Leu Gln Ala His Arg Gln Leu Glu Glu Arg Gly
            420                 425                 430

Tyr Val Phe Val Gly Tyr His Gly Thr Phe Leu Glu Ala Ala Gln Ser
        435                 440                 445
```

```
Ile Val Phe Gly Gly Val Arg Ala Arg Ser Gln Asp Leu Asp Ala Ile
    450                 455                 460

Trp Arg Gly Phe Tyr Ile Ala Gly Asp Pro Ala Leu Ala Tyr Gly Tyr
465                 470                 475                 480

Ala Gln Asp Gln Glu Pro Asp Ala Arg Gly Arg Ile Arg Asn Gly Ala
                485                 490                 495

Leu Leu Arg Val Tyr Val Pro Arg Ser Ser Leu Pro Gly Phe Tyr Arg
            500                 505                 510

Thr Ser Leu Thr Leu Ala Ala Pro Glu Ala Ala Gly Glu Val Glu Arg
        515                 520                 525

Leu Ile Gly His Pro Leu Pro Leu Arg Leu Asp Ala Ile Thr Gly Pro
    530                 535                 540

Glu Glu Glu Gly Gly Arg Leu Glu Thr Ile Leu Gly Trp Pro Leu Ala
545                 550                 555                 560

Glu Arg Thr Val Val Ile Pro Ser Ala Ile Pro Thr Asp Pro Arg Asn
                565                 570                 575

Val Gly Gly Asp Leu Asp Pro Ser Ser Ile Pro Asp Lys Glu Gln Ala
            580                 585                 590

Ile Ser Ala Leu Pro Asp Tyr Ala Ser Gln Pro Gly Lys Pro Pro Arg
        595                 600                 605

Glu Asp Leu Lys
    610


<210> SEQ ID NO 17
<211> LENGTH: 633
<212> TYPE: PRT
<213> ORGANISM: Vibrio Cholerae

<400> SEQUENCE: 17

Glu Asp Glu Leu Asn Ile Phe Asp Glu Cys Arg Ser Pro Cys Ser Leu
1               5                   10                  15

Thr Pro Glu Pro Gly Lys Pro Ile Gln Ser Lys Leu Ser Ile Pro Ser
            20                  25                  30

Asp Val Val Leu Asp Glu Gly Val Leu Tyr Tyr Ser Met Thr Ile Asn
        35                  40                  45

Asp Glu Gln Asn Asp Ile Lys Asp Glu Asp Lys Gly Glu Ser Ile Ile
    50                  55                  60

Thr Ile Gly Glu Phe Ala Thr Val Arg Ala Thr Arg His Tyr Val Asn
65                  70                  75                  80

Gln Asp Ala Pro Phe Gly Val Ile His Leu Asp Ile Thr Thr Glu Asn
                85                  90                  95

Gly Thr Lys Thr Tyr Ser Tyr Asn Arg Lys Glu Gly Glu Phe Ala Ile
            100                 105                 110

Asn Trp Leu Val Pro Ile Gly Glu Asp Ser Pro Ala Ser Ile Lys Ile
        115                 120                 125

Ser Val Asp Glu Leu Asp Gln Gln Arg Asn Ile Ile Glu Val Pro Lys
    130                 135                 140

Leu Tyr Ser Ile Asp Leu Asp Asn Gln Thr Leu Glu Gln Trp Lys Thr
145                 150                 155                 160

Gln Gly Asn Val Ser Phe Ser Val Thr Arg Pro Glu His Asn Ile Ala
                165                 170                 175

Ile Ser Trp Pro Ser Val Ser Tyr Lys Ala Ala Gln Lys Glu Gly Ser
            180                 185                 190

Arg His Lys Arg Trp Ala His Trp His Thr Gly Leu Ala Leu Cys Trp
        195                 200                 205
```

-continued

```
Leu Val Pro Met Asp Ala Ile Tyr Asn Tyr Ile Thr Gln Gln Asn Cys
    210                 215                 220

Thr Leu Gly Asp Asn Trp Phe Gly Gly Ser Tyr Glu Thr Val Ala Gly
225                 230                 235                 240

Thr Pro Lys Val Ile Thr Val Lys Gln Gly Ile Glu Gln Lys Pro Val
                245                 250                 255

Glu Gln Arg Ile His Phe Ser Lys Gly Asn Ala Met Ser Ala Leu Ala
            260                 265                 270

Ala His Arg Val Cys Gly Val Pro Leu Glu Thr Leu Ala Arg Ser Arg
        275                 280                 285

Lys Pro Arg Asp Leu Thr Asp Asp Leu Ser Cys Ala Tyr Gln Ala Gln
    290                 295                 300

Asn Ile Val Ser Leu Phe Val Ala Thr Arg Ile Leu Phe Ser His Leu
305                 310                 315                 320

Asp Ser Val Phe Thr Leu Asn Leu Asp Glu Gln Glu Pro Glu Val Ala
                325                 330                 335

Glu Arg Leu Ser Asp Leu Arg Arg Ile Asn Glu Asn Asn Pro Gly Met
            340                 345                 350

Val Thr Gln Val Leu Thr Val Ala Arg Gln Ile Tyr Asn Asp Tyr Val
        355                 360                 365

Thr His His Pro Gly Leu Thr Pro Glu Gln Thr Ser Ala Gly Ala Gln
    370                 375                 380

Ala Ala Asp Ile Leu Ser Leu Phe Cys Pro Asp Ala Asp Lys Ser Cys
385                 390                 395                 400

Val Ala Ser Asn Asn Asp Gln Ala Asn Ile Asn Ile Glu Ser Arg Ser
                405                 410                 415

Gly Arg Ser Tyr Leu Pro Glu Asn Arg Ala Val Ile Thr Pro Gln Gly
            420                 425                 430

Val Thr Asn Trp Thr Tyr Gln Glu Leu Glu Ala Thr His Gln Ala Leu
        435                 440                 445

Thr Arg Glu Gly Tyr Val Phe Val Gly Tyr His Gly Thr Asn His Val
    450                 455                 460

Ala Ala Gln Thr Ile Val Asn Arg Ile Ala Pro Val Pro Arg Gly Asn
465                 470                 475                 480

Asn Thr Glu Asn Glu Glu Lys Trp Gly Gly Leu Tyr Val Ala Thr His
                485                 490                 495

Ala Glu Val Ala His Gly Tyr Ala Arg Ile Lys Glu Gly Thr Gly Glu
            500                 505                 510

Tyr Gly Leu Pro Thr Arg Ala Glu Arg Asp Ala Arg Gly Val Met Leu
        515                 520                 525

Arg Val Tyr Ile Pro Arg Ala Ser Leu Glu Arg Phe Tyr Arg Thr Asn
    530                 535                 540

Thr Pro Leu Glu Asn Ala Glu Glu His Ile Thr Gln Val Ile Gly His
545                 550                 555                 560

Ser Leu Pro Leu Arg Asn Glu Ala Phe Thr Gly Pro Glu Ser Ala Gly
                565                 570                 575

Gly Glu Asp Glu Thr Val Ile Gly Trp Asp Met Ala Ile His Ala Val
            580                 585                 590

Ala Ile Pro Ser Thr Ile Pro Gly Asn Ala Tyr Glu Glu Leu Ala Ile
        595                 600                 605

Asp Glu Glu Ala Val Ala Lys Glu Gln Ser Ile Ser Thr Lys Pro Pro
    610                 615                 620
```

Tyr Lys Glu Arg Lys Asp Glu Leu Lys
625 630

<210> SEQ ID NO 18
<211> LENGTH: 10
<212> TYPE: PRT
<213> ORGANISM: Artificial Sequence
<220> FEATURE:
<223> OTHER INFORMATION: synthetic construct

<400> SEQUENCE: 18

Ala Arg Ser Arg Lys Pro Arg Asp Leu Thr
1 5 10

<210> SEQ ID NO 19
<211> LENGTH: 10
<212> TYPE: PRT
<213> ORGANISM: Artificial Sequence
<220> FEATURE:
<223> OTHER INFORMATION: synthetic construct

<400> SEQUENCE: 19

Thr Arg His Arg Gln Pro Arg Gly Trp Glu
1 5 10

<210> SEQ ID NO 20
<211> LENGTH: 10
<212> TYPE: PRT
<213> ORGANISM: Artificial Sequence
<220> FEATURE:
<223> OTHER INFORMATION: synthetic construct

<400> SEQUENCE: 20

Ala Gly Asn Arg Val Arg Arg Ser Val Gly
1 5 10

<210> SEQ ID NO 21
<211> LENGTH: 8
<212> TYPE: PRT
<213> ORGANISM: Artificial Sequence
<220> FEATURE:
<223> OTHER INFORMATION: synthetic construct

<400> SEQUENCE: 21

Leu Pro Glu Thr Gly Gly Val Glu
1 5

<210> SEQ ID NO 22
<211> LENGTH: 10
<212> TYPE: PRT
<213> ORGANISM: Artificial Sequence
<220> FEATURE:
<223> OTHER INFORMATION: synthetic construct

<400> SEQUENCE: 22

Gly Lys Gly Gly Ser Asn Ser Ala Ala Ser
1 5 10

<210> SEQ ID NO 23
<211> LENGTH: 13
<212> TYPE: PRT
<213> ORGANISM: Artificial Sequence
<220> FEATURE:
<223> OTHER INFORMATION: synthetic construct

<400> SEQUENCE: 23

Glu Ser Lys Gly Ile Glu Pro Asp Ser Gly Val Glu Gly 1 5 10

<210> SEQ ID NO 24
<211> LENGTH: 14
<212> TYPE: PRT
<213> ORGANISM: Artificial Sequence
<220> FEATURE:
<223> OTHER INFORMATION: synthetic construct

<400> SEQUENCE: 24

Leu Pro Glu Thr Gly Lys Gly Gly Ser Asn Ser Ala Ala Ser
1 5 10

<210> SEQ ID NO 25
<211> LENGTH: 5
<212> TYPE: PRT
<213> ORGANISM: Artificial Sequence
<220> FEATURE:
<223> OTHER INFORMATION: synthetic construct

<400> SEQUENCE: 25

Asp Asp Asp Asp Lys
1 5

<210> SEQ ID NO 26
<211> LENGTH: 4
<212> TYPE: PRT
<213> ORGANISM: Artificial Sequence
<220> FEATURE:
<223> OTHER INFORMATION: synthetic construct

<400> SEQUENCE: 26

Arg Ser Arg Arg
1

<210> SEQ ID NO 27
<211> LENGTH: 10
<212> TYPE: PRT
<213> ORGANISM: Artificial Sequence
<220> FEATURE:
<223> OTHER INFORMATION: synthetic construct

<400> SEQUENCE: 27

Asn Ser Ser Tyr Lys Asp Asp Asp Asp Lys
1 5 10

<210> SEQ ID NO 28
<211> LENGTH: 14
<212> TYPE: PRT
<213> ORGANISM: Artificial Sequence
<220> FEATURE:
<223> OTHER INFORMATION: synthetic construct

<400> SEQUENCE: 28

Asn Ser Ser Tyr Lys Asp Asp Asp Asp Lys Arg Ser Arg Arg
1 5 10

<210> SEQ ID NO 29
<211> LENGTH: 7
<212> TYPE: PRT
<213> ORGANISM: Artificial Sequence
<220> FEATURE:
<223> OTHER INFORMATION: synthetic construct

<400> SEQUENCE: 29

Arg Val Arg Arg Ala Ser Val
1 5

<210> SEQ ID NO 30
<211> LENGTH: 7
<212> TYPE: PRT
<213> ORGANISM: Artificial Sequence
<220> FEATURE:
<223> OTHER INFORMATION: synthetic construct

<400> SEQUENCE: 30

Arg Val Arg Arg Ser Ser Val
1 5

<210> SEQ ID NO 31
<211> LENGTH: 7
<212> TYPE: PRT
<213> ORGANISM: Artificial Sequence
<220> FEATURE:
<223> OTHER INFORMATION: synthetic construct

<400> SEQUENCE: 31

Arg Val Arg Arg Ala Thr Val
1 5

<210> SEQ ID NO 32
<211> LENGTH: 7
<212> TYPE: PRT
<213> ORGANISM: Artificial Sequence
<220> FEATURE:
<223> OTHER INFORMATION: synthetic construct

<400> SEQUENCE: 32

Glu Asn Leu Tyr Phe Gln Gly
1 5

<210> SEQ ID NO 33
<211> LENGTH: 7
<212> TYPE: PRT
<213> ORGANISM: Artificial Sequence
<220> FEATURE:
<223> OTHER INFORMATION: synthetic construct

<400> SEQUENCE: 33

Arg Val Arg Arg Ala Ser Gly
1 5

<210> SEQ ID NO 34
<211> LENGTH: 12
<212> TYPE: PRT
<213> ORGANISM: Artificial Sequence
<220> FEATURE:
<223> OTHER INFORMATION: synthetic construct

<400> SEQUENCE: 34

Tyr Ser Ala Tyr Pro Asp Ser Val Pro Met Met Ser
1 5 10

<210> SEQ ID NO 35
<211> LENGTH: 8
<212> TYPE: PRT
<213> ORGANISM: Artificial Sequence
<220> FEATURE:
<223> OTHER INFORMATION: synthetic construct

<400> SEQUENCE: 35

Leu Pro Glu Thr Gly Gly Val Glu
1 5

-continued

<210> SEQ ID NO 36
<211> LENGTH: 6
<212> TYPE: PRT
<213> ORGANISM: Artificial Sequence
<220> FEATURE:
<223> OTHER INFORMATION: synthetic construct

<400> SEQUENCE: 36

Gly Lys Gly Gly Gly Ser
1               5

<210> SEQ ID NO 37
<211> LENGTH: 10
<212> TYPE: PRT
<213> ORGANISM: Artificial Sequence
<220> FEATURE:
<223> OTHER INFORMATION: synthetic construct

<400> SEQUENCE: 37

Leu Pro Glu Thr Gly Lys Gly Gly Gly Ser
1               5                   10

<210> SEQ ID NO 38
<211> LENGTH: 5
<212> TYPE: PRT
<213> ORGANISM: Artificial Sequence
<220> FEATURE:
<223> OTHER INFORMATION: synthetic construct

<400> SEQUENCE: 38

Leu Pro Glu Thr Gly
1               5

<210> SEQ ID NO 39
<211> LENGTH: 8
<212> TYPE: PRT
<213> ORGANISM: Artificial Sequence
<220> FEATURE:
<223> OTHER INFORMATION: synthetic construct

<400> SEQUENCE: 39

Gly Lys Gly Gly Ser Asn Ser Ala
1               5

<210> SEQ ID NO 40
<211> LENGTH: 14
<212> TYPE: PRT
<213> ORGANISM: Artificial Sequence
<220> FEATURE:
<223> OTHER INFORMATION: synthetic construct

<400> SEQUENCE: 40

Gly Gly His Arg Asp Gln Arg Ser Glu Arg Ser Ala Ser Ser
1               5                   10

<210> SEQ ID NO 41
<211> LENGTH: 7
<212> TYPE: PRT
<213> ORGANISM: Artificial Sequence
<220> FEATURE:
<223> OTHER INFORMATION: synthetic construct

<400> SEQUENCE: 41

Arg Asp Gln Arg Ser Glu Arg
1               5

<210> SEQ ID NO 42
<211> LENGTH: 5
<212> TYPE: PRT
<213> ORGANISM: Artificial Sequence
<220> FEATURE:
<223> OTHER INFORMATION: synthetic construct

<400> SEQUENCE: 42

Lys Asp Glu Leu Lys
1               5

<210> SEQ ID NO 43
<211> LENGTH: 5
<212> TYPE: PRT
<213> ORGANISM: Artificial Sequence
<220> FEATURE:
<223> OTHER INFORMATION: synthetic construct

<400> SEQUENCE: 43

Arg Asp Glu Leu Lys
1               5

<210> SEQ ID NO 44
<211> LENGTH: 5
<212> TYPE: PRT
<213> ORGANISM: Artificial Sequence
<220> FEATURE:
<223> OTHER INFORMATION: synthetic construct

<400> SEQUENCE: 44

Lys Asp Glu Leu Arg
1               5

<210> SEQ ID NO 45
<211> LENGTH: 5
<212> TYPE: PRT
<213> ORGANISM: Artificial Sequence
<220> FEATURE:
<223> OTHER INFORMATION: synthetic construct

<400> SEQUENCE: 45

Arg Asp Glu Leu Arg
1               5

<210> SEQ ID NO 46
<211> LENGTH: 6
<212> TYPE: PRT
<213> ORGANISM: Artificial Sequence
<220> FEATURE:
<223> OTHER INFORMATION: synthetic construct

<400> SEQUENCE: 46

Arg Lys Pro Arg Asp Leu
1               5

<210> SEQ ID NO 47
<211> LENGTH: 6
<212> TYPE: PRT
<213> ORGANISM: Artificial Sequence
<220> FEATURE:
<223> OTHER INFORMATION: synthetic construct

<400> SEQUENCE: 47

Arg Val Arg Arg Ser Val
1               5

<210> SEQ ID NO 48

<211> LENGTH: 4
<212> TYPE: PRT
<213> ORGANISM: Artificial Sequence
<220> FEATURE:
<223> OTHER INFORMATION: synthetic construct

<400> SEQUENCE: 48

Ile Ala Pro Asp
1

<210> SEQ ID NO 49
<211> LENGTH: 4
<212> TYPE: PRT
<213> ORGANISM: Artificial Sequence
<220> FEATURE:
<223> OTHER INFORMATION: synthetic construct

<400> SEQUENCE: 49

Arg Lys Lys Arg
1

<210> SEQ ID NO 50
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa = Trp or Tyr
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Gly, Ala, Thr, Ser, or Asn

<400> SEQUENCE: 50

Xaa Glu Xaa Asp Xaa
1               5

<210> SEQ ID NO 51
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa = Ile or Leu
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Gly, Ala, Thr, Ser, or Asn

<400> SEQUENCE: 51

Xaa Glu Xaa Asp Xaa
1               5

<210> SEQ ID NO 52
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Gly, Ala, Thr, Ser, or Asn

<400> SEQUENCE: 52

Asp Glu Xaa Asp Xaa
1               5

<210> SEQ ID NO 53
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Gly, Ala, Thr, Ser, or Asn

<400> SEQUENCE: 53

Val Glu Xaa Asp Xaa
1               5

<210> SEQ ID NO 54
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa = Val or Leu
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = Gly, Ala, Thr, Ser, or Asn

<400> SEQUENCE: 54

Xaa Asp Glu Xaa Asp Xaa
1               5

<210> SEQ ID NO 55
<211> LENGTH: 6
<212> TYPE: PRT
<213> ORGANISM: Artificial Sequence
<220> FEATURE:
<223> OTHER INFORMATION: synthetic construct

<400> SEQUENCE: 55

Gly Ser Gly Arg Ser Ala
1               5

<210> SEQ ID NO 56
<211> LENGTH: 6
<212> TYPE: PRT

<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa = Tyr or Phe

<400> SEQUENCE: 56

Ser Ser Xaa Tyr Ser Gly
1               5

<210> SEQ ID NO 57
<211> LENGTH: 8
<212> TYPE: PRT
<213> ORGANISM: Artificial Sequence
<220> FEATURE:
<223> OTHER INFORMATION: synthetic construct

<400> SEQUENCE: 57

His Pro Phe His Leu Val Ile His
1               5

<210> SEQ ID NO 58
<211> LENGTH: 8
<212> TYPE: PRT
<213> ORGANISM: Artificial Sequence
<220> FEATURE:
<223> OTHER INFORMATION: synthetic construct

<400> SEQUENCE: 58

His Pro Val Gly Leu Leu Ala Arg
1               5

<210> SEQ ID NO 59
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Ser or Gly

<400> SEQUENCE: 59

Glu Xaa Xaa Tyr Xaa Gln Xaa
1               5

<210> SEQ ID NO 60
<211> LENGTH: 7
<212> TYPE: PRT
<213> ORGANISM: Artificial Sequence
<220> FEATURE:
<223> OTHER INFORMATION: synthetic construct

<400> SEQUENCE: 60

Ser Gln Asn Tyr Pro Ile Val
1               5

<210> SEQ ID NO 61

<211> LENGTH: 8
<212> TYPE: PRT
<213> ORGANISM: Artificial Sequence
<220> FEATURE:
<223> OTHER INFORMATION: synthetic construct

<400> SEQUENCE: 61

Pro Val Ile Leu Pro Ile Gln Ala
1 5

<210> SEQ ID NO 62
<211> LENGTH: 7
<212> TYPE: PRT
<213> ORGANISM: Artificial Sequence
<220> FEATURE:
<223> OTHER INFORMATION: synthetic construct

<400> SEQUENCE: 62

Ala Val Leu Gln Ser Gly Phe
1 5

<210> SEQ ID NO 63
<211> LENGTH: 6
<212> TYPE: PRT
<213> ORGANISM: Artificial Sequence
<220> FEATURE:
<223> OTHER INFORMATION: synthetic construct

<400> SEQUENCE: 63

Ala Leu Phe Gln Gly Pro
1 5

<210> SEQ ID NO 64
<211> LENGTH: 4
<212> TYPE: PRT
<213> ORGANISM: Artificial Sequence
<220> FEATURE:
<223> OTHER INFORMATION: synthetic construct

<400> SEQUENCE: 64

Arg Val Arg Arg
1

<210> SEQ ID NO 65
<211> LENGTH: 5
<212> TYPE: PRT
<213> ORGANISM: Artificial Sequence
<220> FEATURE:
<223> OTHER INFORMATION: synthetic construct

<400> SEQUENCE: 65

Asp Pro Pro Ile Val
1 5

<210> SEQ ID NO 66
<211> LENGTH: 7
<212> TYPE: PRT
<213> ORGANISM: Artificial Sequence
<220> FEATURE:
<223> OTHER INFORMATION: synthetic construct

<400> SEQUENCE: 66

Arg Val Arg Arg Ser Val Gly
1 5

<210> SEQ ID NO 67
<211> LENGTH: 6

<212> TYPE: PRT
<213> ORGANISM: Artificial Sequence
<220> FEATURE:
<223> OTHER INFORMATION: synthetic construct

<400> SEQUENCE: 67

Lys Val Pro Leu Ser Gly
1 5

<210> SEQ ID NO 68
<211> LENGTH: 12
<212> TYPE: PRT
<213> ORGANISM: Artificial Sequence
<220> FEATURE:
<223> OTHER INFORMATION: synthetic construct

<400> SEQUENCE: 68

Asp Ser Lys Val Arg Arg Ala Arg Ser Val Asp Gly
1 5 10

<210> SEQ ID NO 69
<211> LENGTH: 11
<212> TYPE: PRT
<213> ORGANISM: Artificial Sequence
<220> FEATURE:
<223> OTHER INFORMATION: synthetic construct

<400> SEQUENCE: 69

Ala Ser His Ser Ser Arg Ala Arg Asn Leu Ser
1 5 10

<210> SEQ ID NO 70
<211> LENGTH: 13
<212> TYPE: PRT
<213> ORGANISM: Artificial Sequence
<220> FEATURE:
<223> OTHER INFORMATION: synthetic construct

<400> SEQUENCE: 70

Glu Ser Lys Gly Ile Glu Pro Asp Ser Gly Val Glu Gly
1 5 10

<210> SEQ ID NO 71
<211> LENGTH: 13
<212> TYPE: PRT
<213> ORGANISM: Artificial Sequence
<220> FEATURE:
<223> OTHER INFORMATION: synthetic construct

<400> SEQUENCE: 71

Glu Ser Lys Glu Asn Leu Tyr Phe Gln Gly Val Glu Gly
1 5 10

<210> SEQ ID NO 72
<211> LENGTH: 6
<212> TYPE: PRT
<213> ORGANISM: Artificial Sequence
<220> FEATURE:
<223> OTHER INFORMATION: synthetic construct

<400> SEQUENCE: 72

Arg Val Arg Arg Ala Ser
1 5

<210> SEQ ID NO 73
<211> LENGTH: 7
<212> TYPE: PRT

<213> ORGANISM: Artificial Sequence
<220> FEATURE:
<223> OTHER INFORMATION: synthetic construct

<400> SEQUENCE: 73

Glu Leu Asn Tyr Phe Gln Gly
1 5

<210> SEQ ID NO 74
<211> LENGTH: 666
<212> TYPE: PRT
<213> ORGANISM: Vibrio Cholerae

<400> SEQUENCE: 74

Met Tyr Leu Thr Phe Tyr Leu Glu Lys Val Met Lys Lys Met Leu Leu
1 5 10 15

Ile Ala Gly Ala Thr Val Ile Ser Ser Met Ala His Pro Thr Phe Ala
20 25 30

Val Glu Asp Glu Leu Asn Ile Phe Asp Glu Cys Arg Ser Pro Cys Ser
35 40 45

Leu Thr Pro Glu Pro Gly Lys Pro Ile Gln Ser Lys Leu Ser Ile Pro
50 55 60

Ser Asp Val Val Leu Asp Glu Gly Val Leu Tyr Tyr Ser Met Thr Ile
65 70 75 80

Asn Asp Glu Gln Asn Asp Ile Lys Asp Glu Asp Lys Gly Glu Ser Ile
85 90 95

Ile Thr Ile Gly Glu Phe Ala Thr Val Arg Ala Thr Arg His Tyr Val
100 105 110

Asn Gln Asp Ala Pro Phe Gly Val Ile His Leu Asp Ile Thr Thr Glu
115 120 125

Asn Gly Thr Lys Thr Tyr Ser Tyr Asn Arg Lys Glu Gly Glu Phe Ala
130 135 140

Ile Asn Trp Leu Val Pro Ile Gly Glu Asp Ser Pro Ala Ser Ile Lys
145 150 155 160

Ile Ser Val Asp Glu Leu Asp Gln Gln Arg Asn Ile Ile Glu Val Pro
165 170 175

Lys Leu Tyr Ser Ile Asp Leu Asp Asn Gln Thr Leu Glu Gln Trp Lys
180 185 190

Thr Gln Gly Asn Val Ser Phe Ser Val Thr Arg Pro Glu His Asn Ile
195 200 205

Ala Ile Ser Trp Pro Ser Val Ser Tyr Lys Ala Ala Gln Lys Glu Gly
210 215 220

Ser Arg His Lys Arg Trp Ala His Trp His Thr Gly Leu Ala Leu Cys
225 230 235 240

Trp Leu Val Pro Met Asp Ala Ile Tyr Asn Tyr Ile Thr Gln Gln Asn
245 250 255

Cys Thr Leu Gly Asp Asn Trp Phe Gly Gly Ser Tyr Glu Thr Val Ala
260 265 270

Gly Thr Pro Lys Val Ile Thr Val Lys Gln Gly Ile Glu Gln Lys Pro
275 280 285

Val Glu Gln Arg Ile His Phe Ser Lys Gly Asn Ala Met Ser Ala Leu
290 295 300

Ala Ala His Arg Val Cys Gly Val Pro Leu Glu Thr Leu Ala Arg Ser
305 310 315 320

Arg Lys Pro Arg Asp Leu Thr Asp Asp Leu Ser Cys Ala Tyr Gln Ala
325 330 335

```
Gln Asn Ile Val Ser Leu Phe Val Ala Thr Arg Ile Leu Phe Ser His
            340                 345                 350

Leu Asp Ser Val Phe Thr Leu Asn Leu Asp Glu Gln Glu Pro Glu Val
        355                 360                 365

Ala Glu Arg Leu Ser Asp Leu Arg Arg Ile Asn Glu Asn Asn Pro Gly
    370                 375                 380

Met Val Thr Gln Val Leu Thr Val Ala Arg Gln Ile Tyr Asn Asp Tyr
385                 390                 395                 400

Val Thr His His Pro Gly Leu Thr Pro Glu Gln Thr Ser Ala Gly Ala
                405                 410                 415

Gln Ala Ala Asp Ile Leu Ser Leu Phe Cys Pro Asp Ala Asp Lys Ser
            420                 425                 430

Cys Val Ala Ser Asn Asn Asp Gln Ala Asn Ile Asn Ile Glu Ser Arg
        435                 440                 445

Ser Gly Arg Ser Tyr Leu Pro Glu Asn Arg Ala Val Ile Thr Pro Gln
    450                 455                 460

Gly Val Thr Asn Trp Thr Tyr Gln Glu Leu Glu Ala Thr His Gln Ala
465                 470                 475                 480

Leu Thr Arg Glu Gly Tyr Val Phe Val Gly Tyr His Gly Thr Asn His
                485                 490                 495

Val Ala Ala Gln Thr Ile Val Asn Arg Ile Ala Pro Val Pro Arg Gly
            500                 505                 510

Asn Asn Thr Glu Asn Glu Glu Lys Trp Gly Gly Leu Tyr Val Ala Thr
        515                 520                 525

His Ala Glu Val Ala His Gly Tyr Ala Arg Ile Lys Glu Gly Thr Gly
    530                 535                 540

Glu Tyr Gly Leu Pro Thr Arg Ala Glu Arg Asp Ala Arg Gly Val Met
545                 550                 555                 560

Leu Arg Val Tyr Ile Pro Arg Ala Ser Leu Glu Arg Phe Tyr Arg Thr
                565                 570                 575

Asn Thr Pro Leu Glu Asn Ala Glu Glu His Ile Thr Gln Val Ile Gly
            580                 585                 590

His Ser Leu Pro Leu Arg Asn Glu Ala Phe Thr Gly Pro Glu Ser Ala
        595                 600                 605

Gly Gly Glu Asp Glu Thr Val Ile Gly Trp Asp Met Ala Ile His Ala
    610                 615                 620

Val Ala Ile Pro Ser Thr Ile Pro Gly Asn Ala Tyr Glu Glu Leu Ala
625                 630                 635                 640

Ile Asp Glu Glu Ala Val Ala Lys Glu Gln Ser Ile Ser Thr Lys Pro
                645                 650                 655

Pro Tyr Lys Glu Arg Lys Asp Glu Leu Lys
            660                 665
```

<210> SEQ ID NO 75
<211> LENGTH: 1923
<212> TYPE: DNA
<213> ORGANISM: Artificial Sequence
<220> FEATURE:
<223> OTHER INFORMATION: synthetic

<400> SEQUENCE: 75

```
atggaagatg agctgaatat ttttgacgag tgccgtagcc cgtgttctct gaccccagaa      60

cctggcaaac cgatccagag taaactgtca attccatccg atgtggttct ggacgaaggt     120

gtcctgtatt actcgatgac gatcaacgat gaacaaaatg acattaaaga tgaggataaa     180
```

ggggaaagca tcattactat cggagagttc gcgacagtac gcgccacccg tcattatgtg 240
aaccaggacg caccttttgg cgttattcac ctggatatca cgactgaaaa tggtacaaaa 300
acctactctt ataaccgcaa agaaggggag ttcgctatta attggctggt cccgatcgga 360
gaggacagtc cggcgtcaat taaaatctcc gtagatgagc tggaccaaca gcgtaacatt 420
atcgaagtgc caaaactgta ctcgattgat ctggataatc agacgctgga acaatggaaa 480
acccagggca acgttagctt ttctgtcact cgccctgagc ataatattgc catcagttgg 540
ccgtcagtgt cctataaagc agctcaaaaa gaaggttcgc gtcacaaacg ctgggcgcat 600
tggcacacag gcctggccct gtgctggctg gtaccgatgg acgcaattta caactatatc 660
acgcagcaga attgtaccct gggtgataac tggttcgggg gaagctatga gactgttgct 720
ggcacaccaa aagtgattac cgtcaaacaa ggtatcgaac agaaacctgt tgaacaacgt 780
attcattttg ctagcaaagg caatgccatg agtgcactgg ctgcgcaccg cgtatgcggt 840
gtgccgctgg agacactggc ccgttcacgc aaaccacgtg acctgaccga tgacctgagc 900
tgcgcgtatc aggcccaaaa tattgtgtct ctgtttgttg caacgcgtat cctgttcagt 960
catctggatt cagtctttac tctgaacctg gacgaacagg agccggaagt agctgagcgc 1020
ctgtccgatc tgcgtcgcat taatgaaaac aatccaggca tggtgacaca agttctgacc 1080
gtcgcgcgtc agatctacaa cgactatgta acgcaccatc ctggtctgac tccggaacag 1140
acatcggccg gggcacaagc tgcggatatt ctgagcctgt tctgtccaga tgccgacaaa 1200
tcttgcgtgg caagtaataa cgatcaggct aatatcaaca ttgagtcacg ctccggacgt 1260
tcgtacctgc ctgaaaatcg cgcggttatc accccgcaag gcgtcacgaa ctggacctat 1320
caggagctgg aagccactca ccaggcactg acacgtgaag gttacgtgtt tgtagggtat 1380
catggaacga atcacgttgc tgcgcaaacc attgtgaacc gcatcgcccc ggtcccacgt 1440
ggcaataaca ctgagaatga agagaaatgg ggtggcctgt acgttgcaac acatgcggaa 1500
gtagctcacg gttatgcccg cattaaagaa gggaccggag agtatggcct gcctacgcgt 1560
gcagaacgcg acgcgcgtgg tgtgatgctg cgcgtctaca tcccgcgtgc ttcgctggag 1620
cgcttctatc gtaccaacac tccgctggaa aatgccgaag agcatattac acaggttatc 1680
ggccactctc tgccactgcg caacgaagca tttacgggtc ctgaaagtgc gggggggagag 1740 gatgaaaccg tgattggctg ggacatggct atccatgccg tagcaattcc gtcaactatt 1800
ccaggtaatg cgtacgagga actggccatc gatgaagagg cagtcgcgaa agaacaatcc 1860
atttcgacaa aaccgcctta taaagagcgt caccatcatc accatcacaa agatgaactg 1920
taa 1923

<210> SEQ ID NO 76
<211> LENGTH: 639
<212> TYPE: PRT
<213> ORGANISM: Artificial Sequence
<220> FEATURE:
<223> OTHER INFORMATION: synthetic construct

<400> SEQUENCE: 76

Met Glu Asp Glu Leu Asn Ile Phe Asp Glu Cys Arg Ser Pro Cys Ser
1 5 10 15

Leu Thr Pro Glu Pro Gly Lys Pro Ile Gln Ser Lys Leu Ser Ile Pro
20 25 30

Ser Asp Val Val Leu Asp Glu Gly Val Leu Tyr Tyr Ser Met Thr Ile
35 40 45

```
Asn Asp Glu Gln Asn Asp Ile Lys Asp Glu Asp Lys Gly Glu Ser Ile
    50                  55                  60

Ile Thr Ile Gly Glu Phe Ala Thr Val Arg Ala Thr Arg His Tyr Val
65                  70                  75                  80

Asn Gln Asp Ala Pro Phe Gly Val Ile His Leu Asp Ile Thr Thr Glu
                85                  90                  95

Asn Gly Thr Lys Thr Tyr Ser Tyr Asn Arg Lys Glu Gly Glu Phe Ala
            100                 105                 110

Ile Asn Trp Leu Val Pro Ile Gly Glu Asp Ser Pro Ala Ser Ile Lys
        115                 120                 125

Ile Ser Val Asp Glu Leu Asp Gln Gln Arg Asn Ile Ile Glu Val Pro
    130                 135                 140

Lys Leu Tyr Ser Ile Asp Leu Asp Asn Gln Thr Leu Glu Gln Trp Lys
145                 150                 155                 160

Thr Gln Gly Asn Val Ser Phe Ser Val Thr Arg Pro Glu His Asn Ile
                165                 170                 175

Ala Ile Ser Trp Pro Ser Val Ser Tyr Lys Ala Ala Gln Lys Glu Gly
            180                 185                 190

Ser Arg His Lys Arg Trp Ala His Trp His Thr Gly Leu Ala Leu Cys
        195                 200                 205

Trp Leu Val Pro Met Asp Ala Ile Tyr Asn Tyr Ile Thr Gln Gln Asn
    210                 215                 220

Cys Thr Leu Gly Asp Asn Trp Phe Gly Gly Ser Tyr Glu Thr Val Ala
225                 230                 235                 240

Gly Thr Pro Lys Val Ile Thr Val Lys Gln Gly Ile Glu Gln Lys Pro
                245                 250                 255

Val Glu Gln Arg Ile His Phe Ser Lys Gly Asn Ala Met Ser Ala Leu
            260                 265                 270

Ala Ala His Arg Val Cys Gly Val Pro Leu Glu Thr Leu Ala Arg Ser
        275                 280                 285

Arg Lys Pro Arg Asp Leu Thr Asp Asp Leu Ser Cys Ala Tyr Gln Ala
    290                 295                 300

Gln Asn Ile Val Ser Leu Phe Val Ala Thr Arg Ile Leu Phe Ser His
305                 310                 315                 320

Leu Asp Ser Val Phe Thr Leu Asn Leu Asp Glu Gln Glu Pro Glu Val
                325                 330                 335

Ala Glu Arg Leu Ser Asp Leu Arg Arg Ile Asn Glu Asn Asn Pro Gly
            340                 345                 350

Met Val Thr Gln Val Leu Thr Val Ala Arg Gln Ile Tyr Asn Asp Tyr
        355                 360                 365

Val Thr His His Pro Gly Leu Thr Pro Glu Gln Thr Ser Ala Gly Ala
    370                 375                 380

Gln Ala Ala Asp Ile Leu Ser Leu Phe Cys Pro Asp Ala Asp Lys Ser
385                 390                 395                 400

Cys Val Ala Ser Asn Asn Asp Gln Ala Asn Ile Asn Ile Glu Ser Arg
                405                 410                 415

Ser Gly Arg Ser Tyr Leu Pro Glu Asn Arg Ala Val Ile Thr Pro Gln
            420                 425                 430

Gly Val Thr Asn Trp Thr Tyr Gln Glu Leu Glu Ala Thr His Gln Ala
        435                 440                 445

Leu Thr Arg Glu Gly Tyr Val Phe Val Gly Tyr His Gly Thr Asn His
    450                 455                 460
```

```
Val Ala Ala Gln Thr Ile Val Asn Arg Ile Ala Pro Val Pro Arg Gly
465                 470                 475                 480

Asn Asn Thr Glu Asn Glu Glu Lys Trp Gly Gly Leu Tyr Val Ala Thr
                485                 490                 495

His Ala Glu Val Ala His Gly Tyr Ala Arg Ile Lys Glu Gly Thr Gly
            500                 505                 510

Glu Tyr Gly Leu Pro Thr Arg Ala Glu Arg Asp Ala Arg Gly Val Met
        515                 520                 525

Leu Arg Val Tyr Ile Pro Arg Ala Ser Leu Glu Arg Phe Tyr Arg Thr
    530                 535                 540

Asn Thr Pro Leu Glu Asn Ala Glu Glu His Ile Thr Gln Val Ile Gly
545                 550                 555                 560

His Ser Leu Pro Leu Arg Asn Glu Ala Phe Thr Gly Pro Glu Ser Ala
                565                 570                 575

Gly Gly Glu Asp Glu Thr Val Ile Gly Trp Asp Met Ala Ile His Ala
            580                 585                 590

Val Ala Ile Pro Ser Thr Ile Pro Gly Asn Ala Tyr Glu Glu Leu Ala
        595                 600                 605

Ile Asp Glu Glu Ala Val Ala Lys Glu Gln Ser Ile Ser Thr Lys Pro
    610                 615                 620

Pro Tyr Lys Glu Arg His His His His His His Lys Asp Glu Leu
625                 630                 635
```

<210> SEQ ID NO 77
<211> LENGTH: 660
<212> TYPE: DNA
<213> ORGANISM: Artificial Sequence
<220> FEATURE:
<223> OTHER INFORMATION: synthetic construct

<400> SEQUENCE: 77

```
atgggccctg aaaatcgcgc ggttatcacc ccgcaaggcg tcacgaactg gacctatcag     60

gagctggaag ccactcacca ggcactgaca cgtgaaggtt acgtgtttgt agggtatcat    120

ggaacgaatc acgttgctgc gcaaaccatt gtgaaccgca tcgccccggt cccacgtggc    180

aataacactg agaatgaaga gaaatggggt ggcctgtacg ttgcaacaca tgcggaagta    240

gctcacggtt atgcccgcat taaagaaggg accggagagt atggcctgcc tacgcgtgca    300

gaacgcgacg cgcgtggtgt gatgctgcgc gtctacatcc cgcgtgcttc gctggagcgc    360

ttctatcgta ccaacactcc gctggaaaat gccgaagagc atattacaca ggttatcggc    420

cactctctgc cactgcgcaa cgaagcattt acgggtcctg aaagtgcggg gggagaggat    480

gaaaccgtga ttggctggga catggctatc catgccgtag caattccgtc aactattcca    540

ggtaatgcgt acgaggaact ggccatcgat gaagaggcag tcgcgaaaga acaatccatt    600

tcgacaaaac cgccttataa agagcgtcac catcatcacc atcacaaaga tgaactgtaa    660
```

<210> SEQ ID NO 78
<211> LENGTH: 219
<212> TYPE: PRT
<213> ORGANISM: Artificial Sequence
<220> FEATURE:
<223> OTHER INFORMATION: synthetic construct

<400> SEQUENCE: 78

```
Met Gly Pro Glu Asn Arg Ala Val Ile Thr Pro Gln Gly Val Thr Asn
1               5                   10                  15

Trp Thr Tyr Gln Glu Leu Glu Ala Thr His Gln Ala Leu Thr Arg Glu
```

-continued

```
            20                  25                  30

Gly Tyr Val Phe Val Gly Tyr His Gly Thr Asn His Val Ala Ala Gln
        35                  40                  45

Thr Ile Val Asn Arg Ile Ala Pro Val Pro Arg Gly Asn Asn Thr Glu
    50                  55                  60

Asn Glu Glu Lys Trp Gly Gly Leu Tyr Val Ala Thr His Ala Glu Val
65                  70                  75                  80

Ala His Gly Tyr Ala Arg Ile Lys Glu Gly Thr Gly Glu Tyr Gly Leu
                85                  90                  95

Pro Thr Arg Ala Glu Arg Asp Ala Arg Gly Val Met Leu Arg Val Tyr
            100                 105                 110

Ile Pro Arg Ala Ser Leu Glu Arg Phe Tyr Arg Thr Asn Thr Pro Leu
        115                 120                 125

Glu Asn Ala Glu Glu His Ile Thr Gln Val Ile Gly His Ser Leu Pro
    130                 135                 140

Leu Arg Asn Glu Ala Phe Thr Gly Pro Glu Ser Ala Gly Gly Glu Asp
145                 150                 155                 160

Glu Thr Val Ile Gly Trp Asp Met Ala Ile His Ala Val Ala Ile Pro
                165                 170                 175

Ser Thr Ile Pro Gly Asn Ala Tyr Glu Glu Leu Ala Ile Asp Glu Glu
            180                 185                 190

Ala Val Ala Lys Glu Gln Ser Ile Ser Thr Lys Pro Pro Tyr Lys Glu
        195                 200                 205

Arg His His His His His His Lys Asp Glu Leu
    210                 215
```

<210> SEQ ID NO 79
<211> LENGTH: 1328
<212> TYPE: DNA
<213> ORGANISM: Artificial Sequence
<220> FEATURE:
<223> OTHER INFORMATION: synthetic construct

<400> SEQUENCE: 79

```
atgggctcca acgaactgca tcaggtgccg agcaactgcg attgtctgaa cggcggtacc      60

tgcgtttcca acaaatattt ttctaacatt cactggtgta actgcccgaa aaaattcggt     120

ggacaacatt gtgaaatcga cggcggtggt ggttcgggcg gtggcggttc gggtggcggt     180

ggcagctcta gcaaaggcaa tgccatgagt gcactggctg cgcaccgcgt atgcggtgtg     240

ccgctggaga cactggcccg ttcacgcaaa ccacgtgacc tgaccgatga cctgagctgc     300

gcgtatcagg cccaaaatat tgtgtctctg tttgttgcaa cgcgtatcct gttcagtcat     360

ctggattcag tctttactct gaacctggac gaacaggagc cggaagtagc tgagcgcctg     420

tccgatctgc gtcgcattaa tgaaaacaat ccaggcatgg tgacacaagt tctgaccgtc     480

gcgcgtcaga tctacaacga ctatgtaacg caccatcctg gtctgactcc ggaacagaca     540

tcggccgggg cacaagctgc ggatattctg agcctgttct gtccagatgc cgacaaatct     600

tgcgtggcaa gtaataacga tcaggctaat atcaacattg agtcacgctc cggacgttcg     660

tacctgcctg aaaatcgcgc ggttatcacc ccgcaaggcg tcacgaactg gacctatcag     720

gagctggaag ccactcacca ggcactgaca cgtgaaggtt acgtgtttgt agggtatcat     780

ggaacgaatc acgttgctgc gcaaaccatt gtgaaccgca tcgccccggt cccacgtggc     840

aataacactg agaatgaaga gaaatggggt ggcctgtacg ttgcaacaca tgcggaagta     900

gctcacggtt atgcccgcat taaagaaggg accggagagt atggcctgcc tacgcgtgca     960
```

```
gaacgcgacg cgcgtggtgt gatgctgcgc gtctacatcc cgcgtgcttc gctggagcgc   1020

ttctatcgta ccaacactcc gctggaaaat gccgaagagc atattacaca ggttatcggc   1080

cactctctgc cactgcgcaa cgaagcattt acgggtcctg aaagtgcggg gggagaggat   1140

gaaaccgtga ttggctggga catggctatc catgccgtag caattccgtc aactattcca   1200

ggtaatgcgt acgaggaact ggccatcgat gaagaggcag tcgcgaaaga acaatccatt   1260

tcgacaaaac cgccttataa agagcgtcac catcatcacc atcacaaaga tgaactgtaa   1320

gcggccgc                                                            1328


<210> SEQ ID NO 80
<211> LENGTH: 438
<212> TYPE: PRT
<213> ORGANISM: Artificial Sequence
<220> FEATURE:
<223> OTHER INFORMATION: synthetic construct

<400> SEQUENCE: 80

Met Ser Asn Glu Leu His Gln Val Pro Ser Asn Cys Asp Cys Leu Asn
1               5                   10                  15

Gly Gly Thr Cys Val Ser Asn Lys Tyr Phe Ser Asn Ile His Trp Cys
            20                  25                  30

Asn Cys Pro Lys Lys Phe Gly Gly Gln His Cys Glu Ile Asp Gly Gly
        35                  40                  45

Gly Gly Ser Gly Gly Gly Gly Ser Gly Gly Gly Gly Ser Ser Ser Lys
    50                  55                  60

Gly Asn Ala Met Ser Ala Leu Ala Ala His Arg Val Cys Gly Val Pro
65                  70                  75                  80

Leu Glu Thr Leu Ala Arg Ser Arg Lys Pro Arg Asp Leu Thr Asp Asp
                85                  90                  95

Leu Ser Cys Ala Tyr Gln Ala Gln Asn Ile Val Ser Leu Phe Val Ala
            100                 105                 110

Thr Arg Ile Leu Phe Ser His Leu Asp Ser Val Phe Thr Leu Asn Leu
        115                 120                 125

Asp Glu Gln Glu Pro Glu Val Ala Glu Arg Leu Ser Asp Leu Arg Arg
    130                 135                 140

Ile Asn Glu Asn Asn Pro Gly Met Val Thr Gln Val Leu Thr Val Ala
145                 150                 155                 160

Arg Gln Ile Tyr Asn Asp Tyr Val Thr His His Pro Gly Leu Thr Pro
                165                 170                 175

Glu Gln Thr Ser Ala Gly Ala Gln Ala Ala Asp Ile Leu Ser Leu Phe
            180                 185                 190

Cys Pro Asp Ala Asp Lys Ser Cys Val Ala Ser Asn Asn Asp Gln Ala
        195                 200                 205

Asn Ile Asn Ile Glu Ser Arg Ser Gly Arg Ser Tyr Leu Pro Glu Asn
    210                 215                 220

Arg Ala Val Ile Thr Pro Gln Gly Val Thr Asn Trp Thr Tyr Gln Glu
225                 230                 235                 240

Leu Glu Ala Thr His Gln Ala Leu Thr Arg Glu Gly Tyr Val Phe Val
                245                 250                 255

Gly Tyr His Gly Thr Asn His Val Ala Ala Gln Thr Ile Val Asn Arg
            260                 265                 270

Ile Ala Pro Val Pro Arg Gly Asn Asn Thr Glu Asn Glu Glu Lys Trp
        275                 280                 285
```

```
Gly Gly Leu Tyr Val Ala Thr His Ala Glu Val Ala His Gly Tyr Ala
    290                 295                 300

Arg Ile Lys Glu Gly Thr Gly Glu Tyr Gly Leu Pro Thr Arg Ala Glu
305                 310                 315                 320

Arg Asp Ala Arg Gly Val Met Leu Arg Val Tyr Ile Pro Arg Ala Ser
                325                 330                 335

Leu Glu Arg Phe Tyr Arg Thr Asn Thr Pro Leu Glu Asn Ala Glu Glu
            340                 345                 350

His Ile Thr Gln Val Ile Gly His Ser Leu Pro Leu Arg Asn Glu Ala
        355                 360                 365

Phe Thr Gly Pro Glu Ser Ala Gly Gly Glu Asp Glu Thr Val Ile Gly
    370                 375                 380

Trp Asp Met Ala Ile His Ala Val Ala Ile Pro Ser Thr Ile Pro Gly
385                 390                 395                 400

Asn Ala Tyr Glu Glu Leu Ala Ile Asp Glu Glu Ala Val Ala Lys Glu
                405                 410                 415

Gln Ser Ile Ser Thr Lys Pro Pro Tyr Lys Glu Arg His His His His
            420                 425                 430

His His Lys Asp Glu Leu
        435


<210> SEQ ID NO 81
<211> LENGTH: 438
<212> TYPE: PRT
<213> ORGANISM: Artificial Sequence
<220> FEATURE:
<223> OTHER INFORMATION: synthetic construct

<400> SEQUENCE: 81

Met Ser Asn Glu Leu His Gln Val Pro Ser Asn Cys Asp Cys Leu Asn
1               5                   10                  15

Gly Gly Thr Cys Val Ser Asn Lys Tyr Phe Ser Asn Ile His Trp Cys
            20                  25                  30

Asn Cys Pro Lys Lys Phe Gly Gly Gln His Cys Glu Ile Asp Gly Gly
        35                  40                  45

Gly Gly Ser Gly Gly Gly Gly Ser Gly Gly Gly Gly Ser Ser Ser Lys
    50                  55                  60

Gly Asn Ala Met Ser Ala Leu Ala Ala His Arg Val Cys Gly Val Pro
65                  70                  75                  80

Leu Glu Thr Leu Ala Arg Ser Ile Glu Pro Asp Asp Leu Thr Asp Asp
                85                  90                  95

Leu Ser Cys Ala Tyr Gln Ala Gln Asn Ile Val Ser Leu Phe Val Ala
            100                 105                 110

Thr Arg Ile Leu Phe Ser His Leu Asp Ser Val Phe Thr Leu Asn Leu
        115                 120                 125

Asp Glu Gln Glu Pro Glu Val Ala Glu Arg Leu Ser Asp Leu Arg Arg
    130                 135                 140

Ile Asn Glu Asn Asn Pro Gly Met Val Thr Gln Val Leu Thr Val Ala
145                 150                 155                 160

Arg Gln Ile Tyr Asn Asp Tyr Val Thr His His Pro Gly Leu Thr Pro
                165                 170                 175

Glu Gln Thr Ser Ala Gly Ala Gln Ala Ala Asp Ile Leu Ser Leu Phe
            180                 185                 190

Cys Pro Asp Ala Asp Lys Ser Cys Val Ala Ser Asn Asn Asp Gln Ala
        195                 200                 205
```

```
Asn Ile Asn Ile Glu Ser Arg Ser Gly Arg Ser Tyr Leu Pro Glu Asn
    210                 215                 220

Arg Ala Val Ile Thr Pro Gln Gly Val Thr Asn Trp Thr Tyr Gln Glu
225                 230                 235                 240

Leu Glu Ala Thr His Gln Ala Leu Thr Arg Glu Gly Tyr Val Phe Val
                245                 250                 255

Gly Tyr His Gly Thr Asn His Val Ala Ala Gln Thr Ile Val Asn Arg
            260                 265                 270

Ile Ala Pro Val Pro Arg Gly Asn Asn Thr Glu Asn Glu Glu Lys Trp
        275                 280                 285

Gly Gly Leu Tyr Val Ala Thr His Ala Glu Val Ala His Gly Tyr Ala
    290                 295                 300

Arg Ile Lys Glu Gly Thr Gly Glu Tyr Gly Leu Pro Thr Arg Ala Glu
305                 310                 315                 320

Arg Asp Ala Arg Gly Val Met Leu Arg Val Tyr Ile Pro Arg Ala Ser
                325                 330                 335

Leu Glu Arg Phe Tyr Arg Thr Asn Thr Pro Leu Glu Asn Ala Glu Glu
            340                 345                 350

His Ile Thr Gln Val Ile Gly His Ser Leu Pro Leu Arg Asn Glu Ala
        355                 360                 365

Phe Thr Gly Pro Glu Ser Ala Gly Gly Glu Asp Glu Thr Val Ile Gly
    370                 375                 380

Trp Asp Met Ala Ile His Ala Val Ala Ile Pro Ser Thr Ile Pro Gly
385                 390                 395                 400

Asn Ala Tyr Glu Glu Leu Ala Ile Asp Glu Glu Ala Val Ala Lys Glu
                405                 410                 415

Gln Ser Ile Ser Thr Lys Pro Pro Tyr Lys Glu Arg His His His His
            420                 425                 430

His His Lys Asp Glu Leu
        435
```

<210> SEQ ID NO 82
<211> LENGTH: 1869
<212> TYPE: DNA
<213> ORGANISM: Artificial Sequence
<220> FEATURE:
<223> OTHER INFORMATION: synthetic construct

<400> SEQUENCE: 82

```
atggccaaca tccagctggt gcagtctggt cctgagctga agaagcctgg tgagactgtc      60

aaaatctcct gcaaggcttc tgggtatacc ttcactaact atggtatgaa ctgggtgaag     120

caggctcctg gtaagggtct gcgttggatg ggctggatta acacccacac tggtgagcct     180

acttatgctg atgacttcaa gggacgtttt gccttctctc tggaaacttc tgccagcact     240

gcctatctcc agatcaacaa cctcaaaaat gaggacactg ctacttactt ctgtacacgt     300

cgtggttacg actggtactt cgatgtctgg ggtgctggga ccacggtgac cgtgttctcc     360

gggggaggtg gcagcggggg aggtggcagc ggcggcggga gctccgacat caagatgacc     420

cagtctcctt cttccatgta tgcttctctg ggtgagcgtg tcactatcac ttgcaaggcc     480

agccaggaca ttaatagcta tctgagctgg ttccatcata aacctgggaa atctcctaag     540

accctgatct atcgtgctaa ccgtctggtt gatggggtcc cttctcgttt cagcggctct     600

ggttctgggc aagattattc tctcaccatc agcagcctgg actatgaaga tatgggtatt     660

tattattgtc aacagtatga tgagtctcct tggactttcg gtggtggcac caagctggag     720
```

atgaaaggct ctggcgctag caaaggcaat gccatgagtg cactggctgc gcaccgcgta 780
tgcggtgtgc cgctggagac actggcccgt tcacgcaaac cacgtgacct gaccgatgac 840
ctgagctgcg cgtatcaggc ccaaaatatt gtgtctctgt ttgttgcaac gcgtatcctg 900
ttcagtcatc tggattcagt ctttactctg aacctggacg aacaggagcc ggaagtagct 960
gagcgcctgt ccgatctgcg tcgcattaat gaaaacaatc caggcatggt gacacaagtt 1020
ctgaccgtcg cgcgtcagat ctacaacgac tatgtaacgc accatcctgg tctgactccg 1080
gaacagacat cggccggggc acaagctgcg gatattctga gcctgttctg tccagatgcc 1140
gacaaatctt gcgtggcaag taataacgat caggctaata tcaacattga gtcacgctcc 1200
ggacgttcgt acctgcctga aaatcgcgcg gttatcaccc cgcaaggcgt cacgaactgg 1260
acctatcagg agctggaagc cactcaccag gcactgacac gtgaaggtta cgtgtttgta 1320
gggtatcatg gaacgaatca cgttgctgcg caaaccattg tgaaccgcat cgccccggtc 1380
ccacgtggca ataacactga gaatgaagag aaatggggtg gcctgtacgt tgcaacacat 1440
gcggaagtag ctcacggtta tgcccgcatt aaagaaggga ccggagagta tggcctgcct 1500
acgcgtgcag aacgcgacgc gcgtggtgtg atgctgcgcg tctacatccc gcgtgcttcg 1560
ctggagcgct tctatcgtac caacactccg ctggaaaatg ccgaagagca tattacacag 1620
gttatcggcc actctctgcc actgcgcaac gaagcattta cgggtcctga aagtgcgggg 1680
ggagaggatg aaaccgtgat tggctgggac atggctatcc atgccgtagc aattccgtca 1740
actattccag gtaatgcgta cgaggaactg gccatcgatg aagaggcagt cgcgaaagaa 1800
caatccattt cgacaaaacc gccttataaa gagcgtcacc atcatcacca tcacaaagat 1860
gaactgtaa 1869

<210> SEQ ID NO 83
<211> LENGTH: 624
<212> TYPE: PRT
<213> ORGANISM: Artificial Sequence
<220> FEATURE:
<223> OTHER INFORMATION: synthetic construct

<400> SEQUENCE: 83

Met Ala Asn Ile Gln Leu Val Gln Ser Gly Pro Glu Leu Lys Lys Pro
1 5 10 15

Gly Glu Thr Val Lys Ile Ser Cys Lys Ala Ser Gly Tyr Thr Phe Thr
20 25 30

Asn Tyr Gly Met Asn Trp Val Lys Gln Ala Pro Gly Lys Gly Leu Arg
35 40 45

Trp Met Gly Trp Ile Asn Thr His Thr Gly Glu Pro Thr Tyr Ala Asp
50 55 60

Asp Phe Lys Gly Arg Phe Ala Phe Ser Leu Glu Thr Ser Ala Ser Thr
65 70 75 80

Ala Tyr Leu Gln Ile Asn Asn Leu Lys Asn Glu Asp Thr Ala Thr Tyr
85 90 95

Phe Cys Thr Arg Arg Gly Tyr Asp Trp Tyr Phe Asp Val Trp Gly Ala
100 105 110

Gly Thr Thr Val Thr Val Phe Ser Gly Gly Gly Gly Ser Gly Gly Gly
115 120 125

Gly Ser Gly Gly Gly Gly Gly Ser Ser Asp Ile Lys Met Thr Gln Ser
130 135 140

Pro Ser Ser Met Tyr Ala Ser Leu Gly Glu Arg Val Thr Ile Thr Cys
145 150 155 160

-continued

```
Lys Ala Ser Gln Asp Ile Asn Ser Tyr Leu Ser Trp Phe His His Lys
                165                 170                 175

Pro Gly Lys Ser Pro Lys Thr Leu Ile Tyr Arg Ala Asn Arg Leu Val
            180                 185                 190

Asp Gly Val Pro Ser Arg Phe Ser Gly Ser Gly Ser Gly Gln Asp Tyr
        195                 200                 205

Ser Leu Thr Ile Ser Ser Leu Asp Tyr Glu Asp Met Gly Ile Tyr Tyr
    210                 215                 220

Cys Gln Gln Tyr Asp Glu Ser Pro Trp Thr Phe Gly Gly Gly Thr Lys
225                 230                 235                 240

Leu Glu Met Lys Gly Ser Gly Ala Ser Lys Gly Asn Ala Met Ser Ala
                245                 250                 255

Leu Ala Ala His Arg Val Cys Gly Val Pro Leu Glu Thr Leu Ala Arg
            260                 265                 270

Ser Arg Lys Pro Arg Asp Leu Thr Asp Asp Leu Ser Cys Ala Tyr Gln
        275                 280                 285

Ala Gln Asn Ile Val Ser Leu Phe Val Ala Thr Arg Ile Leu Phe Ser
    290                 295                 300

His Leu Asp Ser Val Phe Thr Leu Asn Leu Asp Glu Gln Glu Pro Glu
305                 310                 315                 320

Val Ala Glu Arg Leu Ser Asp Leu Arg Arg Ile Asn Glu Asn Asn Pro
                325                 330                 335

Gly Met Val Thr Gln Val Leu Thr Val Ala Arg Gln Ile Tyr Asn Asp
            340                 345                 350

Tyr Val Thr His His Pro Gly Leu Thr Pro Glu Gln Thr Ser Ala Gly
        355                 360                 365

Ala Gln Ala Ala Asp Ile Leu Ser Leu Phe Cys Pro Asp Ala Asp Lys
    370                 375                 380

Ser Cys Val Ala Ser Asn Asn Asp Gln Ala Asn Ile Asn Ile Glu Ser
385                 390                 395                 400

Arg Ser Gly Arg Ser Tyr Leu Pro Glu Asn Arg Ala Val Ile Thr Pro
                405                 410                 415

Gln Gly Val Thr Asn Trp Thr Tyr Gln Glu Leu Glu Ala Thr His Gln
            420                 425                 430

Ala Leu Thr Arg Glu Gly Tyr Val Phe Val Gly Tyr His Gly Thr Asn
        435                 440                 445

His Val Ala Ala Gln Thr Ile Val Asn Arg Ile Ala Pro Val Pro Arg
    450                 455                 460

Gly Asn Asn Thr Glu Asn Glu Glu Lys Trp Gly Gly Leu Tyr Val Ala
465                 470                 475                 480

Thr His Ala Glu Val Ala His Gly Tyr Ala Arg Ile Lys Glu Gly Thr
                485                 490                 495

Gly Glu Tyr Gly Leu Pro Thr Arg Ala Glu Arg Asp Ala Arg Gly Val
            500                 505                 510

Met Leu Arg Val Tyr Ile Pro Arg Ala Ser Leu Glu Arg Phe Tyr Arg
        515                 520                 525

Thr Asn Thr Pro Leu Glu Asn Ala Glu Glu His Ile Thr Gln Val Ile
    530                 535                 540

Gly His Ser Leu Pro Leu Arg Asn Glu Ala Phe Thr Gly Pro Glu Ser
545                 550                 555                 560

Ala Gly Gly Glu Asp Glu Thr Val Ile Gly Trp Asp Met Ala Ile His
                565                 570                 575
```

-continued

```
Ala Val Ala Ile Pro Ser Thr Ile Pro Gly Asn Ala Tyr Glu Glu Leu
            580                 585                 590

Ala Ile Asp Glu Glu Ala Val Ala Lys Glu Gln Ser Ile Ser Thr Lys
        595                 600                 605

Pro Pro Tyr Lys Glu Arg His His His His His His Lys Asp Glu Leu
    610                 615                 620


<210> SEQ ID NO 84
<211> LENGTH: 1908
<212> TYPE: DNA
<213> ORGANISM: Artificial Sequence
<220> FEATURE:
<223> OTHER INFORMATION: synthetic construct

<400> SEQUENCE: 84

atggcccagg tgcagctgca gcagtccggc gctgagctgg tgcgccctgg ctcctccgtg     60

aaaatctcct gcaaggcttc cggctacgct ttctcctcct actggatgaa ctgggtgaag    120

cagcgccctg gccagggcct ggagtggatc ggccaaatct ggccgggcga cggcgacacc    180

aactacaacg gcaagttcaa gggcaaggct accctgaccg ctgacgagtc ctcctccacc    240

gcttacatgc agctgtcctc cctggcttcc gaggactccg ctgtgtactt ctgcgctcgc    300

cgcgagacca ccaccgtggg ccgctactac tacgctatgg actactgggg ccagggcacc    360

tcggtgaccg tgtcctccgg cggcggcggc tccggcggcg gcggctccgg cggcgggtcc    420

gggagctccg acatcctgct gacccagacc ccggcttccc tggctgtgtc cctgggccag    480

cgcgctacca tctcctgcaa ggcttcccag tccgtggact acgacggcga ctcctacctg    540

aactggtacc agcagatccc gggccagccg ccgaagctgc tgatctacga cgcttccaac    600

ctggtgtccg gcatcccgcc gcgcttctcc ggctccggct ccggcaccga cttcaccctg    660

aacatccacc cggtggagaa ggtggacgct gctacctacc actgccagca gtccaccgag    720

gacccgtgga ccttcggcgg cggcaccaag ctggagatca agcgcggctc tggcgctagc    780

aaaggcaatg ccatgagtgc actggctgcg caccgcgtat gcggtgtgcc gctggagaca    840

ctggcccgtt cacgcaaacc acgtgacctg accgatgacc tgagctgcgc gtatcaggcc    900

caaaatattg tgtctctgtt tgttgcaacg cgtatcctgt tcagtcatct ggattcagtc    960

tttactctga acctggacga acaggagccg gaagtagctg agcgcctgtc cgatctgcgt   1020

cgcattaatg aaaacaatcc aggcatggtg acacaagttc tgaccgtcgc gcgtcagatc   1080

tacaacgact atgtaacgca ccatcctggt ctgactccgg aacagacatc ggccggggca   1140

caagctgcgg atattctgag cctgttctgt ccagatgccg acaaatcttg cgtggcaagt   1200

aataacgatc aggctaatat caacattgag tcacgctccg gacgttcgta cctgcctgaa   1260

aatcgcgcgg ttatcacccc gcaaggcgtc acgaactgga cctatcagga gctggaagcc   1320

actcaccagg cactgacacg tgaaggttac gtgtttgtag ggtatcatgg aacgaatcac   1380

gttgctgcgc aaaccattgt gaaccgcatc gccccggtcc cacgtggcaa taacactgag   1440

aatgaagaga aatggggtgg cctgtacgtt gcaacacatg cggaagtagc tcacggttat   1500

gcccgcatta aagaagggac cggagagtat ggcctgccta cgcgtgcaga acgcgacgcg   1560

cgtggtgtga tgctgcgcgt ctacatcccg cgtgcttcgc tggagcgctt ctatcgtacc   1620

aacactccgc tggaaaatgc cgaagagcat attacacagg ttatcggcca ctctctgcca   1680

ctgcgcaacg aagcatttac gggtcctgaa agtgcggggg gagaggatga aaccgtgatt   1740

ggctgggaca tggctatcca tgccgtagca attccgtcaa ctattccagg taatgcgtac   1800
```

gaggaactgg ccatcgatga agaggcagtc gcgaaagaac aatccatttc gacaaaaccg 1860
ccttataaag agcgtcacca tcatcaccat cacaaagatg aactgtaa 1908

<210> SEQ ID NO 85
<211> LENGTH: 635
<212> TYPE: PRT
<213> ORGANISM: Artificial Sequence
<220> FEATURE:
<223> OTHER INFORMATION: synthetic construct

<400> SEQUENCE: 85

```
Met Ala Gln Val Gln Leu Gln Gln Ser Gly Ala Glu Leu Val Arg Pro
1               5                   10                  15

Gly Ser Ser Val Lys Ile Ser Cys Lys Ala Ser Gly Tyr Ala Phe Ser
            20                  25                  30

Ser Tyr Trp Met Asn Trp Val Lys Gln Arg Pro Gly Gln Gly Leu Glu
        35                  40                  45

Trp Ile Gly Gln Ile Trp Pro Gly Asp Gly Asp Thr Asn Tyr Asn Gly
    50                  55                  60

Lys Phe Lys Gly Lys Ala Thr Leu Thr Ala Asp Glu Ser Ser Ser Thr
65                  70                  75                  80

Ala Tyr Met Gln Leu Ser Ser Leu Ala Ser Glu Asp Ser Ala Val Tyr
                85                  90                  95

Phe Cys Ala Arg Arg Glu Thr Thr Thr Val Gly Arg Tyr Tyr Tyr Ala
            100                 105                 110

Met Asp Tyr Trp Gly Gln Gly Thr Ser Val Thr Val Ser Ser Gly Gly
        115                 120                 125

Gly Gly Ser Gly Gly Gly Gly Ser Gly Gly Gly Ser Gly Ser Ser Asp
    130                 135                 140

Ile Leu Leu Thr Gln Thr Pro Ala Ser Leu Ala Val Ser Leu Gly Gln
145                 150                 155                 160

Arg Ala Thr Ile Ser Cys Lys Ala Ser Gln Ser Val Asp Tyr Asp Gly
                165                 170                 175

Asp Ser Tyr Leu Asn Trp Tyr Gln Gln Ile Pro Gly Gln Pro Pro Lys
            180                 185                 190

Leu Leu Ile Tyr Asp Ala Ser Asn Leu Val Ser Gly Ile Pro Pro Arg
        195                 200                 205

Phe Ser Gly Ser Gly Ser Gly Thr Asp Phe Thr Leu Asn Ile His Pro
    210                 215                 220

Val Glu Lys Val Asp Ala Ala Thr Tyr His Cys Gln Gln Ser Thr Glu
225                 230                 235                 240

Asp Pro Trp Thr Phe Gly Gly Gly Thr Lys Leu Glu Ile Lys Arg Gly
                245                 250                 255

Ser Gly Ala Ser Lys Gly Asn Ala Met Ser Ala Leu Ala Ala His Arg
            260                 265                 270

Val Cys Gly Val Pro Leu Glu Thr Leu Ala Arg Ser Arg Lys Pro Arg
        275                 280                 285

Asp Leu Thr Asp Asp Leu Ser Cys Ala Tyr Gln Ala Gln Asn Ile Val
    290                 295                 300

Ser Leu Phe Val Ala Thr Arg Ile Leu Phe Ser His Leu Asp Ser Val
305                 310                 315                 320

Phe Thr Leu Asn Leu Asp Glu Gln Glu Pro Glu Val Ala Glu Arg Leu
                325                 330                 335

Ser Asp Leu Arg Arg Ile Asn Glu Asn Asn Pro Gly Met Val Thr Gln
            340                 345                 350
```

```
Val Leu Thr Val Ala Arg Gln Ile Tyr Asn Asp Tyr Val Thr His His
        355                 360                 365

Pro Gly Leu Thr Pro Glu Gln Thr Ser Ala Gly Ala Gln Ala Ala Asp
    370                 375                 380

Ile Leu Ser Leu Phe Cys Pro Asp Ala Asp Lys Ser Cys Val Ala Ser
385                 390                 395                 400

Asn Asn Asp Gln Ala Asn Ile Asn Ile Glu Ser Arg Ser Gly Arg Ser
                405                 410                 415

Tyr Leu Pro Glu Asn Arg Ala Val Ile Thr Pro Gln Gly Val Thr Asn
            420                 425                 430

Trp Thr Tyr Gln Glu Leu Glu Ala Thr His Gln Ala Leu Thr Arg Glu
        435                 440                 445

Gly Tyr Val Phe Val Gly Tyr His Gly Thr Asn His Val Ala Ala Gln
    450                 455                 460

Thr Ile Val Asn Arg Ile Ala Pro Val Pro Arg Gly Asn Asn Thr Glu
465                 470                 475                 480

Asn Glu Glu Lys Trp Gly Gly Leu Tyr Val Ala Thr His Ala Glu Val
                485                 490                 495

Ala His Gly Tyr Ala Arg Ile Lys Glu Gly Thr Gly Glu Tyr Gly Leu
            500                 505                 510

Pro Thr Arg Ala Glu Arg Asp Ala Arg Gly Val Met Leu Arg Val Tyr
        515                 520                 525

Ile Pro Arg Ala Ser Leu Glu Arg Phe Tyr Arg Thr Asn Thr Pro Leu
    530                 535                 540

Glu Asn Ala Glu Glu His Ile Thr Gln Val Ile Gly His Ser Leu Pro
545                 550                 555                 560

Leu Arg Asn Glu Ala Phe Thr Gly Pro Glu Ser Ala Gly Gly Glu Asp
                565                 570                 575

Glu Thr Val Ile Gly Trp Asp Met Ala Ile His Ala Val Ala Ile Pro
            580                 585                 590

Ser Thr Ile Pro Gly Asn Ala Tyr Glu Glu Leu Ala Ile Asp Glu Glu
        595                 600                 605

Ala Val Ala Lys Glu Gln Ser Ile Ser Thr Lys Pro Pro Tyr Lys Glu
    610                 615                 620

Arg His His His His His His Lys Asp Glu Leu
625                 630                 635
```

<210> SEQ ID NO 86
<211> LENGTH: 1887
<212> TYPE: DNA
<213> ORGANISM: Artificial Sequence
<220> FEATURE:
<223> OTHER INFORMATION: synthetic construct

<400> SEQUENCE: 86

```
atggactaca aggacgacga cgacaagggc atggccaaca tccagctggt gcagtctggt      60

cctgagctga agaagcctgg tgagactgtc aaaatctcct gcaaggcttc tgggtatacc     120

ttcactaact atggtatgaa ctgggtgaag caggctcctg gtaagggtct gcgttggatg     180

ggctggatta acacccacac tggtgagcct acttatgctg atgacttcaa gggacgtttt     240

gccttctctc tggaaacttc tgccagcact gcctatctcc agatcaacaa cctcaaaaat     300

gaggacactg ctacttactt ctgtacacgt cgtggttacg actggtactt cgatgtctgg     360

ggtgctggga ccacggtgac cgtgttctcc gggggaggtg gcagcggggg aggtggcagc     420
```

ggcggcggga gctccgacat caagatgacc cagtctcctt cttccatgta tgcttctctg 480
ggtgagcgtg tcactatcac ttgcaaggcc agccaggaca ttaatagcta tctgagctgg 540
ttccatcata aacctgggaa atctcctaag accctgatct atcgtgctaa ccgtctggtt 600
gatggggtcc cttctcgttt cagcggctct ggttctgggc aagattattc tctcaccatc 660
agcagcctgg actatgaaga tatgggtatt tattattgtc aacagtatga tgagtctcct 720
tggactttcg gtggtggcac caagctggag atgaaaggag gcggaggctc cggaggagga 780
ggcgggtccg ctagcctgat cgccctgacc gcccaccagg cctgccacct gccgctggag 840
accttcaccg ctagcatcga gccggacggc tgggagcagc tggagcagtg cggctacccg 900
gtgcagcgcc tggtggccct gtacctggcc gcccgcctgt cctggaacca ggtggaccag 960
gtgatccgca acgccctggc ctccccgggc tccggcggcg acctgggcga ggccatccgc 1020
gagcagccgg agcaggcccg cctggccctg accctggccg ccgccgagtc cgagcgcttc 1080
gtgcgccagg gcaccggcaa cgacgaggcc ggcgccgcca acgccgacgt ggtgtccctg 1140
acctgcccgg tggccgccgg cgagtgcgcc ggcccggccg actccggcga cgccctgctg 1200
gagcgcaact acccgaccgg cgccgagttc ctgggcgacg gcggcgacgt gtccttctcc 1260
acccgcggca cccagacctg gaccgtggag cgcctgctgc aggcccaccg ccagctggag 1320
gagcgcggct acgtgttcgt gggctaccac ggcaccttcc tggaggccgc ccagtccatc 1380
gtgttcggcg gcgtgcgcgc ccgctcccag gacctggacg ccatctggcg cggcttctac 1440
atcgccggcg acccggccct ggcctacggc tacgcccagg accaggagcc ggacgcccgc 1500
ggtcgcatcc gcaacggcgc cctgctgcgc gtgtacgtgc cgcgctcctc cctgccgggc 1560
ttctaccgca cctccctgac cctggccgcc ccggaggccg ccggcgaggt ggagcgcctg 1620
atcggccacc cgctgccgct gcgcctggac gccatcaccg gcccggagga ggagggcggt 1680
cgcctggaga ccatcctggg ctggccgctg gccgagcgca ccgtggtgat cccgtccgcc 1740
atcccgaccg acccgcgcaa cgtgggcggc gacctggacc cgtcctccat cccggacaag 1800
gagcaggcca tctccgccct gccggactac gcctctcagc cgggcaagcc gccgcaccac 1860
caccaccacc acaaggacga gctgtag 1887

<210> SEQ ID NO 87
<211> LENGTH: 628
<212> TYPE: PRT
<213> ORGANISM: Artificial Sequence
<220> FEATURE:
<223> OTHER INFORMATION: synthetic construct

<400> SEQUENCE: 87

Met Asp Tyr Lys Asp Asp Asp Asp Lys Gly Met Ala Asn Ile Gln Leu
1 5 10 15

Val Gln Ser Gly Pro Glu Leu Lys Lys Pro Gly Glu Thr Val Lys Ile
20 25 30

Ser Cys Lys Ala Ser Gly Tyr Thr Phe Thr Asn Tyr Gly Met Asn Trp
35 40 45

Val Lys Gln Ala Pro Gly Lys Gly Leu Arg Trp Met Gly Trp Ile Asn
50 55 60

Thr His Thr Gly Glu Pro Thr Tyr Ala Asp Asp Phe Lys Gly Arg Phe
65 70 75 80

Ala Phe Ser Leu Glu Thr Ser Ala Ser Thr Ala Tyr Leu Gln Ile Asn
85 90 95

Asn Leu Lys Asn Glu Asp Thr Ala Thr Tyr Phe Cys Thr Arg Arg Gly

-continued

```
            100                 105                 110

Tyr Asp Trp Tyr Phe Asp Val Trp Gly Ala Gly Thr Thr Val Thr Val
        115                 120                 125

Phe Ser Gly Gly Gly Gly Ser Gly Gly Gly Gly Ser Gly Gly Gly Ser
    130                 135                 140

Ser Asp Ile Lys Met Thr Gln Ser Pro Ser Ser Met Tyr Ala Ser Leu
145                 150                 155                 160

Gly Glu Arg Val Thr Ile Thr Cys Lys Ala Ser Gln Asp Ile Asn Ser
                165                 170                 175

Tyr Leu Ser Trp Phe His His Lys Pro Gly Lys Ser Pro Lys Thr Leu
            180                 185                 190

Ile Tyr Arg Ala Asn Arg Leu Val Asp Gly Val Pro Ser Arg Phe Ser
        195                 200                 205

Gly Ser Gly Ser Gly Gln Asp Tyr Ser Leu Thr Ile Ser Ser Leu Asp
    210                 215                 220

Tyr Glu Asp Met Gly Ile Tyr Tyr Cys Gln Gln Tyr Asp Glu Ser Pro
225                 230                 235                 240

Trp Thr Phe Gly Gly Gly Thr Lys Leu Glu Met Lys Gly Gly Gly Gly
                245                 250                 255

Ser Gly Gly Gly Gly Gly Ser Ala Ser Leu Ile Ala Leu Thr Ala His
            260                 265                 270

Gln Ala Cys His Leu Pro Leu Glu Thr Phe Thr Ala Ser Ile Glu Pro
        275                 280                 285

Asp Gly Trp Glu Gln Leu Glu Gln Cys Gly Tyr Pro Val Gln Arg Leu
    290                 295                 300

Val Ala Leu Tyr Leu Ala Ala Arg Leu Ser Trp Asn Gln Val Asp Gln
305                 310                 315                 320

Val Ile Arg Asn Ala Leu Ala Ser Pro Gly Ser Gly Gly Asp Leu Gly
                325                 330                 335

Glu Ala Ile Arg Glu Gln Pro Glu Gln Ala Arg Leu Ala Leu Thr Leu
            340                 345                 350

Ala Ala Ala Glu Ser Glu Arg Phe Val Arg Gln Gly Thr Gly Asn Asp
        355                 360                 365

Glu Ala Gly Ala Ala Asn Ala Asp Val Val Ser Leu Thr Cys Pro Val
    370                 375                 380

Ala Ala Gly Glu Cys Ala Gly Pro Ala Asp Ser Gly Asp Ala Leu Leu
385                 390                 395                 400

Glu Arg Asn Tyr Pro Thr Gly Ala Glu Phe Leu Gly Asp Gly Gly Asp
                405                 410                 415

Val Ser Phe Ser Thr Arg Gly Thr Gln Thr Trp Thr Val Glu Arg Leu
            420                 425                 430

Leu Gln Ala His Arg Gln Leu Glu Glu Arg Gly Tyr Val Phe Val Gly
        435                 440                 445

Tyr His Gly Thr Phe Leu Glu Ala Ala Gln Ser Ile Val Phe Gly Gly
    450                 455                 460

Val Arg Ala Arg Ser Gln Asp Leu Asp Ala Ile Trp Arg Gly Phe Tyr
465                 470                 475                 480

Ile Ala Gly Asp Pro Ala Leu Ala Tyr Gly Tyr Ala Gln Asp Gln Glu
                485                 490                 495

Pro Asp Ala Arg Gly Arg Ile Arg Asn Gly Ala Leu Leu Arg Val Tyr
            500                 505                 510

Val Pro Arg Ser Ser Leu Pro Gly Phe Tyr Arg Thr Ser Leu Thr Leu
        515                 520                 525
```

```
Ala Ala Pro Glu Ala Ala Gly Glu Val Glu Arg Leu Ile Gly His Pro
    530                 535                 540

Leu Pro Leu Arg Leu Asp Ala Ile Thr Gly Pro Glu Glu Glu Gly Gly
545                 550                 555                 560

Arg Leu Glu Thr Ile Leu Gly Trp Pro Leu Ala Glu Arg Thr Val Val
                565                 570                 575

Ile Pro Ser Ala Ile Pro Thr Asp Pro Arg Asn Val Gly Gly Asp Leu
            580                 585                 590

Asp Pro Ser Ser Ile Pro Asp Lys Glu Gln Ala Ile Ser Ala Leu Pro
        595                 600                 605

Asp Tyr Ala Ser Gln Pro Gly Lys Pro Pro His His His His His His
    610                 615                 620

Lys Asp Glu Leu
625


<210> SEQ ID NO 88
<211> LENGTH: 1608
<212> TYPE: DNA
<213> ORGANISM: Artificial Sequence
<220> FEATURE:
<223> OTHER INFORMATION: synthetic construct

<400> SEQUENCE: 88

atgggcgtga aggtgctgtt cgccctgatc tgcatcgccg tggcgctcgc cgacaactcg     60

agctacaagg acgacgacga caagatcatc gggggacatg aggccaagcc ccactcccgc    120

ccctacatgg cttatcttat gatctgggat cagaagtctc tgaagaggtg cggtggcttc    180

ctgatacaag acgacttcgt gctgacagct gctcactgtt ggggaagctc cataaatgtc    240

accttggggg cccacaatat caaagaacag gagccgaccc agcagtttat ccctgtgaaa    300

agacccatcc cccatccagc ctataatcct aagaacttct ccaacgacat catgctactg    360

cagctggaga gaaaggccaa gcggaccaga gctgtgcagc ccctcaggct acctagcaac    420

aaggcccagg tgaagccagg gcagacatgc agtgtggccg gctgggggca gacggccccc    480

ctgggaaaac actcacacac actacaagag gtgaagatga cagtgcagga agatcgaaag    540

tgcgaatctg acttacgcca ttattacgac agtaccattg agttgtgcgt gggggaccca    600

gagattaaaa agacttcctt taagggggac tctggaggcc ctcttgtgtg taacaaggtg    660

gcccagggca ttgtctccta tggacgaaac aatggcatgc ctccacgagc ctgcaccaaa    720

gtctcaagct ttgtacactg gataaagaaa accatgaaac gctacgccat gggaggcgga    780

ggctccggag gaggagggtc cgggggcggc ggaagcatgg cccaggtgca gctgcagcag    840

tccggcgctg agctggtgcg ccctggctcc tccgtgaaaa tctcctgcaa ggcttccggc    900

tacgctttct cctcctactg gatgaactgg gtgaagcagc gccctggcca gggcctggag    960

tggatcggcc aaatctggcc gggcgacggc gacaccaact acaacggcaa gttcaagggc   1020

aaggctaccc tgaccgctga cgagtcctcc tccaccgctt acatgcagct gtcctccctg   1080

gcttccgagg actccgctgt gtacttctgc gctcgccgcg agaccaccac cgtgggccgc   1140

tactactacg ctatggacta ctggggccag ggcacctcgg tgaccgtgtc ctccggcggc   1200

ggcggctccg gcggcggcgg ctccggcggc gggagctccg acatcctgct gacccagacc   1260

ccggcttccc tggctgtgtc cctgggccag cgcgctacca tctcctgcaa ggcttcccag   1320

tccgtggact acgacggcga ctcctacctg aactggtacc agcagatccc gggccagccg   1380

ccgaagctgc tgatctacga cgcttccaac ctggtgtccg gcatcccgcc gcgcttctcc   1440
```

```
ggctccggct ccggcaccga cttcaccctg aacatccacc cggtggagaa ggtggacgct   1500

gctacctacc actgccagca gtccaccgag gacccgtgga ccttcggcgg cggcaccaag   1560

ctggagatca agcgcggtgg tgacatgcat caccatcacc atcactga                1608


<210> SEQ ID NO 89
<211> LENGTH: 535
<212> TYPE: PRT
<213> ORGANISM: Artificial Sequence
<220> FEATURE:
<223> OTHER INFORMATION: synthetic construct

<400> SEQUENCE: 89

Met Gly Val Lys Val Leu Phe Ala Leu Ile Cys Ile Ala Val Ala Leu
1               5                   10                  15

Ala Asp Asn Ser Ser Tyr Lys Asp Asp Asp Asp Lys Ile Ile Gly Gly
            20                  25                  30

His Glu Ala Lys Pro His Ser Arg Pro Tyr Met Ala Tyr Leu Met Ile
        35                  40                  45

Trp Asp Gln Lys Ser Leu Lys Arg Cys Gly Gly Phe Leu Ile Gln Asp
    50                  55                  60

Asp Phe Val Leu Thr Ala Ala His Cys Trp Gly Ser Ser Ile Asn Val
65                  70                  75                  80

Thr Leu Gly Ala His Asn Ile Lys Glu Gln Glu Pro Thr Gln Gln Phe
                85                  90                  95

Ile Pro Val Lys Arg Pro Ile Pro His Pro Ala Tyr Asn Pro Lys Asn
            100                 105                 110

Phe Ser Asn Asp Ile Met Leu Leu Gln Leu Glu Arg Lys Ala Lys Arg
        115                 120                 125

Thr Arg Ala Val Gln Pro Leu Arg Leu Pro Ser Asn Lys Ala Gln Val
    130                 135                 140

Lys Pro Gly Gln Thr Cys Ser Val Ala Gly Trp Gly Gln Thr Ala Pro
145                 150                 155                 160

Leu Gly Lys His Ser His Thr Leu Gln Glu Val Lys Met Thr Val Gln
                165                 170                 175

Glu Asp Arg Lys Cys Glu Ser Asp Leu Arg His Tyr Tyr Asp Ser Thr
            180                 185                 190

Ile Glu Leu Cys Val Gly Asp Pro Glu Ile Lys Lys Thr Ser Phe Lys
        195                 200                 205

Gly Asp Ser Gly Gly Pro Leu Val Cys Asn Lys Val Ala Gln Gly Ile
    210                 215                 220

Val Ser Tyr Gly Arg Asn Asn Gly Met Pro Pro Arg Ala Cys Thr Lys
225                 230                 235                 240

Val Ser Ser Phe Val His Trp Ile Lys Lys Thr Met Lys Arg Tyr Ala
                245                 250                 255

Met Gly Gly Gly Gly Ser Gly Gly Gly Gly Ser Gly Gly Gly Gly Ser
            260                 265                 270

Met Ala Gln Val Gln Leu Gln Gln Ser Gly Ala Glu Leu Val Arg Pro
        275                 280                 285

Gly Ser Ser Val Lys Ile Ser Cys Lys Ala Ser Gly Tyr Ala Phe Ser
    290                 295                 300

Ser Tyr Trp Met Asn Trp Val Lys Gln Arg Pro Gly Gln Gly Leu Glu
305                 310                 315                 320

Trp Ile Gly Gln Ile Trp Pro Gly Asp Gly Asp Thr Asn Tyr Asn Gly
                325                 330                 335
```

```
Lys Phe Lys Gly Lys Ala Thr Leu Thr Ala Asp Glu Ser Ser Ser Thr
            340                 345                 350

Ala Tyr Met Gln Leu Ser Ser Leu Ala Ser Glu Asp Ser Ala Val Tyr
        355                 360                 365

Phe Cys Ala Arg Arg Glu Thr Thr Thr Val Gly Arg Tyr Tyr Tyr Ala
    370                 375                 380

Met Asp Tyr Trp Gly Gln Gly Thr Ser Val Thr Val Ser Ser Gly Gly
385                 390                 395                 400

Gly Gly Ser Gly Gly Gly Gly Ser Gly Gly Gly Ser Ser Asp Ile Leu
                405                 410                 415

Leu Thr Gln Thr Pro Ala Ser Leu Ala Val Ser Leu Gly Gln Arg Ala
            420                 425                 430

Thr Ile Ser Cys Lys Ala Ser Gln Ser Val Asp Tyr Asp Gly Asp Ser
        435                 440                 445

Tyr Leu Asn Trp Tyr Gln Gln Ile Pro Gly Gln Pro Pro Lys Leu Leu
    450                 455                 460

Ile Tyr Asp Ala Ser Asn Leu Val Ser Gly Ile Pro Pro Arg Phe Ser
465                 470                 475                 480

Gly Ser Gly Ser Gly Thr Asp Phe Thr Leu Asn Ile His Pro Val Glu
                485                 490                 495

Lys Val Asp Ala Ala Thr Tyr His Cys Gln Gln Ser Thr Glu Asp Pro
            500                 505                 510

Trp Thr Phe Gly Gly Gly Thr Lys Leu Glu Ile Lys Arg Gly Gly Asp
        515                 520                 525

Met His His His His His His
    530                 535
```

<210> SEQ ID NO 90
<211> LENGTH: 1977
<212> TYPE: DNA
<213> ORGANISM: Artificial Sequence
<220> FEATURE:
<223> OTHER INFORMATION: synthetic construct

<400> SEQUENCE: 90

```
atgggtgccg acgacgtggt ggactcctcc aagtccttcg tgatggaaaa cttcgcttcc      60

taccacggta ccaagcctgg ttacgtggat tccatccaga agggtatcca gaagcctaag     120

tccggtaccc agggtaacta cgacgatgat tggaagggtt tttactccac cgacaacaag     180

tacgacgccg ccggttactc cgtggataac gaaaaccctc tgtccggtaa ggccggtggt     240

gtggtgaaag tgacctaccc tggtctgacc aaggtgctgg ccctgaaggt ggataacgcc     300

gaaaccatca agaaggagct gggtctgtcc ctgaccgaac ctctgatgga gcaggtgggt     360

accgaagagt ttatcaagag attcggtgat ggtgcctcca gagtggtgct gtccctgcct     420

ttcgccgagg gttcctcctc cgtggaatac atcaacaact gggaacaggc caaggccctg     480

tccgtggaac tggagatcaa ctttgaaacc agaggtaaga gaggtcagga tgccatgtac     540

gagtacatgg cccaggcctg tgccggcaac atcgagcctg acaccggttc ctccctgtcc     600

tgcatcaacc tggactggga cgtgatcaga gacaagacca agaccaagat cgagtccctg     660

aaggagcacg gtcctatcaa gaacaagatg tccgagtccc ctgccaagac cgtgtccgag     720

gagaaggcca agcagtacct ggaggagttc caccagaccg ccctggagca ccctgagctg     780

tccgagctga agaccgtgac tggtaccaac cctgtgttcg ccggtgccaa ctacgccgcc     840

tgggccgtga acgtggccca ggtgatcgac tccgagaccg ccgacaacct ggagaagacc     900
```

```
accgccgccc tgtccatcct gcctggtatc ggttccgtga tgggtatcgc cgacggtgcc    960

gtgcaccaca acaccgagga gatcgtggcc cagtccatcg ccctgtcctc cctgatggtg   1020

gcccaggcca tccctctggt gggtgagctg gtggacatcg gtttcgccgc ctacaacttc   1080

gtggagtcca tcatcaacct gttccaggtg gtgcacaact cctacaacag acctgcctac   1140

tcccctggtc acaagaccca gcctgccatg ggaggcggag gctccggagg aggagggtcc   1200

gggggcggcg gaagcatggc ccaggtgcag ctgcagcagt ccggtgccga gctggtgaga   1260

cctggtgcct ccgtgaagct gtcctgcaag acctccgcct acaccttcac caactactgg   1320

atcaactggg tgaagcagag acctggtcag ggtctggagt ggatcggtaa catctaccct   1380

tccgactcct acaccaacta caaccagaag ttcaaggaca aggccaccct gaccgtggac   1440

aagtcctcct ccaccgccta catccagctg tcctccccta cctccgagga ctccgccgtg   1500

tactactgca ccagaggtgg tgcctactac agatccttcg actactgggc ccagggtacc   1560

acggtgaccg tgtcctccgg tggcggtggc tccgggggcg gtggttccgg tggtgggagc   1620

tccgacatcg tgctgaccca gtcccctgcc atcctgtccg cctcccctgg tgagaaagtg   1680

accatgacct gcagagccac ctcctccgtg tcctacatgc actggtacca gcagaagcct   1740

ggttcctccc ctaagccttg gatctacgcc acctccaacc tggcctccgg tgtgcctgcc   1800

agattctccg gttccggttc cggtacctcc tactccctga ccatctccag agtggaggcc   1860

gaggacgccg ccacctacta ctgccagcag tggtcctcca accctcctac cttcggtgcc   1920

ggtaccatgc tggagctgaa gagaggtggt cacatgcacc atcaccatca tcactaa      1977
```

<210> SEQ ID NO 91
<211> LENGTH: 658
<212> TYPE: PRT
<213> ORGANISM: Artificial Sequence
<220> FEATURE:
<223> OTHER INFORMATION: synthetic construct

<400> SEQUENCE: 91

```
Met Gly Ala Asp Asp Val Val Asp Ser Ser Lys Ser Phe Val Met Glu
1               5                   10                  15

Asn Phe Ala Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175
```

-continued

```
Asp Ala Met Tyr Glu Tyr Met Ala Gln Ala Cys Ala Gly Asn Ile Glu
            180                 185                 190

Pro Asp Thr Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Ala Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Ala Met Gly Gly Gly Gly Ser Gly Gly Gly Gly Ser
385                 390                 395                 400

Gly Gly Gly Gly Ser Met Ala Gln Val Gln Leu Gln Gln Ser Gly Ala
                405                 410                 415

Glu Leu Val Arg Pro Gly Ala Ser Val Lys Leu Ser Cys Lys Thr Ser
            420                 425                 430

Ala Tyr Thr Phe Thr Asn Tyr Trp Ile Asn Trp Val Lys Gln Arg Pro
        435                 440                 445

Gly Gln Gly Leu Glu Trp Ile Gly Asn Ile Tyr Pro Ser Asp Ser Tyr
    450                 455                 460

Thr Asn Tyr Asn Gln Lys Phe Lys Asp Lys Ala Thr Leu Thr Val Asp
465                 470                 475                 480

Lys Ser Ser Ser Thr Ala Tyr Ile Gln Leu Ser Ser Pro Thr Ser Glu
                485                 490                 495

Asp Ser Ala Val Tyr Tyr Cys Thr Arg Gly Gly Ala Tyr Tyr Arg Ser
            500                 505                 510

Phe Asp Tyr Trp Ala Gln Gly Thr Thr Val Thr Val Ser Ser Gly Gly
        515                 520                 525

Gly Gly Ser Gly Gly Gly Gly Ser Gly Gly Gly Ser Ser Asp Ile Val
    530                 535                 540

Leu Thr Gln Ser Pro Ala Ile Leu Ser Ala Ser Pro Gly Glu Lys Val
545                 550                 555                 560

Thr Met Thr Cys Arg Ala Thr Ser Ser Val Ser Tyr Met His Trp Tyr
                565                 570                 575

Gln Gln Lys Pro Gly Ser Ser Pro Lys Pro Trp Ile Tyr Ala Thr Ser
            580                 585                 590
```

Asn Leu Ala Ser Gly Val Pro Ala Arg Phe Ser Gly Ser Gly Ser Gly
595 600 605

Thr Ser Tyr Ser Leu Thr Ile Ser Arg Val Glu Ala Glu Asp Ala Ala
610 615 620

Thr Tyr Tyr Cys Gln Gln Trp Ser Ser Asn Pro Pro Thr Phe Gly Ala
625 630 635 640

Gly Thr Met Leu Glu Leu Lys Arg Gly Gly His Met His His His His
645 650 655

His His

<210> SEQ ID NO 92
<211> LENGTH: 470
<212> TYPE: PRT
<213> ORGANISM: Artificial Sequence
<220> FEATURE:
<223> OTHER INFORMATION: synthetic construct

<400> SEQUENCE: 92

Ala Glu Pro Val Tyr Pro Asp Gln Leu Arg Leu Phe Ser Leu Gly Gln
1 5 10 15

Gly Val Cys Gly Asp Lys Tyr Arg Pro Val Asn Arg Glu Glu Ala Gln
20 25 30

Ser Val Lys Ser Asn Ile Val Gly Met Met Gly Gln Trp Gln Ile Ser
35 40 45

Gly Leu Ala Asn Gly Trp Val Ile Met Gly Pro Gly Tyr Asn Gly Glu
50 55 60

Ile Lys Pro Gly Thr Ala Ser Asn Thr Trp Cys Tyr Pro Thr Asn Pro
65 70 75 80

Val Thr Gly Glu Ile Pro Thr Leu Ser Ala Leu Asp Ile Pro Asp Gly
85 90 95

Asp Glu Val Asp Val Gln Trp Arg Leu Val His Asp Ser Ala Asn Phe
100 105 110

Ile Lys Pro Thr Ser Tyr Leu Ala His Tyr Leu Gly Tyr Ala Trp Val
115 120 125

Gly Gly Asn His Ser Gln Tyr Val Gly Glu Asp Met Asp Val Thr Arg
130 135 140

Asp Gly Asp Gly Trp Val Ile Arg Gly Asn Asn Asp Gly Gly Cys Asp
145 150 155 160

Gly Tyr Arg Cys Gly Asp Lys Thr Ala Ile Lys Val Ser Asn Phe Ala
165 170 175

Tyr Asn Leu Asp Pro Asp Ser Phe Lys His Gly Asp Val Thr Gln Ser
180 185 190

Asp Arg Gln Leu Val Lys Thr Val Val Gly Trp Ala Val Asn Asp Ser
195 200 205

Asp Thr Pro Gln Ser Gly Tyr Asp Val Thr Leu Arg Tyr Asp Thr Ala
210 215 220

Thr Asn Trp Ser Lys Thr Asn Thr Tyr Gly Leu Ser Glu Lys Val Thr
225 230 235 240

Thr Lys Asn Lys Phe Lys Trp Pro Leu Val Gly Glu Thr Glu Leu Ser
245 250 255

Ile Glu Ile Ala Ala Asn Gln Ser Trp Ala Ser Gln Asn Gly Gly Ser
260 265 270

Thr Thr Thr Ser Leu Ser Gln Ser Val Arg Pro Thr Val Pro Ala Arg
275 280 285

Ser Lys Ile Pro Val Lys Ile Glu Leu Tyr Lys Ala Asp Ile Ser Tyr 290 295 300

Pro Tyr Glu Phe Lys Ala Asp Val Ser Tyr Asp Leu Thr Leu Ser Gly
305 310 315 320

Phe Leu Arg Trp Gly Gly Asn Ala Trp Tyr Thr His Pro Asp Asn Arg
325 330 335

Pro Asn Trp Asn His Thr Phe Val Ile Gly Pro Tyr Lys Asp Lys Ala
340 345 350

Ser Ser Ile Arg Tyr Gln Trp Asp Lys Arg Tyr Ile Pro Gly Glu Val
355 360 365

Lys Trp Trp Asp Trp Asn Trp Thr Ile Gln Gln Asn Gly Leu Ser Thr
370 375 380

Met Gln Asn Asn Leu Ala Arg Val Leu Arg Pro Val Arg Ala Gly Ile
385 390 395 400

Thr Gly Asp Phe Ser Ala Glu Ser Gln Phe Ala Gly Asn Ile Glu Ile
405 410 415

Gly Ala Pro Val Pro Leu Ala Ala Asp Ser Lys Val Arg Arg Ala Arg
420 425 430

Ser Val Asp Gly Ala Gly Gln Gly Leu Arg Leu Glu Ile Pro Leu Asp
435 440 445

Ala Gln Glu Leu Ser Gly Leu Gly Phe Asn Asn Val Ser Leu Ser Val
450 455 460

Thr Pro Ala Ala Asn Gln
465 470

<210> SEQ ID NO 93
<211> LENGTH: 407
<212> TYPE: PRT
<213> ORGANISM: Artificial Sequence
<220> FEATURE:
<223> OTHER INFORMATION: synthetic construct

<400> SEQUENCE: 93

Gly Lys Gly Gly Ser Asn Ser Ala Ala Ser Gly Glu Ile Pro Thr Leu
1 5 10 15

Ser Ala Leu Asp Ile Pro Asp Gly Asp Glu Val Asp Val Gln Trp Arg
20 25 30

Leu Val His Asp Ser Ala Asn Phe Ile Lys Pro Thr Ser Tyr Leu Ala
35 40 45

His Tyr Leu Gly Tyr Ala Trp Val Gly Gly Asn His Ser Gln Tyr Val
50 55 60

Gly Glu Asp Met Asp Val Thr Arg Asp Gly Asp Gly Trp Val Ile Arg
65 70 75 80

Gly Asn Asn Asp Gly Gly Cys Asp Gly Tyr Arg Cys Gly Asp Lys Thr
85 90 95

Ser Ile Lys Val Ser Asn Phe Ala Tyr Asn Leu Asp Pro Asp Ser Phe
100 105 110

Lys His Gly Asp Val Thr Gln Ser Asp Arg Gln Leu Val Lys Thr Val
115 120 125

Val Gly Trp Ala Ile Asn Asp Ser Asp Thr Pro Gln Ser Gly Tyr Asp
130 135 140

Val Thr Leu Arg Tyr Asp Thr Ala Thr Asn Trp Ser Lys Thr Asn Thr
145 150 155 160

Tyr Gly Leu Ser Glu Lys Val Thr Thr Lys Asn Lys Phe Lys Trp Pro
165 170 175

Leu Val Gly Glu Thr Glu Leu Ser Ile Glu Ile Ala Ala Asn Gln Ser

-continued

```
            180                 185                 190

Trp Ala Ser Gln Asn Gly Gly Ser Thr Thr Thr Ser Leu Ser Gln Ser
        195                 200                 205

Val Arg Pro Thr Val Pro Ala His Ser Lys Ile Pro Val Lys Ile Glu
    210                 215                 220

Leu Tyr Lys Ala Asp Ile Ser Tyr Pro Tyr Glu Phe Lys Ala Asp Val
225                 230                 235                 240

Ser Tyr Asp Leu Thr Leu Ser Gly Phe Leu Arg Trp Gly Gly Asn Ala
                245                 250                 255

Trp Tyr Thr His Pro Asp Asn Arg Pro Asn Trp Asn His Thr Phe Val
            260                 265                 270

Ile Gly Pro Tyr Lys Asp Lys Ala Ser Ser Ile Arg Tyr Gln Trp Asp
        275                 280                 285

Lys Arg Tyr Ile Pro Gly Glu Val Lys Trp Trp Asp Trp Asn Trp Thr
    290                 295                 300

Ile Gln Gln Asn Gly Leu Pro Thr Met Gln Asn Asn Leu Ala Arg Val
305                 310                 315                 320

Leu Arg Pro Val Arg Ala Gly Ile Thr Gly Asp Phe Ser Ala Glu Ser
                325                 330                 335

Gln Phe Ala Gly Asn Ile Glu Ile Gly Ala Pro Val Pro Val Ala Ala
            340                 345                 350

Glu Ser Lys Gly Ile Glu Pro Asp Ser Gly Val Glu Gly Ala Gly Gln
        355                 360                 365

Gly Leu Arg Leu Glu Ile Pro Leu Asp Ala Gln Glu Leu Ser Gly Leu
    370                 375                 380

Gly Phe Asn Asn Val Ser Leu Ser Val Thr Pro Ala Ala Asn Gln Val
385                 390                 395                 400

Glu His His His His His His
                405
```

<210> SEQ ID NO 94
<211> LENGTH: 1221
<212> TYPE: DNA
<213> ORGANISM: Artificial Sequence
<220> FEATURE:
<223> OTHER INFORMATION: synthetic construct

<400> SEQUENCE: 94

```
ggtaaaggtg gttcgaattc tgcagctagc ggagaaatac cgactctgtc tgccctggat     60

attccagatg gtgatgaagt agatgtgcaa tggcggctgg tacatgacag tgcgaatttc    120

atcaaaccaa ccagttatct ggcccattat ctcggctatg cctgggtagg ggggaatcac    180

agtcaatatg tcggcgaaga catggatgtg acccgtgatg gtgatggctg ggtgatccgt    240

ggcaacaatg acggtggctg cgatggttat cgctgtggtg acaagacctc catcaaggtg    300

agcaattttg cctacaacct ggatcctgac agtttcaagc atggcgatgt gacccagtcc    360

gaccgccaac tggtcaagac ggtggtgggg tgggctatca acgacagcga cacgcctcaa    420

tccggttatg acgtcaccct gcgctacgac acggccacca actggtccaa gaccaacacc    480

tatggtctga gcgagaaggt gaccaccaag aacaagttca agtggccgct ggtgggggaa    540

accgagctct ccatcgagat tgctgccaac cagtcctggg cctcccagaa cgggggctcg    600

accaccacct ctttgtccca gtccgtgcgc ccgacagtgc cggcccactc caagatcccg    660

gtgaagatag agctctacaa agccgacatc tcctacccct acgagttcaa ggccgatgtc    720

agctatgacc tgaccctgag cggtttcctg cgttggggcg gtaatgcctg gtataccat    780
```

```
ccggacaacc gtccgaactg gaaccacacc ttcgtcatag ggccatacaa ggacaaggcc    840

agcagtatcc gctaccagtg ggacaagcgt tatatcccgg gtgaagtgaa gtggtgggat    900

tggaactgga ccatacagca gaacggtctg cctaccatgc agaataacct ggccagggtg    960

ctgcgcccgg tgcgggccgg gatcaccggt gatttcagtg ccgagagcca gtttgccggc   1020

aacatcgaaa tcggcgctcc cgtgccggtc gctgccgaat ctaagggtat cgagccagat   1080

tctggtgttg aaggtgccgg tcagggtctg agactggaga tcccgctcga tgcacaagag   1140

ctctccgggc ttggcttcaa caatgtcagc ctcagcgtga cccctgctgc caaccaagtc   1200

gagcaccacc accaccacca c                                             1221


<210> SEQ ID NO 95
<211> LENGTH: 264
<212> TYPE: PRT
<213> ORGANISM: Artificial Sequence
<220> FEATURE:
<223> OTHER INFORMATION: synthetic construct

<400> SEQUENCE: 95

Ala Asn Ile Gln Leu Val Gln Ser Gly Pro Glu Leu Lys Lys Pro Gly
1               5                   10                  15

Glu Thr Val Lys Ile Ser Cys Lys Ala Ser Gly Tyr Thr Phe Thr Asn
            20                  25                  30

Tyr Gly Met Asn Trp Val Lys Gln Ala Pro Gly Lys Gly Leu Arg Trp
        35                  40                  45

Met Gly Trp Ile Asn Thr His Thr Gly Glu Pro Thr Tyr Ala Asp Asp
    50                  55                  60

Phe Lys Gly Arg Phe Ala Phe Ser Leu Glu Thr Ser Ala Ser Thr Ala
65                  70                  75                  80

Tyr Leu Gln Ile Asn Asn Leu Lys Asn Glu Asp Thr Ala Thr Tyr Phe
                85                  90                  95

Cys Thr Arg Arg Gly Tyr Asp Trp Tyr Phe Asp Val Trp Gly Ala Gly
            100                 105                 110

Thr Thr Val Thr Val Phe Ser Gly Gly Gly Gly Ser Gly Gly Gly Gly
        115                 120                 125

Ser Gly Gly Gly Ser Ser Asp Ile Lys Met Thr Gln Ser Pro Ser Ser
    130                 135                 140

Met Tyr Ala Ser Leu Gly Glu Arg Val Thr Ile Thr Cys Lys Ala Ser
145                 150                 155                 160

Gln Asp Ile Asn Ser Tyr Leu Ser Trp Phe His His Lys Pro Gly Lys
                165                 170                 175

Ser Pro Lys Thr Leu Ile Tyr Arg Ala Asn Arg Leu Val Asp Gly Val
            180                 185                 190

Pro Ser Arg Phe Ser Gly Ser Gly Ser Gly Gln Asp Tyr Ser Leu Thr
        195                 200                 205

Ile Ser Ser Leu Asp Tyr Glu Asp Met Gly Ile Tyr Tyr Cys Gln Gln
    210                 215                 220

Tyr Asp Glu Ser Pro Trp Thr Phe Gly Gly Gly Thr Lys Leu Glu Met
225                 230                 235                 240

Arg Leu Glu Arg Pro His Gly Gly Gly Ser Leu Pro Glu Thr Gly Gly
                245                 250                 255

Val Glu His His His His His His
            260
```

<210> SEQ ID NO 96
<211> LENGTH: 792
<212> TYPE: DNA
<213> ORGANISM: Artificial Sequence
<220> FEATURE:
<223> OTHER INFORMATION: synthetic construct

<400> SEQUENCE: 96
gccaacatcc agctggtgca gtctggtcct gagctgaaga agcctggtga gactgtcaaa 60
atctcctgca aggcttctgg gtataccttc actaactatg gtatgaactg ggtgaagcag 120
gctcctggta agggtctgcg ttggatgggc tggattaaca cccacactgg tgagcctact 180
tatgctgatg acttcaaggg acgttttgcc ttctctctgg aaacttctgc cagcactgcc 240
tatctccaga tcaacaacct caaaaatgag gacactgcta cttacttctg tacacgtcgt 300
ggttacgact ggtacttcga tgtctggggt gctgggacca cggtgaccgt gttctccggg 360
ggaggtggca gcgggggagg tggcagcggc ggcgggagct ccgacatcaa gatgacccag 420
tctccttctt ccatgtatgc ttctctgggt gagcgtgtca ctatcacttg caaggccagc 480
caggacatta atagctatct gagctggttc catcataaac ctgggaaatc tcctaagacc 540
ctgatctatc gtgctaaccg tctggttgat ggggtccctt ctcgtttcag cggctctggt 600
tctgggcaag attattctct caccatcagc agcctggact atgaagatat gggtatttat 660
tattgtcaac agtatgatga gtctccttgg actttcggtg gtggcaccaa gctggagatg 720
cgtctcgagc ggccgcatgg cggcggctcc ctgccagaga ctggcggggt cgagcaccac 780
caccaccacc ac 792

<210> SEQ ID NO 97
<211> LENGTH: 661
<212> TYPE: PRT
<213> ORGANISM: Artificial Sequence
<220> FEATURE:
<223> OTHER INFORMATION: synthetic construct

<400> SEQUENCE: 97

Ala Asn Ile Gln Leu Val Gln Ser Gly Pro Glu Leu Lys Lys Pro Gly
1               5                   10                  15

Glu Thr Val Lys Ile Ser Cys Lys Ala Ser Gly Tyr Thr Phe Thr Asn
            20                  25                  30

Tyr Gly Met Asn Trp Val Lys Gln Ala Pro Gly Lys Gly Leu Arg Trp
        35                  40                  45

Met Gly Trp Ile Asn Thr His Thr Gly Glu Pro Thr Tyr Ala Asp Asp
    50                  55                  60

Phe Lys Gly Arg Phe Ala Phe Ser Leu Glu Thr Ser Ala Ser Thr Ala
65                  70                  75                  80

Tyr Leu Gln Ile Asn Asn Leu Lys Asn Glu Asp Thr Ala Thr Tyr Phe
                85                  90                  95

Cys Thr Arg Arg Gly Tyr Asp Trp Tyr Phe Asp Val Trp Gly Ala Gly
            100                 105                 110

Thr Thr Val Thr Val Phe Ser Gly Gly Gly Gly Ser Gly Gly Gly Gly
        115                 120                 125

Ser Gly Gly Gly Ser Ser Asp Ile Lys Met Thr Gln Ser Pro Ser Ser
    130                 135                 140

Met Tyr Ala Ser Leu Gly Glu Arg Val Thr Ile Thr Cys Lys Ala Ser
145                 150                 155                 160

Gln Asp Ile Asn Ser Tyr Leu Ser Trp Phe His His Lys Pro Gly Lys
                165                 170                 175

-continued

```
Ser Pro Lys Thr Leu Ile Tyr Arg Ala Asn Arg Leu Val Asp Gly Val
            180                 185                 190

Pro Ser Arg Phe Ser Gly Ser Gly Ser Gly Gln Asp Tyr Ser Leu Thr
        195                 200                 205

Ile Ser Ser Leu Asp Tyr Glu Asp Met Gly Ile Tyr Tyr Cys Gln Gln
    210                 215                 220

Tyr Asp Glu Ser Pro Trp Thr Phe Gly Gly Gly Thr Lys Leu Glu Met
225                 230                 235                 240

Arg Leu Glu Arg Pro His Gly Gly Gly Ser Leu Pro Glu Thr Gly Lys
                245                 250                 255

Gly Gly Ser Asn Ser Ala Ala Ser Gly Glu Ile Pro Thr Leu Ser Ala
            260                 265                 270

Leu Asp Ile Pro Asp Gly Asp Glu Val Asp Val Gln Trp Arg Leu Val
        275                 280                 285

His Asp Ser Ala Asn Phe Ile Lys Pro Thr Ser Tyr Leu Ala His Tyr
    290                 295                 300

Leu Gly Tyr Ala Trp Val Gly Gly Asn His Ser Gln Tyr Val Gly Glu
305                 310                 315                 320

Asp Met Asp Val Thr Arg Asp Gly Asp Gly Trp Val Ile Arg Gly Asn
                325                 330                 335

Asn Asp Gly Gly Cys Asp Gly Tyr Arg Cys Gly Asp Lys Thr Ser Ile
            340                 345                 350

Lys Val Ser Asn Phe Ala Tyr Asn Leu Asp Pro Asp Ser Phe Lys His
        355                 360                 365

Gly Asp Val Thr Gln Ser Asp Arg Gln Leu Val Lys Thr Val Val Gly
    370                 375                 380

Trp Ala Ile Asn Asp Ser Asp Thr Pro Gln Ser Gly Tyr Asp Val Thr
385                 390                 395                 400

Leu Arg Tyr Asp Thr Ala Thr Asn Trp Ser Lys Thr Asn Thr Tyr Gly
                405                 410                 415

Leu Ser Glu Lys Val Thr Thr Lys Asn Lys Phe Lys Trp Pro Leu Val
            420                 425                 430

Gly Glu Thr Glu Leu Ser Ile Glu Ile Ala Ala Asn Gln Ser Trp Ala
        435                 440                 445

Ser Gln Asn Gly Gly Ser Thr Thr Thr Ser Leu Ser Gln Ser Val Arg
    450                 455                 460

Pro Thr Val Pro Ala His Ser Lys Ile Pro Val Lys Ile Glu Leu Tyr
465                 470                 475                 480

Lys Ala Asp Ile Ser Tyr Pro Tyr Glu Phe Lys Ala Asp Val Ser Tyr
                485                 490                 495

Asp Leu Thr Leu Ser Gly Phe Leu Arg Trp Gly Gly Asn Ala Trp Tyr
            500                 505                 510

Thr His Pro Asp Asn Arg Pro Asn Trp Asn His Thr Phe Val Ile Gly
        515                 520                 525

Pro Tyr Lys Asp Lys Ala Ser Ser Ile Arg Tyr Gln Trp Asp Lys Arg
    530                 535                 540

Tyr Ile Pro Gly Glu Val Lys Trp Trp Asp Trp Asn Trp Thr Ile Gln
545                 550                 555                 560

Gln Asn Gly Leu Pro Thr Met Gln Asn Asn Leu Ala Arg Val Leu Arg
                565                 570                 575

Pro Val Arg Ala Gly Ile Thr Gly Asp Phe Ser Ala Glu Ser Gln Phe
            580                 585                 590
```

Ala Gly Asn Ile Glu Ile Gly Ala Pro Val Pro Val Ala Ala Glu Ser
595 600 605

Lys Gly Ile Glu Pro Asp Ser Gly Val Glu Gly Ala Gly Gln Gly Leu
610 615 620

Arg Leu Glu Ile Pro Leu Asp Ala Gln Glu Leu Ser Gly Leu Gly Phe
625 630 635 640

Asn Asn Val Ser Leu Ser Val Thr Pro Ala Ala Asn Gln Val Glu His
645 650 655

His His His His His
660

<210> SEQ ID NO 98
<211> LENGTH: 305
<212> TYPE: PRT
<213> ORGANISM: Artificial Sequence
<220> FEATURE:
<223> OTHER INFORMATION: synthetic construct

<400> SEQUENCE: 98

Met Lys Tyr Leu Leu Pro Thr Ala Ala Ala Gly Leu Leu Leu Leu Ala
1 5 10 15

Ala Gln Pro Ala Met Ala Ala Asn Ser Ala Gln Val Gln Leu Gln Gln
20 25 30

Ser Gly Ala Glu Leu Val Arg Pro Gly Ser Ser Val Lys Ile Ser Cys
35 40 45

Lys Ala Ser Gly Tyr Ala Phe Ser Ser Tyr Trp Met Asn Trp Val Lys
50 55 60

Gln Arg Pro Gly Gln Gly Leu Glu Trp Ile Gly Gln Ile Trp Pro Gly
65 70 75 80

Asp Gly Asp Thr Asn Tyr Asn Gly Lys Phe Lys Gly Lys Ala Thr Leu
85 90 95

Thr Ala Asp Glu Ser Ser Ser Thr Ala Tyr Met Gln Leu Ser Ser Leu
100 105 110

Ala Ser Glu Asp Ser Ala Val Tyr Phe Cys Ala Arg Arg Glu Thr Thr
115 120 125

Thr Val Gly Arg Tyr Tyr Tyr Ala Met Asp Tyr Trp Gly Gln Gly Thr
130 135 140

Ser Val Thr Val Ser Ser Gly Gly Gly Gly Ser Gly Gly Gly Gly Ser
145 150 155 160

Gly Gly Gly Gly Ser Gly Ser Ser Asp Ile Leu Leu Thr Gln Thr Pro
165 170 175

Ala Ser Leu Ala Val Ser Leu Gly Gln Arg Ala Thr Ile Ser Cys Lys
180 185 190

Ala Ser Gln Ser Val Asp Tyr Asp Gly Asp Ser Tyr Leu Asn Trp Tyr
195 200 205

Gln Gln Ile Pro Gly Gln Pro Pro Lys Leu Leu Ile Tyr Asp Ala Ser
210 215 220

Asn Leu Val Ser Gly Ile Pro Pro Arg Phe Ser Gly Ser Gly Ser Gly
225 230 235 240

Thr Asp Phe Thr Leu Asn Ile His Pro Val Glu Lys Val Asp Ala Ala
245 250 255

Thr Tyr His Cys Gln Gln Ser Thr Glu Asp Pro Trp Thr Phe Gly Gly
260 265 270

Gly Thr Lys Leu Glu Ile Lys Arg Gly Gly Leu Glu Arg Pro His Gly
275 280 285

```
Gly Gly Ser Leu Pro Glu Thr Gly Gly Val Glu His His His His His
    290                 295                 300

His
305


<210> SEQ ID NO 99
<211> LENGTH: 915
<212> TYPE: DNA
<213> ORGANISM: Artificial Sequence
<220> FEATURE:
<223> OTHER INFORMATION: synthetic construct

<400> SEQUENCE: 99

atgaaatacc tgctgccgac cgctgctgct ggtctgctgc tcctcgctgc ccagccggcg      60

atggccgcga attctgccca ggtgcagctg cagcagtccg gcgctgagct ggtgcgccct     120

ggctcctccg tgaaaatctc ctgcaaggct tccggctacg ctttctcctc ctactggatg     180

aactgggtga agcagcgccc tggccagggc ctggagtgga tcggccaaat ctggccgggc     240

gacggcgaca ccaactacaa cggcaagttc aagggcaagg ctaccctgac cgctgacgag     300

tcctcctcca ccgcttacat gcagctgtcc tccctggctt ccgaggactc cgctgtgtac     360

ttctgcgctc gccgcgagac caccaccgtg ggccgctact actacgctat ggactactgg     420

ggccagggca cctcggtgac cgtgtcctcc gggggaggtg gcagcggtgg aggtggcagc     480

ggcggcgggg gttccgggag ctccgacatc ctgctgaccc agaccccggc ttccctggct     540

gtgtccctgg gccagcgcgc taccatctcc tgcaaggctt cccagtccgt ggactacgac     600

ggcgactcct acctgaactg gtaccagcag atcccgggcc agccgccgaa gctgctgatc     660

tacgacgctt ccaacctggt gtccggcatc ccgccgcgct tctccggctc cggctccggc     720

accgacttca ccctgaacat ccacccggtg gagaaggtgg acgctgctac ctaccactgc     780

cagcagtcca ccgaggaccc gtggaccttc ggcggcggca ccaagctgga gatcaagcgc     840

ggtggtctcg agcggccgca tggcggcggc tccctgccag agactggcgg ggtcgagcac     900

caccaccacc accac                                                      915


<210> SEQ ID NO 100
<211> LENGTH: 680
<212> TYPE: PRT
<213> ORGANISM: Artificial Sequence
<220> FEATURE:
<223> OTHER INFORMATION: synthetic construct

<400> SEQUENCE: 100

Ala Asn Ser Ala Gln Val Gln Leu Gln Gln Ser Gly Ala Glu Leu Val
1               5                   10                  15

Arg Pro Gly Ser Ser Val Lys Ile Ser Cys Lys Ala Ser Gly Tyr Ala
            20                  25                  30

Phe Ser Ser Tyr Trp Met Asn Trp Val Lys Gln Arg Pro Gly Gln Gly
        35                  40                  45

Leu Glu Trp Ile Gly Gln Ile Trp Pro Gly Asp Gly Asp Thr Asn Tyr
    50                  55                  60

Asn Gly Lys Phe Lys Gly Lys Ala Thr Leu Thr Ala Asp Glu Ser Ser
65                  70                  75                  80

Ser Thr Ala Tyr Met Gln Leu Ser Ser Leu Ala Ser Glu Asp Ser Ala
                85                  90                  95

Val Tyr Phe Cys Ala Arg Arg Glu Thr Thr Thr Val Gly Arg Tyr Tyr
            100                 105                 110
```

```
Tyr Ala Met Asp Tyr Trp Gly Gln Gly Thr Ser Val Thr Val Ser Ser
        115                 120                 125

Gly Gly Gly Gly Ser Gly Gly Gly Gly Ser Gly Gly Gly Gly Ser Gly
    130                 135                 140

Ser Ser Asp Ile Leu Leu Thr Gln Thr Pro Ala Ser Leu Ala Val Ser
145                 150                 155                 160

Leu Gly Gln Arg Ala Thr Ile Ser Cys Lys Ala Ser Gln Ser Val Asp
                165                 170                 175

Tyr Asp Gly Asp Ser Tyr Leu Asn Trp Tyr Gln Gln Ile Pro Gly Gln
            180                 185                 190

Pro Pro Lys Leu Leu Ile Tyr Asp Ala Ser Asn Leu Val Ser Gly Ile
        195                 200                 205

Pro Pro Arg Phe Ser Gly Ser Gly Ser Gly Thr Asp Phe Thr Leu Asn
    210                 215                 220

Ile His Pro Val Glu Lys Val Asp Ala Ala Thr Tyr His Cys Gln Gln
225                 230                 235                 240

Ser Thr Glu Asp Pro Trp Thr Phe Gly Gly Gly Thr Lys Leu Glu Ile
                245                 250                 255

Lys Arg Gly Gly Leu Glu Arg Pro His Gly Gly Gly Ser Leu Pro Glu
            260                 265                 270

Thr Gly Lys Gly Gly Ser Asn Ser Ala Ala Ser Gly Glu Ile Pro Thr
        275                 280                 285

Leu Ser Ala Leu Asp Ile Pro Asp Gly Asp Glu Val Asp Val Gln Trp
    290                 295                 300

Arg Leu Val His Asp Ser Ala Asn Phe Ile Lys Pro Thr Ser Tyr Leu
305                 310                 315                 320

Ala His Tyr Leu Gly Tyr Ala Trp Val Gly Gly Asn His Ser Gln Tyr
                325                 330                 335

Val Gly Glu Asp Met Asp Val Thr Arg Asp Gly Asp Gly Trp Val Ile
            340                 345                 350

Arg Gly Asn Asn Asp Gly Gly Cys Asp Gly Tyr Arg Cys Gly Asp Lys
        355                 360                 365

Thr Ser Ile Lys Val Ser Asn Phe Ala Tyr Asn Leu Asp Pro Asp Ser
    370                 375                 380

Phe Lys His Gly Asp Val Thr Gln Ser Asp Arg Gln Leu Val Lys Thr
385                 390                 395                 400

Val Val Gly Trp Ala Ile Asn Asp Ser Asp Thr Pro Gln Ser Gly Tyr
                405                 410                 415

Asp Val Thr Leu Arg Tyr Asp Thr Ala Thr Asn Trp Ser Lys Thr Asn
            420                 425                 430

Thr Tyr Gly Leu Ser Glu Lys Val Thr Thr Lys Asn Lys Phe Lys Trp
        435                 440                 445

Pro Leu Val Gly Glu Thr Glu Leu Ser Ile Glu Ile Ala Ala Asn Gln
    450                 455                 460

Ser Trp Ala Ser Gln Asn Gly Gly Ser Thr Thr Thr Ser Leu Ser Gln
465                 470                 475                 480

Ser Val Arg Pro Thr Val Pro Ala His Ser Lys Ile Pro Val Lys Ile
                485                 490                 495

Glu Leu Tyr Lys Ala Asp Ile Ser Tyr Pro Tyr Glu Phe Lys Ala Asp
            500                 505                 510

Val Ser Tyr Asp Leu Thr Leu Ser Gly Phe Leu Arg Trp Gly Gly Asn
        515                 520                 525

Ala Trp Tyr Thr His Pro Asp Asn Arg Pro Asn Trp Asn His Thr Phe
```

```
    530                 535                 540

Val Ile Gly Pro Tyr Lys Asp Lys Ala Ser Ser Ile Arg Tyr Gln Trp
545                 550                 555                 560

Asp Lys Arg Tyr Ile Pro Gly Glu Val Lys Trp Trp Asp Trp Asn Trp
                565                 570                 575

Thr Ile Gln Gln Asn Gly Leu Pro Thr Met Gln Asn Asn Leu Ala Arg
            580                 585                 590

Val Leu Arg Pro Val Arg Ala Gly Ile Thr Gly Asp Phe Ser Ala Glu
        595                 600                 605

Ser Gln Phe Ala Gly Asn Ile Glu Ile Gly Ala Pro Val Pro Val Ala
    610                 615                 620

Ala Glu Ser Lys Gly Ile Glu Pro Asp Ser Gly Val Glu Gly Ala Gly
625                 630                 635                 640

Gln Gly Leu Arg Leu Glu Ile Pro Leu Asp Ala Gln Glu Leu Ser Gly
                645                 650                 655

Leu Gly Phe Asn Asn Val Ser Leu Ser Val Thr Pro Ala Ala Asn Gln
            660                 665                 670

Val Glu His His His His His His
        675                 680


<210> SEQ ID NO 101
<211> LENGTH: 429
<212> TYPE: PRT
<213> ORGANISM: Artificial Sequence
<220> FEATURE:
<223> OTHER INFORMATION: synthetic construct

<400> SEQUENCE: 101

Met Lys Tyr Leu Leu Pro Thr Ala Ala Ala Gly Leu Leu Leu Leu Ala
1               5                   10                  15

Ala Gln Pro Ala Met Ala Gly Lys Gly Gly Ser Asn Ser Ala Ala Ser
            20                  25                  30

Gly Glu Ile Pro Thr Leu Ser Ala Leu Asp Ile Pro Asp Gly Asp Glu
        35                  40                  45

Val Asp Val Gln Trp Arg Leu Val His Asp Ser Ala Asn Phe Ile Lys
    50                  55                  60

Pro Thr Ser Tyr Leu Ala His Tyr Leu Gly Tyr Ala Trp Val Gly Gly
65                  70                  75                  80

Asn His Ser Gln Tyr Val Gly Glu Asp Met Asp Val Thr Arg Asp Gly
                85                  90                  95

Asp Gly Trp Val Ile Arg Gly Asn Asn Asp Gly Gly Cys Asp Gly Tyr
            100                 105                 110

Arg Cys Gly Asp Lys Thr Ser Ile Lys Val Ser Asn Phe Ala Tyr Asn
        115                 120                 125

Leu Asp Pro Asp Ser Phe Lys His Gly Asp Val Thr Gln Ser Asp Arg
    130                 135                 140

Gln Leu Val Lys Thr Val Val Gly Trp Ala Ile Asn Asp Ser Asp Thr
145                 150                 155                 160

Pro Gln Ser Gly Tyr Asp Val Thr Leu Arg Tyr Asp Thr Ala Thr Asn
                165                 170                 175

Trp Ser Lys Thr Asn Thr Tyr Gly Leu Ser Glu Lys Val Thr Thr Lys
            180                 185                 190

Asn Lys Phe Lys Trp Pro Leu Val Gly Glu Thr Glu Leu Ser Ile Glu
        195                 200                 205

Ile Ala Ala Asn Gln Ser Trp Ala Ser Gln Asn Gly Gly Ser Thr Thr
```

```
    210                 215                 220

Thr Ser Leu Ser Gln Ser Val Arg Pro Thr Val Pro Ala His Ser Lys
225                 230                 235                 240

Ile Pro Val Lys Ile Glu Leu Tyr Lys Ala Asp Ile Ser Tyr Pro Tyr
                245                 250                 255

Glu Phe Lys Ala Asp Val Ser Tyr Asp Leu Thr Leu Ser Gly Phe Leu
            260                 265                 270

Arg Trp Gly Gly Asn Ala Trp Tyr Thr His Pro Asp Asn Arg Pro Asn
        275                 280                 285

Trp Asn His Thr Phe Val Ile Gly Pro Tyr Lys Asp Lys Ala Ser Ser
    290                 295                 300

Ile Arg Tyr Gln Trp Asp Lys Arg Tyr Ile Pro Gly Glu Val Lys Trp
305                 310                 315                 320

Trp Asp Trp Asn Trp Thr Ile Gln Gln Asn Gly Leu Pro Thr Met Gln
                325                 330                 335

Asn Asn Leu Ala Arg Val Leu Arg Pro Val Arg Ala Gly Ile Thr Gly
            340                 345                 350

Asp Phe Ser Ala Glu Ser Gln Phe Ala Gly Asn Ile Glu Ile Gly Ala
        355                 360                 365

Pro Val Pro Val Ala Ala Glu Ser Lys Glu Asn Leu Tyr Phe Gln Gly
    370                 375                 380

Val Glu Gly Ala Gly Gln Gly Leu Arg Leu Glu Ile Pro Leu Asp Ala
385                 390                 395                 400

Gln Glu Leu Ser Gly Leu Gly Phe Asn Asn Val Ser Leu Ser Val Thr
                405                 410                 415

Pro Ala Ala Asn Gln Val Glu His His His His His His
            420                 425
```

<210> SEQ ID NO 102
<211> LENGTH: 1287
<212> TYPE: DNA
<213> ORGANISM: Artificial Sequence
<220> FEATURE:
<223> OTHER INFORMATION: synthetic construct

<400> SEQUENCE: 102

```
atgaaatacc tgctgccgac cgctgctgct ggtctgctgc tcctcgctgc ccagccggcg      60

atggccggta aaggtggttc gaattctgca gctagcggag aaataccgac tctgtctgcc     120

ctggatattc cagatggtga tgaagtagat gtgcaatggc ggctggtaca tgacagtgcg     180

aatttcatca aaccaaccag ttatctggcc cattatctcg gctatgcctg ggtaggggggg     240

aatcacagtc aatatgtcgg cgaagacatg gatgtgaccc gtgatggtga tggctgggtg     300

atccgtggca acaatgacgg tggctgcgat ggttatcgct gtggtgacaa gacctccatc     360

aaggtgagca attttgccta caacctggat cctgacagtt tcaagcatgg cgatgtgacc     420

cagtccgacc gccaactggt caagacggtg gtggggtggg ctatcaacga cagcgacacg     480

cctcaatccg gttatgacgt caccctgcgc tacgacacgg ccaccaactg gtccaagacc     540

aacacctatg gtctgagcga gaaggtgacc accaagaaca agttcaagtg gccgctggtg     600

ggggaaaccg agctctccat cgagattgct gccaaccagt cctgggcctc ccagaacggg     660

ggctcgacca ccacctcttt gtcccagtcc gtgcgcccga cagtgccggc ccactccaag     720

atcccggtga agatagagct ctacaaagcc gacatctcct acccctacga gttcaaggcc     780

gatgtcagct atgacctgac cctgagcggt ttcctgcgtt ggggcggtaa tgcctggtat     840
```

-continued

```
acccatccgg acaaccgtcc gaactggaac cacaccttcg tcatagggcc atacaaggac    900

aaggccagca gtatccgcta ccagtgggac aagcgttata tcccgggtga agtgaagtgg    960

tgggattgga actggaccat acagcagaac ggtctgccta ccatgcagaa taacctggcc   1020

agggtgctgc gcccggtgcg ggccgggatc accggtgatt tcagtgccga gagccagttt   1080

gccggcaaca tcgaaatcgg cgctcccgtg ccggtcgctg ccgaatctaa ggagaacctg   1140

tacttccaag gtgttgaagg tgccggtcag ggtctgagac tggagatccc gctcgatgca   1200

caagagctct ccgggcttgg cttcaacaat gtcagcctca gcgtgacccc tgctgccaac   1260

caagtcgagc accaccacca ccaccac                                        1287
```

<210> SEQ ID NO 103
<211> LENGTH: 429
<212> TYPE: PRT
<213> ORGANISM: Artificial Sequence
<220> FEATURE:
<223> OTHER INFORMATION: synthetic construct

<400> SEQUENCE: 103

```
Met Lys Tyr Leu Leu Pro Thr Ala Ala Ala Gly Leu Leu Leu Leu Ala
1               5                   10                  15

Ala Gln Pro Ala Met Ala Gly Lys Gly Gly Ser Asn Ser Ala Ala Ser
            20                  25                  30

Gly Glu Ile Pro Thr Leu Ser Ala Leu Asp Ile Pro Asp Gly Asp Glu
        35                  40                  45

Val Asp Val Gln Trp Arg Leu Val His Asp Ser Ala Asn Phe Ile Lys
    50                  55                  60

Pro Thr Ser Tyr Leu Ala His Tyr Leu Gly Tyr Ala Trp Val Gly Gly
65                  70                  75                  80

Asn His Ser Gln Tyr Val Gly Glu Asp Met Asp Val Thr Arg Asp Gly
                85                  90                  95

Asp Gly Trp Val Ile Arg Gly Asn Asn Asp Gly Gly Cys Asp Gly Tyr
            100                 105                 110

Arg Cys Gly Asp Lys Thr Ser Ile Lys Val Ser Asn Phe Ala Tyr Asn
        115                 120                 125

Leu Asp Pro Asp Ser Phe Lys His Gly Asp Val Thr Gln Ser Asp Arg
    130                 135                 140

Gln Leu Val Lys Thr Val Val Gly Trp Ala Ile Asn Asp Ser Asp Thr
145                 150                 155                 160

Pro Gln Ser Gly Tyr Asp Val Thr Leu Arg Tyr Asp Thr Ala Thr Asn
                165                 170                 175

Trp Ser Lys Thr Asn Thr Tyr Gly Leu Ser Glu Lys Val Thr Thr Lys
            180                 185                 190

Asn Lys Phe Lys Trp Pro Leu Val Gly Glu Thr Glu Leu Ser Ile Glu
        195                 200                 205

Ile Ala Ala Asn Gln Ser Trp Ala Ser Gln Asn Gly Gly Ser Thr Thr
    210                 215                 220

Thr Ser Leu Ser Gln Ser Val Arg Pro Thr Val Pro Ala His Ser Lys
225                 230                 235                 240

Ile Pro Val Lys Ile Glu Leu Tyr Lys Ala Asp Ile Ser Tyr Pro Tyr
                245                 250                 255

Glu Phe Lys Ala Asp Val Ser Tyr Asp Leu Thr Leu Ser Gly Phe Leu
            260                 265                 270

Arg Trp Gly Gly Asn Ala Trp Tyr Thr His Pro Asp Asn Arg Pro Asn
        275                 280                 285
```

Trp Asn His Thr Phe Val Ile Gly Pro Tyr Lys Asp Lys Ala Ser Ser
    290                 295                 300

Ile Arg Tyr Gln Trp Asp Lys Arg Tyr Ile Pro Gly Glu Val Lys Trp
305                 310                 315                 320

Trp Asp Trp Asn Trp Thr Ile Gln Gln Asn Gly Leu Pro Thr Met Gln
                325                 330                 335

Asn Asn Leu Ala Arg Val Leu Arg Pro Val Arg Ala Gly Ile Thr Gly
            340                 345                 350

Asp Phe Ser Ala Glu Ser Gln Phe Ala Gly Asn Ile Glu Ile Gly Ala
        355                 360                 365

Pro Val Pro Val Ala Ala Glu Ser Lys Gly Ile Glu Pro Asp Ser Gly
    370                 375                 380

Val Glu Gly Ala Gly Gln Gly Leu Arg Leu Glu Ile Pro Leu Asp Ala
385                 390                 395                 400

Gln Glu Leu Ser Gly Leu Gly Phe Asn Asn Val Ser Leu Ser Val Thr
                405                 410                 415

Pro Ala Ala Asn Gln Val Glu His His His His His His
            420                 425

<210> SEQ ID NO 104
<211> LENGTH: 1287
<212> TYPE: DNA
<213> ORGANISM: Artificial Sequence
<220> FEATURE:
<223> OTHER INFORMATION: synthetic construct

<400> SEQUENCE: 104
atgaaatacc tgctgccgac cgctgctgct ggtctgctgc tcctcgctgc ccagccggcg 60
atggccggta aaggtggttc gaattctgca gctagcggag aaataccgac tctgtctgcc 120
ctggatattc cagatggtga tgaagtagat gtgcaatggc ggctggtaca tgacagtgcg 180
aatttcatca aaccaaccag ttatctggcc cattatctcg gctatgcctg ggtaggggg 240 aatcacagtc aatatgtcgg cgaagacatg gatgtgaccc gtgatggtga tggctgggtg 300
atccgtggca acaatgacgg tggctgcgat ggttatcgct gtggtgacaa gacctccatc 360
aaggtgagca attttgccta caacctggat cctgacagtt tcaagcatgg cgatgtgacc 420
cagtccgacc gccaactggt caagacggtg gtggggtggg ctatcaacga cagcgacacg 480
cctcaatccg gttatgacgt caccctgcgc tacgacacgg ccaccaactg gtccaagacc 540
aacacctatg gtctgagcga gaaggtgacc accaagaaca agttcaagtg gccgctggtg 600
ggggaaaccg agctctccat cgagattgct gccaaccagt cctgggcctc ccagaacggg 660
ggctcgacca ccacctcttt gtcccagtcc gtgcgcccga cagtgccggc ccactccaag 720
atcccggtga agatagagct ctacaaagcc gacatctcct acccctacga gttcaaggcc 780
gatgtcagct atgacctgac cctgagcggt ttcctgcgtt ggggcggtaa tgcctggtat 840
acccatccgg acaaccgtcc gaactggaac cacaccttcg tcatagggcc atacaaggac 900
aaggccagca gtatccgcta ccagtgggac aagcgttata tcccgggtga agtgaagtgg 960
tgggattgga actggaccat acagcagaac ggtctgccta ccatgcagaa taacctggcc 1020
agggtgctgc gcccggtgcg ggccgggatc accggtgatt tcagtgccga gagccagttt 1080
gccggcaaca tcgaaatcgg cgctcccgtg ccggtcgctg ccgaatctaa gggtatcgag 1140
ccagattctg gtgttgaagg tgccggtcag ggtctgagac tggagatccc gctcgatgca 1200
caagagctct ccgggcttgg cttcaacaat gtcagcctca gcgtgacccc tgctgccaac 1260
caagtcgagc accaccacca ccaccac 1287

<210> SEQ ID NO 105
<211> LENGTH: 265
<212> TYPE: PRT
<213> ORGANISM: Artificial Sequence
<220> FEATURE:
<223> OTHER INFORMATION: synthetic construct

<400> SEQUENCE: 105

Met Ala Asn Ile Gln Leu Val Gln Ser Gly Pro Glu Leu Lys Lys Pro
1               5                   10                  15

Gly Glu Thr Val Lys Ile Ser Cys Lys Ala Ser Gly Tyr Thr Phe Thr
            20                  25                  30

Asn Tyr Gly Met Asn Trp Val Lys Gln Ala Pro Gly Lys Gly Leu Arg
        35                  40                  45

Trp Met Gly Trp Ile Asn Thr His Thr Gly Glu Pro Thr Tyr Ala Asp
    50                  55                  60

Asp Phe Lys Gly Arg Phe Ala Phe Ser Leu Glu Thr Ser Ala Ser Thr
65                  70                  75                  80

Ala Tyr Leu Gln Ile Asn Asn Leu Lys Asn Glu Asp Thr Ala Thr Tyr
                85                  90                  95

Phe Cys Thr Arg Arg Gly Tyr Asp Trp Tyr Phe Asp Val Trp Gly Ala
            100                 105                 110

Gly Thr Thr Val Thr Val Phe Ser Gly Gly Gly Gly Ser Gly Gly Gly
        115                 120                 125

Gly Ser Gly Gly Gly Ser Ser Asp Ile Lys Met Thr Gln Ser Pro Ser
    130                 135                 140

Ser Met Tyr Ala Ser Leu Gly Glu Arg Val Thr Ile Thr Cys Lys Ala
145                 150                 155                 160

Ser Gln Asp Ile Asn Ser Tyr Leu Ser Trp Phe His His Lys Pro Gly
                165                 170                 175

Lys Ser Pro Lys Thr Leu Ile Tyr Arg Ala Asn Arg Leu Val Asp Gly
            180                 185                 190

Val Pro Ser Arg Phe Ser Gly Ser Gly Ser Gly Gln Asp Tyr Ser Leu
        195                 200                 205

Thr Ile Ser Ser Leu Asp Tyr Glu Asp Met Gly Ile Tyr Tyr Cys Gln
    210                 215                 220

Gln Tyr Asp Glu Ser Pro Trp Thr Phe Gly Gly Gly Thr Lys Leu Glu
225                 230                 235                 240

Met Arg Leu Glu Arg Pro His Gly Gly Gly Ser Leu Pro Glu Thr Gly
                245                 250                 255

Gly Val Glu His His His His His His
            260                 265

<210> SEQ ID NO 106
<211> LENGTH: 795
<212> TYPE: DNA
<213> ORGANISM: Artificial Sequence
<220> FEATURE:
<223> OTHER INFORMATION: synthetic construct

<400> SEQUENCE: 106
atggccaaca tccagctggt gcagtctggt cctgagctga agaagcctgg tgagactgtc 60
aaaatctcct gcaaggcttc tgggtatacc ttcactaact atggtatgaa ctgggtgaag 120
caggctcctg gtaagggtct gcgttggatg ggctggatta acacccacac tggtgagcct 180

```
actttatgctg atgacttcaa gggacgtttt gccttctctc tggaaacttc tgccagcact    240

gcctatctcc agatcaacaa cctcaaaaat gaggacactg ctacttactt ctgtacacgt    300

cgtggttacg actggtactt cgatgtctgg ggtgctggga ccacggtgac cgtgttctcc    360

gggggaggtg gcagcggggg aggtggcagc ggcggcggga gctccgacat caagatgacc    420

cagtctcctt cttccatgta tgcttctctg ggtgagcgtg tcactatcac ttgcaaggcc    480

agccaggaca ttaatagcta tctgagctgg ttccatcata aacctgggaa atctcctaag    540

accctgatct atcgtgctaa ccgtctggtt gatggggtcc cttctcgttt cagcggctct    600

ggttctgggc aagattattc tctcaccatc agcagcctgg actatgaaga tatgggtatt    660

tattattgtc aacagtatga tgagtctcct tggactttcg gtggtggcac caagctggag    720

atgcgtctcg agcggccgca tggcggcggc tccctgccag agactggcgg ggtcgagcac    780

caccaccacc accac                                                      795


<210> SEQ ID NO 107
<211> LENGTH: 704
<212> TYPE: PRT
<213> ORGANISM: Artificial Sequence
<220> FEATURE:
<223> OTHER INFORMATION: synthetic construct

<400> SEQUENCE: 107

Met Gly Ser Asp Lys Ile Ile His Leu Thr Asp Asp Ser Phe Asp Thr
1               5                   10                  15

Asp Val Leu Lys Ala Asp Gly Ala Ile Leu Val Asp Phe Trp Ala His
            20                  25                  30

Trp Cys Gly Pro Cys Lys Met Ile Ala Pro Ile Leu Asp Glu Ile Ala
        35                  40                  45

Asp Glu Tyr Gln Gly Lys Leu Thr Val Ala Lys Leu Asn Ile Asp His
    50                  55                  60

Asn Pro Gly Thr Ala Pro Lys Tyr Gly Ile Arg Gly Ile Pro Thr Leu
65                  70                  75                  80

Leu Leu Phe Lys Asn Gly Glu Val Ala Ala Thr Lys Val Gly Ala Leu
                85                  90                  95

Ser Lys Gly Gln Leu Lys Glu Phe Leu Asp Ala Asn Leu Ala Gly Ser
            100                 105                 110

Gly Ser Gly Asp Asp Asp Asp Lys Leu Gly Ile Asp Pro Phe Thr Glu
        115                 120                 125

Asn Leu Tyr Phe Gln Gly Gly Ala Asp Asp Val Val Asp Ser Ser Lys
    130                 135                 140

Ser Phe Val Met Glu Asn Phe Ala Ser Tyr His Gly Thr Lys Pro Gly
145                 150                 155                 160

Tyr Val Asp Ser Ile Gln Lys Gly Ile Gln Lys Pro Lys Ser Gly Thr
                165                 170                 175

Gln Gly Asn Tyr Asp Asp Asp Trp Lys Gly Phe Tyr Ser Thr Asp Asn
            180                 185                 190

Lys Tyr Asp Ala Ala Gly Tyr Ser Val Asp Asn Glu Asn Pro Leu Ser
        195                 200                 205

Gly Lys Ala Gly Gly Val Val Lys Val Thr Tyr Pro Gly Leu Thr Lys
    210                 215                 220

Val Leu Ala Leu Lys Val Asp Asn Ala Glu Thr Ile Lys Lys Glu Leu
225                 230                 235                 240

Gly Leu Ser Leu Thr Glu Pro Leu Met Glu Gln Val Gly Thr Glu Glu
```

-continued

```
                245                 250                 255

Phe Ile Lys Arg Phe Gly Asp Gly Ala Ser Arg Val Val Leu Ser Leu
            260                 265                 270

Pro Phe Ala Glu Gly Ser Ser Ser Val Glu Tyr Ile Asn Asn Trp Glu
        275                 280                 285

Gln Ala Lys Ala Leu Ser Val Glu Leu Glu Ile Asn Phe Glu Thr Arg
    290                 295                 300

Gly Lys Arg Gly Gln Asp Ala Met Tyr Glu Tyr Met Ala Gln Ala Cys
305                 310                 315                 320

Ala Gly Asn Ile Glu Pro Asp Thr Gly Ser Ser Leu Ser Cys Ile Asn
                325                 330                 335

Leu Asp Trp Asp Val Ile Arg Asp Lys Thr Lys Thr Lys Ile Glu Ser
            340                 345                 350

Leu Lys Glu His Gly Pro Ile Lys Asn Lys Met Ser Glu Ser Pro Ala
        355                 360                 365

Lys Thr Val Ser Glu Glu Lys Ala Lys Gln Tyr Leu Glu Glu Phe His
    370                 375                 380

Gln Thr Ala Leu Glu His Pro Glu Leu Ser Glu Leu Lys Thr Val Thr
385                 390                 395                 400

Gly Thr Asn Pro Val Phe Ala Gly Ala Asn Tyr Ala Ala Trp Ala Val
                405                 410                 415

Asn Val Ala Gln Val Ile Asp Ser Glu Thr Ala Asp Asn Leu Glu Lys
            420                 425                 430

Thr Thr Ala Ala Leu Ser Ile Leu Pro Gly Ile Gly Ser Val Met Gly
        435                 440                 445

Ile Ala Asp Gly Ala Val His His Asn Thr Glu Glu Ile Val Ala Gln
    450                 455                 460

Ser Ile Ala Leu Ser Ser Leu Met Val Ala Gln Ala Ile Pro Leu Val
465                 470                 475                 480

Gly Glu Leu Val Asp Ile Gly Phe Ala Ala Tyr Asn Phe Val Glu Ser
                485                 490                 495

Ile Ile Asn Leu Phe Gln Val Val His Asn Ser Tyr Asn Arg Pro Ala
            500                 505                 510

Tyr Ser Pro Gly His Lys Thr Gln Pro Ala Met Gly Gly Gly Gly Ser
        515                 520                 525

Gly Gly Gly Gly Ser Gly Gly Gly Gly Ser Lys Gly Glu Leu Glu Arg
    530                 535                 540

Cys Val Leu Thr Val Pro Ser Thr Asp Ile Glu Lys Glu Ile Leu Asp
545                 550                 555                 560

Leu Ala Ala Ala Thr Glu Arg Leu Asn Leu Thr Asp Ala Leu Asn Ser
                565                 570                 575

Asn Pro Ala Gly Asn Leu Tyr Asp Trp Arg Ser Ser Asn Ser Tyr Pro
            580                 585                 590

Trp Thr Gln Lys Leu Asn Leu His Leu Thr Ile Thr Ala Thr Gly Gln
        595                 600                 605

Lys Tyr Arg Ile Leu Ala Ser Lys Ile Val Asp Phe Asn Ile Tyr Ser
    610                 615                 620

Asn Asn Phe Asn Asn Leu Val Lys Leu Glu Gln Ser Leu Gly Asp Gly
625                 630                 635                 640

Val Lys Asp His Tyr Val Asp Ile Ser Leu Asp Ala Gly Gln Tyr Val
                645                 650                 655

Leu Val Met Lys Ala Asn Ser Ser Tyr Ser Gly Asn Tyr Pro Tyr Ser
            660                 665                 670
```

Ile Leu Phe Gln Lys Phe Lys Leu Glu Gly Lys Pro Ile Pro Asn Pro
675 680 685

Leu Leu Gly Leu Asp Ser Thr Arg Thr Gly His His His His His His
690 695 700

<210> SEQ ID NO 108
<211> LENGTH: 2125
<212> TYPE: DNA
<213> ORGANISM: Artificial Sequence
<220> FEATURE:
<223> OTHER INFORMATION: synthetic construct

<400> SEQUENCE: 108
ccatgggatc tgataaaatt attcatctga ctgatgattc ttttgatact gatgtactta 60
aggcagatgg tgcaatcctg gttgatttct gggcacactg gtgcggtccg tgcaaaatga 120
tcgctccgat tctggatgaa atcgctgacg aatatcaggg caaactgacc gttgcaaaac 180
tgaacatcga tcacaacccg ggcactgcgc cgaaatatgg catccgtggt atcccgactc 240
tgctgctgtt caaaaacggt gaagtggcgg caaccaaagt gggtgcactg tctaaaggtc 300
agttgaaaga gttcctcgac gctaacctgg ccggctctgg atccggtgat gacgatgaca 360
agctgggaat tgatcccttc accgagaacc tgtacttcca gggcggtgcc gacgacgtgg 420
tggactcctc caagtccttc gtgatggaaa acttcgcttc ctaccacggt accaagcctg 480
gttacgtgga ttccatccag aagggtatcc agaagcctaa gtccggtacc cagggtaact 540
acgacgatga ttggaagggt tttactcca ccgacaacaa gtacgacgcc gccggttact 600
ccgtggataa cgaaaaccct ctgtccggta aggccggtgg tgtggtgaaa gtgacctacc 660
ctggtctgac caaggtgctg gccctgaagg tggataacgc cgaaaccatc aagaaggagc 720
tgggtctgtc cctgaccgaa cctctgatgg agcaggtggg taccgaagag tttatcaaga 780
gattcggtga tggtgcctcc agagtggtgc tgtccctgcc tttcgccgag ggttcctcct 840
ccgtggaata catcaacaac tgggaacagg ccaaggccct gtccgtggaa ctggagatca 900
actttgaaac cagaggtaag agaggtcagg atgccatgta cgagtacatg gcccaggcct 960
gtgccggcaa catcgagcct gacaccggtt cctccctgtc ctgcatcaac ctggactggg 1020
acgtgatcag agacaagacc aagaccaaga tcgagtccct gaaggagcac ggtcctatca 1080
agaacaagat gtccgagtcc cctgccaaga ccgtgtccga ggagaaggcc aagcagtacc 1140
tggaggagtt ccaccagacc gccctggagc accctgagct gtccgagctg aagaccgtga 1200
ctggtaccaa ccctgtgttc gccggtgcca actacgccgc ctgggccgtg aacgtggccc 1260
aggtgatcga ctccgagacc gccgacaacc tggagaagac caccgccgcc ctgtccatcc 1320
tgcctggtat cggttccgtg atgggtatcg ccgacggtgc cgtgcaccac aacaccgagg 1380
agatcgtggc ccagtccatc gccctgtcct ccctgatggt ggcccaggcc atccctctgg 1440
tgggtgagct ggtggacatc ggtttcgccg cctacaactt cgtggagtcc atcatcaacc 1500
tgttccaggt ggtgcacaac tcctacaaca gacctgccta ctcccctggt cacaagaccc 1560
agcctgccat gggaggcgga ggctccggag gaggagggtc cgggggcggc ggaagcaagg 1620
gcgagctcga aagatgtgtt ttaacagttc catctacaga tatagaaaaa gaaatccttg 1680
atttagctgc tgctacagaa agattaaatt taactgatgc attaaactca aatccagctg 1740
gtaatttata tgattggcgt tcttctaact catacccttg gactcaaaag ctcaatttac 1800
acttaacaat tacagctact ggacaaaaat atagaatctt agctagcaaa attgttgatt 1860
ttaatattta ttcaaataat tttaataatc tagtgaaatt agaacagtcc ttaggtgatg 1920
gagtaaaaga tcattatgtt gatataagtt tagatgctgg acaatatgtt cttgtaatga 1980
aagctaattc atcatatagt ggaaattacc cttattcaat attatttcaa aaatttaagc 2040
ttgaaggtaa gcctatccct aaccctctcc tcggtctcga ttctacgcgt accggtcatc 2100
atcaccatca ccattgagtt taaac 2125

<210> SEQ ID NO 109
<211> LENGTH: 571
<212> TYPE: PRT
<213> ORGANISM: Artificial Sequence
<220> FEATURE:
<223> OTHER INFORMATION: synthetic construct

<400> SEQUENCE: 109

Gly Gly Ala Asp Asp Val Val Asp Ser Ser Lys Ser Phe Val Met Glu
1 5 10 15

Asn Phe Ala Ser Tyr His Gly Thr Lys Pro Gly Tyr Val Asp Ser Ile
20 25 30

Gln Lys Gly Ile Gln Lys Pro Lys Ser Gly Thr Gln Gly Asn Tyr Asp
35 40 45

Asp Asp Trp Lys Gly Phe Tyr Ser Thr Asp Asn Lys Tyr Asp Ala Ala
50 55 60

Gly Tyr Ser Val Asp Asn Glu Asn Pro Leu Ser Gly Lys Ala Gly Gly
65 70 75 80

Val Val Lys Val Thr Tyr Pro Gly Leu Thr Lys Val Leu Ala Leu Lys
85 90 95

Val Asp Asn Ala Glu Thr Ile Lys Lys Glu Leu Gly Leu Ser Leu Thr
100 105 110

Glu Pro Leu Met Glu Gln Val Gly Thr Glu Glu Phe Ile Lys Arg Phe
115 120 125

Gly Asp Gly Ala Ser Arg Val Val Leu Ser Leu Pro Phe Ala Glu Gly
130 135 140

Ser Ser Ser Val Glu Tyr Ile Asn Asn Trp Glu Gln Ala Lys Ala Leu
145 150 155 160

Ser Val Glu Leu Glu Ile Asn Phe Glu Thr Arg Gly Lys Arg Gly Gln
165 170 175

Asp Ala Met Tyr Glu Tyr Met Ala Gln Ala Cys Ala Gly Asn Ile Glu
180 185 190

Pro Asp Thr Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly
210 215 220

Pro Ile Lys Asn Lys Met Ser Glu Ser Pro Ala Lys Thr Val Ser Glu
225 230 235 240

Glu Lys Ala Lys Gln Tyr Leu Glu Glu Phe His Gln Thr Ala Leu Glu
245 250 255

His Pro Glu Leu Ser Glu Leu Lys Thr Val Thr Gly Thr Asn Pro Val
260 265 270

Phe Ala Gly Ala Asn Tyr Ala Ala Trp Ala Val Asn Val Ala Gln Val
275 280 285

Ile Asp Ser Glu Thr Ala Asp Asn Leu Glu Lys Thr Thr Ala Ala Leu
290 295 300

Ser Ile Leu Pro Gly Ile Gly Ser Val Met Gly Ile Ala Asp Gly Ala
305 310 315 320

```
Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Ala Met Gly Gly Gly Gly Ser Gly Gly Gly Gly Ser
385                 390                 395                 400

Gly Gly Gly Gly Ser Lys Gly Glu Leu Glu Arg Cys Val Leu Thr Val
                405                 410                 415

Pro Ser Thr Asp Ile Glu Lys Glu Ile Leu Asp Leu Ala Ala Ala Thr
            420                 425                 430

Glu Arg Leu Asn Leu Thr Asp Ala Leu Asn Ser Asn Pro Ala Gly Asn
        435                 440                 445

Leu Tyr Asp Trp Arg Ser Ser Asn Ser Tyr Pro Trp Thr Gln Lys Leu
    450                 455                 460

Asn Leu His Leu Thr Ile Thr Ala Thr Gly Gln Lys Tyr Arg Ile Leu
465                 470                 475                 480

Ala Ser Lys Ile Val Asp Phe Asn Ile Tyr Ser Asn Asn Phe Asn Asn
                485                 490                 495

Leu Val Lys Leu Glu Gln Ser Leu Gly Asp Gly Val Lys Asp His Tyr
            500                 505                 510

Val Asp Ile Ser Leu Asp Ala Gly Gln Tyr Val Leu Val Met Lys Ala
        515                 520                 525

Asn Ser Ser Tyr Ser Gly Asn Tyr Pro Tyr Ser Ile Leu Phe Gln Lys
    530                 535                 540

Phe Lys Leu Glu Gly Lys Pro Ile Pro Asn Pro Leu Leu Gly Leu Asp
545                 550                 555                 560

Ser Thr Arg Thr Gly His His His His His His
                565                 570


<210> SEQ ID NO 110
<211> LENGTH: 328
<212> TYPE: PRT
<213> ORGANISM: Artificial Sequence
<220> FEATURE:
<223> OTHER INFORMATION: synthetic construct

<400> SEQUENCE: 110

Gly Gln Arg Ala Gly Cys Cys Ala Val Ser Ser Phe Trp Gln Arg Ile
1               5                   10                  15

Ala Arg Gly Gln Gln Lys Leu Ala Ala Thr Met Gly Val Lys Val Leu
            20                  25                  30

Phe Ala Leu Ile Cys Ile Ala Val Ala Leu Ala Asp Asn Ser Ser Tyr
        35                  40                  45

Lys Asp Asp Asp Asp Lys Ile Ile Gly Gly His Glu Ala Lys Pro His
    50                  55                  60

Ser Arg Pro Tyr Met Ala Tyr Leu Met Ile Trp Asp Gln Lys Ser Leu
65                  70                  75                  80

Lys Arg Cys Gly Gly Phe Leu Ile Gln Asp Asp Phe Val Leu Thr Ala
                85                  90                  95

Ala His Cys Trp Gly Ser Ser Ile Asn Val Thr Leu Gly Ala His Asn
            100                 105                 110
```

```
Ile Lys Glu Gln Glu Pro Thr Gln Gln Phe Ile Pro Val Lys Arg Pro
        115                 120                 125

Ile Pro His Pro Ala Tyr Asn Pro Lys Asn Phe Ser Asn Asp Ile Met
    130                 135                 140

Leu Leu Gln Leu Glu Arg Lys Ala Lys Arg Thr Arg Ala Val Gln Pro
145                 150                 155                 160

Leu Arg Leu Pro Ser Asn Lys Ala Gln Val Lys Pro Gly Gln Thr Cys
                165                 170                 175

Ser Val Ala Gly Trp Gly Gln Thr Ala Pro Leu Gly Lys His Ser His
            180                 185                 190

Thr Leu Gln Glu Val Lys Met Thr Val Gln Glu Asp Arg Lys Cys Glu
        195                 200                 205

Ser Asp Leu Arg His Tyr Tyr Asp Ser Thr Ile Glu Leu Cys Val Gly
    210                 215                 220

Asp Pro Glu Ile Lys Lys Thr Ser Phe Lys Gly Asp Ser Gly Gly Pro
225                 230                 235                 240

Leu Val Cys Asn Lys Val Ala Gln Gly Ile Val Ser Tyr Gly Arg Asn
                245                 250                 255

Asn Gly Met Pro Pro Arg Ala Cys Thr Lys Val Ser Ser Phe Val His
            260                 265                 270

Trp Ile Lys Lys Thr Met Lys Arg Tyr Ala Met Gly Gly Gly Gly Ser
        275                 280                 285

Tyr Ser Ala Tyr Pro Asp Ser Val Pro Met Met Ser Gly Gly Gly Gly
    290                 295                 300

Ser Tyr Ser Ala Tyr Pro Asp Ser Val Pro Met Met Ser Gly Gly Gly
305                 310                 315                 320

Gly Ser His His His His His His
                325
```

<210> SEQ ID NO 111
<211> LENGTH: 1029
<212> TYPE: DNA
<213> ORGANISM: Artificial Sequence
<220> FEATURE:
<223> OTHER INFORMATION: synthetic construct

<400> SEQUENCE: 111

```
gggcaacgtg ctggttgttg tgctgtctca tcattttggc aaagaattgc acgaggtcag     60

cagaagcttg ccgccaccat gggcgtgaag gtgctgttcg ccctgatctg catcgccgtg    120

gcgctcgccg acaactcgag ctacaaggac gacgacgaca agatcatcgg gggacatgag    180

gccaagcccc actcccgccc ctacatggct tatcttatga tctgggatca gaagtctctg    240

aagaggtgcg gtggcttcct gatacaagac gacttcgtgc tgacagctgc tcactgttgg    300

ggaagctcca taaatgtcac cttgggggcc cacaatatca aagaacagga gccgacccag    360

cagtttatcc ctgtgaaaag acccatcccc catccagcct ataatcctaa gaacttctcc    420

aacgacatca tgctactgca gctggagaga aaggccaagc ggaccagagc tgtgcagccc    480

ctcaggctac ctagcaacaa ggcccaggtg aagccagggc agacatgcag tgtggccggc    540

tgggggcaga cggcccccct gggaaaacac tcacacacac tacaagaggt gaagatgaca    600

gtgcaggaag atcgaaagtg cgaatctgac ttacgccatt attacgacag taccattgag    660

ttgtgcgtgg gggacccaga gattaaaaag acttccttta agggggactc tggaggccct    720

cttgtgtgta acaaggtggc ccagggcatt gtctcctatg gacgaaacaa tggcatgcct    780
```

-continued ccacgagcct gcaccaaagt ctcaagcttt gtacactgga taaagaaaac catgaaacgc 840
tacgccatgg gtggcggtgg ctcttactcc gcttatcctg attccgttcc aatgatgtct 900
ggcggtggcg gttcctattc tgcctaccca gactccgtcc ctatgatgtc tggtggcggt 960
ggctcccatc accatcacca tcacaaggat taaaagcttg aagtccgagg aattcgggac 1020
agcggccgc 1029

<210> SEQ ID NO 112
<211> LENGTH: 274
<212> TYPE: PRT
<213> ORGANISM: Artificial Sequence
<220> FEATURE:
<223> OTHER INFORMATION: synthetic construct

<400> SEQUENCE: 112

```
Ile Ile Gly Gly His Glu Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Gln Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Pro Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr Ala Met Gly Gly Gly Gly Ser Tyr Ser Ala Tyr Pro Asp
225                 230                 235                 240

Ser Val Pro Met Met Ser Gly Gly Gly Gly Ser Tyr Ser Ala Tyr Pro
                245                 250                 255

Asp Ser Val Pro Met Met Ser Gly Gly Gly Gly Ser His His His His
            260                 265                 270

His His
```

<210> SEQ ID NO 113
<211> LENGTH: 837
<212> TYPE: DNA
<213> ORGANISM: Artificial Sequence
<220> FEATURE:

<223> OTHER INFORMATION: synthetic construct

<400> SEQUENCE: 113

```
atcatcgggg gacatgaggc caagccccac tcccgcccct acatggctta tcttatgatc     60

tgggatcaga agtctctgaa gaggtgcggt ggcttcctga tacaagacga cttcgtgctg    120

acagctgctc actgttgggg aagctccata aatgtcacct tgggggccca caatatcaaa    180

gaacaggagc cgacccagca gtttatccct gtgaaaagac ccatccccca tccagcctat    240

aatcctaaga acttctccaa cgacatcatg ctactgcagc tggagagaaa ggccaagcgg    300

accagagctg tgcagcccct caggctacct agcaacaagg cccaggtgaa gccagggcag    360

acatgcagtg tggccggctg gggggcagacg gcccccctgg gaaaacactc acacacacta    420

caagaggtga agatgacagt gcaggaagat cgaaagtgcg aatctgactt acgccattat    480

tacgacagta ccattgagtt gtgcgtgggg gacccagaga ttaaaaagac ttcctttaag    540

ggggactctg gaggccctct tgtgtgtaac aaggtggccc agggcattgt ctcctatgga    600

cgaaacaatg gcatgcctcc acgagcctgc accaaagtct caagctttgt acactggata    660

aagaaaacca tgaaacgcta cgccatgggt ggcggtggct cttactccgc ttatcctgat    720

tccgttccaa tgatgtctgg cggtggcggt tcctattctg cctacccaga ctccgtccct    780

atgatgtctg gtggcggtgg ctcccatcac catcaccatc acaaggatta aaagctt       837
```

<210> SEQ ID NO 114
<211> LENGTH: 780
<212> TYPE: PRT
<213> ORGANISM: Artificial Sequence
<220> FEATURE:
<223> OTHER INFORMATION: synthetic construct

<400> SEQUENCE: 114

```
Met Gly Ser Asp Lys Ile Ile His Leu Thr Asp Asp Ser Phe Asp Thr
1               5                   10                  15

Asp Val Leu Lys Ala Asp Gly Ala Ile Leu Val Asp Phe Trp Ala His
            20                  25                  30

Trp Cys Gly Pro Cys Lys Met Ile Ala Pro Ile Leu Asp Glu Ile Ala
        35                  40                  45

Asp Glu Tyr Gln Gly Lys Leu Thr Val Ala Lys Leu Asn Ile Asp His
    50                  55                  60

Asn Pro Gly Thr Ala Pro Lys Tyr Gly Ile Arg Gly Ile Pro Thr Leu
65                  70                  75                  80

Leu Leu Phe Lys Asn Gly Glu Val Ala Ala Thr Lys Val Gly Ala Leu
                85                  90                  95

Ser Lys Gly Gln Leu Lys Glu Phe Leu Asp Ala Asn Leu Ala Gly Ser
            100                 105                 110

Gly Ser Gly Asp Asp Asp Asp Lys Leu Gly Ile Asp Pro Phe Thr Gly
        115                 120                 125

Ala Asp Asp Val Val Asp Ser Ser Lys Ser Phe Val Met Glu Asn Phe
    130                 135                 140

Ala Ser Tyr His Gly Thr Lys Pro Gly Tyr Val Asp Ser Ile Gln Lys
145                 150                 155                 160

Gly Ile Gln Lys Pro Lys Ser Gly Thr Gln Gly Asn Tyr Asp Asp Asp
                165                 170                 175

Trp Lys Gly Phe Tyr Ser Thr Asp Asn Lys Tyr Asp Ala Ala Gly Tyr
            180                 185                 190

Ser Val Asp Asn Glu Asn Pro Leu Ser Gly Lys Ala Gly Gly Val Val
```

-continued 195 200 205

Lys Val Thr Tyr Pro Gly Leu Thr Lys Val Leu Ala Leu Lys Val Asp
210 215 220

Asn Ala Glu Thr Ile Lys Lys Glu Leu Gly Leu Ser Leu Thr Glu Pro
225 230 235 240

Leu Met Glu Gln Val Gly Thr Glu Glu Phe Ile Lys Arg Phe Gly Asp
245 250 255

Gly Ala Ser Arg Val Val Leu Ser Leu Pro Phe Ala Glu Gly Ser Ser
260 265 270

Ser Val Glu Tyr Ile Asn Asn Trp Glu Gln Ala Lys Ala Leu Ser Val
275 280 285

Glu Leu Glu Ile Asn Phe Glu Thr Arg Gly Lys Arg Gly Gln Asp Ala
290 295 300

Met Tyr Glu Tyr Met Ala Gln Ala Cys Ala Gly Asn Arg Val Arg Arg
305 310 315 320

Ala Ser Val Gly Ser Ser Leu Ser Cys Ile Asn Leu Asp Trp Asp Val
325 330 335

Ile Arg Asp Lys Thr Lys Thr Lys Ile Glu Ser Leu Lys Glu His Gly
340 345 350

Pro Ile Lys Asn Lys Met Ser Glu Ser Pro Asn Lys Thr Val Ser Glu
355 360 365

Glu Lys Ala Lys Gln Tyr Leu Glu Glu Phe His Gln Thr Ala Leu Glu
370 375 380

His Pro Glu Leu Ser Glu Leu Lys Thr Val Thr Gly Thr Asn Pro Val
385 390 395 400

Phe Ala Gly Ala Asn Tyr Ala Ala Trp Ala Val Asn Val Ala Gln Val
405 410 415

Ile Asp Ser Glu Thr Ala Asp Asn Leu Glu Lys Thr Thr Ala Ala Leu
420 425 430

Ser Ile Leu Pro Gly Ile Gly Ser Val Met Gly Ile Ala Asp Gly Ala
435 440 445

Val His His Asn Thr Glu Glu Ile Val Ala Gln Ser Ile Ala Leu Ser
450 455 460

Ser Leu Met Val Ala Gln Ala Ile Pro Leu Val Gly Glu Leu Val Asp
465 470 475 480

Ile Gly Phe Ala Ala Tyr Asn Phe Val Glu Ser Ile Ile Asn Leu Phe
485 490 495

Gln Val Val His Asn Ser Tyr Asn Arg Pro Ala Tyr Ser Pro Gly His
500 505 510

Lys Thr Gln Pro Lys Gly Glu Leu Lys Leu Ala Asn Ile Gln Leu Val
515 520 525

Gln Ser Gly Pro Glu Leu Lys Lys Pro Gly Glu Thr Val Lys Ile Ser
530 535 540

Cys Lys Ala Ser Gly Tyr Thr Phe Thr Asn Tyr Gly Met Asn Trp Val
545 550 555 560

Lys Gln Ala Pro Gly Lys Gly Leu Arg Trp Met Gly Trp Ile Asn Thr
565 570 575

His Thr Gly Glu Pro Thr Tyr Ala Asp Asp Phe Lys Gly Arg Phe Ala
580 585 590

Phe Ser Leu Glu Thr Ser Ala Ser Thr Ala Tyr Leu Gln Ile Asn Asn
595 600 605

Leu Lys Asn Glu Asp Thr Ala Thr Tyr Phe Cys Thr Arg Arg Gly Tyr
610 615 620

-continued

Asp Trp Tyr Phe Asp Val Trp Gly Ala Gly Thr Thr Val Thr Val Phe
625 630 635 640

Ser Gly Gly Gly Gly Ser Gly Gly Gly Gly Ser Gly Gly Gly Ser Ser
645 650 655

Asp Ile Lys Met Thr Gln Ser Pro Ser Ser Met Tyr Ala Ser Leu Gly
660 665 670

Glu Arg Val Thr Ile Thr Cys Lys Ala Ser Gln Asp Ile Asn Ser Tyr
675 680 685

Leu Ser Trp Phe His His Lys Pro Gly Lys Ser Pro Lys Thr Leu Ile
690 695 700

Tyr Arg Ala Asn Arg Leu Val Asp Gly Val Pro Ser Arg Phe Ser Gly
705 710 715 720

Ser Gly Ser Gly Gln Asp Tyr Ser Leu Thr Ile Ser Ser Leu Asp Tyr
725 730 735

Glu Asp Met Gly Ile Tyr Tyr Cys Gln Gln Tyr Asp Glu Ser Pro Trp
740 745 750

Thr Phe Gly Gly Gly Thr Lys Leu Glu Met Lys Glu Gln Lys Leu Ile
755 760 765

Ser Glu Glu Asp Leu Gly His His His His His His
770 775 780

<210> SEQ ID NO 115
<211> LENGTH: 2360
<212> TYPE: DNA
<213> ORGANISM: Artificial Sequence
<220> FEATURE:
<223> OTHER INFORMATION: synthetic construct

<400> SEQUENCE: 115
atgggatctg ataaaattat tcatctgact gatgattctt ttgatactga tgtacttaag 60
gcagatggtg caatcctggt tgatttctgg gcacactggt gcggtccgtg caaaatgatc 120
gctccgattc tggatgaaat cgctgacgaa tatcagggca aactgaccgt tgcaaaactg 180
aacatcgatc acaacccggg cactgcgccg aaatatggca tccgtggtat cccgactctg 240
ctgctgttca aaaacggtga agtggcggca accaaagtgg gtgcactgtc taaaggtcag 300
ttgaaagagt tcctcgacgc taacctggcc ggctctggat ccggtgatga cgatgacaag 360
ctgggaattg atcccttcac cggcgccgac gacgtggtgg actcctccaa gtccttcgtc 420
atggaaaact tcgcttccta ccacgggact aaacctggtt atgtagattc cattcaaaaa 480
ggtatacaaa agccaaaatc tggtacacaa ggaaattatg acgatgattg gaaagggttt 540
tatagtaccg acaataaata cgacgctgcg ggatactctg tagataatga aaacccgctc 600
tctggaaaag ctggaggcgt ggtcaaagtg acgtatccag gactgacgaa ggttctcgca 660
ctaaaagtgg ataatgccga aactattaag aaagagttag gtttaagtct cactgaaccg 720
ttgatggagc aagtcggaac ggaagagttt atcaaaaggt tcggtgatgg tgcttcgcgt 780
gtagtgctca gccttccctt cgctgagggg agttctagcg ttgaatatat taataactgg 840
gaacaggcga aagcgttaag cgtagaactt gagattaatt ttgaaacccg tggaaaacgt 900
ggccaagatg cgatgtatga gtatatggct caagcctgtg ccggcaatcg cgtgcgccgc 960
gctagcgtgg ggagctcatt gtcatgcatc aacctggact gggacgtgat ccgcgacaag 1020
accaagacca agatcgagtc cctgaaggag cacggcccga tcaagaacaa gatgtccgag 1080
tccccgaaca agaccgtgtc cgaggagaag gctaagcagt acctggagga gttccaccag 1140

```
accgctctgg agcacccgga gctgtccgag ctgaaaaccg tgaccggcac caacccggtg   1200

ttcgctggcg ctaactacgc tgcttgggct gtgaacgtgg ctcaggtgat cgactccgag   1260

actgctgaca acctggagaa aaccaccgct gctctgtcca tcctgccggg catcggctcc   1320

gtgatgggca tcgctgacgg cgctgtgcac cacaacaccg aggagatcgt ggctcagtcc   1380

atcgctctgt cctccctgat ggtggctcag gctatcccgc tggtgggcga gctggtggac   1440

atcggcttcg ctgcttacaa cttcgtggag tccatcatca acctgttcca ggtggtgcac   1500

aactcctaca accgcccggc ttactccccg ggccacaaga cccagcccaa gggcgagctc   1560

aagcttgccc aggtgcagct gcagcagtcc ggcgctgagc tggtgcgccc tggctcctcc   1620

gtgaaaatct cctgcaaggc ttccggctac gctttctcct cctactggat gaactgggtg   1680

aagcagcgcc ctggccaggg cctggagtgg atcggccaaa tctggccggg cgacggcgac   1740

accaactaca acggcaagtt caagggcaag gctaccctga ccgctgacga gtcctcctcc   1800

accgcttaca tgcagctgtc ctccctggct tccgaggact ccgctgtgta cttctgcgct   1860

cgccgcgaga ccaccaccgt gggccgctac tactacgcta tggactactg gggccagggc   1920

acctcggtga ccgtgtcctc cggcggcggc ggctccggcg gcggcggctc cggcggcggg   1980

agctccgaca tcctgctgac ccagaccccg gcttccctgg ctgtgtccct gggccagcgc   2040

gctaccatct cctgcaaggc ttcccagtcc gtggactacg acggcgactc ctacctgaac   2100

tggtaccagc agatcccggg ccagccgccg aagctgctga tctacgacgc ttccaacctg   2160

gtgtccggca tcccgccgcg cttctccggc tccggctccg gcaccgactt caccctgaac   2220

atccacccgg tggagaaggt ggacgctgct acctaccact gccagcagtc caccgaggac   2280

ccgtggacct tcggcggcgg caccaagctg gagatcaagc gcggtggtga catgcatcac   2340

catcaccatc actgaagctt                                                2360
```

<210> SEQ ID NO 116
<211> LENGTH: 696
<212> TYPE: PRT
<213> ORGANISM: Artificial Sequence
<220> FEATURE:
<223> OTHER INFORMATION: synthetic construct

<400> SEQUENCE: 116

```
Met Gly Ser Asp Lys Ile Ile His Leu Thr Asp Asp Ser Phe Asp Thr
1               5                   10                  15

Asp Val Leu Lys Ala Asp Gly Ala Ile Leu Val Asp Phe Trp Ala His
            20                  25                  30

Trp Cys Gly Pro Cys Lys Met Ile Ala Pro Ile Leu Asp Glu Ile Ala
        35                  40                  45

Asp Glu Tyr Gln Gly Lys Leu Thr Val Ala Lys Leu Asn Ile Asp His
    50                  55                  60

Asn Pro Gly Thr Ala Pro Lys Tyr Gly Ile Arg Gly Ile Pro Thr Leu
65                  70                  75                  80

Leu Leu Phe Lys Asn Gly Glu Val Ala Ala Thr Lys Val Gly Ala Leu
                85                  90                  95

Ser Lys Gly Gln Leu Lys Glu Phe Leu Asp Ala Asn Leu Ala Gly Ser
            100                 105                 110

Gly Ser Gly Glu Asn Leu Tyr Phe Gln Leu Gly Ile Asp Pro Phe Thr
        115                 120                 125

Gly Ala Asp Asp Val Val Asp Ser Ser Lys Ser Phe Val Met Glu Asn
    130                 135                 140
```

Phe Ala Ser Tyr His Gly Thr Lys Pro Gly Tyr Val Asp Ser Ile Gln
145 150 155 160

Lys Gly Ile Gln Lys Pro Lys Ser Gly Thr Gln Gly Asn Tyr Asp Asp
165 170 175

Asp Trp Lys Gly Phe Tyr Ser Thr Asp Asn Lys Tyr Asp Ala Ala Gly
180 185 190

Tyr Ser Val Asp Asn Glu Asn Pro Leu Ser Gly Lys Ala Gly Gly Val
195 200 205

Val Lys Val Thr Tyr Pro Gly Leu Thr Lys Val Leu Ala Leu Lys Val
210 215 220

Asp Asn Ala Glu Thr Ile Lys Lys Glu Leu Gly Leu Ser Leu Thr Glu
225 230 235 240

Pro Leu Met Glu Gln Val Gly Thr Glu Glu Phe Ile Lys Arg Phe Gly
245 250 255

Asp Gly Ala Ser Arg Val Val Leu Ser Leu Pro Phe Ala Glu Gly Ser
260 265 270

Ser Ser Val Glu Tyr Ile Asn Asn Trp Glu Gln Ala Lys Ala Leu Ser
275 280 285

Val Glu Leu Glu Ile Asn Phe Glu Thr Arg Gly Lys Arg Gly Gln Asp
290 295 300

Ala Met Tyr Glu Tyr Met Ala Gln Ala Cys Ala Gly Asn Arg Val Arg
305 310 315 320

Arg Ala Ser Val Gly Ser Ser Leu Ser Cys Ile Asn Leu Asp Trp Asp
325 330 335

Val Ile Arg Asp Lys Thr Lys Thr Lys Ile Glu Ser Leu Lys Glu His
340 345 350

Gly Pro Ile Lys Asn Lys Met Ser Glu Ser Pro Asn Lys Thr Val Ser
355 360 365

Glu Glu Lys Ala Lys Gln Tyr Leu Glu Glu Phe His Gln Thr Ala Leu
370 375 380

Glu His Pro Glu Leu Ser Glu Leu Lys Thr Val Thr Gly Thr Asn Pro
385 390 395 400

Val Phe Ala Gly Ala Asn Tyr Ala Ala Trp Ala Val Asn Val Ala Gln
405 410 415

Val Ile Asp Ser Glu Thr Ala Asp Asn Leu Glu Lys Thr Thr Ala Ala
420 425 430

Leu Ser Ile Leu Pro Gly Ile Gly Ser Val Met Gly Ile Ala Asp Gly
435 440 445

Ala Val His His Asn Thr Glu Glu Ile Val Ala Gln Ser Ile Ala Leu
450 455 460

Ser Ser Leu Met Val Ala Gln Ala Ile Pro Leu Val Gly Glu Leu Val
465 470 475 480

Asp Ile Gly Phe Ala Ala Tyr Asn Phe Val Glu Ser Ile Ile Asn Leu
485 490 495

Phe Gln Val Val His Asn Ser Tyr Asn Arg Pro Ala Tyr Ser Pro Gly
500 505 510

His Lys Thr Gln Pro Lys Gly Glu Leu Lys Leu Phe Leu His Asp Gly
515 520 525

Tyr Ala Val Ser Trp Asn Thr Val Glu Asp Ser Ile Ile Arg Thr Gly
530 535 540

Phe Gln Gly Glu Ser Gly His Asp Ile Lys Ile Thr Ala Glu Asn Thr
545 550 555 560

Pro Leu Pro Ile Ala Gly Val Leu Leu Pro Thr Ile Pro Gly Lys Leu

```
                565                 570                 575

Asp Val Asn Lys Ser Lys Thr His Ile Ser Val Asn Gly Arg Lys Ile
            580                 585                 590

Arg Met Arg Cys Arg Ala Ile Asp Gly Asp Val Thr Phe Cys Arg Pro
        595                 600                 605

Lys Ser Pro Val Tyr Val Gly Asn Gly Val His Ala Asn Leu His Val
    610                 615                 620

Ala Phe His Arg Ser Ser Ser Glu Lys Ile His Ser Asn Glu Ile Ser
625                 630                 635                 640

Ser Asp Ser Ile Gly Val Leu Gly Tyr Gln Lys Thr Val Asp His Thr
                645                 650                 655

Lys Val Asn Ser Lys Leu Ser Leu Phe Phe Glu Ile Lys Ser Lys Leu
            660                 665                 670

Glu Gly Lys Pro Ile Pro Asn Pro Leu Leu Gly Leu Asp Ser Thr Arg
        675                 680                 685

Thr Gly His His His His His His
    690                 695


<210> SEQ ID NO 117
<211> LENGTH: 2019
<212> TYPE: DNA
<213> ORGANISM: Artificial Sequence
<220> FEATURE:
<223> OTHER INFORMATION: synthetic construct

<400> SEQUENCE: 117

atgggatctg ataaaattat tcatctgact gatgattctt ttgatactga tgtacttaag      60

gcagatggtg caatcctggt tgatttctgg gcacactggt gcggtccgtg caaaatgatc     120

gctccgattc tggatgaaat cgctgacgaa tatcagggca aactgaccgt tgcaaaactg     180

aacatcgatc acaacccggg cactgcgccg aaatatggca tccgtggtat cccgactctg     240

ctgctgttca aaaacggtga agtggcggca accaaagtgg gtgcactgtc taaaggtcag     300

ttgaaagagt tcctcgacgc taacctggcc ggctctggat ccggtgaaaa cctgtatttt     360

cagggcctgg gaattgatcc cttcaccggc gccgacgacg tggtggactc ctccaagtcc     420

ttcgtcatgg aaaacttcgc ttcctaccac gggactaaac ctggttatgt agattccatt     480

caaaaaggta tacaaaagcc aaaatctggt acacaaggaa attatgacga tgattggaaa     540

gggttttata gtaccgacaa taaatacgac gctgcgggat actctgtaga taatgaaaac     600

ccgctctctg gaaaagctgg aggcgtggtc aaagtgacgt atccaggact gacgaaggtt     660

ctcgcactaa aagtggataa tgccgaaact attaagaaag agttaggttt aagtctcact     720

gaaccgttga tggagcaagt cggaacggaa gagtttatca aaaggttcgg tgatggtgct     780

tcgcgtgtag tgctcagcct tcccttcgct gaggggagtt ctagcgttga atatattaat     840

aactgggaac aggcgaaagc gttaagcgta gaacttgaga ttaattttga aacccgtgga     900

aaacgtggcc aagatgcgat gtatgagtat atggctcaag cctgtgccgg caatcgcgtg     960

cgccgcgcta gcgtggggag ctcattgtca tgcatcaacc tggactggga cgtgatccgc    1020

gacaagacca agaccaagat cgagtccctg aaggagcacg gcccgatcaa gaacaagatg    1080

tccgagtccc cgaacaagac cgtgtccgag gagaaggcta agcagtacct ggaggagttc    1140

caccagaccg ctctggagca cccggagctg tccgagctga aaaccgtgac cggcaccaac    1200

ccggtgttcg ctggcgctaa ctacgctgct tgggctgtga acgtggctca ggtgatcgac    1260

tccgagactg ctgacaacct ggagaaaacc accgctgctc tgtccatcct gccgggcatc    1320
```

ggctccgtga tgggcatcgc tgacggcgct gtgcaccaca acaccgagga gatcgtggct 1380
cagtccatcg ctctgtcctc cctgatggtg gctcaggcta tcccgctggt gggcgagctg 1440
gtggacatcg gcttcgctgc ttacaacttc gtggagtcca tcatcaacct gttccaggtg 1500
gtgcacaact cctacaaccg cccggcttac tccccgggcc acaagaccca gcccaagggc 1560
gagctcaagc tttttcttca tgacgggtat gctgtcagtt ggaacactgt tgaagattcg 1620
ataatccgaa ctggttttca aggggagagt gggcacgaca taaaaattac tgctgaaaat 1680
accccgcttc caatcgcggg tgtcctacta ccgactattc ctggaaagct ggacgttaat 1740
aagtccaaga ctcatatttc cgtaaatggt cggaaaataa ggatgcgttg cagagctata 1800
gacggtgatg taactttttg tcgccctaaa tctcctgttt atgttggtaa tggtgtgcat 1860
gcgaatcttc acgtggcatt tcacagaagc agctcggaga aaattcattc taatgaaatt 1920
tcgtcggatt ccataggcgt tcttgggtac cagaaaacag tagatcacac caaggttaat 1980
tctaagctat cgctattttt tgaaatcaaa agcaagctt 2019

<210> SEQ ID NO 118
<211> LENGTH: 921
<212> TYPE: PRT
<213> ORGANISM: Artificial Sequence
<220> FEATURE:
<223> OTHER INFORMATION: synthetic construct

<400> SEQUENCE: 118

Met Gly Ala Asp Asp Val Val Asp Ser Ser Lys Ser Phe Val Met Glu
1 5 10 15

Asn Phe Ala Ser Tyr His Gly Thr Lys Pro Gly Tyr Val Asp Ser Ile
20 25 30

Gln Lys Gly Ile Gln Lys Pro Lys Ser Gly Thr Gln Gly Asn Tyr Asp
35 40 45

Asp Asp Trp Lys Gly Phe Tyr Ser Thr Asp Asn Lys Tyr Asp Ala Ala
50 55 60

Gly Tyr Ser Val Asp Asn Glu Asn Pro Leu Ser Gly Lys Ala Gly Gly
65 70 75 80

Val Val Lys Val Thr Tyr Pro Gly Leu Thr Lys Val Leu Ala Leu Lys
85 90 95

Val Asp Asn Ala Glu Thr Ile Lys Lys Glu Leu Gly Leu Ser Leu Thr
100 105 110

Glu Pro Leu Met Glu Gln Val Gly Thr Glu Glu Phe Ile Lys Arg Phe
115 120 125

Gly Asp Gly Ala Ser Arg Val Val Leu Ser Leu Pro Phe Ala Glu Gly
130 135 140

Ser Ser Ser Val Glu Tyr Ile Asn Asn Trp Glu Gln Ala Lys Ala Leu
145 150 155 160

Ser Val Glu Leu Glu Ile Asn Phe Glu Thr Arg Gly Lys Arg Gly Gln
165 170 175

Asp Ala Met Tyr Glu Tyr Met Ala Gln Ala Cys Ala Gly Asn Ile Glu
180 185 190

Pro Asp Thr Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly
210 215 220

Pro Ile Lys Asn Lys Met Ser Glu Ser Pro Ala Lys Thr Val Ser Glu
225 230 235 240

```
Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Ala Met Glu Val Gln Leu Val Glu Ser Gly Gly Gly
385                 390                 395                 400

Leu Val Lys Pro Gly Gly Ser Leu Lys Leu Ser Cys Ala Ala Ser Gly
                405                 410                 415

Phe Ala Phe Ser Ile Tyr Asp Met Ser Trp Val Arg Gln Thr Pro Glu
            420                 425                 430

Lys Arg Leu Glu Trp Val Ala Tyr Ile Ser Ser Gly Gly Gly Thr Thr
        435                 440                 445

Tyr Tyr Pro Asp Thr Val Lys Gly Arg Phe Thr Ile Ser Arg Asp Asn
    450                 455                 460

Ala Lys Asn Thr Leu Tyr Leu Gln Met Ser Ser Leu Lys Ser Glu Asp
465                 470                 475                 480

Thr Ala Met Tyr Tyr Cys Ala Arg His Ser Gly Tyr Gly Thr His Trp
                485                 490                 495

Gly Val Leu Phe Ala Tyr Trp Gly Gln Gly Thr Leu Val Thr Val Ser
            500                 505                 510

Ala Gly Gly Gly Gly Ser Gly Gly Gly Gly Ser Gly Gly Gly Ser Ser
        515                 520                 525

Asp Ile Gln Met Thr Gln Thr Thr Ser Ser Leu Ser Ala Ser Leu Gly
    530                 535                 540

Asp Arg Val Thr Ile Ser Cys Arg Ala Ser Gln Asp Ile Ala Arg Tyr
545                 550                 555                 560

Leu Asn Trp Tyr Gln Gln Lys Pro Asp Gly Thr Val Lys Leu Leu Ile
                565                 570                 575

Tyr Tyr Thr Ser Ile Leu His Ser Gly Val Pro Ser Arg Phe Ser Gly
            580                 585                 590

Ser Gly Ser Gly Thr Asp Tyr Ser Leu Thr Ile Ser Asn Leu Glu Gln
        595                 600                 605

Glu Asp Phe Ala Thr Tyr Phe Cys Gln Gln Gly Asn Thr Leu Pro Trp
    610                 615                 620

Thr Phe Gly Gly Gly Thr Lys Leu Glu Ile Lys Thr Gly Pro Ser Gly
625                 630                 635                 640

Gln Ala Gly Ala Ala Ala Ser Glu Ser Leu Phe Val Ser Asn His Ala
                645                 650                 655
```

-continued

```
Tyr Thr Met Ala Gln Val Gln Leu Gln Gln Ser Gly Ala Glu Leu Val
            660                 665                 670

Arg Pro Gly Ser Ser Val Lys Ile Ser Cys Lys Ala Ser Gly Tyr Ala
        675                 680                 685

Phe Ser Ser Tyr Trp Met Asn Trp Val Lys Gln Arg Pro Gly Gln Gly
    690                 695                 700

Leu Glu Trp Ile Gly Gln Ile Trp Pro Gly Asp Gly Asp Thr Asn Tyr
705                 710                 715                 720

Asn Gly Lys Phe Lys Gly Lys Ala Thr Leu Thr Ala Asp Glu Ser Ser
                725                 730                 735

Ser Thr Ala Tyr Met Gln Leu Ser Ser Leu Ala Ser Glu Asp Ser Ala
            740                 745                 750

Val Tyr Phe Cys Ala Arg Arg Glu Thr Thr Thr Val Gly Arg Tyr Tyr
        755                 760                 765

Tyr Ala Met Asp Tyr Trp Gly Gln Gly Thr Ser Val Thr Val Ser Ser
    770                 775                 780

Gly Gly Gly Gly Ser Gly Gly Gly Gly Ser Gly Gly Gly Ser Ser Asp
785                 790                 795                 800

Ile Leu Leu Thr Gln Thr Pro Ala Ser Leu Ala Val Ser Leu Gly Gln
                805                 810                 815

Arg Ala Thr Ile Ser Cys Lys Ala Ser Gln Ser Val Asp Tyr Asp Gly
            820                 825                 830

Asp Ser Tyr Leu Asn Trp Tyr Gln Gln Ile Pro Gly Gln Pro Pro Lys
        835                 840                 845

Leu Leu Ile Tyr Asp Ala Ser Asn Leu Val Ser Gly Ile Pro Pro Arg
    850                 855                 860

Phe Ser Gly Ser Gly Ser Gly Thr Asp Phe Thr Leu Asn Ile His Pro
865                 870                 875                 880

Val Glu Lys Val Asp Ala Ala Thr Tyr His Cys Gln Gln Ser Thr Glu
                885                 890                 895

Asp Pro Trp Thr Phe Gly Gly Gly Thr Lys Leu Glu Ile Lys Arg Gly
            900                 905                 910

Gly Asp Met His His His His His His
        915                 920
```

<210> SEQ ID NO 119
<211> LENGTH: 2766
<212> TYPE: DNA
<213> ORGANISM: Artificial Sequence
<220> FEATURE:
<223> OTHER INFORMATION: synthetic construct

<400> SEQUENCE: 119

```
atgggtgccg acgacgtggt ggactcctcc aagtccttcg tgatggaaaa cttcgcttcc      60

taccacggta ccaagcctgg ttacgtggat tccatccaga agggtatcca gaagcctaag     120

tccggtaccc agggtaacta cgacgatgat tggaagggtt tttactccac cgacaacaag     180

tacgacgccg ccggttactc cgtggataac gaaaaccctc tgtccggtaa ggccggtggt     240

gtggtgaaag tgacctaccc tggtctgacc aaggtgctgg ccctgaaggt ggataacgcc     300

gaaaccatca agaaggagct gggtctgtcc ctgaccgaac ctctgatgga gcaggtgggt     360

accgaagagt ttatcaagag attcggtgat ggtgcctcca gagtggtgct gtccctgcct     420

ttcgccgagg gttcctcctc cgtggaatac atcaacaact gggaacaggc caaggccctg     480

tccgtggaac tggagatcaa ctttgaaacc agaggtaaga gaggtcagga tgccatgtac     540
```

```
gagtacatgg cccaggcctg tgccggcaac atcgagcctg acaccggttc ctccctgtcc    600
tgcatcaacc tggactggga cgtgatcaga gacaagacca agaccaagat cgagtccctg    660
aaggagcacg gtcctatcaa gaacaagatg tccgagtccc ctgccaagac cgtgtccgag    720
gagaaggcca agcagtacct ggaggagttc caccagaccg ccctggagca ccctgagctg    780
tccgagctga agaccgtgac tggtaccaac cctgtgttcg ccggtgccaa ctacgccgcc    840
tgggccgtga acgtggccca ggtgatcgac tccgagaccg ccgacaacct ggagaagacc    900
accgccgccc tgtccatcct gcctggtatc ggttccgtga tgggtatcgc cgacggtgcc    960
gtgcaccaca acaccgagga gatcgtggcc cagtccatcg ccctgtcctc cctgatggtg   1020
gcccaggcca tccctctggt gggtgagctg gtggacatcg gtttcgccgc ctacaacttc   1080
gtggagtcca tcatcaacct gttccaggtg gtgcacaact cctacaacag acctgcctac   1140
tcccctggtc acaagaccca gcctgccatg gaggttcagc tggttgagtc cggtggtggt   1200
ctggttaagc caggtggttc cctgaagctg tcctgtgctg cttccggttt cgctttctcc   1260
atctacgata tgtcctgggt tagacagacc ccagagaaga gactggagtg ggttgcttac   1320
atctcctccg gtggtggtac cacctactac ccagacaccg ttaagggtag attcaccatc   1380
tccagagata acgctaagaa caccctgtac ctgcagatgt cctccctgaa gtccgaggac   1440
accgctatgt actactgtgc tagacattcc ggttacggta cccattgggg tgttctgttc   1500
gcttactggg gtcagggtac cctggttacc gtttccgctg gtggtggtgg ttccggtggt   1560
ggtggttccg gtggtgggag ctccgatatc cagatgaccc agaccacctc ctccctgtcc   1620
gcttccctgg gtgacagagt taccatctcc tgtagagctt cccaggatat cgctagatac   1680
ctgaactggt accagcagaa gccagacggt accgttaagc tgctgatcta ctacacctcc   1740
atcctgcatt ccggtgttcc atccagattc tccggttccg gttccggtac cgattactcc   1800
ctgaccatct ccaacctgga gcaggaggac ttcgctacct acttctgtca gcagggtaac   1860
accctgcctt ggaccttcgg tggtggtacc aagctggaga tcaagactgg tccatccggt   1920
caggctggtg ctgctgcttc cgagtccttg ttcgtttcca accacgctta caccatggcc   1980
caggttcagt tgcagcagtc cggtgctgag ttggttagac caggttcctc tgttaagatc   2040
tcttgtaagg cctctggcta tgctttttcc tcttactgga tgaactgggt taagcagaga   2100
ccaggtcagg gcttggaatg gatcggtcaa atttggccag gtgatggtga tactaactac   2160
aacggtaagt tcaagggtaa ggctactttg actgctgacg aatcctcctc tactgcctat   2220
atgcaactgt cctctctggc ttctgaagat tctgctgttt acttctgcgc tagaagagaa   2280
accactaccg ttggtagata ctactatgct atggattact ggggtcaagg tacctcggtg   2340
accgtttctt ccggtggcgg tggttctggt ggtggtggct ctggtggtgg gagctccgat   2400
atcttgttga ctcaaacccc agcttctttg gctgtgtctc tgggtcaaag agctactatt   2460
tcctgcaagg cttctcaatc tgtggattac gatggtgact cctacttgaa ttggtatcag   2520
cagattccag gtcagcctcc taagctgttg atctacgatg cttccaactt ggtctccggt   2580
atcccaccaa gattctccgg ttctggttcc ggtactgact tcactttgaa catccaccca   2640
gttgagaaag tggatgctgc cacttaccac tgccaacaat ctaccgagga tccttggact   2700
ttcggtggtg gtaccaagtt ggagatcaaa agaggtggtg acatgcacca tcaccaccac   2760
cattaa                                                              2766
```

<210> SEQ ID NO 120
<211> LENGTH: 769

<212> TYPE: PRT
<213> ORGANISM: Artificial Sequence
<220> FEATURE:
<223> OTHER INFORMATION: synthetic construct

<400> SEQUENCE: 120

```
Ile Ile Gly Gly His Glu Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Gln Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Pro Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr Ala Met Gly Gly Gly Gly Ser Gly Gly Gly Gly Ser Gly
225                 230                 235                 240

Gly Gly Gly Ser Ala Gln Val Gln Leu Gln Gln Ser Gly Ala Glu Leu
                245                 250                 255

Val Arg Pro Gly Ser Ser Val Lys Ile Ser Cys Lys Ala Ser Gly Tyr
            260                 265                 270

Ala Phe Ser Ser Tyr Trp Met Asn Trp Val Lys Gln Arg Pro Gly Gln
        275                 280                 285

Gly Leu Glu Trp Ile Gly Gln Ile Trp Pro Gly Asp Gly Asp Thr Asn
    290                 295                 300

Tyr Asn Gly Lys Phe Lys Gly Lys Ala Thr Leu Thr Ala Asp Glu Ser
305                 310                 315                 320

Ser Ser Thr Ala Tyr Met Gln Leu Ser Ser Leu Ala Ser Glu Asp Ser
                325                 330                 335

Ala Val Tyr Phe Cys Ala Arg Arg Glu Thr Thr Thr Val Gly Arg Tyr
            340                 345                 350

Tyr Tyr Ala Met Asp Tyr Trp Gly Gln Gly Thr Ser Val Thr Val Ser
        355                 360                 365

Ser Gly Gly Gly Gly Ser Gly Gly Gly Gly Ser Gly Gly Gly Ser Ser
    370                 375                 380
```

```
Asp Ile Leu Leu Thr Gln Thr Pro Ala Ser Leu Ala Val Ser Leu Gly
385                 390                 395                 400

Gln Arg Ala Thr Ile Ser Cys Lys Ala Ser Gln Ser Val Asp Tyr Asp
                405                 410                 415

Gly Asp Ser Tyr Leu Asn Trp Tyr Gln Gln Ile Pro Gly Gln Pro Pro
            420                 425                 430

Lys Leu Leu Ile Tyr Asp Ala Ser Asn Leu Val Ser Gly Ile Pro Pro
        435                 440                 445

Arg Phe Ser Gly Ser Gly Ser Gly Thr Asp Phe Thr Leu Asn Ile His
    450                 455                 460

Pro Val Glu Lys Val Asp Ala Ala Thr Tyr His Cys Gln Gln Ser Thr
465                 470                 475                 480

Glu Asp Pro Trp Thr Phe Gly Gly Gly Thr Lys Leu Glu Ile Lys Arg
                485                 490                 495

Gly Gly Asp Met Gly Asn Ser Gly Gly Gly Ala Gln Val Gln Leu
            500                 505                 510

Gln Gln Ser Gly Ala Glu Leu Val Arg Pro Gly Ser Ser Val Lys Ile
        515                 520                 525

Ser Cys Lys Ala Ser Gly Tyr Ala Phe Ser Ser Tyr Trp Met Asn Trp
    530                 535                 540

Val Lys Gln Arg Pro Gly Gln Gly Leu Glu Trp Ile Gly Gln Ile Trp
545                 550                 555                 560

Pro Gly Asp Gly Asp Thr Asn Tyr Asn Gly Lys Phe Lys Gly Lys Ala
                565                 570                 575

Thr Leu Thr Ala Asp Glu Ser Ser Ser Thr Ala Tyr Met Gln Leu Ser
            580                 585                 590

Ser Leu Ala Ser Glu Asp Ser Ala Val Tyr Phe Cys Ala Arg Arg Glu
        595                 600                 605

Thr Thr Thr Val Gly Arg Tyr Tyr Tyr Ala Met Asp Tyr Trp Gly Gln
    610                 615                 620

Gly Thr Ser Val Thr Val Ser Ser Gly Gly Gly Gly Ser Gly Gly Gly
625                 630                 635                 640

Gly Ser Gly Gly Gly Ser Ser Asp Ile Leu Leu Thr Gln Thr Pro Ala
                645                 650                 655

Ser Leu Ala Val Ser Leu Gly Gln Arg Ala Thr Ile Ser Cys Lys Ala
            660                 665                 670

Ser Gln Ser Val Asp Tyr Asp Gly Asp Ser Tyr Leu Asn Trp Tyr Gln
        675                 680                 685

Gln Ile Pro Gly Gln Pro Pro Lys Leu Leu Ile Tyr Asp Ala Ser Asn
    690                 695                 700

Leu Val Ser Gly Ile Pro Pro Arg Phe Ser Gly Ser Gly Ser Gly Thr
705                 710                 715                 720

Asp Phe Thr Leu Asn Ile His Pro Val Glu Lys Val Asp Ala Ala Thr
                725                 730                 735

Tyr His Cys Gln Gln Ser Thr Glu Asp Pro Trp Thr Phe Gly Gly Gly
            740                 745                 750

Thr Lys Leu Glu Ile Lys Arg Gly Gly Asp Met His His His His His
        755                 760                 765

His
```

<210> SEQ ID NO 121
<211> LENGTH: 2312
<212> TYPE: DNA
<213> ORGANISM: Artificial Sequence
<220> FEATURE:
<223> OTHER INFORMATION: synthetic construct

<400> SEQUENCE: 121

```
atcatcgggg gacatgaggc caagccccac tcccgcccct acatggctta tcttatgatc     60
tgggatcaga agtctctgaa gaggtgcggt ggcttcctga tacaagacga cttcgtgctg    120
acagctgctc actgttgggg aagctccata aatgtcacct tgggggccca caatatcaaa    180
gaacaggagc cgacccagca gtttatccct gtgaaaagac ccatcccccca tccagcctat    240
aatcctaaga acttctccaa cgacatcatg ctactgcagc tggagagaaa ggccaagcgg    300
accagagctg tgcagcccct caggctacct agcaacaagg cccaggtgaa gccagggcag    360
acatgcagtg tggccggctg gggggcagacg gcccccctgg gaaaacactc acacacacta    420
caagaggtga agatgacagt gcaggaagat cgaaagtgcg aatctgactt acgccattat    480
tacgacagta ccattgagtt gtgcgtgggg gacccagaga ttaaaaagac ttcctttaag    540
ggggactctg gaggccctct tgtgtgtaac aaggtggccc agggcattgt ctcctatgga    600
cgaaacaatg gcatgcctcc acgagcctgc accaaagtct caagctttgt acactggata    660
aagaaaacca tgaaacgcta cgccatggga ggcggaggct ccggaggagg agggtccggg    720
ggcggcggaa gcgcccaggt tcagttgcag cagtccggtg ctgagttggt tagaccaggt    780
tcctctgtta agatctcttg taaggcctct ggctatgctt tttcctctta ctggatgaac    840
tgggttaagc agagaccagg tcagggcttg gaatggatcg gtcaaatttg gccaggtgat    900
ggtgatacta actacaacgg taagttcaag ggtaaggcta ctttgactgc tgacgaatcc    960
tcctctactg cctatatgca actgtcctct ctggcttctg aagattctgc tgtttacttc   1020
tgcgctagaa gagaaaccac taccgttggt agatactact atgctatgga ttactggggt   1080
caaggtacct cggtgaccgt ttcttccggt ggcggtggtt ctggtggtgg tggctctggt   1140
ggtgggagct ccgatatctt gttgactcaa accccagctt ctttggctgt gtctctgggt   1200
caaagagcta ctatttcctg caaggcttct caatctgtgg attacgatgg tgactcctac   1260
ttgaattggt atcagcagat tccaggtcag cctcctaagc tgttgatcta cgatgcttcc   1320
aacttggtct ccggtatccc accaagattc tccggttctg gttccggtac tgacttcact   1380
ttgaacatcc acccagttga gaaagtggat gctgccactt accactgcca acaatctacc   1440
gaggatcctt ggactttcgg tggtggtacc aagttggaga tcaaaagagg tggtgacatg   1500
gggaattctg gaggcggagg cgcccaggtt cagttgcagc agtccggtgc tgagttggtt   1560
agaccaggtt cctctgttaa gatctcttgt aaggcctctg gctatgcttt ttcctcttac   1620
tggatgaact gggttaagca gagaccaggt cagggcttgg aatggatcgg tcaaatttgg   1680
ccaggtgatg gtgatactaa ctacaacggt aagttcaagg gtaaggctac tttgactgct   1740
gacgaatcct cctctactgc ctatatgcaa ctgtcctctc tggcttctga agattctgct   1800
gtttacttct gcgctagaag agaaaccact accgttggta gatactacta tgctatggat   1860
tactggggtc aaggtacctc ggtgaccgtt tcttccggtg gcggtggttc tggtggtggt   1920
ggctctggtg gtgggagctc cgatatcttg ttgactcaaa ccccagcttc tttggctgtg   1980
tctctgggtc aaagagctac tatttcctgc aaggcttctc aatctgtgga ttacgatggt   2040
gactcctact tgaattggta tcagcagatt ccaggtcagc ctcctaagct gttgatctac   2100
gatgcttcca acttggtctc cggtatccca ccaagattct ccggttctgg ttccggtact   2160
gacttcactt tgaacatcca cccagttgag aaagtggatg ctgccactta ccactgccaa   2220
```

caatctaccg aggatccttg gactttcggt ggtggtacca agttggagat caaaagaggt 2280
ggtgacatgc accatcacca ccaccattaa gc 2312

<210> SEQ ID NO 122
<211> LENGTH: 658
<212> TYPE: PRT
<213> ORGANISM: Artificial Sequence
<220> FEATURE:
<223> OTHER INFORMATION: synthetic construct

<400> SEQUENCE: 122

```
Met Pro Pro Ser His Met Lys Thr Glu Glu Gly Lys Leu Val Ile Trp
1               5                   10                  15

Ile Asn Gly Asp Lys Gly Tyr Asn Gly Leu Ala Glu Val Gly Lys Lys
            20                  25                  30

Phe Glu Lys Asp Thr Gly Ile Lys Val Thr Val Glu His Pro Asp Lys
        35                  40                  45

Leu Glu Glu Lys Phe Pro Gln Val Ala Ala Thr Gly Asp Gly Pro Asp
    50                  55                  60

Ile Ile Phe Trp Ala His Asp Arg Phe Gly Gly Tyr Ala Gln Ser Gly
65                  70                  75                  80

Leu Leu Ala Glu Ile Thr Pro Asp Lys Ala Phe Gln Asp Lys Leu Tyr
                85                  90                  95

Pro Phe Thr Trp Asp Ala Val Arg Tyr Asn Gly Lys Leu Ile Ala Tyr
            100                 105                 110

Pro Ile Ala Val Glu Ala Leu Ser Leu Ile Tyr Asn Lys Asp Leu Leu
        115                 120                 125

Pro Asn Pro Pro Lys Thr Trp Glu Glu Ile Pro Ala Leu Asp Lys Glu
    130                 135                 140

Leu Lys Ala Lys Gly Lys Ser Ala Leu Met Phe Asn Leu Gln Glu Pro
145                 150                 155                 160

Tyr Phe Thr Trp Pro Leu Ile Ala Ala Asp Gly Gly Tyr Ala Phe Lys
                165                 170                 175

Tyr Glu Asn Gly Lys Tyr Asp Ile Lys Asp Val Gly Val Asp Asn Ala
            180                 185                 190

Gly Ala Lys Ala Gly Leu Thr Phe Leu Val Asp Leu Ile Lys Asn Lys
        195                 200                 205

His Met Asn Ala Asp Thr Asp Tyr Ser Ile Ala Glu Ala Ala Phe Asn
    210                 215                 220

Lys Gly Glu Thr Ala Met Thr Ile Asn Gly Pro Trp Ala Trp Ser Asn
225                 230                 235                 240

Ile Asp Thr Ser Lys Val Asn Tyr Gly Val Thr Val Leu Pro Thr Phe
                245                 250                 255

Lys Gly Gln Pro Ser Lys Pro Phe Val Gly Val Leu Ser Ala Gly Ile
            260                 265                 270

Asn Ala Ala Ser Pro Asn Lys Glu Leu Ala Lys Glu Phe Leu Glu Asn
        275                 280                 285

Tyr Leu Leu Thr Asp Glu Gly Leu Glu Ala Val Asn Lys Asp Lys Pro
    290                 295                 300

Leu Gly Ala Val Ala Leu Lys Ser Tyr Glu Glu Glu Leu Ala Lys Asp
305                 310                 315                 320

Pro Arg Ile Ala Ala Thr Met Glu Asn Ala Gln Lys Gly Glu Ile Met
                325                 330                 335

Pro Asn Ile Pro Gln Met Ser Ala Phe Trp Tyr Ala Val Arg Thr Ala
            340                 345                 350
```

```
Val Ile Asn Ala Ala Ser Gly Arg Gln Thr Val Asp Glu Ala Leu Lys
        355                 360                 365

Asp Ala Gln Thr Asn Ser Ser Asn Asn Ser Arg Arg Ala Ser Val Ala
    370                 375                 380

Met Leu Arg Gln Ile Leu Asp Ser Gln Lys Met Glu Trp Arg Ser Asn
385                 390                 395                 400

Ala Met Thr Gly Gly Gly Ser Lys Leu Gly Asp Asp Asp Asp Lys Gly
                405                 410                 415

Lys Gly Gly Gly Ser Lys Gly Pro Arg Asp Tyr Asn Pro Ile Ser Ser
            420                 425                 430

Ala Ile Cys His Leu Thr Asn Glu Ser Asp Gly His Thr Thr Ser Leu
        435                 440                 445

Tyr Gly Ile Gly Phe Gly Pro Phe Ile Ile Thr Asn Lys His Leu Phe
    450                 455                 460

Arg Arg Asn Asn Gly Thr Leu Leu Val Gln Ser Leu His Gly Val Phe
465                 470                 475                 480

Lys Val Lys Asn Thr Thr Thr Leu Gln Gln His Leu Ile Asp Gly Arg
                485                 490                 495

Asp Met Met Leu Ile Arg Met Pro Lys Asp Phe Pro Pro Phe Pro Gln
            500                 505                 510

Lys Leu Lys Phe Arg Glu Pro Gln Arg Glu Glu Arg Ile Cys Leu Val
        515                 520                 525

Thr Thr Asn Phe Gln Thr Lys Ser Met Ser Ser Met Val Ser Asp Thr
    530                 535                 540

Ser Cys Thr Phe Pro Ser Ser Asp Gly Ile Phe Trp Lys His Trp Ile
545                 550                 555                 560

Gln Thr Lys Asp Gly His Cys Gly Ser Pro Leu Val Ser Thr Arg Asp
                565                 570                 575

Gly Phe Ile Val Gly Ile His Ser Ala Ser Asn Phe Thr Asn Thr Asn
            580                 585                 590

Asn Tyr Phe Thr Ser Val Pro Lys Asp Phe Met Asp Leu Leu Thr Asn
        595                 600                 605

Gln Glu Ala Gln Gln Trp Val Ser Gly Trp Arg Leu Asn Ala Asp Ser
    610                 615                 620

Val Leu Trp Gly Gly His Lys Val Phe Met Asn Lys Pro Glu Glu Pro
625                 630                 635                 640

Phe Gln Pro Val Lys Glu Ala Thr Gln Leu Met Ser His His His His
                645                 650                 655

His His
```

<210> SEQ ID NO 123
<211> LENGTH: 1991
<212> TYPE: DNA
<213> ORGANISM: Artificial Sequence
<220> FEATURE:
<223> OTHER INFORMATION: synthetic construct

<400> SEQUENCE: 123

```
atgccaccct cccatatgaa aactgaagaa ggtaaactgg taatctggat taacggcgat      60

aaaggctata acggtctcgc tgaagtcggt aagaaattcg agaaagatac cggaattaaa     120

gtcaccgttg agcatccgga taaactggaa gagaaattcc cacaggttgc ggcaactggc     180

gatggccctg acattatctt ctgggcacac gaccgctttg gtggctacgc tcaatctggc     240

ctgttggctg aaatcacccc ggacaaagcg ttccaggaca agctgtatcc gtttacctgg     300
```

```
gatgccgtac gttacaacgg caagctgatt gcttacccga tcgctgttga agcgttatcg    360

ctgatttata acaaagatct gctgccgaac ccgccaaaaa cctgggaaga gatcccggcg    420

ctggataaag aactgaaagc gaaaggtaag agcgcgctga tgttcaacct gcaagaaccg    480

tacttcacct ggccgctgat tgctgctgac gggggttatg cgttcaagta tgaaaacggc    540

aagtacgaca ttaaagacgt gggcgtggat aacgctggcg cgaaagcggg tctgaccttc    600

ctggttgacc tgattaaaaa caaacacatg aatgcagaca ccgattactc catcgcagaa    660

gctgccttta ataaaggcga aacagcgatg accatcaacg gcccgtgggc atggtccaac    720

atcgacacca gcaaagtgaa ttatggtgta acggtactgc cgaccttcaa gggtcaacca    780

tccaaaccgt tcgttggcgt gctgagcgca ggtattaacg ccgccagtcc gaacaaagag    840

ctggcaaaag agttcctcga aaactatctg ctgactgatg aaggtctgga agcggttaat    900

aaagacaaac cgctgggtgc cgtagcgctg aagtcttacg aggaagagtt ggcgaaagat    960

ccacgtattg ccgccactat ggaaaacgcc cagaaaggtg aaatcatgcc gaacatcccg   1020

cagatgtccg ctttctggta tgccgtgcgt actgcggtga tcaacgccgc cagcggtcgt   1080

cagactgtcg atgaagccct gaaagacgcg cagactaatt cgagcaacaa ctcacggcgg   1140

gctagtgtcg ccatgctgcg tcaaattctg gattctcaaa aatggaatg gcgctctaac    1200

gccatgaccg gtggcgggag caagcttggg gatgacgatg acaagggcaa aggcggcggg   1260

agcaaaggtc cgcgtgacta caacccgatc tcctccgcta tctgccacct gaccaacgaa   1320

tccgacggtc acaccacctc cctgtacggt atcggtttcg gtccgttcat catcaccaac   1380

aaacacctgt tccgtcgtaa caacgggacc ctgctggttc agtccctgca cggtgttttc   1440

aaagttaaaa acaccaccac cctccagcag cacctgatcg acggtcgtga catgatgctg   1500

atccgtatgc cgaaagactt cccgccgttc ccgcagaaac tgaaattccg tgaaccgcag   1560

cgtgaagaac gtatctgcct cgttaccacc aacttccaga ccaaatccat gtcctctatg   1620

gtttccgaca cctcctgcac cttcccgtcc tccgacggta tcttctggaa acactggatt   1680

cagaccaaag acggtcactg cggttccccg ctggtttcca cccgtgacgg tttcatcgtt   1740

ggtatccact ccgcttccaa cttcaccaac accaacaact acttcacctc cgttccgaaa   1800

gacttcatgg acctcctgac caaccaggaa gctcagcagt gggtttccgg ttggcgtctg   1860

aacgctgact ccgttctgtg gggtggtcac aaagttttta tgaacaaacc ggaagaaccg   1920

ttccagccgg ttaaagaagc tacccagctc atgtcccacc atcaccacca ccattaagcg   1980

gccgcgaatt c                                                        1991
```

<210> SEQ ID NO 124
<211> LENGTH: 496
<212> TYPE: PRT
<213> ORGANISM: Artificial Sequence
<220> FEATURE:
<223> OTHER INFORMATION: synthetic construct

<400> SEQUENCE: 124

```
Ile Ile Gly Gly Arg Glu Val Ile Pro His Ser Arg Pro Tyr Met Ala
1               5                   10                  15

Ser Leu Gln Arg Asn Gly Ser His Leu Cys Gly Gly Val Leu Val His
            20                  25                  30

Pro Lys Trp Val Leu Thr Ala Ala His Cys Leu Ala Gln Arg Met Ala
        35                  40                  45

Gln Leu Arg Leu Val Leu Gly Leu His Thr Leu Asp Ser Pro Gly Leu
```

```
    50                  55                  60

Thr Phe His Ile Lys Ala Ala Ile Gln His Pro Arg Tyr Lys Pro Val
65                  70                  75                  80

Pro Ala Leu Glu Asn Asp Leu Ala Leu Leu Gln Leu Asp Gly Lys Val
                85                  90                  95

Lys Pro Ser Arg Thr Ile Arg Pro Leu Ala Leu Pro Ser Lys Arg Gln
            100                 105                 110

Val Val Ala Ala Gly Thr Arg Cys Ser Met Ala Gly Trp Gly Leu Thr
        115                 120                 125

His Gln Gly Gly Arg Leu Ser Arg Val Leu Arg Glu Leu Asp Leu Gln
    130                 135                 140

Val Leu Asp Thr Arg Met Cys Asn Asn Ser Arg Phe Trp Asn Gly Ser
145                 150                 155                 160

Leu Ser Pro Ser Met Val Cys Leu Ala Ala Asp Ser Lys Asp Gln Ala
                165                 170                 175

Pro Cys Lys Gly Asp Ser Gly Gly Pro Leu Val Cys Gly Lys Gly Arg
            180                 185                 190

Val Leu Ala Gly Val Leu Ser Phe Ser Ser Arg Val Cys Thr Asp Ile
        195                 200                 205

Phe Lys Pro Pro Val Ala Thr Ala Val Ala Pro Tyr Val Ser Trp Ile
    210                 215                 220

Arg Lys Val Thr Gly Arg Ser Ala Ala Met Ala Gln Val Gln Leu Gln
225                 230                 235                 240

Gln Ser Gly Ala Glu Leu Val Arg Pro Gly Ser Ser Val Lys Ile Ser
                245                 250                 255

Cys Lys Ala Ser Gly Tyr Ala Phe Ser Ser Tyr Trp Met Asn Trp Val
            260                 265                 270

Lys Gln Arg Pro Gly Gln Gly Leu Glu Trp Ile Gly Gln Ile Trp Pro
        275                 280                 285

Gly Asp Gly Asp Thr Asn Tyr Asn Gly Lys Phe Lys Gly Lys Ala Thr
    290                 295                 300

Leu Thr Ala Asp Glu Ser Ser Ser Thr Ala Tyr Met Gln Leu Ser Ser
305                 310                 315                 320

Leu Ala Ser Glu Asp Ser Ala Val Tyr Phe Cys Ala Arg Arg Glu Thr
                325                 330                 335

Thr Thr Val Gly Arg Tyr Tyr Tyr Ala Met Asp Tyr Trp Gly Gln Gly
            340                 345                 350

Thr Ser Val Thr Val Ser Ser Gly Gly Gly Gly Ser Gly Gly Gly Gly
        355                 360                 365

Ser Gly Gly Gly Ser Ser Asp Ile Leu Leu Thr Gln Thr Pro Ala Ser
    370                 375                 380

Leu Ala Val Ser Leu Gly Gln Arg Ala Thr Ile Ser Cys Lys Ala Ser
385                 390                 395                 400

Gln Ser Val Asp Tyr Asp Gly Asp Ser Tyr Leu Asn Trp Tyr Gln Gln
                405                 410                 415

Ile Pro Gly Gln Pro Pro Lys Leu Leu Ile Tyr Asp Ala Ser Asn Leu
            420                 425                 430

Val Ser Gly Ile Pro Pro Arg Phe Ser Gly Ser Gly Ser Gly Thr Asp
        435                 440                 445

Phe Thr Leu Asn Ile His Pro Val Glu Lys Val Asp Ala Ala Thr Tyr
    450                 455                 460

His Cys Gln Gln Ser Thr Glu Asp Pro Trp Thr Phe Gly Gly Gly Thr
465                 470                 475                 480
```

Lys Leu Glu Ile Lys Arg Gly Gly Asp Met His His His His His His
485 490 495

<210> SEQ ID NO 125
<211> LENGTH: 1521
<212> TYPE: DNA
<213> ORGANISM: Artificial Sequence
<220> FEATURE:
<223> OTHER INFORMATION: synthetic construct

<400> SEQUENCE: 125
ctcgagctac aaggacgacg acgacaagat catcgggggc cgggaggtga tcccccactc 60
gcgcccgtac atggcctcac tgcagagaaa tggctcccac ctgtgcgggg gtgtcctggt 120
gcacccaaag tgggtgctga cggctgccca ctgcctggcc cagcggatgg cccagctgag 180
gctggtgctg ggctccacac ccctggacag ccccggtctc accttccaca tcaaggcagc 240
catccagcac cctcgctaca agcccgtccc tgccctggag aacgacctcg cgctgcttca 300
gctggacggg aaagtgaagc ccagccggac catccggccg ttggccctgc ccagtaagcg 360
ccaggtggtg gcagcaggga ctcggtgcag catggccggc tgggggctga cccaccaggg 420
cgggcgcctg tcccgggtgc tgcgggagct ggacctccaa gtgctggaca cccgcatgtg 480
taacaacagc cgcttctgga acggcagcct ctcccccagc atggtctgcc tggcggccga 540
ctccaaggac caggctccct gcaagggtga ctcgggcggg cccctggtgt gtggcaaagg 600
ccgggtgttg gccggagtcc tgtccttcag ctccagggtc tgcactgaca tcttcaagcc 660
tcccgtggcc accgctgtgg cgccttacgt gtcctggatc aggaaggtca ccggccgatc 720
ggccgccatg gcccaggtgc agctgcagca gtccggcgct gagctggtgc gccctggctc 780
ctccgtgaaa atctcctgca aggcttccgg ctacgctttc tcctcctact ggatgaactg 840
ggtgaagcag cgccctggcc agggcctgga gtggatcggc caaatctggc cgggcgacgg 900
cgacaccaac tacaacggca agttcaaggg caaggctacc ctgaccgctg acgagtcctc 960
ctccaccgct tacatgcagc tgtcctccct ggcttccgag gactccgctg tgtacttctg 1020
cgctcgccgc gagaccacca ccgtgggccg ctactactac gctatggact actggggcca 1080
gggcacctcg gtgaccgtgt cctccggcgg cggcggctcc ggcggcggcg gctccggcgg 1140
cgggagctcc gacatcctgc tgacccagac cccggcttcc ctggctgtgt ccctgggcca 1200
gcgcgctacc atctcctgca aggcttccca gtccgtggac tacgacggcg actcctacct 1260
gaactggtac cagcagatcc cgggccagcc gccgaagctg ctgatctacg acgcttccaa 1320
cctggtgtcc ggcatcccgc cgcgcttctc cggctccggc tccggcaccg acttcaccct 1380
gaacatccac ccggtggaga aggtggacgc tgctacctac cactgccagc agtccaccga 1440
ggacccgtgg accttcggcg gcggcaccaa gctggagatc aagcgcggtg gtgacatgca 1500
ccatcaccac caccattaag c 1521

<210> SEQ ID NO 126
<211> LENGTH: 2338
<212> TYPE: DNA
<213> ORGANISM: Artificial Sequence
<220> FEATURE:
<223> OTHER INFORMATION: synthetic construct

<400> SEQUENCE: 126
atgggatctg ataaaattat tcatctgact gatgattctt ttgatactga tgtacttaag 60
gcagatggtg caatcctggt tgatttctgg gcacactggt gcggtccgtg caaaatgatc 120

```
gctccgattc tggatgaaat cgctgacgaa tatcagggca aactgaccgt tgcaaaactg    180
aacatcgatc acaacccggg cactgcgccg aaatatggca tccgtggtat cccgactctg    240
ctgctgttca aaaacggtga agtggcggca accaaagtgg gtgcactgtc taaaggtcag    300
ttgaaagagt tcctcgacgc taacctggcc ggctctggat ccggtgatga cgatgacaag    360
ctgggaattg atcccttcac catgggagca tttttagaca agccaaagat ggaaaagcat    420
aatgcccagg ggcagggtaa tgggttgcga tatgggctaa gcagcatgca aggctggcgt    480
gttgaaatgg aggatgcaca tacggctgtg atcggtttgc caagtggact tgaatcgtgg    540
tcattctttg ctgtgtatga tgggcatgct ggttctcagg ttgccaaata ctgctgtgag    600
catttgttag atcacatcac caataaccag gattttaaag ggtctgcagg agcaccttct    660
gtggaaaatg taaagaatgg aatcagaaca ggttttctgg agattgatga acacatgaga    720
gttatgtcag agaagaaaca tggtgcagat agaagtgggt caacagctgt aggtgtctta    780
atttctcccc aacatactta tttcattaac tgtggagact caagaggttt actttgtagg    840
aacaggaaag ttcatttctt cacacaagat cacaaaccaa gtaatccgct ggagaaagaa    900
cgaattcaga atgcaggtgg ctctgtaatg attcagcgtg tgaatggctc tctggctgta    960
tcgagggccc ttggggattt tgattacaaa tgtgtccatg gaaaaggtcc tactgagcag   1020
cttgtctcac cagagcctga agtccatgat attgaaagat ctgaagaaga tgatcagttc   1080
attatccttg catgtgatgg tatctgggat gttatgggaa atgaagagct ctgtgatttt   1140
gtaagatcca gacttgaagt cactgatgac cttgagaaag tttgcaatga agtagtcgac   1200
acctgtttgt ataagggaag tcgagacaac atgagtgtga ttttgatctg ttttccaaat   1260
gcacccaaag tatcgccaga agcagtgaag aaggaggcag agttggacaa gtacctggaa   1320
tgcagagtag aagaaatcat aaagaagcag ggggaaggcg tccccgactt agtccatgtg   1380
atgcgcacat tagcgagtga gaacatcccc agcctcccac caggggggtga attggcaagc   1440
aagaggaatg ttattgaagc cgtttacaat agactgaatc cttacaaaaa tgacgacact   1500
gactctacat caacagatga tatgtggaag ggcgagctca agcttgccaa catccagctg   1560
gtgcagtctg gtcctgagct gaagaagcct ggtgagactg tcaaaatctc ctgcaaggct   1620
tctgggtata ccttcactaa ctatggtatg aactgggtga agcaggctcc tggtaagggt   1680
ctgcgttgga tgggctggat taacacccac actggtgagc ctacttatgc tgatgacttc   1740
aagggacgtt ttgccttctc tctggaaact tctgccagca ctgcctatct ccagatcaac   1800
aacctcaaaa atgaggacac tgctacttac ttctgtacac gtcgtggtta cgactggtac   1860
ttcgatgtct ggggtgctgg gaccacggtg accgtgttct ccgggggagg tggcagcggg   1920
ggaggtggca gcggcggcgg gagctccgac atcaagatga cccagtctcc ttcttccatg   1980
tatgcttctc tgggtgagcg tgtcactatc acttgcaagg ccagccagga cattaatagc   2040
tatctgagct ggttccatca taaacctggg aaatctccta agaccctgat ctatcgtgct   2100
aaccgtctgg ttgatggggt cccttctcgt ttcagcggct ctggttctgg gcaagattat   2160
tctctcacca tcagcagcct ggactatgaa gatatgggta tttattattg tcaacagtat   2220
gatgagtctc cttggacttt cggtggtggc accaagctgg agatgaaaga acaaaagttg   2280
atctccgaag aggatttggg tcatcatcac catcaccatt aagcggccgc ataagctt     2338
```

<210> SEQ ID NO 127
<211> LENGTH: 773
<212> TYPE: PRT

<213> ORGANISM: Artificial Sequence
<220> FEATURE:
<223> OTHER INFORMATION: synthetic construct

<400> SEQUENCE: 127

```
Met Gly Ser Asp Lys Ile Ile His Leu Thr Asp Asp Ser Phe Asp Thr
1               5                   10                  15

Asp Val Leu Lys Ala Asp Gly Ala Ile Leu Val Asp Phe Trp Ala His
            20                  25                  30

Trp Cys Gly Pro Cys Lys Met Ile Ala Pro Ile Leu Asp Glu Ile Ala
        35                  40                  45

Asp Glu Tyr Gln Gly Lys Leu Thr Val Ala Lys Leu Asn Ile Asp His
    50                  55                  60

Asn Pro Gly Thr Ala Pro Lys Tyr Gly Ile Arg Gly Ile Pro Thr Leu
65                  70                  75                  80

Leu Leu Phe Lys Asn Gly Glu Val Ala Ala Thr Lys Val Gly Ala Leu
                85                  90                  95

Ser Lys Gly Gln Leu Lys Glu Phe Leu Asp Ala Asn Leu Ala Gly Ser
            100                 105                 110

Gly Ser Gly Asp Asp Asp Asp Lys Leu Gly Ile Asp Pro Phe Thr Met
        115                 120                 125

Gly Ala Phe Leu Asp Lys Pro Lys Met Glu Lys His Asn Ala Gln Gly
    130                 135                 140

Gln Gly Asn Gly Leu Arg Tyr Gly Leu Ser Ser Met Gln Gly Trp Arg
145                 150                 155                 160

Val Glu Met Glu Asp Ala His Thr Ala Val Ile Gly Leu Pro Ser Gly
                165                 170                 175

Leu Glu Ser Trp Ser Phe Phe Ala Val Tyr Asp Gly His Ala Gly Ser
            180                 185                 190

Gln Val Ala Lys Tyr Cys Cys Glu His Leu Leu Asp His Ile Thr Asn
        195                 200                 205

Asn Gln Asp Phe Lys Gly Ser Ala Gly Ala Pro Ser Val Glu Asn Val
    210                 215                 220

Lys Asn Gly Ile Arg Thr Gly Phe Leu Glu Ile Asp Glu His Met Arg
225                 230                 235                 240

Val Met Ser Glu Lys Lys His Gly Ala Asp Arg Ser Gly Ser Thr Ala
                245                 250                 255

Val Gly Val Leu Ile Ser Pro Gln His Thr Tyr Phe Ile Asn Cys Gly
            260                 265                 270

Asp Ser Arg Gly Leu Leu Cys Arg Asn Arg Lys Val His Phe Phe Thr
        275                 280                 285

Gln Asp His Lys Pro Ser Asn Pro Leu Glu Lys Glu Arg Ile Gln Asn
    290                 295                 300

Ala Gly Gly Ser Val Met Ile Gln Arg Val Asn Gly Ser Leu Ala Val
305                 310                 315                 320

Ser Arg Ala Leu Gly Asp Phe Asp Tyr Lys Cys Val His Gly Lys Gly
                325                 330                 335

Pro Thr Glu Gln Leu Val Ser Pro Glu Pro Glu Val His Asp Ile Glu
            340                 345                 350

Arg Ser Glu Glu Asp Asp Gln Phe Ile Ile Leu Ala Cys Asp Gly Ile
        355                 360                 365

Trp Asp Val Met Gly Asn Glu Glu Leu Cys Asp Phe Val Arg Ser Arg
    370                 375                 380

Leu Glu Val Thr Asp Asp Leu Glu Lys Val Cys Asn Glu Val Val Asp
```

-continued

```
385                 390                 395                 400

Thr Cys Leu Tyr Lys Gly Ser Arg Asp Asn Met Ser Val Ile Leu Ile
                405                 410                 415

Cys Phe Pro Asn Ala Pro Lys Val Ser Pro Glu Ala Val Lys Lys Glu
            420                 425                 430

Ala Glu Leu Asp Lys Tyr Leu Glu Cys Arg Val Glu Glu Ile Ile Lys
        435                 440                 445

Lys Gln Gly Glu Gly Val Pro Asp Leu Val His Val Met Arg Thr Leu
    450                 455                 460

Ala Ser Glu Asn Ile Pro Ser Leu Pro Pro Gly Gly Glu Leu Ala Ser
465                 470                 475                 480

Lys Arg Asn Val Ile Glu Ala Val Tyr Asn Arg Leu Asn Pro Tyr Lys
                485                 490                 495

Asn Asp Asp Thr Asp Ser Thr Ser Thr Asp Asp Met Trp Lys Gly Glu
            500                 505                 510

Leu Lys Leu Ala Asn Ile Gln Leu Val Gln Ser Gly Pro Glu Leu Lys
        515                 520                 525

Lys Pro Gly Glu Thr Val Lys Ile Ser Cys Lys Ala Ser Gly Tyr Thr
    530                 535                 540

Phe Thr Asn Tyr Gly Met Asn Trp Val Lys Gln Ala Pro Gly Lys Gly
545                 550                 555                 560

Leu Arg Trp Met Gly Trp Ile Asn Thr His Thr Gly Glu Pro Thr Tyr
                565                 570                 575

Ala Asp Asp Phe Lys Gly Arg Phe Ala Phe Ser Leu Glu Thr Ser Ala
            580                 585                 590

Ser Thr Ala Tyr Leu Gln Ile Asn Asn Leu Lys Asn Glu Asp Thr Ala
        595                 600                 605

Thr Tyr Phe Cys Thr Arg Arg Gly Tyr Asp Trp Tyr Phe Asp Val Trp
    610                 615                 620

Gly Ala Gly Thr Thr Val Thr Val Phe Ser Gly Gly Gly Gly Ser Gly
625                 630                 635                 640

Gly Gly Gly Ser Gly Gly Gly Ser Ser Asp Ile Lys Met Thr Gln Ser
                645                 650                 655

Pro Ser Ser Met Tyr Ala Ser Leu Gly Glu Arg Val Thr Ile Thr Cys
            660                 665                 670

Lys Ala Ser Gln Asp Ile Asn Ser Tyr Leu Ser Trp Phe His His Lys
        675                 680                 685

Pro Gly Lys Ser Pro Lys Thr Leu Ile Tyr Arg Ala Asn Arg Leu Val
    690                 695                 700

Asp Gly Val Pro Ser Arg Phe Ser Gly Ser Gly Ser Gly Gln Asp Tyr
705                 710                 715                 720

Ser Leu Thr Ile Ser Ser Leu Asp Tyr Glu Asp Met Gly Ile Tyr Tyr
                725                 730                 735

Cys Gln Gln Tyr Asp Glu Ser Pro Trp Thr Phe Gly Gly Gly Thr Lys
            740                 745                 750

Leu Glu Met Lys Glu Gln Lys Leu Ile Ser Glu Glu Asp Leu Gly His
        755                 760                 765

His His His His His
    770
```

METHODS, COMPOSITIONS, AND KITS FOR THE SELECTIVE ACTIVATION OF PROTOXINS THROUGH COMBINATORIAL TARGETING

CROSS-REFERENCE TO RELATED APPLICATIONS

This application is the U.S. National Stage of International Application No. PCT/US2007/16475, filed Jul. 20, 2007, which in turn, claims the benefit of U.S. Provisional Application No. 60/832,022, filed Jul. 20, 2006, each of which is incorporated by reference.

FIELD OF THE INVENTION

In general, the present invention relates to a therapeutic strategy for targeting cyotoxic or cytostatic agents to particular cell types while reducing systemic adverse effects. More specifically, the present invention involves the use of a therapeutic modality comprising two or more individually inactive components with independent targeting principles, which are activated through their specific interaction at the targeted cells. The invention also provides related methods and compositions.

BACKGROUND OF THE INVENTION

Selective killing of particular types of cells is desirable in a variety of clinical settings, including the treatment of cancer, which is usually manifested through growth and accumulation of malignant cells. An established treatment for cancer is chemotherapy, which kills tumor cells by inhibiting DNA synthesis or damaging DNA (Chabner and Roberts, Nat. Rev. Cancer 5:65 (2005)). However, such treatments often cause severe systemic toxicity due to nondiscriminatory killing of normal cells. Because many cancer chemotherapeutics exert their efficacy through selective destruction of proliferating cells, increased toxicities to normal tissues with high proliferation rates, such as bone marrow, gastrointestinal tract, and hair follicles have usually prevented their use in optimal doses. Such treatments often fail, resulting in drug resistance, disease relapse, and/or metastasis. To reduce systemic toxicity, different strategies have been explored to selectively target a particular cell population. Antibodies and other ligands that recognize tumor-associated antigens have been coupled with small molecule drugs or protein toxins, generating conjugates and fusion proteins that are often referred to as immunoconjugates and immunotoxins, respectively (Allen, Nat. Rev. Cancer 2:750 (2002)).

In addition to dose-limiting toxicities, another limitation for chemotherapy is its ineffectiveness for treatment of cancers that do not involve accelerated proliferation, but rather prolonged survival of malignant cells due to defective apoptosis (Kitada et al., Oncogene 21:3459 (2002)). For example, B cell chronic lymphocytic leukemia (B-CLL) is a disease characterized by slowly accumulating apoptosis-resistant neoplastic B cells, for which currently there is no cure (Munk and Reed, Leuk. Lymphoma 45:2365 (2004)).

Cancer stem cells (CSCs) are a small fraction of tumor cells that have a capacity for self-renewal and unlimited growth, and therefore are distinct from their progeny in their capacity to initiate cancers (Schulenburg et al., Cancer 107:2512 (2006)). Current cancer therapies do not target these cancer stem cells specifically, and it is hypothesized that the persistence of CSCs results in an ineradicable subset of cells that can give rise to progeny cells exhibiting drug resistance and/ or contributing to the formation of metastases. In those tumors which harbor CSCs it is highly attractive to be able to eliminate these cells. CSCs have been thought to possess many properties similar to that of normal stems cells, e.g., long life span, relative mitotic quiescence, and active DNA repair capacity, as well as resistance to apoptosis and to drug/toxins through high level expression of ATP-binding cassette drug transporters such as P-glycoprotein. Consequently, CSCs are thought to be difficult to target and destroy by conventional cancer therapies (Dean et al., Nat. Rev. Cancer 5:275 (2005)). Conversely, it is critically important to distinguish CSCs from normal stem cells because of the essential roles that normal stem cells play in the renewal of normal tissues.

To increase the selectivity of highly toxic anti-tumor agents, various attempts have been made to take advantage of specific features of the tumor microenvironment, such as the low pH, low oxygen tension, or increased density of tumor specific enzymes, that are not found in the vicinity of normal cells in well-perfused tissues. Environmentally sensitive antitumor agents have been developed that are hypothesized to exhibit increased toxicity in the solid tumor. For example "bioreductive prodrugs" are agents that can be activated to cytotoxic agents in the hypoxic environment of a solid tumor (Ahn and Brown, Front Biosci. May 1, 2007; 12:3483-501.) Similarly Kohchi et al. describe the synthesis of chemotherapeutic prodrugs that can be activated by membrane dipeptidases found in tumors (Bioorg Med Chem Lett. Apr. 15, 2007; 17(8):2241-5.) The use of selective antibody conjugated enzymes to alter the tumor microenvironment has also been explored by many groups. In the strategy known as antibody-directed enzyme prodrug therapy (ADEPT), enzymes conjugated to tumor-specific antibodies are intended to be delivered to the patient, followed by a chemotherapeutic agent that is inactive until subject to the action of the conjugated enzyme (see for example Bagshawe, Expert Rev Anticancer Ther. October 2006; 6(10):1421-31 or Rooseboome et al. Pharmacol Rev. March 2004; 56(1):53-102) To date the clinical advantages of these strategies remain undocumented and there remains a high interest in developing more selective and more potent agents that can show therapeutic utility.

SUMMARY OF THE INVENTION

In one aspect, the invention features a protoxin activator fusion protein including one or more cell-targeting moieties and a modification domain. In one embodiment of this aspect, the protoxin activator fusion protein can also include a natively activatable domain. In this embodiment, the modification domain is inactive prior to activation of the natively activatable domain. Desirably, the protoxin activator fusion protein is non-toxic to a target cell (e.g., the protoxin activator fusion protein has less than 10% of the cytotoxic or cytostatic activity of the combination of the protoxin activator fusion protein and the protoxin upon which the protoxin activator fusion protein acts).

In the above aspects, the modification domain can be a protease containing the catalytic domain of a human protease (desirably an exogenous human protease), or a non-human protease, including a viral protease (e.g., retroviral protease, a potyviral protease, a picornaviral protease, or a coronaviral protease). In a related aspect, the modification domain can be a phosphatase.

In another aspect, the invention features a protoxin fusion protein including one or more non-native cell-targeting moieties, a selectively modifiable activation domain, and a toxin domain (e.g., an activatable toxin domain). In this aspect, the modifiable activation domain may include a substrate for an exogenous enzyme.

In this aspect, the exogenous enzyme can be, for example, a protease or phosphatase. Examples of proteases include an exogenous human protease or a non-human (or non-mammalian) protease, including a viral protease (e.g., a retroviral protease, a potyviral protease, a picornaviral protease, or a coronaviral protease).

Also in this aspect, the activatable toxin domain can include an activatable pore forming toxin or an activatable enzymatic toxin. Examples of such domains include an AB toxin, a cyotoxic necrotizing factor toxin, a dermonecrotic toxin, and an activatable ADP-ribosylating toxin. Further examples include aerolysin, *Vibrio cholerae* exotoxin, *Pseudomonas* exotoxin, and diphtheria toxin.

In the above protoxin fusion proteins, the modifiable activation domain may further include a post-translational modification of a protease cleavage site. In this aspect, the modifiable activation domain can include a substrate for an enzyme (e.g., an exogenous enzyme).

In another aspect, the invention features a proactivator fusion protein including one or more non-native cell-targeting moieties, a selectively modifiable activation domain, and an activator domain. In this aspect, the modifiable activation domain may include a substrate for an enzyme (e.g., a protease or phosphatase). The modifiable activation domain may include a post-translational modification of a protease cleavage site or a substrate for an enzyme capable of removing a post-translational modification.

In this aspect, the protease may be an exogenous human protease, a non-human protease (e.g., a non-mammalian protease), or a viral protease.

Any of the above compositions can be formulated for administration to a subject (e.g., a human, dog, cat, monkey, horse, or rat) in order to kill a desired population of target cells.

In yet another aspect, the invention features a method of destroying or inhibiting a target cell (e.g., a human cell or a human cancer cell), by contacting the target cell with (i) a protoxin fusion protein including a first cell-targeting moiety, a selectively modifiable activation domain (e.g. a protease domain heterologous to the target cell), and a toxin domain; and (ii) a protoxin activator fusion protein including a second cell-targeting moiety and a modification domain. In this aspect, the first cell-targeting moiety of the protoxin fusion protein and the second cell-targeting moiety of the protoxin activator fusion protein each recognize and bind the target cell. Upon binding of both fusion proteins to the target cell, the modifiable activation moiety is selectively activated by the modification domain resulting in toxin activity; and thereby destroying or inhibiting the target cell. In a separate embodiment, absent the selective activation of the modifiable activation domain, the protoxin fusion protein is not natively activatable by the target cell or the environment surrounding the target cell, and wherein the selective activation of the modifiable activation domains renders the protoxin fusion protein natively activatable.

In a related aspect, the invention features a method of destroying or inhibiting a target cell in a subject, by administering to the subject (e.g., a human) (i) a protoxin fusion protein including a first cell-targeting moiety, a selectively modifiable activation domain, and a toxin domain; and (ii) a protoxin activator fusion protein including a second cell-targeting moiety, a natively activatable domain, and a modification domain. In this aspect the natively activatable domain becoming active upon administration of the protoxin activator fusion protein to the subject, whereby the activity of the natively activatable domain results in activation of the modification domain. In this aspect, the first cell-targeting domain of the protoxin fusion protein and the second cell-targeting domain of the protoxin activator fusion protein each recognize and bind the target cell and, upon binding of both fusion proteins to the target cell, the modifiable activation moiety is selectively activated by the modification domain resulting in toxin activity; and thereby destroying or inhibiting the target cell.

In the above-related aspects, the toxin domain can include an AB toxin, a cyotoxic necrotizing factor toxin, a dermonecrotic toxin, activatable pore forming toxin, activatable enzymatic toxin, and an activatable ADP-ribosylating toxin. Additional examples of toxin domains include *Vibrio Cholerae* exotoxin, aerolysin, a caspase, Ricin, Abrin, and Modeccin.

Also in the above-related aspects, the heterologous proteases can include an exogenous human protease (e.g., human granzyme B, including amino acids 21-247 of human granzyme B), a non-human protease, a non-mammalian protease, or a viral protease. In this aspect the selectively modifiable activation domain can be IEPD.

Also in the above-related aspects, the toxin domain can include Diphtheria toxin (e.g., amino-acids 1-389 of Diphtheria toxin), where the Diphtheria toxin furin cleavage site is replaced by a cleavage site of a protease heterologous to the target cell.

Also in the above-related aspects, the protoxin fusion protein can be contacted with the target cell prior to, simultaneous with, or after the protoxin activator fusion protein is contacted with the cell.

In yet another aspect, the invention features a kit having a (i) protoxin fusion protein and (ii) a protoxin activator fusion protein, and (iii) instructions for administering the two fusion proteins to a patient diagnosed with cancer.

In another related aspect, the invention features a kit having a (i) protoxin fusion protein and (ii) instructions for administering (i) with a protoxin activator fusion protein to a patient diagnosed with cancer.

In yet another related aspect, the invention features a kit having a (i) protoxin activator fusion protein and (ii) instructions for administering (i) with a protoxin fusion protein to a patient diagnosed with cancer.

In any of the forgoing aspects, the one or more of the fusion proteins can be modified by PEGylation, glycosylation, or both.

Also in any of the forgoing aspects, the one ore more cell-targeting domains or non-native cell-targeting domains can be a polypeptide, an antibody (e.g., an antibody, an antibody-like molecule, an antibody fragment, and a single antibody domain, including an anti-CD5 ScFv, anti-CD19 ScFv, and an anti-CD22 ScFv), a ligand for a receptor, a matrix fragment, a soluble receptor fragment, a cytokine, a soluable mediator, or an artificially diversified binding protein. The cell-targeting moiety may derived from a bacterial source (e.g., derived from a bacterial toxin). Alternatively, the cell targeting moiety can be a carbohydrate, a lipid, or a synthetic ligand.

Further, the cell-targeting domains or non-native cell targeting domains of the invention can recognize a cancer cell, a hematopoietic cell (e.g., a lymphocyte), or a nociceptive neuron.

As used herein in the specification, "a" or "an" may mean one or more; "another" may mean at least a second or more.

The term "polypeptide" or "peptide" as used herein refers to two or more amino acids linked by an amide bond between the carboxyl terminus of one amino acid and the amino terminus of another.

The term "amino acid" as used herein refers to a naturally occurring or unnatural alpha or beta amino acid, wherein such natural or unnatural amino acids may be optionally substituted by one to four substituents, such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

The term "modified" as used herein refers to a composition that has been operably changed from one or more predominant forms found naturally to an altered form by any of a variety of methods, including genetic alteration or chemical substitution or degradation and comprising addition, subtraction, or alteration of biological components or substituents such as amino acid or nucleic acid residues, as well as the addition, subtraction or modification of protein post-translational modifications such as, without limitation, glycan, lipid, phosphate, sulfate, methyl, acetyl, ADP-ribosyl, ubiquitinyl, sumoyl, neddoyl, hydroxyl, carboxyl, amino, or formyl. "Modified" also comprises alteration by chemical or enzymatic substitution or degradation to add, subtract, or alter chemical moieties to provide a form not found in the composition as it exists in its natural abundance comprising a proportion of greater than 10%, or greater than 1%, or greater than 0.1%. The term "modified" is not intended to refer to a composition that has been altered incidentally as a consequence of manufacturing, purification, storage, or expression in a novel host and for which such alteration does not operably change the character of the composition.

The terms "fusion protein," "protoxin fusion," "toxin fusion," "protoxin activator fusion" "protoxin proactivator fusion," or "proactivator activator fusion" as used herein refer to a protein that has a peptide component operably linked to at least one additional component and that differs from a natural protein in the composition and/or organization of its domains. The additional component can be peptide or non-peptide in nature. Additional peptide components can be derived by natural production or by chemical synthesis, and in the case of a peptide component that acts as an inhibitor moiety, a cell-targeting moiety, or a cleavage site, the additional peptide components need not be based on any natural template but may be selected for the desired purpose from an artificial scaffold or random sequence or by diversification of an existing template such that substantially all of the primary sequence similarity is lost but the functional attributes are preserved. Non-peptide additional components can include one or more functional chemical species. The chemical species may comprise a linker or a cleavage site, each optionally substituted with one or more linkers that may provide flexible attachment of the chemical species to a polypeptide or to another chemical species.

The terms "operably linked" or "operable linkage" encompass the joining of two or more peptide components covalently or noncovalently or both covalently and noncovalently as well as the joining of one or more peptide components with one or more chemical species covalently or noncovalently or both covalently and noncovalently, as well as the joining of two or more chemical species covalently. Among suitable form of covalent linkage for peptide components are direct translational fusion, in which a single polypeptide is formed upon translation of mRNA, or post-translational fusion, achieved by operable linkage through chemical or enzymatic means or by operable linkage through natural intermolecular reactions such as the formation of disulfide bonds. Operable linkage may be performed through chemical or enzymatic activation of various portions of a donor molecule to result in the attachment of the activated donor molecule to a recipient molecule. Following operable linkage two moieties may have additional linker species between them, or no additional species, or may have undergone covalent joining that results in the loss of atoms from one or more moieties, for example as may occur following enzymatically induced operable linkage.

The term "transglutaminase" refers to a protein that catalyzes the formation of a covalent bond between a free amine group (e.g., protein- or peptide-bound lysine, or substituted aminoalkane such as a substituted cadaverine) and the gamma-carboxamide group of protein- or peptide bound glutamine. Examples of this family of proteins are transglutaminases of many different origins, including thrombin, factor XIII, and tissue transglutaminase from human and animals. A preferred embodiment comprises the use of a microbial transglutaminase (Yokoyama et al., Appl. Microbiol. Biotechnol. 64(4):447-454 (2004)) to catalyze an acyl transfer reaction between a first moiety containing a glutamine residue (acyl donor), located within a preferred sequence such as LLQG (SEQ ID NO:1), and a second moiety containing a primary amine group (acyl acceptor). It is preferable that the reactive glutamine residue is solvent exposed and located in an unstructured, i.e. flexible, segment of the polypeptide.

The term "sortase" refers to a protein from gram-positive bacteria that can recognize a conserved carboxylic sorting motif and catalyze a transpeptidation reaction to anchor surface proteins to the cell wall envelope (Dramsi et al., Res. Microbiol. 156(3):289-297 (2005)). A preferred embodiment comprises the use of *Staphylococcus aureus* sortase A or B to catalyze a transpeptidation reaction between a first moiety that is tagged with LPXTG (SEQ ID NO:2) or NPQTN (SEQ ID NO:3) at or near C-terminus, respectively for sortase A and sortase B, and a second moiety containing the dipeptide GG or GK at the N-terminus, or a primary amine group.

The term "immobilized sortase" refers to purified and active sortase enzyme that has been absorbed covalently or non-covalently to a solid support such as agarose. The enzyme can be chemically or enzymatically immobilized as described herein to matrices bearing a chemical functional group such as a free sulfhydril or amine. Alternatively, the enzyme can be modified and then immobilized through some specific interaction. For example, the sortase enzyme could be biotinylated and then immobilized via an indirect interaction with immobilized streptavidin.

The term "intein" refers to a protein that undergoes autoreaction resulting in the formation of novel peptide or amide linkages. Intein-mediated ligation is a well established method to perform protein-protein conjugation (Xu and Evans Methods 24(3):257-277 (2001)) as well as protein-small molecule conjugation (Wood, et al., Bioconjug. Chem. 15(2):366-372 (2004)). A self-splicing intein may be added to the C-terminus of a protein to be conjugated, and treated with a conjugation partner that contains cysteine that can undergo acyl transfer followed by S—N acyl shift to provide a stable amide linkage.

The term "toxin" or "protoxin" as used herein refers to a protein comprising one or more moieties that have the latent (protoxin) or manifest (toxin) ability to inhibit cell growth (cytostasis) or to cause cell death (cytotoxicity). Examples of such toxins or protoxins include, without limitation, Diphtheria toxin, *Pseudomonas* exotoxin A, Shiga toxin, and Shiga-like toxin, anthrax lethal factor toxin, anthrax edema factor toxin, pore-forming toxins or protoxins such as Proaerolysin, hemolysins, pneumolysin, Cryl toxins, *Vibrio* pro-cytolysin, or listeriolysin; *Cholera* toxin, *Clostridium* septicum alpha-toxin, *Clostridial* neurotoxins including tetanus toxin and botulinum toxin; gelonin; nucleic acid modifying agents such as ribonuclease A, human pancreatic ribonuclease, angiogenin, and pierisin-1, apoptosis-inducing enzymes such as caspases, and ribosome-inactivating proteins (RIPs) such as Ricin, Abrin, and Modeccin. A protoxin is a toxin precursor that must undergo modification to become an active toxin. Preferable forms of protoxins for the present invention include those that can be activated by a protoxin activator.

The term "selectively modifiable activation moiety" refers to an unnatural or not naturally found moiety of a protoxin or protoxin activator that, upon modification, converts a protoxin to a toxin or natively activatable protoxin or activates a protoxin proactivator or modifies the protoxin proactivator so that it becomes natively activatable. When the selectively modifiable activation moiety is a component of the protoxin fusion protein, modification of the modifiable activation moiety by the protoxin activator can result directly in the protoxin becoming toxic to the target cell, or can result in the protoxin assuming a form that is natively activatable to become toxic to the target cell. When the selectively modifiable activation moiety is a component of the protoxin proactivator protein, modification of the modifiable activation moiety by the proactivator activator can result directly in the proactivator becoming activated to a form that can modify the protoxin, or can result in the proactivator assuming a form that is natively activatable to become a form that can modify the protoxin. Natively activatable protoxins or proactivators comprise, for example, modification of the modifiable activation moiety such that it is sensitive to endogenous components of the target cell, or the environment surrounding the target cells. (e.g., a target cell specific protease or a ubiquitous protease).

The term "cell targeting moiety" as used herein refers to one or more protein domains that can bind to one or more cell surface targets, and thus can direct protoxins, protoxin activators, protoxin proactivators or proactivator activators to those cells. Such cell targeting moieties include, among others, antibodies or antibody-like molecules such as monoclonal antibodies, polyclonal antibodies, antibody fragments, single antibody domains and related molecules, such as scFv, diabodies, engineered lipocalins, camelbodies, nanobodies and related structures. Also included are soluble mediators, cytokines, growth factors, soluble receptor fragments, matrix fragments, or other structures that are known to have cognate binding structures on the targeted cell. In addition, protein domains that have been selected by diversification of an invariant or polymorphic scaffold, for example, in the formation of binding principles from fibronectin, anticalins, titin and other structures, are also included. Cell targeting moieties can also include combinations of moieties (e.g., an scFv with a cytokine and an scFv with a second scFv).

The term "artificially diversified polypeptide binder" as used herein refers to a peptide or polypeptide comprising at least one domain that has been made to comprise multiple embodiments as a result of natural or synthetic mutation, including addition, deletion and substitution, so as to provide an ensemble of peptides or polypeptides from which a high affinity variant capable of binding to the desired cell surface target can be isolated. Such artificially diversified binders can comprise peptides, for example as selected by phage display, ribosome display, RNA display, yeast display, cell surface display or related methods, or polypeptides, similarly selected, and typically diversified in flexible loops of robust scaffolds so as to provide antibody variable region mimetics or related binding molecules.

The term "cell surface target" as used herein refers to any structure operably exposed on the surface of a cell, including transient exposure as for example may be the consequence of fusion of intracellular vesicles with the plasma membrane, and that can be specifically recognized by a cell targeting moiety. A cell surface target may include one or more optionally substituted polypeptide, carbohydrate, nucleic acid, sterol or lipid moieties, or combinations thereof, as well as modifications of polypeptides, carbohydrate, nucleic acid, sterol or lipid moieties separately or in combination. A cell surface target may comprise a combination of optionally substituted polypeptide and optionally substituted carbohydrate, an optionally substituted carbohydrate and optionally substituted lipid or other structures operably recognized by a cell-targeting moiety. A cell surface target may comprise one or more such optionally substituted polypeptides, carbohydrates, nucleic acid, sterol or lipids in complexes, for example heteromultimeric proteins, glycan-substituted heteromultimeric proteins, or other complexes, such as the complex of a peptide with a major histocompatibility complex antigen. A cell surface target may exist in a form operably linked to the target cell through another binding intermediary. A cell surface target may be created by some intervention to modify particular cells with an optionally substituted small molecule, polypeptide, carbohydrate, nucleic acid, sterol or lipid. For example a cell surface target may be created by the administration of a species that binds to a cell of interest and thereby affords a binding surface for any of the protoxins, protoxin activators, protoxin proactivators or proactivator activators of the present invention.

The term "targeted cell" or "target cell" is used herein to refer to any cell that expresses at least two cell surface targets, which are the intended targets of one or more protoxins or protoxin activators or protoxin proactivators or proactivator activators.

The phrase "non toxic to a target cell" is used herein to refer to compositions that, when contacted with a target cell (i.e., the target cell to which the cell-targeting moiety of the protoxin activator is directed) under the conditions of use described in the present invention, do not significantly destroy or inhibit the growth of a target cell, that is do not reduce the proportion of viable cells in a target population, or the proportion of dividing cells in a target population, or the total proportion of cells in a target population by more than 50%, or 10%, or 1% or 0.1% under the preferred conditions of use. This phrase does not include fusion proteins that, when administered to a subject or contacted with a target cell, become activated by an endogenous factor, rendering them toxic to a target cell. By "target population" is meant cells that express targets for the cell targeting moieties of the present invention.

The term "natively activatable" as used herein refers to a composition or state that can be converted from an inactive form to an active form by the action of natural factors or environmental variables on, in, or in the vicinity of a target cell. In one embodiment "natively activatable" refers to toxins or protoxin activators that, either as a consequence of modification on a modifiable activation moiety, or not, have the property of being converted from an inactive form to an active form as a result of natural factors on, in, or in the vicinity of a target cell. In one embodiment, the natively activatable protein possesses a cleavage site for a ubiquitously distributed protease such as a furin/kexin protease. In another embodiment, the natively activatable protein possesses a cleavage site for a target cell-specific protease, such as a tumor-enriched protease. In yet another embodiment, the natively activatable protein can be activated by low pH in, on, or in the vicinity of, a target cell. In another embodiment, the natively activatable protein possesses a post-translational modification that is removable by an enzyme found in, on, or in the vicinity of a target cell. In another embodiment the natively activatable protein posesses a modifiable activation moiety that can be modified by an enzyme found in, on, or in the vicinity of a target cell. Examples of such non-protease enzymes include phosphatases, nucleases, and glycohydrolases.

The phrase "substantially promote" as used herein means to improve the referenced action or activity by 50%, or by 100%, or by 300%, or by 700% or more.

The term "natively targetable toxin" as used herein refers to a toxins that possess native cell-targeting moieties that permit the toxin to bind to cell surface targets.

The term "bacterial toxin" refers to a toxin that is selected from a repertoire that comprises at least 339 members including natural variants, serotypes, isoforms, and allelic forms, of which at least 160 are from Gram-positive bacteria and 179 are from Gram-negative bacteria. Most are extracellular or cell-associated and the rest are intracellular. Many bacterial toxins are enzymes, including ADP-ribosyltransferases, phospholipases, adenylate cyclases, metalloproteases, RNA N-glycosidase, glucosyl transferases, deamidases, proteases, and deoxyribonucleases (Alouf and Popoff, Eds. "The Comprehensive Sourcebook of Bacterial Protein Toxins, 3$^{rd}$ Ed." Academic Press. 2006).

The term "intracellular bacterial toxin" refers to bacterial toxins that enter cells through various trafficking pathways and act on targets in the intracellular compartment of eukaryotic cells.

The term "activatable AB toxin" as used herein refers to any protein that comprises a cell-targeting and translocation domain (B domain) as well as a biologically active domain (A domain) and that requires the action of an endogenous target cell protease on an activation sequence to substantially promote their toxic effect. AB toxins have the capability to intoxicate target cells without requirement for accessory proteins or protein-delivery structures such as the type III secretion system of gram negative bacteria. AB toxins typically contain a site that is sensitive to the action of ubiquitous furin/kexin-like proteases, and must undergo cleavage to become activated. According to the present invention, the term "activatable AB toxin" is meant to include modified AB toxins in which the endogenous cell-targeting domain is replaced by one or more heterologous cell-targeting moiety or in which one or more heterologous cell-targeting moiety is added to an intact endogenous cell-targeting domain, and the activation sequence is replaced with a modifiable activation moiety that may be modified by an exogenous activator.

The term "ribosome-inactivating protein" or "RIP" as used herein refers to enzymes that trigger the catalytic inactivation of ribosomes and other substrates. Such toxins are present in a large number of plants and have been found also in fungi, algae and bacteria. RIPs are currently classified as belonging to one of two types: type 1, comprising a single polypeptide chain with enzymatic activity, and type 2, comprising two distinct polypeptide chains, an. A chain equivalent to the polypeptide of a type 1 RIPs and a B chain with lectin activity. Type 2 RIPs known in the art may be represented by the formulae A-B, $(A-B)_2$, $(A-B)_4$ and or by polymeric forms comprising multiple B chains per A chain. Linkage of the A chain with B chain is through a disulfide bond. The toxic activity of RIPs is due to translational inhibition, a consequence of the hydrolysis of an N-glycosidic bond of a specific adenine base in a highly conserved loop region of the 28 S rRNA of the eukaryotic ribosome (Girbes et al, Mini Rev. Med. Chem. 4(5):461-76 (2004)).

The term "ADP-ribosylating toxin" refers to enzymes that transfer the ADP ribose moiety of β-$NAD^+$ to a eukaryotic target protein. This process impairs essential functions of target cells, leading to cytostasis or cytotoxicity. Examples of bacterial ADP-ribosylating toxins include Diphtheria toxin, *Pseudomonas aeruginosa* exotoxin A, *P. aeruginosa* cytotoxic exotoxin S, pertussis toxin, cholera toxin, and heat-labile enterotoxins LT-I and LT-II from *E. coil* (Krueger and Barbieri, Clin. Microbiol. Rev. 8:34-47 (1995)). Examples of nonbacterial ADP-ribosylating toxins include the DNA ADP-ribosylating enzymes pierisin-1, pierisin-2, CARP-1 and the related toxins of the clams Ruditapes philippinarum and Corbicula japonica (Nakano et al. Proc Natl Acad Sci USA. 103(37):13652-7 (2006)). In addition, the application of in silico analyses have allowed the prediction of putative ADP-ribosylating toxins (Pallen et al. Trends Microbiol. 9:302-307 (2001).

ADP-ribosylating toxins of the present invention include those that can induce their own translocation across the target cell membranes, herein referred to as "autonomously acting ADP-ribosylating toxins," which have no requirement for a type III secretion system or similar structure expressed by bacteria to convey the translocation of the toxin into the host cytoplasm by an injection pilus or related structure. Such autonomously acting ADP-ribosylating toxins can be modified with respect to their activation moiety and cell-targeting moiety and produced by methods well known in the art.

The term "dermonecrotic toxin" or "DNT" as used herein refers to virulence factors known as *Bordetella* dermonecrotic toxin and described in *Bordetella* species such as, without limitation, *B. pertussis, B. parapertussis*, or *B. bronchoseptica*.

The term "cytotoxic necrotizing factor" or "CNF" or "CNF1" or "CNF2" or "CNFY" as used herein refers to any virulence factor known as a cytotoxic necrotizing factor and described in gram-negative species such as, without limitation, *Escherichia coli* or *Yersinia pseudotuberculosis*.

The term "activatable ADP-ribosylating toxin" or "activatable ADPRT" as used herein refers to toxins that are functionally conserved enzymes produced by a variety of species that share the ability to transfer the ADP ribose moiety of β-$NAD^+$ to a eukaryotic target protein and that require the action of an endogenous target cell protease on an activation sequence to substantially promote their toxic effect. This process impairs essential functions of target cells, leading to cytostasis or cytotoxicity. Examples of activatable bacterial ADPRTs are Diphtheria toxin, *Pseudomonas aeruginosa* exotoxin A, pertussis toxin, cholera toxin, and heat-labile enterotoxins LT-I and LT-II from *E. coli* (Krueger and Barbieri, Clin. Microbiol. Rev. 8:34-47 (1995); Holbourn et al. The FEBS J. 273:4579-4593(2006)). Examples of activatable nonbacterial ADP-ribosylating toxins include the DNA ADP-ribosylating enzymes from Cabbage butterfly, *Pieris Rapae* (Kanazawa et al Proc. Natl. Acad. Sci. 98:2226-2231 (2001)) and, by sequence homology, *Pieris brassicae* (Takamura-Enya et al., Biochem. Biophys. Res. Commun. 32:579-582 (2004)).

The term "activatable enzymatic toxin" refers to toxins that exert their toxic effect by enzymatic action and that require the action of an endogenous target cell protease on an activation sequence (e.g., a native or heterologous activation sequence) to substantially promote their toxic effect. The enzymatic action can be, for example and without limitation, an ADP-ribosyltransferase, a protease, a transglutaminase, a deamidase, a lipase, a phospholipase, a sphingomyelinase or a glycosyltransferase.

The term "pore-forming toxin" refers to toxins that create channels (pores) in the membrane of cells. The pore allows exchange of small molecules or ions between the extracellular and cytosolic space with an accompanying deleterious effect on the target cell incurred by such events as potassium efflux, sodium and calcium influx, the passage of essential small molecules through the membrane, cell lysis, or induced apoptosis. Some pore forming toxins are expressed as inactive toxins "protoxins" and become active only when modified in some manner at the cell surface while some pore-forming toxins require no modifications other than aggregation at the cell surface.

The term "activatable pore-forming toxins" refers to naturally occurring toxins that are expressed as inactive protoxins, and require an activation step in order for pore formation to occur. For example, many toxins require a furin cleavage event between a pro-domain and active pore-forming domain, essentially removing the pro-domain, in order for oligomerization and pore formation to occur.

Representative pore-forming toxins that require modification to become active include, *Aeromonas hydrophila* aerolysin, *Clostridium perfringens* ϵ-toxin, *Clostridium septicum* α-toxin, *Escherichia coil* prohaemolysin, hemolysins of *Vibrio cholerae*, and *B. pertussis* AC toxin (CyaA). The eukaryotic pore-forming protein, perforin, is inactive during the synthetic stage and activated by cleaving off a prodomain during maturation inside CTL and NK cells.

The term "reengineered activatable pore-forming toxin" or "RAPFT" refers to pore-forming toxins that have been modified to target only specific cell types in the context of combinatorial targeting. Typically, pore-forming agents are not specifically targeted towards diseased cells but act on healthy cells. Pore-forming agents often bind to common cellular markers such as carbohydrate groups, membrane proteins, glycosyl phosphatidylinositol anchors, and cholesterol. RAPFTs still retain the the cytolytic pore-forming activity, but the cell recognition and activation sites have been modified to specifically target cells possessing the targeted combination of surface markers.

The embodiments described herein comprise but are not limited to two types modifications. The first is a modification of the native cell-targeting portion of the toxin in order to target a specific class of cells using one or more optionally substituted cell-targeting moieties. The second modification introduces a modifiable activation moiety that can affect the pore-forming ability of the protoxin. When paired with a second targeting principle that can modify the modifiable activation moiety in a manner that activates the pore-forming toxin or converts it to a form that can be natively activated, the RAPFT can cause rapid loss of ion and small molecule gradients causing increased permeability, cytolysis, or apoptosis. These embodiments are unique with respect to previously reported pore-forming immunotoxins in that the activity that can convert the protoxin to the active toxin need not be endogenous to the target cell (Buckley, MacKenzie. 2006. Patent WO2007056867A1, Buckley. 2003. Patent WO03018611A2). An exogenous modifying moiety must be brought to the target cell via a second interaction between one or more cell-targeting moieties and one or more cell surface targets.

The term "translocation domain" of a toxin as used herein refers to an optional domain of a toxin (for example, a naturally occurring or modified toxin) that is necessary for translocation into the cytoplasm or a cytoplasm-contiguous compartment an active domain of a toxin. Prior to translocation the active domain may be located on the cell surface, or may have been conveyed from the cell surface into an intracellular space excluded from the cytoplasm, for example a vesicular compartment such as the endosome, lysosome, *Golgi*, or endoplasmic reticulum. Examples of such domains are the translocation domain of DT (residues 187-389) and the translocation domain of *Pseudomonas* exotoxin A (residues 253-364). Not all toxins contain translocation domains (e.g., pore forming toxins).

The term "Diphtheria toxin" or "DT" as used herein a protein selected from the family of protoxins, the prototype of which is a 535 amino acid polypeptide encoded by lysogenic bacteriophage of *Corynebacterium diphtheriae*. The prototypical diphtheria toxin contains three domains: a catalytic domain (residues 1-186), a translocation domain (residues 187-389), and a cell-targeting moiety (residues 390-535). The catalytic domain and the translocation domain are linked through a furin cleavage site (residues 190-195: RVRR↓SV (SEQ ID NO:4). Diphtheria toxin binds to a widely expressed growth factor expressed on the cell surface via its cell-targeting moiety and is internalized into the endosomal compartment of the cell, where furin cleaves at RVRR↓SV and the catalytic domain is translocated to the cytosol. In the cytosol, the catalytic domain catalyzes ADP-ribosylation of elongation factor 2 (EF-2), thereby inhibiting protein synthesis and inducing cytotoxicity or cytostasis.

The terms "modified DT," or "engineered DT" are used interchangeably herein to describe a recombinant or synthetic DT that is modified to confer amino acid sequence changes as compared with that of any natural DT, including extending, shortening, and replacing amino acid sequences within the original sequence. In particular, the terms may refer to DT proteins with sequence changes at the furin cleavage site to provide a modifiable activation moiety that is a recognition site for proteases other than furin, and/or DT fusion proteins with their native cell-targeting moiety removed or changed to other cell-targeting ligands. The term may also refer to DT with modifications such as glycosylation and PEGylation.

The term "DT fusion" as used herein refers to a fusion protein containing a DT or modified DT, for example, and a polypeptide that can bind to a targeted cell surface. The DT or modified DT is preferably located at the N-terminus of the fusion protein and the cell-targeting polypeptide attached to the C-terminus of the DT or modified DT. When discussed in the context of fusion toxins, "modified DT" may simply be referred to as "DT."

The term "*Pseudomonas* exotoxin A," "PE" or "PEA" as used herein refers to a protein selected from the family of protoxins, the prototype of which is an ADP-ribosyltransferase produced by *Pseudomonas aeruginosa*. The prototypical PEA is a 638 amino acid protein and has the following domain organization: an N-terminus receptor binding moiety (residues 1-252), a translocation domain (residues 253-364) and a C-terminal catalytic domain (residues 405-613). PEA is internalized into eukaryotic cells via receptor-mediated endocytosis and transported to ER, where it was cleaved at the furin cleavage site (residues 276-281: RQPR↓GW (SEQ ID NO:5)). The catalytic domain is translocated into the cytosol, where it catalyzes ADP-ribosylation of EF2, resulting in cell killing.

The term "modified PEA" or "engineered PEA" are used interchangeably herein to describe a recombinant or synthetic PEA protein that is modified to confer amino acid sequence changes compared with that of natural PEA, including extending, shortening, and replacing amino acid sequences within the original sequence, addition of linkers, of modifiable activation moieties or cell-targeting moieties. In particular, the terms may refer to PEA proteins with sequence changes at the furin cleavage site to provide a modifiable activation moiety that is capable of being modified by a protoxin activator, and/or PEA fusion proteins with their native cell-targeting moieties removed or changed to therapeutically desirable cell-targeting moieties. The term may also refer to PEA with amino acid covalent modifications or containing unnatural amino acids and or variants derived by optional substitution with other moieties such as to induce glycosylation and/or PEGylation. The term may also refer to PEA with alterations to the C terminus to increase specificity or activity, for example to the C-terminal endoplasmic reticulum retention sequence, more specifically to consensus versions of such sequence and variants.

The term "PEA fusion" as used herein refers to a fusion protein containing a PEA or modified PEA, for example, and a cell-targeting moiety that can bind to a targeted cell surface. The PEA or modified PEA is preferably located at the C-terminus of the fusion protein and the cell-targeting moiety is preferably attached to the N-terminus of the PEA or modified PE. When discussed in the context of fusion toxins, "modified PEA" may simply be referred to as "PEA".

The term "*Vibrio Cholerae* exotoxin A" or "VCE" as used herein refers to a protein selected from the family of protoxins, the prototype of which is a diphthamide-specific toxin encoded by the toxA gene of *Vibrio cholerae*. The prototypical VCE possesses a conserved DT-like ADP-ribosylation domain, and adopts an overall domain structure very similar to that of *Pseudomonas* exotoxin A (PEA), with moderate amino acid sequence identity (~33%). Like PEA, the VCE possesses an N-terminal cell-targeting moiety, followed by a translocation domain and a C-terminal ADP-ribosyltransferase. A putative furin cleavage site (RKPK↓DL (SEQ ID NO:6)) is located near the N-terminus of the putative translocation domain.

The term "modified VCE", "modified VCE", or "engineered VCE" are used interchangeably herein to describe a recombinant or synthetic VCE protein that is modified to confer amino acid sequence changes as compared with that of VCE, including extending, shortening, and replacing amino acid sequences within the original sequence. In particular, the terms may refer to VCE proteins with sequence changes at the furin cleavage site to provide a mutated sequence that is a recognition site for proteases other than furin, and/or VCE fusion proteins with their native cell-targeting moiety removed or changed to cell-targeting ligands. The term may also refer to VCE with amino acid covalent modifications such as glycosylation and PEGylation.

The term "VCE fusion" as used herein refers to a fusion protein containing a VCE or modified VCE, for example, and a polypeptide that can bind to a targeted cell surface. The VCE or modified VCE is preferably located at the C-terminus of the fusion protein and the cell-targeting polypeptide attached to the N-terminus of the VCE or modified VCE. When discussed in the context of fusion toxins, "modified VCE" may simply be referred to as "VCE."

The terms "proaerolysin" or "aerolysin" as used herein refers a protein selected from the family of bacterial pore forming toxin encoded by *Aeromonas* species, the prototype of which is a pore-forming toxin from *Aeromonas hydrophila*. The prototypical proaerolysin is composed of four domains: N-terminus Domain 1 (residues 1-82) that can bind to N-linked glycan of its glycosylated GPI-anchored receptors, Domain 2 (residues 83-178 & 311-398) that binds to the glycan core of the GPI-anchor, and non-contiguous Domains 3 and 4 (residues 179-470) that are involved in heptamerization and pore formation. Located at the C-terminus of Domain 4 is a propeptide that is sensitive to furin cleavage at its recognition sequence just upstream (residues 427-432 KVRR↓AR (SEQ ID NO:7)). Furin removal of the propeptide promotes formation of a ring-like heptamer structure, which insert into a lipid membrane to form a pore and cause cell death. Domain I is also known as the small lobe, and Domains 2, 3, and 4 as a whole are known as the large lobe.

The terms "modified aerolysin", or "engineered aerolysin" are used interchangeably herein to describe a recombinant or synthetic aerolysin protein that is modified to confer amino acid sequence changes as compared with that of aerolysin, including extending, shortening, and replacing amino acid sequences within the original sequence. In particular, the terms may refer to aerolysin proteins with sequence changes at the furin cleavage site to provide a mutated sequence that is a recognition site for proteases other than furin, and/or aerolysin fusion proteins with the native cell-targeting moiety 1 (small lobe) removed or changed to cell-targeting ligands. The term may also refer to aerolysin with amino acid covalent modifications such as glycosylation and PEGylation. The term may also refer to functional fragments of aerolysin.

The term "aerolysin fusion" as used herein refers to a fusion protein containing an aerolysin or modified aerolysin, for example, and a polypeptide that can bind to a targeted cell surface. The aerolysin or modified aerolysin is preferably located at the C-terminus of the fusion protein and the cell-targeting polypeptide attached to the N-terminus of the aerolysin or modified aerolysin. When discussed in the context of fusion toxins, "modified aerolysin" may simply be referred to as "aerolysin."

The term "protoxin activator" is meant to include a protein that modifies a protoxin such that the toxin becomes able to inhibit cell growth or to cause cell death.

The term "modification domain" as used herein refers to a polypeptide that selectively modifies a selectively modifiable activation domain on a target molecule. Such modification is meant to include modification of the polypeptide structure of the target molecule or the addition or removal of a chemical moiety. Examples of modification domains are polypeptides that contain protease activity, phosphatase activity, kinase activity, and other modifications as described herein.

The term "enzyme" as used herein refers to a catalyst that mediates a specific chemical modification (i.e., the addition, removal, or substitution of a chemical component) of a "substrate". The term enzyme is meant to include proteases, phophatases, kinases, or other chemical modifications as described herein.

The term "substrate" as used herein refers to the specific molecule, or portion of a molecules, that is recognized and chemically modified by a particular enzyme.

The term "protease" as used herein refers to compositions that possess proteolytic activity, and preferably those that can recognize and cleave certain peptide sequences specifically. In one particular embodiment, the specific recognition site is equal to or longer than that of the native furin cleavage sequence of four amino acids, thus providing activation stringency comparable to, or greater than, that of native toxins. A protease may be a native, engineered, or synthetic molecule having the desired proteolytic activity. Proteolytic specificity can be enhanced by genetic mutation, in vitro modification, or addition or subtraction of binding moieties that control activity.

The term "heterologous" as used herein refers to a composition or state that is not native or naturally found, for example, that may be achieved by replacing an existing natural composition or state with one that is derived from another source. Thus replacement of a naturally existing, for example, furin-sensitive, cleavage site with the cleavage site for another enzyme, constitutes the replacement of the native site with a heterologous site. Similarly the expression of a protein in an organism other than the organism in which that protein is naturally expressed constitutes a heterologous expression system and a heterologous protein.

The term "exogenous" as used herein refers to any protein that is not operably present in, on, or in the vicinity of, a targeted host cell. By operably present it is meant that the protein, if present, is not present in a form that allows it to act in the way that the therapeutically supplied protein is capable of acting. Examples of protoxin-activating moiety that may be present but not operably present include, for example, intracellular proteases, phosphatases or ubiquitin C-terminal hydrolases, which are not operably present because they are in a different compartment than the therapeutically supplied protease, phosphatase or ubiquitin C-terminal hydrolase (which when therapeutically supplied is either present on the surface of the cell or in a vesicular compartment topologically equivalent to the exterior of the cell) and cannot act on the protoxin in a way that would cause its activation. A protein may also be present but not operably present if it is found in such low quantities as not to significantly affect the rate of activation of the protoxin or protoxin proactivator, for example to provide a form not operably found in, on, or in the vicinity of, a targeted cell in a proportion of greater than 10%, or greater than 1%, or greater than 0.1% of the proportion that can be achieved by exogenous supply of a minimum therapeutically effective dose. As a further non-limiting example, replacement of a furin-sensitive site in a therapeutic protein with a site for a protease naturally found operably present on, in, or In the vicinity of a targeted host cell constitutes a heterologous replacement that can be acted on by an endogenous protease. Replacement of a furin-sensitive site in a therapeutic protein with a site for a protease not naturally found operably present in the vicinity of a targeted host cell constitutes a heterologous replacement that can be acted on by an exogenous protease.

The term "PEGylation" refers to covalent or noncovalent modifications of proteins with polyethylene glycol polymers of various sizes and geometries, such as linear, branched and dendrimer and may refer to block copolymers incorporating polyethylene glycol polymers or modified polymers with additional functionality, such as may be useful for the therapeutic action of a modified toxin. For example a polyethylene glycol moiety may join a modifiable activation sequence to an optional inhibitor sequence or may join one or more cell-targeting moieties to a modified toxin. Many strategies for PEGylating proteins in a manner that is consistent with retention of activity of the conjugated protein have been described in the art. These include conjugation to a free thiol such as a cysteine by alkylation or Michael addition, attachment to the N-terminus by acylation or reductive alkylation, attachment to the side chain amino groups of lysine residues, attachment to glutamine residues using transglutaminase, attachment to the N-terminus by native ligation or Staudinger ligation, or attachment to endogenous glycans, such as N-linked glycans or O-liked glycans. Numerous glycan addition strategies are known, including hydrazone formation with aldehydes generated by periodate oxidation, Staudinger ligation with glycan azides incorporated by metabolic labeling, and glycan substitution technology. Examples of noncovalent modification include the reaction of a high affinity ligand-substituted PEG with a protein domain binding such ligand, as for example the reaction of a biotin-substituted PEG moiety with a streptavidin or avidin fusion protein.

The term "PEG" refers to an optionally substituted polyethylene glycol moiety that may exist in various sizes and geometries, such as linear, branched or dendrimer and may refer to block copolymers or modified polymers with additional functionality, such as may be useful for the therapeutic action of a modified toxin. The number of optionally substituted or unsubstituted ethylene glycol moieties in a PEG moiety is at least two.

The term "PEGylated" refers to a composition that has undergone reversible or irreversible attachment of a PEG moiety.

The term "thiol-specific PEGylation" refers to attachment of an optionally substituted thiol-reactive PEG moiety to one or more thiol groups of a protein or protein substituent. The target of thiol-directed PEGylation can be a cysteine residue, or a thiol group introduced by chemical reaction, such as by the reaction of iminothiolane with lysine epsilon amino groups or N-terminal alpha amino or imino groups. A number of highly specific chemistries have been developed for thiol-directed PEGylation, i.e., PEG-ortho-pyridyl-disulfide, PEG-maleimide, PEG-vinylsulfone, and PEG-iodoacetamide. In addition to the type of thiol specific conjugation chemistry, commercially available thiol-reactive PEGs also vary in terms of size, linear or branched, and different end groups including hydroxyl, carboxylic acid, methoxy, or other alkoxy groups.

The term "carboxyl-reactive PEGylation" refers to the reaction of a protein or protein substituent with an optionally substituted PEG moiety capable of reacting with a carboxyl group, such as a glutamate or aspartate side chain or the C-terminus of a protein. The carboxyl groups of a protein can be subjected to carboxyl-reactive PEGylation using PEG-hydrazide when the carboxyl groups are activated by coupling agents such as N-(3-dimethylaminopropyl)-N'-ethylcarbodiimide hydrochloride (EDC) at acidic pH.

The term "amine-reactive PEGylation" refers to the reaction of a protein or protein substituent with an optionally substituted PEG moiety capable of reacting with an amine, such as a primary amine or a secondary amine. A common route for amine-reactive PEGylation of proteins is to use a PEG containing a functional group that reacts with lysines and/or an N-terminal amino or imino group (Roberts et al. Adv. Drug Deliv. Rev. 54(4):459-476 (2002)). Examples of amine-reactive PEGs include PEG dichlorotriazine, PEG tresylate, PEG succinimidyl carbonate, PEG benzotriazole carbonate, PEG p-nitrophenyl carbonate, PEG carbonylimidazole, PEG succinimidyl succinate, PEG propionaldehyde, PEG acetaldehyde, and PEG N-hydroxysuccinimide.

The term "N-terminal PEGylation" refers to attachment of an optionally substituted PEG moiety to the amino terminus of a protein. Preferred protein fusions or protein hybrids for N-terminal PEGylation have at least one N-terminal amino group. N-terminal PEGylation can be carried out by reaction of an amine-reactive PEG with a protein, or by reaction of a thioester-terminated PEG with an N-terminal cysteine in the reaction known as native chemical ligation, or by reaction of a hydrazide, hydrazine or hydroxylamine terminated PEG with an N terminal aldehyde formed by periodate oxidation of an N-terminal serine or threonine residue. Preferably, a PEG-protein conjugate contains 1-5 PEG substituents, and may be optimized experimentally. Multiple attachments may occur if the protein is exposed to PEGylation reagents in excess. Reaction conditions, including protein:PEG ratio, pH, and incubation time and temperature may be adjusted to limit the number and/or sites of the attachments. Modification at active site(s) within a fusion protein may be prevented by conducting PEGylation in the presence of a substrate, reversible inhibitor, or a binding protein. A fusion protein with the desired number of PEG substitutions may also be obtained by isolation from a more complex PEGylated fusion protein mixture using column chromatography fractionation.

The term "unnatural amino acid-reactive PEGylation" refers to the reaction of a protein or protein substituent with an optionally substituted PEG moiety capable of reacting with unnatural amino acids bearing reactive functional groups that may be introduced into a protein at certain sites utilizing modified tRNAs. In particular, para-azidophenylalanine and azidohomoalanine may be specifically incorporated into proteins by expression in yeast (Deiters et al. Bioorg. Med. Chem. Lett. 14(23):5743-5 (2004)) and in *E. coli* (Kiick et al. Proc. Natl. Acad. Sci. USA. 99(1):19-24 (2002)), respectively. These azide modified residues can selectively react with an alkyne derivatized PEG reagent to allow site specific PEGylation.

The term "glycan-reactive PEGylation" refers to the reaction of a protein or protein substituent with an optionally substituted PEG moiety capable of reacting with a glycosylated protein and the proteins containing N-terminus serine or threonine may be PEGylated followed by selective oxidation. Carbohydrate side chains may be oxidized enzymatically, or chemically using sodium periodate to generate reactive aldehyde groups. N-terminus serine or threonine may similarly undergo periodate oxidation to afford a glyoxylyl derivative. Both aldehyde and glyoxylyl groups can selectively react with PEG-hydrazine or PEG-amine.

The term "enzyme-catalyzed PEGylation" refers to the reaction of a protein or protein substituent with an optionally substituted PEG moiety through one or more enzyme catalyzed reactions. One such approach is to use transglutaminases, a family of proteins that catalyze the formation of a covalent bond between a free amine group and the gamma-carboxamide group of protein- or peptide-bound glutamine. Examples of this family of proteins include transglutaminases of many different origins, including thrombin, factor XIII, and tissue transglutaminase from human and animals. A preferred embodiment comprises the use of a microbial transglutaminase, to catalyze a conjugation reaction between a protein substrate containing a glutamine residue embedded within a peptide sequence of LLQG (SEQ ID NO:8) and a PEGylating reagent containing a primary amino group (Sato Adv. Drug Deliv. Rev. 54(4):487-504 (2002)). Another example is to use a sortase to induce the same conjugation. Accordingly a substituted PEG moiety is provided that is endowed with LPXTG (SEQ ID NO:2) or NPQTN (SEQ ID NO:3), respectively for sortase A and sortase B, and a second moiety such as a polypeptide containing the dipeptide GG or GK at the N-terminus, or a primary amine group, or the dipeptide GG or GK attached to a linker, and said sortase A or sortase B is then provided to accomplish the joining of the PEG moiety to the second moiety. Alternatively, said LPXTG (SEQ ID NO:2) or NPQTN (SEQ ID NO:3) can be provided at the C-terminus of a polypeptide to be modified and the PEG moiety can be supplied that is substituted with a GG or GK or a primary amine, and the sortase reaction performed.

The term "glycoPEGylation" refers to the reaction of a protein with an optionally substituted PEG moiety through enzymatic GalNAc glycosylation at specific serine and threonine residues in proteins expressed in a prokaryotic host, followed by enzymatic transfer of sialic acid conjugated PEG to the introduced GalNAc (Defrees et al. Glycobiology. 16(9):833-843 (2006)).

The term "intein-mediated PEGylation" refers to the reaction of a protein with an optionally substituted PEG moiety through an intein domain that may be attached to the C-terminus of the protein to be PEGylated, and is subsequently treated with a cysteine terminated PEG to afford PEGylated protein. Such intein-mediated protein conjugation reactions are promoted by the addition of thiophenol or triarboxylethylphosphine (Wood, et al., Bioconjug. Chem. 15(2):366-372 (2004)).

The term "reversible PEGylation" refers to the reaction of a protein or protein substituent with an optionally substituted PEG moiety through a linker that can be cleaved or eliminated, liberating the PEG moiety. Preferable forms of reversible PEGylation involve the use of linkers that are susceptible to various activities present at the cell surface or in intracellular compartments, and allow the useful prolongation of plasma half-life and/or reduction of immunogenicity while still permitting the internalized or cell-surface-bound protoxin or protoxin proactivator or proactivator activator to carry out their desired action without inhibition or impediment by the PEG substitution. Examples of reversible PEGylation linkers include linkers susceptible to the action of cathepsins, furin/kexin proteases, and lysosomal hydrolases such as neuraminidases, nucleases and glycol hydrolases.

The term "administering" and "co-administering" as used herein refer to the application of two or more fusion proteins, simultaneously and/or sequentially to an organism in need of treatment. The sequential order, time interval, and relative quantity of the application may be varied to achieve an optimized selective cytotoxic or cytostatic effect. It may be preferable to use one agent in large excess, or to use two agents in similar quantities. One agent may be applied significantly before the addition of the second agent, or they may be applied in closer intervals or at the same time. In addition administering and co-administering may include injection or delivery from more than one site, for example by injection into two different anatomical locations or by delivery by more than one modality, such as by aerosol and intravenous injection, or by intravenous and intramuscular injection.

The term "selective killing" is used herein to refer to the killing, destroying, or inhibiting of more cells of one particular population than another, e.g., by a margin of 99:1 or above, 95:5 or above, 90:10 or above, 85:15 or above, 80:20 or above, 75:25 or above, 70:30 or above, 65:35 or above, or 60:40 or above.

The term "destroying or inhibiting a target cell" is used herein to refer to reducing the rate of cellular division (cytostasis) or causing cell death (cytotoxicity) of a particular cell type (e.g., a cell expressing the desired cell surface targets). Cytostasis or cytotoxicity may be achieved, for example, by the induction of differentiation of the cell, apoptosis of the cell, death by necrosis of the cell, or impairment of the processes of cellular division.

The term "glycosylation" refers to covalent modifications of proteins with carbohydrates. Glycosylation can be achieved through N-glycosylation or O-glycosylation. An introduction of consensus N-linked glycosylation sites may be preferred when the proteins are to be produced in a mammalian cell line or cell lines that create a glycosylation pattern that are innocuous to humans.

Human "granzyme B" (GrB) is a member of the granzyme family of serine proteases known to be involved in apoptosis. Specifically, GrB has been shown to cleave only a limited number of natural substrates, e.g., pro-caspase-3 and Bid. It has been shown that GrB is an enzyme with high substrate sequence specificity because of the requirement for interactions with an extended peptide sequence in the substrate for efficient catalysis, i.e., a consensus recognition sequence of IEPD (SEQ ID NO:9). GrB is a single chain and single domain serine protease and is synthesized in a pro-form, which is activated by removal of the two amino acid propeptide by dipeptidyl peptidase I (DPPI (SEQ ID NO:10). In the present invention, the term GrB for example refers to the mature form, i.e., the form without the propeptide.

Human "Granzyme M" (GrM) is another member of the granzyme family of serine proteases that is specifically found in granules of natural killer cells and is implicated in the induction of target cell death. It has been shown that GrM is an enzyme with high substrate sequence specificity because of the requirement for interactions with at least four amino acids in the peptide substrate for efficient catalysis, i.e., a preferred recognition sequence of KVPL (SEQ ID NO:11).

The term "potyviral protease" refers to any of a variety of proteases encoded by members of the plant virus family Potyviridae and exhibiting high cleavage specificity. "Potyviral protease" encompasses the natural proteases as well as engineered variants generated by genetic mutation or chemical modification. The term "tobacco etch virus protease" or "TEV protease" refers to natural or engineered variants of a 27 kDa cysteine protease exhibiting stringent sequence specificity. It is widely used in biotechnology for removal of affinity tags of recombinant proteins. TEV protease recognizes a seven amino acid recognition sequence EXXYXQ↓S/G (SEQ ID NO:12), where X is any residue.

The term "picornaviral protease" refers to any of a variety of proteases encoded by members of the animal virus family Picornaviridae and exhibiting high cleavage specificity. "picornaviral protease" encompasses the natural proteases as well as engineered variants generated by genetic mutation or chemical or enzymatic modification. The term "human Rhinovirus 3C consensus protease" refers to a synthetic picornaviral protease that is created by choice of a consensus sequence derived from multiple examples of specific rhinoviral proteases.

The term "retroviral protease" refers to any of a variety of proteases encoded by members of the virus family Retroviridae. "HIV protease" encompasses the natural proteases as well as engineered variants generated by genetic mutation or chemical or enzymatic modification.

The term "coronaviral protease" refers to any of a variety of proteases encoded by members of the animal virus family Coronaviridae and exhibiting high cleavage specificity. "coronaviral protease" encompasses the natural proteases as well as engineered variants generated by genetic mutation or chemical or enzymatic modification. The term "SARS protease" refers to a coronaviral protease encoded by any of the members of the family Coronaviridae inducing the human syndrome SARS.

By "substantially identical" is meant a nucleic acid or amino acid sequence that, when optimally aligned, for example using the methods described below, share at least 60%, 65%, 70%, 75%, 80%, 85%, 90%, 95%, 96%, 97%, 98%, 99%, or 100% sequence identity with a second nucleic acid or amino acid sequence, e.g., a SAA sequence. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By the term "cancer cell" is meant a component of a cell population characterized by inappropriate accumulation in a tissue. This inappropriate accumulation may be the result of a genetic or epigenetic variation that occurs in one or more cells of the cell population. This genetic or epigenetic variation causes the cells of the cell population to grow faster, die slower, or differentiate slower than the surrounding, normal tissue. The term "cancer cell" as used herein also encompasses cells that support the growth or survival of a malignant cell. Such supporting cells may include fibroblasts, vascular or lymphatic endothelial cells, inflammatory cells or co-expanded nonneoplastic cells that favor the growth or survival of the malignant cell. The term "cancer cell" is meant to include cancers of hematopoietic, epithelial, endothelial, or solid tissue origin. The term "cancer cell" is also meant to include cancer stem cells. The cancer cells targeted by the fusion proteins of the invention include those set forth in Table 1.

A major limitation of all previously described approaches to targeting cells is their reliance on endogenous proteases, which may not be present on all tumors, or may be present in inadequate abundance, or may be shed in substantial quantities, leading to nonspecific activation of the toxin. The present invention differs from existing methods by its independence from endogenous tumor proteases. The combinatorial toxins of the present invention can be used on tumor cells or other undesired cells that have no appropriate endogenous protease activity.

BRIEF DESCRIPTION OF THE DRAWINGS

FIG. 6A, Jurkat or $CD19^+$ Jurkat cells were incubated with 1.0 nM GrB-anti-CD19 and various concentrations of DT-anti-CD5 as shown in the graph. FIG. 6B, Jurkat or $CD19^+$Jurkat cells were pre-treated with 1.0 nM GrB-anti-CD19 at 4° C. for 30 min. GrB-anti-CD19 was then washed away, replaced with a medium with or without 10 nM DT-anti-CD5, and incubated at 37° C. for 20 hours. For control experiments, cells were treated with 10 nM DT-anti-CD5±1.0 nM GrB-anti-CD19 and incubated at 37° C. for 20 hours.

FIG. 13A shows FACS analysis of purified PBMNC from a B-CLL patient with anti-CD5 and anti-CD19 antibodies. FIG. 13B shows 1.0 nM GrB-anti-CD19 alone was not toxic to either PBMNC or $CD5^+$Raji. FIG. 13C shows that anti-CD5-VCE selectively kill $CD5^+$Raji cells and a fraction of PBMNC only in the presence of GrB-anti-CD19.

FIG. 18A illustrates the effect of GrB-anti-CD19 (2 nM) on the cytotoxicity of anti-CD5-Aerolysin$_{GrB}$ towards $CD5^+$Raji and $CD19^+$Jurkat cells. FIG. 18B illustrates the effect of anti-CD5 ScFv domain for cytotoxicity, as well as the requirement of CD5 surface antigen for cytotoxicity of the combinatorial targeting reagents.

DETAILED DESCRIPTION OF THE INVENTION

Figure 1:
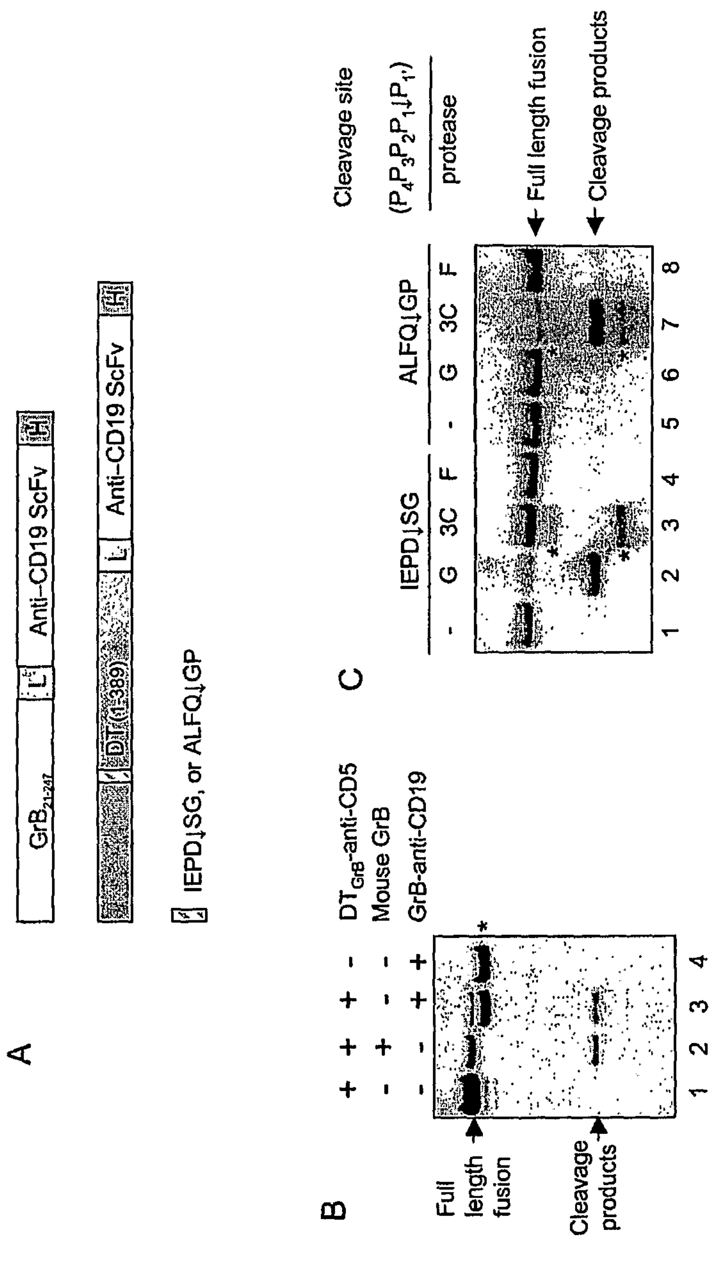
FIG. 1A is a schematic depiction of expression cassettes for GrB-anti-CD19 and DT-anti-CD5 fusion proteins. GrB-anti-CD19 was produced from 293ETN cells as secreted protein and an N-terminal FLAG tag (N), which was removed by enterokinase to yield an enzymatically active fusion protein. Mature human Granzyme B and anti-CD19 ScFv are linked via a $(G_4S)_3$ linker (L). A polyhistidine tag (H) is added to the C-terminus of anti-CD19 ScFv for detection and purification. Expression of DT-anti-CD5 fusion protein is driven by the AOX1 promoter. The fusion protein is constructed in a form to be secreted into culture media by attachment of the yeast α factor signal peptide at the N-terminus (S). The α factor signal peptide is removed by protease Kex2 during the process of secretion. The endogenous furin cleavage site of the DT gene is replaced by a granzyme B cleavage site (IEPD↓SG (SEQ ID NO:13)) or an HRV 3C protease cleavage site (ALFQ↓GP (SEQ ID NO:14)). The toxin moiety and anti-CD5 ScFv are linked via a $(G_4S_3)$ linker (L). A polyhistidine tag (H) is present at the C-terminus of anti-CD5 ScFv for detection and purification.
FIG. 1B is an electrophoretic gel showing cleavage of DT-anti-CD5 fusion protein by granzyme B proteolytic activity. Purified DT-anti-CD5 fusion protein with an additional N-terminal FLAG tag was incubated with either mouse granzyme B or purified GrB-anti-CD19 fusion protein at room temperature overnight. Reaction products were separated by 4-12% SDS-PAGE and immunoblotted with anti-FLAG antibody. Full length protein and cleaved products are indicated by arrows.
FIG. 1C is an electrophoretic gel showing cleavage of DT-anti-CD5 with a granzyme B site (lanes 1 to 4) or an HRV 3C protease site (lanes 5 to 8) with various proteases. Reactions were carried out at room temperature overnight. The products were detected with anti-His tag antibody. Full length protein and cleaved products are indicated by arrows. Asterisks in lanes 3 and 7 indicate unknown proteins present in the HRV 3C protease sample. G: granzyme B; 3C: HRV 3C protease; F: furin.

The present invention provides methods and compositions for treating various diseases through selective killing of targeted cells using a combinatorial targeting approach. In one aspect, the invention features protoxin fusion proteins containing a cell targeting moiety and, a modifiable activation moiety which is activated by an activation moiety not naturally operably found in, on, or in the vicinity of a target cell. These methods also include the combinatorial use of two or more therapeutic agents, at minimum comprising a protoxin and a protoxin activator, to target and destroy a specific cell population. Each agent contains at least one cell targeting moiety that binds to an independent cell surface target of the targeted cells. The protoxin contains a modifiable activation moiety that may be acted upon by the protoxin activator. The protoxin activator comprises an enzymatic activity that upon acting on the modifiable activation moiety converts, or allows to be converted, the protoxin to an active toxin or a natively activatable toxin. The targeted cells are then inhibited or destroyed by the activated toxin.

The present invention also provides for the use of multiple independent targeting events to further restrict or make selective the recognition of cells that are desired to be inhibited or destroyed, through the use of modified protoxins and protoxin activators. The protoxin activators of the invention may contain an activation domain. Prior to activation of the activation domain by a proactivator, these protoxin activators are inactive (i.e., they cannot activate the protoxin). Examples of such protoxin proactivators include proteases specific for the protoxin modifiable activation moiety that are presented in zymogen form, such that the cleavage of the zymogen to activate the proactivator requires a second protease. Examples of moieties provided by this invention include targeted granzyme B bearing an enterokinase-susceptible peptide blocking the active site, and targeted granzyme B bearing a furin-susceptible peptide blocking the active site. A suitable example of a protoxin proactivator, would be an enterokinase fusion protein that can be independently targeted to the target cell and act upon the granzyme B bearing an enterokinase-susceptible peptide blocking the active site.

The present invention also provides for the activation of protoxins or proactivators by modifiable activation moieties that allow said protoxins or proactivators to be activated or converted to a form that may be natively activated. Modifiable activation moieties may be polypeptide cleavage sequences, altered polypeptide cleavage sequences, or cleavable linkers, that restrict or make selective the activation of the protoxin or proactivator. Each modifiable activation moiety must have a corresponding activator capable of modifying such modifiable activation moiety in a way that causes the protoxins or proactivators bearing such modifiable activation moiety to be activated or converted to a form that may be natively activated.

I. Disease Indications and Targeted Cell Surface Markers

The protoxin/toxin activator combinations of the invention target and kill specific cell subsets while sparing closely related cells. The utility of the invention lies in the selective elimination of subsets of cells to achieve a desired therapeutic effect. In particular the combinations of the present invention can target cancer cells while sparing closely related normal cells, thereby providing a more specific and effective treatment for cancer. The cell-targeting moieties can target cell surface targets on the targeted cancer cells, or on targeted noncancer cells that are preferably eliminated to achieve a therapeutic benefit.

A. Cell Surface Targets

One or both of the cell-targeting moieties can target a cell surface target typical of a specific type of cells, for example, by recognizing lineage-specific markers found on subsets of cells and representing their natural origin, such as markers of the various organs of the body or specific cell types within such organs, or cells of the hematopoietic, nervous, or vascular systems. Alternatively one or both of the cell-targeting moieties can target cell surface markers aberrantly expressed on a diseased tissue, such as a cancer cell or a cell eliciting or effecting an autoimmune activity (e.g., B cells, T cells, dendritic cells, NK cells, neutrophils, leukocytes, macrophages, platelets, macrophages, myeloid cells, and granulocytes). One or both agents can target a cell surface marker that is aberrantly overexpressed by a cancer cell. This multi-agent targeting strategy is used to target neoplastic or undesired cells selectively without severe damage to normal or desired cells, thereby providing treatments for cancers including leukemias and lymphomas, such as chronic B cell leukemia, mantle cell lymphoma, Acute myelogenous leukemia, chronic myelogenous leukemia, acute lymphocytic leukemia, chronic lymphocytic leukemia, multiple myeloma, acute lymphoblastic leukemia, adult T-cell leukemia, Hodgkin's lymphoma, and non-Hodgkin's lymphoma; as well as solid tumors, including melanoma, colon cancer, breast cancer, prostate cancer, ovarian cancer, lung cancer, pancreatic cancer, kidney cancer, stomach cancer, liver cancer, bladder cancer, thyroid cancer, brain cancer, bone cancer, testicular cancer, uterus cancer, soft tissue tumors, nervous system tumors, and head and neck cancer.

The combination of protoxin and protoxin activator proteins can also be used to target non-cancerous cells, including autoreactive B or T cells, providing treatment for chronic inflammatory diseases including multiple sclerosis, rheumatoid arthritis, systemic lupus erythematosus, Sjogren's syndrome, scleroderma, primary biliary cirrhosis, Graves' disease, Hashimoto's thyroiditis, type 1 diabetes, pernicious anemia, myasthenia gravis, Reiter's syndrome, immune thrombocytopenia, celiac disease, inflammatory bowel disease, and asthma and atopic disorders.

In addition the combinatorial therapeutic composition can be used to ablate cells in the nervous system that are responsible for pathological or undesired activity, for example nociceptive neurons in the peripheral nervous system, or to treat sensory phantom sensation, or to control neuropathic pain, such as the pain caused by diabetic neuropathy or viral reactivation.

The combination can also target cells infected by viral, microbial, or parasitic pathogens that are difficult to eradicate, providing treatment for acquired syndromes such as HIV, HBV, HCV or papilloma virus infections, tuberculosis, malaria, dengue, Chagas' disease, trypanosomiasis, leishmaniasis, or Lyme disease.

Furthermore, the combination can target specific cell types including, without limitation, parenchymal cells of the major organs of the body, as well as adipocytes, endothelial cells, cells of the nervous system, pneumocytes, B cells or T cells of specific lineage, dendritic cells, NK cells, neutrophils, leukocytes, macrophages, platelets, macrophages, myeloid cells, granulocytes, adipocyte, and any other specific tissue cells.

The combination can further target cells that produce disease through benign proliferation, such as prostate cells in benign prostatic hypertrophy, or in various syndromes leading to hyperproliferation of normal tissues or the expansion of undesired cellular compartments as for example of adipocytes in obesity.

It will be well recognized by those skilled in the art that there are many cell surface targets that may be used for targeting the protoxins or protoxin activators of the invention to tumor tissues. For example, breast cancer cells may be targeted using overexpressed surface antigens such as claudin-3 (Soini, Hum. Pathol. 35:1531 (2004)), claudin-4 (Soini, Hum. Pathol. 35:1531 (2004)), MUC1 (Taylor-Papadimitriou et al., J. Mammary Gland Biol. Neoplasia 7:209 (2002)), EpCAM (Went et al., Hum. Pathol. 35:122 (2004)), CD24 (Kristiansen et al., J. Mol. Histol. 35:255 (2004)), and EphA2 (Ireton and Chen, Curr. Cancer Drug Targets 5:149 (2005); Zelinski et al., Cancer Res. 61:2301 (2001)), as well as HER2 (Stem, Exp. Cell Res. 284:89 (2003)), EGFR (Stern, Cell Res. 284:89 (2003)), CEA, and uPAR (Han et al., Oncol. Rep. 14:105 (2005)). Colorectal cancer may be targeted using upregulated surface antigens such as A33 (Sakamoto et al., Cancer Chemother. Pharmacol. 46:S27 (2000)), EpCAM (Went et al., Hum. Pathol. 35:122 (2004)), EphA2 (Ireton and Chen, Curr. Cancer Drug Targets 5:149 (2005); Kataoka et al., Cancer Sci. 95:136 (2004)), CEA (Hammarstrom, Semin. Cancer Biol. 9:67 (1999)), CSAp, EGFR (Wong, Clin. Ther. 27:684 (2005)), and EphB2 (Jubb et al., Clin. Cancer Res. 11:5181 (2005)). Non-small cell lung cancer may be targeted using EphA2 (Kinch et al., Clin. Cancer Res. 9:613 (2003)), CD24 (Kristiansen et al., Br. J. Cancer 88:231 (2003)), EpCAM (Went et al., Hum. Pathol. 35:122 (2004)), HER2 (Hirsch et al., Br. J. Cancer 86:1449 (2002)), and EGFR (Dacic et al., Am. J. Clin. Pathol. 125:860 (2006)). Mesothelin has been targeted by a PEA based immunotoxin for the treatment of NSCLC (Ho et al., Clin. Cancer Res. 13(5):1571 (2007)). Ovarian cancer may be targeted using upregulated claudin-3 (Morin, Cancer Res. 65:9603 (2005)), claudin-4 (ibid.), EpCAM (Went et al., Hum. Pathol. 35:122 (2004)), CD24 (Kristiansen et al., J. Mol. Histol. 35:255 (2004)), MUC1 (Feng et al., Jpn. J. Clin. Oncol. 32:525 (2002)), EphA2 (Ireton and Chen, Curr. Cancer Drug Targets 5:149 (2005)), B7-H4 (Simon et al., Cancer Res. 66:1570 (2006)), and mesothelin (Hassan et al., Appl. Immunohistochem Mol. Morphol. 13:243 (2005)), as well as CXCR4 (Jiang et al., Gynecol. Oncol. 20:20 (2006)) and MUC16/CA125. Pancreatic cancer may be targeted using overexpressed mesothelin (Rodriguez et al., World J. Surg. 29:297 (2005)), PSCA (Rodriguez et al., World J. Surg. 29:297 (2005)), CD24 (Kristiansen et al., J. Mol. Histol. 35:255 (2004)), HER2 (Garcea et al., Eur. J. Cancer 41:2213 (2005)), and EGFR (Garcea et al., Eur. J. Cancer 41:2213 (2005)). Prostate cancer may be targeted using PSMA (Kinoshita et al., World J. Surg. 30:628 (2006)), PSCA (Hari et al., J. Urol. 171:1117 (2004)), STEAP (Hubert et al., Proc. Natl. Acad. Sci. USA 96:14523 (1999)), and EphA2 (Ireton and Chen, Curr. Cancer Drug Targets 5:149 (2005)). EpCAM is also upregulated in prostate cancer and has been targeted for its antibody-based treatment (Oberneder et al., Eu. J. Cancer 42:2530 (2006)). The expression of activated leukocyte cell adhesion molecule (ALCAM, as known as CD166) is a prognostic and diagnostic marker for prostate cancer (Kristiansen et al., J. Pathol. 205:359 (2005)), colorectal cancer (Weichert et al., J. Clin. Pathol. 57:1160 (2004)), and melanoma (van Kempen et al. Am. J. Pathol. 156(3):769 (2000)). All cancers that have been treated with chemotherapy and developed multidrug resistance (MDR) can be targeted using the transmembrane transporter proteins involved, including P-glycoprotein (P-gp), the multidrug resistance associated protein (MRP1), the lung resistance protein (LRP), and the breast cancer resistance protein (BCRP) (Tan et al., Curr. Opin. Oncol. 12:450 (2000)). Any of the above markers may be targeted by the fusion proteins of the invention.

Significant advances have been made during the past decade in the identification of unique cell surface marker profiles of cancer stem cells from various cancers, distinguishing them from the bulk of corresponding tumor cells. For example, in acute myeloid leukemia (AML) it has been observed that the CD133+/CD38−. AML cells, which constitute a small fraction of CD34+/CD38− AML cells, are responsible for initiating human AML in animal models (Yin et al., Blood 12:5002 (1997)). In addition, CD133 has been recently determined as a cancer stem cell surface marker for several solid tumors as well, including brain tumor (Singh et al., Nature 432:395 (2004) and Bao et al., Nature 444:756 (2006)), colon cancer (O'Brien et al., Nature 445:106 (2007) and Ricci-Vitiani et al, Nature 445:111 (2007)), prostate cancer (Rizzo et al., Cell Prolif. 38:363 (2005)), and heptocellular carcinoma (Suetsugu et al., Biochem. Biophys. Res. Commun. 351:820 (2006) and Yin et al., Int. J. Cancer 120:1444 (2007)). In the case of colon cancer, the CD133+ tumorgenic cells were found to bind antibody Ber-EP4 (Ricci-Vitiani et al, Nature 445:111 (2007)), which recognizes the epithelial cell adhesion molecules (EpCAM), also known as ESA and CD326. More recently, it was reported that CD44+ may more accurately define the CSC population of colorectal cancer than CD133+ does, and the CSCs for colorectal cancer have been identified as $EpCAM^{high}$/CD44+/CD166+ (Dalerba et al., Proc. Natl. Acad. Sci. USA 104(24):10158 (2007)). Based on this information, EpCAM/CD133, EpCAM/CD44, EpCAM/CD166, and CD44/CD166 are possible combinations for combinatorial targeting of colon cancer CSCs. In addition to CD133, prostate cancer stem cells have been separately identified to be CD44+ (Gu et al. Cancer Res. 67:4807 (2007)), thus they may be targetable by using the CD44/CD133 pair of surface markers. Furthermore, CXCR4 was detected in the CD44+/CD133+ putative prostate CSCs, suggesting that the combination of CXCR4 with either CD44 or CD133 may provide useful pairs of targets for combinatorial targeting strategy. In other CSCs where the only currently known surface antigen is CD133, additional surface antigens may be identified through comprehensive antibody screening and then used to complement CD133 in a combinatorial targeting scheme. Likewise, tumorigenic cells for breast cancer have been identified as CD44+/CD24− subpopulation of breast cancer cells. Further analysis revealed that the CD44+/CD24−/EpCAM+ fraction has even higher tumorigenicity (Al-Hajj et al., Proc. Natl. Acad. Sci. USA 100:3983 (2003)). A combinatorial targeting approach using CD44+ and EpCAM+ as targeted surface markers could specifically kill these CSCs while leaving normal CD44+ leukocytes/erythrocytes and normal EpCAM+ epithelial cells unharmed. Another recent study has shown that pancreatic CSCs are CD44+/CD24+/EpCAM+ (Li et al., Cancer Res. 67:1030 (2007)). Consequently, the pancreatic CSCs may be targeted using a combination of CD44/CD24, CD44/EpCAM, or CD24/EpCAM.

B cell chronic lymphocytic leukemia (B-CLL) is characterized by slowly accumulating $CD5^+$ B cells (Guipaud et al., Lancet Oncol. 4:505 (2003)). CD5 is a cell surface protein found on normal T cells and a small fraction of B cells, known as B1 cells. Immunotoxins that target CD5 have shown high efficacy in killing T cells (Better et al., J. Biol. Chem. 270: 14951 (1995)). The combinatorial targeting strategy described in this invention makes it possible to use CD5 in combination with a B cell marker such as CD19, CD20, CD21, or CD22, thereby distinguishing B-CLL cells or other B cells in the B1 subset from T cells. The B1 subset is thought to give rise to low affinity polyreactive antibodies that are frequently found in the setting of autoimmune disorders, hence ablation of this population without significantly impairing the remainder of B cells could favorably impact the course of autoimmune disease without comprising the immune response of an individual to the same extent that ablation of all B cells would induce.

Examples of combinations of surface antigens that can be useful targets for the protoxin activator (e.g., protease) fusion and toxin fusion proteins of the invention are set forth in Table 1.

TABLE 1

| Antigen Pair | Antigen | Target Availability | Normal Distribution | Cancer Marker | Targeted Cells | Antibody Sequences | Antibody Immunotoxins | ScFv Immunotoxins |
|---|---|---|---|---|---|---|---|---|
| Targeted Cancer: Breast Cancer | | | | | | | | |
| [Claudin-3 & 4]/ [EpCAM] [Caludin-3 & 4]/ [EphA2] [Claudin-3 & 4]/ [MUC1] Etc. | Claudin-3 Claudin-4 | Abnova Corporation: H00001365-P01 (claudin-3) H00001364-Q01 (Claudin-4) | Tight junctions at the apical junctional complex in epithelial and endothelial cellular sheets; gut, lungs, and kidneys | Expression in 92-100% of breast carcinomas, claudin-3 and -4 overexpressed in 62% or 26% of breast carcinomas, respectively | Carcinoma cells | C-terminal domain of *C. perfringens* enterotoxin (C-CPE) can bind claudin-3 and -4 specifically | None | C-CPE-PEA fusion: J Pharmacol Exp Ther. 2006, 316(1): 255 |
| | MUC1 (Mucin 1) | Abnova Corporation: H00004582-Q01 (partial sequence) | Expressed at the luminal surface of most simple epithelial cells | Expression in ~90% breast carcinomas; correlates with lower grade tumors | Breast carcinoma cells | Cancer Immunol Immunother. 1999, 48(1): 29 Mol Immunol. 2005, 42(1): 55 U.S. Pat. No. 6,506,881 ($V_H$ & $V_L$) | Calicheamicin conjugate: Bioconjug Chem. 2005, 16(2): 346 & 354 | Ribonuclease fusion: Br J Cancer. 2004, 90(9): 1863 |
| | EpCAM (Epithelial cell adhesion molecule) | R&D Systems: 960-EP-050 | Expressed on the baso-lateral cell surface in most human simple epithelia | Upregulated in ~35% breast carcinomas, and by Taxol or Navelbine; IHC positive in 74% samples; >100-fold increase in mRNA; correlates w/ poor prognosis | Epithelial cells and breast cancer cells | Cancer Immunol Immunother. 2001, 50(1): 51. Cancer Res. 1999 59(22): 5758 ($V_H$ & $V_L$) | IL2 fusion: J Immunother. 2004, 27(3): 211 | β-glucuronidase fusion: Br J Cancer. 2002, 86(5): 811 |
| | EphA2 (Ephrin receptor A2) | R&D Systems: 3035-A2-100 | Weak or negative IHC in normal breast tissues | Overexpressed in ~92% of breast tumor cells (by IHC, diffused into cytoplasm); certain epitopes more exposed than in normal cells | Breast cancer cells | Methods. 2005, 36(1): 43 (B233: $V_H$ & $V_L$) Mol. Immunol 2007, 44: 3049 (EA2 & 47: $V_H$ & $V_L$) | None | None; Ephrin memetic peptides can be phage selected to bind EphA2 specifically |
| | HER2 | R&D Systems: 1129-ER-050 | Liver, kidneys, spleen, etc. Br J Pharmacol. 2004, 143(1): 99 | Upregulated in ~20-30% breast cancer; correlates w/ poor prognosis; only partially overlaps with EpCAM overexpression | HER2+ cells | Biochemistry 1994, 33: 5451 (dcFv $V_H$ & $V_L$) J Mol Biol. 1996, 255(1): 28 (scFv $V_H$ & $V_L$) | Herceptin-geldanamycin conjugate: Cancer Res. 2004 64(4): 1460 | PEA fusion: J Biol Chem. 1994, 269(28): 18327. Breast Cancer Res Treat. 2003, 82(3): 155. GrB fusion: Cell Death Differ. 2006 13(4): 576. |

TABLE 1-continued

| | | | | | | | | |
|---|---|---|---|---|---|---|---|---|
| | EGFR (Epidermal growth factor receptor) | R&D Systems: 1095-ER-002 | Kidneys, liver, intestine, bone, etc. J Nucl Med. 2006, 47(6): 1023 | Only positive in ~10% breast cancer tissue | EGFR+ cells | Int J Cancer. 1995, 60: 137 ($V_H$ & $V_L$) Jpn J Cancer Res. 2000 91(10): 1035 (vIII $V_H$ & $V_L$) | Taxol conjugate: Bioconjug Chem. 2003, 14(2): 302 Methotrexate conjugate: Mol Cancer Ther. 2006, 5(1): 52 | PEA fusion: Int J Cancer. 2000, 86(2): 269. GrB-TGFα fusion: Cell Death Differ. 2006 13(4): 576. |
| | CEA (Carcino-embryonic antigen) | ProSpec-Tany TechnoGene Ltd: PRO-287 GenScript Corporation: Z00239 | Limited tissue distribution: colon, neck, stomach, tohue esophagus, cervix, prostate | Overexpressed in gastro-intestinal, breast, & lung cancers; upregulated by drugs; also a serum marker; detected in only 19% of breast cancers | Breast carcinoma cells | Immunotech. 1996, 2: 181 ($V_H$ & $V_L$) U.S. Pat. No. 2,316,2709A1 U.S. Pat. No. 2,524,4333A1 | Doxorubicin conjugate: Cancer Immunol Immunother. 1994, 38(2): 92 | PEA fusion: Clin Cancer Res. 1998, 4(11): 2825 |
| | uPAR | R&D Systems: 807-UK-100; 807-UK-100/CF | Low expression in normal breast tissue | Overexpressed by leukemias and breast cancer | Breast carcinoma cells | U.S. Pat. No. 5,891,664 | None | None |
| | CD24 (aka HSA: Heat stable antagen) | Abnova Corporation: H00000934-P01 | B cells, granulocytes | High IHC staining in 85% breast cancer | Normal B cells and carcinoma cells | None | Ricin A conjugate: Int J Cancer. 1996, 66(4): 526 | None |
| | p-Glyco-protein (MDR1 gene product) | Abnova Corporation: H00005243-Q01 (partial sequence) | Low expression | Upregulated after chemotherapy | Drug-resistant cancer cells | MRK-16: Biol Chem. 1999, 274(39): 27371 C219: J Biol Chem. 1997, 272(47): 29784 | PEA conjugate: J Urol. 1993, 149(1): 174 | PEA fusion: Int J Cancer. 2001. 94(6): 864 |
| Targeted Cancer: Colorectal Cancer (CRC) | | | | | | | | |
| [A33]/ [EGFR-HER2] [A33]/ [CEA] [A33]/ [CD15] [EpCAM]/ [EGFR-HER2] Etc. | A33 | N/A Recombinant expression in insect cells: Biotechnol Prog. 2004, 20(4): 1273 | Epithelia of gastrointestinal tract (colonic, small intestinal, and duodenal epithelium) | Carcinomas of the colon and rectum; a glycoprotein found in 95% CRC cancers | Colorectal epithelial cells | J Biol Chem. 2000, 275(18): 13668 ($V_H$ & $V_L$) | Carboxypeptidase A fusion: Int J Oncol. 2004, 24(5): 1289 | Cytosine-deaminase fusion: Br J Cancer. 2003, 88(6): 937. Pichia expression of scFv: Protein Expr. Purif. 2004, 37: 18 |
| | EpCAM (Epithelial cell adhesion molecule) | R&D Systems: 960-EP-050 | Expressed on the baso-lateral cell surface in most human simple epithelia | Upregulated in colon epithelia; upregulated by Taxol and Navelbine; IHC positive in 100% tissue samples | Colorectal epithelial cells | Cancer Immunol Immunother. 2001, 50(1): 51 Cancer Res. 1999 59(22): 5758 ($V_H$ & $V_L$) | IL2 fusion: J Immunother. 2004, 27(3): 211 | β-glucuronidase fusion: Br J Cancer. 2002, 86(5): 811 |
| | EphA2 (Ephrin receptor A2) | R&D Systems: 3035-A2-100 | Some expression in normal colon tissue | Upregulated in 50-70% of primary colorectal tumor cells (IHC); downregulated in metastasis | Colon cancer cells | Methods. 2005, 36(1): 43 ($V_H$ & $V_L$) | None | None; Ephrin memetic peptides can be phage selected to bind EphA2 specifically |

TABLE 1-continued

| | | | | | | | |
|---|---|---|---|---|---|---|---|
| CEA (Carcino-embryonic antigen) | ProSpec-Tany TechnoGene Ltd: PRO-287 GenScript Corporation: Z00239 | Limited tissue distribution: colon, neck, stomach, tohue, esophagus, cervix, prostate | Overexpressed in many cancers, e.g., gastrointestinal, breast, and lung cancers. Can be further upregulated by drugs. Elevated levels in serum. | Colorectal epithelial cells Colorectal carcinoma cells | Immunotech. 1996, 2: 181 ($V_H$ & $V_L$) U.S. Pat. No. 2,316,2709A1 U.S. Pat. No. 2,524,4333A1 | Doxorubicin conjugate: Cancer Immunol Immunother. 1994, 38(2): 92 | PEA fusion: Clin Cancer Res. 1998, 4(11): 2825 |
| CD15 (Sialyl lewis X) | N/A | Neutrophils, eosinophiles, monocytes | Expressed in CRC, AML, and other cancers; correlated with EpCAM+ and CEA+ CRC cells: Proteomics. 2006, 6(6): 1791 | CEA+ and EpCAM+ CRC cells | Proc Natl Acad Sci USA. 1999, 96(12): 6953 (scFv $V_H$ & $V_L$) U.S. Pat. No. 5,723,583A2 | None | None |
| CSAp (Colon specific antigen-p) | N/A | Restricted to the intestines | Present in 60% colorectal carcinomas | Colorectal carcinoma cells | Cancer. 1997, 80(12 Suppl): 2667 | $^{131}$I conjugate: Cancer. 1994, 73(3 Suppl): 864- | None |
| CD166 (ALCAM: Activated leukocyte cell adhesion molecule) | R&D Systems: 656-AL | Broad distribution, in epithelia, neurons, lymphoid and myeloid cells, hematopoietic and mesenchymal stem cells | Strong cell surface expression in 31% colorectal carcinoma; mRNA overexpression in 86% prostate carcinoma | Epithelial cells and other normal cells, and colorectal cancer cells | Reported in J. Cell Biol. 2005, 118(7): 1515 & Liu B., et al. J. Mol. Med. 2007, but sequences were not disclosed | None | Saporin S6 conjugate: J. Cell Biol. 2005, 118(7): 1515 |
| EGFR (Epidermal growth factor receptor) | R&D Systems: 1095-ER-002 | Kidneys, liver, intestine, bone, etc. J Nucl Med. 2006, 47(6): 1023 | Upregulated in cancers of colon, breast, etc. Level correlates with tumor progression | EGFR+ cancer cells EGFRvIII mutant in PCa | Int J Cancer. 1995, 60: 137 ($V_H$ & $V_L$) Jpn J Cancer Res. 2000 91(10): 1035 (vIII $V_H$ & $V_L$ ) | Taxol conjugate: Bioconjug Chem. 2003, 14(2): 302 Methotrexate conjugate: Mol Cancer Ther. 2006, 5(1): 52 | PEA fusion: Int J Cancer. 2000, 86(2): 269. GrB-TGFα fusion: Cell Death Differ. 2006 13(4): 576. |
| HER2 | R&D Systems: 1129-ER-050 | Liver, kidneys, spleen, etc. Br J Pharmacol. 2004, 143(1): 99 | Upregulated in cancers of colon, breast, etc. | HER2+ cancer cells | Biochemistry 1994, 33: 5451 (dcFv $V_H$ & $V_L$) J Mol Biol. 1996, 255(1): 28 ($V_H$ & $V_L$ ) | Herceptin-geldanamycin conjugate: Cancer Res. 2004 64(4): 1460 | PEA fusion: J Biol Chem. 1994, 269(28): 18327. Breast Cancer Res Treat. 2003, 82(3): 155. GrB fusion: Cell Death Differ. 2006 13(4): 576. |
| EGFR-HER2 | See above | Advantages of bispecific targeting: not limited by a single marker and higher target density, neither is achievable by natural protease system, e.g., uPA/uPAR | | EGFR+ or HER2+ cancer cells | US20060099205 A1: Bispecific single chain FVs ($V_H$ & $V_L$) | None | Bivalent PEA fusion: Br J Cancer. 1996, 74(6): 853. Int J Cancer. 1996, 65(4): 538: |
| p-Glyco-protein (MDR1 gene | Abnova Corporation: H00005243-Q01 (partial | Low expression | Upregulated after chemotherapy | Drug-resistant cancer cells | MRK-16: Biol Chem. 1999, 274(39): 27371 C219: J Biol | PEA conjugate: J Urol. 1993, 149(1): 174 | PEA fusion: Int J Cancer. 2001, 94(6): 864 |

TABLE 1-continued

| | | | | | | | | |
|---|---|---|---|---|---|---|---|---|
| | product) | sequence) | | | | Chem. 1997, 272(47): 29784 | | |
| Targeted Cancer: Non-Small Cell Lung Cancer (NSCLC) | | | | | | | | |
| [EphA2]/ [CD24] [EphA2]/ [EpCAM] etc. | EphA2 (Ephrin receptor A2) | R&D Systems: 3035-A2-100 | | Overexpressed in ~74% (moderate-high) and detectable in 96% of NSCLC tissue (by IHC, in cytoplasm and membrane) | NSCLC cells | Methods. 2005, 36(1): 43 ($V_H$ & $V_L$) | None | None; Ephrin memetic peptides can be phage selected to bind EphA2 specifically |
| | CD24 (aka HSA: Heat stable antagen) | Abnova Corporation: H00000934-P01 (full length) | B cells, granulocytes | ~40-60% of cancer tissue samples with high IHC staining; higher expression level corresponds to poor prognosis | Normal B cells and carcinoma cells | None | Ricin A conjugate: Int J Cancer. 1996, 66(4): 526 | None |
| | EpCAM (Epithelial cell adhesion molecule) | R&D Systems: 960-EP-050 | Expressed on the baso-lateral cell surface in most human simple epithelia | IHC positive in 92% tissue samples | | Cancer Immunol Immunother. 2001, 50(1): 51 Cancer Res. 1999 59(22): 5758 ($V_H$ & $V_L$) | IL2 fusion: J Immunother. 2004, 27(3): 211 | β-glucuronidase fusion: Br J Cancer. 2002, 86(5): 811 |
| | HER2 | R&D Systems: 1129-ER-050 | Liver, kidneys, spleen, etc. Br J Pharmacol. 2004, 143(1): 99 | Overexpression in 16% and detection in 43% NSCLC tumor samples | HER2+ cancer cells | Biochemistry 1994, 33: 5451 (dcFv $V_H$ & $V_L$) J Mol Biol. 1996, 255(1): 28 ($V_H$ & $V_L$) | Herceptin-geldanamycin conjugate: Cancer Res. 2004 64(4): 1460 | PEA fusion: J Biol Chem. 1994, 269(28): 18327. Breast Cancer Res Treat. 2003, 82(3): 155. GrB fusion: Cell Death Differ. 2006 13(4): 576. |
| | EGFR | R&D Systems: 1095-ER-002 | Kidneys, liver, intestine, bone, etc. J Nucl Med. 2006, 47(6): 1023 | Detection in 11-26% NSCLC tissue samples | EGFR+ cancer cells | Int J Cancer. 1995, 60: 137 ($V_H$ & $V_L$) Jpn J Cancer Res. 2000 91(10): 1035 (vIII $V_H$ & $V_L$) | Taxol conjugate: Bioconjug Chem. 2003, 14(2): 302 Methotrexate conjugate: Mol Cancer Ther. 2006, 5(1): 52 | PEA fusion: Int J Cancer. 2000, 86(2): 269. GrB-TGFα fusion: Cell Death Differ. 2006 13(4): 576. |
| | EGFR-HER2 | See above | Advantages of bispecific targeting: not limited by a single marker and higher target density, neither is achievable by natural protease system, e.g., uPA/uPAR | | EGFR+ or HER2+ cancer cells | US20060099205 A1: Bispecific single chain FVs ($V_H$ & $V_L$) | None | Bivalent PEA fusion: Br J Cancer. 1996, 74(6): 853. Int J Cancer. 1996, 65(4): 538. |

TABLE 1-continued

| | | | | | | | | |
|---|---|---|---|---|---|---|---|---|
| | MSLN (Mesothelin) | Abnova Corporation: H00010232-Q01 (partial sequence) | Methothelial cells; Stomach, peritoneum, and ovary | Upregulated for >16-fold in pancreatic cancer tissues and cell lines; detected in 100% patients | Lung cancer cells, methothelial cells | J Mol Biol. 1998, 281(5): 917 ($V_H$ & $V_L$) Mol. Immunol. 1997, 34(1): 9 ($V_H$ & $V_L$) | PEA conjugate: J Immunother. 2000, 23(4): 473 | PEA fusion: J Mol Biol. 1998, 281(5): 917 |
| | p-Glyco-protein (MDR1 gene product) | Abnova Corporation: H00005243-Q01 (partial sequence) | Low expression | Upregulated after chemotherapy | Drug-resistant cancer cells | MRK-16: Biol Chem. 1999, 274(39): 27371 C219: J Biol Chem. 1997, 272(47): 29784 | PEA conjugate: J Urol. 1993, 149(1): 174 | PEA fusion: Int J Cancer. 2001, 94(6): 864 |
| Targeted Cancer: Ovarian Cancer | | | | | | | | |
| [Claudin-3 & 4]/ [EpCAM] [Claudin-3 & 4]/ [CD24] [MUC1]/ [EpCAM] [EpCAM]/ [CA125-B7-H4] Etc. | Claudin-3 Claudin-4 | Abnova Corporation: H00001365-P01 (claudin-3, full length) H00001364-Q01 (Claudin-4, full length) | Tight junctions at the apical junctional complex in epithelial and endothelial cellular sheets; gut, lungs, and kidneys; low claudin-3 in normal ovarian tissue | Claudin-3 upregulated in ovarian cancers for ~2-10 fold | Ovarian cancer cells | C-terminal domain of *C. perfringens* enterotoxin (C-CPE) can bind claudin-3 and -4 specifically | None | C-CPE-PEA fusion: J Pharmacol Exp Ther. 2006, 316(1): 255 |
| | EpCAM (Epithelial cell adhesion molecule) | R&D Systems: 960-EP-050 | Expressed on the baso-lateral cell surface in most human simple epithelia, very low exoression in normal ovaries | Highly upregulated in ovarian cancer, breast cancer, etc; in 100% ovarian cancer tissue samples | Epithelial cells and ovarian cancer cells | Cancer Immunol Immunother. 2001, 50(1): 51. Cancer Res. 1999 59(22): 5758 ($V_H$ & $V_L$) | IL2 fusion: J Immunother. 2004, 27(3): 211 | β-glucuronidase fusion: Br J Cancer. 2002, 86(5): 811 |
| | CD24 (aka HSA: Heat stable antagen) | Abnova Corporation: H00000934-P01 (full length) | B cells, granulocytes | Highly upregulated mRNA in ovarian cancer; IHC positive in 75-91% ovarian tumors | Normal B cells and carcinoma cells | N/A | Ricin A conjugate: Int J Cancer. 1996, 66(4): 526 | None |
| | MUC1 (mucin 1) | Abnova Corporation: H00004582-Q01 (partial sequence) | Expressed at the apical surface of most simple epithelia | IHC positive in 100% serous and 75% mucinous ovarian carcinomas; correlates with higer grade ovarian cancer | Ovarian cancer cells | Cancer Immunol Immunother. 1999, 48(1): 29 Mol Immunol. 2005, 42(1): 55 U.S. Pat. No. 6,506,881 ($V_H$ & $V_L$) | Calicheamicin conjugate: Bioconjug Chem. 2005, 16(2): 346 & 354 | Ribonuclease fusion: Br J Cancer. 2004, 90(9): 1863 |

TABLE 1-continued

| | | | | | | | | |
|---|---|---|---|---|---|---|---|---|
| | EphA2 (Ephrin receptor A2) | R&D Systems: 3035-A2-100 | Little to none IHC staining in normal ovarian tissue | Upregulated in ~76% of ovarianl tumor cells judging by IHC | Ovarian cancer cells | Methods. 2005, 36(1): 43 ($V_H$ & $V_L$) Mol. Immunol 2007, 44: 3049 (EA2 & 47: $V_H$ & $V_L$) | None | None; Ephrin memetic peptides can be phage selected to bind EphA2 specifically |
| | B7-H4 | Abnova Corporation: Mouse B7-H4 2154-B7-050 91% homologous to human extracellular sequence | Tightly controled in normal tissues: no detection | Highly upregulated in 85-100% ovarian cancer tissue; a serum marker that seems to complement CA125 | B7-H4+ T cells, dentric cells, B cells, macrophage, & ovarian cancer cells | N/A | None | None |
| | MSLN (Mesothelin) | Abnova Corporation: H00010232-Q01 (partial sequence) | Methothelial cells; Stomach, peritoneum, and ovary | Upregulated in ovarian cancer methothelioma; upregulated in ~70% serous cancer | Ovarian cancer cells, methothelial cells | J Mol Biol. 1998, 281(5): 917 ($V_H$ & $V_L$) Mol. Immunol. 1997, 34(1): 9 ($V_H$ & $V_L$) | PEA conjugate: J Immunother. 2000, 23(4): 473 | PEA fusion: J Mol Biol. 1998, 281(5): 917 |
| | CXCR4 | Abnova Corporation: H00007852-Q01 (partial sequence) | | Expressed in 60-70% ovarian cancers | Ovarian cancer cells | U.S. Pat. No. 7,005,503 | None | None |
| | MUC16/ CA125 | Sigma-Aldrich: O6008 (from human fluids) | Expressed on mesothelial cells in fetal coelomic epithelium and its derivatives in the fetus and the adult | Upregulated mRNA in 84% ovarian cancer tissues; but IHC equally positive for both normal & cancer tissues | | Hybridoma 1997, 16(1): 47 ($V_H$ & $V_L$) | Daunorubicin conjugate: Gynecol Oncol. 1989, 34(3): 305 | IL6 fusion: Cancer Res. 2003, 63(12): 3234 |
| | p-Glyco-protein (MDR1 gene product) | Abnova Corporation: H00005243-Q01 (partial sequence) | Low expression | Upregulated after chemotherapy | Drug-resistant cancer cells | MRK-16: Biol Chem. 1999, 274(39): 27371 C219: J Biol Chem. 1997, 272(47): 29784 | PEA conjugate: J Urol. 1993, 149(1): 174 | PEA fusion: Int J Cancer. 2001, 94(6): 864 |
| Targeted Cancer: Pancreatic Cancer | | | | | | | | |
| [MSLN]/ [PSCA] Etc. | MSLN (Mesothelin) | Abnova Corporation: H00010232-Q01 (partial sequence) | Methothelial cells; Stomach, peritoneum, and ovary | Upregulated for >16-fold-in pancreatic cancer tissues and cell lines; detected in 100% patients | Pancreatic cancer cells, methothelial cells | J Mol Biol. 1998, 281(5): 917 ($V_H$ & $V_L$) Mol. Immunol. 1997, 34(1): 9 ($V_H$ & $V_L$) | PEA conjugate: J Immunother. 2000, 23(4): 473 | PEA fusion: J Mol Biol. 1998, 281(5): 917 |

TABLE 1-continued

| | | | | | | | | |
|---|---|---|---|---|---|---|---|---|
| | PSCA (Prostate stem cell antigen) | Abnova Corporation: H00008000-Q01 (partial sequence) | Prostate:kidney = 4084:152 per 10k actin mRNA | Upregulated for >16-fold in Pancreatic cell lines | Pancreatic cancer cells | U.S. Pat. No. 06/824,780 | Maytansinoid conjugate: Cancer Res. 2002, 62: 2546 | None |
| | Claudin4 | Abnova Corporation: H00001364-Q01 (full length) | Lung, breast, colon | mRNA upregulated for >32-fold in pancreatic cell lines; no IHC observation | Pancreatic cancer cells | C-terminal domain of *C. perfringens* enterotoxin (C-CPE) can bind specifically | None | C-CPE-PEA fusion: J Pharmacol Exp Ther. 2006, 316(1): 255 |
| | CD24 | Abnova Corporation: H00000934-P01 (full length) | B cells, granulocytes | IHC positive in 72% pancreatic tumors | Normal B cells and carcinoma cells | N/A | Ricin A conjugate: Int J Cancer. 1996, 66(4): 526 | None |
| | EGFR | R&D Systems: 1095-ER-002 | Kidneys, liver, intestine, bone, etc. J Nucl Med. 2006, 47(6): 1023 | Upregulated in ~ 31-68% pancreatic cancer patients | EGFR+ cancer cells | Int J Cancer. 1995, 60: 137 ($V_H$ & $V_L$) Jpn J Cancer Res. 2000 91(10): 1035 (vIII $V_H$ & $V_L$) | Taxol conjugate: Bioconjug Chem. 2003, 14(2): 302 Methotrexate conjugate: Mol Cancer Ther. 2006, 5(1): 52 | PEA fusion: Int J Cancer. 2000, 86(2): 269. GrB-TGFα fusion: Cell Death Differ. 2006 13(4): 576. |
| | HER2 | R&D Systems: 1129-ER-050 | Liver, kidneys, spleen, etc. Br J Pharmacol. 2004, 143(1): 99 | Upregulated in ~ 28% pancreatic cancer patients | HER2+ cancer cells | Biochemistry 1994, 33: 5451 (dcFv $V_H$ & $V_L$) J Mol Biol. 1996, 255(1): 28 ($V_H$ & $V_L$) | Herceptin-geldanamycin conjugate: Cancer Res. 2004 64(4): 1460 | PEA fusion: J Biol Chem. 1994, 269(28): 18327. Breast Cancer Res Treat. 2003, 82(3): 155. GrB fusion: Cell Death Differ. 2006 13(4): 576. |
| | EGFR-HER2 | See above | Advantages of bispecific targeting: not limited by a single marker and higher target density, neither is achievable by natural protease system, e.g., uPA/uPAR | | EGFR+ or HER2+ cancer cells | US20060099205 A1: Bispecific single chain FVs ($V_H$ & $V_L$) | None | Bivalent PEA fusion: Br J Cancer. 1996, 74(6): 853. Int J Cancer. 1996, 65(4): 538. |
| | p-Glyco-protein (MDR1 gene product) | Abnova Corporation: H00005243-Q01 (partial sequence) | Low expression | Upregulated after chemotherapy | Drug-resistant cancer cells | MRK-16: Biol Chem. 1999, 274(39): 27371 C219: J Biol Chem. 1997, 272(47): 29784 | PEA conjugate: J Urol. 1993, 149(1): 174 | PEA fusion: Int J Cancer. 2001, 94(6): 864 |
| Targeted Cancer: Prostate Cancer (Pca) | | | | | | | | |
| [STEAP]/ [PSCA] [STEAP]/ [PSMA-PSCA] | PSMA (Prostate specific membrane antigen) | N/A Baculovirus expression described in Protein Expr | Prostate:liver:kidney = 174:14:11 per 10k actin mRNA; Strong IHC stain for 15/23 prostate, | Upregulated in higher grade Pca; Strong IHC stain for 8/19 prostate samples. | Prostate epithelial cells (apically localized) | U.S. Pat. No. 07/045,605 ($V_H$ & $V_L$) | (1) Maytansinoid conjugate: Cancer Res. 2004, 64: 7995 (2) Ricin A fusion: Prostate 2004, 61: 1 | PEA fusion: Cancer Immunol. Immunother. 2006 pub on web |

TABLE 1-continued

| | | | | | | | | |
|---|---|---|---|---|---|---|---|---|
| [PSMA/ PSCA] [PSCA/ EphA2] Etc. | | Purif. 2000, 19(1): 12 | 22/22 kidney, & 11/18 bladder samples | (Apical localization) | | | | |
| | PSCA (Prostate stem cell antigen) | Abnova Corporation: H00008000-Q01 (partial sequence) | Prostate:kidney = 4084:152 per 10k actin mRNA | Detected in 94% Pca samples and overexpressed in ~40% Pca; correlates with higher grade (Non-polarized distribution) | Prostate epithelial cells | U.S. Pat. No. 06/824,780 | Maytansinoid conjugate: Cancer Res. 2002, 62: 2546 | None |
| | STEAP 1 (Six-trans-membrane epithelial antigen of the prostate) | Abnova Corporation: H00026872-P01 (full length) | Predominantly in prostate; some presence in bladder; low level in colon, pancrease, stomach, and uterus | Overexpressed in prostate cancer (98%-positive in Pca, 97% positive in BPH) | Prostate epithelial cells | WO05113601A2 ($V_H$ & $V_L$) anti-STEAP-1 | None | None |
| | EphA2 (Ephrin receptor A2) | R&D Systems: 3035-A2-100 | No normal prostate IHC staining | Overexpressed in ~93% of prostate cance samples by IHC (diffused into cytoplasm) | Prostate cancer cells | Methods. 2005, 36(1): 43 ($V_H$ & $V_L$) Mol. Immunol 2007, 44: 3049 (EA2 & 47: $V_H$ & $V_L$) | None | None |
| | EpCAM (Epithelial cell adhesion molecule) | R&D Systems: 960-EP-050 | Expressed on the baso-lateral cell surface in most human simple epithelia, very low exoression in normal ovaries | Highly upregulated in ovarian cancer, breast cancer, etc; increased in prostate cancer | Epithelial cells and prostate cancer cells | Cancer Immunol Immunother. 2001, 50(1): 51. Cancer Res. 1999 59(22): 5758 ($V_H$ & $V_L$) | IL2 fusion: J Immunother. 2004, 27(3): 211 | β-glucuronidase fusion: Br J Cancer. 2002, 86(5): 811 |
| | ALCAM (Activated leukocyte cell adhesion molecule, CD166) | R&D Systems: 656-AL | Broad distribution, in epithelia, neurons, lymphoid and myeloid cells, hematopoietic and mesenchymal stem cells | Strong cell surface expression in 31% colorectal carcinoma; mRNA overexpression in 86% prostate carcinoma | Epithelial cells and other normal cells, and prostate cancer cells | Reported in J. Cell Biol. 2005, 118(7): 1515 & Liu B., et al. J. Mol. Med. 2007, but sequences were not disclosed | None | Saporin S6 conjugate: J. Cell Biol. 2005, 118(7): 1515 |
| | EGFR? | R&D Systems: 1095-ER-002 | Kidneys, liver, intestine, bone, etc. J Nucl Med. 2006, 47(6): 1023 | Upregulated in cancers of colon, breast, pancreas, etc. Mutated to EGFRvIII in Pca. | EGFR+ cancer cells | Int J Cancer. 1995, 60: 137 ($V_H$ & $V_L$) Jpn J Cancer Res. 2000 91(10): 1035 (vIII $V_H$ & $V_L$) | Taxol conjugate: Bioconjug Chem. 2003, 14(2): 302 Methotrexate conjugate: Mol Cancer Ther. 2006, 5(1): 52 | PEA fusion: Int J Cancer. 2000, 86(2): 269. GrB-TGFα fusion: Cell Death Differ. 2006 13(4): 576. |

TABLE 1-continued

| Antigen Pair | Antigen | Target Availability | Normal Distribution | Cancer Stem Cell Marker | Antibody Sequences | Antibody Immunotoxins | ScFc Immunotoxins |
|---|---|---|---|---|---|---|---|
| | HER2? | R&D Systems: 1129-ER-050 | Liver, kidneys, spleen, etc. Br J Pharmacol. 2004, 143(1): 99 | Upregulated in cancers of colon, breast, prostate, etc. | HER2+ cancer cells | Biochemistry 1994, 33: 5451 (dcFv $V_H$ & $V_L$) J Mol Biol. 1996, 255(1): 28 ($V_H$ & $V_L$) | Herceptin-geldanamycin conjugate: Cancer Res. 2004 64(4): 1460 | PEA fusion: J Biol Chem. 1994, 269(28): 18327. Breast Cancer Res Treat. 2003, 82(3): 155. GrB fusion: Cell Death Differ. 2006 13(4): 576. |
| | EGFR-HER2? | See above | Advantages of bispecific targeting: not limited by a single marker and higher target density, neither is achievable by natural protease system, e.g., uPA/uPAR | | EGFR+ or HER2+ cancer cells | US20060099205 A1: Bispecific single chain FVs ($V_H$ & $V_L$) | None | Bivalent PEA fusion: Br J Cancer. 1996, 74(6): 853. Int J Cancer. 1996, 65(4): 538. |
| | p-Glyco-protein (MDR1 gene product) | Abnova Corporation: H00005243-Q01 (partial sequence) | Low expression | Upregulated after chemotherapy | Drug-resistant cancer cells | MRK-16: Biol Chem. 1999, 274(39): 27371 C219: J Biol Chem. 1997, 272(47): 29784 | PEA conjugate: J Urol. 1993, 149(1): 174 | PEA fusion: Int J Cancer. 2001, 94(6): 864 |
| Targeting Cancer Causing Stem Cells | | | | | | | |
| [CD44]/[EpCAM] & [CD133]/[EpCAM] Etc. | CD44 | R&D Systems: 3660-CD-050 | Ubiquitously expressed on different cell surfaces | Metastatic cancer cells, breast cancer stem cells, prostate stem cells, colorectal cancer stem cells, pancreatic cancer stem cells, and head & neck cancer stem cells | WO05049082A2 (H90: $V_H$ & $V_L$) Int. J. Cancer 1996, 68: 232 (CD44v6 $V_H$ & $V_L$) Gyn. Oncol. 1997, 66: 209 (CD44v7v8 $V_H$ & $V_L$) | None | None |
| | EpCAM (aka ESA, Ber-EP4, B38.1, and CD326) | R&D Systems: 960-EP-050 | Expressed on the baso-lateral cell surface in most human simple epithelia | Breast cancer stem cells, colon cancer stem cells, colorectal cancer stem cells, and pancreatic cancer stem cells | Cancer Immunol Immunother. 2001, 50(1): 51 Cancer Res. 1999 59(22): 5758 ($V_H$ & $V_L$) | IL2 fusion: J Immunother. 2004, 27(3): 211 | β-glucuronidase fusion: Br J Cancer. 2002, 86(5): 811 |
| | CD133 (aka AC133 and prominin-1) | Abnova Corporation: H00008842-Q01 (partial sequence) | Hematopoitic stem cells | Colon cancer stem cells, glioblastoma stem cells, prostate cancer stem cells, and heptocellular carcinoma stem cells | N/A | None | None |

TABLE 1-continued

| | | | | | | |
|---|---|---|---|---|---|---|
| CD34 | Prospec: Pro-292 | Hematopoitic stem cells | AML stem cells | J. Immunonol. Methods 1997, 201: 223 ($V_H$ & $V_L$) | None | None |
| CD24 | Abnova Corporation: H00000934-P01 (full length) | B cells, granulocytes | Pancreatic cancer stem cells | N/A | Ricin A conjugate: Int J Cancer. 1996, 66(4): 526 | None |
| CXCR4 | Abnova Corporation: H00007852-Q01 (partial sequence) | Widely expressed in normal tissues | Prostate stem cells | U.S. Pat. No. 7,005,503 | None | None |
| CD166 (ALCAM: Activated leukocyte cell adhesion molecule) | R&D Systems: 656-AL | Broad-distribution, in epithelia, neurons, lymphoid and myeloid cells, hematopoietic and mesenchymal stem cells | Colorectal cancer stem cells | Reported in J. Cell Biol. 2005, 118(7): 1515 & Liu B., et al. J. Mol. Med. 2007, but sequences were not disclosed | None | Saporin S6 conjugate: J. Cell Biol. 2005, 118(7): 1515 |
| p-Glyco-protein (MDR1 gene product) | Abnova Corporation: H00005243-Q01 (partial sequence) | Low expression | Higher expression in stem cells | MRK-16: Biol Chem. 1999, 274(39): 27371 C219: J Biol Chem. 1997, 272(47): 29784 | PEA conjugate: J Urol. 1993, 149(1): 174 | PEA fusion: Int J Cancer. 2001, 94(6): 864 |

B. Cell Targeting Moieties

The invention features protoxin fusion proteins and protoxin activator fusion proteins each containing a cell-targeting moiety. Such cell targeting moieties of the invention include proteins derived from antibodies, antibody mimetics, ligands specific for certain receptors expressed on a target cell surface, carbohydrates, and peptides that specifically bind cell surface molecules.

One embodiment of the cell-targeting moiety is a protein that can specifically recognize a target on the cell surface. The most common form of target recognition by proteins is antibodies. One embodiment employs intact antibodies in all isotypes, such as IgG, IgD, IgM, IgA, and IgE. Alternatively, the cell-targeting moiety can be a fragment or reengineered version of a full length antibody such as Fabs, Fab', Fab2, or scFv fragments (Huston, et al. 1991. Methods Enzymol. 203: 46-88, Huston, et al. 1988. Proc Natl Acad Sci USA. 85:5879-83). In one embodiment the binding antibody is of human, murine, goat, rat, rabbit, or camel antibody origin. In another embodiment the binding antibody is a humanized version of animal antibodies in which the CDR regions have grafted onto a human antibody framework (Queen and Harold. 1996. U.S. Pat. No. 5,530,101). Human antibodies to human epitopes can be isolated from transgenic mice bearing human antibodies as well as from phage display libraries based on human antibodies (Kellermann and Green. 2002. Curr Opin Biotechnol. 13:593-7, Mendez, et al. 1997. Nat Genet. 15:146-56, Knappik, et al. 2000. J Mol Biol. 296:57-86). The binding moiety may also be molecules from the immune system that are structurally related to antibodies such as reengineered T-cell receptors, single chain T-cell receptors, CTLA-4, monomeric Vh or Vl domains (nanobodies), and camelized antibodies (Berry and Davies. 1992. J Chromatogr. 597:239-45, Martin, et al. 1997. Protein Eng. 10:607-14, Tanha, et al. 2001. J Biol Chem. 276:24774-80, Nuttall, et al. 1999. Proteins. 36:217-27). A further embodiment may contain diabodies which are genetic fusions of two single chain variable fragments that have specificity for two distinct epitopes on the same cell. As an example, a diabody with an anti-CD19 and anti-CD22 scFv can be fused to a protoxin or protoxin activator in order to increase the affinity to B-cell targets (Kipriyanov. 2003. Methods Mol Biol. 207:323-33).

In another embodiment the cell-targeting moiety can also be diversified proteins that act as antibody mimetics. Diversified proteins have portions of their native sequence replaced by sequences that can bind to heterologous targets. Diversified proteins may be superior to antibodies in terms of stability, production, and size. One example is fibronectin type III domain, which has been used previously to isolate affinity reagents to various targets (Lipovsek and Pluckthun. 2004. J Immunol Methods. 290:51-67, Lipovsek, et al. 2007. J Mol Biol. 368:1024-41, Lipovsek, Wagner, and Kuimelis. 2004. U.S. Patent 20050038229). Lipocalins have been used for molecular diversification and selection (Skerra et al. 2005. U.S. Patent 20060058510). Lipocalins are a class of proteins that bind to steroids and metabolites in the serum. Functional binders to CTLA4 and VEGF have been isolated using phage display techniques (Vogt and Skerra. 2004. Chembiochem. 5:191-9). C-type lectin domains, A-domains and ankyrin repeats provide frameworks that can be oligomerized in order to increase the binding surface of the scaffold (Mosavi, et al. 2004. Protein Sci. 13:1435-48). Other diversified proteins include but are not limited to human serum albumin, green fluorescent protein, PDZ domains, Kunitz domains, charybdotoxin, plant homeodomain, and β-lactamase. A comprehensive review of protein scaffolds is described in (Hosse, et al. 2006. Protein Sci. 15:14-27, Lipovsek. 2005.). Those skilled in the art understand that many diverse proteins or protein domains have the potential to be diversified and may be developed and used as affinity reagents, and these may serve as bell-binding moieties in the context of combinatorial targeting therapy.

In another embodiment, the cell-targeting moiety can be a naturally occurring ligand, adhesion molecule, or receptor for an epitope expressed on the cell surface. Compositions of the ligand may be a peptide, lectin, hormone, fatty acid, nucleic acid, or steroid. For example, human growth hormone could be used as a cell-targeting moiety for cells expressing human growth hormone receptor. Solubilized receptor ligands may also be used in cases in which the natural ligand is an integral membrane protein. Such solubilized integral membrane proteins are well-known in the art and are easily prepared by the formation of a functional fragment of a membrane protein by removing the transmembrane or membrane anchoring domains to afford a soluble active ligand; for example, soluble CD72 may be used as a ligand to localize engineered protoxins to CD5 containing cells. Another example is the binding of urokinase type plasminogen activator (uPA) to its receptor uPAR. It has been shown that the region of u-PA responsible for high affinity binding ($K_d \approx 0.5$ nM) to uPAR is entirely localized within the first 46 amino acids called N-terminal growth factor like domain (N-GFD) (Appella, et al. 1987. J Biol Chem. 262:4437-40). Avemers refer to multiple receptor binder domains that have been shuffled in order to increase the avidity and specificity to specific targets (Silverman, et al. 2005. Nat Biotechnol. 23:1556-61). These receptor binding domains and ligands may be genetically fused and produced as a contiguous polypeptide with the protoxin or protoxin activator or they can be isolated separately and then chemically or enzymatically attached. They may also be non-covalently associated with the protoxin or protoxin activator.

In a previously reported example, Denileukin difitox is a fusion protein of DT and human interleukin (IL)-2 (Fenton and Perry. 2005 Drugs 65:2405). Denileukin difitox targets any cells that express IL-2 receptor (IL2R), including the intended target CTCL cells. Acute hypersensitivity-type reactions, vascular leak syndrome, and loss of visual acuity have been reported as side effects. Because human normal non-hematopoietic cells of mesenchymal and neuroectodermal origin may express functional IL2R, some cytotoxic effects observed could be due to a direct interaction between IL-2 and non-hematopoietic tissues. In order to overcome this toxicity, the invention features, for example, addition of a T cell marker as a second targeting element, e.g., CD3.

If the moiety is a carbohydrate such as mannose, mannose 6-phosphate, galactose, N-acetylglucosamine, or sialyl-Lewis X, it can target the mannose receptor, mannose 6-phosphate receptor, asialoglycoprotein receptor, N-acetylglucosamine receptor, or E-selectin, respectively. If the moiety comprises a sialyl-Lewis X glycan operably linked to a tyrosine sulfated peptide or a sulfated carbohydrate it can target the P-selectin or L-selectin, respectively.

As another example, the binding partners may be from known interactions between different organisms, as in a pathogen host interaction. The C-terminal domain of the *Clostridium perfringens* enterotoxin (C-CPE) binds with high affinity and specificity to the mammalian claudin3/4 adhesion molecules. Although claudins are components of most cells tight junctions, they are not typically exposed on the apical surface. The C-CPE can be appended to the protoxin or activator in order to localize one of the components of the combinatorial targeting to cells overexpressing unengaged claudin3/4, a condition of many types of cancers (Takahashi, et al. 2005. J Control Release. 108:56-62, Ebihara, et al. 2006. J Pharmacol Exp Ther. 316:255-60).

An example of a peptide moiety is the use of angiotensin to localize complexes to cells expressing angiotensin receptor. In another embodiment, the binding peptide could be an unnatural peptide selected from a random sequence library. One group has identified a peptide using phage display, termed YSA, which can specifically recognize EphA2 receptors. EphA2 is overexpressed in many breast cancers (Koolpe, et al. 2005. J Biol Chem. 280:17301-11, Koolpe, et al. 2002. J Biol Chem. 277:46974-9). In order to increase binding affinity, peptides may be multimerized through sequential repeated fusions or attachment to a dendrimer which can then be attached to the protoxin or protoxin activator.

In another embodiment, the cell-targeting moiety can be a nucleic acid that consists of DNA, RNA, PNA or other analogs thereof. Nucleic acid aptamers have been identified to many protein targets and bind with very high affinity through a process of in vitro evolution (Gold. 1991. U.S. Pat. No. 5,475,096, Wilson and Szostak. 1999. Annu Rev Biochem. 68:611-47). RNA aptamers specific for PSMA were shown to specifically localized conjugated gelonin toxin to cells overexpressing PSMA (Chu, et al. 2006. Cancer Res. 66:5989-92). The nucleic acid can be chemically synthesized or biochemically transcribed and then modified to include an attachment group for conjugation to the reengineered toxin. The nucleic acid may be directly conjugated using common crosslinking reagents or enzymatically coupled by processes known in the art. The nucleic acid can also be non-covalently associated with the protoxin.

The cell-targeting moiety may be identified using a number of techniques described in the art. Typically natural hormones and peptide ligands can be identified through reported interactions in the reported literature. Additionally, antibody mimics and nucleic acid aptamers can be identified using selection technologies that can isolate rare binding molecules toward epitopes of interest, such as those expressed on cancer cells or other diseased states. These techniques include SELEX, phage display, bacterial display, yeast display, mRNA display, in vivo complementation, yeast two-hybrid system, and ribosome display (Roberts and Szostak. 1997. Proc Natl Acad Sci USA. 94:12297-302, Boder and Wittrup. 1997. Nat Biotechnol. 15:553-7, Ellington and Szostak. 1990. Nature. 346:818-22, Tuerk and MacDougal-Waugh. 1993. Gene. 137:33-9, Gyuris, et al. 1993. Cell. 75:791-803, Fields and Song. 1989. Nature. 340:245-6, Mattheakis, et al. 1994. Proc Natl Acad Sci USA. 91:9022-6). Antibodies can be generated using the aforementioned techniques or in a traditional fashion through immunizing animals and isolating the resultant antibodies or creating monoclonal antibodies from plasma cells.

The targets of the cell-targeting moieties may be protein receptors, carbohydrates, or lipids on or around the cell surface. Examples of polypeptide modifications known in the art that may advantageously comprise elements of a cell surface target include glycosylation, sulfation, phosphorylation, ADP-ribosylation, and ubiquitination. Examples of carbohydrate modifications that may be distinctive for a specific lineage of cells include sulfation, acetylation, dehydrogenation and dehydration. Examples of lipid modification include glycan substitution and sulfation. Examples of lipids that may be distinctive for a specific targeted cell include sphingolipids and their derivatives, such as gangliosides, globosides, ceramides and sulfatides, or lipid anchor moieties, such as the glycosyl phosphatidyl inositol-linked protein anchor.

The cell-targeting moiety may indirectly bind to the target cell through another binding intermediary that directly binds to a cell surface epitope, as long as the cell-targeting moiety acts to localize the reengineered toxin to the cell surface. The targets of these binding modules may be resident proteins, receptors, carbohydrates, lipids, cholesterol, and other modifications to the target cell surface. The cell-targeting moiety can be joined to the protoxin either through direct translational fusions if the DNA encoding both species is joined. Alternatively, chemical coupling methods and enzymatic crosslinking can also join the two components. The cell-targeting moiety may contain sequences not involved in the structure or binding of the agent, but involved with other processes such as attachment or interaction with the protoxin.

Disclosed herein are cell-targeting moieties that act to localize modified toxins to the surface of target cells. In one embodiment, the cell-targeting moiety is one or more single-chain variable fragment (scFv) that specifically recognize epitopes on cells of patients with B-CLL. In another embodiment the cell-targeting moiety is one or more single-chain variable fragments (scFv) that specifically recognize CD5. In yet another embodiment the cell-targeting moiety is a single-chain variable fragment (scFv) that specifically recognizes B-cell markers CD19 and CD22. In one embodiment the scFv fragment includes one or more specific tag sequence (LPETG (SEQ ID NO:38)) that is used for enzymatic crosslinking induced by SortaseA. The tag sequence may be at the N-terminus, C-terminus, or at an internal position. In another embodiment the LPETG (SEQ ID NO:38) tag sequence is located near or at the C-terminus. The expression and functional reproduction of scFv is well-known in the art. The scFvs were produced through the expression in the *E. coli* periplasm and refolded in vitro using reported procedures for obtaining functional scFvs.

Described herein are examples of using known natural receptor ligands as cell-targeting moieties. Specifically the N-terminal domain of u-PA was fused directly to a protoxin in order to specifically target u-PAR. Also, a toxin based on the fusion between the C-terminal domain of the *Clostridium perfringens* enterotoxin (C-CPE) and toxins are also described herein that can target claudin3/4.

II. Protoxins

The protoxins of the invention are designed to be independently targeted to one or more preselected cell surface targets. In order to become active, the protoxin of the invention must be modified by a corresponding protoxin activator. In one embodiment, the invention features a protoxin containing a cytotoxic domain of one toxin and a translocation domain of the same or another toxin, and an intervening peptide containing a proteolytic cleavage sequence specifically recognized by an exogenous protease. Alternatively, or additionally, the toxin activity may be blocked by a chemical or peptide moiety. In these cases, the toxin will only become active when this chemical or peptide moiety is modified by either an exogenous enzyme (i.e., a protoxin activator) or by an activator natively present at or around the target cell. The toxin or protoxin fusion can be derived from any toxin known in the art, including, without limitation, Diphtheria toxin, *Pseudomonas* exotoxin A, Shiga toxin, and Shiga-like toxin, anthrax toxin, pore-forming toxins or protoxins such as proaerolysin, hemolysins, pneumolysin, Cryl toxins, *Vibrio* pro-cytolysin, or listeriolysin; *Cholera* toxin, *Clostridium* septicum alpha-toxin, *Clostridial* neurotoxins including tetanus toxin and botulinum toxin; gelonin; nucleic acid modifying agents such as pierisin-1, and ribosome-inactivating proteins (RIPs) such as Ricin, Abrin, and Modeccin.

A. Proteolytic Toxins

Because many proteases play an essential role in targeted cell death in vivo, they may be used as the toxin moiety for the present invention. For example, granzymes are exogenous serine proteases that are released by cytoplasmic granules within cytotoxic T cells and natural killer cells, and can induce apoptosis within virus-infected cells, thus destroying them; caspases are cysteine proteases that play a central role in the initiation and execution phases of apoptosis; and a proteolytic cascade during complement activation results in complement-mediated inflammation, leukocyte migration, and phagocytosis of complement-opsonized particles and cells, which eventually leads to a direct lysis of target cells and microorganisms as a consequence of membrane-penetrating lesions.

Most proteases involved in apoptosis or complement activation exist in the form of a zymogen until activated. Zymogens are proenzymes that are inhibited by a propeptide component within its own sequence, usually located at the N-terminus. One embodiment of the present invention utilizes such a proteolytic zymogen as the protoxin moiety, and a second proteolytic activity acting as an activator of the zymogen. Both the protoxin and protease fusions comprise a cell-targeting domain, and optionally a translocation domain to assist endocytosis. Examples of the cleavage site within the first zymogen and the protease within the activator fusion include, but are not limited to, a protease cleavage site targeted by Factor Xa, IEGR↓; and a protease cleavage site targeted by Enterokinase, DDDDK↓ (SEQ ID NO:25). Additional examples include granzymes, caspases, elastase, kallikreins, the matrix metalloprotease (MMP) family, the plasminogen activator family, as well as fibroblast activation protein.

Granzymes

U.S. Pat. No. 7,101,977 discloses that a chimeric protein comprising an apoptosis-inducing factor such as granzyme B and a cell-specific targeting moiety can induce cell death. GrB induces cell death by cleaving caspases (especially caspase-3), which in turn activates caspase-activated DNase. This enzyme degrades DNA, irreversibly inactivating the apoptotic cell. GrB also cleaves the protein Bid, which recruits the protein Bax and Bak to change the membrane permeability of mitochondria, causing the release of cytochrome c (which activates caspase 9), Smac/Diablo and Omi/HtrA2 (which suppress the inhibitor of apoptosis proteins (IAPs)), among other proteins.

In a preferred embodiment of the present invention, an apoptosis-inducing granzyme (e.g., granzyme B) may be constructed as the cytotoxic part of a protoxin. For example, in constructing a GrB-based protoxin, a proteolytic substrate sequence may be placed in the immediate front of granzyme B sequence, resulting in a GrB fusion that is activatable by a protease fusion that can specifically cleave the proteolytic substrate sequence.

Caspases

There are two types of apoptotic caspases: initiator (apical) caspases and effector (executioner) caspases. Initiator caspases (e.g. caspase-2, -8, -9 and -10) cleave inactive pro-forms of effector caspases, thereby activating them. Effector caspases (e.g. caspase-3, -6, -7) in turn cleave other protein substrates within the cell resulting in the apoptotic process. In vivo the initiation of this cascade reaction is regulated by caspase inhibitors. The caspase cascade can be activated by Granzyme B, released by cytotoxic T lymphocytes, which activates caspase-3 and -7; by death receptors (like FAS, TRAIL receptors and TNF receptor) which activate caspase-8 and -10; and by the apoptosome, regulated by cytochrome c and the Bcl-2 family, which activates caspase-9.

Because caspases are critically involved in the later stages of apoptosis regardless of the initial stimulus of apoptosis, the invention features the direct use of these activities, particularly the effector caspases, to initiate an apoptotic cascade independent of upstream cellular events. For example, in constructing a caspase-6 based protoxin, a procaspase-6 is used. The procaspase-6 comprises the mature caspase-6 sequence, an inhibitory sequence, and a proteolytic substrate sequence placed in between. The procaspase fusion is selectively activated by a protease fusion that can specifically cleave the proteolytic substrate sequence.

Proteases of the Complement System

The complement system is a biochemical cascade that helps clear pathogens from an organism. The complement system includes of a number of small proteins found in the blood, which work together to kill target cells by disrupting the target cell's plasma membrane. Over 20 proteins and protein fragments make up the complement system, including serum proteins, serosal proteins, and cell membrane receptors. The complement system is not adaptable and does not change over the course of an individual's lifetime, and, as such, it belongs to the innate immune system. However, it can be recruited and brought into action by the adaptive immune system.

There are three distinct pathways of complement activation—the classical pathway, the lectin pathway, and the alternative pathway. Complement activation proceeds in a sequential fashion, through the proteolytic cleavage of a series of proteins, and leads to the generation of active products that mediate various biological activities through their interaction with specific cellular receptors and other serum proteins. During the course of this cascade, a number of biological processes are initiated by the various complement components, which eventually lead to direct lysis of target cells. C1-C9 and factors B and D are the reacting components of the complement system. One preferred embodiment of the present invention involves the use of a protease involved in the complement activation cascade (e.g., proteolytic component of the C1-C9 and Factors B and D, preferably C3) as the toxin moiety within the protoxin fusion.

B. Bacterial Toxins

Examples of bacterial toxins that may be used in the protoxin fusion proteins of the invention are set forth below.

Pore Forming Toxins

In another aspect, the invention features a protoxin fusion protein containing a pore-forming toxin domain. These toxins bind to cellular membranes and upon an activation trigger, create channels (pores) in which essential ions and metabolites may diffuse. Representative pore-forming toxins that require modification to become active include but are not limited to *Aeromonas hydrophila* aerolysin, *Clostridium perfringens* ε-toxin, *Clostridium septicum* α-toxin, *Escherichia coli* prohaemolysin, hemolysins of *Vibrio cholerae*, and *B. pertussis* AC toxin (CyaA).

In the reengineered activatable pore-forming toxins "RAPFTs" of the invention, the trigger to convert the toxin from an inactive form to an active form can be altered from the native mechanism to an alternative mechanism. A preferred manner of alteration is to replace a native proteolytic activation site with an heterologous proteolytic site that is not normally operationally resident on the target cell. The heterologous proteolytic site may be added to or replace the original activation site, while either mutating or preserving the original residues as long as the endogenous activation does not occur prior to activation by the exogenous protease. Alternative sequences or chemical compositions that may be used in the RAPFT include substrates for proteases from the activating moiety other than those previously reported. These alternative substrates may be used as the modified proteolytic site in the RAPFT.

Other modifications to the activation site include but are not limited to phosphorylation, glycosylation, lipoylation, biotinylation, acetylation, ubiquitination, sumoylation, and esterification. These modifications must be paired with activating groups that can reverse, remove, or further alter these modifications in order to switch the RAPFT from the inactive to the active state or to a natively activatable state when used in a therapeutic context. In another embodiment, RAPFTs can possess a modification to a vital portion of the toxin other than the native activation site that inhibits pore formation unless that modification is reversed. An example of this would be phosphorylation of a residue in the hydrophobic loop that forms part of the pore and which interferes with native pore-forming activity. Only when the phosphate group is removed, for example, with a phosphatase, can the protoxin form functional pores.

The RAPFTs can also contain an optionally substituted cell targeting moiety described herein in addition to the native targeting domain as long as the substituted cell-targeting moiety operably replaces the localizing function of the targeting domain. Additionally, the native targeting domain can be eliminated or replaced partially or entirely by an optionally substituted cell-targeting moiety. Those skilled in the art understand methods to make deletions, insertions, site-directed mutations, and random mutations to the native pore-forming toxin within the encoding DNA sequences that are then represented as changes in the encoded amino acid sequences using established molecular cloning techniques. Optionally substituted cell-targeting moieties can be appended to the protoxin as a direct genetic fusion, or can be added through chemical or enzymatic crosslinking. The cell-targeting moieties may also be non-covalently associated with the protoxin through hydrophobic, metal binding, and other affinity-based interactions. Additional variants of cell-targeting moieties are described herein.

Other modifications of RAPFT include single amino acid substitutions or combinations of multiple substitutions that may aid in the synthesis of functional immunotoxins as well as modify the properties of the reengineered protein, such as solubility, immunogenicity, or pharmacokinetics (Sambrook J. 2001. Cold-Spring Harbor Press., Ausubel F. 1997 and updates. Wiley and Sons.).

Modifications can include the addition of purification tags for the purpose of preparation of the RAPFT. The protoxin can be modified to include modifiable amino acids such as cysteines and lysines in specific positions in the toxin. Modifying groups such as binding or inhibitory domains can be added to these amino acids through alkylation of the sulfhydryl or epsilon amino group. Mutations that affect the natural activity of the RAPFT can be introduced. For example, mutations such as C159S and W324A can be made that disrupt the GPI-binding site within the aerolysin pore-forming toxin. These mutations would reduce the non-specific binding of the reengineered toxin (MacKenzie, et al. 1999. J Biol Chem. 274:22604-9).

In one embodiment, the RAPFT may encode sequences that allow for posttranslational modifications in vivo or in vitro. These post translational modifications include but are not limited to protease cleavage sites, lipoylation signals, phosphorylation, glycosylation, ubiquitination, sumoylation sites, and a BirA biotinylation target sequences for the addition of biotin. The biotinylation can occur during protein synthesis within the host organism or afterwards in an in vitro reaction. Streptavidin-biotin interactions can be used to couple the pore-forming function with other desired functionalities.

In another embodiment, an artificial inhibitory region may be substituted for a natural inhibitory sequence. In the case of aerolysin, residues between 433-470 may be replaced with an alternative sequence or chemical moiety that exhibits an analogous regulatory role. This region may be an alternative polypeptide sequence or small molecule, carbohydrate, lipid, or nucleic acid modification. Only when this non-native region is removed or inactivated will the toxin be activated or converted to a form that can be easily activated by the target cell. For example, an inhibitory peptide that is distinct in its primary sequence can be attached to the native inhibitory pro-peptide, and pore-forming activity can be restored upon removal of said inhibitory pro-peptide.

In another embodiment, the functioning portions of the RAPFT (e.g., the binding domain, pore-forming domain, and inhibitory pro-region) are linked together through non-peptide bonds. These domains are may be connected covalently using disulfide bonds, chemically crosslinked with bireactive alkylating reagents, or enzymatically through the conjugation with SortaseA or transglutaminase (Parthasarathy, et al. 2007. Bioconjug Chem. 18:469-76, Tanaka, et al. 2004. Bioconjug Chem. 15:491-7). Alternatively, a pore-forming toxin may contain functioning portions that are non-covalently associated (e.g., hydrophobic interactions like leucine zippers or binding interactions like SH2 domain-phosphate interaction) in order to achieve a functioning complex of associated pore-forming agents.

Another embodiment features RAPFTs in which one or more amino acids are substituted with unnatural amino acids (e.g., f 4-fluorotryptophan in place of tryptophan (Bacher and Ellington. 2007. Methods Mol Biol. 352:23-34, Bacher and Ellington. 2001. J Bacteriol. 183:5414-25)).

The functional RAPFT, without limitation, may have one or more of the following modifications: single or multiple amino acid mutations, altered activation moieties, optionally substituted cell-targeting domains, non-native inhibitory pro-regions, and unnatural amino acids.

In one preferred embodiment the RAPFT is based on the aerolysin pore-forming toxin. Aerolysin is produced by the species *Aeromonas* and causes cytolysis in a non-cell-specific manner. The toxin is comprised of four distinct domains and the superstructure exists as a dimer in the non-membrane bound form (Parker, et al. 1994. Nature. 367:292-5). Once the toxin is localized to cell membrane, furin cleaves a target sequence between residues 427-432, a C-terminal pro-domain which inhibits pore formation when present (residues 433-470) is removed, and the toxin can oligomerize with other activated toxins on the surface of the same cell. A hydrophobic segment is then inserted across the lipid bilayer to create a channel between the extracellular domain and cytosol. In the wild type aerolysin toxin, Domain 1 contains an N-glycan binding domain that targets the natural toxin to cells, and domain 2 contains a glycosyl-phosphatidylinositol (GPI) binding domain. Domain 3 contains the pore-forming loop and Domain 4 contains the pro-domain, separated from the pore-forming section by a cleavable linker with a furin recognition site.

The invention features modifications of pore-forming toxins to make them more suitable for administration as part of a RAPFT. In one embodiment of the reengineered aerolysin toxin, Domain 1 which is the native N-glycan binding domain can be removed. In another embodiment, Domain 1 can be optionally substituted with a cell-targeting moiety, with or without removing Domain 1. If Domain 1 is not removed, the toxin may or may not contain mutations in the binding site that affect the affinity toward the target molecule on the cell surface. The cell-targeting moiety may be attached to the N-terminus, C-terminus, or to an internal residue, provided it does not interfere with pore-forming activity once the RAPFT is activated. The optionally substituted protoxin can be synthesized by a variety of methods described herein.

The present invention also features a modified aerolysin with the residues between the pore-forming section and the pro-domain that inhibits pore formation (residues 427-432) changed from the native protease cleavage site to a modifiable activation moiety. Some embodiments comprise a mutated activation moiety in which the native furin activation moiety is substituted by one or more alternative protease recognition sequences. The native furin cleavage sequence KVRR↓AR (SEQ ID NO:7) (residues 427-432) can be replaced with the granzyme B activation moiety (IEPD (SEQ ID NO:9)). In this case, the therapeutic regimen would pair this embodiment with a granzyme B moiety as the protoxin activator. Alternatively, the native furin sequence can be replaced by the tobacco etch virus protease (TEV). The different protease activation sites include but are not limited to those described herein. The DNA encoding the native activation moiety can be replaced with a modified sequence using standard molecular biology methods (Sambrook J. 2001. Cold-Spring Harbor Press. Ausubel F. 1997 and updates. Wiley and Sons.). Sequences that can be cleaved by exogenous proteases, but have not been yet identified as substrates, can also be used.

In another embodiment, the first 82 residues of aerolysin are removed through DNA mutagenesis. Here, the small lobe is replaced by a DNA encoded linker sequence in which a peptide sequence which can be recognized and modified by SortaseA is added (GKGGSNSAAS (SEQ ID NO:22)). A cell-binding moiety which has at its C-terminus a sortase A acceptor sequence (LPETG SEQ ID NO:38)) is coupled to the mutated toxin using immobilized sortaseA. Sortase A forms a covalent attachment between the C-terminus of the threonine from the single chain Fv and the N-terminus of the GKGGSNSAAS (SEQ ID NO:22). In a preferred embodiment the cell-binding moiety is a single chain Fv fragment. In another embodiment, the single chain Fv fragment has specificity towards the cell surface receptor CD5, which is normally found on T-cells and not B-cells. In the case of chronic B-cell chronic lymphoid leukemia (B-CLL), B-cells are found to have the receptor on the cell surface. In addition to this mutation, the reengineered aerolysin contains an alternative proteolytic activation site recognized by human Granzyme B in place of the native furin active (residues 427-432). When this reengineered aerolysin is paired with an activating moiety which has a granzyme B protease associated with a targeting module that also targets the diseased cell, as an example a granzyme B that has been functionally fused with a single-chain antibody fragment that can recognize CD19, a common B-cell marker, the reengineered aerolysin can become activated and destroy the cell expressing both CD5 and CD19 through the formation of a heptameric pore. In yet another embodiment the anti-CD5 and anti-CD19 moieties are swapped between the protoxin and protoxin activator. The aerolysin based RAPFT is modified with anti-CD19 and the the activating protease is modified with anti-CD5.

In another embodiment, the invention features RAPFTs based on homologous toxins to aerolysin such as *Clostridium septicum* alpha-toxin. This pore-forming toxin does not have a native N-glycan binding region, domain1, and thus can be modified to have a cell-targeting moiety apart from the GPI-binding domain. Analagous mutations to the activation region of alpha-toxin can be made as described for aerolysin.

Those skilled in the art understand how to express RAPFTs in a variety of host systems. In one embodiment the protoxin may be produced in the organism, or related organism from which the natural toxin is normally found. In order to simplify the production process reengineered toxins can also be produced in heterologous expression systems such as *E. coli*, yeast (e.g. *Pichia pastoris, Kluvermyces lactis*), insect cells, in vitro translation systems, and mammalian cells (eg. 293, 3T3, CHO, HeLa, Cos, BHK, MDCK) as described in standard molecular biology guides. Transcriptional regulators and translational signals can be incorporated within the commercially available vector systems that accompany the various heterologous expression systems. Expression of the protoxin can be targeted to the intracellular or extracellular compartments of the host cell through the manipulation of signal peptides. The reengineered toxins may be expressed in fragments in different expression systems or created synthetically and then subsequently reconstituted into functional RAPFTs using purified components.

PCT Application Publication No. WO 20071056867 teaches the use of modified pore-forming protein toxins (MPPTs). MPPTs are derived from naturally-occurring pore-forming protein toxins (nPPTs) such as aerolysin and aerolysin-related toxins, and comprise a modified activation moiety that permits activation of the MPPTs in a variety of different cancer types. WO 2007/056867 distinguishes MPPTs from the pore-forming molecules described in PCT Application Publication No. WO 03/1018611, which have been engineered to selectively target a specific type of cancer. The MPPTs of WO 2007/056867 are intended to be used as broad spectrum anti-cancer agents and accordingly are constructed to be activated by proteolytic enzymes found in a plurality of cancer types. The activation moieties of the present invention are cognate to exogenous proteases that are not native to the tumor or expected to be enriched in the vicinity of the tumor.

Bacterial Activatable ADP-Ribosylating Toxins (ADPRTs)

Several groups of bacterial ADPRTs are known to be proteolytically activated. *Cholera* toxin, pertussis toxin and the *E. coli* enterotoxin are members of the $AB_5$ family that target small regulatory G-proteins. The enzymatically active A subunit binds non-covalently to pentamers of B subunits (Zhang et al. *J. Mol Biol.* 251: 563-573 (1995)). Members of the AB5 family of ADP-ribosylating toxins, including pertussis toxin, *E coli* heat labile enterotoxin and cholera toxin, require that the catalytic domain (A) undergo proteolytic cleavage of the disulfide linked A1-A2 domain. Proteolytic cleavage of the A subunit results in the A1 domain being released from the A2-B5 complex, rendering the A2-B5 complex cytotoxic in the presence of a cellular cofactor (Holboum et al. *FEBS J.* 273:4579-4593 (2006))

Diphtheria toxin, *Pseudomonas* exotoxin, and *Vibrio Cholera* Exotoxin presented in the present invention are members of the AB family. AB family toxins are multi-domain proteins consisting of a cell targeting domain, a translocation domain and an ADRPT domain by which the toxin ADP ribosylates a diphthamide residue on eukaryotic elongation factor 2 (Hwang et al. Cell 48:229-236(1987); Collier. *Bacteriol. Rev.* 87:828-832(1980)).

The third group comprises the actin-targeting AB combinatorial toxins that, unlike the more common $AB_5$ combinatorial toxins, comprise two domains, an active catalytic domain and a cell-targeting domain. This group includes a wide range of clostridial toxins including C2 toxin from *Clostridium botulinum, Clostridium perfringens* Iota toxin, *Clostridium spiroforme* toxin, *Clostridium difficile* toxin and the vegetative insecticidal protein (VIP2) from *Bacillus cereus* (Aktories et al. *Nature* 322:390-392(1986); Stiles & Wilkins Infect and Immun 54: 683-688 (1986); Han et al. Nature Struct Biol 6:932-936 (1999)). Combinatorial toxins do not bind cells as complete A-B units. Instead proteolytically activated B monomers bind to cell surface receptors as homoheptamers. These homoheptamers then bind to the A domains and are taken into cells via endocytosis. Once inside acidic endosomes, the low pH activates the translocation function of the B domain heptamers and they translocate the catalytic A domains across the endosomal membrane into the cytoplasm where they ADP-ribosylate actin and cause cell death (Barth et al. *Microbiol. Mol. Biol. Rev.* 68:373-402 (2004))

ADP-ribosylating toxins of the present invention include those that can induce their own translocation across the target cell membranes, herein referred to as "autonomously acting ADP-ribosylating toxins," which have no requirement for a type III secretion system or similar structure expressed by bacteria to convey the translocation of the toxin into the host cytoplasm by an injection pilus or related structure. Such autonomously acting ADP-ribosylating toxins can be modified with respect to their activation moiety and cell-targeting moiety and produced by methods well known in the art.

Like the autonomously acting ADP-ribosylating toxins from bacterial sources, the pierisin-1 toxin from the butterfly *Pieris rapae* can be activated by proteolytic cleavage at a trypsin-sensitive site, Arg-233; cleavage results in a nicked toxin that shows enhanced cytolytic activity and the fragment 1-233 is cytotoxic if electroporated into HeLa cells (Kanazawa et al. Proc Natl Acad Sci USA. 98(5):2226-31 (2001)). Arg-233 lies in a predicted disordered loop of sequence GGHRDQRSERSASS (SEQ ID NO:40) in which the third arginine residue is Arg-233. Pierisin-1 contains a C-terminal sphingolipid binding region that targets the toxin to eukaryotic membranes and is believed to consist of four repeats of a lectin-like domain similar to that found in the plant toxin ricin (Matsushima-Hibiya et al. J Biol Chem. Mar. 14, 2003; 278(II):9972-8). Mutation of tryptophan residues thought to comprise the carbohydrate-binding motif results in reduced activity of the toxin (Matsushima-Hibiya et al. J Biol Chem. Mar. 14, 2003; 278(11):9972-8). Hence the redirection of the toxin to novel cell surface targets can be achieved by addition of an exogenous cell-targeting moiety to an engineered variant of pierisin-1 or related toxin that lacks carbohydrate-binding capacity as a result of mutational modification to the coding sequence. Such redirected pierisin can be additionally modified in the activation moiety to replace the arginine-rich RDQRSER (SEQ ID NO:41) sequence with a sequence cognate to a protoxin-activating protease.

Another aspect of the present invention is the provision of a new protoxin moiety derived from *Vibrio cholerae*, hereinafter known as *Vibrio cholerae* exotoxin or VCE. Like the catalytic moieties of diphtheria toxin and *Pseudomonas* exotoxin A, the VCE catalytic moiety specifically ADP-ribosylates diphthamide on eEF2. ADP-ribosylation of diphthamide impairs the function of eEF2 and leads to inhibition of protein synthesis which results in profound physiological changes and ultimately cell death. The mechanism whereby VCE enters the cell is not fully understood, but the related toxin PEA binds to the $\alpha_2$-macroglobulin receptor on the cell surface and undergoes receptor-mediated endocytosis, becoming internalized into endosomes where the low pH creates a conformational change in the toxin leaving it open to furin protease cleavage that removes the binding domain. The catalytic domain then undergoes retrograde transport to the endoplasmic reticulum, translocates into the cytoplasm and can enzymatically ribosylate eEF2. DT by contrast binds to the heparin binding epidermal growth factor-like growth factor precursor (HB-EGF) and is cleaved on the cell surface before uptake through receptor mediated endocytosis. Once in the early endosome, the DT catalytic fragment is not processed and penetrates the membrane of the endosome to pass directly into the host cell cytoplasm where it can ADP-ribosylate eEF2. The receptor responsible for binding of VCE is currently unknown. In several regards, VCE resembles PEA more closely than it resembles DT. First, the domain organization of VCE appears similar to that of PEA, in which the cell-targeting domain is followed by the translocation domain and then the enzymatic domain. VCE and PEA both possess a masked ER retention signal at the C-terminus, suggesting that VCE and PEA enter the cytosol of target cells via endoplasmic reticulum. Both VCE and PEA have low lysine content, thought to be consistent with the mechanism of introduction of toxin into the cytoplasm through the endoplasmic reticulum associated degradation (ERAD) pathway. The present data support the view that the proteolytic event that activates PEA and VCE occurs in an acidic endosomal compartment, whereas furin cleavage of DT might take place in a more neutral environment.

The C-terminus of VCE bears a characteristic endoplasmic reticulum retention signal (KDEL (SEQ ID NO:15)) followed by a lysine residue at the very C-terminus of the VCE which presumably will be removed by a ubiquitous carboxylpeptidase activity such as carboxypeptidase B, suggesting that VCE enters the cytosol of target cell in a manner similar to PEA and that the C-terminal sequence of VCE is essential for full cytotoxicity. Thus, for maximum cytotoxic properties of a preferred VCE molecule, an appropriate carboxyl terminal sequence is preferred to translocate the molecule into the cytosol of target cells. Such preferred amino acid sequences include, without limitation, KDELK (SEQ ID NO:42), RDELK (SEQ ID NO:43), KDELR (SEQ ID NO:44) and RDELR (SEQ ID NO:45).

Generic methods similar to those described below for DT fusion proteins may be applied to prepare recombinant DNA constructs and to express modified VCE fusion proteins they encode. Specifically for VCE fusions, the cell-targeting moiety (residues 1-295) of wild type VCE is replaced by a polypeptide sequence that binds to a different, selected target cell surface target, and the furin cleavage sequence (residues 321-326: RKPR↓DL (SEQ ID NO:46)) is displaced by a recognition sequence of an exogenous protease such as GrB, GrM, and TEV protease.

In another embodiment the invention includes the use of modified *Pseudomonas* exotoxin A as an element of a protoxin. Many useful improvements of PEA are known in the art. For example deletion and substitution analyses have indicated that the C-terminus of PEA contains an element essential for the cytotoxic effect of PEA. Mutational analyses of the region between amino acid 602 and 613 identified the last 5 amino acid residues (RDELK (SEQ ID NO:43)) as essential for toxicity and a basic residue at 609 and acidic amino acid at 610, 611, and a leucine at 612 as required for full cytotoxicity, whereas the lysine at 613 was identified to be dispensable (Chaudhary et al. Proc. Natl. Acad. Sci. 87:308-312 (1990)). A mutant PEA in which the C-terminus RDELK (SEQ ID NO:43) sequence was replaced with KDEL (SEQ ID NO: 15), a well defined endoplasmic reticulum retention signal, is fully functional, suggesting that intoxication by PEA requires cellular factor(s) present in the target cells and that PEA protein might travel to the lumen of the endoplasmic reticulum. Subsequently, it was found that immunotoxins engineered to have a consensus endoplasmic reticulum retention signal at the C-termini exhibit higher toxicity that those with the wild type PEA sequences (Seetharam et al., J. Biol. Chem. 266:17376-17381 (1991); U.S. Pat. No. 5,705,163; U.S. Pat. No. 5,821,238). Hence one embodiment of the present invention includes modified PEA bearing C-terminal sequence changes that favorably improve the toxicity to tumor cells.

Generic methods similar to those described below for DT fusion proteins may be applied to prepare recombinant DNA constructs and to express modified PEA fusion proteins they encode. Specifically for PEA fusions, the cell-targeting moiety (residues 1-252) of wild type PEA is replaced by a polypeptide sequence that binds to a different, selected target cell surface target, and the furin cleavage sequence (residues 276-281: RQPR↓GW (SEQ ID NO:5)) is displaced by a recognition sequence of an exogenous protease such as GrB, GrM, and TEV protease.

Various modifications have been described in the art that improved toxicity of PEA. These modification are also useful for improving the toxicity of VCE immunotoxins. Mere et al. J. Biol. Chem. 280: 21194-21201 (2005) teach that exposure to low endosomal pH during internalization of *Pseudomonas* exotoxin A (PE) triggers membrane insertion of its translocation domain, a process that is a prerequisite for PEA translocation to the cytosol where it inactivates protein synthesis. Membrane insertion is promoted by exposure of a key tryptophan residue (Trp 305). At neutral pH, this residue is buried in a hydrophobic pocket closed by the smallest α-helix (helix F) of the translocation domain. Upon acidification, protonation of the Asp that is the N-cap residue of the helix leads to its destabilization, enabling Trp side chain insertion into the endosome membrane. A mutant PEA in which the first two N-terminal amino acids (Asp 358 and Glu 359) of helix F replaced with non-acidic amino acids, showed destabilization of helix F, leading to exposure of tryptophan 305 to the outside of the molecule in the absence of an acidic environment and resulting in 7-fold higher toxicity than wild type PEA. Similarly, the mutant PEA in which the entire helix F is removed was shown to exhibit 3-fold higher toxicity than wild type PEA. Hence one embodiment of the present invention includes modified PEA bearing sequence changes to helix F or Trp 305 that favorably improve the toxicity to tumor cells. Although by sequence alignment, we did not find a helix corresponding to the helix F of PE, we found that, similar to the proteolytic cleavage of PEA, cleavage of VCE by furin is favored in mildly acidic conditions, suggesting that a similar acid triggered conformational change might take place during membrane insertion of VCE. Mutations that facilitate membrane insertion of VCE, and thereby enhance cytotoxicity, might be found through means such as random mutagenesis. Thus, preferable forms of VCE molecules for the present invention include those that exhibit more efficient membrane insertion, leading to higher toxicity.

One of the important factors determining the toxicity of the PEA-based or VCE-based immunotoxins depends on whether the immunotoxins are internalized by the target cell upon receptor binding. The internalization is considered the rate-limiting step in immunotoxin-mediated cytotoxicity (Li and Ramakrishnan. *J. Biol. Chem.* 269: 2652-2659 (1994)). He et al. fused $Arg_9$-peptide, a well known membrane translocational signal, to an anti-CEA (carcinoembryonic antigen) immunotoxin, PE35/CEA(Fv)/KDEL, at the position between the toxin moiety and the binding moiety. Strong binding and internalization of this fusion protein was observed in all detected cell lines, but little cytotoxicity to the cells that lack the CEA molecules on the cell surface was detected. However, the cytotoxicity besides the binding activity of the fusion protein to specific tumor cells expressing large amount of CEA molecules on the cell surface was improved markedly, indicating that the $Arg_9$-peptide is capable of facilitating the receptor-mediated endocytosis of this immunotoxin, which leads to the increase of the specific cytotoxicity of this immunotoxin (He et al. *International Journal of Biochemistry and Cell Biology,* 37:192-205 (2005)). Accordingly, one preferred embodiment of protoxins that depend on translocation to the endoplasmic reticulum for intoxication includes the operable linkage of Arg9-peptide or related membrane translocation signals, such as, without limitation, those derived from HIV-Tat, Antennapedia, or Herpes simplex VP22, to such protoxins. A further preferred embodiment of the present invention includes modified PEA or VCE protoxins operably linked to Arg9-peptide or related membrane translocation signals, such as, without limitation, those derived from HIV-Tat, Antennapedia, or Herpes simplex VP22.

Toxicities that are independent of ligand binding have been observed with most targeted toxins. These include either hepatocyte injury causing abnormal liver function tests or vascular endothelial damage with resultant vascular leak syndrome (VLS). Both the hepatic lesion and the vascular lesion may relate to nonspecific uptake of targeted toxins by normal human tissues. U.S. Patent Application Publication No. 2006/0159708 A1 and U.S. Pat. No. 6,566,500 describe methods and compositions relating to modified variants of diphtheria toxin and immunotoxins in general that reduce binding to vascular endothelium or vascular endothelial cells, and therefore reduce the incidence of Vascular Leak Syndrome (VLS), wherein the (X)D(Y) sequence is GDL, GDS, GDV, IDL, IDS, IDV, LDL, LDS, and LDV. In one example, avariant of DT, V7AV29A, in which two (X)D(Y) motifs are mutated is shown to maintain full cytotoxicity, but to exhibit reduced binding activity to human vascular endothelial cells (HUVECs). U.S. Pat. No. 5,705,156 teaches the use of modified PEA molecules in which 4 amino acids (57, 246, 247, 249) in domain I are mutated to glutamine or glycine to reduce nonspecific toxicity of PEA to animals. Hence one embodiment of the present invention includes modified PEA, VCE, or DT protoxins bearing sequence changes that favorably reduce toxicity to normal tissues.

The plasma half-lives of several therapeutic proteins have been improved using a variety of techniques such as those described by Collen et al., Bollod 71:216-219 (1998); Hotchkiss et al., Thromb. Haemostas. 60:255-261 (1988); Browne wt al., J. Biol. Chem. 263:1599-1602 (1988); Abuchowski et al., Cancer Biochem. Biophys. 7:175 (1984)). Antibodies have been chemically conjugated to toxins to generate immunotoxins which have increased half-lives in serum as compared with unconjugated toxins and the increased half-life is attributed to the native antibody. WO94/04689 teaches the use of modified immunotoxins in which the immunotoxin is linked to the IgG constant region domain having the property of increasing the half-life of the protein in mammalian serum. The IgG constant region domain is CH2 or a fragment thereof. Similar strategy can be applied to creating variants of VCE immunotoxin with increased serum half-life. In addition operable linkage to albumin, polyethylene glycol, or related nonimmunogenic polymers may promote the plasma persistence of therapeutic toxins.

Upon repeated treatment of immunotoxins, patients may develop antibodies that neutralize, hence lessen the effectiveness of immunotoxins. To circumvent the problem of high titer antibodies to a given immunotoxin, U.S. Pat. No. 6,099,842 teaches the use of a combination of immunotoxins bearing the same targeting principle, but differing in their cytotoxic moieties. In one example, anti-Tac(Fv)-PE40 and DT(1-388)-anti-Tac(Fv) immunotoxins are used in combination to reduce the possibility of inducing human anti-toxin antibodies. A similar strategy may be applied to the present invention where the protoxins of a combinatory strategy can be alternated between two or more protoxins, for example, those described herein.

One particular type of toxin fusion protein, the DT fusion protein, can be produced from nucleic acid constructs encoding amino acid residues 1-389 of DT, in which the native furin cleavage site is replaced by a recognition sequence of an exogenous protease and a polypeptide that can bind to a cell surface target. Those skilled in the art will recognize a variety of methods to introduce mutations into the nucleic acid sequence encoding DT or to synthesize nucleic acid sequences that encode the mutant DT. Methods for making nucleic acid constructs are well known and well documented in publications such as *Current Protocols in Molecular Biology* (Ausubel et al., eds., 2005). The nucleic acid constructs can be generated using PCR. For example, the construct encoding the DT fusion protein can be produced by mutagenic PCR, where primers encoding an alternative protease recognition site can be used to substitute the DNA sequence coding the furin cleavage site RVRRSV (SEQ ID NO:47). Constructs containing the mutations can also be made through sequence assembly of oligonucleotides. Either approach can be used to introduce nucleic acid sequences encoding the granzyme B cleavage site IEPD (SEQ ID NO:9) in place of that which encodes RVRRSV (SEQ ID NO:47). In addition to IEPD (SEQ ID NO:9), GrB has been shown to recognize and cleave other similar peptide sequences with high efficiency, including IAPD (SEQ ID NO:48) and IETD (SEQ ID NO:49). These and other sequences specifically cleavable by GrB may be incorporated. Genetically modified proteases of higher than natural specificity or displaying a different specificity than the naturally occurring protease may be of use in avoiding undesirable side effects attributable to the normal action of the protease.

DNA sequences encoding a cell-targeting polypeptide can be similarly cloned using PCR, and the full-length construct encoding the DT fusion protein can be assembled by restriction digest of PCR products and the DT construct followed by ligation. The construct may be designed to position a nucleic acid sequence encoding the modified DT near the translation start site and the DNA sequence encoding the cell-targeting moiety close to the translation termination site. Such a sequence arrangement uses native Diphtheria toxin to confer optimal translocation efficiency of the catalytic domain of DT to the cytosol.

DT fusion proteins may be expressed in bacterial, insect, yeast, or mammalian cells, using established methods known to those skilled in the art, many of which are described in *Current Protocols in Protein Science* (Coligan et al., eds., 2006). DNA constructs intended for expression in each of these hosts may be modified to accommodate preferable codons for each host (Gustafsson et al., Trends Biotechnol. 22:346 (2004)), which may be achieved using established methods, for example, as described in *Current Protocols in Molecular Biology* (Ausubel et al., eds., 2005), e.g., site-directed mutagenesis. To quickly identify an appropriate host system for the production of a particular DT fusion, the Gateway cloning method (Invitrogen) may also be applied for shuffling a gene to be cloned among different expression vectors by in vitro site-specific recombination.

In addition to codon changes, other sequence modifications to the construct of a DT fusion protein may include naturally occurring variations of DT sequences that do not significantly affect its cytotoxicity and variants of the cell-targeting domain that do hot abolish its ability to selectively bind to targeted cells.

Further, the sequence of the cell-targeting domain can be modified to select for variants with improved characteristics, e.g., reduced immunogenicity, higher binding affinity and/or specificity, superior pharmacokinetic profile, or improved production of the DT fusion protein. Libraries of cell-targeting domains and/or DT fusions can be generated using site-directed mutagenesis, error-prone PCR, or PCR using degenerate oligonucleotide primers. Sequence modifications may be necessary to remove or add consensus glycosylation sites, for maintaining desirable protein function or introducing sites of glycosylation to reduce immunogenicity.

For high yield expression of DT fusion proteins, the encoding polynucleotide may be subcloned into one of many commercially available expression vectors, which typically contain a selectable marker, a controllable transcriptional promoter, and a transcription/translation terminator. In addition, signal peptides are often used to direct the localization of the expressed proteins, while other peptide sequences such as 6 His tags, FLAG tags, and myc tags may be introduced to facilitate detection, isolation, and purification of fusion proteins. To help successful folding of each domain within the DT fusion, a flexible linker may be inserted between the modified DT domain and the cell-targeting moiety in the expression construct.

DT fusion proteins may be expressed in the bacterial expression system *Escherichia coli*. In this system a ribosome-binding site is used to enhance translation initiation. To increase the likelihood of obtaining soluble protein fusion, its expression construct may include DNA that encodes a carrier protein such as MBP, GST, or thioredoxin, either 5' or 3' to the DT fusion, to assist protein folding. The carrier protein(s) may be proteolytically removed after expression. Proteolytic cleavage sites are routinely incorporated to remove protein or peptide tags and generate active fusion proteins. Most reports on successful *E. coli* expression of fusion proteins containing a DT moiety have been in the form of inclusion bodies, which may be refolded to afford soluble proteins.

DT fusion proteins may be expressed in the methylotrophic yeast expression system *Pichia pastoris*. The expression vectors for this purpose may contain several common features, including a promoter from the *Pichia* alcohol oxidase (AOX1) gene, transcription termination sequences derived from the native *Pichia* AOX1 gene, a selectable marker wild-type gene for histidinol dehydrogenase HIS4, and the 3'AOX1 sequence derived from a region of the native gene that lies 3' to the transcription termination sequences, which is required for integration of vector sequence by gene replacement or gene insertion 3' to the chromosomal AOX1 gene. Although *P. pastoris* has been used successfully to express a wide range of heterologous proteins as either intracellular or secreted proteins, secretion is more commonly used because *Pichia* secretes very low levels of native proteins. A secretion signal peptide MAT factor prepro peptide (MF-$\alpha$1) is often used to direct the expressed protein to the secretory pathway.

Post-translational modification such as N-linked glycosylation in *Pichia* occurs by adding approximately 8-14 mannose residues per side chain. Although considered less antigenic than the extensive modifications in *S. cerevisiae* (50-150 mannose residues per side chain), there is still a possibility that such glycosylation could elicit immune responses in human. Therefore, any consensus N-glycosylation sites NXS(T) within an expression construct are typically mutated to avoid glycosylation.

DT is potently toxic to eukaryotic cells if the catalytic domain translocates to or is localized to the cytosol. Although *Pichia* is sensitive to diphtheria toxin, it has a tolerance to levels of DT that were observed to intoxicate other wild type eukaryotic cells and the expression of DT fusion by the secretory route has been successful (Woo et al., Protein Expr. Purif. 25:270 (2002)). Because the secretion of expressed heterologous protein in *Pichia* involves cleavage of signal peptide MF-α1 by Kex2, a furin-like protease, a DT fusion protein with its furin cleavage site replaced should be less toxic to *Pichia* than wild type DT fusion proteins. Alternatively, DT fusion proteins can be expressed in a mutant strain of *Pichia*, whose chromosomal EF-2 locus has been mutated to resist GDP ribosylation by catalytic domain of DT (Liu et al., Protein Expr. Purif. 30:262 (2003)).

DT fusion proteins may also be expressed in mammalian cells. Mutant cell lines that confer resistance to ADP-ribosylation have been described (Kohno and Uchida, J. Biol. Chem. 262:12298 (1987); Liu et al., Protein Expr. Purif. 19:304 (2000); Shulga-Morskoy and Rich, Protein Eng. Des. Sel. 18:25 (2005)) and can be used to express soluble DT fusion proteins. For example, a toxin-resistant cell line CHO—K1 RE1.22c has been selected and used to express a DT-ScFv fusion protein (Liu et al., Protein Expr. Purif. 19:304 (2000)) and a mutant 293T cell line has been selected and used to express a DT-IL7 fusion protein (Shulga-Morskoy and Rich, Protein Eng. Des. Sel. 18:25 (2005)). It has been determined that a G-to-A transition in the first position of codon 717 of the EP-2 gene results in substitution of arginine for glycine and prevents post-translational modification of diphthamide at histidine 715 of EF-2, which is the target amino acid for ADP-ribosylation by DT. EF-2 produced by the mutant gene is fully functional in protein synthesis (Foley et al., Somat. Cell Mol. Genet. 18:227 (1992)). Based on this information and established methods such as described in *Current Protocols in Molecular Biology* (Ausubel et al., eds., 2005), different mammalian cells may be transfected with vectors containing G717A mutant of EF-2 gene and select for cells that are resistant to DT.

Stable expression in mammalian cells also requires the transfer of the foreign DNA encoding the fusion protein and transcription signals into the chromosomal DNA of the host cell. A variety of vectors are commercially available, which typically contain phenotypic markers for selection in *E. coli* ($Ap^r$) and CHO cells (DHFR), a replication origin for *E. coli*, a polyadenylation sequence from SV40, a eukaryotic origin of replication such as SV40, and promoter and enhancer sequences. Based on methods described in *Current Protocols in Protein Science* (Coligan et al., eds., 2006), and starting with the DT-resistant cell lines, vectors containing DNA encoding DT fusion proteins may be used to transfect host cells, which may be screened for high producers of the fusion proteins.

Although mammalian expression systems are often used to take advantage of its post-translational modifications that are innocuous to human, this is not necessarily applicable to DT fusion proteins involved in the present invention. Because DT is of bacterial origin, potential N-glycosylation sites within its sequence may need to be mutated in order to retain the cytotoxicity potential of native DT. Further, glycosylation within cell-targeting domain may need to be avoided to maintain its desirable binding characteristics. However, consensus N-glycosylation sites may be introduced to linkers or terminal sequences so that such glycosylation do not hamper the functions of DT and cell-targeting moiety.

Proteinaceous Toxins

A common property of many proteinaceous toxins that might be deployed as therapeutic agents is their requirement for activation by proteolytic cleavage through the action of ubiquitous proteases such as furin/kexin proteases found in, on, or in the vicinity of, the target cell. One promising approach to increase the selectivity of highly active proteinaceous toxins has been the introduction of proteolytic cleavage sites to replace the endogenous recognition sequence with that of proteases hypothesized or known to be enriched in the tumor. For example a variant anthrax toxin has been engineered to replace the endogenous furin cleavage site with a site easily cleaved by urokinase, a protease often highly expressed by malignant cells (Liu et al. J Biol Chem. May 25, 2001; 276(21):17976-84.) The formation of a chimeric toxin consisting of anthrax lethal factor fused to the ADP-ribosylation domain of *Pseudomonas* exotoxin A resulted in an agent that selectively killed tumor cells (Liu et al. J Biol Chem. May 25, 2001; 276(21):17976-84.) The recombinant toxin in this case was natively targeted, i.e. did not comprise an independent tumor-specific targeting moiety. A recombinant anthrax toxin variant activatable by urokinase has been disclosed that may have broad applicability to various human solid tumors (Abi-Habib et al., Mol Cancer Ther. 5(10):2556-62 (2006)) Singh et al. Anticancer Drugs. 18(7):809-16 (2007) disclose the creation of recombinant aerolysins that can be activated by the chymotrypsin-like protease, prostate specific antigen.

*Bacillus anthracis* produces three proteins which when combined appropriately form two potent toxins, collectively designated anthrax toxin. Protective antigen (PA) and edema factor combine (EF) to form edema toxin (ET), while PA and lethal factor (LF) combine to form lethal toxin (LT) (Leppla et al. Academic Press, London 277-302 (1991)). A unique feature of these toxins is that LF and EF have no toxicity in the absence of PA, apparently because they cannot gain access to the cytosol of eukaryotic cells. PA is responsible for targeting of LT and ET to cells and is capable of binding to the surface of many types of cells. After PA binds to a specific receptor, it is cleaved at a single site by furin or furin-like proteases, to produce an amino-terminal 19 kD fragment that is released from the receptor/PA complex (Singh et al. *J. Biol. Chem.* 264:19103-19107 (1989)). Removal of this fragment from PA exposes a high affinity binding site for LF and EF on the receptor-bound 63 kD carboxyl-terminal fragment (PA63). The complex of PA63 and LF or EF enter cells and probably passes through acidified endosomes to reach the cytosol.

U.S. Pat. No. 5,677,274 teaches the use of modified PA in which the furin cleavage site is replaced with intracellular protease activatable sequences. Once cleaved by protease resident in target cells, cleaved PA presents a high affinity binding domain for a second fusion protein comprising a fragment of LF which binds to PA and a toxin moiety such as *pseudomonas* exotoxin which kills target cells. In one embodiment of the invention, the furin cleavage site was replaced with a HIV protease site, rendering the modified PA proteins to be activated specifically by HIV-infected cells or cells expressing HIV protease. Thus allows the fusion protein comprising a PA binding domain of LF and the translocation domain and ADPRT domain of PE to enter and kill target cells. In another embodiment, the furin cleavage sequence is replaced with an HIV cleavage sequence so that two proteolytic events are required to activate modified LF.

Anthrax lethal toxin, a protoxin of *Bacillus anthracis*, may also be employed according to the present invention. Anthrax lethal toxin has two components, a catalytic moiety that is a protease specific for mitogen-activated protein kinase kinases (MAPKK), and a cell-targeting and translocation moiety. The latter is referred to as protective antigen, and binds cells through widely distributed cell surface targets known as anthrax toxin receptors. Following activation by proteolytic cleavage at a furin-like recognition sequence, RKKR(SEQ ID NO:49), spanning residues 164 to 167 of the protective antigen, an inhibitory fragment is liberated and the remaining protective antigen fragment forms a heptamer that binds three catalytic moieties that are subsequently endocytosed. The activated protective antigen forms a pore in the acidic environment of the endosome, allowing the toxic catalytic moiety to enter the cell, where it causes the cleavage of mitogen activated protein kinase kinases, (MAPKKs), resulting in cell cycle arrest. Protective antigen can also bind anthrax edema factor and fusion proteins of lethal toxin and another toxin, such as PEA, have been exemplified in the art (Liu et al. J Biol Chem. 276(21):17976-84 (2001)).

Accordingly, replacement of the furin-like recognition sequence with that of an exogenous protease will result in a protoxin that is activatable by a second protoxin activating moiety. The protective antigen can be made to target specific cells through the replacement of the endogenous receptor binding domain with a cell target binding moiety that is selective for a target desirable for therapeutic purposes.

AB Toxins

A large class of bacterial toxins well-known in the art and particularly suitable for the purposes of this invention are known as AB toxins. AB toxins consist of a cell-targeting and translocation domain (B domain) as well as a enzymatically active domain (A domain) and undergo translocation into the cytoplasm following the action of an endogenous target cell protease on an activation sequence.

The AB toxins *Bordetella* dermonecrotic toxin (DNT), *E. coli* cytotoxic necrotizing factor 1 or 2 (CNF1 or CNF2) and *Yersinia* cytotoxic necrotizing factor (CNFY) may accordingly be used for the purposes of the present invention. These toxins are similar in structure and mechanism of action (Hoffmann and Schmidt, Rev Physiol Biochem Pharmacol. 152: 49-63 (2004)). DNT is a transglutaminase that inactivates Rho GTPases by polyamination or deamidation (Schmidt et al. J Biol Chem. 274(45):31875-81 (1999); Fukui and Horiuchi, J Biochem (Tokyo). 136(4):415-9 (2004)). CNF1, CNF2 and CNFY are deamidases that deamidate Gln 63 or Rho GTPase (Schmidt et al., Nature 387(6634):725-9 (1997), Hoffmann and Schmidt, Rev Physiol Biochem Pharmacol. 152:49-63 (2004)). DNT comprises a membrane targeting domain at the N terminus known as the B domain, a furin-like protease cleavage site, a translocation domain, and a catalytic domain; to enter the cytoplasm DNT must bind its target cells, undergo internalization and cleavage, and be translocated across the membrane (Fukui and Horiuchi, J Biochem (Tokyo). 136(4):415-9 (2004)). According to the present invention, modified DNT can be provided in which the B domain is replaced by a heterologous cell-targeting moiety, or in which a heterologous cell-targeting moiety is added to an intact B domain, and the furin-like protease cleavage site is replaced with a modifiable activation sequence that may be modified by an exogenous activator. CNFY and CNF1 exhibit 61% sequence identity in a pattern of uniform divergence throughout the molecule. CNFY and CNF1 target the same residue of RhoA but use different cell surface receptors to enter the cell (Blumenthal et al. Infect Immun. 75(7):3344-53 (2007)). Entry appears to be through an acidified endosomal compartment (Blumenthal et al. Infect Immun. 75(7):3344-53 (2007)). According to the present invention, modified DNT, CNF1, CNF2, or CNFY can be provided in which the endogenous cell-targeting domain is replaced by a heterologous cell-targeting moiety, or in which a heterologous cell-targeting moiety is added to an intact endogenous cell-targeting domain, and the furin-like protease cleavage site is replaced with a modifiable activation sequence that may be modified by an exogenous activator.

*Clostridial glucosylating* cytotoxins may also be used for the purposes of the present invention. Toxins in this family transfer glucose or N-acetylglucosamine to Rho family GTPases following internalization and translocation of the toxin enzymatic moiety into the cytoplasm (Schirmer and Aktories, Biochim Biophys Acta. 1673(1-2):66-74 (2004)). Like AB toxins, the glucosylating cytotoxins undergo proteolytic cleavage to transfer the catalytic N-terminus into the host (Pfeiffer et al. J Biol Chem. 278(45):44535-41 (2003)).

Additional Modifications

In addition to the above, functional toxins may be generated through refolding insoluble toxins through rapid dilution or stepwise removal of denaturant in the presence of additives that prevent aggregation (Middelberg. 2002. Trends Biotechnol. 20:437-43).

Reengineered toxins may have encoded affinity tags from which one can use affinity chromatography methods to obtain purified samples. These tags can be used for purification and may also aid in the soluble expression of some embodiments. Examples include and are not limited to histidine tags, avidin/streptavidin interacting sequences, glutathione-S-transferase (GST), maltose-bining protein, thioredoxin, and FLAG encoding sequence tags. The protoxins may be purified from host cells by standard techniques known in the art, such as gel filtration, ion exchange, metal chelating, and affinity purification. The optionally substituted cell-targeting moiety may be attached to the pore-forming-agent through a linker that provides conformational freedom or spatial separation for the pore-forming agent to function properly. This linker can be a polypeptide and may be directly encoded on the DNA by means of a genetic fusion at the N or C-terminus, or at an internal position such as an exposed loop. The linker may possess specific features that will allow attachments to binding or regulatory moieties, such as target sequences for crosslinking enzymes such as transglutaminase or sortaseA (see conjugation methods). The linker may be synthetic such as a poly-ethylene glycol group or a long hydrocarbon chain and can be attached to the toxin (pore-forming agent) through chemical or enzymatic means such as alkylation or transglutaminase reaction. The linker need not be covalently associated with either the toxin or the cell-targeting moiety. The interactions can be through metal chelation, hydrophobic interactions, and small molecule protein interactions like biotin-streptavidin as long as the association does not interfere with the toxin upon activation.

C. Other Toxins

RIPs are enzymes that trigger the catalytic inactivation of ribosomes and other substrates. Such toxins are present in a large number of plants and have been found also in fungi, algae, and bacteria. RIPs are currently classified as belonging to one of two types: type 1, comprising a single polypeptide chain with enzymatic activity, and type 2, comprising two distinct polypeptide chains, an A chain equivalent to the polypeptide of a type 1 RIPs and a B chain with lectin activity. Type 2 RIPs known in the art may be represented by the formulae A-B, $(A-B)_2$, $(A-B)_4$ and or by polymeric forms comprising multiple B chains per A chain. Linkage of the A chain with B chain is through a disulfide bond. The toxic activity of RIPs is due to translational inhibition, a consequence of the hydrolysis of an N-glycosidic bond of a specific adenine base in a highly conserved loop region of the 28 S rRNA of the eukaryotic ribosome (Girbes et al, Mini Rev. Med. Chem. 4(5):461-76 (2004)).

RIPs are often initially produced in an inactive, precursor form. For example, ricin is initially produced as a single polynucleotide (preproricin) with a 35 amino acid N-terminal presequence and a 12 amino acid linker between the A and B chains. The presequence is removed during translocation of the ricin precursor into the endoplasmic reticulum. The protoxin is then translocated into specialized organelles called protein bodies where a plant protease cleaves at the linker region between A and B chains. U.S. Pat. No. 6,803,358 discloses a protoxin comprising ricin A chain, ricin B chain, and a heterologous protease-sensitive peptide linker that may be selectively activated by a tumor-associated protease (e.g., MMP-9) that cleaves the peptide linker.

The toxicity of RIPs to animals is highly variable, although type 1 RIP and the A-chains of type 2 RIP share the same catalytic activity. Although some type 1 RIPs are highly active in cell free translation systems, they may be much less toxic than the type 2 RIPs in vivo. This is thought to be due to the absence of the lectin chain, resulting in a low rate of penetration into cells. Among the toxic type 2 RIPs are some of the most potent toxins known, but the lethal doses of toxic type 2 RIP may also vary greatly among different toxins, as reported for abrin and ricin, modeccin, and volkensin (Battelli Mini Rev. Med. Chem. 4(5):513-21 (2004)).

One embodiment of the present invention uses a protoxin comprising a type 1 RIP or the A chain of type 2 RIP as toxin moiety, a cell-targeting moiety, and a linker containing an exogenous protease cleavage site linking the two moiety. This protoxin is used in conjunction with an activator, which comprises a protease that cleaves the heterologous protease cleavage site and a cell-targeting domain.

Another embodiment of the present invention is to use a protoxin comprising a type 1 or the A chain of type 2 RIP containing a presequence mutated to include an exogenous protease sensitive site and a cell-targeting moiety. This protoxin is used in conjunction with an activator, which comprises a protease that can cleave the heterologous protease cleavage site and a cell-targeting domain.

Examples of type 1 RIPs include, but not limited to bryodin, gelonin, momordin, PAP-S, saporin-S6, trichokirin and momorcochin-S. Examples of toxic type 2 RIP include, but not limited to Abrin, Modeccin, Ricin, Viscumin, and Volkensin.

Like the autonomously acting ADP-ribosylating toxins from bacterial sources, the pierisin-1 toxin from the butterfly *Pieris rapae* can be activated by proteolytic cleavage at a trypsin-sensitive site, Arg-233; cleavage results in a nicked toxin that shows enhanced cytolytic activity and the fragment 1-233 is cytotoxic if electroporated into HeLa cells (Kanazawa et al. Proc Natl Acad Sci USA. 98(5):2226-31 (2001)). Arg-233 lies in a predicted disordered loop of sequence GGHRDQRSERSASS (SEQ ID NO:40) in which the third arginine residue is Arg-233. Pierisin-1 contains a C-terminal sphingolipid binding region that targets the toxin to eukaryotic membranes and is believed to consist of four repeats of a lectin-like domain similar to that found in the plant toxin ricin (Matsushima-Hibiya et al. J Biol Chem. Mar. Mar. 14, 2003; 278(11):9972-8). Mutation of tryptophan residues thought to comprise the carbohydrate-binding motif results in reduced activity of the toxin (Matsushima-Hibiya et al. J Biol Chem. Mar. 14, 2003; 278(11):9972-8). Hence the redirection of the toxin to novel cell surface targets can be achieved by addition of an exogenous cell-targeting moiety to an engineered variant of pierisin-1 or related toxin that lacks carbohydrate-binding capacity as a result of mutational modification to the coding sequence. Such redirected pierisin can be additionally modified in the activation moiety to replace the arginine-rich RDQRSER (SEQ ID NO:41) sequence with a modifiable activation moiety that can be activated by an exogenous activator.

D. Toxin Modifications and Methods of Expressing Fusion Proteins

Expressing reengineered pore-forming toxins in a variety of host systems is well known in the art. In one embodiment the protoxin may be produced in the organism, or related organism from which the natural toxin is normally found. In order to simplify the production process reengineered toxins can also be produced in heterologous expression systems such as *E. coli*, yeast (e.g. *Pichia pastoris, Kluvermyces lactis*), insect cells, in vitro translation systems, and mammalian cells (eg. 293, 3T3, CHO, HeLa, Cos, BHK, MDCK) as described in standard molecular biology guides. Transcriptional regulators and translational signals can be incorporated within the commercially available vector systems that accompany the various heterologous expression systems. Expression of the toxin can be targeted to the intracellular or extracellular compartments of the host cell through the manipulation of signal peptides. The reengineered toxins may be expressed in fragments in different expression systems or created synthetically and then subsequently reconstituted into functional reengineered pore-forming toxins using purified components.

Due to the challenges of expressing large fusion proteins in soluble form, it may be advantageous to separately express different domains of these fusion proteins followed by chemical conjugation or enzymatic ligation. Either the toxin fusion or the protease fusion may be prepared using this strategy. For example, the cell-targeting moiety replacing the small lobe and the large lobe of aerolysin may be expressed in properly tagged subunits, which can then be crosslinked using various protein conjugation and ligation methods, including native chemical ligation (Yeo et al., Chem. Eur. J. 10:4664 (2004)), transglutaminase catalyzed ligation through the formation of a $\gamma$-glutamyl-$\epsilon$-lysyl bond (Ota et al., Biopolymers 50(2):193 (1999)), and sortase-mediated ligation through a sequence specific transpeptidation (Mao et al., J. Am. Chem. Soc. 126: 2670 (2004)).

In another embodiment, functional toxins may be generated through refolding insoluble toxins through rapid dilution or stepwise removal of denaturant in the presence of additives that prevent aggregation.

III. Protoxin Activator Fusion Protein Constructs

As described above, the invention features protoxin activator fusion proteins containing a cell targeting moiety and a modification domain. In a preferred embodiment, the modification domain includes the activity of an exogenous protease.

A. Exogenous Protease Selection

An exogenous protease and corresponding cleavage site may be chosen for the present invention based on the following considerations. The protease is preferably capable of cleaving a protoxin activation moiety without significantly inactivating the protoxin or itself. The protease is preferably not naturally found in or on cells that are desired to be spared, with the exception that the protease can be naturally found in such cells if its natural location does not allow it to activate an externally administered protoxin. For example, an intracellular protease such as a caspase may be used if the toxin must be activated at the surface of the cell or in some intracellular vesicular compartment that does not naturally contain the intracellular protease, such as the endosome, golgi, or endoplasmic reticulum. In such cases the cells that are desired to be spared could contain the protease but the protease would not activate the protoxin.

The catalytic activity of the protease Is preferably stable to in vivo conditions for the time required to exert its therapeutic effect in vivo. If the therapeutic program requires the repeat administration of the protease, the protease is preferably resistant to interference by the formation of antibodies that impair its function, for example neutralizing antibodies. In some embodiments the protease has low immunogenicity or can be optionally substituted to reduce immunogenicity or can be optionally substituted to reduce the effect of antibodies on its activity. The protease preferably has low toxicity itself or has low toxicity in the form of its operable linkage with one or more cell surface binding moieties. The protease is preferably stable or can be made to be stable to conditions associated with the manufacturing and distribution of therapeutic products. The protease is preferably a natural protease, a modified protease, or an artificial enzyme.

Desirable proteases of the present invention include those known to have highly specific substrate selectivities, either by virtue of an extended catalytic site or by the presence of specific substrate-recognition modules that endow a relatively nonselective protease with appropriate specificity. Proteases of limited selectivity can also be made more selective by genetic mutation or chemical modification of residues close to the substrate-binding pocket.

As is known in the art, many proteases recognize certain cleavage sites, and some specific, non-limiting examples are given below. One of skill in the art would understand that cleavage sites other than those listed are recognized by the listed proteases, and can be used as a general protease cleavage site according to the present invention.

Proteases of human origin are preferred embodiments of the present invention due to reduced risk of immunogenicity. A human protease utilizing any catalytic mechanism, i.e., the nature of the amino acid residue or cofactor at the active site that is involved in the hydrolysis of the peptides and proteins, including aspartic proteases, cysteine proteases, metalloproteases, serine proteases, and threonine proteases, may be useful for the present invention.

Because model studies of a potential therapeutic agent must be conducted in animals to determine such properties as toxicity, efficacy, and pharmacokinetics prior to clinical trials in human, the presence of proteinase inhibitors in the plasma of animals could also limit the development of therapeutics comprising proteolytic activities. The proteinase inhibitors in animal plasma can possess inhibitory properties that are different from their human counterparts. For example human GrB has been found to be inhibited by mouse serpina3n, which is secreted by cultured Sertoli cells and is the major component of serpina3 ($\alpha_1$-antichymotrypsin) present in mouse plasma (Sipione et at., J. Immunol. 177:5051-5058 (2006)). However, the human $\alpha_1$-antichymotrypsin has not been shown to be an inhibitor of human GrB. The difference between mouse and human plasma protease inhibitors may be traced to their genetic differences. Whereas the major human plasma protease inhibitors, $\alpha_1$-antitrypsin and $\alpha_1$-antichymotrypsin, are each encoded by a single gene, in the mouse they are represented by clusters of 5 and 14 genes, respectively. Even though there is a high degree of overall sequence similarity within these clusters of inhibitors, the reactive-center loop (RCL) domain, which determines target protease specificity, is markedly divergent. To overcome inhibition by mouse proteases, the screening and mutagenesis strategies described herein can be applied to identify mutant proteases that are resistant to inhibition by inhibitors present in the animal model of choice.

Human Granzymes

Recombinant human granzyme B (GrB) may be used as an exogenous protease within the protease fusion protein. GrB has high substrate sequence specificity with a consensus recognition sequence of IEPD and is known to cleave only a limited number of natural substrates. GrB is found in cytoplasmic granules of cytotoxic T-lymphocytes and natural killer cells, and thus should be useful for the present invention provided these cells are not the targeted cells. The optimum pH for GrB activity is around pH 8, but it retains its activity between pH 5.5 and pH 9.5 (Fynbo et al., Protein Expr. Purif. 39:209 (2005)). GrB cleaves peptides containing IEPD with high efficiency and specificity (Harris et al., J. Biol. Chem. 273:27364 (1998)). Because GrB is involved in regulating programmed cell death, it is tightly regulated in vivo. In addition, GrB is a single chain and single domain serine protease, which could contribute to a simpler composite structure of the fusion protein. Moreover, GrB has recently been found to be very stable in general, and it performs very well in the cleavage of different fusion proteins (Fynbo et al., Protein Expr. Purif. 39:209 (2005)).

Any member of the granzyme family of serine proteases, e.g., granzyme A and granzyme M, may be used as the recombinant protease component of the protease fusion in this invention. For example, granzyme M (GrM) is specifically found in the granules of natural killer cells and can hydrolyze the peptide sequence KV(Y)PL(M) with high efficiency and specificity (Mahrus et al., J: Biol. Chem. 279:54275 (2004)).

In designing and utilizing protease fusions of the invention, it should be noted that proteinase inhibitors may hamper the proteolytic activities of protease fusion proteins. For example, GrB is specifically inhibited by intracellular proteinase inhibitor 9 (PI-9), a member of the serpin superfamily that primarily exists in cytotoxic lymphocytes (Sun et al., J. Biol. Chem. 271:27802 (1996)) and has been detected in human plasma. GrB can also be inhibited by $\alpha_1$-protease inhibitor ($\alpha_1$PI) that is present in human plasma (Poe et al., J. Biol. Chem. 266:98 (1991)). GrM is inhibited by $\alpha_1$-antichymotrypsin (ACT) and $\alpha_1$PI (Mahrus et al., J. Biol. Chem. 279:54275 (2004)), and GrA is inhibited in vitro by protease inhibitors antithrombin III (ATIII) and $\alpha$2-macroglobulin ($\alpha_2$M) (Spaeny-Dekking et al., Blood 95:1465 (2000)). These proteinase inhibitors are also present in human plasma (Travis and Salvesen, Annu. Rev. Biochem. 52:655 (1983)).

One approach to preserve proteolytic activities of granzymes is to utilize complexation with proteoglycan, since the mature and active form of GrA has been observed in human plasma as a complex with serglycin, a granule-associated proteoglycan (Spaeny-Dekking et al., Blood 95:1465 (2000)). Glycosaminglycan complexes of GrB have also been found proteolytically active (Galvin et al., J. Immunol. 162: 5345 (1999)). Thus, it may be possible to keep granzyme fusion proteins active in plasma through formulations using chondroitin sulfates.

Cathepsins and Caspases

Any member of the cathepsins (Chwieralski et al., Apoptosis 11:143 (2006)), e.g., cathepsin A, B, C, D, E, F, G, H, K, L, S, W, and X, may also be used as the recombinant protease for the present invention. Cathepsins are proteases that are localized intralysosomally under physiologic conditions, and therefore have optimum activity in acidic environments. Cathepsins comprise proteases of different enzyme classes; e.g., cathepsins A and G are serine proteases, cathepsins D and E are aspartic proteases. Certain cathepsins are caspases, a unique family of cysteine proteases that play a central role in the initiation and execution phases of apoptosis. Among all known mammalian proteases, only the serine protease granzyme B has substrate specificity similar to the caspases.

A cathepsin or caspase can be used as an exogenous activator or proactivator only if the protoxin to be activated is not exposed to that cathepsin or caspase prior to internalization (in the case of toxins that must be internalized) or during the course of the natural formation of the active toxin. For example, the protoxins of pore-forming toxins are activated at the cell surface, followed by oligomerization and pore formation. Because pore forming toxins do not localize to lysosome, cathepsins and caspases can be applied as exogenous activators. On the other hand, because the A-B toxin DT is known to be translocated directly into the cytosol through the endosome and/or lysosome, where cathepsins naturally reside, cathepsins should not be used as exogenous activators for DT-based protoxins. Other A-B toxins such as PEA may be compatible with the use of lysosomal proteases as exogenous activators, because they are transported to the trans-Golgi network and the ER before the translocation into cytosol. The bacterial toxins that can utilize cathepsins or other lysosomal proteases as exogenous activators include, but not limited to, PEA, shiga toxin, cholera toxin, and pertussis toxin. The bacterial toxins that are not suited for such use include DT, anthrax toxin, and clostridial neurotoxins (Falnes and Sandvig, Curr. Opin. Cell Biol. 2000, 12(4):407-13).

All caspases, including caspase-1, -2, -3, -4, -5, -6, -7, -8, -9 and more, show high selectivity and cleave proteins adjacent to an aspartate residue (Timmer and Salvesen, Cell Death Diff. 14:66-72 (2007)). The preferred cleavage site for caspase-1, 4, -5, and -14 are (W/Y)EXD↓Φ, where X is any residue and Φ represents a Gly, Ala, Thr, Ser, or Asn (SEQ ID NO:50). The preferred substrate for caspase-8, -9, and -10 contains the sequence of (I/L)EXD↓Φ (SEQ ID NO:51), and that of caspase-3 and -7 contains DEXD↓Φ (SEQ ID NO:52). Caspase-6 preferably cleaves at VEXD↓Φ (SEQ ID NO:53), while caspase-2 selectively targets (V/L)DEXD↓Φ(SEQ ID NO:54). Because the naturally occurring inhibitors of caspases, e.g., IAPs, are usually located intracellularly (LeBlanc, Prog. Neuropsychopharmacol. Biol. Psychiatry 27:215 (2003)), the probability of inhibition in plasma is dramatically reduced. Although caspase-1 and caspase-4 can be inhibited by PI-9 at moderate rates, it does not inhibit caspase-3 (Annand et al., Biochem. J. 342:655 (1999)).

Other Human Proteases

Many human proteases, including those have been identified as certain disease markers secreted by diseased cells, or associated with cancer invasion and metastasis, may be useful for the present invention as the heterologous protease. These proteases are well studied and detailed information on proteolytic activity and sequence selectivity is available. Examples of such proteases include urokinase plasminogen activator (uPA), which recognizes and cleaves GSGR↓SA (SEQ ID NO:55); prostate-specific antigen (PSA), which prefers substrate sequence SS(Y/F)Y↓SG (SEQ ID NO:56); renin, which cleaves at HPFHL↓VIH (SEQ ID NO:57); and MMP-2, which can cleave at HPVG↓LLAR (SEQ ID NO:58). Additional examples include the caspases, elastase, kallikreins, the matrix metalloprotease (MMP) family, the plasminogen activator family, as well as fibroblast activation protein.

In certain cases, the protease involved in one disease may be useful for the treatment of another disease that does not usually involve its overexpression. In other instances, the concentration of the secreted protease at native level may not be sufficient to activate corresponding toxin fusion to the extent that is necessary for targeted cell killing, i.e., is not operably present on the targeted cells. Additional proteolytic activity delivered to the cells through targeted protease fusion would provide desired toxin activation. In one embodiment, the protease fusion could have the same sequence specificity as the protease secreted by the diseased cells. In another embodiment, it may be desirable to use a combination of multiple, different, proteolytic cleavage activities to increase overall cleavage efficiency, with at least one of the proteolytic activity being provided by a targeted protease fusion.

Additional examples of endogenous proteases include those have been identified as certain disease markers, which are upregulated in certain disease. Non-limiting examples of such proteases include urokinase plasminogen activator (uPA), which recognizes and cleaves GSGR↓SA (SEQ ID NO:55); prostate-specific antigen (PSA), which prefers substrate sequence SS(Y/F)Y↓SG (SEQ ID NO:56); renin, which cleaves at HPFHL↓VIH (SEQ ID NO:57); and MMP-2, which can cleave at HPVG↓LLAR (SEQ ID NO:58).

Alternatively, potential candidate proteases may be screened in vitro by interactions with known proteinase inhibitors in plasma or with human plasma directly to avoid potential complications posed by these proteinase inhibitors. Alternatively, proteases for which cognate inhibitors are found in plasma can be engineered to provide mutant forms that resist inhibition. For example, in vitro *E. coli* expression-screening methods have been developed to select mutant proteases that are resistant to known HIV-1 protease inhibitors (Melnick et al., Antimicrob. Agents Chemother. 42:3256 (1998)).

Retroviral proteases may also be used for the present invention. Human retroviral proteases, including that of human immunodeficiency virus type 1 (HIV-1) (Beck et al., 2002), human T cell leukemia viruses (HTLV) (Shuker et al., Chem. Biol. 10:373 (2003)), and have been extensively studied as targets of anti-viral therapy. These proteases often have long recognition sequences and high substrate selectivity.

Picornaviral proteases may also be used for the present invention. Such picornaviral proteases have been studied as targets of anti-viral therapy, for example human Rhinovirus (HRV) (Binford et al., Antimicrob. Agents Chemother. 49:619 (2005)).

Recombinant heterologous proteases of any origin may be engineered to possess the aforementioned qualities and be used for the present invention. For example, tobacco etch virus (TEV) protease has very high substrate specificity and catalytic efficiency, and is used widely as a tool to remove peptide tags from recombinant proteins (Nunn et al., J. Mol. Biol. 350:145 (2005)). TEV protease recognizes an extended seven amino acid residue long consensus sequence E-X-X-Y-X-Q↓S/G (where X is any residue) (SEQ ID NO:59) that is present at protein junctions. Those skilled in the art would recognize that it is possible to engineer a particular protease such that its sequence specificity is altered to prefer another substrate sequence (Tozser et al., FEBS J. 272:514 (2005)).

Further modifications can be engineered to increase the activity and/or specificity of proteases. These modifications include PEGylation to increase stability to serum or to lower immunogenicity, and genetic engineering/selection may produce mutant proteases that possess altered properties such as resistance to certain inhibitors, increased thermal stability, and improved solubility.

Additional human proteases are set forth in Table 2.

| Clan | Family | MEROPS ID | Peptidase or homologue (subtype) | MERNUM | Gene | Link | Locus |
|---|---|---|---|---|---|---|---|
| AA | A1 | A01.001 | pepsin A | MER00885 | PGA3 | 5220 | 11q13 |
| | | A01.003 | gastricsin | MER00894 | PGC | 5225 | 6p21.3-p21.1 |
| | | A01.004 | memapsin-2 | MER05870 | BACE1 | 23621 | 11q23.3-q24.1 |
| | | A01.006 | chymosin | MER02929 | CYMP | 1542 | 1 |
| | | A01.007 | renin | MER00917 | REN | 5972 | 1q32 |
| | | A01.009 | cathepsin D | MER00911 | CTSD | 1509 | 11p15.5 |
| | | A01.010 | cathepsin E | MER00944 | CTSE | 1510 | 1q31 |
| | | A01.041 | memapsin-1 | MER05534 | BACE2 | 25825 | 21pter-qter |
| | | A01.046 | napsin A | MER04981 | NAPSA | 9476 | 19q13.33 |
| | | A01.057 | Mername-AA034 peptidase (deduced from nucleotide sequence by MEROPS) | MER14038 | | | 1q23.3-24.3 |
| | | A01.071 | pepsin A5 (*Homo sapiens*) | MER37291 | PGA5 | 5222 | 11q13 |
| | | A01.P01 | napsin B pseudogene (napsin B pseudogene) | MER04982 | NAPSB | 256236 | 19q13.33 |
| | A2 | A02.010 | mouse mammary tumor virus retropepsin (deduced from nucleotide sequence by MEROPS) | MER48030 | | | |
| | | A02.011 | human endogenous retrovirus K retropepsin (deduced from nucleotide sequence by MEROPS) | MER47534 | | | 5 |
| | | | human endogenous retrovirus K retropepsin | MER49453 | | | |
| | | | human endogenous retrovirus K retropepsin | MER00968 | | | 7 |
| | | A02.019 | multiple-sclerosis-associated retrovirus retropepsin (deduced from nucleotide sequence by MEROPS) | MER47079 | | | 16 |
| | | | multiple-sclerosis-associated retrovirus retropepsin (deduced from nucleotide sequence by MEROPS) | MER47096 | | | 4 |
| | | | multiple-sclerosis-associated retrovirus retropepsin (deduced from nucleotide sequence by MEROPS) | MER47119 | | | 19 |
| | | | multiple-sclerosis-associated retrovirus retropepsin (deduced from nucleotide sequence by MEROPS) | MER47124 | | | 7 |
| | | | multiple-sclerosis-associated retrovirus retropepsin (deduced from nucleotide sequence by MEROPS) | MER47138 | | | 7 |
| | | | multiple-sclerosis-associated retrovirus retropepsin (deduced from nucleotide sequence by MEROPS) | MER47145 | | | 2 |
| | | | multiple-sclerosis-associated retrovirus retropepsin (deduced from nucleotide sequence by MEROPS) | MER47153 | | | 19 |
| | | | multiple-sclerosis-associated retrovirus retropepsin (deduced from nucleotide sequence by MEROPS) | MER47162 | | | 5 |
| | | | multiple-sclerosis-associated retrovirus retropepsin (deduced from nucleotide sequence by MEROPS) | MER47241 | | | 4 |
| | | | multiple-sclerosis-associated retrovirus retropepsin (deduced from nucleotide sequence by MEROPS) | MER47244 | | | 15q21 |
| | | | multiple-sclerosis-associated retrovirus retropepsin (deduced from nucleotide sequence by MEROPS) | MER47256 | | | 8 |
| | | | multiple-sclerosis-associated retrovirus retropepsin (deduced from nucleotide sequence by MEROPS) | MER47257 | | | 8 |
| | | | multiple-sclerosis-associated retrovirus retropepsin (deduced from nucleotide sequence by MEROPS) | MER47264 | | | 11 |
| | | | multiple-sclerosis-associated retrovirus retropepsin (deduced from nucleotide sequence by MEROPS) | MER47271 | | | 12 |
| | | | multiple-sclerosis-associated retrovirus retropepsin (deduced from nucleotide sequence by MEROPS) | MER47313 | | | 3 |
| | | | multiple-sclerosis-associated retrovirus retropepsin (deduced from nucleotide sequence by MEROPS) | MER47390 | | | 2 |
| | | | multiple-sclerosis-associated retrovirus retropepsin (deduced from nucleotide sequence by MEROPS) | MER47402 | | | 3 |
| | | | multiple-sclerosis-associated retrovirus retropepsin (deduced from nucleotide sequence by MEROPS) | MER47412 | | | 3 |
| | | | multiple-sclerosis-associated retrovirus retropepsin (deduced from nucleotide sequence by MEROPS) | MER47446 | | | 8 |
| | | | multiple-sclerosis-associated retrovirus retropepsin (deduced from nucleotide sequence by MEROPS) | MER29837 | | | |
| | | | multiple-sclerosis-associated retrovirus retropepsin (deduced from nucleotide sequence by MEROPS) | MER47480 | | | 3 |
| | | | multiple-sclerosis-associated retrovirus retropepsin (deduced from nucleotide sequence by MEROPS) | MER47492 | | | 2 |
| | | | multiple-sclerosis-associated retrovirus retropepsin (deduced from nucleotide sequence by MEROPS) | MER47510 | | | 5 |
| | | | multiple-sclerosis-associated retrovirus retropepsin (deduced from nucleotide sequence by MEROPS) | MER48013 | | | |
| | | A02.024 | rabbit endogenous retrovirus endopeptidase | MER43650 | | | |
| | | A02.053 | S71-related human endogenous retropepsin | MER01812 | | | |
| | | A02.055 | RTVL-H-like putative peptidase (deduced from nucleotide sequence by MEROPS) | MER47133 | | | |
| | | | RTVL-H-like putative peptidase (deduced from nucleotide sequence by MEROPS) | MER47160 | | | 19 |
| | | | RTVL-H-like putative peptidase (deduced from nucleotide sequence by MEROPS) | MER47253 | | | 19 |
| | | | RTVL-H-like putative peptidase (deduced from nucleotide sequence by MEROPS) | MER47260 | | | 3 |

-continued

| Clan | Family | MEROPS ID | Peptidase or homologue (subtype) | MERNUM | Gene | Link | Locus |
|---|---|---|---|---|---|---|---|
| | | | RTVL-H-like putative peptidase (deduced from nucleotide sequence by MEROPS) | MER47418 | | | 4 |
| | | | RTVL-H-like putative peptidase (deduced from nucleotide sequence by MEROPS) | MER47440 | | | 1p33-p32 |
| | | | RTVL-H-like putative peptidase (pseudogene) | MER15446 | | 387590 | 22q11.2 |
| | | A02.056 | human endogenous retrovirus retropepsin homologue 1 (deduced from ESTs by MEROPS) | MER15479 | | | |
| | | A02.057 | human endogenous retrovirus retropepsin homologue 2 (deduced from ESTs by MEROPS) | MER15481 | | | |
| | | A02.P01 | endogenous retrovirus retropepsin pseudogene 1 (*Homo sapiens* chromosome 14) (deduced from nucleotide sequence by MEROPS) | MER29977 | | | 14q32.33 |
| | | A02.P02 | endogenous retrovirus retropepsin pseudogene 2 (*Homo sapiens* chromosome 8) (deduced from nucleotide sequence by MEROPS) | MER29665 | | | 8p21.3-p22 |
| | | A02.P03 | endogenous retrovirus retropepsin pseudogene 3 (*Homo sapiens* chromosome 17) | MER02660 | | | 17 |
| | | | endogenous retrovirus retropepsin pseudogene 3 (*Homo sapiens* chromosome 17) (deduced from nucleotide sequence by MEROPS) | MER30286 | | | |
| | | | endogenous retrovirus retropepsin pseudogene 3 (*Homo sapiens* chromosome 17) (deduced from nucleotide sequence by MEROPS) | MER47144 | | | 2 |
| | | A02.P04 | endogenous retrovirus retropepsin pseudogene 5 (*Homo sapiens* chromosome 12) (deduced from nucleotide sequence by MEROPS) | MER29664 | | | 12q13.1 |
| | | A02.P05 | endogenous retrovirus retropepsin pseudogene 6 (*Homo sapiens* chromosome 7) (deduced from nucleotide sequence by MEROPS) | MER02094 | | | 7 |
| | | A02.P06 | endogenous retrovirus retropepsin pseudogene 7 (*Homo sapiens* chromosome 6) (deduced from nucleotide sequence by MEROPS) | MER29776 | | | 6p21.3 |
| | | A02.P07 | endogenous retrovirus retropepsin pseudogene 8 (*Homo sapiens* chromosome Y) (deduced from nucleotide sequence by MEROPS) | MER30291 | | | Y |
| | | A02.P08 | endogenous retrovirus retropepsin pseudogene 9 (*Homo sapiens* chromosome 19) (deduced from nucleotide sequence by MEROPS) | MER29680 | | | 19 |
| | | A02.P09 | endogenous retrovirus retropepsin pseudogene 10 (*Homo sapiens* chromosome 12) (deduced from nucleotide sequence by MEROPS) | MER02848 | | | 12q23.3 |
| | | A02.P10 | endogenous retrovirus retropepsin pseudogene 11 (*Homo sapiens* chromosome 17) (deduced from nucleotide sequence by MEROPS) | MER04378 | | | 17 |
| | | A02.P11 | endogenous retrovirus retropepsin pseudogene 12 (*Homo sapiens* chromosome 11) (deduced from nucleotide sequence by MEROPS) | MER03344 | | | 11q11 |
| | | A02.P12 | endogenous retrovirus retropepsin pseudogene 13 (*Homo sapiens* chromosome 2 and similar) (deduced from nucleotide sequence by MEROPS) | MER29779 | | | 2 |
| | | A02.P13 | endogenous retrovirus retropepsin pseudogene 14 (*Homo sapiens* chromosome 2) (deduced from nucleotide sequence by MEROPS) | MER29778 | | | 2 |
| | | A02.P14 | endogenous retrovirus retropepsin pseudogene 15 (*Homo sapiens* chromosome 4) (deduced from nucleotide sequence by MEROPS) | MER47158 | | | 19 |
| | | | endogenous retrovirus retropepsin pseudogene 15 (*Homo sapiens* chromosome 4) (deduced from nucleotide sequence by MEROPS) | MER47332 | | | 3 |
| | | | endogenous retrovirus retropepsin pseudogene 15 (*Homo sapiens* chromosome 4) (deduced from nucleotide sequence by MEROPS) | MER03182 | | | 4 |
| | | A02.P15 | endogenous retrovirus retropepsin pseudogene 16 (deduced from nucleotide sequence by MEROPS) | MER47165 | | | 19 |
| | | | endogenous retrovirus retropepsin pseudogene 16 (deduced from nucleotide sequence by MEROPS) | MER47178 | | | Y |
| | | | endogenous retrovirus retropepsin pseudogene 16 (deduced from nucleotide sequence by MEROPS) | MER47200 | | | 19 |
| | | | endogenous retrovirus retropepsin pseudogene 16 (deduced from nucleotide sequence by MEROPS) | MER47315 | | | 10 |
| | | | endogenous retrovirus retropepsin pseudogene 16 (deduced from nucleotide sequence by MEROPS) | MER47405 | | | 8 |
| | | | endogenous retrovirus retropepsin pseudogene 16 (deduced from nucleotide sequence by MEROPS) | MER30292 | | | 4 |

-continued

| Clan | Family | MEROPS ID | Peptidase or homologue (subtype) | MERNUM | Gene | Link | Locus |
|---|---|---|---|---|---|---|---|
| | | A02.P16 | endogenous retrovirus retropepsin pseudogene 17 (*Homo sapiens* chromosome 8) (deduced from nucleotide sequence by MEROPS) | MER05305 | | | 8 |
| | | A02.P17 | endogenous retrovirus retropepsin pseudogene 18 (*Homo sapiens* chromosome 4) (deduced from nucleotide sequence by MEROPS) | MER30288 | | | 4 |
| | | A02.P18 | endogenous retrovirus retropepsin pseudogene 19 (*Homo sapiens* chromosome 16) (deduced from nucleotide sequence by MEROPS) | MER01740 | | | 16p11.2 |
| | | A02.P19 | endogenous retrovirus retropepsin pseudogene 21 (*Homo sapiens*) (deduced from nucleotide sequence by MEROPS) | MER47222 | | | 11 |
| | | | endogenous retrovirus retropepsin pseudogene 21 (*Homo sapiens*) (deduced from nucleotide sequence by MEROPS) | MER47454 | | | 3p24.3 |
| | | | endogenous retrovirus retropepsin pseudogene 21 (*Homo sapiens*) (deduced from nucleotide sequence by MEROPS) | MER47477 | | | 4 |
| | | | endogenous retrovirus retropepsin pseudogene 21 (*Homo sapiens*) (deduced from nucleotide sequence by MEROPS) | MER04403 | | | |
| | | A02.P20 | endogenous retrovirus retropepsin pseudogene 22 (*Homo sapiens* chromosome X) (deduced from nucleotide sequence by MEROPS) | MER30287 | | | Xq22.1 |
| | | non-peptidase homologue | subfamily A2A non-peptidase homologues (deduced from nucleotide sequence by MEROPS) | MER47046 | | | 9q32 |
| | | | subfamily A2A non-peptidase homologues | MER47052 | | | 6q21 |
| | | | subfamily A2A non-peptidase homologues (deduced from nucleotide sequence by MEROPS) | MER47076 | | | X |
| | | | subfamily A2A non-peptidase homologues (deduced from nucleotide sequence by MEROPS) | MER47080 | | | 19 |
| | | | subfamily A2A non-peptidase homologues (deduced from nucleotide sequence by MEROPS) | MER47088 | | | Xq23 |
| | | | subfamily A2A non-peptidase homologues (deduced from nucleotide sequence by MEROPS) | MER47089 | | | 14q24.3 |
| | | | subfamily A2A non-peptidase homologues (deduced from nucleotide sequence by MEROPS) | MER47091 | | | 11 |
| | | | subfamily A2A non-peptidase homologues (deduced from nucleotide sequence by MEROPS) | MER47092 | | | |
| | | | subfamily A2A non-peptidase homologues (deduced from nucleotide sequence by MEROPS) | MER47093 | | | 7 |
| | | | subfamily A2A non-peptidase homologues (deduced from nucleotide sequence by MEROPS) | MER47094 | | | 2 |
| | | | subfamily A2A non-peptidase homologues (deduced from nucleotide sequence by MEROPS) | MER47097 | | | 2 |
| | | | subfamily A2A non-peptidase homologues (deduced from nucleotide sequence by MEROPS) | MER47099 | | | 7q31.3 |
| | | | subfamily A2A non-peptidase homologues (deduced from nucleotide sequence by MEROPS) | MER47101 | | | |
| | | | subfamily A2A non-peptidase homologues (deduced from nucleotide sequence by MEROPS) | MER47102 | | | 17 |
| | | | subfamily A2A non-peptidase homologues (deduced from nucleotide sequence by MEROPS) | MER47107 | | | 7 |
| | | | subfamily A2A non-peptidase homologues (deduced from nucleotide sequence by MEROPS) | MER47108 | | | 4p16 |
| | | | subfamily A2A non-peptidase homologues (deduced from nucleotide sequence by MEROPS) | MER47109 | | | |
| | | | subfamily A2A non-peptidase homologues (deduced from nucleotide sequence by MEROPS) | MER47110 | | | X |
| | | | subfamily A2A non-peptidase homologues (deduced from nucleotide sequence by MEROPS) | MER47111 | | | 17 |
| | | | subfamily A2A non-peptidase homologues (deduced from nucleotide sequence by MEROPS) | MER47114 | | | 18 |
| | | | subfamily A2A non-peptidase homologues (deduced from nucleotide sequence by MEROPS) | MER47118 | | | |
| | | | subfamily A2A non-peptidase homologues (deduced from nucleotide sequence by MEROPS) | MER47121 | | | X |
| | | | subfamily A2A non-peptidase homologues (deduced from nucleotide sequence by MEROPS) | MER47122 | | | 4p16 |
| | | | subfamily A2A non-peptidase homologues (deduced from nucleotide sequence by MEROPS) | MER47126 | | | Y |
| | | | subfamily A2A non-peptidase homologues (deduced from nucleotide sequence by MEROPS) | MER47129 | | | 7 |
| | | | subfamily A2A non-peptidase homologues (deduced from nucleotide sequence by MEROPS) | MER47130 | | | Y |
| | | | subfamily A2A non-peptidase homologues (deduced from nucleotide sequence by MEROPS) | MER47134 | | | 12p13 |
| | | | subfamily A2A non-peptidase homologues (deduced from nucleotide sequence by MEROPS) | MER47135 | | | |

-continued

| Clan | Family | MEROPS ID | Peptidase or homologue (subtype) | MERNUM | Gene | Link | Locus |
|---|---|---|---|---|---|---|---|
| | | | subfamily A2A non-peptidase homologues (deduced from nucleotide sequence by MEROPS) | MER47137 | | | 12p13 |
| | | | subfamily A2A non-peptidase homologues (deduced from nucleotide sequence by MEROPS) | MER47140 | | | 16 |
| | | | subfamily A2A non-peptidase homologues (deduced from nucleotide sequence by MEROPS) | MER47141 | | | 3 |
| | | | subfamily A2A non-peptidase homologues (deduced from nucleotide sequence by MEROPS) | MER47142 | | | Y |
| | | | subfamily A2A non-peptidase homologues (deduced from nucleotide sequence by MEROPS) | MER47148 | | | 2 |
| | | | subfamily A2A non-peptidase homologues (deduced from nucleotide sequence by MEROPS) | MER47149 | | | 3q26.2-27 |
| | | | subfamily A2A non-peptidase homologues (deduced from nucleotide sequence by MEROPS) | MER47151 | | | 5 |
| | | | subfamily A2A non-peptidase homologues (deduced from nucleotide sequence by MEROPS) | MER47154 | | | 5 |
| | | | subfamily A2A non-peptidase homologues (deduced from nucleotide sequence by MEROPS) | MER47155 | | | 5 |
| | | | subfamily A2A non-peptidase homologues (deduced from nucleotide sequence by MEROPS) | MER47156 | | | 5 |
| | | | subfamily A2A non-peptidase homologues (deduced from nucleotide sequence by MEROPS) | MER47157 | | | 19 |
| | | | subfamily A2A non-peptidase homologues (deduced from nucleotide sequence by MEROPS) | MER47159 | | | 19 |
| | | | subfamily A2A non-peptidase homologues (deduced from nucleotide sequence by MEROPS) | MER47161 | | | 19 |
| | | | subfamily A2A non-peptidase homologues (deduced from nucleotide sequence by MEROPS) | MER47163 | | | 5 |
| | | | subfamily A2A non-peptidase homologues (deduced from nucleotide sequence by MEROPS) | MER47166 | | | 2 |
| | | | subfamily A2A non-peptidase homologues (deduced from nucleotide sequence by MEROPS) | MER47171 | | | 18 |
| | | | subfamily A2A non-peptidase homologues (deduced from nucleotide sequence by MEROPS) | MER47173 | | | |
| | | | subfamily A2A non-peptidase homologues (deduced from nucleotide sequence by MEROPS) | MER47174 | | | 2 |
| | | | subfamily A2A non-peptidase homologues (deduced from nucleotide sequence by MEROPS) | MER47179 | | | 2 |
| | | | subfamily A2A non-peptidase homologues (deduced from nucleotide sequence by MEROPS) | MER47183 | | | Y |
| | | | subfamily A2A non-peptidase homologues (deduced from nucleotide sequence by MEROPS) | MER47186 | | | 19 |
| | | | subfamily A2A non-peptidase homologues (deduced from nucleotide sequence by MEROPS) | MER47190 | | | 19 |
| | | | subfamily A2A non-peptidase homologues (deduced from nucleotide sequence by MEROPS) | MER47191 | | | 19 |
| | | | subfamily A2A non-peptidase homologues (deduced from nucleotide sequence by MEROPS) | MER47196 | | | Y |
| | | | subfamily A2A non-peptidase homologues (deduced from nucleotide sequence by MEROPS) | MER47198 | | | 10q22.3 |
| | | | subfamily A2A non-peptidase homologues (deduced from nucleotide sequence by MEROPS) | MER47199 | | | 19 |
| | | | subfamily A2A non-peptidase homologues (deduced from nucleotide sequence by MEROPS) | MER47201 | | | 19 |
| | | | subfamily A2A non-peptidase homologues (deduced from nucleotide sequence by MEROPS) | MER47202 | | | |
| | | | subfamily A2A non-peptidase homologues (deduced from nucleotide sequence by MEROPS) | MER47203 | | | |
| | | | subfamily A2A non-peptidase homologues (deduced from nucleotide sequence by MEROPS) | MER47204 | | | 8 |
| | | | subfamily A2A non-peptidase homologues (deduced from nucleotide sequence by MEROPS) | MER47205 | | | Y |
| | | | subfamily A2A non-peptidase homologues (deduced from nucleotide sequence by MEROPS) | MER47207 | | | 3 |
| | | | subfamily A2A non-peptidase homologues (deduced from nucleotide sequence by MEROPS) | MER47208 | | | 12p11.22 |
| | | | subfamily A2A non-peptidase homologues (deduced from nucleotide sequence by MEROPS) | MER47210 | | | 2 |
| | | | subfamily A2A non-peptidase homologues (deduced from nucleotide sequence by MEROPS) | MER47211 | | | 3 |
| | | | subfamily A2A non-peptidase homologues (deduced from nucleotide sequence by MEROPS) | MER47212 | | | 5 |
| | | | subfamily A2A non-peptidase homologues (deduced from nucleotide sequence by MEROPS) | MER47213 | | | 5 |
| | | | subfamily A2A non-peptidase homologues (deduced from nucleotide sequence by MEROPS) | MER47215 | | | 15q25 |

-continued

| Clan | Family | MEROPS ID | Peptidase or homologue (subtype) | MERNUM | Gene | Link | Locus |
|---|---|---|---|---|---|---|---|
| | | | subfamily A2A non-peptidase homologues (deduced from nucleotide sequence by MEROPS) | MER47216 | | | 10p11.2-q21 |
| | | | subfamily A2A non-peptidase homologues (deduced from nucleotide sequence by MEROPS) | MER47218 | | | 8 |
| | | | subfamily A2A non-peptidase homologues (deduced from nucleotide sequence by MEROPS) | MER47219 | | | 11p14.3 |
| | | | subfamily A2A non-peptidase homologues (deduced from nucleotide sequence by MEROPS) | MER47221 | | | 15q21.3 |
| | | | subfamily A2A non-peptidase homologues (deduced from nucleotide sequence by MEROPS) | MER47224 | | | 2 |
| | | | subfamily A2A non-peptidase homologues (deduced from nucleotide sequence by MEROPS) | MER47225 | | | 2q33 |
| | | | subfamily A2A non-peptidase homologues (deduced from nucleotide sequence by MEROPS) | MER47226 | | | 8 |
| | | | subfamily A2A non-peptidase homologues (deduced from nucleotide sequence by MEROPS) | MER47227 | | | 8 |
| | | | subfamily A2A non-peptidase homologues (deduced from nucleotide sequence by MEROPS) | MER47230 | | | 10 |
| | | | subfamily A2A non-peptidase homologues (deduced from nucleotide sequence by MEROPS) | MER47232 | | | 7 |
| | | | subfamily A2A non-peptidase homologues (deduced from nucleotide sequence by MEROPS) | MER47233 | | | 16 |
| | | | subfamily A2A non-peptidase homologues (deduced from nucleotide sequence by MEROPS) | MER47234 | | | 11p15.4 |
| | | | subfamily A2A non-peptidase homologues (deduced from nucleotide sequence by MEROPS) | MER47236 | | | 2 |
| | | | subfamily A2A non-peptidase homologues (deduced from nucleotide sequence by MEROPS) | MER47238 | | | 2 |
| | | | subfamily A2A non-peptidase homologues (deduced from nucleotide sequence by MEROPS) | MER47239 | | | 7 |
| | | | subfamily A2A non-peptidase homologues (deduced from nucleotide sequence by MEROPS) | MER47240 | | | 2 |
| | | | subfamily A2A non-peptidase homologues (deduced from nucleotide sequence by MEROPS) | MER47242 | | | 4 |
| | | | subfamily A2A non-peptidase homologues (deduced from nucleotide sequence by MEROPS) | MER47243 | | | 4 |
| | | | subfamily A2A non-peptidase homologues (deduced from nucleotide sequence by MEROPS) | MER47249 | | | 5 |
| | | | subfamily A2A non-peptidase homologues (deduced from nucleotide sequence by MEROPS) | MER47251 | | | 18 |
| | | | subfamily A2A non-peptidase homologues (deduced from nucleotide sequence by MEROPS) | MER47252 | | | 12p13 |
| | | | subfamily A2A non-peptidase homologues (deduced from nucleotide sequence by MEROPS) | MER47254 | | | 17 |
| | | | subfamily A2A non-peptidase homologues (deduced from nucleotide sequence by MEROPS) | MER47255 | | | 15q15 |
| | | | subfamily A2A non-peptidase homologues (deduced from nucleotide sequence by MEROPS) | MER47263 | | | 5 |
| | | | subfamily A2A non-peptidase homologues (deduced from nucleotide sequence by MEROPS) | MER47265 | | | 12 |
| | | | subfamily A2A non-peptidase homologues (deduced from nucleotide sequence by MEROPS) | MER47266 | | | 10 |
| | | | subfamily A2A non-peptidase homologues (deduced from nucleotide sequence by MEROPS) | MER47267 | | | 5 |
| | | | subfamily A2A non-peptidase homologues (deduced from nucleotide sequence by MEROPS) | MER47268 | | | 3 |
| | | | subfamily A2A non-peptidase homologues (deduced from nucleotide sequence by MEROPS) | MER47269 | | | 5 |
| | | | subfamily A2A non-peptidase homologues (deduced from nucleotide sequence by MEROPS) | MER47272 | | | 3 |
| | | | subfamily A2A non-peptidase homologues (deduced from nucleotide sequence by MEROPS) | MER47273 | | | 10 |
| | | | subfamily A2A non-peptidase homologues (deduced from nucleotide sequence by MEROPS) | MER47274 | | | 10q23.32 |
| | | | subfamily A2A non-peptidase homologues (deduced from nucleotide sequence by MEROPS) | MER47275 | | | 3 |
| | | | subfamily A2A non-peptidase homologues (deduced from nucleotide sequence by MEROPS) | MER47276 | | | 3 |
| | | | subfamily A2A non-peptidase homologues (deduced from nucleotide sequence by MEROPS) | MER47279 | | | 5 |
| | | | subfamily A2A non-peptidase homologues (deduced from nucleotide sequence by MEROPS) | MER47280 | | | 5 |
| | | | subfamily A2A non-peptidase homologues (deduced from nucleotide sequence by MEROPS) | MER47281 | | | 5 |
| | | | subfamily A2A non-peptidase homologues (deduced from nucleotide sequence by MEROPS) | MER47282 | | | 5 |

-continued

| Clan | Family | MEROPS ID | Peptidase or homologue (subtype) | MERNUM | Gene | Link | Locus |
|---|---|---|---|---|---|---|---|
| | | | subfamily A2A non-peptidase homologues (deduced from nucleotide sequence by MEROPS) | MER47284 | | | 15q26.2 |
| | | | subfamily A2A non-peptidase homologues (deduced from nucleotide sequence by MEROPS) | MER47285 | | | 11q11 |
| | | | subfamily A2A non-peptidase homologues (deduced from nucleotide sequence by MEROPS) | MER47289 | | | 16 |
| | | | subfamily A2A non-peptidase homologues (deduced from nucleotide sequence by MEROPS) | MER47290 | | | 2 |
| | | | subfamily A2A non-peptidase homologues (deduced from nucleotide sequence by MEROPS) | MER47294 | | | 2 |
| | | | subfamily A2A non-peptidase homologues (deduced from nucleotide sequence by MEROPS) | MER47295 | | | 3p |
| | | | subfamily A2A non-peptidase homologues (deduced from nucleotide sequence by MEROPS) | MER47298 | | | 2 |
| | | | subfamily A2A non-peptidase homologues (deduced from nucleotide sequence by MEROPS) | MER47300 | | | 2 |
| | | | subfamily A2A non-peptidase homologues (deduced from nucleotide sequence by MEROPS) | MER47302 | | | 8 |
| | | | subfamily A2A non-peptidase homologues (deduced from nucleotide sequence by MEROPS) | MER47304 | | | 15q15 |
| | | | subfamily A2A non-peptidase homologues (deduced from nucleotide sequence by MEROPS) | MER47305 | | | 11p15 |
| | | | subfamily A2A non-peptidase homologues (deduced from nucleotide sequence by MEROPS) | MER47306 | | | 3 |
| | | | subfamily A2A non-peptidase homologues (deduced from nucleotide sequence by MEROPS) | MER47307 | | | 3 |
| | | | subfamily A2A non-peptidase homologues (deduced from nucleotide sequence by MEROPS) | MER47310 | | | Y |
| | | | subfamily A2A non-peptidase homologues (deduced from nucleotide sequence by MEROPS) | MER47311 | | | 3 |
| | | | subfamily A2A non-peptidase homologues (deduced from nucleotide sequence by MEROPS) | MER47314 | | | 2 |
| | | | subfamily A2A non-peptidase homologues (deduced from nucleotide sequence by MEROPS) | MER47318 | | | 2 |
| | | | subfamily A2A non-peptidase homologues (deduced from nucleotide sequence by MEROPS) | MER47320 | | | Xp |
| | | | subfamily A2A non-peptidase homologues (deduced from nucleotide sequence by MEROPS) | MER47321 | | | 2 |
| | | | subfamily A2A non-peptidase homologues (deduced from nucleotide sequence by MEROPS) | MER47322 | | | 7 |
| | | | subfamily A2A non-peptidase homologues (deduced from nucleotide sequence by MEROPS) | MER47326 | | | 12 |
| | | | subfamily A2A non-peptidase homologues (deduced from nucleotide sequence by MEROPS) | MER47327 | | | Xp |
| | | | subfamily A2A non-peptidase homologues (deduced from nucleotide sequence by MEROPS) | MER47330 | | | 4 |
| | | | subfamily A2A non-peptidase homologues (deduced from nucleotide sequence by MEROPS) | MER47333 | | | 18 |
| | | | subfamily A2A non-peptidase homologues (deduced from nucleotide sequence by MEROPS) | MER47362 | | | 15 |
| | | | subfamily A2A non-peptidase homologues (deduced from nucleotide sequence by MEROPS) | MER47366 | | | 8 |
| | | | subfamily A2A non-peptidase homologues (deduced from nucleotide sequence by MEROPS) | MER47369 | | | 11 |
| | | | subfamily A2A non-peptidase homologues (deduced from nucleotide sequence by MEROPS) | MER47370 | | | 18 |
| | | | subfamily A2A non-peptidase homologues (deduced from nucleotide sequence by MEROPS) | MER47371 | | | 18 |
| | | | subfamily A2A non-peptidase homologues (deduced from nucleotide sequence by MEROPS) | MER47375 | | | 11p15.2-p15.1 |
| | | | subfamily A2A non-peptidase homologues (deduced from nucleotide sequence by MEROPS) | MER47376 | | | 15q22-q24 |
| | | | subfamily A2A non-peptidase homologues (deduced from nucleotide sequence by MEROPS) | MER47381 | | | Xq23 |
| | | | subfamily A2A non-peptidase homologues (deduced from nucleotide sequence by MEROPS) | MER47383 | | | 15 |
| | | | subfamily A2A non-peptidase homologues (deduced from nucleotide sequence by MEROPS) | MER47384 | | | 7 |
| | | | subfamily A2A non-peptidase homologues (deduced from nucleotide sequence by MEROPS) | MER47385 | | | 12p13 |
| | | | subfamily A2A non-peptidase homologues (deduced from nucleotide sequence by MEROPS) | MER47388 | | | 3 |
| | | | subfamily A2A non-peptidase homologues (deduced from nucleotide sequence by MEROPS) | MER47389 | | | 3 |
| | | | subfamily A2A non-peptidase homologues (deduced from nucleotide sequence by MEROPS) | MER47391 | | | 12p |

-continued

| Clan | Family | MEROPS ID | Peptidase or homologue (subtype) | MERNUM | Gene | Link | Locus |
|---|---|---|---|---|---|---|---|
| | | | subfamily A2A non-peptidase homologues (deduced from nucleotide sequence by MEROPS) | MER47394 | | | 2 |
| | | | subfamily A2A non-peptidase homologues (deduced from nucleotide sequence by MEROPS) | MER47396 | | | 2 |
| | | | subfamily A2A non-peptidase homologues (deduced from nucleotide sequence by MEROPS) | MER47400 | | | 12 |
| | | | subfamily A2A non-peptidase homologues (deduced from nucleotide sequence by MEROPS) | MER47401 | | | 3 |
| | | | subfamily A2A non-peptidase homologues (deduced from nucleotide sequence by MEROPS) | MER47403 | | | 3 |
| | | | subfamily A2A non-peptidase homologues (deduced from nucleotide sequence by MEROPS) | MER47406 | | | 2 |
| | | | subfamily A2A non-peptidase homologues (deduced from nucleotide sequence by MEROPS) | MER47407 | | | 1 |
| | | | subfamily A2A non-peptidase homologues (deduced from nucleotide sequence by MEROPS) | MER47410 | | | 5 |
| | | | subfamily A2A non-peptidase homologues (deduced from nucleotide sequence by MEROPS) | MER47411 | | | 5 |
| | | | subfamily A2A non-peptidase homologues (deduced from nucleotide sequence by MEROPS) | MER47413 | | | 1q42.12 |
| | | | subfamily A2A non-peptidase homologues (deduced from nucleotide sequence by MEROPS) | MER47414 | | | 8 |
| | | | subfamily A2A non-peptidase homologues (deduced from nucleotide sequence by MEROPS) | MER47416 | | | 4 |
| | | | subfamily A2A non-peptidase homologues (deduced from nucleotide sequence by MEROPS) | MER47417 | | | 4 |
| | | | subfamily A2A non-peptidase homologues (deduced from nucleotide sequence by MEROPS) | MER47420 | | | 5 |
| | | | subfamily A2A non-peptidase homologues (deduced from nucleotide sequence by MEROPS) | MER47423 | | | 4 |
| | | | subfamily A2A non-peptidase homologues (deduced from nucleotide sequence by MEROPS) | MER47424 | | | 4 |
| | | | subfamily A2A non-peptidase homologues (deduced from nucleotide sequence by MEROPS) | MER47428 | | | 4 |
| | | | subfamily A2A non-peptidase homologues (deduced from nucleotide sequence by MEROPS) | MER47429 | | | 4 |
| | | | subfamily A2A non-peptidase homologues (deduced from nucleotide sequence by MEROPS) | MER47431 | | | 4 |
| | | | subfamily A2A non-peptidase homologues (deduced from nucleotide sequence by MEROPS) | MER47434 | | | 2 |
| | | | subfamily A2A non-peptidase homologues (deduced from nucleotide sequence by MEROPS) | MER47439 | | | 7 |
| | | | subfamily A2A non-peptidase homologues (deduced from nucleotide sequence by MEROPS) | MER47442 | | | 11 |
| | | | subfamily A2A non-peptidase homologues (deduced from nucleotide sequence by MEROPS) | MER47445 | | | 18 |
| | | | subfamily A2A non-peptidase homologues (deduced from nucleotide sequence by MEROPS) | MER47449 | | | 8 |
| | | | subfamily A2A non-peptidase homologues (deduced from nucleotide sequence by MEROPS) | MER47450 | | | 8 |
| | | | subfamily A2A non-peptidase homologues (deduced from nucleotide sequence by MEROPS) | MER47452 | | | 1q44 |
| | | | subfamily A2A non-peptidase homologues (deduced from nucleotide sequence by MEROPS) | MER47455 | | | 4 |
| | | | subfamily A2A non-peptidase homologues (deduced from nucleotide sequence by MEROPS) | MER47457 | | | 4 |
| | | | subfamily A2A non-peptidase homologues (deduced from nucleotide sequence by MEROPS) | MER47458 | | | 3 |
| | | | subfamily A2A non-peptidase homologues (deduced from nucleotide sequence by MEROPS) | MER47459 | | | 8 |
| | | | subfamily A2A non-peptidase homologues (deduced from nucleotide sequence by MEROPS) | MER47463 | | | 4 |
| | | | subfamily A2A non-peptidase homologues (deduced from nucleotide sequence by MEROPS) | MER47468 | | | 4 |
| | | | subfamily A2A non-peptidase homologues (deduced from nucleotide sequence by MEROPS) | MER47469 | | | 4 |
| | | | subfamily A2A non-peptidase homologues (deduced from nucleotide sequence by MEROPS) | MER47470 | | | 3 |
| | | | subfamily A2A non-peptidase homologues (deduced from nucleotide sequence by MEROPS) | MER47476 | | | 4 |
| | | | subfamily A2A non-peptidase homologues (deduced from nucleotide sequence by MEROPS) | MER47478 | | | 5 |
| | | | subfamily A2A non-peptidase homologues (deduced from nucleotide sequence by MEROPS) | MER47483 | | | 16 |
| | | | subfamily A2A non-peptidase homologues (deduced from nucleotide sequence by MEROPS) | MER47488 | | | 2 |

-continued

| Clan | Family | MEROPS ID | Peptidase or homologue (subtype) | MERNUM | Gene | Link | Locus |
|---|---|---|---|---|---|---|---|
| | | | subfamily A2A non-peptidase homologues (deduced from nucleotide sequence by MEROPS) | MER47489 | | | 4 |
| | | | subfamily A2A non-peptidase homologues (deduced from nucleotide sequence by MEROPS) | MER47490 | | | 2 |
| | | | subfamily A2A non-peptidase homologues (deduced from nucleotide sequence by MEROPS) | MER47493 | | | 3 |
| | | | subfamily A2A non-peptidase homologues (deduced from nucleotide sequence by MEROPS) | MER47494 | | | 5 |
| | | | subfamily A2A non-peptidase homologues (deduced from nucleotide sequence by MEROPS) | MER47495 | | | 4 |
| | | | subfamily A2A non-peptidase homologues (deduced from nucleotide sequence by MEROPS) | MER47496 | | | 4 |
| | | | subfamily A2A non-peptidase homologues (deduced from nucleotide sequence by MEROPS) | MER47497 | | | 4 |
| | | | subfamily A2A non-peptidase homologues (deduced from nucleotide sequence by MEROPS) | MER47499 | | | 11p15.4 |
| | | | subfamily A2A non-peptidase homologues (deduced from nucleotide sequence by MEROPS) | MER47502 | | | 3 |
| | | | subfamily A2A non-peptidase homologues (deduced from nucleotide sequence by MEROPS) | MER47504 | | | 3 |
| | | | subfamily A2A non-peptidase homologues (deduced from nucleotide sequence by MEROPS) | MER47511 | | | 5 |
| | | | subfamily A2A non-peptidase homologues (deduced from nucleotide sequence by MEROPS) | MER47513 | | | 5 |
| | | | subfamily A2A non-peptidase homologues (deduced from nucleotide sequence by MEROPS) | MER47514 | | | 5 |
| | | | subfamily A2A non-peptidase homologues (deduced from nucleotide sequence by MEROPS) | MER47515 | | | 11p11.2 |
| | | | subfamily A2A non-peptidase homologues (deduced from nucleotide sequence by MEROPS) | MER47516 | | | 4 |
| | | | subfamily A2A non-peptidase homologues (deduced from nucleotide sequence by MEROPS) | MER47520 | | | X |
| | | | subfamily A2A non-peptidase homologues (deduced from nucleotide sequence by MEROPS) | MER47533 | | | 3 |
| | | | subfamily A2A non-peptidase homologues (deduced from nucleotide sequence by MEROPS) | MER47537 | | | 3 |
| | | | subfamily A2A non-peptidase homologues (deduced from nucleotide sequence by MEROPS) | MER47569 | | | 3 |
| | | | subfamily A2A non-peptidase homologues (deduced from nucleotide sequence by MEROPS) | MER47570 | | | 3 |
| | | | subfamily A2A non-peptidase homologues (deduced from nucleotide sequence by MEROPS) | MER47584 | | | 3 |
| | | | subfamily A2A non-peptidase homologues (deduced from nucleotide sequence by MEROPS) | MER47603 | | | 4 |
| | | | subfamily A2A non-peptidase homologues (deduced from nucleotide sequence by MEROPS) | MER47604 | | | 5 |
| | | | subfamily A2A non-peptidase homologues (deduced from nucleotide sequence by MEROPS) | MER47606 | | | 12q15-q21 |
| | | | subfamily A2A non-peptidase homologues (deduced from nucleotide sequence by MEROPS) | MER47609 | | | 3 |
| | | | subfamily A2A non-peptidase homologues (deduced from nucleotide sequence by MEROPS) | MER47616 | | | 3 |
| | | | subfamily A2A non-peptidase homologues (deduced from nucleotide sequence by MEROPS) | MER47619 | | | 5 |
| | | | subfamily A2A non-peptidase homologues (deduced from nucleotide sequence by MEROPS) | MER47648 | | | 5 |
| | | | subfamily A2A non-peptidase homologues (deduced from nucleotide sequence by MEROPS) | MER47649 | | | 16 |
| | | | subfamily A2A non-peptidase homologues (deduced from nucleotide sequence by MEROPS) | MER47662 | | | 12q24.11 |
| | | | subfamily A2A non-peptidase homologues (deduced from nucleotide sequence by MEROPS) | MER48004 | | | |
| | | | subfamily A2A non-peptidase homologues (deduced from nucleotide sequence by MEROPS) | MER48018 | | | |
| | | | subfamily A2A non-peptidase homologues (deduced from nucleotide sequence by MEROPS) | MER48019 | | | |
| | | | subfamily A2A non-peptidase homologues (deduced from nucleotide sequence by MEROPS) | MER48023 | | | 21q21 |
| | | | subfamily A2A non-peptidase homologues (deduced from nucleotide sequence by MEROPS) | MER48037 | | | 8q21-q23 |
| | | unassigned | subfamily A2A unassigned peptidases (deduced from nucleotide sequence by MEROPS) | MER47117 | | | 7 |
| | | | subfamily A2A unassigned peptidases (deduced from nucleotide sequence by MEROPS) | MER47164 | | | 19 |
| | | | subfamily A2A unassigned peptidases (deduced from nucleotide sequence by MEROPS) | MER47206 | | | Y |

-continued

| Clan | Family | MEROPS ID | Peptidase or homologue (subtype) | MERNUM | Gene | Link | Locus |
|---|---|---|---|---|---|---|---|
| | | | subfamily A2A unassigned peptidases (deduced from nucleotide sequence by MEROPS) | MER47231 | | | 16 |
| | | | subfamily A2A unassigned peptidases (deduced from nucleotide sequence by MEROPS) | MER47291 | | | 8 |
| | | | subfamily A2A unassigned peptidases (deduced from nucleotide sequence by MEROPS) | MER47386 | | | 5 |
| | | | subfamily A2A unassigned peptidases (deduced from nucleotide sequence by MEROPS) | MER47479 | | | X |
| | | | subfamily A2A unassigned peptidases (deduced from nucleotide sequence by MEROPS) | MER47559 | | | 12 |
| | | | subfamily A2A unassigned peptidases (deduced from nucleotide sequence by MEROPS) | MER47583 | | | 16 |
| AD | A22 | A22.001 | presenilin 1 | MER05221 | PSEN1 | 5663 | 14q24.3 |
| | | A22.002 | presenilin 2 | MER05223 | PSEN2 | 5664 | 1q31-q42 |
| | | A22.003 | impas 1 peptidase | MER19701 | HM13 | 81502 | 20q11.21 |
| | | A22.004 | impas 4 peptidase | MER19715 | | 56928 | 19p13.3 |
| | | A22.005 | impas 2 peptidase | MER19708 | | 121665 | 12q24.31 |
| | | A22.006 | impas 5 peptidase | MER19712 | | 162540 | 17q21.31 |
| | | A22.007 | impas 3 peptidase | MER19711 | | 84888 | 15q21.2 |
| | | A22.P01 | possible family A22 pseudogene (*Homo sapiens* chromosome 18) (deduced from nucleotide sequence by MEROPS) | MER29974 | | | 18 |
| | | A22.P02 | possible family A22 pseudogene (*Homo sapiens* chromosome 11) | MER23159 | | | 11q12.2 |
| CA | C1 | C01.009 | cathepsin V | MER04437 | CTSL2 | 1515 | 9q22.2 |
| | | C01.013 | cathepsin X | MER04508 | CTSZ | 1522 | 20q13 |
| | | C01.014 | cathepsin L-like peptidase 2 | MER05210 | CTSLL2 | 1517 | 10q |
| | | C01.015 | cathepsin L-like peptidase 3 | MER05209 | CTSLL3 | 1518 | 10q22.3-q23.1 |
| | | C01.018 | cathepsin F | MER04980 | CTSF | 8722 | 11q13.1-q13.3 |
| | | C01.032 | cathepsin L | MER00622 | CTSL | 1514 | 9q21-q22 |
| | | C01.034 | cathepsin S | MER00633 | CTSS | 1520 | 1q21 |
| | | C01.035 | cathepsin O | MER01690 | CTSO | 1519 | 4q31-q32 |
| | | C01.036 | cathepsin K | MER00644 | CTSK | 1513 | 1q21 |
| | | C01.037 | cathepsin W | MER03756 | CTSW | 1521 | 11q13.1 |
| | | C01.040 | cathepsin H | MER00629 | CTSH | 1512 | 15q24-q25 |
| | | C01.060 | cathepsin B | MER00686 | CTSB | 1508 | 8p22 |
| | | C01.070 | dipeptidyl-peptidase I | MER01937 | CTSC | 1075 | 11q14.1-q14.3 |
| | | C01.084 | bleomycin hydrolase (animal) | MER02481 | BLMH | 642 | 17q11.1-q11.2 |
| | | C01.973 | tubulointerstitial nephritis antigen | MER16137 | TINAG | 27283 | 6p11.2p12 |
| | | C01.975 | tubulointerstitial nephritis antigen-related protein | MER21799 | LCN7 | 64129 | 1p34.3 |
| | | C01.P02 | cathepsin L-like pseudogene 1 (*Homo sapiens*) (pseudogene) | MER02789 | CTSLL1 | 1516 | 10q |
| | | C01.P03 | cathepsin B-like pseudogene (chromosome 4, *Homo sapiens*) | MER29469 | | | 4 |
| | | C01.P04 | cathepsin B-like pseudogene (chromosome 1, (*Homo sapiens*) | MER29457 | | | 1q42.11 |
| | C2 | C02.001 | calpain-1 | MER00770 | CAPN1 | 823 | 11q13 |
| | | C02.002 | calpain-2 | MER00964 | CAPN2 | 824 | 1q41-q42 |
| | | C02.004 | calpain-3 | MER01446 | CAPN3 | 825 | 15q15.1-q21.1 |
| | | C02.006 | calpain-9 | MER04042 | CAPN9 | 10753 | 1q42.11-q42.3 |
| | | C02.007 | calpain-8 | MER21474 | | | 1q41 |
| | | C02.008 | calpain-7 | MER05537 | CAPN7 | 23473 | 3p24 |
| | | C02.010 | calpain-15 | MER04745 | SOLH | 6650 | 16p13.3 |
| | | C02.011 | calpain-5 | MER02939 | CAPN5 | 726 | 11q14 |
| | | C02.013 | calpain-11 | MER05844 | CAPN11 | 11131 | 6p12 |
| | | C02.017 | calpain-12 (deduced from nucleotide sequence by MEROPS) | MER29889 | CAPN12 | 147968 | 19q13.2 |
| | | C02.018 | calpain-10 | MER13510 | CAPN10 | 11132 | 2q37.3 |
| | | C02.020 | calpain-13 | MER20139 | CAPN13 | 92291 | 2p21-22 |
| | | C02.021 | calpain-14 | MER29744 | CAPN14 | 114773 | 2p23.1-p21 |
| | | C02.971 | calpamodulin (calpamodulin) | MER00718 | CAPN6 | 827 | Xq23 |
| | | C02.972 | hypothetical protein flj40251 | MER03201 | C6orf103 | 79747 | 6q24.2 |
| | C12 | C12.001 | ubiquitinyl hydrolase-L1 | MER00832 | UCHL1 | 7345 | 4p14 |
| | | C12.003 | ubiquitinyl hydrolase-L3 | MER00836 | UCHL3 | 7347 | 13q21.2-q22.1 |
| | | C12.004 | ubiquitinyl hydrolase-BAP1 (KIAA0272 protein) | MER03989 | BAP1 | 8314 | 3p21.2-p21.31 |
| | | C12.005 | ubiquitinyl hydrolase-UCH37 | MER05539 | UCHL5 | 51377 | 1q32 |
| CD | C13 | C13.002 | legumain (plant alpha form) | MER44591 | | | |
| | | C13.004 | legumain | MER01800 | LGMN | 5641 | 14q32.1 |
| | | C13.005 | glycosylphosphatidylinositol:protein transamidase | MER02479 | PIGK | 10026 | 1 |
| | | C13.P01 | legumain pseudogene (*Homo sapiens*) | MER29741 | LGMN2P | 122199 | 13q21.2 |
| | C14 | C14.001 | caspase-1 | MER00850 | CASP1 | 834 | 11q22.2-q22.3 |
| | | C14.003 | caspase-3 | MER00853 | CASP3 | 836 | 4q33-q35.1 |
| | | C14.004 | caspase-7 | MER02705 | CASP7 | 840 | 10q25.1-q25.2 |
| | | C14.005 | caspase-6 | MER02708 | CASP6 | 839 | 4q25 |
| | | C14.006 | caspase-2 | MER01644 | CASP2 | 835 | 7q34-q35 |
| | | C14.007 | caspase-4 | MER01938 | CASP4 | 837 | 11q22.2-q22.3 |

-continued

| Clan | Family | MEROPS ID | Peptidase or homologue (subtype) | MERNUM | Gene | Link | Locus |
|---|---|---|---|---|---|---|---|
| | | C14.008 | caspase-5 | MER02240 | CASP5 | 838 | 11q22.2-q22.3 |
| | | C14.009 | caspase-8 | MER02849 | CASP8 | 841 | 2q33-q34 |
| | | C14.010 | caspase-9 | MER02707 | CASP9 | 842 | 1p36.1-p36.3 |
| | | C14.011 | caspase-10 | MER02579 | CASP10 | 843 | 2q33-q34 |
| | | C14.018 | caspase-14 | MER12083 | CASP14 | 23581 | 19p13.1 |
| | | C14.026 | paracaspase | MER19325 | MALT1 | 10892 | 18q21 |
| | | C14.028 | Mername-AA143 peptidase | MER21304 | | | 11q22.3 |
| | | C14.029 | Mername-AA186 peptidase | MER20516 | | | 11q22.3 |
| | | C14.032 | putative caspase (*Homo sapiens*) | MER21463 | | | |
| | | C14.971 | FLIP protein (casper) | MER03026 | CFLAR | 8837 | 2q33-q34 |
| | | C14.976 | Mername-AA142 protein | MER21316 | | | 11q22.3 |
| | | C14.P01 | caspase-12 pseudogene (*Homo sapiens*) | MER19698 | CASP12P1 | 120329 | 11q22.3 |
| | | C14.P02 | Mername-AA093 caspase pseudogene | MER14766 | | 197350 | 16p13.3 |
| CF | C15 | C15.010 | pyroglutamyl-peptidase I (chordate) | MER11032 | PGPEP1 | 54858 | 19p13.11 |
| | | C15.011 | Mername-AA073 peptidase (deduced from nucleotide sequence by MEROPS) | MER29978 | | 145814 | 15q26.3 |
| CA | C19 | C19.001 | ubiquitin-specific peptidase 5 | MER02066 | USP5 | 8078 | 12p13 |
| | | C19.009 | ubiquitin-specific peptidase 6 | MER00863 | USP6 | 9098 | 17q11 |
| | | C19.010 | ubiquitin-specific peptidase 4 (ubiquitin carboxy-terminal hydrolase UNP) | MER01795 | USP4 | 7375 | 3p21.31 |
| | | C19.011 | ubiquitin-specific peptidase 8 (KIAA0055 protein) | MER01884 | USP8 | 9101 | 15q11.2-q21.1 |
| | | C19.012 | ubiquitin-specific peptidase 13 | MER02627 | USP13 | 8975 | 3q26.2-q26.3 |
| | | C19.013 | ubiquitin-specific peptidase 2 | MER04834 | USP2 | 9099 | 11q23.3 |
| | | C19.014 | ubiquitin-specific peptidase 11 | MER02693 | USP11 | 8237 | Xp11.23 |
| | | C19.015 | ubiquitin-specific peptidase 14 | MER02667 | USP14 | 9097 | 18p11.32 |
| | | C19.016 | ubiquitin-specific peptidase 7 (ubiquitin carboxyl-terminal hydrolase HAUSP) | MER02896 | USP7 | 7874 | 16p13.3 |
| | | C19.017 | ubiquitin-specific peptidase 9X | MER05877 | USP9X | 8239 | Xp11.4 |
| | | C19.018 | ubiquitin-specific peptidase 10 (KIAA0190 protein) | MER04439 | USP10 | 9100 | 16q23.1 |
| | | C19.019 | ubiquitin-specific peptidase 1 | MER04978 | USP1 | 7398 | 1p31.3-p32.1 |
| | | C19.020 | ubiquitin-specific peptidase 12 | MER05454 | USP12 | 9959 | 5q33-q34 |
| | | C19.021 | ubiquitin-specific peptidase 16 | MER05493 | USP16 | 10600 | 21q22.11 |
| | | C19.022 | ubiquitin-specific peptidase 15 | MER05427 | USP15 | 9958 | 12q14 |
| | | C19.023 | ubiquitin-specific peptidase 17 | MER02900 | USP17 | 23661 | 4p15 |
| | | C19.024 | ubiquitin-specific peptidase 19 | MER05428 | USP19 | 10869 | 3p21.31 |
| | | C19.025 | ubiquitin-specific peptidase 20 | MER05494 | USP20 | 10868 | 9q34.13 |
| | | C19.026 | ubiquitin-specific peptidase 3 | MER05513 | USP3 | 9960 | 15q22.3 |
| | | C19.028 | ubiquitin-specific peptidase 9Y | MER04314 | USP9Y | 8287 | Yq11.2 |
| | | C19.030 | ubiquitin-specific peptidase 18 | MER05641 | USP18 | 11274 | 22q11.21 |
| | | C19.034 | ubiquitin-specific peptidase 21 | MER06258 | USP21 | 27005 | 1q22 |
| | | C19.035 | ubiquitin-specific peptidase 22 | MER12130 | USP22 | 23326 | 17p13.2 |
| | | C19.037 | ubiquitin-specific peptidase 33 | MER14335 | USP33 | 23032 | 1p31.1 |
| | | C19.040 | ubiquitin-specific peptidase 29 | MER12093 | USP29 | 57663 | 19q13.43 |
| | | C19.041 | ubiquitin-specific peptidase 25 | MER11115 | USP25 | 29761 | 21q11.2 |
| | | C19.042 | ubiquitin-specific peptidase 36 | MER14033 | USP36 | 57602 | 17q25.3 |
| | | C19.044 | ubiquitin-specific peptidase 32 | MER14290 | USP32 | 84669 | 17q23.3 |
| | | C19.046 | ubiquitin-specific peptidase 26 (human-type) | MER14292 | USP26 | 83844 | Xq26.2 |
| | | C19.047 | ubiquitin-specific peptidase 24 | MER05706 | USP24 | 23358 | 1p32.1 |
| | | C19.048 | ubiquitin-specific peptidase 42 | MER11852 | USP42 | 84132 | 7p22.2 |
| | | C19.052 | ubiquitin-specific peptidase 46 | MER14629 | USP46 | 64854 | 4q11 |
| | | C19.053 | ubiquitin-specific peptidase 37 | MER14633 | USP37 | 57695 | 2q36.1 |
| | | C19.054 | ubiquitin-specific peptidase 28 | MER14634 | USP28 | 57646 | 11q23 |
| | | C19.055 | ubiquitin-specific peptidase 47 | MER14636 | USP47 | 55031 | 11p15.2 |
| | | C19.056 | ubiquitin-specific peptidase 38 | MER14637 | USP38 | 84640 | 4q31.1 |
| | | C19.057 | ubiquitin-specific peptidase 44 | MER14638 | USP44 | 84101 | 12q21.33 |
| | | C19.058 | ubiquitin-specific peptidase 50 | MER30315 | USP50 | 373509 | 15q21.1 |
| | | C19.059 | ubiquitin-specific peptidase 35 | MER14646 | USP35 | 57558 | 11q13.5 |
| | | C19.060 | ubiquitin-specific peptidase 30 | MER14649 | USP30 | 84749 | 12q23.3 |
| | | C19.062 | Mername-AA091 peptidase (deduced from nucleotide sequence by MEROPS) | MER14743 | | | Xq21.31 |
| | | C19.064 | ubiquitin-specific peptidase 45 | MER30314 | USP45 | 85015 | 6q16.3 |
| | | C19.065 | ubiquitin-specific peptidase 51 | MER14769 | USP51 | 158880 | Xp11.21-22 |
| | | C19.067 | ubiquitin-specific peptidase 34 | MER14780 | USP34 | 23021 | 2p15 |
| | | C19.068 | ubiquitin-specific peptidase 48 | MER64620 | USP48 | 84196 | 1p36.12 |
| | | C19.069 | ubiquitin-specific peptidase 40 | MER15483 | USP40 | 55230 | 2q37.1 |
| | | C19.070 | ubiquitin-specific peptidase 41 | MER45268 | USP41 | 150200 | 22q11.22 |
| | | C19.071 | ubiquitin-specific peptidase 31 | MER15493 | USP31 | 57478 | 16p12.3 |
| | | C19.072 | Mername-AA129 peptidase (deduced from ESTs by MEROPS) | MER16485 | | | |
| | | C19.073 | ubiquitin-specific peptidase 49 | MER16486 | USP49 | 25862 | 6pter-p12.1 |
| | | C19.075 | Mername-AA187 peptidase | MER52579 | USP27X | 373504 | Xp11.23 |
| | | C19.078 | USP17-like peptidase | MER30192 | | 401447 | 8p23.1 |
| | | C19.080 | ubiquitin-specific peptidase 54 | MER28714 | USP54 | 159195 | 10q22.3 |
| | | C19.081 | ubiquitin-specific peptidase 53 | MER27329 | USP53 | 54532 | 4q27 |
| | | C19.972 | ubiquitin-specific endopeptidase 39 [misleading] | MER64621 | USP39 | 10713 | 2q11.2 |

-continued

| Clan | Family | MEROPS ID | Peptidase or homologue (subtype) | MERNUM | Gene | Link | Locus |
|---|---|---|---|---|---|---|---|
| | | C19.974 | Mername-AA090 non-peptidase homologue (deduced from nucleotide sequence by MEROPS) | MER14739 | | | 22q11.2 |
| | | C19.976 | ubiquitin-specific peptidase 43 [misleading] | MER30140 | USP43 | 124739 | 17p13.1 |
| | | C19.978 | ubiquitin-specific peptidase 52 [misleading] | MER30317 | USP52 | 9924 | 12q13.2-q13.3 |
| | | C19.980 | Mername-AA088 peptidase (deduced from nucleotide sequence by MEROPS) | MER14750 | USP8P | | 6p21.3 |
| | | C19.P01 | NEK2 pseudogene (deduced from nucleotide sequence by MEROPS) | MER14736 | NEK2P | 326302 | 14q11.2 |
| | | C19.P02 | C19 pseudogene (*Homo sapiens*: chromosome 5) (deduced from nucleotide sequence by MEROPS) | MER29972 | | | 5 |
| PC | C26 | C26.001 | gamma-glutamyl hydrolase | MER02963 | GGH | 8836 | 8q12.23-q13.1 |
| | | C26.950 | guanine 5'-monophosphate synthetase | MER43387 | GMPS | 8833 | 3q24 |
| | | C26.951 | carbamoyl-phosphate synthase (*Homo sapiens*) (CPS1 protein) | MER78640 | | | |
| | | C26.952 | dihydro-orotase (N-terminal unit) (*Homo sapiens*) | MER60647 | CAD | 790 | 2p22-p21 |
| PB | C44 | C44.001 | amidophosphoribosyltransferase precursor | MER03314 | PPAT | 5471 | 4q121 |
| | | C44.970 | glutamine-fructose-6-phosphate transaminase 1 (glucosamine-fructose-6-phosphate aminotransferase) | MER03322 | GFPT1 | 2673 | 2p13 |
| | | C44.972 | glutamine:fructose-6-phosphate amidotransferase | MER12158 | GFPT2 | 9945 | 5q34-q35 |
| | | C44.973 | Mername-AA144 protein | MER21319 | | | Xq13.3 |
| | | C44.974 | asparagine synthetase | MER33254 | ASNS | 440 | 7q21.3 |
| CH | C46 | C46.002 | Sonic hedgehog protein | MER02539 | SHH | 6469 | 7q36 |
| | | C46.003 | Indian hedgehog protein | MER02538 | IHH | 3549 | 2 |
| | | C46.004 | Desert hedgehog protein | MER12170 | DHH | 50846 | 12q12-13.1 |
| CE | C48 | C48.002 | SENP1 peptidase | MER11012 | SENP1 | 29843 | 12q13.1 |
| | | C48.003 | SENP3 peptidase | MER11019 | SENP3 | 26168 | 17p13 |
| | | C48.004 | SENP6 peptidase | MER11109 | SENP6 | 26054 | 6q13-q14.3 |
| | | C48.007 | SENP2 peptidase | MER12183 | SENP2 | 59343 | 3q28 |
| | | C48.008 | SENP5 peptidase | MER14032 | SENP5 | 205564 | 3q29 |
| | | C48.009 | SENP7 peptidase | MER14095 | SENP7 | 57337 | 3q12 |
| | | C48.011 | SENP8 peptidase | MER16161 | SENP8 | 123228 | 15q22.32 |
| | | C48.012 | SENP4 peptidase | MER05557 | | | |
| CD | C50 | C50.001 | separase | MER11775 | ESPL1 | 9700 | 8 |
| | | C50.P01 | separase-like pseudogene (deduced from nucleotide sequence by MEROPS) | MER14797 | | | 8q21.2 |
| CA | C54 | C54.002 | autophagin-2 | MER13564 | ATG4A | 115201 | Xq22.1-22.3 |
| | | C54.003 | autophagin-1 | MER13561 | ATG4B | 23192 | 2 |
| | | C54.004 | autophagin-3 | MER14316 | ATG4C | 84938 | 1p31.3 |
| | | C54.005 | autophagin-4 | MER64622 | ATG4D | 84971 | 19p13.2 |
| PC | C56 | C56.002 | DJ-1 putative peptidase | MER03390 | PARK7 | 11315 | 1p36.2-p36.3 |
| | | C56.003 | Mername-AA100 peptidase (deduced from nucleotide sequence by MEROPS) | MER14802 | | | 12q13 |
| | | C56.971 | Mername-AA101 non-peptidase homologue (deduced from nucleotide sequence by MEROPS) | MER14803 | | | 9q22.32 |
| | | C56.972 | KIAA0361 protein (*Homo sapiens*) | MER42827 | PFAS | 5198 | 17p13.1 |
| | | C56.974 | FLJ34283 protein (*Homo sapiens*) | MER44553 | | 347862 | 11p15.5 |
| CA | C64 | C64.001 | Cezanne deubiquitinylating peptidase | MER29042 | ZA20D1 | 56957 | 1q21.3 |
| | | C64.002 | Cezanne-2 peptidase | MER29044 | C15orf16 | 161725 | 15q13.1 |
| | | C64.003 | tumor necrosis factor alpha-induced protein 3 | MER29050 | TNFAIP3 | 7128 | 6q23-q25 |
| | | C64.004 | TRABID protein | MER29052 | ZRANB1 | 54764 | 10q26.2 |
| | C65 | C65.001 | otubain-1 | MER29056 | OTUB1 | 55611 | 11q13.1 |
| | | C65.002 | otubain-2 | MER29061 | OTUB2 | 78990 | 14q32.13-q32.2 |
| | C67 | C67.001 | CylD protein | MER30104 | CYLD | 1540 | 16q12.1 |
| PB | C69 | C69.003 | secernin 1 | MER45376 | SCRN1 | 9805 | 7p14.3-p14.1 |
| | | C69.004 | secernin 2 (SCRN2 protein) | MER64573 | SCRN2 | 90507 | 17q21.32 |
| | | C69.005 | secernin 3 (SCRN3 protein) | MER64582 | SCRN3 | 79634 | 2q31.1 |
| CA | C78 | C78.001 | UfSP1 peptidase | MER42724 | | | |
| | | C78.002 | UfSP2 peptidase | MER60306 | | | |
| MA | M1 | M01.001 | aminopeptidase N | MER00997 | ANPEP | 290 | 15q25-q26 |
| | | M01.003 | aminopeptidase A | MER01012 | ENPEP | 2028 | 4q25 |
| | | M01.004 | leukotriene A4 hydrolase (LTA4H protein) | MER01013 | LTA4H | 4048 | 12q22 |
| | | M01.008 | pyroglutamyl-peptidase II | MER12221 | TRHDE | 29953 | 12q15-q21 |
| | | M01.010 | cytosol alanyl aminopeptidase | MER02746 | NPEPPS | 9520 | 17q12-q21 |
| | | M01.011 | cystinyl aminopeptidase | MER02060 | LNPEP | 4012 | 5q15 |
| | | M01.014 | aminopeptidase B | MER01494 | RNPEP | 6051 | 1q32.1-q32.2 |
| | | M01.018 | aminopeptidase PILS | MER05331 | | 51752 | 5q15 |
| | | M01.022 | Mername-AA050 peptidase | MER12271 | RNPEPL1 | 57140 | 2q37.3 |
| | | M01.024 | leukocyte-derived arginine aminopeptidase | MER02968 | | 64167 | 16 |
| | | M01.026 | laeverin | MER52595 | | 206338 | 5q23.1 |
| | | M01.028 | aminopeptidase O | MER19730 | C9orf3 | 84909 | 9q22.32 |
| | | M01.972 | Tata binding protein associated factor | MER26493 | TAF2 | 6873 | 8q24.12 |
| | M2 | M02.001 | angiotensin-converting enzyme peptidase unit 1 (peptidase unit 1) | MER04967 | ACE | 1636 | 17q23 |
| | | M02.004 | angiotensin-converting enzyme peptidase unit 2 (peptidase unit 2) | MER01019 | ACE | 1636 | 17q23 |

-continued

| Clan | Family | MEROPS ID | Peptidase or homologue (subtype) | MERNUM | Gene | Link | Locus |
|---|---|---|---|---|---|---|---|
| | | M02.006 | angiotensin-converting enzyme 2 | MER11061 | ACE2 | 5972 | Xp22 |
| | | M02.972 | Mername-AA153 protein | MER20514 | | | 17q21.33 |
| | M3 | M03.001 | thimet oligopeptidase | MER01737 | THOP1 | 7064 | 19q13.3 |
| | | M03.002 | neurolysin | MER10991 | NLN | 57486 | 5q12.3 |
| | | M03.006 | mitochondrial intermediate peptidase | MER03665 | MIPEP | 4285 | 13q12 |
| | | M03.971 | Mername-AA154 protein | MER21317 | | | 7q21.13 |
| | M8 | M08.003 | leishmanolysin-2 | MER14492 | LMLN | 89782 | 3q29 |
| | M10 | M10.001 | matrix metallopeptidase-1 | MER01063 | MMP1 | 4312 | 11q22-q23 |
| | | M10.002 | matrix metallopeptidase-8 | MER01084 | MMP8 | 4317 | 11q21-q22 |
| | | M10.003 | matrix metallopeptidase-2 | MER01080 | MMP2 | 4313 | 16q13 |
| | | M10.004 | matrix metallopeptidase-9 | MER01085 | MMP9 | 4318 | 20q11.2-q13.1 |
| | | M10.005 | matrix metallopeptidase-3 | MER01068 | MMP3 | 4314 | 11q23 |
| | | M10.006 | matrix metallopeptidase-10 (human type) | MER01072 | MMP10 | 4319 | 11q22.3-q23 |
| | | M10.007 | matrix metallopeptidase-11 | MER01075 | MMP11 | 4320 | 22q11.2 |
| | | M10.008 | matrix metallopeptidase-7 | MER01092 | MMP7 | 4316 | 11q21-q22 |
| | | M10.009 | matrix metallopeptidase-12 | MER01089 | MMP12 | 4321 | 11q22.2-q22.3 |
| | | M10.013 | matrix metallopeptidase-13 | MER01411 | MMP13 | 4322 | 11q22.3 |
| | | M10.014 | membrane-type matrix metallopeptidase-1 | MER01077 | MMP14 | 4323 | 14q11-q12 |
| | | M10.015 | membrane-type matrix metallopeptidase-2 | MER02383 | MMP15 | 4324 | 16q13-q21 |
| | | M10.016 | membrane-type matrix metallopeptidase-3 | MER02384 | MMP16 | 4325 | 8q21 |
| | | M10.017 | membrane-type matrix metallopeptidase-4 | MER02595 | MMP17 | 4326 | 12q24.3 |
| | | M10.019 | matrix metallopeptidase-20 | MER03021 | MMP20 | 9313 | 11q22.3 |
| | | M10.021 | matrix metallopeptidase-19 | MER02076 | MMP19 | 4327 | 12q14 |
| | | M10.022 | matrix metallopeptidase-23B | MER04766 | MMP23B | 8510 | 1p36.3 |
| | | M10.023 | membrane-type matrix metallopeptidase-5 | MER05638 | MMP24 | 10893 | 20q11.2 |
| | | M10.024 | membrane-type matrix metallopeptidase-6 | MER12071 | MMP25 | 64386 | 16p13.3 |
| | | M10.026 | matrix metallopeptidase-21 | MER06101 | MMP21 | 118856 | 10q26.2 |
| | | M10.027 | matrix metallopeptidase-22 | MER14098 | MMP27 | 64066 | 11q24 |
| | | M10.029 | matrix metallopeptidase-26 | MER12072 | MMP26 | 56547 | 11p15 |
| | | M10.030 | matrix metallopeptidase-28 | MER13587 | MMP28 | 79148 | 17q21.1 |
| | | M10.037 | matrix metallopeptidase-23A | MER37217 | MMP23A | 8511 | 1p36.3 |
| | | M10.950 | macrophage elastase homologue (chromosome 8, Homo *sapiens*) (deduced from nucleotide sequence by MEROPS) | MER30035 | | | 8 |
| | | M10.971 | Mername-AA156 protein | MER21309 | | | 11q22.2 |
| | | M10.973 | matrix metallopeptidase-like 1 | MER45280 | MMPL1 | 4328 | 16p13.3 |
| | M12 | M12.002 | meprin alpha subunit (alpha) | MER01111 | MEP1A | 4224 | 6p21.2-p21.1 |
| | | M12.004 | meprin beta subunit (beta) | MER05213 | MEP1B | 4225 | 18q12.2-q12.3 |
| | | M12.005 | procollagen C-peptidase | MER01113 | BMP1 | 649 | 8p21 |
| | | M12.016 | mammalian tolloid-like 1 protein | MER05124 | TLL1 | 7092 | 4q32-q33 |
| | | M12.018 | mammalian tolloid-like 2 protein | MER05866 | TLL2 | 7093 | 10q23-q24 |
| | | M12.021 | ADAMTS9 peptidase | MER12092 | ADAMTS9 | 56999 | 3p14.2-p14.3 |
| | | M12.024 | ADAMTS14 peptidase | MER16700 | ADAMTS14 | 140766 | 10q2 |
| | | M12.025 | ADAMTS15 peptidase | MER17029 | ADAMTS15 | 170689 | 11q25 |
| | | M12.026 | ADAMTS16 peptidase | MER15689 | ADAMTS16 | 170690 | 5p15 |
| | | M12.027 | ADAMTS17 peptidase | MER16302 | ADAMTS17 | 170691 | 15q24 |
| | | M12.028 | ADAMTS18 peptidase | MER16090 | ADAMTS18 | 170692 | 16q23 |
| | | M12.029 | ADAMTS19 peptidase | MER15663 | ADAMTS19 | 171019 | 5q31 |
| | | M12.201 | ADAM1 peptidase | MER03912 | ADAM1 | 8759 | 12q24 |
| | | M12.208 | ADAM8 peptidase | MER03902 | ADAM8 | 101 | 10q26.3 |
| | | M12.209 | ADAM9 peptidase | MER01140 | ADAM9 | 8754 | 8p11.22 |
| | | M12.210 | ADAM10 peptidase | MER02382 | ADAM10 | 102 | 15q21.3 |
| | | M12.212 | ADAM12 peptidase | MER05107 | ADAM12 | 8038 | 10q26 |
| | | M12.214 | adamalysin-19 | MER12241 | ADAM19 | 8728 | 5q32-33 |
| | | M12.215 | ADAM15 peptidase | MER02386 | ADAM15 | 8751 | 1q21.3 |
| | | M12.217 | ADAM17 peptidase | MER03094 | ADAM17 | 6868 | 2p25 |
| | | M12.218 | ADAM20 peptidase | MER04725 | ADAM20 | 8748 | 14q24.1 |
| | | M12.219 | ADAMDEC1 peptidase | MER00743 | ADAMDEC1 | 27299 | 8p21.1 |
| | | M12.220 | ADAMTS3 peptidase | MER05100 | ADAMTS3 | 9508 | 4q21 |
| | | M12.221 | ADAMTS4 peptidase | MER05101 | ADAMTS4 | 9507 | 1q31-q32 |
| | | M12.222 | ADAMTS1 peptidase | MER05546 | ADAMTS1 | 9510 | 21q22-q22 |
| | | M12.224 | ADAM28 peptidase (human-type) | MER05495 | ADAM28 | 10863 | 8p21.2 |
| | | M12.225 | ADAMTS5 peptidase | MER05548 | ADAMTS5 | 11096 | 21q22.1-q22 |
| | | M12.226 | ADAMTS8 peptidase | MER05545 | ADAMTS8 | 11095 | 11q25 |
| | | M12.230 | ADAMTS6 peptidase | MER05893 | ADAMTS6 | 11174 | 5pter-qter |
| | | M12.231 | ADAMTS7 peptidase | MER05894 | ADAMTS7 | 11173 | 15pter-qter |
| | | M12.232 | ADAM30 peptidase | MER06268 | ADAM30 | 11085 | 1p11-p13 |
| | | M12.234 | ADAM21 peptidase (*Homo sapiens*) (ADAM 21 protein) | MER04726 | ADAM21 | 8747 | 14q24.1 |
| | | M12.235 | ADAMTS10 peptidase | MER14331 | ADAMTS10 | 81794 | 19p13.3 |
| | | M12.237 | ADAMTS12 peptidase | MER14337 | ADAMTS12 | 81792 | 5q35 |
| | | M12.241 | ADAMTS13 peptidase | MER15450 | ADAMTS13 | 11093 | 9q34 |
| | | M12.244 | ADAM33 peptidase | MER15143 | ADAM33 | 80332 | 20p13 |
| | | M12.245 | ovastacin | MER29996 | ASTL | 431705 | 2q11.1 |
| | | M12.246 | ADAMTS20 peptidase (*Homo sapiens*) | MER26906 | ADAMTS20 | 80070 | 12q12 |
| | | M12.301 | procollagen I N-peptidase | MER04985 | ADAMTS2 | 9509 | 5q23-q24 |
| | | M12.950 | ADAM2 protein (ADAM 2 protein) | MER03090 | ADAM2 | 2515 | 8p11.2 |

-continued

| Clan | Family | MEROPS ID | Peptidase or homologue (subtype) | MERNUM | Gene | Link | Locus |
|---|---|---|---|---|---|---|---|
| | | M12.954 | ADAM6 protein (deduced from nucleotide sequence by MEROPS) | MER47044 | | | 14q32.33 |
| | | | ADAM6 protein (deduced from nucleotide sequence by MEROPS) | MER47250 | | | |
| | | | ADAM6 protein (deduced from nucleotide sequence by MEROPS) | MER47654 | | | 16 |
| | | M12.956 | ADAM7 protein (GP-83 glycoprotein) | MER05109 | ADAM7 | 8756 | 8p21.2 |
| | | M12.957 | ADAM18 protein | MER12230 | ADAM18 | 8749 | 8p22 |
| | | M12.960 | ADAM32 protein | MER26938 | ADAM32 | 203102 | 8p11.21 |
| | | M12.962 | non-peptidase homologue (*Homo sapiens* chromosome 4) (deduced from nucleotide sequence by MEROPS) | MER29973 | | | |
| | | M12.974 | ADAM3A protein (human-type) (ADAM 3A protein) | MER05200 | ADAM3A | 1587 | 8p21-p12 |
| | | M12.975 | ADAM3B protein (human-type) (ADAM 3B protein) | MER05199 | ADAM3B | 1596 | 16q12.1 |
| | | M12.976 | ADAM11 protein (ADAM 11 protein) | MER01146 | ADAM11 | 4185 | 17q21.3 |
| | | M12.978 | ADAM22 protein (ADAM 22 protein) | MER05102 | ADAM22 | 53616 | 7q21 |
| | | M12.979 | ADAM23 protein (ADAM 23 protein) | MER05103 | ADAM23 | 8745 | 2q33 |
| | | M12.981 | ADAM29 protein | MER06267 | ADAM29 | 11086 | 4q34.2-qter |
| | | M12.987 | protein similar to ADAM21 peptidase preproprotein (*Homo sapiens*) | MER26944 | | | |
| | | M12.990 | Mername AA-225 peptidase homologue (*Homo sapiens*) (deduced from nucleotide sequence by MEROPS) | MER47474 | | | 15 |
| | | M12.P01 | putative ADAM pseudogene (chromosome 4, *Homo sapiens*) | MER29975 | | | |
| | M13 | M13.001 | neprilysin | MER01050 | MME | 4311 | 3q21-q27 |
| | | M13.002 | endothelin-converting enzyme 1 | MER01057 | ECE1 | 1889 | 1p36.1 |
| | | M13.003 | endothelin-converting enzyme 2 | MER04776 | ECE2 | 9718 | 3q26.1-q26.33 |
| | | M13.007 | DINE peptidase | MER05197 | ECEL1 | 9427 | 2q37.1 |
| | | M13.008 | neprilysin-2 | MER13406 | MELL1 | 79258 | 1p36 |
| | | M13.090 | Kell blood-group protein | MER01054 | KEL | 3792 | 7q33 |
| | | M13.091 | PHEX peptidase | MER02062 | PHEX | 5251 | Xp22.2-p22.1 |
| MC | M14 | M14.001 | carboxypeptidase A1 | MER01190 | CPA1 | 1357 | 7q32 |
| | | M14.002 | carboxypeptidase A2 | MER01608 | CPA2 | 1358 | 7q32 |
| | | M14.003 | carboxypeptidase B | MER01194 | CPB1 | 1360 | 3q24 |
| | | M14.004 | carboxypeptidase N | MER01198 | CPN1 | 1369 | 10 |
| | | M14.005 | carboxypeptidase E | MER01199 | CPE | 1363 | 4 |
| | | M14.006 | carboxypeptidase M | MER01205 | CPM | 1368 | 12q15 |
| | | M14.009 | carboxypeptidase U | MER01193 | CPB2 | 1361 | 13q14.11 |
| | | M14.010 | carboxypeptidase A3 | MER01187 | CPA3 | 1359 | 3q21-q25 |
| | | M14.011 | metallocarboxypeptidase D peptidase unit 1 (peptidase unit 1) | MER03781 | CPD | 1362 | 17p11.1-q11.2 |
| | | M14.012 | metallocarboxypeptidase Z | MER03428 | CPZ | 8532 | 4p16.1 |
| | | M14.016 | metallocarboxypeptidase D peptidase unit 2 (peptidase unit 2) | MER04963 | CPD | 1362 | 17p11.1-q11.2 |
| | | M14.017 | carboxypeptidase A4 | MER13421 | CPA4 | 51200 | 7q32 |
| | | M14.018 | carboxypeptidase A6 | MER13456 | CPA6 | 57094 | 8q12.3 |
| | | M14.020 | carboxypeptidase A5 | MER17121 | CPA5 | 93979 | 7q32 |
| | | M14.021 | metallocarboxypeptidase O | MER16044 | CPO | 130749 | 2q34 |
| | | M14.025 | Mername-AA216 hypothetical peptidase | MER33174 | | 60509 | 2p23.3 |
| | | M14.026 | Mername-AA213 putative peptidase | MER33176 | AGBL3 | 340351 | 7q33 |
| | | M14.027 | hypothetical protein flj14442 (*Homo sapiens*) and similar | MER33178 | AGBL4 | 84871 | 1p33 |
| | | M14.028 | Mername-AA217 hypothetical peptidase | MER33179 | AGTPBP1 | 23287 | 9q22.1 |
| | | M14.029 | A430081C19RIK (*Mus musculus*)-type protein | MER37713 | AGBL2 | 79841 | 11p11.2 |
| | | M14.950 | metallocarboxypeptidase D non-peptidase unit (peptidase unit 3) | MER04964 | CPD | 1362 | 17p11.1-q11.2 |
| | | M14.951 | adipocyte-enhancer binding protein 1 | MER03889 | AEBP1 | 165 | 7 |
| | | M14.952 | carboxypeptidase-like protein X1 | MER13404 | CPXM | 56265 | 20p12.3-p13 |
| | | M14.954 | cytosolic carboxypeptidase | MER26952 | CPXM2 | 119587 | 10q26.13 |
| ME | M16 | M16.002 | insulysin | MER01214 | IDE | 3416 | 10q23-q25 |
| | | M16.003 | mitochondrial processing peptidase beta-subunit (beta) | MER04497 | PMPCB | 9512 | 7q22.1/ 7q22-q31.1 |
| | | M16.005 | nardilysin | MER03883 | NRD1 | 4898 | 1p32.2/ 1p32.2-p32.1 |
| | | M16.009 | eupitrilysin (MP1 protein) | MER04877 | PITRM1 | 10531 | 10p15.2 |
| | | M16.971 | mitochondrial processing peptidase non-peptidase alpha subunit (alpha) | MER01413 | PMPCA | 23203 | 9q34.3 |
| | | M16.973 | ubiquinol-cytochrome c reductase core protein I (ubiquinol-cytochrome c reductase core protein 1) | MER03543 | UQCRC1 | 7384 | 3p21.3 |
| | | M16.974 | ubiquinol-cytochrome c reductase core protein II (ubiquinol-cytochrome c reductase core protein 2) | MER03544 | UQCRC2 | 7385 | 16p12 |
| | | M16.976 | Mername-AA158 protein | MER21876 | | | 4q22.2 |
| | | M16.980 | mitochondrial processing peptidase beta subunit domain 2 (beta) | MER43988 | PMPCB | 9512 | 7q22.1/ 7q22-q31.1 |
| | | M16.981 | ubiquinol-cytochrome c reductase core protein domain 2 (ubiquinol-cytochrome c reductase core protein 1) | MER43998 | UQCRC1 | 7384 | 3p21.3 |
| | | M16.982 | insulysin unit 2 | MER46821 | IDE | 3416 | 10q23-q25 |

-continued

| Clan | Family | MEROPS ID | Peptidase or homologue (subtype) | MERNUM | Gene | Link | Locus |
|---|---|---|---|---|---|---|---|
| | | M16.983 | nardilysin unit 2 | MER46874 | NRD1 | 4898 | 1p32.2/ 1p32.2-p32.1 |
| | | M16.984 | insulysin unit 3 (*Homo sapiens*) (IDE protein) | MER78753 | IDE | 3416 | 10q23-q25 |
| MF | M17 | M17.001 | leucyl aminopeptidase (animal) | MER03100 | LAP3 | 51056 | 4p15.33 |
| | | M17.005 | Mername-AA040 peptidase | MER03919 | | | 6 |
| | | M17.006 | Mername-AA014 peptidase | MER13416 | NPEPL1 | 79716 | 20q13.32 |
| MH | M18 | M18.002 | aspartyl aminopeptidase | MER03373 | DNPEP | 23549 | 2q36.1 |
| MJ | M19 | M19.001 | membrane dipeptidase | MER01260 | DPEP1 | 1800 | 16q24.3 |
| | | M19.002 | membrane-bound dipeptidase-2 | MER13499 | DPEP2 | 64174 | 16q22.1 |
| | | M19.004 | membrane-bound dipeptidase-3 | MER13496 | DPEP3 | 64180 | 16q22.1 |
| MH | M20 | M20.005 | carnosine dipeptidase II | MER14551 | CNDP2 | 55748 | 18 |
| | | M20.006 | carnosine dipeptidase I (sequenced from cDNA by MEROPS) | MER15142 | CNDP1 | 84735 | 18q22.3 |
| | | M20.011 | Mername-AA218 hypothetical peptidase | MER33182 | | 148811 | 1q32.1 |
| | | M20.971 | Mername-AA161 protein | MER21873 | ACY1L2 | 135293 | 6q15 |
| | | M20.973 | aminoacylase (aminoacylase-1) | MER01271 | ACY1 | 95 | 3p21.1 |
| MK | M22 | M22.003 | Kael putative peptidase | MER01577 | OSGEP | 55644 | 14q11.1 |
| | | M22.004 | Mername-AA018 peptidase | MER13498 | OSGEPL1 | 64172 | 2q32.3 |
| MG | M24 | M24.001 | methionyl aminopeptidase 1 | MER01342 | METAP1 | 23173 | 4q23 |
| | | M24.002 | methionyl aminopeptidase 2 | MER01728 | METAP2 | 10988 | 12q22 |
| | | M24.005 | aminopeptidase P2 | MER04498 | XPNPEP2 | 7512 | Xq25 |
| | | M24.007 | Xaa-Pro dipeptidase (eukaryote) | MER01248 | PEPD | 5184 | 19cen-q13.11 |
| | | M24.009 | aminopeptidase P1 | MER04321 | XPNPEP1 | 7511 | 10q25.3 |
| | | M24.026 | aminopeptidase P homologue | MER13463 | | 63929 | 22q13.31-q13.33 |
| | | M24.028 | Mername-AA021 peptidase | MER14055 | MAP1D | 254042 | 2q31.1 |
| | | M24.950 | Mername-AA020 peptidase homologue | MER10972 | | | 12q11-q12 |
| | | M24.973 | proliferation-association protein 1 (proliferation-associated protein 1) | MER05497 | PA2G4 | 5036 | 12q13 |
| | | M24.974 | chromatin-specific transcription elongation factor 140 kDa subunit | MER26495 | SUPT16H | 11198 | 14q11.2 |
| | | M24.975 | proliferation-associated protein 1-like (*Homo sapiens* chromosome X) | MER29983 | | | Xq23 |
| | | M24.976 | Mername AA-226 peptidase homologue (*Homo sapiens*) | MER56262 | | 442053 | 2q22.3 |
| | | M24.977 | Mername AA-227 peptidase homologue (*Homo sapiens*) (deduced from nucleotide sequence by MEROPS) | MER47299 | | | 18q11.2-q12.1 |
| MH | M28 | M28.010 | glutamate carboxypeptidase II | MER02104 | FOLH1 | 2346 | 11p11.2 |
| | | M28.011 | NAALADASE L peptidase | MER05239 | NAALADL1 | 10004 | 11q12 |
| | | M28.012 | glutamate carboxypeptidase III | MER05238 | NAALAD2 | 10003 | 11q14.3-q21 |
| | | M28.014 | plasma glutamate carboxypeptidase (hematopoietic lineage switch 2) | MER05244 | | 10404 | 8q22.2 |
| | | M28.016 | Mername-AA103 peptidase | MER15091 | QPCTL | 54814 | 19q13.32 |
| | | M28.018 | Fxna peptidase (*Rattus norvegicus*) (sequence assembled by MEROPS) | MER29965 | KIAA1815 | 79956 | 9p24 |
| | | M28.972 | transferrin receptor protein (transferrin receptor) | MER02105 | TFRC | 7037 | 3q26.2 |
| | | M28.973 | transferrin receptor 2 protein (transferrin receptor 2) | MER05152 | TFR2 | 7036 | 7q22 |
| | | M28.974 | glutaminyl cyclase | MER15095 | QPCT | 25797 | 2p22.3 |
| | | M28.975 | glutamate carboxypeptidase II (*Homo sapiens*)-like protein | MER26971 | NAALADL2 | 254827 | 3q26.31 |
| | | M28.978 | nicalin | MER44627 | NCLN | 56926 | 19p13.3 |
| MJ | M38 | M38.972 | dihydro-orotase (dihydroorotase) | MER05767 | CAD | 790 | 2p22-p21 |
| | | M38.973 | dihydropyrimidinase | MER33266 | DPYS | 1807 | 8q22 |
| | | M38.974 | dihydropyrimidinase related protein-1 | MER30143 | CRMP1 | 1400 | 4p16.1-p15 |
| | | M38.975 | dihydropyrimidinase related protein-2 | MER30155 | DPYSL2 | 1808 | 8p22-p21 |
| | | M38.976 | dihydropyrimidinase related protein-3 | MER30151 | DPYSL3 | 1809 | 5q32 |
| | | M38.977 | dihydropyrimidinase related protein-4 | MER30149 | DPYSL4 | 10570 | 10q26 |
| | | M38.978 | dihydropyrimidinase related protein-5 | MER30136 | DPYSL5 | 56896 | 2p23.3 |
| | | M38.979 | hypothetical protein like 5730457F11RIK | MER33184 | | 51005 | 16p13.3 |
| | | M38.980 | 1300019j08rik protein | MER33186 | | 144193 | 12q23.1 |
| | | M38.981 | guanine aminohydrolase | MER37714 | GDA | 9615 | 9q21.11-21.33 |
| MA | M41 | M41.004 | i-AAA peptidase | MER05755 | YME1L1 | 10730 | 10p14 |
| | | M41.006 | paraplegin | MER04454 | SPG7 | 6687 | 16q24.3 |
| | | M41.007 | Afg3-like protein 2 | MER05496 | AFG3L2 | 10939 | 18p11 |
| | | M41.010 | Afg3-like protein 1 (deduced from nucleotide sequence by MEROPS) | MER14306 | AFG3L1 | 172 | 16q24 |
| | | M41.011 | Mername-AA024 peptidase | MER01246 | | | 19 |
| | M43 | M43.004 | pappalysin-1 | MER02217 | PAPPA | 5069 | 9q33.1 |
| | | M43.005 | pappalysin-2 | MER14521 | PAPPA2 | 60676 | 1q23-q25 |
| | M48 | M48.003 | farnesylated-protein converting enzyme 1 | MER02646 | ZMPSTE24 | 10269 | 1p34 |
| | | M48.017 | metalloprotease-related protein-1 | MER30873 | OMA1 | 115209 | 1p32 |
| M- | M49 | M49.001 | dipeptidyl-peptidase III | MER04252 | DPP3 | 10072 | 11q12-q13.1 |
| | | M49.971 | Mername-AA163 protein | MER20074 | | | 9q21.31 |
| | | M49.972 | Mername-AA164 protein | MER20410 | | | 4q13.1 |
| MM | M50 | M50.001 | S2P peptidase | MER04458 | MBTPS2 | 51360 | X |
| MP | M67 | M67.001 | Poh1 peptidase | MER20382 | PSMD14 | 10213 | 2q24.3 |
| | | M67.002 | Jab1/MPN domain metalloenzyme | MER22057 | COPS5 | 10987 | 8q13.1 |
| | | M67.003 | Mername-AA165 peptidase | MER21865 | | 57559 | 10q23.31 |
| | | M67.004 | Mername-AA166 peptidase | MER21890 | CXorf53 | 79184 | Xq28 |

-continued

| Clan | Family | MEROPS ID | Peptidase or homologue (subtype) | MERNUM | Gene | Link | Locus |
|---|---|---|---|---|---|---|---|
| | | M67.005 | Mername-AA167 peptidase | MER21887 | MYSM1 | 114803 | 1p32.1 |
| | | M67.006 | AMSH deubiquitinating peptidase | MER30146 | STAMBP | 10617 | 2p13.1 |
| | | M67.008 | putative peptidase (*Homo sapiens* chromosome 2) | MER29970 | | | 2 |
| | | M67.971 | Mername-AA168 protein | MER21886 | EIF3S3 | 8667 | 8q24.11 |
| | | M67.972 | COP9 signalosome subunit 6 | MER30137 | COPS6 | 10980 | 7q22.1 |
| | | M67.973 | 26S proteasome non-ATPase regulatory subunit 7 | MER30134 | PSMD7 | 5713 | 16q23-q24 |
| | | M67.974 | eukaryotic translation initiation factor 3 subunit 5 | MER30133 | EIF3S5 | 8665 | 11p15.4 |
| | | M67.975 | IFP38 peptidase homologue | MER30132 | EIF3S5 | 83880 | 11p15.4 |
| M- | M76 | M76.001 | Atp23 peptidase | MER60642 | | | |
| PA | S1 | S01.010 | granzyme B, human-type | MER00168 | GZMB | 3002 | 14q11.2 |
| | | S01.011 | testisin | MER05212 | PRSS21 | 10942 | 16p13.3 |
| | | S01.015 | tryptase beta | MER00137 | TPSAB1 | 7177 | 16p13.3 |
| | | | tryptase beta (2) | MER00136 | TPSB2 | 64499 | 16p13.3 |
| | | S01.017 | kallikrein-related peptidase 5 | MER05544 | KLK5 | 25818 | 19q13.3-q13.4 |
| | | S01.019 | corin | MER05881 | CORIN | 10699 | 4p13-p12 |
| | | S01.020 | kallikrein-related peptidase 12 | MER06038 | KLK12 | 43849 | 19q13.3-q13.4 |
| | | S01.021 | DESC1 peptidase | MER06298 | TMPRSS11E | 28983 | 4q13.3 |
| | | S01.028 | tryptase gamma 1 | MER11036 | TPSG1 | 25823 | 16p13.3 |
| | | S01.029 | kallikrein-related peptidase 14 | MER11038 | KLK14 | 43847 | 19q13.3-q13.4 |
| | | S01.033 | hyaluronan-binding peptidase (HGF activator-like protein) | MER03612 | HABP2 | 3026 | 10q25.3 |
| | | S01.034 | transmembrane peptidase, serine 4 | MER11104 | TMPRSS4 | 56649 | 11q23.3 |
| | | S01.047 | adrenal secretory serine peptidase | MER03734 | TMPRSS11D | 9407 | 4q13.2 |
| | | S01.054 | tryptase delta 1 (*Homo sapiens*) | MER05948 | TPSD1 | 23430 | 16p13.3 |
| | | S01.072 | matriptase-3 | MER29902 | TMPRSS7 | 344805 | 3q13 |
| | | S01.074 | marapsin | MER06119 | PRSS27 | 83886 | 16p13.3 |
| | | S01.075 | tryptase homologue 2 (*Homo sapiens*) | MER06118 | PRSS33 | 260429 | 16p13.3 |
| | | S01.076 | tryptase homologue 3 (*Homo sapiens*) | MER00285 | | | |
| | | S01.079 | transmembrane peptidase, serine 3 | MER05926 | TMPRSS3 | 64699 | 21q22.3 |
| | | S01.081 | kallikrein-related peptidase 15 | MER00064 | KLK15 | 55554 | 19q13.41 |
| | | S01.085 | Mername-AA031 peptidase | MER14054 | | 136541 | 7q34 |
| | | S01.087 | mosaic serine peptidase long-form | MER14226 | TMPRSS13 | 84000 | 11q23 |
| | | S01.088 | Mername-AA038 peptidase | MER62848 | | 138652 | 9q22.31 |
| | | S01.098 | Mername-AA128 peptidase (deduced from ESTs by MEROPS) | MER16130 | | 124221 | 16p13.3 |
| | | S01.105 | Mername-AA204 peptidase | MER29980 | | | |
| | | S01.127 | cationic trypsin (*Homo sapiens*-type) (1 (cationic)) | MER00020 | PRSS1 | 5644 | 7q35 |
| | | S01.131 | neutrophil elastase | MER00118 | ELA2 | 1991 | 19p13.3 |
| | | S01.132 | mannan-binding lectin-associated serine peptidase-3 | MER31968 | MASP1 | 5648 | 3q27-q28 |
| | | S01.133 | cathepsin G | MER00082 | CTSG | 1511 | 14q11.2 |
| | | S01.134 | myeloblastin (proteinase 3) | MER00170 | PRTN3 | 5657 | 19p13.3 |
| | | S01.135 | granzyme A | MER01379 | GZMA | 3001 | 5q11-q12 |
| | | S01.139 | granzyme M | MER01541 | GZMM | 3004 | 19p13.3 |
| | | S01.140 | chymase (human-type) | MER00123 | CMA1 | 1215 | 14q11.2 |
| | | S01.143 | tryptase alpha (1) | MER00135 | TPSAB1 | 7176 | 16p13.3 |
| | | S01.146 | granzyme K | MER01936 | GZMK | 3003 | 5q11-q12 |
| | | S01.147 | granzyme H | MER00166 | GZMH | 2999 | 14q11.2 |
| | | S01.152 | chymotrypsin B | MER00001 | CTRB1 | 1504 | 16q23.2-q23.3 |
| | | S01.153 | pancreatic elastase | MER03733 | ELA1 | 1990 | 12q13 |
| | | S01.154 | pancreatic endopeptidase E (A) | MER00149 | ELA3A | 10136 | 1p36.12 |
| | | S01.155 | pancreatic elastase II (IIA) | MER00146 | | 63036 | 1p36.21 |
| | | S01.156 | enteropeptidase | MER02068 | PRSS7 | 5651 | 21q21 |
| | | S01.157 | chymotrypsin C | MER00761 | CTRC | 11330 | 1p36.21 |
| | | S01.159 | prostasin | MER02460 | PRSS8 | 5652 | 16p11.2 |
| | | S01.160 | kallikrein hK1 | MER00093 | KLK1 | 3816 | 19q13.2-q13.4 |
| | | S01.161 | kallikrein-related peptidase 2 | MER00094 | KLK2 | 3817 | 19q13.2-q13.4 |
| | | S01.162 | kallikrein-related peptidase 3 | MER00115 | KLK3 | 354 | 19q13.3-q13.4 |
| | | S01.174 | mesotrypsin | MER00022 | PRSS3 | 5646 | 9p13 |
| | | S01.189 | complement component C1r-like peptidase | MER16352 | C1RL | 51279 | 12p13.31 |
| | | S01.191 | complement factor D | MER00130 | DF | 1675 | 19 |
| | | S01.192 | complement component activated C1r | MER00238 | C1R | 715 | 12p13 |
| | | S01.193 | complement component activated C1s | MER00239 | C1S | 716 | 12p13 |
| | | S01.194 | complement component C2a | MER00231 | C2 | 717 | 6p21.3 |
| | | S01.196 | complement factor B | MER00229 | BF | 629 | 6p21.3 |
| | | S01.198 | mannan-binding lectin-associated serine peptidase 1 | MER00244 | MASP1 | 5648 | 3q27-q28 |
| | | S01.199 | complement factor I | MER00228 | IF | 3426 | 4q24-q25 |
| | | S01.205 | pancreatic endopeptidase E form B (B) | MER00150 | ELA3B | 23436 | 1p36.12 |
| | | S01.206 | pancreatic elastase II form B (*Homo sapiens*) (IIB) | MER00147 | ELA1 | 51032 | 12q13 |
| | | S01.211 | coagulation factor XIIa | MER00187 | F12 | 2161 | 5q33-qter |
| | | S01.212 | plasma kallikrein | MER00203 | KLKB1 | 3818 | 4q35 |
| | | S01.213 | coagulation factor XIa | MER00210 | F11 | 2160 | 4q35 |
| | | S01.214 | coagulation factor IXa | MER00216 | F9 | 2158 | Xq27.1-q27.2 |
| | | S01.215 | coagulation factor VIIa | MER00215 | F7 | 2155 | 13q34 |
| | | S01.216 | coagulation factor Xa | MER00212 | F10 | 2159 | 13q34 |
| | | S01.217 | thrombin | MER00188 | F2 | 2147 | 11p11-q12 |
| | | S01.218 | protein C (activated) | MER00222 | PROC | 5624 | 2q13-q14 |
| | | S01.223 | acrosin | MER00078 | ACR | 49 | 22q13-qter |

-continued

| Clan | Family | MEROPS ID | Peptidase or homologue (subtype) | MERNUM | Gene | Link | Locus |
|---|---|---|---|---|---|---|---|
| | | S01.224 | hepsin | MER00156 | HPN | 3249 | 19q11-q13.2 |
| | | S01.228 | hepatocyte growth factor activator | MER00186 | HGFAC | 3083 | 4p16 |
| | | S01.229 | mannan-binding lectin-associated serine peptidase 2 | MER02758 | MASP2 | 10747 | 1p36.3-p36.2 |
| | | S01.231 | u-plasminogen activator | MER00195 | PLAU | 5328 | 10q24 |
| | | S01.232 | t-plasminogen activator | MER00192 | PLAT | 5327 | 8p12 |
| | | S01.233 | plasmin | MER00175 | PLG | 5340 | 6q26 |
| | | S01.236 | kallikrein-related peptidase 6 (*Homo sapiens*) | MER02580 | KLK6 | 5653 | 19q13.3-q13.4 |
| | | S01.237 | neurotrypsin | MER04171 | PRSS12 | 8492 | 4q25-q26 |
| | | S01.244 | kallikrein-related peptidase 8 | MER05400 | KLK8 | 11202 | 19q13.3-q13.4 |
| | | S01.246 | kallikrein-related peptidase 10 | MER03645 | KLK10 | 5655 | 19q13.33 |
| | | S01.247 | epitheliasin | MER03736 | TMPRSS2 | 7113 | 21q22.3 |
| | | S01.251 | kallikrein-related peptidase 4 | MER05266 | KLK4 | 9622 | 19q13.3-q13.4 |
| | | S01.252 | prosemin | MER04214 | PRSS22 | 64063 | 16p13.3 |
| | | S01.256 | chymopasin | MER01503 | CTRL | 1506 | 16q22.1 |
| | | S01.257 | kallikrein-related peptidase 11 | MER04861 | KLK11 | 11012 | 19q13.3-q13.4 |
| | | S01.258 | trypsin-2 (human-type) (II) | MER00021 | PRSS2 | 5645 | 7q35 |
| | | S01.277 | HtrA1 peptidase | MER02577 | PRSS11 | 5654 | 10q25.3-q26.2 |
| | | S01.278 | HtrA2 peptidase | MER04093 | PRSS25 | 27429 | 2p12 |
| | | S01.284 | HtrA3 peptidase | MER14795 | HTRA3 | 94031 | 4p16.1 |
| | | S01.285 | HtrA4 peptidase | MER16351 | HTRA4 | 203100 | 8p11.23 |
| | | S01.286 | Tysnd1 peptidase | MER50461 | TYSND1 | 219743 | 10q22.1 |
| | | S01.291 | LOC144757 peptidase (*Homo sapiens*) and similar (protein sequence extended by use of MEROPS EST alignment) | MER17085 | TMPRSS12 | 283471 | 12q13.13 |
| | | S01.292 | HAT-like putative peptidase 2 | MER21884 | TMPRSS11A | 339967 | 4q13.3 |
| | | S01.298 | trypsin C | MER21898 | | 154754 | 7q34 |
| | | S01.299 | Mername-AA175 peptidase | MER21930 | | 203074 | 8p23.1 |
| | | S01.300 | kallikrein-related peptidase 7 | MER02001 | KLK7 | 5650 | 19q13.3-q13.4 |
| | | S01.302 | matriptase | MER03735 | ST14 | 6768 | 11q24-q25 |
| | | S01.306 | kallikrein-related peptidase 13 | MER05269 | KLK13 | 26085 | 19q19.3-q19.4 |
| | | S01.307 | kallikrein-related peptidase 9 | MER05270 | KLK9 | 23579 | 19q19.3-q19.4 |
| | | S01.308 | matriptase-2 | MER05278 | TMPRSS6 | 164656 | 22q13.1 |
| | | S01.309 | umbelical vein peptidase | MER05421 | PRSS23 | 11098 | 11q14.1 |
| | | S01.311 | LCLP peptidase (LCLP (N-terminus)) | MER01900 | | | |
| | | S01.313 | spinesin | MER14385 | TMPRSS5 | 80975 | 11q23.3 |
| | | S01.318 | marapsin-2 | MER21929 | | 339501 | 1q42.13 |
| | | S01.319 | complement factor D-like putative peptidase | MER56164 | PRSSL1 | 400668 | 19p13.3 |
| | | S01.320 | Mername-AA180 peptidase | MER22410 | OVCH2 | 341277 | 11p15.4 |
| | | S01.321 | Mername-AA181 peptidase | MER44589 | TMPRSS11F | 389208 | 4q13.2 |
| | | S01.322 | Mername-AA182 peptidase | MER22412 | OVCH1 | 341350 | 12p11.23 |
| | | S01.325 | epidermis-specific SP-like putative peptidase | MER29900 | | 345062 | 4q31.3 |
| | | S01.326 | testis serine peptidase 5 | MER29901 | | 377047 | 3p21 |
| | | S01.327 | testis serine peptidase 1 | MER30190 | | 360226 | 16p13.3 |
| | | S01.357 | polyserase-IA (unit 1) (unit 1) | MER30879 | TMPRSS9 | 360200 | 19p13.3 |
| | | S01.358 | polyserase-IA (unit 2) (unit 2) | MER30880 | TMPRSS9 | 360200 | 19p13.3 |
| | | S01.362 | testis serine peptidase 2 (human-type) | MER33187 | | 339906 | 3p21.31 |
| | | S01.363 | hypothetical acrosin-like peptidase (*Homo sapiens*) | MER33253 | | 284967 | 2q14.1 |
| | | S01.365 | Mername-AA221 putative peptidase | MER28215 | TMPRSS11B | 132724 | 4q13.3 |
| | | S01.374 | polyserase-3 (unit 1) | MER61763 | | | |
| | | S01.375 | polyserase-3 (unit 2) | MER61748 | | | |
| | | S01.376 | peptidase similar to tryptophan/serine protease | MER56263 | | 346702 | 8p23.1 |
| | | S01.414 | polyserase-2 (unit 1) | MER61777 | | | |
| | | S01.940 | polyserase-2 (unit 2) | MER61760 | | | |
| | | S01.941 | polyserase-2 (unit 3) | MER65694 | | | |
| | | S01.957 | secreted trypsin-like serine peptidase homologue (deduced from nucleotide sequence by MEROPS) | MER30000 | | | 4 |
| | | S01.969 | polyserase-1A (unit 3) (unit 3) | MER29880 | TMPRSS9 | 360200 | 19p13.3 |
| | | S01.971 | azurocidin (azurocidin) | MER00119 | AZU1 | 566 | 19p13.3 |
| | | S01.972 | haptoglobin-1 (haptoglobin-2) | MER00233 | HP | 3240 | 16q22.1 |
| | | S01.974 | haptoglobin-related protein (haptoglobin-related protein) | MER00235 | HPR | 3250 | 16q22.1 |
| | | S01.975 | macrophage-stimulating protein (macrophage-stimulating protein) | MER01546 | MST1 | 4485 | 3p21 |
| | | S01.976 | hepatocyte growth factor (hepatocyte growth factor) | MER00185 | HGF | 3082 | 7q21.1 |
| | | S01.977 | hepatocyte growth factor-like protein homologue (hepatocyte growth factor-like protein homologue) | MER03611 | MST1 | 4485 | 3p21 |
| | | S01.979 | protein Z (protein Z) | MER00227 | PROZ | 8858 | 13q34 |
| | | S01.985 | TESP1 protein (deduced from nucleotide sequence by MEROPS) | MER47214 | | 646743/ 646747 | 2q21.1 |
| | | S01.989 | LOC136242 gene product (protein sequence amended by use of MEROPS EST alignment) | MER16132 | | | 7q34 |
| | | S01.992 | Mername-AA199 | MER16346 | | 221191 | 16q21 |
| | | S01.993 | testis-specific protein TSP50 | MER16347 | | 29122 | 3p14-p12 |
| | | S01.994 | dj223e3.1 protein (*Homo sapiens*) | MER16350 | PRSS35 | 167681 | 6q15 |
| | | S01.998 | DKFZp586H2123-like protein | MER66474 | | | |
| | | S01.999 | apolipoprotein | MER00183 | LPA | 4018 | 6q27 |
| | | S01.P08 | psi-KLK1 pseudogene (*Homo sapiens*) | MER33287 | KLKP1 | | 19q13.41 |
| | | S01.P09 | tryptase pseudogene I | MER15077 | | | 16p13.3 |

-continued

| Clan | Family | MEROPS ID | Peptidase or homologue (subtype) | MERNUM | Gene | Link | Locus |
|---|---|---|---|---|---|---|---|
| | | S01.P10 | tryptase pseudogene II | MER15078 | | | 16p13.3 |
| | | S01.P11 | tryptase pseudogene III | MER15079 | | | 16p13.3 |
| SB | S8 | S08.011 | kexin-like peptidase (*Pneumocystis carinii*) (MEROPS assumes this sequence to be derived from a contamination by Pneumocystis carinii) | MER62850 | | 651834 | |
| | | S08.039 | proprotein convertase 9 | MER22416 | PCSK9 | 255738 | 1p32.2 |
| | | S08.063 | site-1 peptidase (KIAA0091 protein) | MER01948 | MBTPS1 | 8720 | 16q24 |
| | | S08.071 | furin | MER00375 | FURIN | 5045 | 15q25-q26 |
| | | S08.072 | proprotein convertase 1 | MER00376 | PCSK1 | 5122 | 5q15-q21 |
| | | S08.073 | proprotein convertase 2 | MER00377 | PCSK2 | 5126 | 20p11.2 |
| | | S08.074 | proprotein convertase 4 | MER28255 | PCSK4 | 54760 | 19p13.3 |
| | | S08.075 | PACE4 proprotein convertase | MER00383 | PCSK6 | 5046 | 15q26 |
| | | S08.076 | proprotein convertase 5 | MER02578 | PCSK5 | 5125 | 9 |
| | | S08.077 | proprotein convertase 7 | MER02984 | PCSK7 | 9159 | 11q23-q24 |
| | | S08.090 | tripeptidyl-peptidase II | MER00355 | TPP2 | 7174 | 13q32-q33 |
| SC | S9 | S09.001 | prolyl oligopeptidase | MER00393 | PREP | 5550 | 6q22 |
| | | S09.003 | dipeptidyl-peptidase IV (eukaryote) | MER00401 | DPP4 | 1803 | 2q23-qter |
| | | S09.004 | acylaminoacyl-peptidase | MER00408 | APEH | 327 | 3p21 |
| | | S09.007 | fibroblast activation protein alpha subunit | MER00399 | FAP | 2191 | 2q23 |
| | | S09.015 | PREPL A protein | MER04227 | PREPL | 9581 | 2 |
| | | S09.018 | dipeptidyl-peptidase 8 | MER13484 | DPP8 | 54878 | 15q22 |
| | | S09.019 | dipeptidyl-peptidase 9 (R26984_1 protein) | MER04923 | DPP9 | 91039 | 19p13.3 |
| | | S09.051 | FLJ1 putative peptidase | MER17240 | C13orf6 | 84945 | 13q33.3 |
| | | S09.052 | Mername-AA194 putative peptidase | MER17353 | C19orf27 | 81926 | 19p13.3 |
| | | S09.053 | Mername-AA195 putative peptidase | MER17367 | | 58489 | 15q25.1 |
| | | S09.054 | Mername-AA196 putative peptidase | MER17368 | C20orf22 | 26090 | 20p11.1 |
| | | S09.055 | Mername-AA197 putative peptidase | MER17371 | C9orf77 | 51104 | 9q21.12 |
| | | S09.061 | C14orf29 protein | MER33244 | C14orf29 | 145447 | 14q22.1 |
| | | S09.062 | hypothetical protein | MER33245 | ABHD10 | 55347 | 3q13.2 |
| | | S09.063 | hypothetical esterase/lipase/thioesterase (deduced from nucleotide sequence by MEROPS) | MER47309 | | | 3 |
| | | S09.065 | protein bat5 | MER37840 | BAT5 | 7920 | 6p21.3 |
| | | S09.958 | hypothetical protein flj40219 | MER33212 | | 79984 | 16q22.1 |
| | | S09.959 | hypothetical protein flj37464 | MER33240 | | 283848 | 16q22.1 |
| | | S09.960 | hypothetical protein flj33678 | MER33241 | | 221223 | 16q12.2 |
| | | S09.966 | hypothetical protein flj90714 (*Homo sapiens*) | MER37720 | C13orf6 | 84945 | 13q33.3 |
| | | S09.973 | dipeptidylpeptidase homologue DPP6 (DPP6 protein) | MER00403 | DPP6 | 1804 | 7 |
| | | S09.974 | dipeptidylpeptidase homologue DPP10 | MER05988 | DPP10 | 57628 | 2q12.3-2q14.2 |
| | | S09.976 | protein similar to chromosome 20 open reading frame 135 (*Mus musculus*) | MER37845 | C20orf135 | 140701 | 20q13.33 |
| | | S09.977 | kynurenine formamidase | MER46020 | AFMID | 125061 | 17q25.3 |
| | | S09.978 | thyroglobulin precursor (thyroglobulin) | MER11604 | TG | 7038 | 8q24.2-q24.3 |
| | | S09.979 | acetylcholinesterase | MER33188 | ACHE | 43 | 7q22 |
| | | S09.980 | cholinesterase | MER33198 | BCHE | 590 | 3q26.1-q26.2 |
| | | S09.981 | carboxylesterase D1 | MER33213 | | | |
| | | S09.982 | liver carboxylesterase | MER33220 | CES1 | 1066 | 16q13-q22.1 |
| | | S09.983 | carboxylesterase 3 | MER33224 | CES3 | 23491 | |
| | | S09.984 | carboxylesterase 2 | MER33226 | CES2 | 8824 | 16q22.1 |
| | | S09.985 | bile salt-dependent lipase | MER33227 | CEL | 1056 | 9q34.3 |
| | | S09.986 | carboxylesterase-related protein | MER33231 | CES4 | 51716 | 16q13 |
| | | S09.987 | neuroligin 3 | MER33232 | NLGN3 | 54413 | Xq13.1 |
| | | S09.988 | neuroligin 4, X-linked | MER33235 | NLGN4X | 57502 | Xp22.33 |
| | | S09.989 | neuroligin 4, Y-linked | MER33236 | NLGN4Y | 22829 | Yq11.221 |
| | | S09.990 | esterase D (*Homo sapiens*) | MER43126 | ESD | 2098 | 13q14.1-q14.2 |
| | | S09.991 | arylacetamide deacetylase | MER33237 | AADAC | 13 | 3q21.3-q25.2 |
| | | S09.992 | KIAA1363-like protein | MER33242 | AADACL1 | 57552 | 3q26.31 |
| | | S09.993 | hormone-sensitive lipase | MER33274 | LIPE | 3991 | 19q13.2 |
| | | S09.994 | neuroligin 1 | MER33280 | NLGN1 | 22871 | 3q26.32 |
| | | S09.995 | neuroligin 2 | MER33283 | NLGN2 | 57555 | 17q13.2 |
| | S10 | S10.002 | serine carboxypeptidase A | MER00430 | PPGB | 5476 | 20q13.1 |
| | | S10.003 | vitellogenic carboxypeptidase-like protein (WUGSC:H_RG113D17.1 protein) | MER05492 | CPVL | 54504 | 7p14-p15.3 |
| | | S10.013 | RISC peptidase | MER10960 | SCPEP1 | 59342 | 17 |
| SE | S12 | S12.004 | LACT-1 peptidase | MER17071 | LACTB | 114294 | 15q22.1 |
| SK | S14 | S14.003 | peptidase Clp (type 3) | MER02211 | CLPP | 8192 | 19 |
| SJ | S16 | S16.002 | PIM1 peptidase | MER00495 | PRSS15 | 9361 | 19p13.2 |
| | | S16.006 | Mername-AA102 peptidase | MER14970 | | 83752 | 16q12.1 |
| SF | S26 | S26.009 | signalase (eukaryote) 18 kDa component (18 kDa) | MER05386 | SEC11L1 | 23478 | 15q25.2 |
| | | S26.010 | signalase (eukaryote) 21 kDa component | MER14880 | SEC11L3 | 90701 | 18q21.31 |
| | | S26.012 | mitochondrial inner membrane peptidase 2 | MER14877 | IMMP2L | 83943 | 7q31 |
| | | S26.013 | mitochondrial signal peptidase (metazoa) | MER13949 | | 196294 | 11p13 |
| | | S26.022 | Mername AA-228 putative peptidase (*Homo sapiens*) (deduced from nucleotide sequence by MEROPS) | MER47379 | | | 8 |
| SC | S28 | S28.001 | lysosomal Pro-Xaa carboxypeptidase | MER00446 | PRCP | 5547 | 11q14 |
| | | S28.002 | dipeptidyl-peptidase II | MER04952 | DPP7 | 29952 | 9q34.3 |
| | | S28.003 | thymus-specific serine peptidase | MER05538 | PRSS16 | 10279 | 6p21.31-p22.2 |

-continued

| Clan | Family | MEROPS ID | Peptidase or homologue (subtype) | MERNUM | Gene | Link | Locus |
|---|---|---|---|---|---|---|---|
| | S33 | S33.011 | epoxide hydrolase-like putative peptidase | MER31614 | ABHD8 | 79575 | 19p13.12 |
| | | S33.012 | Loc328574-like protein | MER33246 | SERHL | 253190 | 22q13.2-q13.31 |
| | | S33.013 | abhydrolase domain-containing protein 4 | MER31616 | ABHD4 | 63874 | 14q11.2 |
| | | S33.971 | epoxide hydrolase (epoxide hydrolase) | MER00432 | EPHX1 | 2052 | 1q42.1 |
| | | S33.972 | mesoderm specific transcript protein | MER17123 | MEST | 4232 | 7q32 |
| | | S33.973 | cytosolic epoxide hydrolase | MER29997 | EPHX2 | 2053 | 8p21-p12 |
| | | S33.974 | similar to hypothetical protein FLJ22408 | MER31608 | ABHD7 | 253152 | 1p22.1 |
| | | S33.975 | CGI-58 putative peptidase | MER30163 | ABHD5 | 51099 | 3p25.3-p24.3 |
| | | S33.976 | Williams-Beuren syndrome critical region protein 21 epoxide hydrolase | MER31610 | ABHD11 | 83451 | 7q11.23 |
| | | S33.977 | epoxide hydrolase | MER31612 | ABHD6 | 57406 | 3p21.2 |
| | | S33.978 | hypothetical protein fli22408 (epoxide hydrolase) (*Homo sapiens*) | MER31617 | ABHD9 | 79852 | 19p13.13 |
| | | S33.980 | monoglyceride lipase | MER33247 | MGLL | 11343 | 3q21.3 |
| | | S33.981 | hypothetical protein | MER33249 | ABHD14A | 25864 | 3p21.1 |
| | | S33.982 | valacyclovir hydrolase | MER33259 | BPHL | 670 | 6p25 |
| | | S33.983 | Ccg1-interacting factor b | MER33263 | | 84836 | 3p21.31 |
| | | S33.984 | protein phosphatase methylesterase 1 | MER37853 | | 51400 | 11q13.4 |
| | | S33.986 | NDRG4 protein | MER42913 | NDRG4 | 65009 | 16q21-q22.1 |
| | | S33.987 | NDRG3 protein | MER42914 | NDRG3 | 57446 | 20q11.21-q11.23 |
| | | S33.988 | Mername AA-229 peptidase homologue (*Homo sapiens*) | MER45809 | NDRG1 | 10397 | 8q24.3 |
| SK | S41 | S41.950 | interphotoreceptor retinoid-binding protein, unit 1 | MER30235 | RBP3 | 5949 | 10q11.2 |
| | | S41.951 | interphotoreceptor retinoid-binding protein, unit 2 | MER59675 | RBP3 | 5949 | 10q11.2 |
| SB | S53 | S53.003 | tripeptidyl-peptidase I | MER03575 | TPP1 | 1200 | 11p15 |
| ST | S54 | S54.002 | rhomboid-like protein 2 | MER15453 | RHBDL2 | 54933 | 1p35.1 |
| | | S54.005 | rhomboid-like protein 1 | MER15454 | RHBDL1 | 9028 | 16p13.3 |
| | | S54.006 | ventrhoid transmembrane protein | MER20285 | RHBDL4 | 162494 | 17q11.2 |
| | | S54.008 | rhomboid-like protein 5 | MER30173 | | 84236 | 2q36.3 |
| | | S54.009 | Rhomboid-7 (*Drosophila melanogaster*) | MER30047 | PSARL | 55486 | 3q27.3 |
| | | S54.952 | RHBDF1 protein | MER04528 | RHBDF1 | 64285 | 16pter-p13 |
| | | S54.953 | peptidase homologue similar to hypothetical protein FLJ22341 | MER02969 | RHBDL6 | 79651 | 17q25.3 |
| | | S54.955 | rhomboid-like protein 7 | MER31620 | RHBDL7 | 57414 | 7q11.23 |
| SP | S59 | S59.001 | nucleoporin 145 | MER20203 | NUP98 | 4928 | 11p15.5 |
| | | S59.951 | nup 36 protein (*Homo sapiens*) and similar | MER20219 | | | |
| SR | S60 | S60.001 | lactoferrin (unit 1) | MER20365 | LTF | 4057 | 3q21-q23 |
| | | S60.970 | lactotransferrin precursor, domain 2 (unit 2) | MER37758 | LTF | 4057 | 3q21-q23 |
| | | S60.972 | serotransferrin precursor (domain 1) (unit 1) | MER33288 | TF | 7018 | 3q22.1 |
| | | S60.973 | melanotransferrin domain 1 (unit 1) | MER33291 | MFI2 | 4241 | 3q28-q29 |
| | | S60.975 | serotransferrin precursor (domain 2) (unit 2) | MER37088 | TF | 7018 | 3q22.1 |
| | | S60.976 | melanotransferrin domain 2 (unit 2) | MER37142 | MFI2 | 4241 | 3q28-q29 |
| S— | S63 | S63.001 | EGF-like module containing mucin-like hormone receptor-like 2 | MER37230 | EMR2 | 30817 | 19p13.1 |
| | | S63.002 | CD97 antigen | MER37286 | CD97 | 976 | 19p13 |
| | | S63.003 | EGF-like module containing mucin-like hormone receptor-like 3 | MER37288 | EMR3 | 84658 | 19p13.1 |
| | | S63.004 | EGF-like module containing mucin-like hormone receptor-like 1 (*Homo sapiens*) | MER37278 | EMR1 | 37278 | 19p13.3 |
| | | S63.008 | EGF-like module containing mucin-ike hormone receptor-like 4 | MER37294 | EMR4 | 326342 | 19p13.3 |
| | | S63.009 | cadherin EGF LAG seven-pass G-type receptor 2 precursor (*Homo sapiens*) | MER45397 | CELSR2 | 1952 | 1p21 |
| | S68 | S68.001 | PIDD auto-processing protein unit 1 | MER20001 | | | 11p15.5 |
| | | S68.002 | PIDD auto-processing protein unit 2 | MER63690 | | | 11p15.5 |
| PB | T1 | T01.010 | proteasome catalytic subunit 1 | MER00556 | PSMB6 | 5694 | 17p13 |
| | | T01.011 | proteasome catalytic subunit 2 | MER02625 | PSMB7 | 5695 | 9q34.11-q34.12 |
| | | T01.012 | proteasome catalytic subunit 3 | MER02149 | PSMB5 | 5693 | 14q11.2 |
| | | T01.013 | proteasome catalytic subunit 1i | MER00552 | PSMB9 | 5698 | 6p21.3 |
| | | T01.014 | proteasome catalytic subunit 2i | MER01515 | PSMB10 | 5699 | 16q22.1 |
| | | T01.015 | proteasome catalytic subunit 3i | MER00555 | PSMB8 | 5696 | 6p21.3 |
| | | T01.016 | RIKEN cDNA 5830406J20 | MER26203 | | 122706 | 14q11.2 |
| | | T01.017 | protein serine kinase c17 (*Homo sapiens*) | MER26497 | | | |
| | | T01.971 | proteasome subunit alpha 6 | MER00557 | PSMA6 | 5687 | 14q13 |
| | | T01.972 | proteasome subunit alpha 2 | MER00550 | PSMA2 | 5683 | 6q27 |
| | | T01.973 | proteasome subunit alpha 4 | MER00554 | PSMA4 | 5685 | 15q11.2 |
| | | T01.974 | proteasome subunit alpha 7 (XAPC7) | MER04372 | PSMA7 | 5688 | 20pter-p12.1 |
| | | | proteasome subunit alpha 7 | MER91448 | | | |
| | | T01.975 | proteasome subunit alpha 5 | MER00558 | PSMA5 | 5686 | 1p13 |
| | | T01.976 | proteasome subunit alpha 1 | MER00549 | PSMA1 | 5682 | 11p15.1 |
| | | T01.977 | proteasome subunit alpha 3 | MER00553 | PSMA3 | 5684 | 14q23 |
| | | T01.978 | 2410072d24rik protein (mouse) | MER33250 | PSMA8 | 143471 | 18q11.2 |
| | | T01.983 | proteasome subunit beta 3 | MER01710 | PSMB3 | 5691 | 2q35 |
| | | T01.984 | proteasome subunit beta 2 | MER02676 | PSMB2 | 5690 | 1p34.2 |
| | | T01.986 | proteasome subunit beta 1 | MER00551 | PSMB1 | 5689 | 7p12-p13 |
| | | | proteasome subunit beta 1 | MER91422 | | | |
| | | T01.987 | proteasome subunit beta 4 | MER01711 | PSMB4 | 5692 | 1q21 |

-continued

| Clan | Family | MEROPS ID | Peptidase or homologue (subtype) | MERNUM | Gene | Link | Locus |
|---|---|---|---|---|---|---|---|
| | | T01.991 | Mername AA-230 peptidase homologue (*Homo sapiens*) (deduced from nucleotide sequence by MEROPS) | MER47329 | | | 2q33 |
| | | T01.P02 | Mername AA-231 pseudogene (*Homo sapiens*) (deduced from nucleotide sequence by MEROPS) | MER47172 | PSMB3P | 121131 | 12q13.2 |
| | | T01.P03 | Mername AA-232 pseudogene (*Homo sapiens*) (deduced from nucleotide sequence by MEROPS) | MER47316 | | 130700 | 2q35 |
| | T2 | T02.001 | glycosylasparaginase precursor | MER03299 | AGA | 175 | 4q23-q27 |
| | | T02.002 | isoaspartyl dipeptidase (threonine type) | MER31622 | ASRGL1 | 80150 | 11q12.3 |
| | | T02.004 | taspase-1 | MER16969 | TASP1 | 55617 | 20p12.1 |
| | T3 | T03.002 | gamma-glutamyltransferase 5 (mammalian) (5) | MER01977 | GGTLA1 | 2687 | 22q11.23 |
| | | T03.006 | gamma-glutamyltransferase 1 (mammalian) (1) | MER01629 | GGT1 | 2678 | 22q11.23 |
| | | T03.015 | gamma-glutamyltransferase 2 (*Homo sapiens*) (2) | MER01976 | GGT2 | 2679 | 22q11.23 |
| | | T03.016 | gamma-glutamyltransferase-like protein 4 (m-type 3) | MER02721 | GGTL4 | 91227 | 22q11.21 |
| | | T03.017 | gamma-glutamyltransferase-like protein 3 | MER16970 | GGTL3 | 2686 | 20q11.22 |
| | | T03.018 | similar to gamma-glutamyltransferase 1 precursor (*Homo sapiens*) | MER26204 | | | 22q11.21 |
| | | T03.019 | similar to gamma-glutamyltransferase 1 precursor (*Homo sapiens*) | MER26205 | | | 22q11.23 |
| | | T03.021 | Mername-AA211 putative peptidase | MER26207 | | | 22 |
| | | T03.971 | gamma-glutamyl transpeptidase homologue (chromosome 2, *Homo sapiens*) | MER37241 | | | 2p11.1 |
| U- | U48 | U48.002 | prenyl peptidase 1 (protein sequence corrected by use of MEROPS EST alignment) | MER04246 | RCE1 | 9986 | 11q13 |

Retroviral Proteases

Recombinant human retroviral proteases nay also be used for the present invention. Human retroviral proteases, including that of human inmmunodeficiency virus type 1 (HIV-1) (Beck et al., 2002), human T cell leukemia viruses (HTLV) (Shuker et al., Chem. Biol. 10:373 (2003)), and severe acute respiratory syndrome coronavirus (SARS), have been extensively studied as targets of anti-viral therapy. These proteases often have long recognition sequences and high substrate selectivity. For example, SQNY↓PIV (SEQ ID NO:60) was determined as a preferred cleavage sequence of HIV-1 protease (Beck et al. Curr. Drug Targets Infect. Disord. 2(1):37-50 (2002), the preferred cleavage sequence for HTLV protease has been determined to be PVIL↓PIQA (SEQ ID NO:61) (Naka et al. Bioorg. Med. Chem. Lett. 16(14):3761-3764 (2006).

Coronaviral Proteases

Coronaviral or toroviral proteases are encoded by members of the animal virus family Coronaviridae and exhibit high cleavage specificity. Such proteases are another preferred embodiment for the present invention. The SARS 3C-like protease has been found to selectively cleave at AVLQ↓SGF (SEQ ID NO:62) (Fan et al. Biochem. Biophys. Res. Commun. 329(3):934-940 (2005)).

Picornaviral Proteases

Picornaviral proteases may also be used for the present invention. Such picornaviral proteases have been studied as targets of anti-viral therapy, for example human Rhinovirus (HRV) (Binford et al., Antimicrob. Agents Chemother. 49:619 (2005)). HRV 3C protease recognizes and cleaves ALFQ↓GP (SEQ ID NO:63) (Cordingley et al. J. Biol. Chem. 265(16):9062-9065 (1990)).

Potyviral Proteases

Potyviral proteases are encoded by members of the plant virus family Potyviridae and exhibiting high cleavage specificity, and are another preferred embodiment for the present invention. For example, tobacco etch virus (TEV) protease has very high substrate specificity and catalytic efficiency, and is used widely as a tool to remove peptide tags from overexpressed recombinant proteins (Nunn et al., J. Mol. Biol. 350:145 (2005)). TEV protease recognizes an extended seven amino acid residue long consensus sequence E-X-X-Y-X-Q↓S/G (where X is any residue) that is present at protein junctions (SEQ ID NO:59). Those skilled in the art would recognize that it is possible to engineer a particular protease such that its sequence specificity is altered to prefer another substrate sequence (Tozser et al., FEBS J. 272:514 (2005)).

Proteases of Other Origins

Since proteases are physiologically necessary for living organisms, they are ubiquitous, being found in a wide range of sources such as plants, animals, and microorganisms (Rao et al. Microbiol. Mol. Biol. Rev. 62(3):597-635 (1998)). All these proteases are potential candidates for the present invention. In a preferred embodiment, PEGylation may be utilized to reduce the immunological potential of fusion proteases for the present invention, particularly for those that are of non-human origins. PEGylation may confer additional benefits to protease fusion proteins, such as improved plasma persistence and reduced non-specific cell binding.

B. Recombinant DNA Construct Design and Sequence Modifications

Methods described above for the construction and sequence modification of fusion proteins, such as DT fusion proteins, are generally applicable to construction of protease fusion proteins as well, except for those techniques specifically dedicated to diphtheria toxin. Many proteases found in nature are synthesized as zymogens, i.e., as catalytically inactive forms in which an inhibitory peptide binds to and masks the active site, or in which the active site is otherwise non-functional because the presence of an inhibitory peptide alters the conformation of the active site. Zymogens are typically activated by cleavage and release of the inhibitory peptide. In one embodiment of the present invention, the exogenous protease of the protoxin activator is in the form of a zymogen, which may be activated by another exogenous protease or by an endogenous protease. Depending on the location of the inhibitory peptide in the primary sequence, such zymogens are either favorably N-terminally situated (when the inhibitory peptide is located at the N-terminus of the zymogen) or C-terminally situated (when the inhibitory peptide is located at the C-terminus of the zymogen). When the protease moiety of the protoxin activator is linked to the cell-targeting moiety by chemical or enzymatic linkage, the inhibitory peptide may be located at either the N-terminus or the C-terminus, since either or both termini may be free as a result of an operable linkage to a cell-targeting moiety taking place at a location other than the N- or C-terminus.

Accordingly, one embodiment of the present invention comprises a recombinant protoxin proactivator that may be activated by another protease. Such a protoxin proactivator comprises an inhibitory peptide, a modifiable activation moiety, a protease moiety, and a cell-targeting moiety. The inhibitory peptide is removed by a modification of the modifiable activation moiety that either directly or indirectly cleaves the modifiable activation moiety to afford an active protease fusion.

Many zymogens comprise active enzymatic moieties in which the inhibitory peptide physically occupies the active site substrate binding cleft, and for which the cleavage site that releases the inhibitory peptide lies distal to the cleft. Among members of a class of proteases for which the active site is composed of residues at the N-terminus of the polypeptide chain, and for which the alpha amino group comprises the active site nucleophile or an important determinant of catalytic efficacy, artificial zymogens can be formed by directly appending a protease cleavage site to the N-terminus. In such cases the activating protease must be capable of cleaving the bond between the recognition site and the desired N-terminal residue. In a preferred embodiment, the activating protease has no sequence requirement for the residue directly following the cleavage location, or preferentially cleaves substrates for which the residue directly following the cleavage location is the same as the reside at the N-terminus of the mature protease. Examples of activating proteases that directly cleave the modifiable activation moiety and their corresponding cleavage sites include, but are not limited to, IEGR↓, a protease cleavage site targeted by Factor Xa; DDDDK↓, (SEQ ID NO:25), a protease cleavage site targeted by enterokinase. Specifically, a GrB fusion containing DDDDK (SEQ ID NO:25), to its N-terminus may be generated and activated by treatment with enterokinase. Specifically, GrB-anti-CD19, GrB-anti-CD5, and GrB-$(YSA)_2$ fusions are so constructed.

Figure 20:
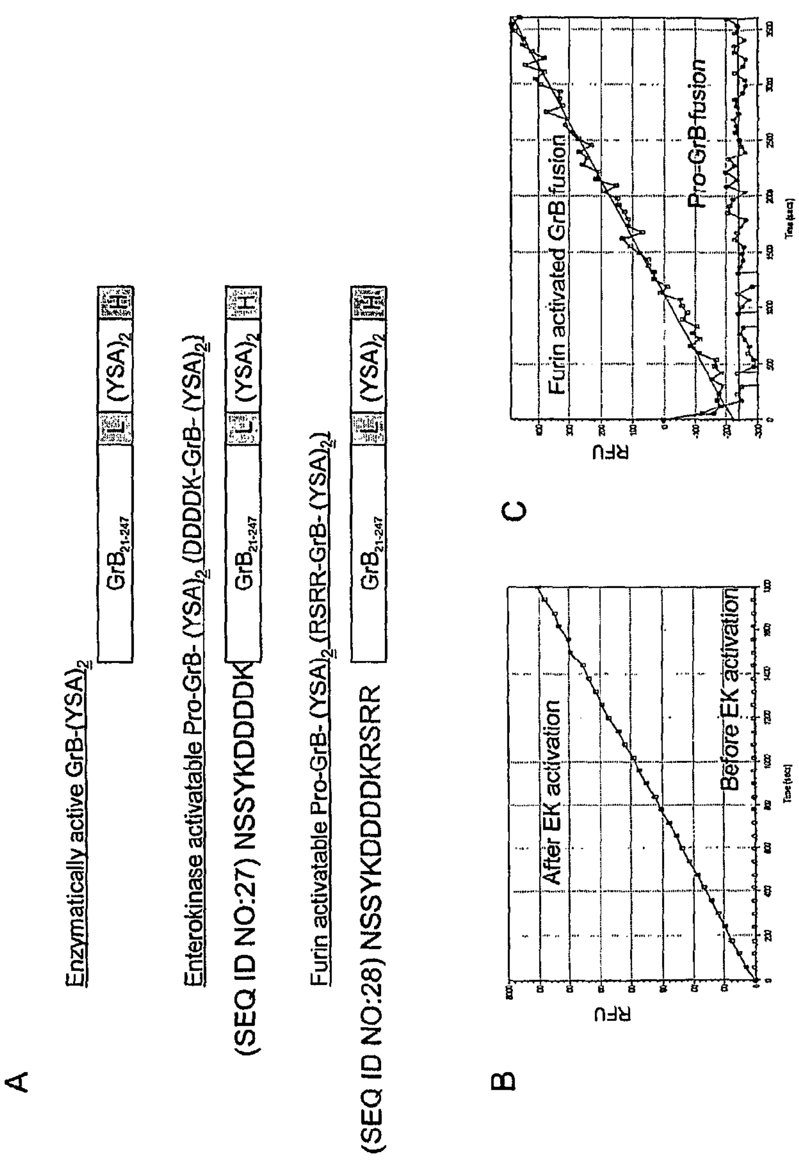
FIG. 20A is a schematic depiction of an enzymatically active GrB-$(YSA)_2$ fusion protein, an enterokinase activatable GrB-$(YSA)_2$ fusion protein DDDDK-GrB-YSA (SEQ ID NO:25), and a furin activatable RSRR-GrB-$(YSA)_2$ (SEQ ID NO:26) fusion protein. The amino acid sequences of the pro-domains are shown.
FIG. 20B is a graph showing that purified DDDDK-GrB-$(YSA)_2$ (SEQ ID NO:25) fusion protein may be activated using enterokinase. The granzyme B activity before (open circles) and after (open rectangles) enterokinase treatment are shown. The GrB activity was monitored using fluorogenic substrate Ac-IEPD-AMC.
FIG. 20C is a graph showing in vivo furin activation of the furin activatable RSRR-GrB-$(YSA)_2$ fusion protein. Both pro-GrB-$(YSA)_2$ fusion proteins were expressed in 293T cells, which naturally express furin. The fusion proteins were collected and their GrB activity measured as described above. Whereas the furin activatable RSRR-GrB-$(YSA)_2$ (SEQ ID NO:26) was active (open rectangles), no GrB activity was observed for the enterokinase activatable DDDDK-GrB-(YSA)2 (SEQ ID NO:25) (open circles).

In another embodiment of the present invention, the proactivator may be activated in vivo by a proteolytic activity that is endogenous to the targeted cells. One example of such endogenous protease is furin, an endosomal protease that is ubiquitously expressed in various mammalian cells. Specifically, a furin recognition site such as RVRR↓ (SEQ ID NO:64) may replace a natural zymogen cleavage site to provide a zymogen that is activated by proximity to the cell surface or by internalization. In the case of proteases for which the N-terminal residues comprise important determinants of the active site, such a furin recognition site can be directly appended to the N-terminus of the proactivator. For example, a furin cleavage site can be added to the N-terminus of Granzyme B or Granzyme M to provide an natively activatable proactivator. Specifically, a GrB fusion construct containing two C-terminal 12 residue cell-targeting YSA peptides and an N-terminal furin cleavage site is prepared for the production of GrB-$(YSA)_2$ (FIG. 20).

Protoxin proactivators containing a furin cleavage site are preferably produced in expression systems that do not contain native furin activity, e.g., in *E. coli*. A protoxin proactivator that is activatable in the targeted human cells by intracellular furin during its internalization process is an example of a natively-activatable protoxin proactivator. One important advantage of such a protoxin proactivator, as compared to a protoxin activator, is that the protoxin proactivator may be combined with a protoxin for simplified therapeutic delivery. Such mixtures of protoxins and protoxin proactivators will show reduced activation prior to accumulation upon the targeted cells.

Protoxin proactivator proteins that are activated by proteolytic cleavage by an endogenous protease activity of the target cell can be designed so that the proteolytic cleavage severs the operable linkage between the cell-targeting moiety and the catalytic or activator moiety. For example in a translational fusion, the inhibitory peptide might lie between the cell-targeting moiety and the catalytic moiety. Or in a chemically or enzymatically induced crosslinking of cell-targeting moiety to catalytic or activator moiety, the crosslinking may be induced via residues on the inhibitory peptide moiety that are not functionally required for inhibition of the catalytic or activator moiety.

Strategies to Reduce Potential Side Effects of Protease Fusions

Application of human proteases for immunotoxin activation may encounter complications if the protease of choice is capable of eliciting unintended biological effects in addition to the designed toxin activation. For example, many proteases, including granzymes and caspases, can promote cell death through involvement in an apoptotic cascade. Immunotoxins composed of granzyme B and a cell surface targeting domain have been developed as cytotoxic agents against certain diseased cell populations (Liu et al. Neoplasia 8:125-135 (2006), Dalken et al. Cell Death Differ. 13:576-585, Zhao et al. J. Biol. Chem. 279:21343-21348 (2004), U.S. Pat. No. 0,710,1977). To eliminate such potential side effects in the context of the present invention, it is preferable to use a cell surface target that does not internalize upon binding as the intended target for the protease fusion protein. In such a case the protoxin activation may be accomplished on the cell surface, but a toxic effect will not be generated by the protoxin activator acting alone.

Another approach is to mutate the candidate proteases so that they confer altered sequence specificity, thus are no longer preferentially bound to and cleaving at the native cleavage sites. Such engineered proteases are likely to have lower toxicities that are caused by biological cascade downstream from the proteolytic processing at the naturally occurring cleavage sequence. Selection or screening methods that are suited for such applications have been developed (e.g., Sices et al. Proc. Natl. Acad. Sci. USA 95:2828-2833 (1998) and Baum et al. Proc. Natl. Acad. Sci. USA 87:10023-10027 (1990)), and have been used select mutant proteases that are capable of cleaving a sequence that is different from the native proteolytic site of the original protease (e.g., O'Loughlin et al. Mol. Biol. Evol. 23:764-722 (2006), Han et al. Biochem. Biophy. Res. Commun. 337:1102-1106 (2005), and Venekei et al. Protein Eng. 9:85-93 (1996)). Because the cleavage site and the inhibitor RCL often possess sequence similarity, changing the proteolytic specificity of a protease may also result in its resistance to inhibition by its known proteinase inhibitors. Examples are available where the selection or screening for altered cleavage site, lower cytotoxicity, and altered inhibition profile are accomplished simultaneously (O'Loughlin et al. Mol. Biol. Evol. 23:764-722 (2006)). Specifically, granzyme B is modified to provide altered forms of granzyme with reduced spontaneous toxicity through altered substrate specificity.

Further modifications can be engineered to increase the activity and/or specificity of proteases. These modifications include PEGylation to increase stability to serum or to lower immunogenicity, and genetic engineering/selection may produce mutant proteases that possess altered properties such as resistance to certain inhibitors, increased thermal stability, and improved solubility.

Strategies to Prevent Inhibition by Proteinase Inhibitors in Plasma and in Cells In designing and utilizing protease fusions of the invention, it should be noted that proteinase inhibitors may hamper the proteolytic activities of protease fusion proteins. For example, GrB is specifically inhibited by intracellular proteinase inhibitor 9 (PI-9), a member of the serpin superfamily that primarily exists in cytotoxic lymphocytes (Sun et al., J. Biol. Chem. 271:27802 (1996)) and has been detected in human plasma. GrB can also be inhibited by $\alpha_1$-protease inhibitor ($\alpha_1$PI) that is present in human plasma (Poe et al., J. Biol. Chem. 266:98(1991)). GrM is inhibited by $\alpha_1$-antichymotrypsin (ACT) and $\alpha_1$PI (Mahrus et al., J. Biol. Chem. 279:54275 (2004)), and GrA is inhibited in vitro by protease inhibitors antithrombin III (ATIII) and $\alpha_2$-macroglobulin ($\alpha_2$M) (Spaeny-Dekking et al., Blood 95:1465 (2000)). These proteinase inhibitors are also present in human plasma (Travis and Salvesen, Annu. Rev. Biochem. 52:655 (1983)).

One approach to preserve proteolytic activities of granzymes is to utilize complexation with proteoglycan, since the mature and active form of GrA has been observed in human plasma as a complex with serglycin, a granule-associated proteoglycan (Spaeny-Dekking et al., Blood 95:1465 (2000)). Glycosaminglycan complexes of GrB have also been found proteolytically active (Galvin et al., J. Immunol. 162: 5345 (1999)). Thus, it may be possible to keep granzyme fusion proteins active in plasma through formulations using chondroitin sulfates.

Alternatively, potential candidate proteases may be screened in vitro by interactions with known proteinase inhibitors in plasma or with human plasma directly to avoid potential complications posed by these proteinase inhibitors. Alternatively, proteases for which cognate inhibitors are found in plasma can be engineered to provide mutant forms that resist inhibition. For example, in vitro *E. coli* expression-screening methods have been developed to select mutant proteases that are resistant to known HIV-1 protease inhibitors (Melnick et al., Antimicrob. Agents Chemother. 42:3256 (1998)).

C. Expression of Protease Fusion Proteins

Methods for the overexpression of large fusion proteins are well known in the art and can be applied to the overexpression of the protease fusion proteins of the invention. Examples of expression systems that may be used in the construction of the fusion proteins of the invention are *E. coli*, baculovirus in insect cells, yeast systems in *Saccharomyces cerevisiae* and *Pichia pastoris*, mammalian cells, and transient expression in vaccinia. Methods described above for the expression of DT fusion proteins are generally applicable for protease fusion proteins, except for those solely applicable to diphtheria toxin.

A mammalian expression system can be used to produce the protease fusion protein, particularly when a protease of human origin such as human granzyme B is selected as the protease portion of the fusion. Expressing proteases of human origin in mammalian cells has certain advantages, notably providing glycosylation patterns that are identical to or closely resemble native forms, which are not immunogenic and may help the folding, solubility, and stability of the recombinant protein.

PEGylation of Proteins

One embodiment of the present invention is the utilization of PEGylated fusion proteins. Preferred embodiments are site-specifically PEGylated fusion proteins. It is known in the art that PEGylated proteins can exhibit a broad range of bioactivities due to the site, number, size, and type of PEG attachment (Harris and Chess Nat. Rev. Drug Discov. 2(3): 214-221 (2003)). A preferred composition of a fusion protein in the present invention is a PEGylated protein that contributes to a desired in vitro or in vivo bioactivity or that is insusceptible to natural actions that would compromise the activity of the fusion protein, such as formation of antibodies, nonspecific adherence to cells or biological surfaces, or degradation or elimination.

A PEG moiety can be attached to the N-terminal amino acid, a cysteine residue (either native or non-native), lysines, or other native or non-native amino acids in a protein's primary sequence. Chemistries for peptide and protein PEGylation have been extensively reviewed (Roberts et al. Adv. Drug Deliv. Rev. 54(4):459-476 (2002)). In addition, specific peptide sequences may be introduced to the primary sequence such that the peptide may be selectively modified by a PEG moiety through a sequence specific enzymatic reaction. Alternatively, a specific peptide sequence may be first modified by a chemically modified group, followed by PEG attachment at the modified group.

Cysteine residues in many proteins may be sequestered in disulfide bonds and are not preferred or available for derivatization. An additional cysteine may be introduced at a location wherein it does not substantially negatively affect the biological activity of the protein, by insertion or substitution through site directed mutagenesis. The free cysteine will serve as the site for the specific attachment of a PEG molecule, thus avoiding the product heterogeneity often observed with amine-specific PEGylation. The preferred site for the added cysteine is exposed on the protein surface and is accessible for PEGylation. The terminal region, C-terminal region, and the linker region of the fusion proteins are potential sites for the cysteine substitution or insertion.

It is also possible to genetically introduce two or more additional cysteines that are not able to form disulfide bonds. In such cases more than one PEG moiety may be specifically attached to the protein. Alternatively, a native, non-essential disulfide bond may be reduced, thus providing two free cysteines for thiol-specific PEGylation.

Free thiol groups may also be introduced by chemical conjugation of a molecule that contains a free cysteine or a thiol group, which may alternatively be modified with a reversible thiol blocking agent.

PEGylation may also be accomplished by using enzyme catalyzed conjugation reactions. One such approach is to use transglutaminases, a family of proteins that catalyze the formation of a covalent bond between a free amine group and the gamma-carboxamide group of protein- or peptide-bound glutamine. Examples of this family of proteins include transglutaminases of many different origins, including thrombin, factor XIII, and tissue transglutaminase from human and animals. A preferred embodiment comprises the use of a microbial transglutaminase, to catalyze a conjugation reaction between a protein substrate containing a glutamine residue embedded within a peptide sequence of LLQG and a PEGylating reagent containing a primary amino group (Sato Adv. Drug Deliv. Rev. 54(4):487-504 (2002)).

Another enzyme-catalyzed PEGylation method involves the use of sortases, a family of enzymes from gram-positive bacteria that can recognize a conserved carboxylic sorting motif and catalyze a transpeptidation reaction to anchor surface proteins to the cell wall envelope (Dramsi et al., Res. Microbiol. 156(3):289-297 (2005)). A preferred embodiment comprises the use of a *S. aureus* sortase to catalyze a transpeptidation reaction between a protein that is tagged with LPXTG or NPQTN, respectively for sortase A and sortase B, and a PEGylating reagent containing a primary amino group (WO06013202A2). The peptide substrate sequences listed above are for example and non-limiting. It is known in the art that these families of enzymes can recognize and utilize different sequences as substrates, and those sequences are included here as embodiments for the present invention. The preferred peptide substrate sequences listed above are for example and non-limiting. It is known in the art that these families of enzymes can recognize and utilize different sequences as substrates, and those sequences are included here as embodiments for the present invention.

Multifunctional PEGs

While a majority of the PEGylated proteins currently available have one or more PEGs per protein, it is also possible to construct protein conjugates with two or more proteins attached to one PEG moiety. Heterofunctional PEGs are commercially available, and may be used to covalently link two proteins, or any two moieties of a protein.

Preferred PEGylation Sites

Because both toxins and activators possess regions or domains that are important for their respective functions, the attachment of the bulky PEG substituents on these domains may be detrimental to their function. Accordingly a preferred embodiment of the present invention is a PEGylating fusion protein wherein the PEG substituent is situated at a position remote from the catalytic site of an activator (either a protoxin activator or a proactivator activator) and the cell surface target recognition surface of a cell-targeting moiety; and in the case of a protoxin, is not situated within the translocation and catalytic domains of the protoxin, because these domains are expected to be involved in translocation through the plasma membrane and/or to be imported into cytoplasm and PEGylation may prevent such translocations.

In one embodiment of the present invention, the preferred sites of PEGylation are located at or near the N- or C-terminal extremities of proteinaceous cell-targeting moieties. In another embodiment of the present invention, PEGylation is directed to a linker region between different moieties within the fusion protein.

In another embodiment of the present invention, reversible PEGylation may be used.

D. Clearing Agents

The invention optionally also includes the use of clearing agents to facilitate the removal of systemic protease fusion protein prior to the administration of toxin fusion protein. The use of clearing agents in ADEPT therapy is well known in the art (see, for example, Syrigos and Epenetos, Anticancer Res. 19:605 (1999)) and may be utilized in the invention.

IV. Linkages

According to the present invention, each moiety within a protoxin fusion protein (e.g., one or more cell targeting moieties, one or more selectively modifiable activations domains, one or more natively activatable domain, and one or more toxin domains) or a protoxin activator fusion, (e.g., one or more cell targeting moieties, one or more modification domains, one or more natively activatable domain, and one or more toxin domains) may function independently but each is operably linked. Within each fusion protein the operable linkage between the two functional moieties acts as a molecular bridge, which may be covalent or non-covalent. The moieties of each fusion protein may be operably linked in any orientation with respect to each other, that is, C-terminal of one to N-terminal of the other, or C-terminal of one to C-terminal of the other, or N-terminal of one to N-terminal of the other, or by internal residues to terminal residues or internal residues to internal residues. An optional linker can serve as a glue to physically join the two moieties, as a separator to allow spatial independence, or as a means to provide additional functionality to each other, or a combination thereof. For example, it may be desirable to separate the cell-targeting moiety from the operably linked enzyme moiety to prevent them from interfering with each other's activity. In this case the linker provides freedom from steric conflict between the operably linked moieties. The linker may also provide, for example, lability to the connection between the two moieties, an enzyme cleavage site (e.g., a cleavage site for protease or a hydrolytic site for esterase), a stability sequence, a molecular tag, a detectable label, or various combinations thereof.

Chemical activation of amino acid residues can be carried out through a variety of methods well known in the art that result in the joining of the side chain of amino acid residues on one molecule with side chains of residues on another molecule, or through the joining of side chains to the alpha amino group or by the joining of two or more alpha amino groups. Typically the joining induced by chemical activation is accomplished through a linker which may be a small molecule, an optionally substituted branched or linear polymer of identical or nonidentical subunits adapted with specific moieties at two or more termini to attach to polypeptides or substitutions on polypeptides, or an optionally substituted polypeptide. Examples of common covalent protein operable linkage are publically available, including those offered for sale by Pierce Chemical Corporation. In general it is preferable to be able to induce operable linkage of components in a site-specific manner, to afford a simple reproducibly manufactured substance. Operable linkage by chemical activation can be the result of chemical activation targeted to specific residues that are functionally unique i.e. are present only once in the moiety to be activated or are preferentially activatable because of a unique chemical environment, for example, such as would produce a reduction in pK of an epsilon amino unit of a lysine residue. Potential groups for chemical activation can be made functionally unique by genetic removal of all other residues having the same properties, for example to remove all but a single cysteine residue, or all but a single lysine reside. Amino terminal residues can be favorably targeted by virtue of the low pK of the alpha amino group, or by suitable chemistry exploiting the increased reactivity of the alpha amino group in close proximity to another activatable group. Examples of the latter include native chemical ligation, Staudinger ligation, and oxidation of amino terminal serine to afford an aldehyde substituent. Chemical activation can also be carried out through reactions that activate naturally occurring protein substituents, such as oxidation of glycans, or other naturally occurring protein modifications such as those formed by biotin or lipoic acid, or can be based on chemical reactions that convert the functionality of one side chain into that of another, or that introduce a novel chemical reactive group that can subsequently activated to produce the desired operable linkage. Examples of the latter include the use of iminodithiolane to endow a lysine residue with a sulfhydryl moiety or the reaction of a cysteine moiety with an appropriate maleimide or haloacetamide to change the functionality of the thiol to another desired reactive moiety. Chemical activation can also be carried out on both species to be operably linked to provide reactive species that interact with one another to provide an operable linkage, for example the introduction of a hydrazide, hydrazine or hydroxylamine on one moiety and an aldehyde on the other.

Noncovalent operable linkage can be obtained by providing a complementary surface between one moiety and another to provide a complex which is stable for the intended useful persistence of the operably linked moieties in therapeutic use. Such noncovalent linkages can be created from either two or more polypeptides that may be the same or dissimilar or one or more polypeptide and a small molecule or ligand attached to the second moiety. Attachment of the small molecule or ligand can take place through in vitro or in vivo processes, such as the incorporation of biotin or lipoic acid into their specific acceptor sequences which may be natural or artificial biotin or lipoic acid acceptor domains and which may be achieved either by natural incorporation in vivo or by enzymatic biotinylation or lipoylation in vitro. Alternatively, the protein may be substituted with biotin or other moieties by chemical reaction with biotin derivatives. Common examples of biotin derivatives used to couple with proteins include aldehydes, amines, haloacetamides, hydrazides, maleimides, and activated esters, such as N-hydroxysuccinimide esters, Examples of commonly employed noncovalent linkage include the linkage induced by binding of biotin and its derivatives or biotin-related substituents such as iminobiotin or diaminobiotin or thiobiotin to streptavidin or avidin or variants thereof, the binding of enzymes to their covalent or noncovalent specific inhibitors, such as the binding of methotrexate to mammalian dihydrofolate reductase, the binding of natural or synthetic leucine zippers to one another, the binding of enzymes to specific or nonspecific inhibitors, such as antitrypsin or leupeptin or alpha-2-macroglobulin, the binding of aryl bis-arsenates to alpha helices bearing appropriately positioned cysteine residues, the binding between a nucleic acid aptamer and its target; between a peptide and a nucleic acid such as Tat-TAR interaction.

Enzymatic activation of one polypeptide to afford coupling with another polypeptide can also be employed. Enzymes or enzyme domains that undergo covalent modification by reaction with substrate-like molecules can also be used to create fusions. Examples of such enzymes or enzyme domains include O6-alkylguanine DNA-alkyltransferase (Gronemeyer et al. Protein Eng Des Sel. 2006 19(7):309-16), thymidylate synthase, or proteases that are susceptible to covalent or stable noncovalent modification of the active site, as for example DPPIV (SEQ ID NO:65).

The present invention also features the use of bifunctional or multifunctional linkers, which contain at least two interactive or reactive functionalities that are positioned near or at opposite ends, each can bind to or react with one of the moieties to be linked. The two or more functionalities can be the same (i.e., the linker is homobifunctional) or they can be different (i.e., the linker is heterobifunctional). A variety of bifunctional or multifunctional cross-linking agents are known in the art are suitable for use as linkers. For example, cystamine, m-maleimidobenzoyl-N-hydroxysuccinimide-ester, N-succinimidyl-3-(2-pyridyldithio)-propionate, methylmercaptobutyrimidate, dithiobis(2-nitrobenzoic acid), and many others are commercially available, e.g., from Pierce Chemical Co. Rockford, Ill. Additional chemically orthogonal reactions suitable for such specific operable linkage reactions include, for example, Staudinger ligation, Cu[I] catalyzed [2+3] cycloaddition, and native ligation.

The bifunctional or multifunctional linkers may be interactive but non-reactive. Such linkers include the composite use of any examples of non-covalent interactions discussed above.

The length and composition of the linker can be varied considerably provided that it can fulfill its purpose as a molecular bridge. The length and composition of the linker are generally selected taking into consideration the intended function of the linker, and optionally other factors such as ease of synthesis, stability, resistance to certain chemical and/or temperature parameters, and biocompatibility. For example, the linker should not significantly interfere with the regulatory ability of the cell-targeting moiety relating to targeting of the toxin, or with the activity of the toxin or enzyme relating to activation and/or cytotoxicity.

Linkers suitable for use according to the present invention may be branched, unbranched, saturated, or unsaturated hydrocarbon chains, including peptides as noted above.

Furthermore, if the linker is a peptide, the linker can be attached to the toxin moiety and enzyme moiety and/or the cell-targeting moiety using recombinant DNA technology.

In one embodiment of the present invention, the linker is a branched or unbranched, saturated or unsaturated, hydrocarbon chain having from 1 to 100 carbon atoms, wherein one or more of the carbon atoms is optionally replaced by —O— or —NR— (wherein R is H, or C1 to C6 alkyl), and wherein the chain is optionally substituted on carbon with one or more substituents selected from the group of (C1-C6) alkoxy, (C3-C6) cycloalkyl, (C1-C6) alkanoyl, (C1-C6) alkanoyloxy, (C1-C6) alkoxycarbonyl, (C1-C6) alkylthio, amide, azido, cyano, nitro, halo, hydroxy, oxo (═O), carboxy, aryl, aryloxy, heteroaryl, and heteroaryloxy.

Examples of suitable linkers include, but are not limited to, peptides having a chain length of 1 to 100 atoms, and linkers derived from groups such as ethanolamine, ethylene glycol, polyethylene with a chain length of 6 to 100 carbon atoms, polyethylene glycol with 3 to 30 repeating units, phenoxyethanol, propanolamide, butylene glycol, butyleneglycolamide, propyl phenyl, and ethyl, propyl, hexyl, steryl, cetyl, and palmitoyl alkyl chains.

In one embodiment, the linker is a branched or unbranched, saturated or unsaturated, hydrocarbon chain, having from 1 to 50 carbon atoms, wherein one or more of the carbon atoms is optionally replaced by —O— or —NR— (wherein R is as defined above), and wherein the chain is optionally substituted on carbon with one or more substituents selected from the group of (C1-C6) alkoxy, (C1-C6) alkanoyl, (C1-C6) alkanoyloxy, (C1-C6) alkoxycarbonyl, (C1-C6) alkylthio, amide, hydroxy, oxo (═O), carboxy, aryl and aryloxy.

In another embodiment, the linker is an unbranched, saturated hydrocarbon chain having from 1 to 50 carbon atoms, wherein one or more of the carbon atoms is optionally replaced by —O— or —NR— (wherein R is as defined above), and wherein the chain is optionally substituted on carbon with one or more substituents selected from the group of (C1-C6) alkoxy, (C1-C6) alkanoyl, (C1-C6) alkanoyloxy, (C1-C6) alkoxycarbonyl, (C1-C6) alkylthio, amide, hydroxy, oxo (═O), carboxy, aryl and aryloxy.

In a specific embodiment of the present invention, the linker is a peptide having a chain length of 1 to 50 atoms. In another embodiment, the linker is a peptide having a chain length of 1 to 40 atoms.

As known in the art, the attachment of a linker to a protoxin moiety (or of a linker element to cell-targeting moiety or a cell-targeting moiety to a protoxin moiety) need not be a particular mode of attachment or reaction. Various non-covalent interactions or reactions providing a product of suitable stability and biological compatibility are acceptable.

One preferred embodiment of the present invention relies on enzymatic reaction to provide an operable linkage between the moieties of a protoxin, protoxin activator, or protoxin proactivator. Among the enzymatic reactions that produce such operable linkage, it is well-known in the art that transglutaminase ligation, sortase ligation, and intein-mediated ligation provide for high specificity.

The preferred peptide substrate sequences listed above are for example and non-limiting. It is known in the art that these families of enzymes can recognize and utilize different sequences as substrates, and those sequences are included here as embodiments for the present invention.

In some aspects, the invention features the use of natively activatable linkers. Such linkers are cleaved by enzymes of the complement system, urokinase, tissue plasminogen activator, trypsin, plasmin, or another enzyme having proteolytic activity may be used in one embodiment of the present invention. According to another embodiment of the present invention, a protoxin is attached via a linker susceptible to cleavage by enzymes having a proteolytic activity such as a urokinase, a tissue plasminogen activator, plasmin, thrombin or trypsin. In addition, protoxins may be attached via disulfide bonds (for example, the disulfide bonds on a cystine molecule) to the cell-targeting moiety. Since many tumors naturally release high levels of glutathione (a reducing agent) this can reduce the disulfide bonds with subsequent release of the protoxin at the site of delivery.

In one embodiment, the cell-targeting moiety is linked to a protoxin by a cleavable linker region. In another embodiment of the invention, the cleavable linker region is a protease-cleavable linker, although other linkers, cleavable for example by small molecules, may be used. Examples of protease cleavage sites are those cleaved by factor Xa, thrombin and collagenase. In one embodiment of the invention, the protease cleavage site is one that is cleaved by a protease that is up-regulated or associated with cancers in general. Examples of such proteases are uPA, the matrix metalloproteinase (MMP) family, the caspases, elastase, and the plasminogen activator family, as well as fibroblast activation protein. In still another embodiment, the cleavage site is cleaved by a protease secreted by cancer-associated cells. Examples of these proteases include matrix metalloproteases, elastase, plasmin, thrombin, and uPA. In another embodiment, the protease cleavage site is one that is up-regulated or associated with a specific cancer. In yet another embodiment, the proteolytic activity may be provided by a protease fusion targeted to the same cell. Various cleavage sites recognized by proteases are known in the art and the skilled person will have no difficulty in selecting a suitable cleavage site. Non-limiting examples of cleavage sites are provided elsewhere in this document. As is known in the art, other protease cleavage sites recognized by these proteases can also be used. In one embodiment, the cleavable linker region is one which is targeted by endocellular proteases.

Chemical linkers may also be designed to be substrates for carboxylesterases, so that they may be selectively cleaved by these carboxyltransferases or corresponding fusion proteins with a cell-targeting moiety. One preferred embodiment comprises the use of a carboxyl transferase activity to activate the cleavage of an ester linker. For example but without limitation, secreted human carboxyltransferase-1, -2, and -3 may be used for this purpose. Additional examples include carboxyl transferase of other origins.

Another embodiment of the cleavable linkers comprises nucleic acid units that are specifically susceptible to endonucleases. Endonucleases are known to be present in human plasma at high levels.

In another embodiment, the modifiable activation moiety is not a peptide, but a cleavable linker that may be acted upon by a cognate enzymatic activity provided by the activator or proactivator. The cleavable linker is preferably situated at the same location as the furin-like cleavage sequence in an activatable protoxin, or at the location of the zymogen inhibitory peptide in an activatable proactivator. The cleavable linker may replace the furin-like cleavage sequence or be attached in parallel to the furin-like cleavage or another modifiable activation moiety, providing a protoxin that requires both a furin-like cleavage or other proteolytic event and a linker cleavage for activation. In one embodiment the cleavable linker joins the ADP ribosyltransferase domain of a DT-based protoxin to the translocation domain of that or another protoxin. In another embodiment the cleavable linker joins the translocation domain of a PEA or VCE-based protoxin to the ADP ribosyltransferase domain of the same or a different toxin. In yet another embodiment the cleavable linker joins the pore-forming domain of a pore-forming toxin with the C-terminal inhibitory peptide.

Preferable cleavable linkers are those which are stable to in vivo conditions but susceptible to the action of an activator. Many examples of suitable linkers have been provided in the context of attempts to develop antibody-directed enzyme prodrug therapy. For example a large class of enzyme substrates that lead to release of an active moiety, such as a fluorophore, have been devised through the use of what are known as self-immolative linkers. Self-immolative linkers are designed to liberate an active moiety upon release of an upstream conjugation linkage, for example between a sugar and an aryl moiety. Such linkers are often based on glycosides of aryl methyl ethers, for example the phenolic glycosides of 3-nitro, 4-hydroxy benzyl alcohol; see for example Ho et al. Chembiochem, Mar. 26, 2007; 8(5):560-6, or the phenolic amides of 4-amino benzyl alcohol, for example Niculescu-Duvaz et al. J Med Chem. Dec. 17, 1998; 41(26):5297-309 or Toki et al. J Org Chem. Mar. 22, 2002; 67(6):1866-72.

To create self-immolative linkers based on glycosides the phenolic hydroxyl is glycated by reaction with a 1-Br-substituted sugar such as alpha-1-Br galactose or alpha-1-Br glucuronic acid to provide the substrate for the activating enzyme, and the benzyl alcohol moiety is then activated with a carbonylation reagent such as phosgene or carbonyl diimidazole and reacted with a primary amine to afford a carbamate linkage. Upon scission of the aryl glycosidic bond or the aryl ester, the aryl moiety eliminates, leaving a carbamoyl moiety that in turn eliminates, affording CO2 and the regenerated amine. Said amine may be the alpha amino group of a polypeptide chain or the epsilon amino of a lysine side chain.

To create self-immolative linkers based on amide bonds the phenyl amine of 4-amino benzyl alcohol is reacted with an activated carboxyl group of a suitable peptide or amino acid to create a phenyl amide that can be a substrate for an appropriate peptidase, for example carboxypeptidase G2 Niculescu-Duvaz et al. J Med Chem. 41(26):5297-309 (1998). The benzyl alcohol moiety is then activated with a carbonylation reagent such as phosgene or carbonyl diimidazole and reacted with a primary amine to afford a carbamate linkage. Upon scission of the aryl amide bond, the aryl moiety eliminates, leaving a carbamoyl moiety that in turn eliminates, affording CO2 and the regenerated amine. Said amine may be the alpha amino group of a polypeptide chain or the epsilon amino of a lysine side chain.

For the creation of an appropriate self-immolating activation moiety according to the present invention the aryl group is substituted with a reactive moiety that provides a linkage to one element of the protoxin or proactivator, such as the toxin moiety or the translocation moiety or the inhibitory peptide moiety.

Similar forms of self-immolative linker are also well-known in the art. For example Papot et al. Bioorg Med Chem Lett. 8(18):2545-8 (1998) teach the creation of glucuronide prodrugs based on aryl malonaldehydes that undergo elimination of the aryl linker moiety upon cleavage by a glucuronidase. Suitable linkers based on aryl malonaldehydes in the context of the present invention provide a modifiable activation moiety in which the aryl substituent is operably linked to one terminus of the toxin moiety, for example at the location of the furin cleavage site, and the carbamoyl functionality is operably linked to the translocation moiety or inhibitory moiety. In the system devised by Papot et al, cleavage by glucuronidase will result in elimination of the aryl malonaldehyde and activation of the protoxin. Similar elimination events are known to take place following hydrolysis of the lactam moiety of linkers based on 7-aminocephalosporanic acid, and enzymatically activated prodrugs based on beta-lactam antibiotics or related structures are well known in the art. For example Alderson et al. Bioconjug Chem. 17(2): 410-8 (2006) teach the creation of a 7-aminocephalosporanic acid-based linker that undergoes elimination and scission of a carbamate moiety in similar fashion to that of the aryl malonaldehydes disclosed by Papot et at. In addition, Harding et al. Mol Cancer Ther. 4(11): 1791-800 (2005) teach a beta-lactamase that has reduced immunogenicity that can be favorably applied as an activator for a prodrug moiety based on a 7-aminocephalosporanic acid nucleus.

In yet another embodiment the modifiable activation moiety is a peptide but is operably linked by a flexible nonpeptide linker at either or both termini in the same location as the natural furin-like protease cleavage site, or in parallel to the natural furin-like cleavage site. In such embodiments the activator is a cognate protease or peptide hydrolase recognizing the peptide of the modifiable activation moiety. In a doubly triggered protoxin, the furin-like cleavage site is replaced by a modifiable activation moiety and a cleavable linker is attached in parallel to the modifiable activation moiety. In such a protoxin the action of two activators is required to activate the protoxin.

V. Isolation and Purification of Toxin Fusion and Protease Fusion Proteins

A. General Strategies for Recombinant Protein Purification

There are many established strategies to isolate and purify recombinant proteins known to those skilled in the art, such as those described in *Current Protocols in Protein Science* (Coligan et al., eds. 2006). Conventional chromatography such as ion exchange chromatography, hydrophobic-interaction (reversed phase) chromatography, and size-exclusion (gel filtration) chromatography, which exploit differences of physicochemical properties between the desired recombinant protein and contaminants, are widely used. HPLC can also been used.

To facilitate the purification of recombinant proteins, a variety of vector systems have been developed to express the target protein as part of a fusion protein appended by an N-terminal or C-terminal polypeptide (tag) that can be subsequently removed using a specific protease. Using such tags, affinity chromatography can be applied to purify the proteins. Examples of such tags include proteins and peptides for which there is a specific antibody (e.g., FLAG fusion purified using anti-FLAG antibody columns), proteins that can specifically bind to columns containing a specific ligand (e.g., GST fusion purified by glutathione affinity gel), polyhistidine tags with affinity to immobilized metal columns (e.g., 6 His tag immobilized on $Ni^{2+}$ column and eluted by imidazole), and sequences that can be biotinylated by the host during expression or in vitro after isolation and enable purification on an avidin column (e.g., BirA).

B. Isolation and Purification of Fusion Proteins Expressed in Insoluble Form

Many recombinant fusion proteins are expressed as inclusion bodies in *Escherichia coli*, i.e., dense aggregates that consist mainly of a desired recombinant product in a nonnative state. In fact, most reported DT-ScFv fusion proteins expressed in *E. coli* are obtained in insoluble forms. Usually the inclusion bodies form because (a) the target protein is insoluble at the concentrations being produced, (b) the target protein is incapable of folding correctly in the bacterial environment, or (c) the target protein is unable to form correct disulfide bonds in the reducing intracellular environment.

Those skilled in the art recognize that different methods that can be used to obtain soluble, active fusion proteins from inclusion bodies. For example, inclusion bodies can be separated by differential centrifugation from other cellular constituents to afford almost pure insoluble product located in the pellet fraction. Inclusion bodies can be partially purified by extracting with a mixture of detergent and denaturant, either urea or guanidine.HCl, followed by gel filtration, ion exchange chromatography, or metal chelate chromatography as an initial purification step in the presence of denaturants. The solubilized and partially purified proteins can be refolded by controlled removal of the denaturant under conditions that minimize aggregation and allow correct formation of disulfide bonds. To minimize nonproductive aggregation, low protein concentrations should be used during refolding. In addition, various additives such as nondenaturing Concentrations of urea or guanidine.HCl, arginine, detergents, and PEG can be used to minimize intermolecular associations between hydrophobic surfaces present in folding intermediates.

C. Isolation and Purification of Fusion Proteins Expressed in Soluble Form

Recombinant proteins can also be expressed and purified in soluble form. Recombinant proteins that are not expressed in inclusion bodies either will be soluble inside the cell or, if using an excretion vector, will be extracellular (or, if *E. coli* is the host, possibly periplasmic). Soluble proteins can be purified using conventional methods afore described.

VI. Assays for Measuring Inhibition of Cell Growth

Various assays well known in the art are useful for determining the efficacy of the protein preparations of the invention, including those assays that measure cell proliferation and death. For example, it has been shown that one molecule of diphtheria toxin catalytic fragment (DTA) introduced into the cytosol of a cell is sufficient to prevent the cell from multiplying and forming a colony (Yamaizumi et al., Cell 15:245 (1978)). The following are examples of many assays that can be used, alone or in combination, for analyzing the cytotoxicity of the reagents in the present invention.

A. Protein Synthesis Inhibition Assays

Because many toxins (e.g., DT) exert their cytotoxicity through inhibition of protein synthesis, an assay that directly quantifies protein being synthesized by the cell after its exposure to the toxin is especially useful. In this assay, cells are exposed to a toxin and then incubated transiently with radioactive amino acids such as $[^3H]$-Leu, $[^{35}S]$-Met or $[^{35}S]$-Met-Cys. The amount of radioactive amino acid incorporated into protein is subsequently determined, usually by lysing cells and precipitating proteins with 10% trichloroacetic acid (TCA), providing a direct measure of how much protein is synthesized. Using such an assay, it was demonstrated that, although the entry of DT into a cell is not associated with an immediate block in protein synthesis, prolonged action (4-24 hours) of single DT catalytic fragment molecules in the cytosol is sufficient to obtain complete protein synthesis inhibition at low toxin concentrations (Falnes et al., J. Biol. Chem. 275:4363 (2000)).

An extension of this method is a luciferase-based assay (Zhao and Haslam, J. Med. Microbiol. 54:1023 (2005)). Luciferase cDNA was incorporated into a wide variety of dividing or non-dividing mammalian cells using an adenoviral expression system, and the resulting cells allowed to constitutively transcribe the luciferase cDNA, which had been engineered to contain an additional PEST sequence for a short intracellular half-life. The assay measures the level of protein synthesis in cells through the light output from D-luciferin reaction catalyzed by the short-lived luciferase. In cells constitutively expressing the luciferase mRNA, inhibition of protein synthesis results in diminished luciferase translation and proportionately reduced light output.

B. Thymidine Incorporation Assay

The rate of proliferation of cells can be measured by determining the incorporation of [$^3$H]-thymidine into cellular nucleic acids. This assay may be used for analyzing cytotoxicity of toxins (e.g., DT-based immunotoxins). Using this method a DT-IL3 immunotoxin was shown to be active in inhibiting growth of IL3-receptor bearing human myeloid leukemia cell lines (Frankel et al., Leukemia. 14:576 (2000)). The toxin fusion and protease fusion proteins of the present invention may be tested using such an assay, individually or combinatorially.

C. Colony Formation Assay

Colony formation may provide a much more sensitive measure of toxicity than certain other commonly employed methods. The reason for this increased sensitivity may be the fact that colony formation is assessed while the cells are in a state of proliferation, and thus more susceptible to toxic effects. The sensitivity of the colony-formation assay, and the fact that dose and time-dependent effects are detectable, enables acute and chronic exposure periods to be investigated as well as permitting recovery studies. For example, the cytotoxicity of a recombinant DT-IL6 fusion protein towards human myeloma cell lines was investigated using methylcellulose colony formation by U266 myeloma cells. In cultures containing both normal bone marrow and U266 cells DT-IL-6 effectively inhibited the growth of U266 myeloma colonies but had little effect on normal bone marrow erythroid, granulocyte and mixed erythroid/granulocyte colony growth (Chadwick et al., Haematol. 85:25 (1993)).

D. MTT Cytotoxicity Assay

The cytotoxicity of a particular fusion protein or a combination of fusion proteins can be assessed using an MTT cytotoxicity assay. The specific cytotoxicity of a DT-GMCSF fusion protein against human leukemia cell lines bearing high affinity receptors for human GMCSF was demonstrated using such an MTT assay, colony formation assay, and protein inhibition assay (Bendel et al., Leuk. Lymphoma. 25:257 (1997)). In a typical MTT assay, the yellow tetrazolium salt (MTT) is reduced in metabolically active cells to form insoluble purple formazan crystals, which are solubilized by the addition of a detergent and quantified by UV-VIS spectrometry. After cells are grown to 80-100% confluence, they are washed with serum-free buffer and treated with cytotoxic agent(s). After incubation of the cells with the MTT reagent for approximately 2 to 4 hours, a detergent solution is added to lyse the cells and solubilize the colored crystals. The samples are analyzed at a wavelength of 570 nm and the amount of color produced is directly proportional to the number of viable cells.

VII. Functional Assays for DT and Protease Fusion Proteins

A. In Vitro Protein Synthesis Inhibition Assay

In eukaryotic cells, DT inhibits protein synthesis because its catalytic domain can inactivate elongation factor 2 (EF-2) by catalyzing its ADP-ribosylation after endocytosis to cytosol. In vitro eukaryotic translation systems, e.g., using rabbit reticulocyte lysate and wheat germ extract, are potentially suited for examining the catalytic function of recombinant DT fusion proteins. For example, TNT-coupled wheat germ extract, supplemented by $NAD^+$, amino acids, [$^{35}$S]-Met, DNA template, and an RNA polymerase, is used to test the inhibition of protein synthesis by a recombinantly expressed catalytic fragment of DT (Epinat and Gilmore, Biochim. Biophys. Acta. 1472:34 (1999)). The level of S-labeled translated protein is an indicator of the extent of DT toxicity.

Because in vitro inhibition of protein synthesis does not require endocytosis of full length DT, it has been shown that its proteolytic activation increased ADP-ribosylation of EF-2 (Drazin et al., J. Biol. Chem. 246:1504 (1971)). Thus these in vitro assays can be used to screen inhibitory effects of DT fusions in the absence or presence of certain proteolytic activity, providing a facile assay to analyze the functional integrity of engineered DT fusion proteins as well as that of protease fusion proteins.

B. In Vitro EF-2 ADP-Ribosylation Assay

DT inhibits protein synthesis by catalyzing the transfer of ADP-ribose moiety of NAD to a post-translationally modified His715 of EF-2 called diphthamide. Thus the function of DT fusions can also be directly assayed in vitro by correlating its catalytic activity to rate of transfer of radiolabeled ADP-ribose to recombinant EF-2 (Parikh and Schramm, Biochemistry 43:1204 (2004)). This assay has been applied for testing the inhibition of ADP-ribosyltransferase activity, and is often used as one of the assays for DT-based immunotoxins (Frankel et al., Leukemia. 14:576 (2000)). Non-radioactively labeled NAD, such as biotinylated NAD or etheno-NAD, may also be used as a substrate (Zhang. Method Enzymol. 280: 255-265 (1997)).

C. In Vitro Proteolytic Activity Assay

The functional activity of recombinant protease fusion proteins may be assayed in vitro either using a peptide or protein substrate containing the recognition sequence of the protease. Various protocols are well known to those skilled in the art.

VIII. Administration of Fusion Proteins

The fusion proteins of the invention are typically administered to the subject by means of injection using any route of administration such as by intrathecal, subcutaneous, submucosal, or intracavitary injection as well as by intravenous or intraarterial injection. Thus, the fusion proteins may be injected systemically, for example, by the intravenous injection of the fusion proteins into the patient's bloodstream or alternatively, the fusion proteins can be directly injected at a specific site.

The protoxin of the invention can be administered prior to, simultaneously with, or following the administration of the protoxin activator or protoxin proactivator and optionally administered prior to, simultaneously with, or following the administration of the proactivator activator of the invention. In preferred embodiments the components are administered in such a way as to minimize spontaneous activation during administration. When administered separately, the administration of two or more fusion proteins can be separated from one another by, for example, one minute, 15 minutes, 30 minutes, one hour, two hours, six hours, 12 hours, one day, two days, one week, or longer. Furthermore, one or more of the fusion proteins of the invention may be administered to the subject in a single dose or in multiple doses. When multiple doses are administered, the doses may be separated from one another by, for example, one day, two days, one week, two weeks, or one month. For example, the fusion proteins may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the fusion proteins. For example, the dosage of the fusion proteins can be increased if the lower dose does not sufficiently destroy or inhibit the growth of the desired target cells. Conversely, the dosage of the fusion proteins can be decreased if the target cells are effectively destroyed or inhibited.

While the attending physician ultimately will decide the appropriate amount and dosage regimen, a therapeutically effective amount of the fusion proteins may be, for example, in the range of about 0.0035 μg to 20 μg/kg body weight/day or 0.010 μg to 140 μg/kg body weight/week. A therapeutically effective amount may be in the range of about 0.025 μg to 10 μg/kg, for example, about 0.025, 0.035, 0.05, 0.075, 0.1, 0.25, 0.5, 1.0, 1.5, 2.0, 2.5, 3.0, 3.5, 4.0, 5.0, 6.0, 7.0, 8.0, or 9.0 μg/kg body weight administered daily, every other day, or twice a week. In addition, a therapeutically effective amount may be in the range of about 0.05, 0.7, 0.15, 0.2, 1.0, 2.0, 3.0, 4.0, 5.0, 6.0, 7.0, 8.0, 10.0, 12.0, 14.0, 16.0, or 18.0 μg/kg body weight administered weekly, every other week, or once a month. Furthermore, a therapeutically effective amount of the fusion proteins may be, for example in the range of about 100 $\mu g/m^2$ to 100,000 $\mu g/m^2$ administered every other day, once weekly, or every other week. The therapeutically effective amount may be in the range of about 1000 $\mu g/m^2$ to 20,000 $\mu g/m^2$, for example, about 1000, 1500, 4000, or 14,000 $\mu g/m^2$ of the fusion proteins administered daily, every other day, twice weekly, weekly, or every other week.

In some cases it may be desirable to modify the plasma half-life of a component of the combinatorial therapeutic agent of the present invention. The plasma half-lives of therapeutic proteins have been extended using a variety of techniques such as those described by Collen et al., Bollod 71:216-219 (1998); Hotchkiss et al., Thromb. Haemostas. 60:255-261 (1988); Browne wt al., J. Biol. Chem. 263:1599-1602 (1988); Abuchowski et al., Cancer Biochem. Biophys. 7:175 (1984)). Antibodies have been chemically conjugated to toxins to generate immunotoxins which have increased half-lives in serum as compared with unconjugated toxins and the increased half-life is attributed to the native antibody. WO94/04689 teaches the use of modified immunotoxins in which the immunotoxin is linked to IgG constant region domain having the property of increasing the half-life of the protein in mammalian serum. The IgG constant region domain is CH2 or a fragment thereof.

The administration the fusion proteins of the invention may be by any suitable means that results in a concentration of the fusion proteins that, combined with other components, effectively destroys or inhibits the growth of target cells. The fusion proteins may be contained in any appropriate amount in any suitable carrier substance, and is generally present in an amount of 1-95% by weight of the total weight of the composition. The composition may be provided in a dosage form that is suitable for any parenteral (e.g., subcutaneous, intravenous, intramuscular, topical, or intraperitoneal) administration route. The pharmaceutical compositions are formulated according to conventional pharmaceutical practice (see, e.g., Remington: The Science and Practice of Pharmacy (20th ed.), ed. Gennaro, Williams & Wilkins, 2000 and Encyclopedia of Pharmaceutical Technology, eds. Swarbrick and Boylan, 1988-1999, Marcel Dekker, New York).

IX: Experimental Results

A. Construction of Fusion Proteins and Cell Lines

Construction of a Human Granzyme B-Anti-CD19 ScFv (GrB-Anti-CD19) Fusion Gene

The sequence corresponding to the mature human Granzyme B (amino acids 21 to 247) was amplified from a full length Granzyme B cDNA clone obtained from OriGene Inc. and inserted into the pEAK15 vector together with synthetic anti-CD19 ScFv DNA fragment by a three-piece ligation (pEAK15 GrB-anti-CD19L). The promoter for the fusion gene is a CMV/chicken β-actin hybrid promoter. The open reading frame encoding the fusion protein directs the formation of a signal peptide derived from the Gaussia princeps luciferase, a synthetic N-linked glycosylation site, a FLAG tag and an enterokinase cleavage sequence followed by the mature human granzyme B sequence, a flexible linker $(Gly\text{-}Gly\text{-}Gly\text{-}Ser)_3$, the anti-CD19 ScFv, and a C-terminal 6 His tag (See FIG. 1A for schematic depiction of the fusion protein). The DNA sequences encoding all fusion proteins were confirmed by DNA sequencing.

Construction of Diphtheria Toxin Anti-CD5 ScFv (DT-Anti-CD5) Fusion Gene

The DT-anti-CD5 fusion gene was made synthetically by Retrogen Co. (San Diego) with codons optimized for expression in *Pichia Pastoris* and human cell lines. The sequence encoding the furin recognition site ($_{190}$RVRRSVG$_{196}$ (SEQ ID NO:66)) was replaced with a consensus granzyme B recognition sequence ($_{190}$IEPDSG$_{195}$ (SEQ ID NO:13)). Two potential N-glycosylation sites were mutated as described (Thompson et al. Protein Eng. 14(12):1035-41 (2001)) and a 6 His tag sequence was added to the C-terminus of the fusion gene for detection and purification. The fusion gene was cloned into XhoI and NotI sites of the pPIC9 vector (Invitrogen) while maintaining the α-factor signal peptide and the Kex2 cleavage site.

Generation of $CD19^+$Jurkat, $CD5^+$Raji, and $CD5^+$JVM3 Cells

Jurkat SVT35 cells were maintained in IMDM (Invitrogen) supplemented with 10% fetal calf serum (Hyclone). JVM-3 (DSMZ, Germany) was maintained in RPMI 1640 (Invitrogen) supplemented with 10% Fetal bovine serum (Hyclone), 2 mM L-Glutamine.

To prepare the recombinant viruses, we replaced the GFP gene in the retroviral vector M3P-GFP with CD19 or CD5 full length cDNA. To produce viral particles, linearized M3P-CD19 plasmid was cotransfected with pMD-MLV, and pMD-VSVG to 293 ETN cells, which were seeded at $5\times10^6$ per 10 $cm^2$ plate a day before transfection. The DNA concentrations of M3P-CD19, pMD-MLV-G/P and pMD-VSVG were 10 μg, 7 μg and 3 μg, respectively. The volume (μl) of TransFectin was 2.5 times of the total DNA concentration (μg). Viral particles were collected 48 hours after transfection and filtered through a 0.45 μm filter (Corning).

For infection, 5 $10^5$ Jurkat cells were suspended in 1.5 ml culture medium and mixed with 1.5 ml filtered virus in a 6-well plate. Three μl of 8 mg/ml polybrene was added to the mixture to the final concentration of 8 μg/ml. The plate was centrifuged at 2000 rpm for 1 hour before culturing in 37° C. incubator containing 5% $CO_2$. To isolate Jurkat cells expressing CD19, the infected cells were sorted after staining with FITC conjugated anti-human CD19 antibody (Pharmingen, San Diego, Calif. Jurkat cells expressing high concentrations of CD19 were collected and used for the cytotoxicity assay.

Flow Cytometric Analysis

The presence of CD5 and CD19 on cell surface was analyzed using indirect immunofluorescence staining. Cells were first incubated with mouse anti-human CD5 or mouse anti-human CD19 (eBioscience) at a concentration of 0.5 μg per one million cells. Goat F $(ab')_2$ anti-mouse IgG1 conjugated with RPEA (Southern Biotechnology) was used as secondary antibody at a concentration of 0.25 μg per million of cells. The stained cells were analyzed by flow cytometry (FAXCaliber).

B. Expression and Purification GrB-Anti-CD19 Fusion from 293ETN Cells

293ETN cells were seeded at 5 $10^6$-6 $10^6$ cells per 10 cm plate and were transfected with 12 μg of pEAK15 GrB-anti-CD19L and 25 μl of TransFectin (Bio-Rad) according to the manufacturer's protocol. Transfected cells were cultured in Opti-MEM (Invitrogen) for 3 days to allow fusion proteins to accumulate. Supernatants were collected and incubated with pre-equilibrated Ni-NTA resin (Qiagen) and the fusion proteins were eluted with the buffer containing 50 mM HEPES pH7.5, 150 mM NaCl, 250 mM imidazole and 5% glycerol. The purified GrB-anti-CD19 fusion proteins were incubated with enterokinase (New England Biolabs) at room temperature overnight to activate the proteolytic activity of Granzyme B. To remove enterokinase and N-terminal peptide released by enterokinase, the reaction mixture was subjected to affinity purification with Ni-NTA resin. In another form of preparation, the enterokinase and N-terminal peptide released by enterokinase, were removed by gel filtration purification (superdex 200, G E Healthcare). The proteolytic activity of the granzyme B-anti-CD19 ScFv was measured by incubating the purified proteins with a fluorogenic peptide substrate (Ac-IEPD-AMC, Sigma Aldrich). Accumulation of fluorescent product was monitored every 30 s at excitation and emission wavelengths of 380 and 460 nm respectively for 15 min.

C. Expression and Purification of DT-Anti-CD5 Fusion from *P. Pastoris*

*Pichia Pastoris* KM71 cells (Invitrogen) were transformed with the expression plasmid by electroporation. Positive clones were selected according to manufacturer's protocol. For large scale purification, a single colony was cultured at 28° C. overnight in 10 ml Buffer Minimal Glycerol pH 6.0 medium (BMG). The overnight culture was transferred to 1 L BMG pH 6.0 and cultured at 28° C. until OD600 reached 6.0. To induce protein expression, the culture was spun down and resuspended with 100 ml Buffered (pH6.6) Methanol-complex Medium containing 1% casamino acids (BMMYC) and cultured at 15° C. for 48 hours. Supernatants were collected and adjusted to pH 7.6 with 5% NaOH. Clarified supernatants were subjected to affinity purification as described above for the purification of the GrB-anti-CD19 fusion protein.

D. Expression and Purification of DT-Anti-CD5, Anti-CD5-PEA, and Anti-CD5-VCE Fusion Proteins from *E. Coli*

DNA sequence corresponding to αCD5-PEA, αCD5-VCE and their variants were cloned into NcoI and NotI of the pET28 vector (Novagen). Transformed bacterial cells (BL21) were cultured with LB medium at 37° C. To induce expression of insoluble fusion proteins, protein expression was induced with 1 mM IPTG at 37° C. for 4 hours at $OD_{600}$=0.8-1.0. The 40 ml of harvested cell pellet was re-suspended in 5 ml of B-PER II (Pierce) and the inclusion body was purified with B-PER II according the manufacturer's instruction. Purified inclusion body was dissolved with 20 mM Tris 8.0, 150 mM NaCl, 6 M GuCl and 1 mM β-ME and further purified with Ni-NTA resin. Final purified fusion proteins were refolded at the concentration of 0.2 mg/ml with the protocol described previously (Umetsu M. et al. J. Biol. Chem. 278:8979-8987 (2003)). To induce expression of soluble ScFv-VCE fusion proteins, the synthetic genes were cloned into NcoI and NotI of the pET22b vector. Protein expression was induced with 0.2 mM IPTG for overnight at 17° C. at OD60=0.3-0.5. Periplasmic fraction of bacteria was collected as described (Malik et al. Prot. Exp. Pur. Advanced electronic publication (2007)) and fusion protein was purified with Ni-NTA resin.

E. Specific Proteolytic Activity of GrB-Anti-CD19 Fusion Protein

To evaluate the enzymatic activity of purified GrB-anti-CD19 fusion protein, a fluorogenic peptide substrate (Ac-IEPD-AMC) (SEQ ID NO:9) was used to compare the activity of the fusion protein with that of purified mouse granzyme B purchased from Sigma. Purified GrB-anti-CD19 exhibited activity similar to that of the commercial mouse granzyme B preparation, suggesting that addition of a ScFv moiety to the C-terminal of human granzyme B did not impair the proteolytic activity and that enterokinase treatment effectively removed the terminal sequence preceding the first isoleucine of mature granzyme B, allowing the enzymatic activity of the fusion protein to be expressed.

To establish whether the DT-anti-CD5 fusion protein bearing a granzyme B cleavage site could be recognized as a substrate by either mouse granzyme B or GrB-anti-CD19 fusion protein, the DT-anti-CD5 fusion protein containing an N-terminal FLAG tag was incubated with either mouse granzyme B (FIGS. 1B and C, lanes 2) or GrB-anti-CD19 fusion protein (FIG. 1B, lane3). The reaction yielded an N-terminal 25 kD fragment corresponding to the A chain of the diphtheria toxin (FIG. 1B) and a C-terminal 50 kD fragment corresponding the B chain of diphtheria toxin and the ScFv moiety (FIG. 1C), consistent with the interpretation that the DT-anti-CD5 fusion protein could be cleaved specifically at the engineered granzyme B site IEPD↓SG (SEQ ID NO:13).

Figure 14:
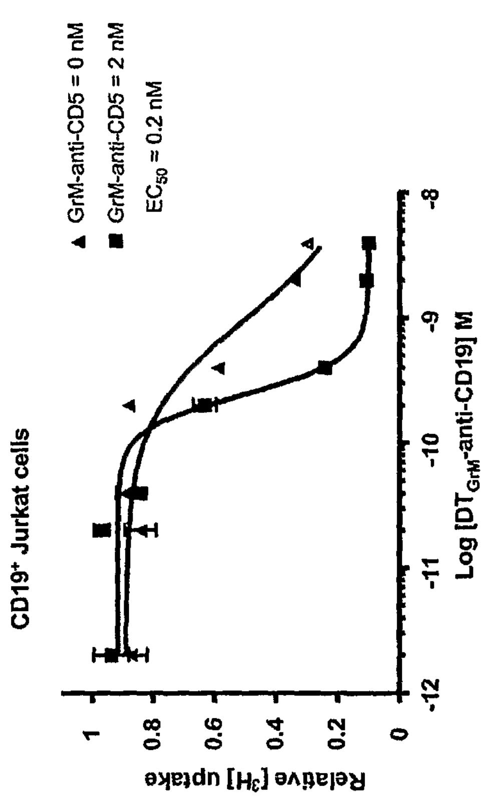
FIG. 14 is a graph showing cytotoxicity assay results of a $DT_{GrM}$-anti-CD19 and GrM-anti-CD5 combination toward a $CD19^+$Jurkat cell line. $CD19^+$ Jurkat cells were treated with 2 nM of GrM-anti-CD5 and various concentrations of $DT_{GrM}$-anti-CD19. The presence of GrM-anti-CD5 increased the toxicity of $DT_{GrM}$-anti-CD19.
Figure 15:
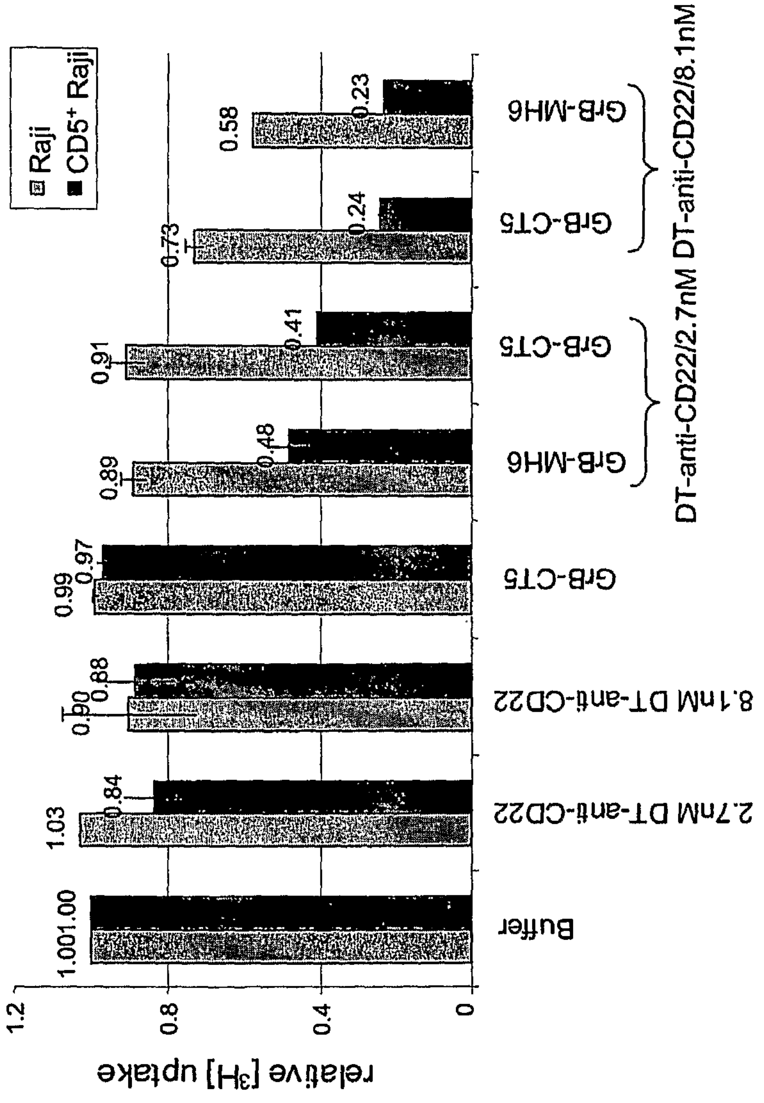
FIG. 15 is a graph showing selective killing of $CD5^+$Raji cells using DT-anti-CD22 and GrB-anti-CD5 (anti-CD5=CT5 ScFv or MH6 ScFv) fusion proteins. Protein synthesis inhibition was analyzed by quantitation of $^3$[H]-leucine uptake in comparison to buffer treated controls.

To further study the cleavage specificity of various DT-anti-CD5 fusion proteins by different proteases, the furin cleavage site of the DT-anti-CD5 fusion protein was replaced with that of a human rhinovirus 3C protease (HRV 3C) cleavage site (ALFQ↓GPLQ) (SEQ ID NO:14) (FIG. 1C, lanes 5 to 8). DT-anti-CD5 bearing an HRV 3C protease cleavage sequence can only be cleaved by HRV 3C protease, not granzyme B or furin (FIG. 1C, lanes 6, 7 and 8). Furthermore, when the furin cleavage site was replaced by a granzyme M recognition site KVPL↓SG SEQ ID NO:67), the resulting toxin $DT_{GrM}$-anti-CD19 showed synergistic toxicity with fusion protein GrM-anti-CD5 to $CD19^+$Jurkat cells (FIG. 14). The toxicity of $DT_{GrM}$-anti-CD19 suggests that this particular toxin fusion may be more susceptible to activation by endogenous proteolytic activities.

The present results demonstrate that replacing the furin cleavage sequence with other protease cleavage sequences renders the mutant DT inactive (or less active in the case of GrM) and that the mutant DT fusion proteins can be selectively activated by proteases that recognize engineered cleavage sequences.

F. Mutant form of Granzyme B with Altered Cleavage Site Specificity

The redirection of the proteolytic specificity of a protease through mutational alteration of residues surrounding the catalytic pocket is well-known in the art. In particular, previous studies involving the site directed mutagenesis of granzyme B, as well as studies of granzyme B proteins from different species, have identified residues that define the substrate specificity of the enzyme, and have provided mutant forms that have altered cleavage specificity (Harris et al. J. Biol. Chem. 273: 27364-27373 (1998); Ruggles et al. J. Biol. Chem. 279:30751-30759 (2004); Casciola-Rosen et al. J biol. Chem. 282:4545-4552(2007)). Similarly, mouse granzyme B isoforms have been found to exhibit much reduced cleavage activity on human Bid, mouse Bid and human caspase 3 than human granzyme B. As a result, mouse granzyme B is thought to be less likely to induce apoptosis in human cells (Casciola-Rosen et al. J Biol. Chem. 282:4545-4552(2007)). Several mutant forms of granzyme B from the Harris et al. study were presumed to have impaired ability to initiate apoptotic pathway due to their altered cleavage sequence specificity. We generated a fusion protein from one such mutant form of granzyme B in which Asn218 of is replaced with Thr (N218T) and showed that the N218T granzyme B exhibited an cleavage site preference toward IAPD (SEQ ID NO:48), a sequence which is not considered a preferred substrate for the wild type granzyme B. Furthermore, we found that the cleavage activity of N218T toward the IAPD (SEQ ID NO:48) sequence is higher than the cleavage activity of wild type granzyme B toward IEDP (SEQ ID NO:9). Thus, in one embodiment of the present invention, a granzyme B fusion protein can be modified to lessen/abrogate the ability to induce apoptosis of target cells, while possessing full (or improved) proteolytic activity toward the optimal cleavage sequences.

Figure 28:
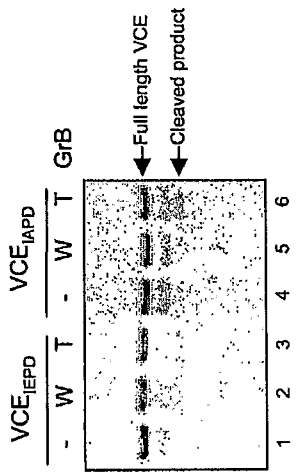
FIG. 28 is an SDS gel showing susceptibility of engineered VCE molecules to granzyme B. $VCE_{IEPD}$: the native furin cleavage site RKPR is replaced by IEPD; $VCE_{IAPD}$: the native furin cleavage site is replaced by IAPD; W: wild type GrB; T: N218T mutant of GrB.

We compared the ability of granzyme B fusion proteins bearing wild type human granzyme B sequence with one bearing the N218T mutation to cleave substrates bearing IEPD (SEQ ID NO:9) or IAPD sequence (SEQ ID NO:48). Under the conditions where only 20% of the substrate was cleaved, we found that N218T cleaved IEPD (SEQ ID NO:9) substrate at comparable capacity as its wild type counterpart (FIG. 28 compare lanes 5 and 6). As expected, we found that N218T cleaved IAPD (SEQ ID NO:48) substrate more efficiently than its wild type counterpart (FIG. 28 compare lanes 5 and 6). Consistent with the in vitro cleavage results, we found that combination of IADP (SEQ ID NO:48) bearing protoxin and N218T mutant granzyme B protoxin activator exhibited higher toxicity to target cells among all the possible combinations of the IEDP/IAPD (SEQ ID NO:48) bearing protoxin and two different forms of granzyme B protoxins activators (data not shown).

G. Cytotoxicity Assay of DT, PEA, or VCE Based Toxin Fusions

The cytotoxicity of combinatorial immunotoxins was tested on cell lines that express both CD5 and CD19, as well as on the corresponding parental cell lines. Cells were placed in a 96-well plate at 5 $10^4$ cells per well in 90 μl leucine-free RPMI and were incubated with 10 μl leucine-free RPMI containing various concentrations of GrB-anti-CD19 ScFv and/or DT-anti-CD5 ScFv fusion proteins at 37° C. for 20 hours in 5% $CO_2$. Inhibition of protein synthesis was measured by adding 0.33 μCi of [$^3$H]-leucine for 1 hour at 37° C. Cells were harvested by filtration onto glass fiber papers by cell harvester (InoTek 96 well cell harvester) and the rate of [$^3$H]-leucine incorporation was determined by scintillation counting. Cell viability was normalized to control wells treated with protein storage buffer. The [$^3$H] incorporation background was obtained by treating cells with 1 mM cycloheximide for 30 min before adding [$^3$H]-leucine. Each point shown represents the average value of duplicate wells.

Figure 2:
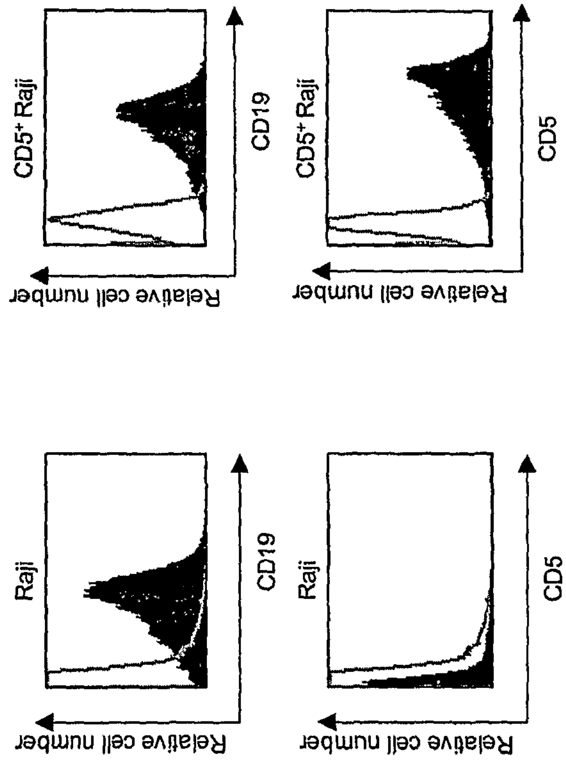
FIG. 2 shows generation of the reporter cell line. Cultured cells from sorted CD5 expressing Raji cells ($CD5^+$Raji) were analyzed by cytometry for CD5 and CD19 expression. The Raji cells only express CD19, whereas $CD5^+$Raji cells express both CD5 and CD19.

Combination of GrB-Anti-CD19 and DT-Anti-CD5Fusion Proteins Exhibits Specific Cytotoxicity Having established the protease fusion protein is functional in vitro, we then asked if the pair of fusion proteins could specifically target cells that express both CD5 and CD19. To this end, we generated a reporter cell B cell line, $CD5^+$Raji, expressing CD5 from a human Raji B cell line. Cytometric analyses using anti-CD5 and anti-CD19 antibodies indicated that both CD5 and CD19 were expressed from the $CD5^+$Raji cell line (FIG. 2), whereas the parental Raji cells express only CD19. The expression of CD5 from the $CD5^+$Raji cell line appeared to be stable, as no significant changes in CD5 level were observed over a long period of culturing.

Figure 3:
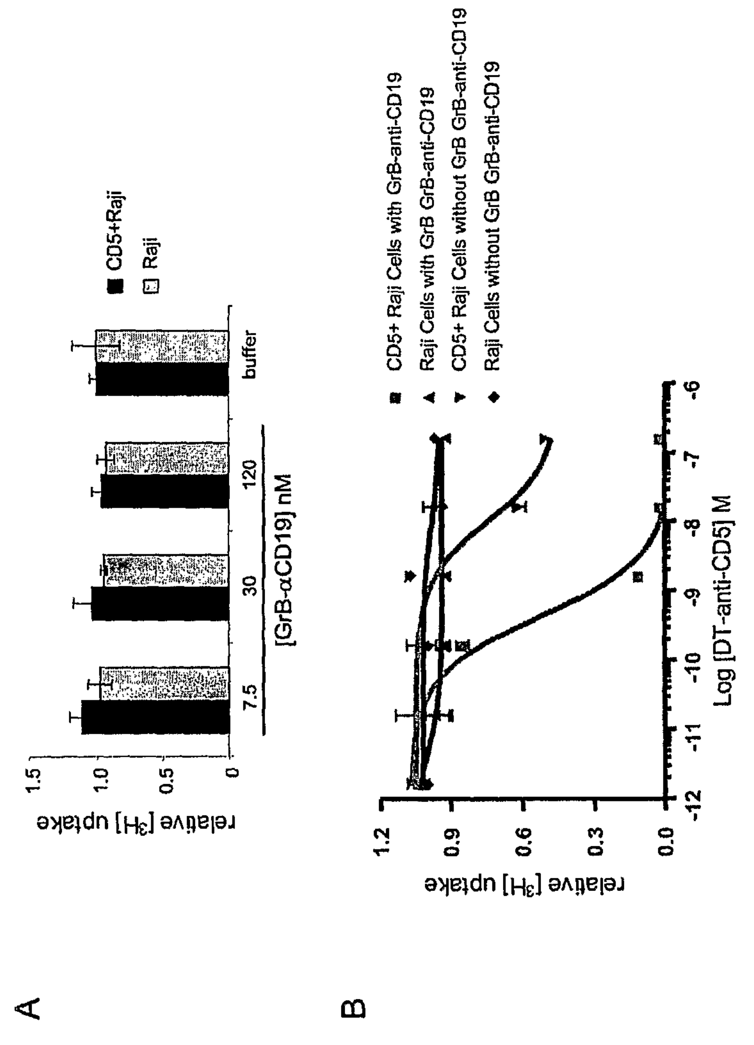
FIG. 3A is a graph showing GrB-anti-CD19 alone was not toxic to cells. The cells were incubated with GrB-anti-CD19 at the concentrations indicated below the graph. The relative cytotoxicity of the fusion proteins in comparison to buffer treated controls was determined by $[^3H]$-leucine uptake.
FIG. 3B is a graph showing DT-anti-CD5 selectively kills $CD5^+$Raji cells in the presence of GrB-anti-CD19. The cells were treated with 1.3 nM GrB-anti-CD19 and various concentrations of DT-anti-CD5. Nonlinear regression analysis was performed using the GraphPad Prism 4 program.
Figure 4:
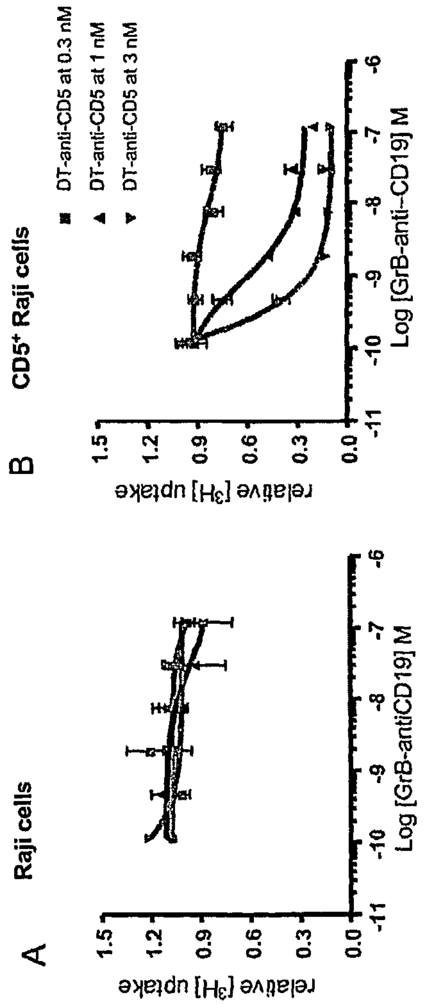
FIG. 4A and FIG. 4B are graphs showing cytotoxicity assays to determine the EC50 of GrB-anti-CD19 in the presence of fixed concentrations of DT-anti-CD5 (0.3 nM, 1.0 nM, and 3.0 nM) using non-target Raji cells (FIG. 4A) and target $CD5^+$Raji cells (FIG. 4B). Nonlinear regression analysis was performed using the GraphPad Prism 4 program.
Figure 5:
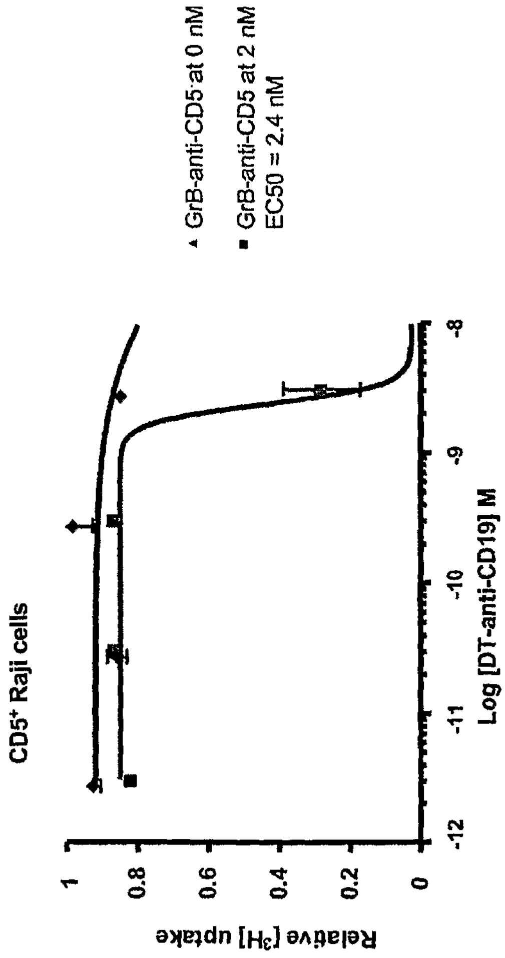
FIG. 5 is a graph showing cytotoxicity assays to determine the EC50 of DT-anti-CD5 in the presence of a fixed concentration of GrB-anti-CD19 (2 nM) using $CD5^+$Raji cells. Nonlinear regression analysis was performed using the GraphPad Prism 4 program.

To evaluate the ability of the fusion proteins to kill specific target cells, we incubated the fusion proteins singly or jointly with either Raji or $CD5^+$Raji cells, and then measured protein synthesis activity. We found that GrB-anti-CD19 alone did not exhibit discernable cytotoxicity toward Raji or $CD5^+$Raji cells at all concentrations tested and that DT-anti-CD5 was not toxic to Raji cells and exhibited only limited toxicity toward $CD5^+$Raji cells at higher concentrations. However, the combination of DT-anti-CD5 and GrB-anti-CD19 fusion proteins was able to arrest protein synthesis in $CD5^+$Raji cells with the EC50 of 423.3 pM, while the parental Raji B cell line was not sensitive to the same treatment (FIG. 3B). GrB-anti-CD19 activated DT-anti-CD5 in a dose-dependent manner (FIG. 4) and fully activated the engineered DT-anti-CD5 at about 1.0 nM, which is well below the concentrations where GrB alone exhibits apoptotic activity (Liu et al. Mol. Cancer Ther. 2(12):1341-50 (2003)). Together, these results demonstrate that DT-anti-CD5 can be targeted to $CD5^+$ cell through anti-CD5 ScFv domain and can be activated efficiently by GrB-anti-CD19.

Figure 6:
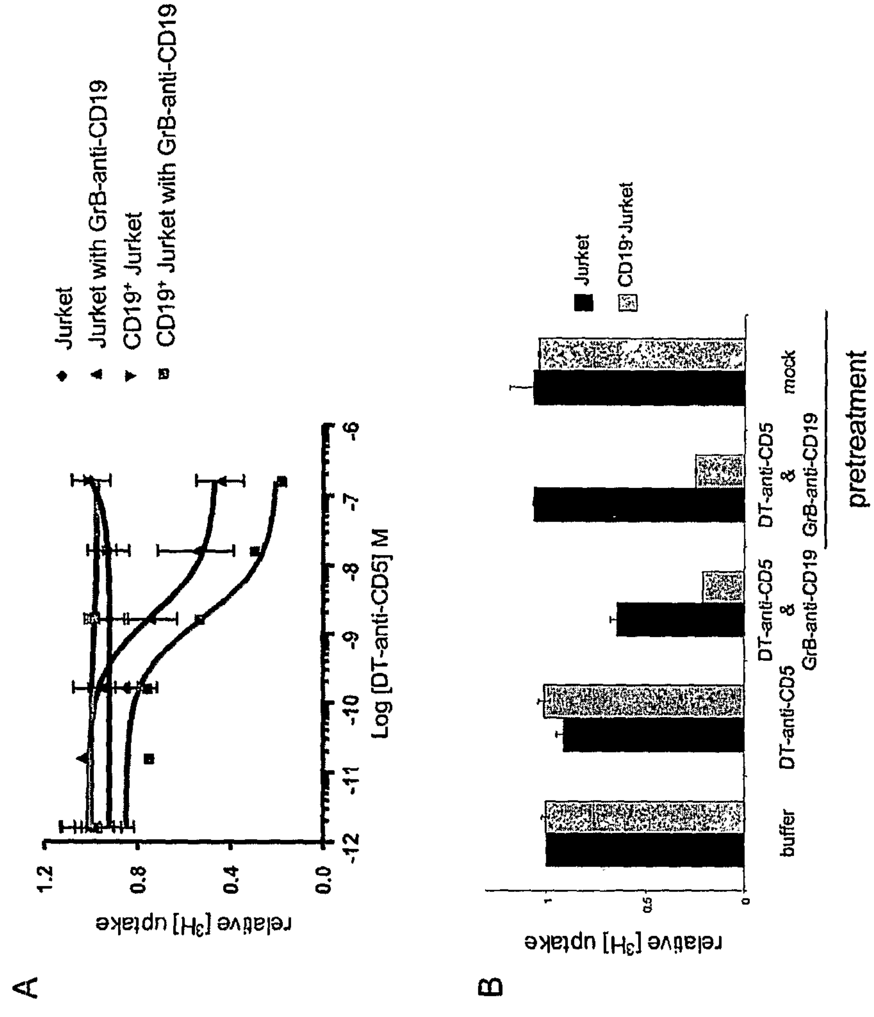
FIG. 6A and FIG. 6B are graphs showing that the combination of DT-anti-CD5 and GrB-anti-CD19 is selectively toxic to $CD19^+$Jurkat cells. The relative cytotoxicity of the fusion protein(s) in comparison to buffer treated controls was determined by $[^3H]$-leucine uptake.

To address if the anti-CD19 ScFv domain of the GrB-anti-CD19 is required for efficient targeting of granzyme B activity to the target cells, we performed additional cytotoxicity assays using Jurkat and $CD19^+$Jurkat cell lines. We found that $CD19^+$Jurkat cells were much more sensitive to the combination of DT-anti-CD5 and GrB-anti-CD19 than Jurkat cells (FIG. 6A), indicating that DT-anti-CD5 was preferentially activated by GrB-anti-CD19 localized to the targeted $CD19^+$ Jurkat cell surface through CD19 binding interaction. The observed lower but significant cytotoxicity to Jurkat cells ($CD19^-$) by these agents suggests that the targeted DT-anti-CD5 may be activated by free GrB-anti-CD19 in media. This hypothesis was confirmed by a separate experiment where both Jurkat and $CD19^+$Jurkat cells were first treated with GrB-anti-CD19 at 4° C. for 30 min., and then washed with buffer to remove the unbound GrB-anti-CD19 from the media. Additional treatment with DT-anti-CD5 at 37° C. for 20 hours induced cytotoxicity in $CD19^+$Jurkat cells, but not in Jurkat cells (FIG. 6B), indicating that the GrB-anti-CD19 bound to the $CD19^+$Jurkat cells were responsible for DT activation. These results indicate that both anti-CD5 and anti-CD19 are necessary for selective killing of the target cells.

*Pseudomonas* Exotoxin (PEA) as the Cytotoxic Agent for Combinatorial Targeting

Figure 7:
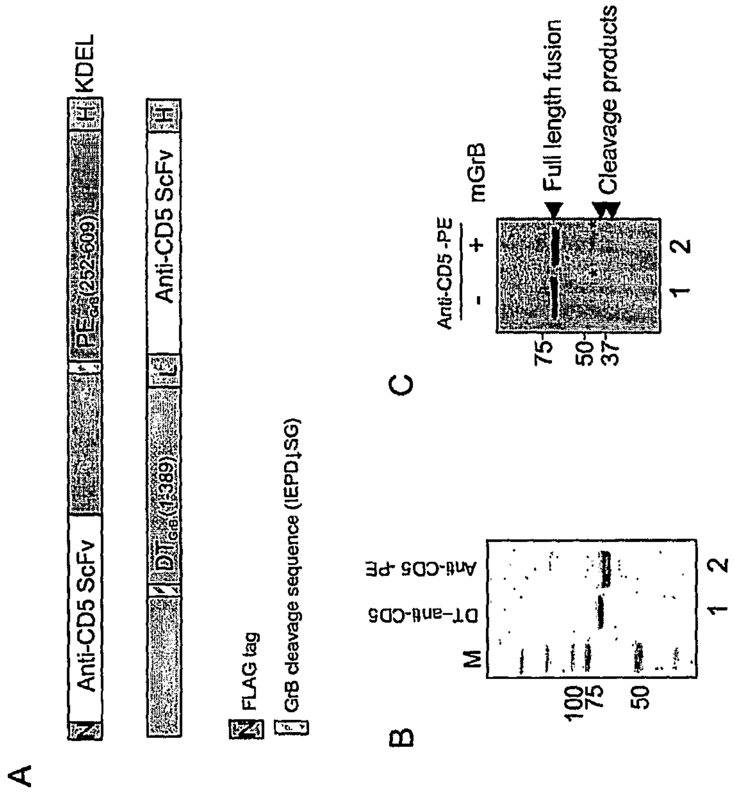
FIG. 7A is a schematic depiction of anti-CD5-PE and DT-anti-CD5 fusion proteins. Artificially synthesized PE gene was fused with the anti-CD5 ScFv gene used in the construction of DT-anti-CD5. Several key features of anti-CD5-PE, including a granzyme B site that replaces the furin site of PE, a C-terminal 6 His tag (H), an N-terminal FLAG tag (N), and an ER retention signal (KDEL (SEQ ID NO:15)) are shown.
FIG. 7B and FIG. 7C are photographs showing 4-12% gradient SDS-PAGE analysis of purified anti-CD5-PE and proteolytic products after mouse GrB treatment, respectively. Anti-CD5-PE was expressed in *E. coli* and was purified from the inclusion body. After refolding, the protein was further purified by gel filtration (Sephadex 75) or by using M2 anti-FLAG tag antibody beads. The refolded anti-CD5-PE is incubated with mouse granzyme B digestion at 30° C. for 3 hours.

To broaden the scope of the combinatorial targeting strategy, we examined the use of a different bacterial toxin, *Pseudomonas* exotoxin A (PEA) in such a context. PEA intoxicates target cells in a manner similar to DT. Upon internalization through receptor-mediated endocytosis, PEA is cleaved by furin at the target cells. The ADP-ribosyl transferase domain is then translocated to cytosol assisted by the translocation domain of PEA and impairs protein translation machinery of the target cells by ADP-ribosylating elongation factor 2. We designed anti-CD5-PEA fusion protein based in part on a published strategy (Di Paolo C. et al., Clin. Cancer Res. 9:2837-48 (2003)), and additionally, replaced the furin cleavage site (RQPR↓SW) with a granzyme B cleavage sequence (IEPD↓SG) (FIG. 7A). The anti-CD5-PEA fusion protein was prepared by refolding the aggregated fusion proteins from bacterial inclusion body using a refolding protocol described by Umetsu M. et al. (J. Biol. Chem. 278:8979-8987 (2003)). The purified anti-CD5-PEA fusion protein was highly pure, as judged by Coomassie Blue staining of the refolded anti-CD5-PEA by SDS-PAGE (FIG. 7B). It is susceptible to proteolytic cleavage by mouse granzyme B, yielding expected products (FIG. 7C).

Figure 8:
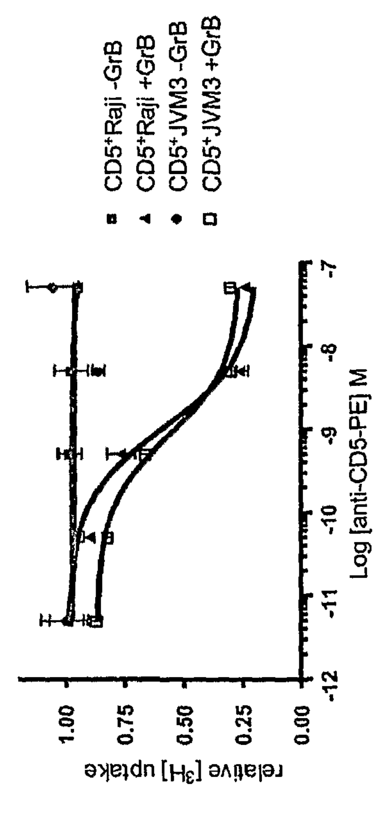
FIG. 8 is graph showing the use of anti-CD5-PE in the context of combinatorial targeting. Cytotoxicity assays were performed with 1.0 nM GrB-anti-CD19 and various concentrations of anti-CD5-PE using four different cell lines, among them $CD5^+$Raji and $CD5^+$JVM3 as target cell lines and Raji and JVM3 as non-target cell lines. Nonlinear regression data analysis was performed as described above. Selective killing of the target cell lines was observed.

To evaluate the ability of anti-CD5-PEA to kill target cells, we performed cytotoxicity assays as described above. We found that anti-CD5-PEA alone was not toxic to either target ($CD5^+$Raji and $CD5^+$JVM3) or non-target (Raji and JVM3) cells (FIG. 8), and that αCD5-PEA selectively killed target cells ($CD5^+$Raji and $CD5^+$JVM3) only in the presence of the second component of combinatorial targeting agents, GrB-anti-CD19, with apparent EC50 of 1.07 nM and 0.81 nM for $CD5^+$Raji and $CD5^+$JVM3 cells, respectively (FIG. 8).

Figure 9:
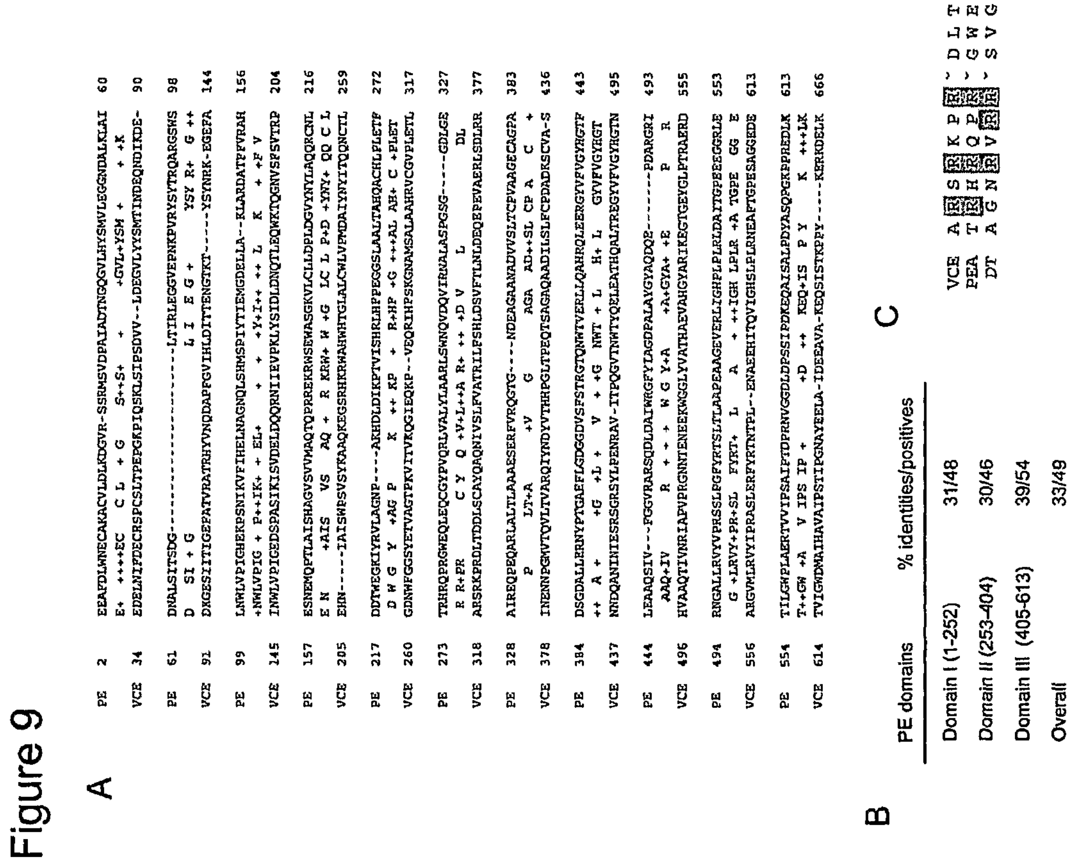
FIG. 9A is a sequence alignment showing the sequence comparison of *pseudomonas* exotoxin A (PE) (SEQ ID NO:16) with a PE-like toxin from a *Vibrio Cholerae* environmental isolate (SEQ ID NO:17) TP using BLAST.
FIG. 9B is a table showing an analysis of overall sequence identity between PE and VCE as well as sequence identity of individual domains of PE and VCE.
FIG. 9C is a sequence alignment showing the sequence of the putative furin cleavage site in VCE (SEQ ID NO:18) in comparison with the furin cleavage sites of PE (SEQ ID NO:19) and DT (SEQ ID NO:20). Residues that are critical for efficient in vitro furin cleavage are highlighted in gray.

Identification and Characterization a PEA-Like Protein from *Vibrio Cholerae* TP Strain In the course of studying anti-CD5-PEA, we identified a putative toxin (GenBank accession number-AY876053) found in an environmental isolate (TP strain) of *Vibrio Cholerae* (Purdy A. et al., J. of Bacteriology 187:2992-3001 (2005)). Although this putative *Vibrio Cholerae* Exotoxin (VCE) only shares moderate protein sequence homology to PEA (33% identities and 49% positives), the residues that are critical for the function of PEA are conserved in VCE, including the active site residues (H440, Y481, E553 in PE), a furin cleavage site in the domain II, and an ER retention signal at the C-terminus (FIG. 9). Furthermore, using molecular simulation tools the VCE catalytic domain sequence was successfully threaded onto the structure of the PEA catalytic domain, consistent with the notion that VCE folds into a structure similar to that of PEA and thus may possess a similar enzymatic activity (Yates S. P., TIBS 31:123-133 (2006)).

Figure 10:
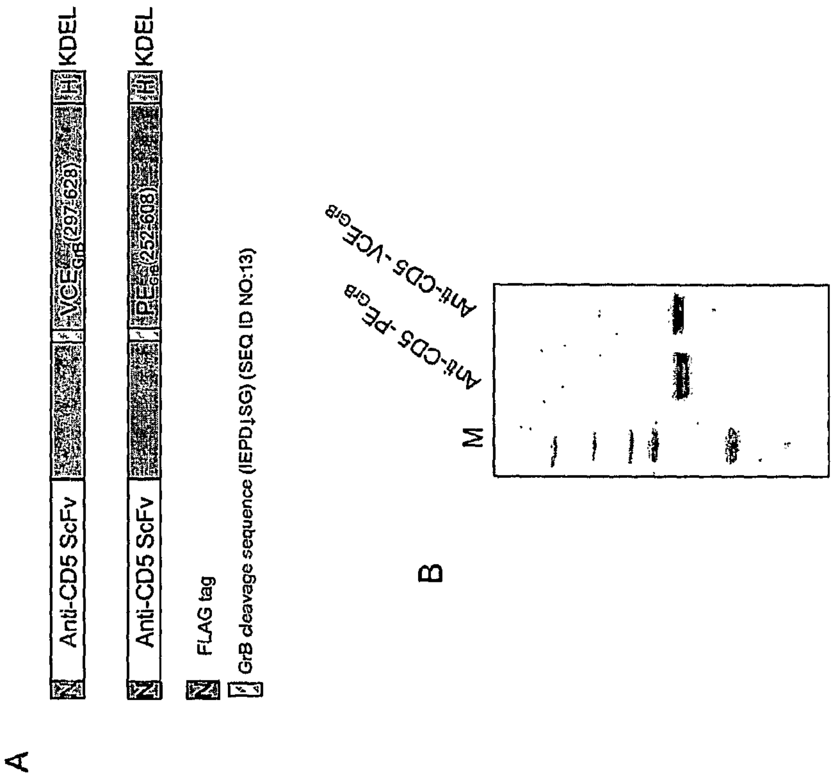
FIG. 10A is a schematic depiction of anti-CD5-VCE. For comparison, the structure of anti-CD5-PE is also shown.
FIG. 10B is a photograph showing a 4-12% SDS-PAGE analysis of purified anti-CD5-VCE and anti-CD5-PE visualized by Coomassie Blue staining. Expression, purification, and refolding of anti-CD5-VCE were carried out following the same protocol that produced functional anti-CD5-PE.
Figure 11:
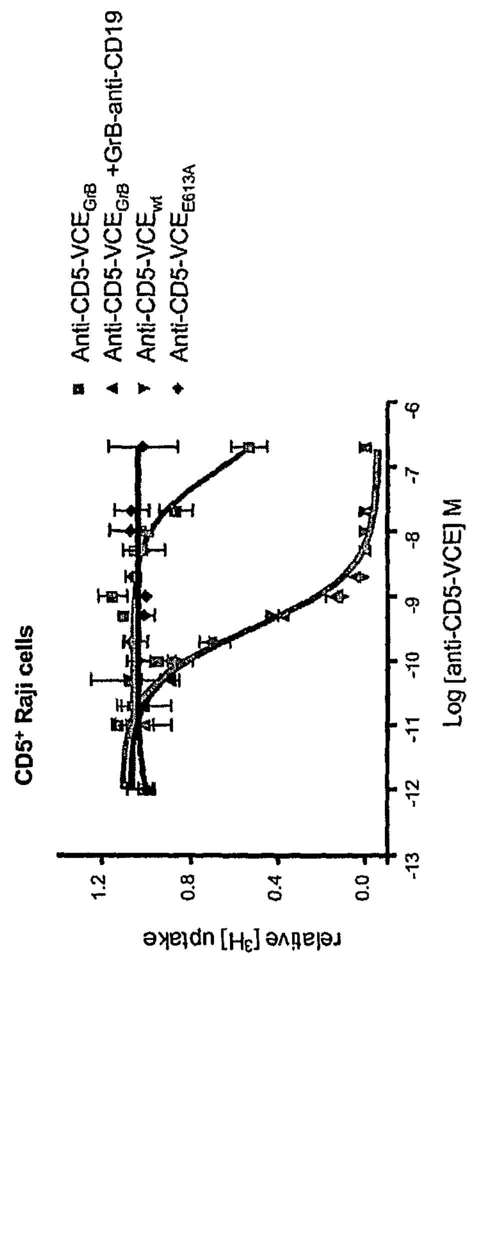
FIG. 11 is a graph showing cytotoxicity assay results of VCE-based combinatorial targeting agents using $CD5^+$Raji cells. The assays were performed with 1.0 nM GrB-anti-CD19 and various concentrations of anti-CD5-VCE. For comparison, we also measured cytotoxicity of anti-CD5-VCE bearing the endogenous furin cleavage sequence (anti-CD5-$VCE_{wt}$) and a mutant anti-CD5-VCE in which one of the predicted active site residues glutamic acid 613 was replaced with alanine (anti-CD5-$VCE_{E613A}$). Nonlinear regression analysis was performed as described above.

To test whether VCE is a PEA-like toxin, we constructed several anti-CD5-VCE synthetic genes and produced anti-CD5-VCE fusion proteins in *E. coli* following the expression and purification protocols for anti-CD5-PEA (FIG. 10B). Like anti-CD5-PEA, the anti-CD5-VCE fusion protein bearing a granzyme B site can be cleaved specifically at the granzyme B cleavage site by both mouse granzyme B and GrB-anti-CD19 fusion protein. We then tested the ability of anti-CD5-VCE to kill target cells in the presence or absence of GrB-anti-CD19 and found that, like DT-anti-CD5 and anti-CD5-PEA fusion proteins, anti-CD5-VCE fusion protein alone was not toxic to target cells, and only in the presence of GrB-anti-CD19 fusion protein it selectively killed target cells (FIG. 11).

Two unexpected advantages of VCE in comparison with PEA relate to expression in *E. coli* and activity. While anti-CD5-PEA could only be produced in *E. coli* in insoluble form, anti-CD5-VCE was solubly expressed in *E. coli*, allowing facile His-tag mediated column purification. In addition, in the presence of GrB-anti-CD19, anti-CD5-VCE showed higher specific toxicity to $CD5^+$Raji cells than anti-CD5-PE. When cytotoxicity profiles of anti-CD5-VCE, anti-CD5-PEA, and DT-anti-CD5 to $CD5^+$Raji cells were determined simultaneously, the relative potency illustrated by observed $EC_{50}$ values were: anti-CD5-VCE (~1.3 nM)<DT-anti-CD5 (~3.0 nM)<anti-CD5-PEA (~4.8 nM). Since VCE and PEA can be predicted to share a similar translocation/intoxication mechanism due to their similar domain structures, it is surprising that VCE is significantly more toxic. The increased toxicity of VCE may be due to more efficient translocation of its ADP-ribosyltransferase by the VCE translocation domain, or the intrinsically higher activity of its ADP-ribosyltransferase. A synthetic toxin comprising the VCE translocation domain and the PEA ADP-ribosyltransferase domain is ~300-fold less toxic to target cells than VCE toxin.

To further assess the efficacy of the combinatorial targeting strategy, we compared the cytotoxicity of three fusion proteins: the anti-CD5-VCE bearing a granzyme B cleavage site, the anti-CD5-VCE fusion protein with the endogenous furin cleavage site, and the anti-CD5-VCE fusion protein in which one of the active sites was mutated (glutamic acid 613 to alanine). As expected, the E613A active site mutation failed to kill target cells at all concentrations tested (FIG. 11). Although replacing the furin cleavage site with a granzyme B cleavage site substantially reduced the toxicity of anti-CD5-VCE fusion protein, the addition of 1.0 nM GrB-anti-CD19 fully restored its cytotoxicity (FIG. 11). These results clearly demonstrate that combinatorial targeting agents are not only highly selective, but also as effective as conventional immunotoxins.

Figure 12:
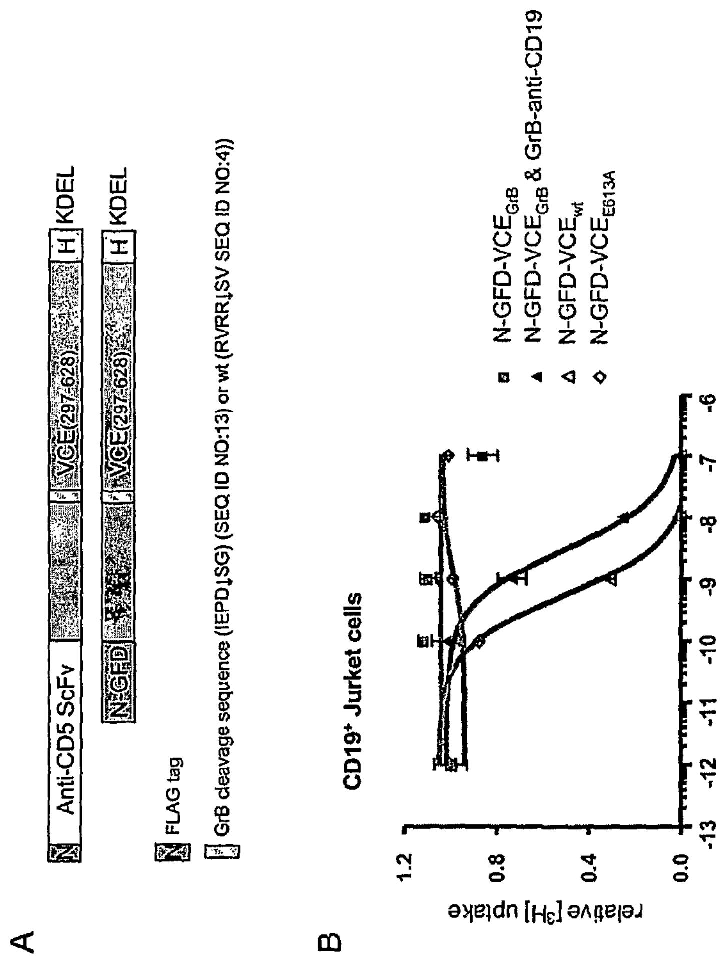
FIG. 12A is a schematic depiction of N-GFD-VCE. For comparison, the structure of anti-CD5-VCE is also shown. N-GFD-VCE was expressed in a soluble form from *E. coli*, and purified by Ni-NTA affinity purification.
FIG. 12B is a graph showing cytotoxicity assay results using $CD19^+$ Jurkat cells. Both N-GFD-$VCE_{wt}$ and the combination of N-GFD-$VCE_{GrB}$ and GrB-anti-CD19 are toxic to the target cells.

N-terminal Growth Factor Like Domain of uPA (Urokinase-Like Plasminogen Activator) as a Targeting Mechanism for Combinatorial Targeting Strategy Naturally occurring peptides has been shown to bind their cognate receptors with high selectivity and affinity. One of such examples is the binding of uPA to its receptor uPAR. It has been shown that the region of u-PA responsible for high affinity binding ($K_d$≈0.5 nM) to uPAR is entirely localized within the first 46 amino acids called N terminal growth factor like domain (N-GFD) (Appella E., et al., J. Biol. Chem. 262:4437 (1987)). To examine if naturally occurring protein sequences such as the N-GFD may be adapted to serve as a targeting principle for the combinatorial targeting strategy, we replaced the ScFv domain of anti-CD5-VCE fusion protein with N-GFD to produce N-GFD-VCE and tested its efficacy in selective killing $uPAR^+$ cells in combination with the GrB-anti-CD19 fusion protein. We chose to use $CD19^+$ Jurkat cells for the cytotoxicity assay since it has been shown that Jurkat cells express a moderate level of uPAR and are sensitive to DTAT, a diphtheria toxin/urokinase fusion protein that targets $uPAR^+$ cells (Ramage J. G. et al. *Leukemia Res.* 27:79-84 (2003)). We found that N-GFD-VCE bearing the native furin cleavage site is toxic to $CD19^+$Jurkat cells, but not to u-PAR negative Raji cells, indicating that cell targeting selectively is achieved exclusively through the N-GFD domain of N-GFD-VCE. N-GFD-VCE fusion protein bearing a granzyme B site alone exhibited only limited toxicity at higher concentrations and was able to kill $CD19^+$Jurkat cell line in the presence of GrB-anti-CD19 at concentrations where N-GFD-VCE itself was not toxic to the target cells (FIG. 12). These results demonstrate that a naturally occurring ligand can serve as targeting mechanism for combinatorial targeting.

Selective Killing of PBMNC from a CLL Patient Using the Combination of Anti-CD5-VCE and GrB-Anti-CD19

Figure 13:
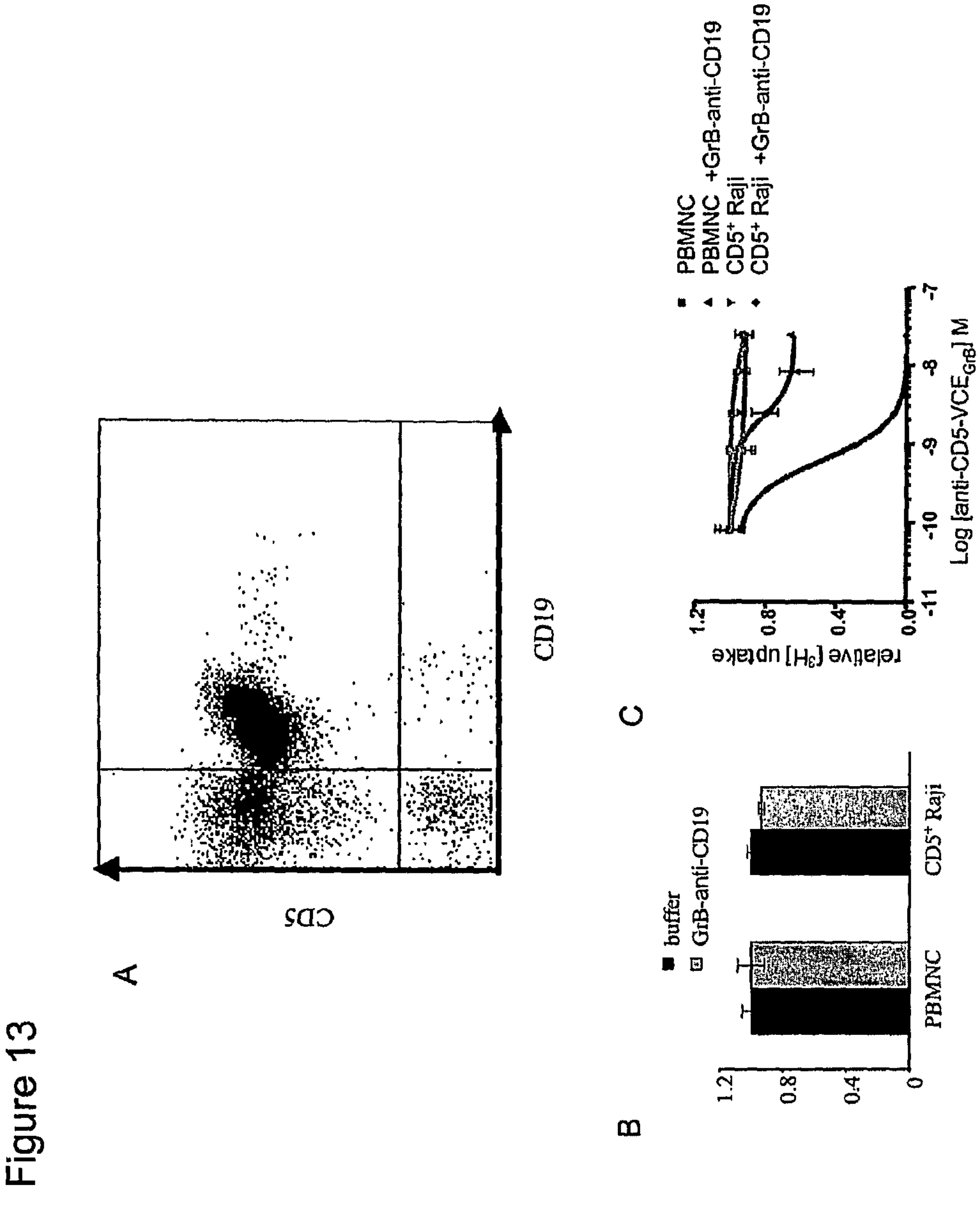
FIG. 13A, FIG. 13B, and FIG. 13C are graphs showing selective cytotoxicity of combinatorial targeting agents to $CD5^+$ B cells in PBMNC from a B-CLL patient.

To test whether combinatorial targeting agents can specifically kill B cell-chronic lymphocytic leukemia cells, we carried out cytotoxicity assay with purified peripheral blood mononuclear cells (PBMNC) from a B-CLL patient. FACS analysis indicated that about 30% of PBMNC was $CD5^+$ B cells (FIG. 13A). We found that each individual component of targeting agents was not toxic to PBMNC (FIGS. 13B and 13C). Furthermore, at the concentrations where combinatorial targeting agents arrested all the protein synthesis activity of the reported cell line ($CD5^+$Raji), about 30% of total protein synthesis activity from PBMNC was arrested. Importantly, no more inhibition of protein synthesis was observed as we increased the concentration of DT-anti-CD5, consistent with the notion that the combinatorial targeting agents might only arrest protein synthesis activity of the target cell population, i.e., $CD5^+$ B cells. Taken together, our data show that combinatorial targeting agents can be deployed to eliminate specific cell populations from heterogeneous mixtures of cells with minimal toxicity to other cell types.

H. Preparation of Anti-CD5-Aerolysin and Anti-CD19-Aerolysin Fusion Proteins

Gene Construction of Tagged, Modified Large Lobe of Aerolysin, Tagged Anti-CD5 ScFv, and Tagged Anti-CD19 ScFv Aerolysin was amplified from the genomic DNA of *Aeromonas hydrophila* (ATCC: 7965D) using Faststart high fidelity PCR mix (Roche). The PCR product was digested with NcoI and XhoI and cloned into a pET22b (Novagen). The 3' end of the clone was subsequently repaired by amplification and digested with NcoI and SalI and recloned into pET22b using NcoI and XhoI sites. There are many different variants of aerolysin and the sequence we obtained most closely resembled an aerolysin clone aer4 (GenBank: X65043). The most significant similarity between our clone and aer4 is in the activation peptide sequence separating the mature pore-forming toxin and the pro-peptide. This differs greatly from the sequence identified from the original aerA gene which is thought to be activated by furin (DSKVRRAR↓SVDG). The activation moiety of our clone was mutated from the native activation moiety (ASHSSRARNLS) to a sequence that could be recognized by human granzyme B (ESKGIEPD↓SGVEG) and tobacco etch virus protease TEV (ESKENLYFQ↓GVEG). We performed site specific mutagenesis using a Phusion polymerase based PCR mutagenesis method (New England Biolabs). These mutants were further modified to delete the small lobe of the native protein and replace it with a sortase substrate sequence (GKGGSNSAAS) using site directed mutagenesis. The resultant clones are referred to as GK-aerolysin$_{GrB}$ and GK-aerolysin$_{TEV}$, respectively.

Anti-CD5 ScFv was PCR amplified, each digested with NcoI and XhoI, and cloned into a pET28a (Novagen) variant modified to carry a sortase attachment signal LPETG upstream of the His-tag. anti-CD19 ScFv was PCR amplified, digested with NcoI and XhoI and cloned into a modified version of pET28a with a periplasmic signal sequence and a sortase attachment signal at the C-terminus.

Figure 16:
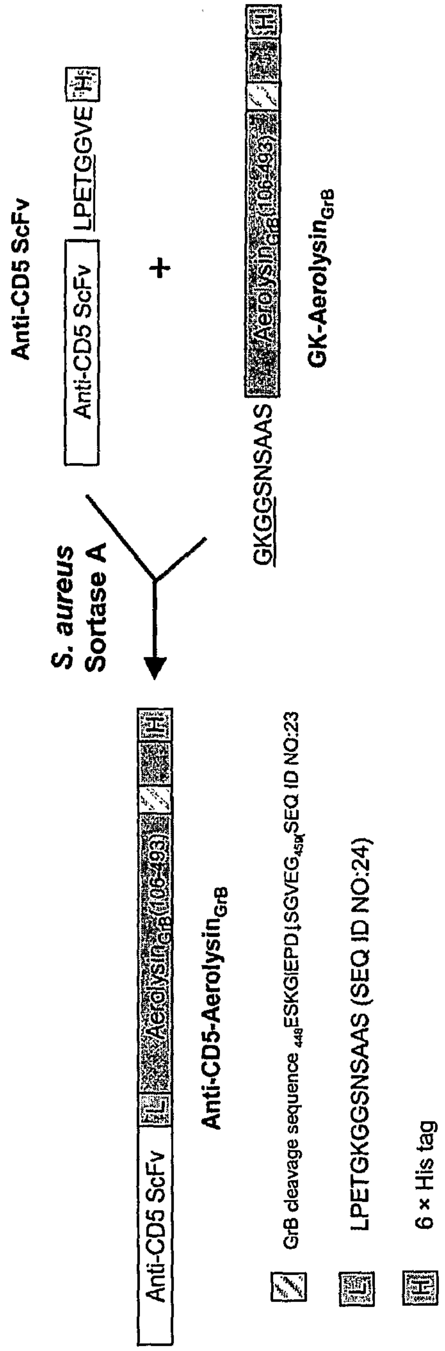
FIG. 16 is a schematic depiction of anti-CD5-Aerolysin$_{GrB}$, which is prepared from anti-CD5 ScFv (LPETGGVE SEQ ID NO:21) and GK-Aerolysin$_{GrB}$ (GKGGSNSAAS SEQ ID NO: 22) through a ligation reaction catalyzed by *S. aureus* Sortase A.

Expression and Purification of Tagged Aerolysin Proteins, Tagged Anti-CD5 ScFv, and Tagged Anti-CD19 ScFv GK-Aerolysin$_{GrB}$ (FIG. 16) and GK-aerolysin$_{TEV}$ were expressed in BL21 star cells at 25° C. after 0.2 mM IPTG induction for 5 hrs. Cells were pelleted and resuspended in lysis buffer (20 mM Tris pH 8, 150 mM NaCl, 0.3 M NH4Cl, 0.1% Triton X-100, 0.2 mg/mL lysozyme) and incubated for 1 hr at 4° C. This was followed by sonication to lyse the bacterial cells and the mixture was spun down and the supernatant was incubated with Ni-NTA agarose (Qiagen). The column was washed with HS buffer (20 mM Tris pH 8, 150 mM NaCl, 1 M NH4Cl, 0.1% Triton X-100) and 20 mM imidazole wash buffer (20 mM Tris pH 8, 150 mM NaCl, 20 mM imidazole) and eluted with 250 mM imidazole elution buffer (20 mM Tris pH 8, 150 mM NaCl, 250 mM imidazole). The protein was then dialyzed against 20 mM Tris pH 7.5 and 150 mM NaCl. Sortase A was purified using a similar protocol.

The ScFvs were expressed as insoluble inclusion bodies in BL21 cells. The inclusion bodies were isolated and then resuspended in redissolving buffer (5M GuCl, 20 mM Tris pH 8, 150 mM NaCl, 0.1% Triton X-100, 5 mM mercaptoethanol). The solution was sonicated to dissolve the protein and then mixed with 4 mL Ni-NTA slurry. The protein was purified under denaturing conditions in the presence of 5M GuCl, and eluted with imidazole (5 mM GuCl, 20 mM Tris pH 8, 150 mM NaCl, 250 mM imidazole, 5 mM mercaptoethanol). The protein was refolded using serial dialysis approach using differing amounts of GuCl and arginine (Umetsu M. et al. J. Biol. Chem. 278:8979-8987 (2003)). The refolded protein was finally dialyzed against 20 mM Tris pH 8, 150 mM NaCl.

Construction of Anti-CD5-Aerolysin and Anti-CD19-Aerolysin$_{GrB}$ Using Sortase A Conjugation

Figure 17:
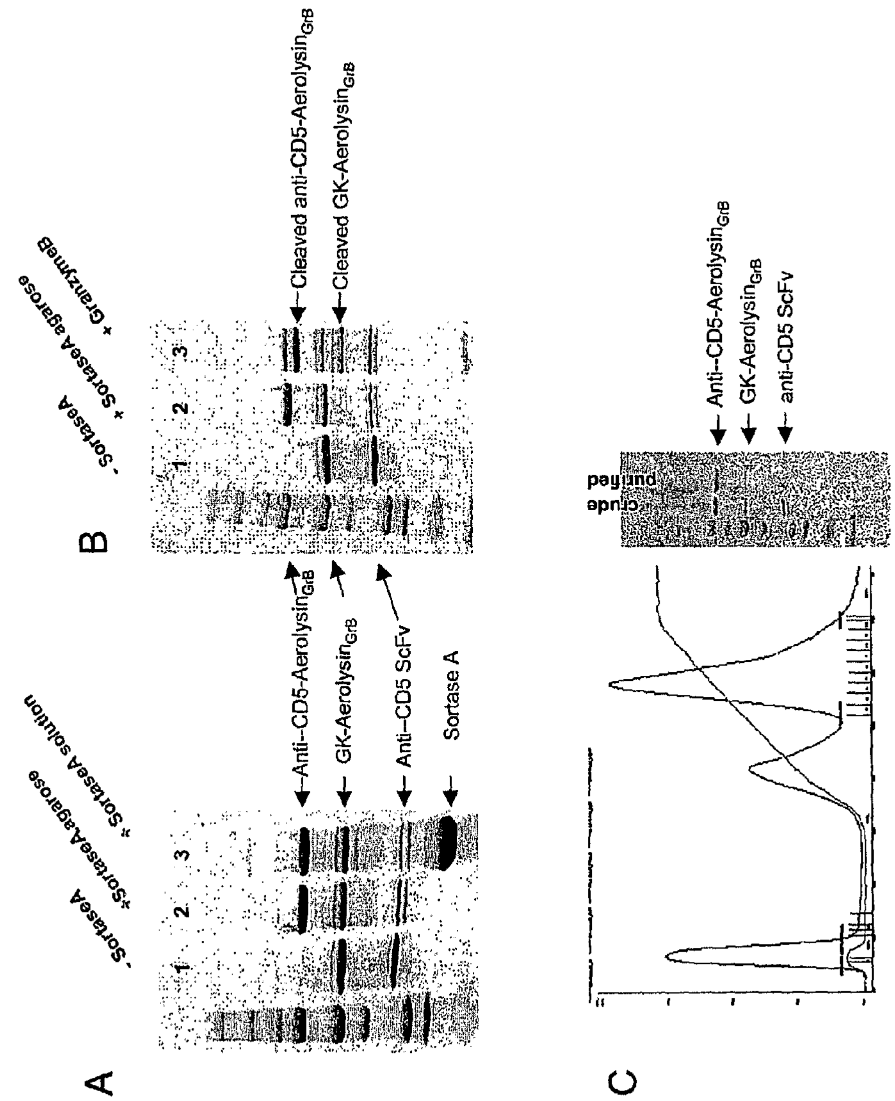
FIG. 17A and FIG. 17B are photographs showing 4-20% gradient SDS-PAGE gels of aerolysin-ScFv conjugation catalyzed by Sortase A. Refolded anti-CD5 ScFv and soluble GK-Aerolysin$_{GrB}$ were mixed (lane 1), treated with immobilized Sortase A (lane 2) or soluble Sortase A (lane 3 of FIG. 17A) and incubated at room temperature overnight. The conjugated mixture was then incubated with mouse GrB for 3 hours at room temperature (lane 3 of FIG. 17B).
FIG. 17C is a graph showing the purification profile of Sortase A conjugated anti-CD5-Aerolysin$_{GrB}$ over a Q-anion exchange column. The purified fusion protein was concentrated and analyzed against the input material using 4-20% gradient SDS-PAGE.

*S. aureus* sortase A is expressed in soluble form from *E. coli* (Zong Y. et al. J. Biol. Chem. 279:31383 (2004)). Purified Sortase A was immobilized on agarose at approximate 10 mg/mL using aminolink plus coupling kit (Pierce). The GK-aerolysin proteins and the refolded scFvs were mixed at 1:2 ratio respectively and incubated with Sortase A-agarose in the presence of 0.1M Tris pH 9, 5 mM $CaCl_2$, 0.01% Tween-20, and incubated overnight at room temperature. The conjugation mix was filtered through a 0.2 micron spin filter and the mixture was purified on a Q-anion exchange column (GE Healthcare) to separate the conjugated aerolysin from the excess ScFv (FIG. 17C). The protein was concentrated and quantified by UV absorbance in preparation for cell based assays.

I. Cytotoxicity Assay (MTS Assay) of Aerolysin Based Toxin Fusions

Promega Cell Titer 96 Aqueous Non-radioactive Cell Proliferation Assay was used to determine cell viability. Cells were placed in a 96-well plate at 5 $10^4$ cells per well in 90 µl RPMI with 10% calf serum (Hyclone, fortified with $Fe^{2+}$). 10 µl of various concentrations of GrB-anti-CD19 ScFv and/or anti-CD5-Aerolysin$_{GrB}$ fusion proteins were added to cells and incubated at 37° C. for 48 hours in 5% $CO_2$ incubator. MTS reagent (25 µl, Promega, G358A) was then added to each well and allowed to incubate for over 4 hours at 37° C. At the end of the incubation period, the $A_{490}$ was recorded using a SPECTRA max ELISA plate reader (Molecular Devices). Cell viability was normalized to control wells treated with protein storage buffer or 1 mM cycloheximide. The reported data represent the average readings from duplicate wells.

Anti-CD5-Aerolysin$_{GrB}$ is Selectively Activated by GrB-anti-CD19

Figure 18:
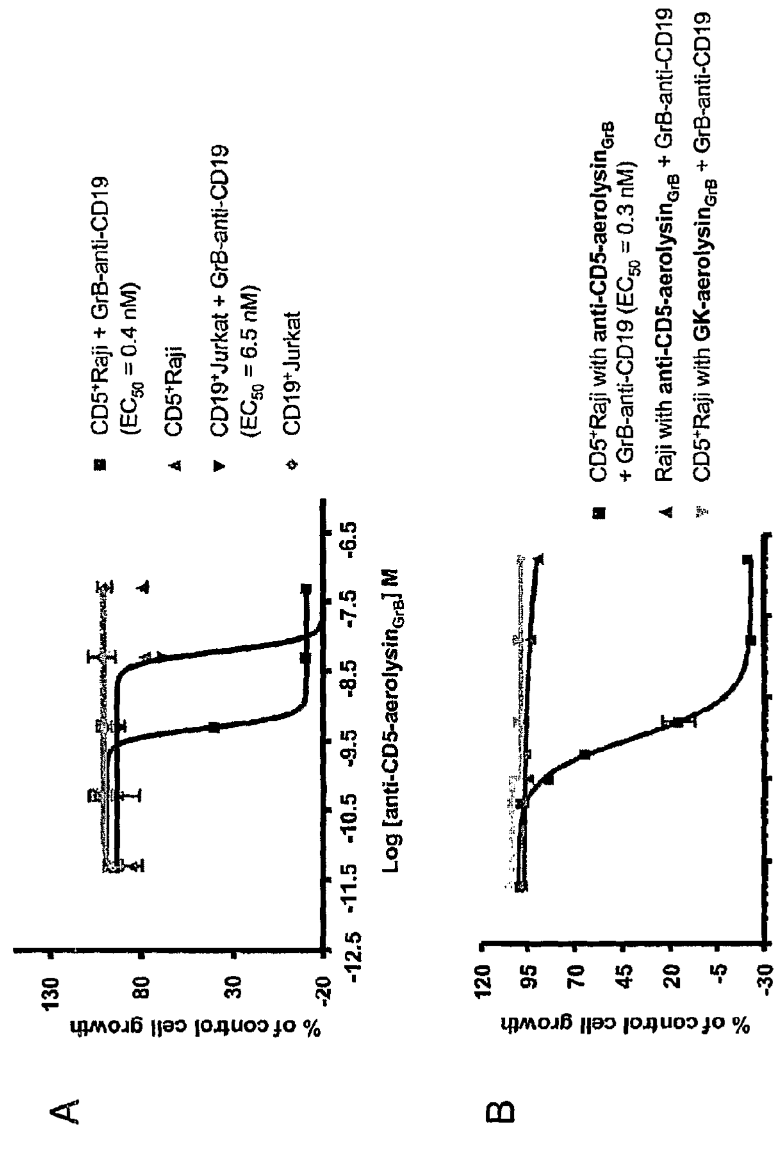
FIG. 18A and FIG. 18B are graphs showing cytotoxicity assay results using aerolysin based immunotoxins.

To investigate whether the engineered aerolysin fusion protein containing a GrB cleavage site and a CD5 binding moiety may be used as the toxin principle in the context of combinatorial targeting of $CD5^+/CD19^+$ cells, the cytotoxicity of anti-CD5-Aerolysin$_{GrB}$ to $CD5^+$Raji and $CD19^+$Jurkat cells was assayed in the presence or absence of 2 nM of GrB-anti-CD19. As shown in FIG. 18, potent cytotoxicity is only observed when GrB-anti-CD19 is present, with $EC_{50}$≈0.3-0.4 nM and 6.5 nM to $CD5^+$Raji and $CD19^+$Jurkat cells, respectively. Virtually no toxicity was observed without the addition of GrB-anti-CD19. Such a low side effect by a aerolysin base protoxin may be attributable to its intoxication mechanism, which involves extracellular proteolytic activation followed by pore formation on cell surface (Howard and Buckley, J. Bateriol. 163:336-340 (1985)). In comparison, DT, PE, or VCE based protoxins are activated inside targeted cells during the translocation process (Ogata et al. J. Biol. Chem. 267:25396-25401 (1992)), during which some intracellular, endogenous proteolytic activities may cleave the heterologous protease cleavage site to activate them, albeit to much less extent than when activated specifically by a targeted activator.

Specific Anti-CD5 ScFv/CD5 Interaction at Cell Surface is Required for the Cytotoxicity of Anti-CD5-Aerolysin$_{GrB}$-Anti-CD19

The necessity of CD5 binding of anti-CD5-Aerolysin$_{GrB}$ for cell targeting was confirmed by the fact that GK-Aerolysin$_{GrB}$, which lacks the anti-CD5 ScFv domain, is not toxic to $CD5^+$Raji cells under the conditions tested. The requirement for specific interaction between anti-CD5 ScFv and cell surface CD5 was further verified by the observation that anti-CD5-Aerolysin$_{GrB}$, in combination to GrB-anti-CD19, is not toxic to Raji cells, which lack the CD5 surface marker (FIG. 18B). Although it is not surprising that a anti-CD5-scFV moiety could direct anti-CD5-Aerolysin$_{GrB}$ fusion protein to CD5$^+$Raji cells, it is not obvious that the anti-CD5-scFV moiety could simply replace the small lobe of aerolysin and successfully function as an integral part of aerolysin. The small lobe of the wild type aerolysin is known to recognize and specifically bind to N-glycans on GPI-anchored proteins, suggesting that it recognizes a site to which both the N-glycan and the GPI-glycan core contribute (MacKenzie et al. J. Biol. Chem. 274:22604-22609 (1999)). Conversely, domain 2 within the large lobe of aerolysin is thought to contribute to the binding of the GPI-core. The specific cytotoxicity to CD5$^+$/CD19$^+$ cells achieved by anti-CD5-Aerolysin$_{GrB}$/GrB-anti-CD19 demonstrated that the contribution of the small lobe to the binding of N-glycan and corresponding GPI-glycan core may be replaced by other interactions between a binder and the surface antigen it recognizes, and the surface marker does not have to be a GPI-anchored protein.

Cytotoxicity to CD5$^+$JVM3 and Jeko-1 Cell Lines

Figure 19:
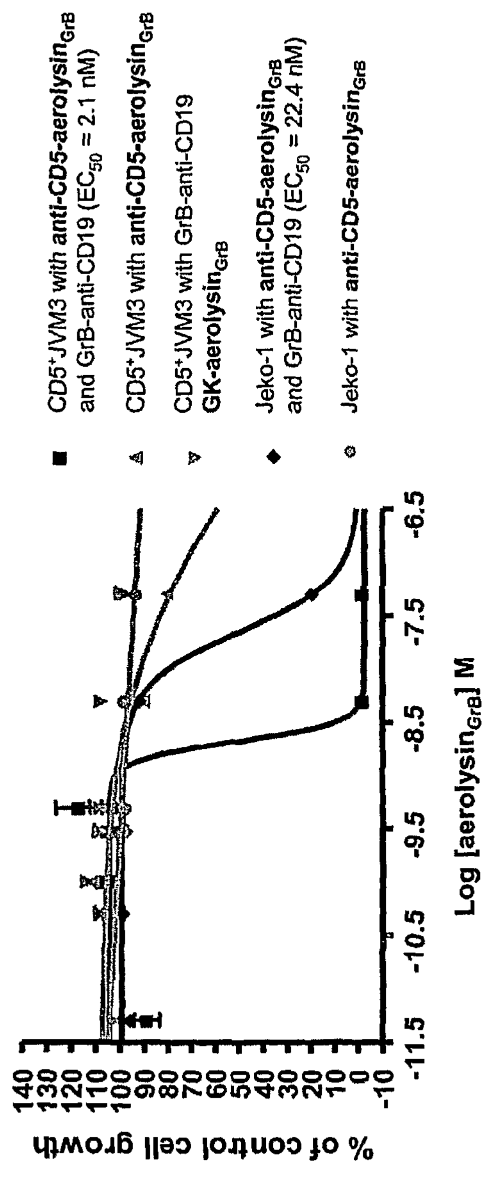
FIG. 19 is a graph showing cytotoxicity assay results using $CD5^+$JVM3 and JeKo-1 cells. $CD5^+$JVM3 or JeKo-1 cells were incubated with anti-CD5-aerolysin$_{GrB}$ with or without 2 nM of GrB-anti-CD19. Anti-CD5-aerolysin$_{GrB}$ shows toxicity to both $CD5^+$JVM3 or JeKo-1 cell lines in the presence of GrB-anti-CD19. GK-Aerolysin$_{GrB}$ is not toxic to $CD5^+$JVM3 cells.

JVM-3 is a cell line that has been used to establish a B-CLL-like xenograft mouse model (Loisel S. et al. Leuk. Res. 29:1347-1352 (2005)), even though it is CD5$^-$. As described above, we have generated a CD5$^+$JVM3 cell line to test combinatorial targeting agents. Jeko-1 cell line is a mantle cell lymphoma cell line that is CD5$^+$/CD19$^+$ (Jeon et al. Brit. J. Haematol. 102:1323-1326 (1998)). Potent cytotoxicity of anti-CD5-Aerolysin$_{GrB}$ to these cells is observed in the presence of 2 nM of GrB-anti-CD19 (FIG. 19), with estimated $EC_{50}$ of 2.1 nM and 22.4 nM, respectively. Since Jeko-1 cells naturally possess both CD5 and CD19 surface antigens, these data illustrate that combinatorial targeting reagents are capable of selectively destroying cancer cells by recognition of cell surface targets present on the cell surface at native levels.

Construction and Expression of Wild Type and Mutant DT Fusion Proteins Bearing Phosphorylation Sites that Block Furin Cleavage when Phosphorylated The gene encoding full length DT (synthesized by Genscript Corporation) was cloned into pBAD102/D-TOPO (Invitrogen Corporation). Single amino acid insertion at the furin cleavage site was achieved using a site-directed mutagenesis kit from Stratagene (QuikChange® 11 Site-Directed Mutagenesis Kit). The original enterokinase recognition sequence in the vector plasmid was changed to a TEV protease recognition sequence using PCR.

All plasmid constructs were transformed into One Shot® TOPO10 competent cells (Invitrogen Corporation). Positive colonies were selected. For protein induction, a single positive bacterial colony was inoculated into 2 ml of LB and transferred into 100 ml LB after overnight incubation. After OD reached 0.6, the culture was moved to 16° C. incubator, to which was added arabinose to a final concentration of 20 ppm and the induction lasted at least for 4 hours. Bacteria were precipitated at 2000 g for 10 minutes and the cell pellet was then suspended in 8 ml buffer of 25 mM $NaH_2PO_4$, 250 mM NaCl at pH 8.0. The cell solution was then incubated with 8 mg of lysozyme on ice for 30 minutes. After sonication, the lysate was centrifuged at 3,000 g for 15 minutes, and the resulting supernatant was purified by Ni-NTA agarose purification following manufacturer's recommended procedures (Invitrogen Corporation).

Figure 21:
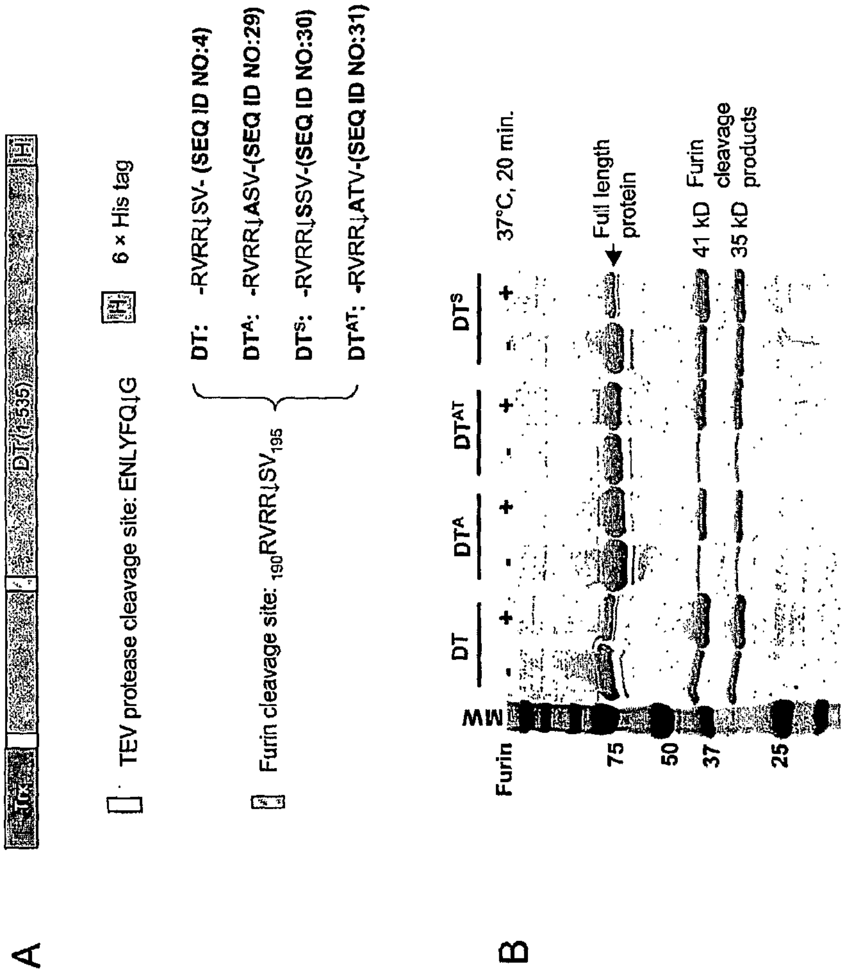
FIG. 21A is a schematic depiction of various thioredoxin-DT fusion proteins containing the wild type or mutated furin cleavage site.
FIG. 21B is a photograph of an SDS PAGE gel showing the site specific cleavage of these fusion proteins by incubating with furin at 37° C. for 20 min.

After purification, the protein solutions were dialyzed against a buffer of 25 mM Tris, 250 mM NaCl and 10% glycerol at pH 7.5 for overnight, to provide a buffer system that is compatible with furin cleavage and phosphorylation reactions. All the fusion proteins made (DT, $DT^A$, $DT^S$, $DT^{AT}$) are depicted in FIG. 21 with the corresponding furin cleavage sites shown.

Phosphorylation of Fusion Proteins

Figure 22:
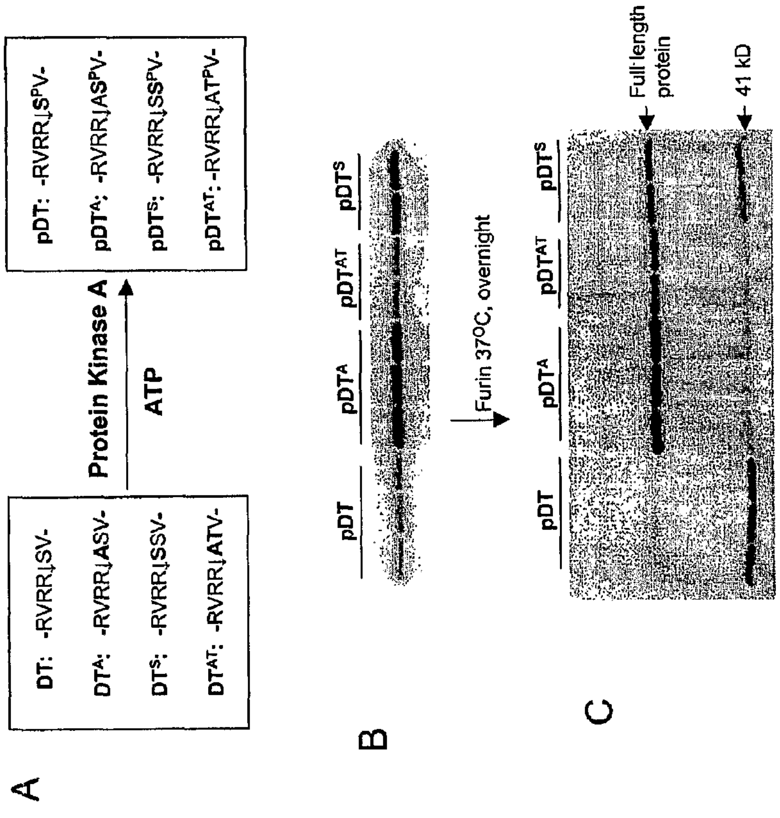
FIG. 22A is a schematic showing the desired phosphorylation reactions (SEQ ID NOs:4, 29-31, from top to bottom).
FIG. 22B is an image showing the radiolabeled fusion proteins after phosphorylation using PKA and $\gamma$-$^{32}$P-ATP.
FIG. 22C shows the reaction mixtures after overnight treatment with furin at 37° C. It is evident that the phosphorylated proteins $pDT^{A}$, $PDT^{AT}$, and $pDT^{S}$ are resistant to furin cleavage.

To examine the efficiency and specificity of site-specific phosphorylation of Trx-DT fusion proteins DT, $DT^A$, $DT^S$, and $DT^{AT}$, a number of commercially available kinases were screened. Protein kinase A (PKA) was identified as the most efficient for these fusions. Phosphorylation reaction was carried out in 20 μl of 50 mM Tris-HCl/10 mM $MgCl_2$ pH 7.5 buffer containing 1 μg of protein, 1 μl of protein kinase A, and 2 μl of 1 mM ATP (New England Biolabs). The mixture was incubated at 30° C. for 20 minutes. In order to visualize the phosphorylation product, in some phosphorylation experiments ATP was supplemented with γ-$^{32}$P-ATP (3000 Ci/mmol, Perkin Elmer Life and Analytical Science) to yield $^{32}$P labeled Trx-DT. It was found that PKA adds the radioactive phosphate group to all the fusion proteins, producing a single product as shown by SDS-PAGE analysis (FIG. 22B, top panel). The labeling efficiency of the Trx-DT fusions, which corresponds to phosphorylation efficiency, is found to be $DT^A>DT^S>DT^{AT}\approx DT$.

Furin Cleavage of Trx-DT and Phosphorylated Trx-DT Fusion Proteins

To analyze whether the phosphorylatlon at furin cleavage site within the Trx-DT fusion proteins have any effect on furin cleavage efficiency, the unlabeled and phosphate-labeled fusion proteins were incubated with furin at 37° C. For each furin digestion, 2 μg of protein was mixed with 2 units of furin (New England Biolabs) in a total reaction volume of 20 μl at 37° C. Reaction buffer contained 100 mM Tris-HCl, 0.5% Triton X-100, 1 mM $CaCl_2$ and 0.5 mM dithiothreitol at pH 7.5. The reaction mixtures were analyzed by SDS-PAGE using the samples without turin treatment as controls. We found that the control samples contained some nicked products of 35 kD and 41 kD, which are consistent with fragmentation at the furin cleavage site. This phenomenon has been observed by others previously and is considered the result of undesired proteolytic cleavage during protein purification. After a 20 minute furin treatment, the DT, $DT^A$, $DT^S$, and $DT^{AT}$ samples showed substantially more cleavage products of 35 kD and 41 kD (FIG. 21B), demonstrating site specific cleavage of non-phosphorylated samples, as expected. However, the phosphorylated proteins $pDT^A$, $pDT^S$, and $pDT^{AT}$ showed reduced sensitivity to furin cleavage. While significant digestion on pDT could be observed after one hour, no obvious digestion could be observed for $pDT^A$, $pDT^S$, and $pDT^{AT}$. The digestion was then continued for overnight. After furin treatment for 20 hours, the cleavage of pDT was near completion, but only about 5%, 10%, and 50% of $pDT^A$, $pDT^{AT}$ and $pDT^S$ were fragmented, respectively (FIG. 22B). The significantly reduced lability of $pDT^A$, $pDT^{AT}$ and pDTs to furin due to phosphorylation suggests that they may potentially be used as protoxins which are activated by dephosphorylation to provide a natively activatable toxin, i.e. one that can be activated by endogenous furin/kexin-like proteases.

Preparation of $DT^A$-Anti-CD19 and $pDT^A$-Anti-CD19 Fusion Proteins

The Trx-DTA-anti-CD19 fusion gene containing an alanine insertion at furin cleavage site $_{190}$RVRR↓<u>A</u>SV$_{195}$ was constructed by subcloning from the corresponding Trx-DT ($DT^A$ in FIG. 21A) and $DT_{GrB}$-anti-CD19 fusion genes. Trx-DTA-anti-CD19 fusion protein was expressed in *E. coli* and the soluble fraction was collected and purified using standard His-tag purification. The purified Trx-$DT^A$-anti-CD19 was treated with TEV protease to remove the Trx tag and afford $DT^A$-anti-CD19.

The purified $DT^A$-anti-CD19 was further phosphorylated using PKA and ATP using the procedure described above to generate $pDT^A$-anti-CD19 (FIG. 22A).

Dephosphorylation of $pDT^A$-Anti-CD19

Fusion protein pDTA-anti-CD19 was treated with recombinant protein phosphatase 2C (PP2C) produced in *E. coli*, and its dephosphorylation was observed by SDS-PAGE. The resulting $DT^A$-anti-CD19 contains the RVRR↓AS sequence, which is activatable by furin that is present in mammalian cells. PP2C was selected for the dephosphorylation because it has been shown that it can remove the phosphate group on $RRAT^PVA$ or $RRAS^PVA$ efficiently (Deana et al., Biochim. Biophy. Acta, 1051:199-202 (1990)), which are very similar to the modified furin cleavage site within $pDT^A$-anti-CD19.

Cytotoxicity Assay of D-Anti-CD19 and $pDT^A$-Anti-CD19 Fusion Proteins

Figure 23:
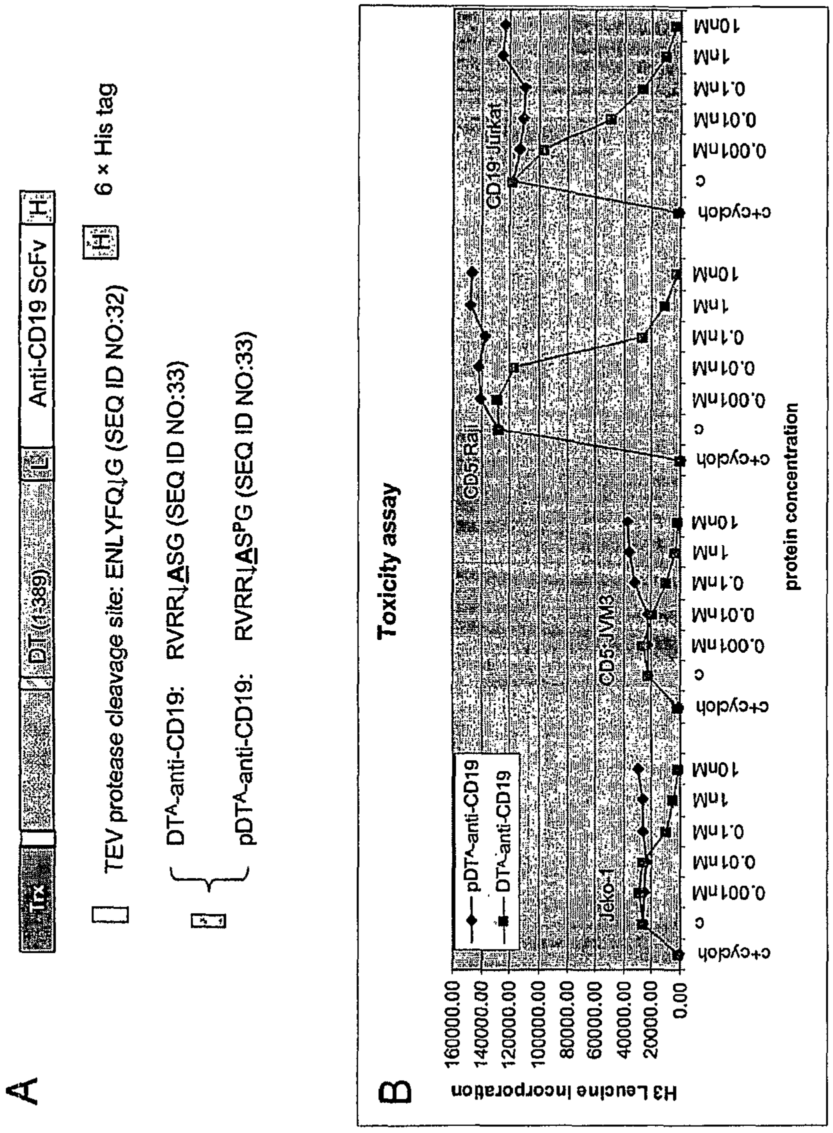
FIG. 23A is a schematic depiction of the Trx-$DT^{A}$-anti-CD19 fusion proteins with mutated and/or modified furin cleavage sites shown.
FIG. 23B is a graph showing that the unphosphorylated Trx-$DT^{A}$-anti-CD19 fusion was toxic to all the cells tested, with IC50~0.01-0.1 nM, whereas the phosphorylated Trx-$DT^{A}$-anti-CD19 fusion was not toxic to these cells under similar conditions.

Both $DT^A$-anti-CD19 and $pDT^A$-anti-CD19 were tested by protein synthesis inhibition cytotoxicity assay as described above, using cells that contain both the CD5 and CD19 surface antigens, i.e. Jeko-1, $CD5^+$JVM3, $CD5^+$Raji, and $CD19^+$ Jurkat cells. Various concentrations of $DT^A$-anti-CD19 and $pDT^A$-anti-CD19 were tested, and a positive inhibition control was provided by adding cycloheximide to each cell line. The results (FIG. 23B) show that the unphosphorylated $DT^A$-anti-CD19 fusion is very toxic to all the cells tested, with IC50~0.01-0.1 nM; whereas the phosphorylated pDTA-anti-CD19 fusion is not toxic to these cells under similar conditions.

These results demonstrate that it is feasible to establish a protoxin activation strategy, in which the proactive moiety (e.g., furin cleavage site RVRR↓AS) within a protoxin (e.g., $DT^A$-anti-CD19) is masked by a chemical modification (e.g., phosphorylation at the Serine) to afford a protoxin (e.g., $pDT^A$ anti-CD19–); the protoxin may be converted by an activator (e.g., phosphatase PP2C) to a natively activatable toxin (e.g., $DT^A$-anti-CD19), which is activated by furin activity natively present in mammalian cells.

This strategy should be applicable to any protoxin that may be naturally activated by intracellular or extracellular proteolysis. Examples of such toxins include but not limited to, ADP-ribosylating toxin such as DT, PE, and VCE, pore-forming toxin such as aerolysin and *Clostridium perfringens* ϵ-toxin, pro-RIP toxin such as pro-ricin, and zymogen-based toxin such as pro-GrB. Examples of enzyme activities that may be used to modify/demodify as protoxin modifying reagent and protoxin proactivator include but are not limited to, kinases and phosphatases for phosphorylation and dephosphorylation, respectively; O-GlcNAc transferase and O-GlcNAcase for glycosylation and deglycosylation, respectively; and E1/E2 and Senp2 for sumoylation and desumoylation, respectively.

Production of Mature GrB-$(YSA)_2$ and Protease Activatable Pro-GrB-$(YSA)_2$

In CTLs and NK cells, GrB is initially expressed as an inactive precursor protein. This pre-pro-GrB carries an N-terminal signal peptide that directs packaging of the protein into secretory granules. The enzymatic activity of GrB is strictly controlled by the activation dipeptide Gly-Glu, which is cleaved by dipeptidyl peptidase/cathepsin C during transport into storage vesicles. We have constructed recombinant GrB in a pro form, which may be matured either by a separate step of proteolytic removal of the extra residues located N-terminal to the first residue Ile of GrB, or by in situ activation conferred by a natively present protease in the host cells.

As shown in FIG. 20A, two pro-GrB-$(YSA)_2$ fusion proteins were designed and constructed, an enterokinase activatable DDDDK-GrB-$(YSA)_2$ fusion protein, and a furin activatable RSRR-GrB-$(YSA)_2$ fusion protein. DDDDK-GrB-$(YSA)_2$ was produced by transfecting 293T cells with plasmids expressing this fusion protein. The pro-enzyme was produced as a secreted form and was first purified with Ni affinity chromatography. Purified DDDDK-GrB-$(YSA)_2$ was activated by adding enterokinase in vitro. Using a fluorogenic peptide (Ac-IEPD-AMC), it was demonstrated that the enzymatically active GrB-$(YSA)_2$ was obtained by proteolytically cleaving the sequences N-terminal to the naturally matured GrB sequence (amino acid 21 to 247) using added enterokinase, which recognizes and cleaves at DDDDK↓ (FIG. 20B).

On the other hand, GrB-$(YSA)_2$ may be isolated in its mature form in 293T cells directly if the fusion construct is designed to be activated by furin, which is naturally present in mammalian cells. Supernant of 293T cells transfected with plasmids expressing RSRR-GrB-$(YSA)_2$ was collected and the activity of GrB was comparable to that of GrB-$(YSA)_2$, which was activated in vitro by enterokinase treatment of DDDDK-GrB-$(YSA)_2$.

These experimental results demonstrate that the status of GrB activity may be manipulated by either exogenbus (e.g., enterokinase) or endogenous (e.g., furin) proteolytic activities. Such controlled activation is particularly useful for the combinatorial targeting described in the present invention. For example, the activation of $DT_{GrB}$-anti-CD5 protoxin fusion may only be achieved when the targeted cells are also bound to the DDDDK-GrB-$(YSA)_2$ fusion, where the exogenous enterokinase is introduced by a cell-targeting moiety recognizing a third cell surface target. On the other hand, in many mammalian cells the availability of RRSR-GrB-$(YSA)_2$ fusion is sufficient to be activated $DT_{GrB}$-anti-CD5 protoxin fusion because these cells natively expresses furin, which can activate proactivator RRSR-GrB-YSA.

J. Targeting Breast Cancer Cells Using Surface Marker EphA2 and Claudin3/4

In one particular example, the protoxin and protoxin activator fusion proteins of the invention were directed towards breast cancer cells expressing EphA3 and claudin3/4.

Construction of a $DT_{GrB}$-CCPE Fusion Gene

The translocation domain and catalytic domain of DT from the $DT_{GrB}$-anti-CD5 gene was cloned into pBAD/D-TOPO-vector (Invitrogen) that contains a His-Patch Thioredoxin. A factor Xa site was also introduced directly upstream of the DT to provide an opportunity to later remove the thioredoxin front the fusion protein. The gene encoding C-CPE was synthesized (Genscript Corporation). The C-CPE insert containing a polyhistidine tag (H6) at C-terminus was ligated into the pBAD/D-TOPO-DT vector described above to generate the fusion gene. A TEV protease cleavage site was introduced using PCR based mutagenesis and Phusion™ High-Fidelity DNA Polymerase (New England Biolabs). The recognition site used was ELNYFQ↓G, and replaced the Factor Xa site (I-E-G-R) in the original construct.

Expression of $DT_{GrB}$-CCPE

A one liter culture of *E. coli* containing the pBAD/D-TOPO-Trx-$DT_{GrB}$-CCPE plasmid was grown to OD600=0.6 in LB containing ampicillan. The culture was induced with 0.02% arabinose at 18° C. overnight. Fusion protein was purified using Ni-NTA agarose resin (Qiagen) and dialyzed against PBS.

TEV protease was used to remove the thioredoxin from the Trx-$DT_{GrB}$-CCPE construct. The $DT_{GrB}$-CCPE was purified from the TEV protease and the thioredoxin using an amylose resin column (New England Biolabs) followed by a Ni-NTA agarose column (Qiagen). The purified protein was dialyzed against PBS.

Construction of GrB-$(YSA)_2$ Gene Fusion

A twelve residue peptide, YSA, having the sequence YSAYPDSVPMMS, has been reported to be a specific binder to EphA2 receptors (Koolpe, et al. J Biol Chem. 280:17301-11 (2005)), which are overexpressed in number of cancers. A DNA encoding the fusion of two YSA peptides was synthesized and cloned into pIC9 vector along with the GrB gene in a 3-piece ligation reaction. The resulting plasmid was confirmed to contain the desired GrB-$(YSA)_2$ DNA, which was then sub-cloned into pEAK15-GrB-CD19L vector that was used for mammalian expression of the GrB-anti-CD19 fusion discussed above. The pEAK15-GrB-$(YSA)_2$ construct contains a leader sequence for secretion of the expressed protein, as well as an enterokinase site directly upstream of the Granzyme B.

Expression and Purification of GrB-$(YSA)_2$

The pEAK15-GrB-$(YSA)_2$ plasmid was transfected into 293ETN cells using TransFectin™ Lipid Reagent (BioRad) following recommended procedure. Cells were incubated for 2 days in OptiMEM (Gibco), and the supernatant was collected. The secreted protein was purified from media supernatant using Ni-NTA resin (Qiagen), then dialyzed against Tris-Cl buffer.

Figure 24:
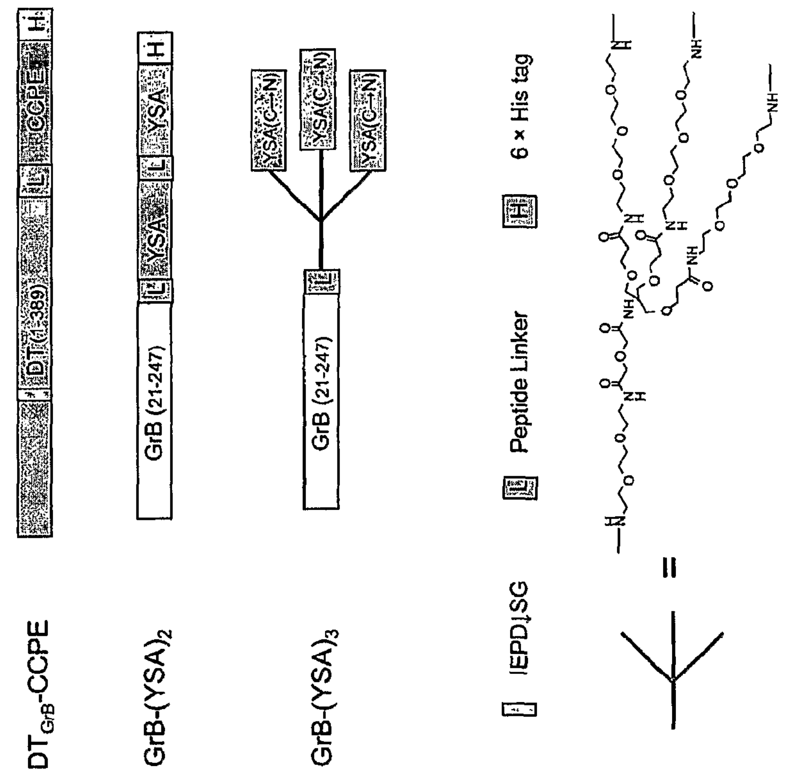
FIG. 24 is a schematic depiction of fusion and hybrid proteins generated to target claudin3/4 or EphA2 surface antigens overexpressed on breast cancer cells. The cell-targeting moiety of $DT_{GrB}$-CCPE fusion protein is C-CPE, the C-terminal domain of the *Clostridium peringens* enterotoxin, which binds with high affinity and specificity to the mammalian claudin3/4 adhesion molecules. The cell-targeting moiety of GrB-$(YSA)_2$ fusion protein is a repeat fusion of YSA peptide, which is a 12 residue peptide YSAYPDSVPMMS (SEQ ID NO:34) that can specifically recognize EphA2 receptors. Hybrid protein GrB-$(YSA)_3$ contains three YSA peptides linked to GrB through a branched chemical linker, to which one GrB molecule and three YSA peptides are linked through their C-terminus carboxyl group.

The purified pro-GrB-$(YSA)_2$ was incubated with Enterokinase to remove the leader sequence and flag-tag from N-terminal side of Granzyme B. Thus activated GrB-$(YSA)_2$ was then separated from the signal peptide using Ni-NTA resin (Qiagen), to be used to activate $DT_{GrB}$-CCPE fusion (FIG. 24).

This system again exemplifies an activation sequence that involves three elements, enterokinase, pro-GrB-$(YSA)_2$, and $DT_{GrB}$-CCPE, with the end result of DT activation at the cells targeted by C-CPE and YSA. It is anticipated a triple-component activation cascade may be established by using an enterokinase that is linked to a cell-targeting moiety that recognizes a third surface antigen. For example, in order to target certain breast cancer cells, EpCAM may be used as the third surface marker (targeted by an anti-EpCAM scFv) for enterokinase, in combination with claudin3/4 (targeted by C-CPE) and EphA2 (targeted by multimerized YSA or anti-EphA2 scFv).

Cytotoxicity of Protoxin $DT_{GrB}$-CCPE Activated by GrB

Protoxin $DT_{GrB}$-CCPE fusion protein was activated in vitro using mouse GrB (Sigma) prior to exposing it to cells. Equal numbers of HT-29 cells, which express Claudin-3/-4, were seeded in a 96 well plates and allowed to settle for 24 hours. Activated $DT_{GrB}$-CCPE was added directly to the wells in concentrations ranging from 0.03 nM up to 0.6 μM, each concentration in triplicate. Cycloheximide was used as a cell growth inhibition control, and PBS was added to wells as a buffer control. Cells were incubated in the presence of the activated $DT_{GrB}$-CCPE fusion for 48 hours, and cytotoxicity was then measured with CellTiter 96® AQueous One Solution Cell Proliferation Assay (MTS) (Promega) as outlined in product manual. Results were analyzed using GraphPad Prism 4.

K. Multistep Synthesis of Branched Chemical Linker JL10

The invention features the use of branched chemical linkers between the various domains of the protoxin and protoxin activator fusion proteins. An example of the synthesis of one such linker is described below.

Synthesis of 14-amino-5-oxo-3,9,12-trioxa-6-azatetradecan-1-oic acid (JL01)

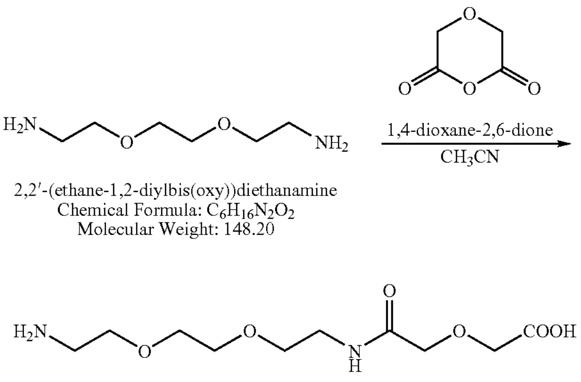

2,2'-(ethane-1,2-diylbis(oxy))diethanamine
Chemical Formula: $C_6H_{16}N_2O_2$
Molecular Weight: 148.20

14-amino-5-oxo-3,9,12-trioxa-6-azatetradecan-1-oic acid (JL01)
Chemical Formula: $C_{10}H_{20}N_2O_6$
Molecular Weight: 264.28

To a solution of 2,2'-(ethane-1,2-diylbis(oxy))diethanamine (1.4830 g, 10.0 mmol) in $CH_3CN$ (15 mL) was added dropwise a solution of 1,4-dioxane-2,6-dione (1.1560 g, 10.0 mmol) in $CH_3CN$ (5 mL) over 5 minutes and the mixture was stirred for 5 hours at room temperature. A colorless supernatant was discarded by decantation. 5 mL of $CH_3CN$ was added and the mixture was vortexed for 30 seconds. The supernatant was decanted. The remaining residue was dissolved in 1M HCl (20 mL) and chromatographed with Dowex 50W 8 ion-exchange resin (15 mL resin, $H^+$-form). The mono-acid product was eluted with water and followed by 0.15M of $NH_4OH$. The reaction afforded 37% yield of the mono-acid product as light yellow gum (JL01). $^1H$-NMR (400 MHz, DMSO-$d_6$) $\delta_H$ 9.69 (t, J=5.20 Hz, 1H), 8.27 (br, 3H), 3.87 (s, 2H), 3.73 (s, 2H), 3.66 (t, J=5.40 Hz, 2H), 3.58 (m, 2H), 3.53 (m, 2H), 3.48 (t, J=5.00 Hz, 2H), 3.27 (m, 2H), 2.91 (t, J=5.40 Hz, 2H); $^{13}C$-NMR (101 MHz, DMSO-$d_6$) $\delta_C$ 174.17, 170.48, 72.94, 72.27, 69.89, 69.81, 69.39, 66.98, 48.63, 38.54; MS (ESI) m/z 265 ($M^+$).

Synthesis of 14-(tert-butoxycarbonylamino)-5-oxo-3, 9,12-trioxa-6-azatetradecan-1-oic acid (JL02)

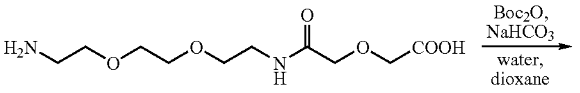

14-amino-5-oxo-3,9,12-trioxa-6-azatetradecan-1-oic acid (JL01)
Chemical Formula: $C_{10}H_{20}N_2O_6$
Molecular Weight: 264.28

-continued

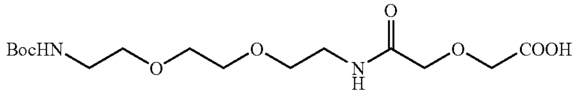

14-(tert-butoxycarbonylamino)-5-oxo-3,9,12-trioxa-6-azatetradecan-1-oic acid (JL02)
Chemical Formula: $C_{15}H_{28}N_2O_8$
Molecular Weight: 364.39

To a solution of 14-amino-5-oxo-3,9,12-trioxa-6-azatetradecan-1-oic acid (0.9650 g, 3.7 mmol) in water (10 mL) was added $NaHCO_3$ (0.3739 g, 4.4 mmol) and the mixture was stirred at room temperature for 10 minutes. A solution of $Boc_2O$ (0.9834 g, 4.5 mmol) in dioxane (5 mL) was added to the mixture and stirred at room temperature for overnight. The reaction crude was concentrated under reduced pressure. The residue was re-dissolved in water and washed with diethyl ether. The ether layer was discarded and the residue was acidified with 1M HCl and extracted with ethyl acetate. The organic layer was saved and dried over $Na_2SO_4$. After ethyl acetated was removed under reduced pressure, a pale yellow gum was obtained as product (JL02) in 1.3111 g. $^1$H-NMR (400 MHz, DMSO-$d_6$) $\delta_H$ 12.79 (brs, 1H), 7.81 (t, J=5.80 Hz, 1H), 6.80 (t, J=5.40 Hz, 1H), 4.10 (s, 2H), 3.96 (s, 2H), 3.49 (s, 4H), 3.43 (t, J=5.80 Hz, 2H), 3.36 (t, J=6.00 Hz, 2H), 3.26 (m, 2H), 3.05 (m, 2H), 1.37 (s, 9H); $^{13}$C-NMR (101 MHz, DMSO-$d_6$) $\delta_C$ 171.43, 168.83, 155.62, 77.63, 70.03, 69.51, 69.49, 69.21, 68.87, 67.48, 38.06, 28.26.

Synthesis of ethyl 21,21-bis((3-ethoxy-3-oxopropoxy)methyl)-2,2-dimethyl-4,15,19-trioxo-3,8,11,17, 23-pentaoxa-5,14,20-triazapentacosane-25-carboxylate (JL04)

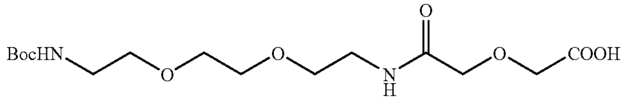

14-(tert-butoxycarbonylamino)-5-oxo-3,9,12-trioxa-6-azatetradecan-1-oic acid (JL02)
Chemical Formula: $C_{15}H_{28}N_2O_8$
Molecular Weight: 364.39

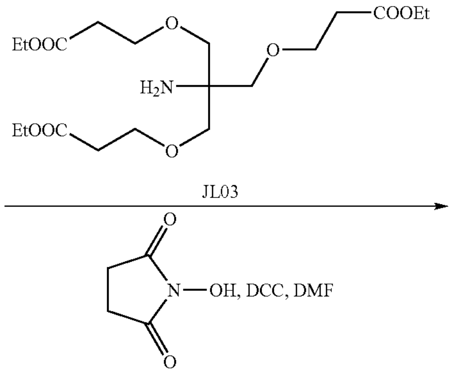

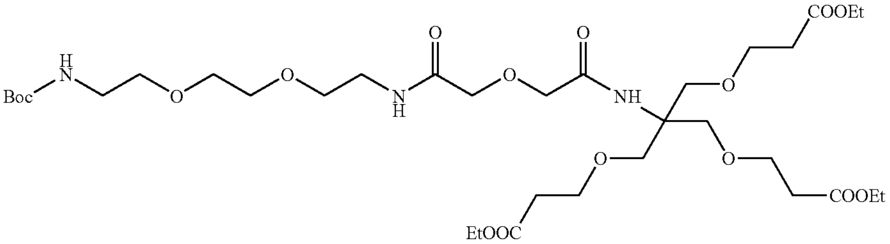

ethyl 21,21-bis((3-ethoxy-3-oxopropoxy)methyl)-2,2-dimethyl-4,15,19-trioxo-3,8,11,17,23-pentaoxa-5,14,20-triazapentacosane-25-carboxylate (JL04)
Chemical Formula: $C_{34}H_{61}N_3O_{16}$
Molecular Weight: 767.86

Compound JL02 (1.2540 g, 3.44 mmol) and N-hydroxysuccinimide (0.5140 g, 4.47 mmol) were dissolved in $CH_2Cl_2$ (10 mL) and DMF (5 mL). The mixture was stirred at room temperature and a solution of DCC (0.8020 g, 3.88 mmol) in $CH_2Cl_2$ (10 mL) was added. The mixture was stirred for overnight and the white precipitates were removed by filtration. The filtrate was concentrated under reduced pressure to afford NHS ester. The NHS ester was re-dissolved in DMF and stirred in ice bath. After addition of a solution of amino triethyl ester[JL05] (JL03, 1.5520 g, 3.68 mmol) in DMF (5 mL), the ice bath was removed and the mixture was stirred at room temperature for 63 hours. The reaction crude was filtered, washed with ethyl acetate and concentrated under reduced pressure. The residue was purified on silica gel column and afforded pale yellow gum product (JL04) in 94% yield. $^1$H-NMR (400 MHz, DMSO-$d_6$) $\delta_H$ 10.57 (brs, 1H), 8.01 (t, J=5.60 Hz, 1H), 6.77 (t, J=5.40 Hz, 1H), 4.05 (q, J=7.20 Hz, 6H), 3.92 (s, 2H), 3.87 (s, 2H), 3.59 (t, J=6.00 Hz, 6H), 3.56 (s, 6H), 3.49 (s, 4H), 3.43 (t, J=6.00 Hz, 2H), 3.36 (t, J=6.20 Hz, 2H), 3.26 (m, 2H), 3.05 (m, 2H), 2.49 (t, J=6.40

Hz, 6H), 1.37 (s, 9H), 1.18 (t, J=7.20 Hz, 9H); $^{13}$C-NMR (101 MHz, DMSO-$d_6$) $\delta_C$ 172.84, 171.06, 168.75, 168.69, 155.61, 77.61, 70.29, 70.20, 69.51, 69.48, 69.20, 68.89, 68.14, 66.54, 59.89, 59.80, 59.39, 38.12, 34.52, 28.24, 25.25, 14.10.

Synthesis of 21,21-bis((2-carboxyethoxy)methyl)-2, 2-dimethyl-4,15,19-trioxo-3,8,11,17,23-pentaoxa-5, 14,20-triazapentacosane-25-carboxylic acid (JL06)

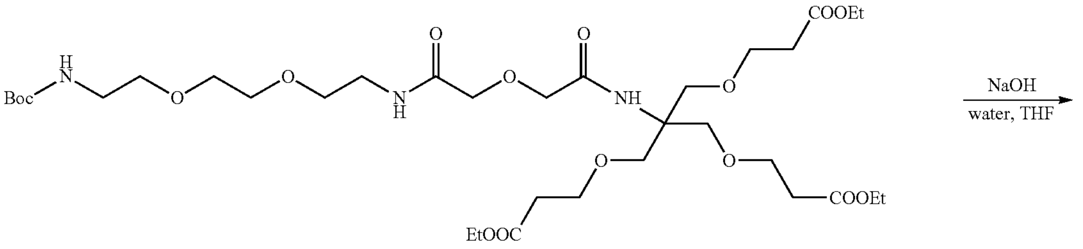

ethyl 21,21-bis((3-ethoxy-3-oxopropoxy)methyl)-2,2-dimethyl-4,15,19-trioxo-3,8,11,17,23-pentaoxa-5,14,20-triazapentacosane-25-carboxylate (JL04)
Chemical Formula: $C_{34}H_{61}N_3O_{16}$
Molecular Weight: 767.86

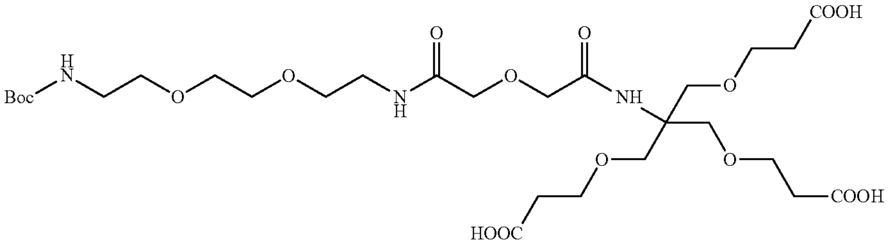

21,21-bis((2-carboxyethoxy)methyl)-2,2-dimethyl-4,15,19-trioxo-3,8,11,17,23-pentaoxa-5,14,20-triazapentacosane-25-carboxylate (JL06)
Chemical Formula: $C_{28}H_{49}N_3O_{16}$
Molecular Weight: 683.70

To a solution of compound JL04 (2.2230 g, 2.90 mmol) in THF (30 mL) was added 1M NaOH aqueous solution (15 mL). The mixture was stirred at room temperature for overnight and THF was removed under reduced pressure. The aqueous solution was acidified with 6M HCl to pH 2 and extracted with $CH_2Cl_2$. The organic layer was saved and dried over $Na_2SO_4$. Pale yellow gum was obtained as product (JL06) in 76% yield. $^1$H-NMR (400 MHz, DMSO-$d_6$) $^{8}{}_{H}$ 12.14 (s, 1H), 8.00 (t, J=5.74 Hz, 1H), 7.05 (s, 1H), 6.75 (t, J=5.52 Hz, 1H), 3.91 (s, 2H), 3.86 (s, 2H), 3.56 (m, 12H), 3.47 (s, 4H), 3.41 (t, J=6.04 Hz, 2H), 3.35 (t, J=6.11 Hz, 2H), 3.25 (q, J=5.87 Hz, 2H), 3.04 (q, J=5.97 Hz, 2H), 2.40 (m, 6H), 1.89 (s, 2H), 1.35 (s, 9H); MS (ESI) m/z 772 ([M+4Na−3H]$^+$), 726 ([M+2Na−3H]$^-$).

Synthesis of 1-azido-2-(2-(2-(2-azidoethoxy)ethoxy) ethoxy)ethane (JL07)

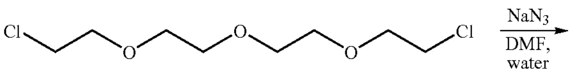

1-chloro-2-(2-(2-(2-chloroethoxy)ethoxy)ethoxy)ethane
Chemical Formula: $C_8H_{16}Cl_2O_3$
Molecular Weight: 231.12

-continued

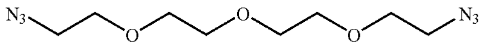

1-azido-2-(2-(2-(2-azidoethoxy)ethoxy)ethoxy)ethane(JL07)
Chemical Formula: $C_8H_{16}N_6O_3$
Molecular Weight: 244.25

To a solution of 1-chloro-2-(2-(2-(2-chloroethoxy)ethoxy) ethoxy)ethane (13.2310 g, 57.2 mmol) in DMF (100 mL) and water (20 mL) was added $NaN_3$ (11.353 g, 175 mmol) and the mixture was stirred at 80° C. for 40 hours. The filtrate was saved after filtration and concentrated under reduced pressure. The white slurry was diluted with ethyl acetate and hexanes (v/v 1:1, 200 mL) and the precipitates were removed by filtration. The filtrate was saved and washed with water (30 mL), brine (30 mL) and dried over $Na_2SO_4$. Pale yellow liquid was obtained as product (JL07) in 99% yield. $^1$H-NMR (400 MHz, $CDCl_3$) $\delta_H$ 3.68 (m, 12H), 3.39 (t, J=5.05 Hz, 4H).

Synthesis of 2-(2-(2-(2-azidoethoxy)ethoxy)ethoxy) ethanamine (JL08)

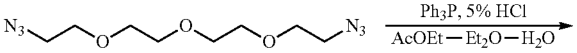

1-azido-2-(2-(2-(2-azidoethoxy)ethoxy)-ethoxy)ethane
(JL07)
Chemical Formula: $C_8H_{16}N_6O_3$
Molecular Weight: 244.25

-continued

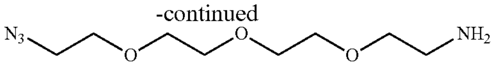

2-(2-(2-(2-azidoethoxy)ethoxy)ethoxy)ethanamine
(JL08)
Chemical Formula: $C_8H_{18}N_4O_3$
Molecular Weight: 218.25

To a solution of compound JL07 (14.4 g, ~57.2 mmol) in ethyl acetate (45 mL) and diethyl ether (45 mL) was added 5% HCl (60 mL), followed by addition of $Ph_3P$ (14.04 g, 53.5 mmol) and the mixture was stirred in ice-bath for over 1 hour. Then the ice-bath was removed and the reaction mixture was stirred at room temperature for 14 hours. The reaction crude was transferred to separatory funnel and the organic phase was removed. The aqueous phase was washed with ethyl acetate and cooled in ice-bath. 1M NaOH was added to adjust pH to 13. The product was extracted into $CH_2Cl_2$ and dried over $Na_2SO_4$. Pale yellow liquid was obtained as product (JL08) in 82% yield. $^1$H-NMR (400 MHz, $CDCl_3$) $\delta_H$ 3.67 (m, 8H), 3.63 (m, 2H), 3.51 (t, J=5.23 Hz, 2H), 3.39 (t, J=5.07 Hz, 2H), 2.87 (t, J=5.21 Hz, 2H), 1.62 (s, 2H).

Synthesis of tert-butyl 33-azido-16,16-bis(17-azido-5-oxo-2,9,12,15-tetraoxa-6-azaheptadecyl)-10,14,21-trioxo-3,6,12,18,25,28,31-heptaoxa-9,15,22-triazatritriacontylcarbamate (JL09)

To a solution of compound JL06 (0.1367 g, 0.2 mmol) in $CH_2Cl_2$ (4 mL) was added a solution of compound JL08 (0.2619 g, 1.2 mmol) in $CH_2Cl_2$ (4 mL), followed by addition of DIEA (209 μL, 1.2 mmol), and the mixture was stirred at room temperature. A solution of DEPC (182 μL, 1.2 mmol) in $CH_2Cl_2$ (4 mL) was added dropwise into above mixture over 1 minute and still stirred at room temperature for overnight. After removal of solvent under reduced pressure, the residue was purified on silica gel column to afford 0.2047 g (80% yield) product JL09 as pale yellow liquid. $^1$H-NMR (400 MHz, $CDCl_3$) $\delta_H$ 7.54 (br, 1H), 7.04 (br, 1H), 6.80 (br, 1H), 5.26 (br, 1H), 4.06 (s, 2H), 3.98 (s, 2H), 3.67 (m, 48H), 3.55 (m, 12H), 3.45 (t, J=5.30 Hz, 6H), 3.41 (t, J=4.97 Hz, 6H), 3.32 (br, 2H), 2.42 (t, J=5.81 Hz, 6H), 1.44 (s, 9H).

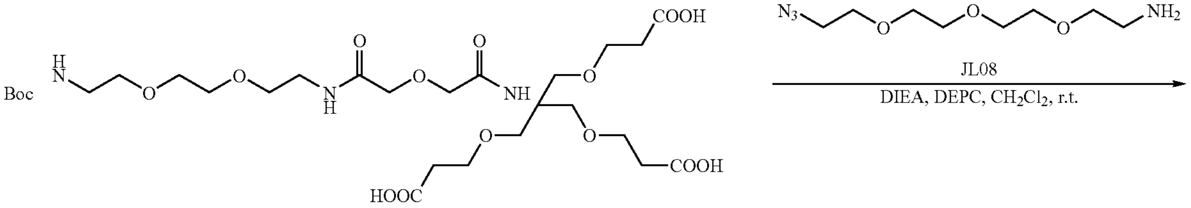

(JL06)
Chemical Formula: $C_{28}H_{49}N_3O_{16}$
Molecular Weight: 683.70

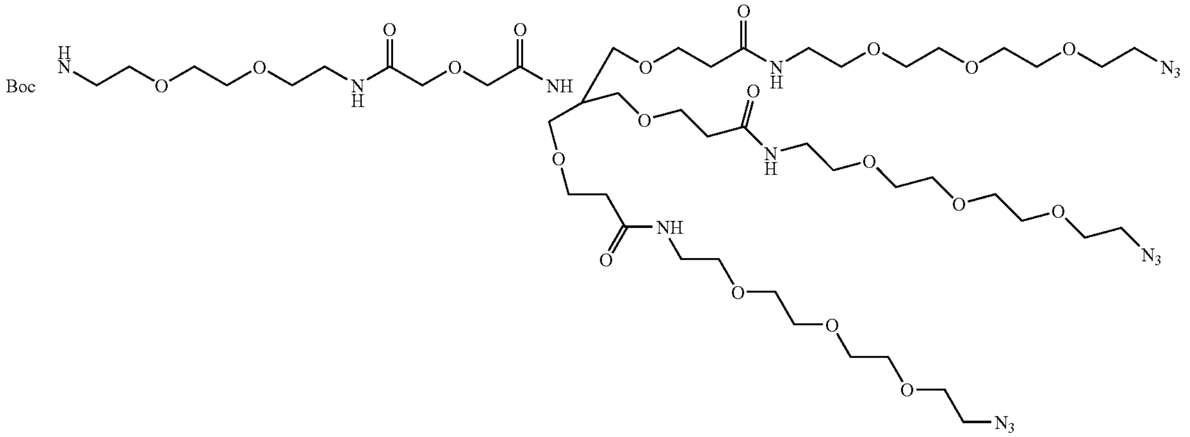

tert-butyl 33-azido-16,16-bis(17-azido-5-oxo-2,9,12,15-tetraoxa-6-azaheptadecyl)-10,14,21-trioxo-3,6,12,18,25,28,31-heptaoxa-9,15,22-triazatritriacontylcarbamate (JL09)
Chemical Formula: $C_{52}H_{97}N_{15}O_{22}$
Molecular Weight: 1284.41

Synthesis of tert-butyl 33-amino-16,16-bis(17-amino-5-oxo-2,9,12,15-tetraoxa-6-azaheptadecyl)-10,14,21-trioxo-3,6,12,18,25,28,31-heptaoxa-9,15,22-triazatritriacontylcarbamate (JL10)

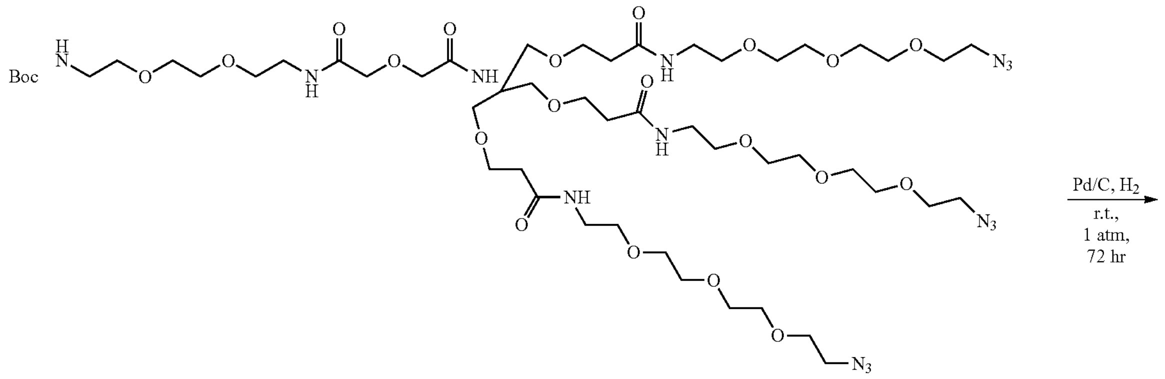

tert-butyl 33-azido-16,16-bis(17-azido-5-oxo-2,9,12,15-tetraoxa-6-azaheptadecyl)-10,14,21-trioxo-3,6,12,18,25,28,31-heptaoxa-9,15,22-triazatritriacontylcarbamate (JL09)
Chemical Formula: $C_{52}H_{97}N_{15}O_{22}$
Molecular Weight: 1284.41

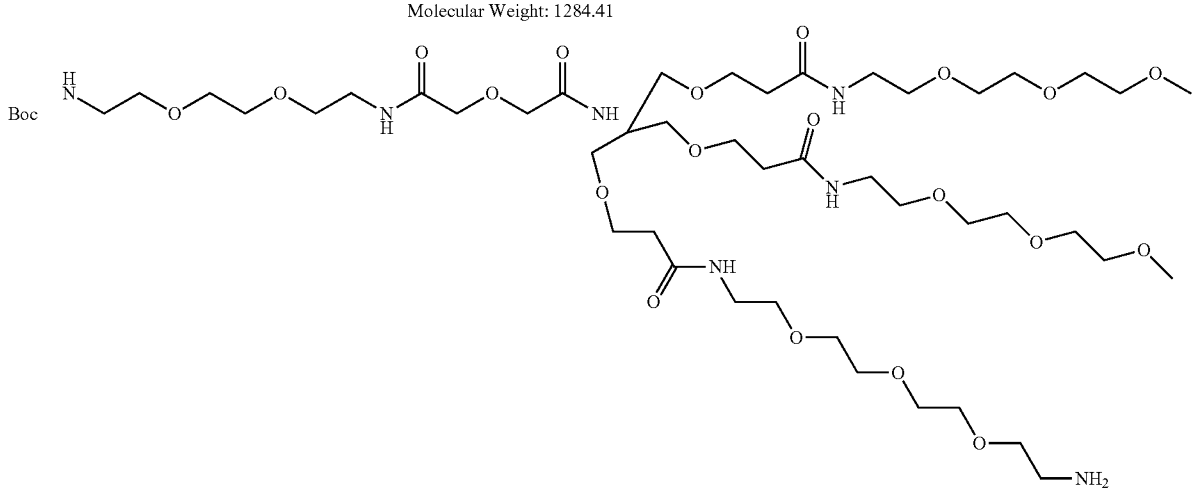

tert-butyl 33-azido-16,16-bis(17-azido-5-ox 2,9,12,15-tetraoxa-6-azaheptadecyl)-10,14,2 trioxo-3,6,12,18,25,28,31-heptaoxa-9,15,22 triazatritriacontylcarbamate (JL10)
Chemical Formula: $C_{52}H_{103}N_9O_{22}$
Molecular Weight: 1206.42

A solution of compound JL09 (0.2047 g, 0.16 mmol) in MeOH (0.64 mL) was added to a 2-neck 50 mL flask. 2 vacuum/Ar cycles were proceeded to replace the air in the flask with Ar. After quick addition of Pd/C to the flask, 2 vacuum/$H_2$ cycles were proceeded to replace Ar with $H_2$. The reaction mixture was vigorously stirred at room temperature under 1 atm $H_2$ pressure (balloon) for 72 hr. Pd/C was filtered off and pale yellow gum was obtained under reduced pressure as product (JL10, 0.1915 g) in 99% yield.

Preparation of JL10-$(YSA)_2$ and Removal of Protection Groups

To a solution of compound JL10 (0.1206 g, 0.1 mmol) in $CH_2Cl_2$ was added a solution of 0.6 mmol of N-terminus- and side-chain-protected YSA peptide in $CH_2Cl_2$, followed by addition of DIEA (105 μL, 0.6 mmol), and the mixture was stirred at room temperature. A solution of DEPC (91 μL, 0.6 mmol) in $CH_2Cl_2$ was added dropwise into above mixture over 1 minute and stirred at room temperature for overnight. After removal of solvent under reduced pressure, the residue was purified by chromatography. The protection groups were removed by sequential treatments of DEA (to remove base labile protecting groups) and TFA (to remove acid-labile protecting groups) and the resulting conjugate is ready for enzymatic ligation reaction.

Preparation of GrB-$(YSA)_3$

Granzyme B fusion proteins with a C-terminal tag LPETG or a LLQG tag are constructed and prepared using methods described above. Each GrB fusion was mixed with fully deprotected JL10-$(YSA)_3$ mixed at 1:2 ratio respectively and incubated with Sortase A-agarose in the presence of 0.1 M Tris pH 9, 5 mM $CaCl_2$, 0.01% Tween-20, and incubated overnight at room temperature. Each conjugation mixture was concentrated using a low MW cutoff spin concentrator, followed by extensive washing with buffer to remove excess JL10-$(YSA)_3$. The conjugate may be further purified using column choromatography. The resulting fusion protein possesses three YSA peptides with exposed N-terminus, as well as the GrB moiety in its active form with the exposed N-terminus (FIG. 24).

Because it is often challenging to discover short peptides that can bind to their cell surface targets with as high an affinity as antibodies, scFvs, or other scaffold-based binders, it may be necessary to multimerize these peptides. Whereas direct, repeated fusion of these peptides with flexible spacers is a convenient strategy for potentially synergistic binding, it does not allow the accessibility to the N-terminus or C-terminus of each peptide motif that is internally located. Since during phage display selection, multiple copies of peptides or proteins are displayed in a configuration that exposes their N-terminus (Kehoe and Kay, Chem. Rev. 2105(11):4056-72 (2005)), the selected peptides or proteins may be the most effective if similar structure is maintained in the targeting agents utilizing them. The use of branched chemical linkers such as described here provides an opportunity to display multiple peptides in any orientation with Respect to the fusion partner, which is critical for the GrB activity and may also be important for YSA-EphA2 interaction.

Construction and Expression of $DT_{GrB}$-Anti-CD2219 and GrB-Anti-CD1919

It has been reported previously that a bispecific scFv fusion protein, DT2219, was assembled consisting of the catalytic and translocation domains of diphtheria toxin fused to two repeating sFv subunits recognizing CD19 and CD22. DT2219 was shown to have greater anticancer activity than monomeric or bivalent immunotoxins made with anti-CD19 and anti-CD22 scFv alone and it showed a higher level of binding to patient leukemia cells and to $CD19^+CD22^+$ Daudi or Raji cells than did anti-CD19 and anti-CD22 parental monoclonal antibodies (Vallera et al., Clin. Cancer Res. 11(10):3879-88 (2005)). We similarly designed a protoxin $DT_{GrB}$-anti-CD2219 and GrB-anti-CD1919 to enhance the binding to targeted B-CLL cells, which are $CD19^+/CD22^+$. Whereas GrB-anti-CD1919 is expected to increase B cell affinity by simple synergistic binding of two binding motifs, $DT_{GrB}$-anti-CD2219 is designed to also take advantage of both CD19 and CD22 populations on the $CD19^+/CD22^+$ B cells.

Figure 25:
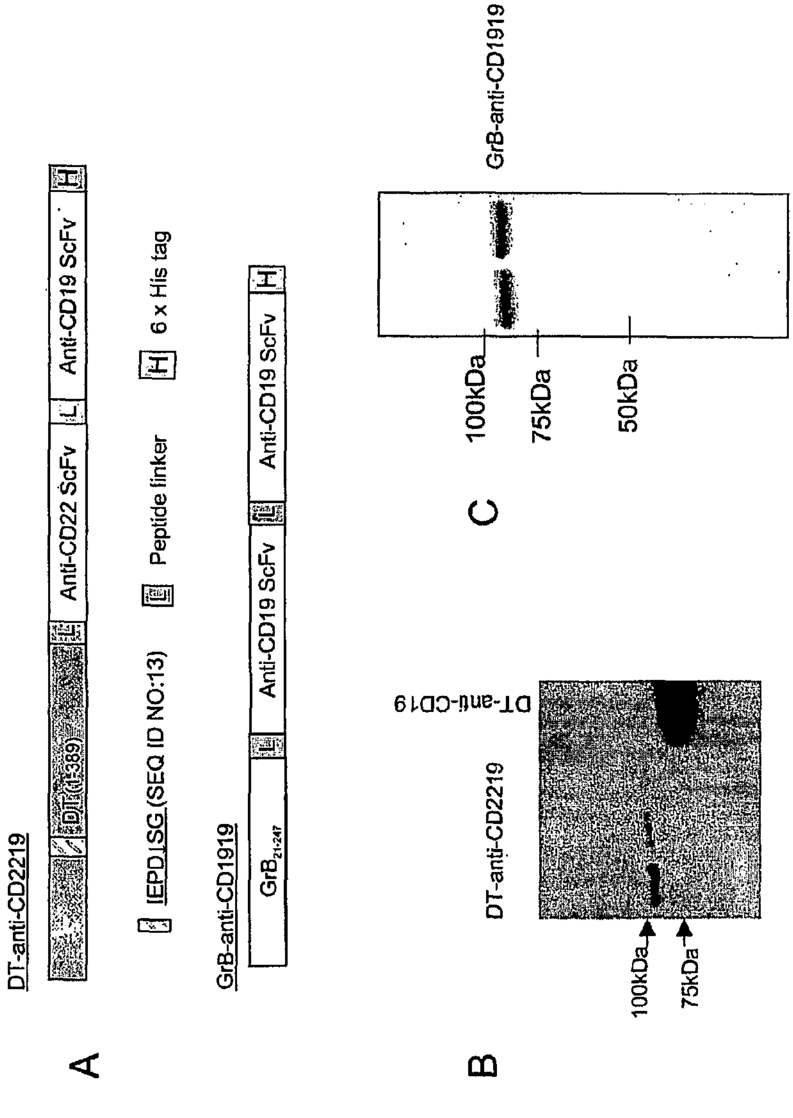
FIG. 25A is a schematic showing the design of fusion proteins DT-anti-CD22-anti-CD19 and GrB-anti-CD19-anti-CD19.
FIG. 25B and FIG. 25C are photographs of SDS PAGE gels showing fusion proteins DT-anti-CD22 anti-CD19 and GrB-anti-CD19-anti-CD19, each containing two fused ScFv binding motifs.

FIG. 25 shows the schematic depictions of $DT_{GrB}$-αCD2219 and GrB-αCD1919 fusion proteins. DT-anti-CD2219 was secreted expressed from *Pichia* KM71. The endogenous furin cleavage site of the DT gene is replaced by a granzyme B cleavage site (IEPD↓SG). The toxin moiety and anti-CD5 ScFv are linked via a $(G_4S)_3$ linker (L). The two ScFv moieties were linked through HMA tag (Vallera et al., Clin. Cancer Res. 11(10):3879-88 (2005)). The secretion expression of GrB-anti-CD1919 was from 293 ETN. The configuration of GrB-anti-CD1919 is same as GrB-anti-CD19, except that an extra anti-CD19 ScFv moiety was fused to GrB-anti-CD19 via $G_4$ linker. In out cytotoxicity experiments, GrB-anti-CD1919 when combined with $DT_{GrB}$-anti-CD5 showed slightly higher selective toxicity to $CD19^+$Jurkat cells than GrB-anti-CD19.

Preparation of NGFD-$VCE_{TEV}$ and Anti-CD5-TEV

Figure 26:
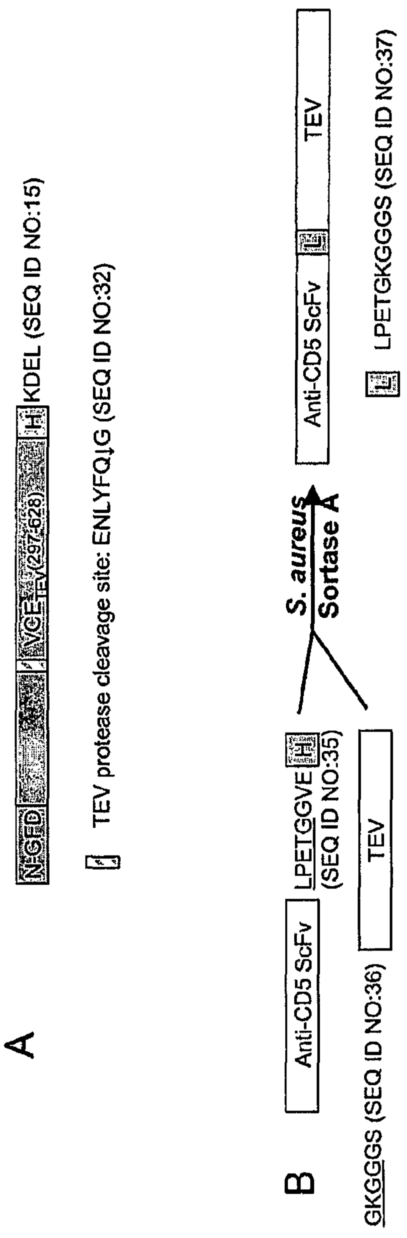
FIG. 26A is a schematic depiction of fusion protein NGFD-$VCE_{TEV}$, which comprises a VCE based protoxin containing a TEV cleavage site in place of the native furin cleavage site and a cell-targeting moiety N-GFD for u-PAR binding.
FIG. 26B is a schematic depiction of the preparation of anti-CD5-TEV hybrid protein using *S. aureus* Sortase A catalyzed ligation of a LEPTG tagged anti-CD5 ScFv moiety and a GKGG tagged TEV protease.

To provide another example of protease activator, NGFD-$VCE_{TEV}$ was constructed from NGFD-VCE by replacing the endogenous furin cleavage site by TEV cleavage site (ENLYFQ↓G), and then expressed using similar procedures. The preparation of anti-CD5 scFv targeted TEV was accomplished using *S. aureus* Sortase A catalyzed ligation, because each moiety was optimally expressed under different conditions, i.e., periplasmic and cytoplamic expressions in *E. coli*, respectively. As illustrated in FIG. 26, LPETG-tagged anti-CD5 scFv was conjugated to GKGG-tagged TEV using standard Sortase A ligation procedures.

Proteolytic Activation of NGFD-$VCE_{TEV}$ and Cytotoxicity Assay

Figure 27:
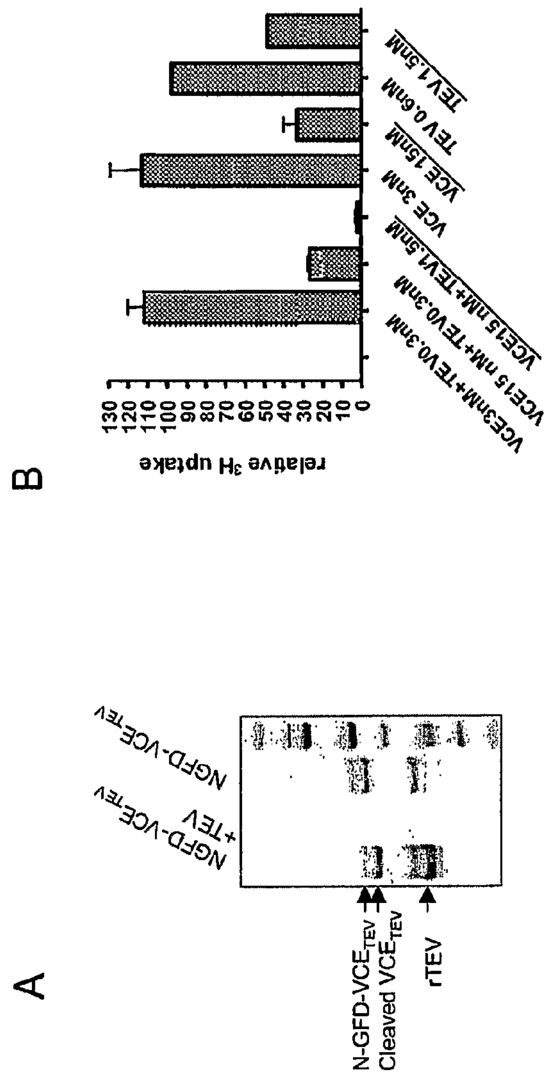
FIG. 27A is an SDS-PAGE analysis of NGFD-$VCE_{TEV}$ fusion protein and its cleavage in a reaction mixture Containing TEV protease. As expected, protoxin NGFD-$VCE_{TEV}$ is specifically cleaved by TEV protease.
FIG. 27B is a graph showing cytotoxicity assay results using $CD19^+$Jurkat cells ($CD5^+$/$uPAR^+$) treated with various concentrations of NGFD-$VCE_{TEV}$ fusion (VCE), anti-CD5-TEV hybrid (TEV), or their mixture. The data illustrates that the combination of 15 nM of NGFD-$VCE_{TEV}$ and 1.5 nM of anti-CD5-TEV is significantly more toxic to the $CD19^+$Jurkat cells than either NGFD-$VCE_{TEV}$ or anti-CD5-TEV alone at the same concentrations.

As shown in FIG. 27A, the NGFD-$VCE_{TEV}$ fusion protein, although not completely purified, was a substrate of recombinant TEV (Invitrogen) and was cleaved to generate a fragment of expected size. FIG. 27B shows the cytotoxicity assay results using $CD19^+$Jurkat cells. When used in combination, 15 nM of NGFD-$VCE_{TEV}$ and 1.5 nM of anti-CD5-TEV inhibited protein synthesis much more effectively than each reagent was used alone at the same concentrations. The observed synergistic effect of the two reagents demonstrates that NGFD-$VCE_{TEV}$ is selectively activatable by anti-CD5-TEV on the same cell.

Cleavage of VCE

Polynucleotide and amino acid sequences for the constructs and proteins described above are set forth in Table 3.

| SEQ ID NO: | NAME | NOTES | SEQUENCE |
|---|---|---|---|
| 74 | VCE Wild type sequence | | gi\|58615288\|gb\|AAW80252.1\| hypothetical exotoxin A [*Vibrio cholerae*]<br>MYLTFYLEKVMKKMLLIAGATVISSMAHPTFAVEDELNIFDECRSPCSLTPEPGKPIQSKLSIPSDV<br>VLDEGVLYYSMTINDEQNDIKDEDKGESIITIGEFATVRATRHYVNQDAPFGVIHLKITTENGTKTY<br>SYNRKEGEFAINWLVPIGEDSPASIKISVDELDQQRNIIEVPKLYSIDLDNQTLEQWKTQGNVSFSV<br>TRPEHNIAISWPSVSYKAAQKEGSRHKRWAHWHTGLALCWLVPMDAIYNYITQQNCTLGDNWFGGSY<br>ETVAGTPKVITVKQGIEQKPVEQRIHFSKGNAMSALAAHRVCGVPLETLARSRKPRDLTDDLSCAYQ<br>AQNIVSLFVATRILFSHLDSVFTLNLDEQEPEVAERLSDLRRINENNPGMVTQVLTVARQIYNDYVT<br>HHPGLTPEQTSAGAQAADILSLFCPDADKSCVASNNDQANINIESRSGRSYLPENRAVITPQGVTNW<br>TYQELEATHQALTREGYVFVGYHGTNHVAAQTIVNRIAPVPRGNNTENEEKWGGLYVATHAEVAHGY<br>ARIKEGTGEYGLPTRAERDARGVMLRVYIPRASLERFYRTNTPLENAEEHITQVIGHSLPLRNEAFT<br>GPESAGGEDETVIGWDMAIHAVAIPSTIPGNAYEELAIDEEAVAKEQSISTKPPYKERKDELK |
| 75 | Synthetic gene encoding VCE | | ATGGAAGATGAGCTGAATATTTTTGACGAGTGCCGTAGCCCGTGTTCTCTGACCCCAGAACCTGGCA<br>AACCGATCCAGAGTAAACTGTCAATTCCATCCGATGTGGTTCTGGACGAAGGTGTCCTGTATTACTC<br>GATGACGATCAACGATGAACAAAATGACATTAAAGATGAGGATAAAGGGGAAAGCATCATTACTATC<br>GGAGAGTTCGCGACAGTACGCGCCACCCGTCATTATGTGAACCAGGACGCACCTTTTGGCGTTATTC<br>ACCTGGATATCACGACTGAAAATGGTACAAAAACCTACTCTTATAACCGCAAAGAAGGGGAGTTCGC<br>TATTAATTGGCTGGTCCCGATCGGAGAGGACAGTCCGGCGTCAATTAAAATCTCCGTAGATGAGCTG<br>GACCAACAGCGTAACATTATCGAAGTGCCAAAACTGTACTCGATTGATCTGGATAATCAGACGCTGG<br>AACAATGGAAAACCCAGGGCAACGTTAGCTTTTCTGTCACTCGCCCTGAGCATAATATTGCCATCAG<br>TTGGCCGTCAGTGTCCTATAAAGCAGCTCAAAAAGAAGGTTCGCGTCACAAACGCTGGGCGCATTGG<br>CACACAGGCCTGGCCCTGTGCTGGCTGGTACCGATGGACGCAATTTACAACTATATCACGCAGCAGA<br>ATTGTACCCTGGGTGATAACTGGTTCGGGGGAAGCTATGAGACTGTTGCTGGCACACCAAAAGTGAT |

-continued

| SEQ ID NO: | NAME | NOTES | SEQUENCE |
|---|---|---|---|
| | | | TACCGTCAAACAAGGTATCGAACAGAAACCTGTTGAACAACGTATTCATTTTGCTAGCAAAGGCAAT GCCATGAGTGCACTGGCTGCGCACCGCGTATGCGGTGTGCCGCTGGAGACACTGGCCCGTTCACGCA AACCACGTGACCTGACCGATGACCTGAGCTGCGCGTATCAGGCCCAAAATATTGTGTCTCTGTTTGT TGCAACGCGTATCCTGTTCAGTCATCTGGATTCAGTCTTTACTCTGAACCTGGACGAACAGGAGCCG GAAGTAGCTGAGCGCCTGTCCGATCTGCGTCGCATTAATGAAAACAATCCAGGCATGGTGACACAAG TTCTGACCGTCGCGCGTCAGATCTACAACGACTATGTAACGCACCATCCTGGTCTGACTCCGGAACA GACATCGGCCGGGGCACAAGCTGCGGATATTCTGAGCCTGTTCTGTCCAGATGCCGACAAATCTTGC GTGGCAAGTAATAACGATCAGGCTAATATCAACATTGAGTCACGCTCCGGACGTTCGTACCTGCCTG AAAATCGCGCGGTTATCACCCCGCAAGGCGTCACGAACTGGACCTATCAGGAGCTGGAAGCCACTCA CCAGGCACTGACACGTGAAGGTTACGTGTTTGTAGGGTATCATGGAACGAATCACGTTGCTGCGCAA ACCATTGTGAACCGCATCGCCCCGGTCCCACGTGGCAATAACACTGAGAATGAAGAGAAATGGGGTG GCCTGTACGTTGCAACACATGCGGAAGTAGCTCACGGTTATGCCCGCATTAAAGAAGGGACCGGAGA GTATGGCCTGCCTACGCGTGCAGAACGCGACGCGCGTGGTGTGATGCTGCGCGTCTACATCCCGCGT GCTTCGCTGGAGCGCTTCTATCGTACCAACACTCCGCTGGAAAATGCCGAAGAGCATATTACACAGG TTATCGGCCACTCTCTGCCACTGCGCAACGAAGCATTTACGGGTCCTGAAAGTGCGGGGGGAGAGGA TGAAACCGTGATTGGCTGGGACATGGCTATCCATGCCGTAGCAATTCCGTCAACTATTCCAGGTAAT GCGTACGAGGAACTGGCCATCGATGAAGAGGCAGTCGCGAAAGAACAATCCATTTCGACAACCGCCT TATAAAGAGCGTCACCATCATCACCATCACAAAGATGAACTGTAA |
| 76 | Protein sequence corresponding to synthetic VCE gene | | medelnifdecrspcsltpepgkpiqskisipsdvvldegvlyysmtindeqndikdedkgesiiti gefatvratrhyflqdapfgvihlditteng tktysynrkegefainwlvpigedspasikisvdel dqqrniievpkiysidldnqtleqwktqgnvsfsvtrpehniaiswpsvsykaaqkegsrhkrwahw htglalcwlvpmdaiynyitqqnctlgdnwfggsyetvagtpkvitvkqgieqkpveqrihfskgna msalaahrvcgvpletlarsrkprdltddlscayqaqnivslfvatrilfshldsvftlnldeqepe vaerlsdlrrinennpgmvtqvltvarqiyndyvthhpgltpeqtsagaqaadilslfcpdadkscv asnndqaniniesrsgrsylpenravitpqgvtnwtyqeleathqaltregyvfvgyhgtnhvaaqt ivnriapvprgnnteneekwgglyvathaevahgyarkegtgeyglptraerdargvmirvyipras lerfyrtntplenaeehitqvighslplrneaftqpesaggedetvigwdmaihavaipstipgnay eelaideeavakegsistkppykerhhhhhhkde 1 |
| 77 | synthetic gene encoding ADPRT domain of VCE | | ATGGGCCCTGAAAATCGCGCGGTTATCACCCCGCAAGGCGTCACGAACTGGACCT ATCAGGAGCTGGAAGCCACTCACCAGGCACTGACACGTGAAGGTTACGTGTTTGTAGGGT ATCATGGAACGAATCACGTTGCTGCGCAAACCATTGTGAACCGCATCGCCCCGGTCCCAC GTGGCAATAACACTGAGAATGAAGAGAAATGGGGTGGCCTGTACGTTGCAACACATGCGG AAGTAGCTCACGGTTATGCCCGCATTAAAGAAGGGACCGGAGAGTATGGCCTGCCTACGC GTGCAGAACGCGACGCGCGTGGTGTGATGCTGCGCGTCTACATCCCGCGTGCTTCGCTGG AGCGCTTCTATCGTACCAACACTCCGCTGGAAAATGCCGAAGAGCATATTACACAGGTTA TCGGCCACTCTCTGCCACTGCGCAACGAAGCATTTACGGGTCCTGAAAGTGCGGGGGGAG AGGATGAAACCGTGATTGGCTGGGACATGGCTATCCATGCCGTAGCAATTCCGTCAACTA TTCCAGGTAATGCGTACGAGGAACTGGCCATCGATGAAGAGGCAGTCGCGAAAGAACAAT CCATTTCGACAAAACCGCCTTATAAAGAGCGTCACCATCATCACCATCACAAAGATGAAC TGTAA |
| 78 | Protein sequence corresponding to ADPRT domain of VCE | | mgpenravitpqgvtnwtyqeleathqaltregyvfvgyhgtnhvaaqtivnriapvprgnntenee lcwgglyvathaevahgyarikegtgeyglptraerdargvmlrvyipraslerfyrtntplenaee hitqvighslplrneaftgpesaggedetvigwdmaihavaipstipgnayeeiaideeavakeqsi stkppykerhhhhhhkdel |
| 79 | N-GFD-VCE Synthetic gene encoding N-GFD-VCE with endogenous furin cleavage site | | ATGGGCTCCAACGAACTGCATCAGGTGCCGAGCAACTGCGATTGTCTGAACGGCGGTACCTGCGTTT CCAACAAATATTTTTCTAACATTCACTGGTGTAACTGCCCGAAAAAATTCGGTGGACAACATTGTGA AATCGACGGCGGTGGTGGTTCGGGCGGTGGCGGTTCGGGTGGCGGTGGCAGCTCTAGCAAAGGCAAT GCCATGAGTGCACTGGCTGCGCACCGCGTATGCGGTGTGCCGCTGGAGACACTGGCCCGTTCACGCA AACCACGTGACCTGACCGATGACCTGAGCTGCGCGTATCAGGCCCAAAATATTGTGTCTCTGTTTGT TGCAACGCGTATCCTGTTCAGTCATCTGGATTCAGTCTTTACTCTGAACCTGGACGAACAGGAGCCG GAAGTAGCTGAGCGCCTGTCCGATCTGCGTCGCATTAATGAAAACAATCCAGGCATGGTGACACAAG TTCTGACCGTCGCGCGTCAGATCTACAACGACTATGTAACGCACCATCCTGGTCTGACTCCGGAACA GACATCGGCCGGGGCACAAGCTGCGGATATTCTGAGCCTGTTCTGTCCAGATGCCGACAAATCTTGC GTGGCAAGTAATAACGATCAGGCTAATATCAACATTGAGTCACGCTCCGGACGTTCGTACCTGCCTG AAAATCGCGCGGTTATCACCCCGCAAGGCGTCACGAACTGGACCTATCAGGAGCTGGAAGCCACTCA CCAGGCACTGACACGTGAAGGTTACGTGTTTGTAGGGTATCATGGAACGAATCACGTTGCTGCGCAA ACCATTGTGAACCGCATCCCCCCGGTCCCACGTGGCAATAACACTGAGAATGAAGAGAAATGGGGTG GCCTGTACGTTGCAACACATGCGGAAGTAGCTCACGGTTATGCCCGCATTAAAGAAGGGACCGGAGA GTATGGCCTGCCTACGCGTGCAGAACGCGACGCGCGTGGTGTGATGCTGCGCGTCTACATCCCGCGT GCTTCGCTGGAGCGCTTCTATCGTACCAACACTCCGCTGGAAAATGCCGAAGAGCATATTACACAGG TTATCGGCCACTCTCTGCCACTGCGCAACGAAGCATTTACGGGTCCTGAAAGTGCGGGGGGAGAGGA TGAAACCGTGATTGGCTGGGACATGGCTATCCATGCCGTAGCAATTCCGTCAACTATTCCAGGTAAT GCGTACGAGGAACTGGCCATCGATGAAGAGGCAGTCGCGAAAGAACAATCCATTTCGACAAACCGCC TTATAAGAGCGTCACCATCATCACCATCACAAAGATGAACTGTAAGCGGCCGC |

-continued

| SEQ ID NO: | NAME | NOTES | SEQUENCE |
| --- | --- | --- | --- |
| 80 | Protein sequence corresponding to synthetic N-GFD-VCE with endogenous furin cleavage site | | MSNELHQVPSN CDCLNGGTCV SNKYFSNIHW CNCPKKFGGQ HCEID<br>GGGGSGGGGSGGGGSSSKGNAMSALAAHRVCGVPLETLARSRKPRDLTDDLSCAYQAQNIVSLFVAT<br>RILFSHLDSVFTLNLDEQEPEVAERLSDLRRINENNPGMVTQVLTVARQIYNDVTHHPGLTPEQTSA<br>GAQAADILSLFCPDADKSCVASNNDQANINIESRSGRSYLPENRAVITPQGVTNWTYQELEATHQAL<br>TREGYVFVGYHGTNHVAAQTIVNRIAPVPRGNNTENEEKWGGLYVATHAEVAHGYARIKEGTGEYGL<br>PTRAERDARGVMLRVYIPRASLERFYRTNTPLENAEEEHITQVIGHSLPLRNEAFTGPESAGGEDET<br>VIGWDMAIRAVAIPSTIPGNAYEELAIDEEAVAKEQSISTKPPYKERHHHHHHKDEL |
| 81 | Protein sequence corresponding to synthetic N-GPD-VCE with a granzyme B cleavage site | Several sequences in place of underlined region have been tested, including IEPDSG and IAPDDL. | MSNELHQVPSNCDCLNGGTCVSNKYFSNIHWCNCPKKFGGQHCEIDGGGGSGGGGSGGGGSSSKGNA<br>MSALAAHRVCGVPLETLARSIEPDDLTDDLSCAYQAQNIVSLFVATRILFSHLDSVFTLNLDEQEPE<br>VAERLSDLRRINENNPGMVTQVLTVARQIYNDYVTHHPGLTPEQTSAGAQAADILSLFCPDADKSCV<br>ASNNDQANINIESRSGRSYLPENRAVITPQGVTNWTYQELEATHQALTREGYVFVGYHGTNHVAAQT<br>IVNRIAPVPRGNNTENEEKWGGLYVATHAEVAHGYARIKEGTGEYGLPTRAERDARGVMLRYIPRAS<br>LERFYRTNTPLENAEEHITQVIGHSLPLRNEAFTGPESAGGEDETVIGWDMAIHAVAIPSTIPGNAY<br>EELAIDEEAVAKEQSISTKPPYKERHHHHHHKDEL |
| 82 | Anti-CD5-VCE synthetic gene encoding anti-CD5-VCE with endogenous furin cleavage site | | ATGgccaacatccagctggtgcagtctggtcctgagctgaagaagcctggtgagactgtcaaaatct<br>cctgcaaggcttctgggtataccttcactaactatgqtatqaactgggtgaagcaggctcctggtaa<br>gggtctgcgttggatgggctggattaacacccacactggtgagcctacttatgctgatgacttcaag<br>ggacgttttgccttctctctggaaacttctgccagcactgcctatctccagatcaacaacctcaaaa<br>atgaggacactgctacttacttctgtacacgtcgtggttacgactggtacttcgatgtctggggtgc<br>tgggaccacggtgaccgtgttctccgggggaqgtggcagcgggggaggtggcagcggcggcgggagc<br>tccgacatcaagatgacccagtctccttcttccatgtatgcttctctgggtgagcgtgtcactatca<br>cttgcaaggccagccaqgacattaatagctatctgagctggttccatcataaacctgggaaatctcc<br>taagaccctgatctatcgtgctaaccgtctggttgatggggtcccttctcgtttcagcggctctggt<br>tctgggcaagattattctctcaccatcagcagcctggactatgaagatatgggtatttattattgtc<br>aacagtatgatgagtctccttggactttcggtggtggcaccaagctggagatgaaaggctctggcGC<br>TAGCAAAGGCAATGCCATGAGTGCACTGGCTGCGCACCGCGTATGCGGTGTGCCGCTGGAGACACTG<br>GCCCGTTCACGCAAACCACGTGACCTGACCGATGACCTGAGCTGCGCGTATCAGGCCCAAAATATTG<br>TGTCTCTGTTTGTTGCAACGCGTATCCTGTTCAGTCATCTGGATTCAGTCTTTACTCTGAACCTGGA<br>CGAACAGGAGCCGGAAGTAGCTGAGCGCCTGTCCGATCTGCGTCGCATTAATGAAAACAATCCAGGC<br>ATGGTGACACAAGTTCTGACCGTCGCGCGTCAGATCTACAACGACTATGTAACGCACCATCCTGGTC<br>TGACTCCGGAACAGACATCGGCCGGGGCACAAGCTGCGGATATTCTGAGCCTGTTCTGTCCAGATGC<br>CGACAAATCTTGCGTGGCAAGTAATAACGATCAGGCTAATATCAACATTGAGTCACGCTCCGGACGT<br>TCGTACCTGCCTGAAAATCGCGCGGTTATCACCCCGCAAGGCGTCACGACTGGAACCTATCAGGAGC<br>TGGAAGCCACTCACCAGGCACTGACACGTGAAGGTTACGTGTTTGTAGGGTATCATGGAACGAATCA<br>CGTTGCTGCGCAAACCATTGTGAACCGCATCGCCCCGGTCCCACGTGGCAATAACACTGAGAATGAA<br>GAGAAATGGGGTGGCCTGTACGTTGCAACACATGCGGAAGTAGCTCACGGTTATGCCCGCATTAAAG<br>AAGGGACCGGAGAGTATGGCCTGCCTACGCGTGCAGAACGCGACGCGCGTGGTGTGATGCTGCGCGT<br>CTACATCCCGCGTGCTTCGCTGGAGCGCTTCTATCGTACCAACACTCCGCTGGAAAATGCCGAAGAG<br>CATATTACACAGGTTATCGGCCACTCTCTGCCACTGCGCAACGAAGCATTTACGGGTCCTGAAAGTG<br>CGGGGGGAGAGGATGAAACCGTGATTGGCTGGGACATGGCTATCCATGCCGTAGCAATTCCGTCAAC<br>TATTCCAGGTAATGCGTACGAGGAACTGGCCATCGATGAAGAGGCAGTCGCGAAAGAACAATCCATT<br>TCGACAAAACCGCCTTATAAAGAGCGTCACCATCATCACCATCACAAAGATGAACTGTAA |
| 83 | Protein sequence of anti-CD5-VCE with a 15 amino acid linker | Proteins with altered underlined sequence, including IEPDDL, IEPDSG, IAPDDL, IAPDSG, RVRRAS, ENLYFQG were also made. | MANIQLVQSGPELKKPGETVKISCKASGYTFTNYGMNWVKQAPGKGLRWMGWINTHTGEPTYADDFK<br>GRFAFSLETSASTAYLQINNLKNEDTATYFCTRRGYDWYFDVWGAGTTVTVFSGGGGSGGGGSGGGG<br>GSSDIKMTQSPSSNYASLGERVTITCKASQDINSYLSWFHHKPGKSPKTLIYRNRLVDGVPSRFSGS<br>GSGQDYSLTISSLDYEDMGIYYCQQYDESPWTFGGGTKLEMKGSGASKGNAMSALAAHRVCGVPLET<br>LARS**RKPRDL**TDDLSCAYQAQNIVSLFVATRILFSHLDSVFTLNLDEQEPEVAERLSDLRRINENNP<br>GMVTQVLTVARQIYNDYVTHRPGLTPEQTSAGAQAADILSLFCPDADKSCVASNNDQANINIESRSG<br>RSYLPENRAVITPQGVTNWTYQELEATHQALTREGYVFVGYHGTNHVAAQTIVNRIAPVPRGNNTEN<br>EEKWGGLYVATHAEVAHGYARIFCEGTGEYGLPTRAERDARGVMLRVYIPRASLERFYRTNTPLENA<br>EEHITQVIGHSLPLRNEAFTGPESAGGEDETVIGWDMAIHAVAIPSTIPGNAYEELAIDEEAVAKEQ<br>SISTKPPYKERHHHHHHKDEL |
| 84 | Anti-CD19-VCE with a 18 amino acid linker | | ATGGCCCAGGTGCAGCTGCAGCAGTCCGGCGCTGAGCTGGTGCGCCCTGGCTCCTCCGTGAAAATCT<br>CCTGCAAGGCTTCCGGCTACGCTTTCTCCTCCTACTGGATGAACTGGGTGAAGCAGCGCCCTGGCCA<br>GGGCCTGGAGTGGATCGGCCAAATCTGGCCGGGCGACGGCGACACCAACTACAACGGCAAGTTCAAG<br>GGCAAGGCTACCCTGACCGCTGACGAGTCCTCCTCCACCGCTTACATGCAGCTGTCCTCCCTGGCTT<br>CCGAGGACTCCGCTGTGTACTTGTGCGCTCGCCGCGAGACCACCACCGTGGGCCGCTACTACTACGC<br>TATGGACTACTGGGGCCAGGGCACCTCGGTGACCGTGTCCTCCGGCGGCGGCGGCTCCGGCGGCGGC<br>GGCTCCGGCGGCGGGTCCGGGAGCTCCGACATCCTGCTGACCCAGACCCCGGCTTCCCTGGCTGTGT<br>CCCTGGGCCAGCGCGCTACCATCTCCTGCAAGGCTTCCCAGTCCGTGGACTACGACGGCGACTCCTA<br>CCTGAACTGGTACCAGCAGATCCCGGGCCAGCCGCCGAAGCTGCTGATCTACGACGCTTCCAACCTG<br>GTGTCCGGCATCCCGCCGCGCTTCTCCGGCTCCGGCTCCGGCACCGACTTCACCCTGAACATCCACC<br>CGGTGGAGAAGGTGGACGCTGCTACCTACCACTGCCAGCAGTCCACCGAGGACCCGTGGACCTTCGG<br>CGGCGGCACCAAGCTGGAGATCAAGCGCGGCTCTGGCGCTAGCAAAGGCAATGCCATGAGTGCACTG<br>GCTGCGCACCGCGTATGCGGTGTGCCGCTGGAGACACTGGCCCGTTCACGCAAACCACGTGACCTGA<br>CCGATGACCTGAGCTGCGCGTATCAGGCCCAAAATATTGTGTCTCTGTTTGTTGCAACGCGTATCCT |

-continued

| SEQ ID NO: | NAME | NOTES | SEQUENCE |
|---|---|---|---|
| | | | GTTCAGTCATCTGGATTCAGTCTTTACTCTGAACCTGGACGAACAGGAGCCGGAAGTAGCTGAGCGC<br>CTGTCCGATCTGCGTCGCATTAATGAAAACAATCCAGGCATGGTGACACAAGTTCTGACCGTCGCGC<br>GTCAGATCTACAACGACTATGTAACGCACCATCCTGGTCTGACTCCGGAACAGACATCGGCCGGGGC<br>ACAAGCTGCGGATATTCTGAGCCTGTTCTGTCCAGATGCCGACAAATCTTGCGTGGCAAGTAATAAC<br>GATCAGGCTAATATCAACATTGAGTCACGCTCCGGACGTTCGTACCTGCCTGAAAATCGCGCGGTTA<br>TCACCCCGCAAGGCGTCACGAACTGGACCTATCAGGAGCTGGAAGCCACTCACCAGGCACTGACACG<br>TGAAGGTTACGTGTTTGTAGGGTATCATGGAACGAATCACGTTGCTGCGCAAACCATTGTGAACCGC<br>ATCGCCCCGGTCCCACGTGGCAATAACACTGAGAATGAAGAGAAATGGGGTGGCCTGTACGTTGCAA<br>CACATGCGGAAGTAGCTCACGGTTATGCCCGCATTAAAGAAGGGACCGGAGAGTATGGCCTGCCTAC<br>GCGTGCAGAACGCGACGCGCGTGCTGTGATGCTGCGCGTCTACATCCCGCGTGCTTCGCTGGAGCGC<br>TTCTATCGTACCAACACTCCGCTGGAAAATGCCGAAGAGCATATTACACAGGTTATCGGCCACTCTC<br>TGCCACTGCGCAACGAAGCATTTACGGGTCCTGAAAGTGCGGGGGGAGAGGATGAAACCGTGATTGG<br>CTGGGACATGGCTATCCATGCCGTAGCAATTCCGTCAACTATTCCAGGTAATGCGTACGAGGAACTG<br>GCCATCGATGAAGAGGCAGTCGCGAAAGAACAATCCATTTCGACAAAACCGCCTTATAAAGAGCGTC<br>ACCATCATCACCATCACAAAGATGAACTGTAA |
| 85 | Anti-CD19-VCE protein sequence | Proteins with altered underlined sequence, including IEPDDL, IEPDSG, IAPDDL, IAPDSG, RVRRAS, ENLYFQG were also made. | MAQVQLQQSGAELVRPGSSVKISCKASGYAESSYWNNWKQRPGQGLEWIGQIWPGDGDTNYNGKFKG<br>KATLTADESSSTAYMQLSSLASEDSAVYFCARRETTTVGRYYYAMDYWGQGTSVTVSSGGGGSGGGG<br>SGGGSGSSDILLTQTPASLAVSLGQRATISCKASQSVDYDGDSYLNWYQQIPGQPPKLLIYDASNLV<br>SGIPPRFSGSGSGTDFTLNIHPVEKVDAATYHCQQSTEDPWTFGGGTKLEIKRGSGASKGNAMSAIA<br>AHRVCGVPLETLARS**RKPRDL**TDDLSCAYQAQNIVSLFVATRILESHLDSVFTLNLDEQEPEVAERL<br>SDLRRINENNPGNVTQVLTVARQIYNDYVTHHPGLTPEQTSAGAQAADILSLFCPDADKSCVASNND<br>QANINIESRSGRSYLPENRAVITPQGVTNWTYQELEATRQALTREGYVFVGYHGTNHVAAQTIVNRI<br>APVPRGNNTENEEKWGGLYVATHAEVAHGYARIKEGTGEYGLPTRAERDARGVMLRVYIPRASLERF<br>YRTNTPLENAEEHITQVIGHSLPLRNEAETGPESAGGEDETVIGWDMAIHAVAIPSTIPGNAYEELA<br>IDEEAVAKEQSISTKPPYKERHHHHRHKDEL |
| 86 | Synthetic gene encoding anti-CD5-PE | | ATGGACTACAAGGACGACGACGACAAGcGCATcgccaacatccagctggtgcagtctggtcctgagc<br>tgaagaagcctggtgagactgtcaaaatctcctgcaaggcttctgggtataccttcactaactatgg<br>tatgaactgggtgaagcaggctcctggtaagggtctgcgttggatgggctggattaacacccacact<br>ggtgagcctacttatgctgatgacttcaagggacgttttgccttctctctggaaacttctgccagca<br>ctgcctatctccagatcaacaacctcaaaaatgaggacactgctacttacttctgtacacgtcgtgg<br>ttacgactggtacttcgatgtctggggtgctgggaccacggtgaccgtgttctccgggggaggtggc<br>agcgggggaggtggcagcggcggcgggagctccgacatcaagatgacccagtctccttcttccatgt<br>atgcttctctgggtgagcgtgtcactatcacttgcaaggccagccaggacattaatagctatctgag<br>ctggttccatcataaacctgggaaatctcctaagaccctgatctatcgtgctaaccgtctggttgat<br>ggggtcccttctcgtttcagcggctctggttctgggcaagattattctctcaccatcagcagcctgg<br>actatgaagatatgggtatttattattgtcaacagtatgatgagtctccttggactttcggtggtgg<br>caccaagctggagatgaaaggaggcggaggctccggaggaggaggcgggtccgctagcctGATCGCC<br>CTGACCGCCCACCAGGCCTGCCACCTGCCGCTGGAGACCTTCACCGCTAGCATCGAGCCGGACGGCT<br>GGGAGCAGCTGGAGCAGTGCGGCTACCCGGTGCAGCGCCTGGTGGCCCTGTACCTGGCCGCCCGCCT<br>GTCCTGGAACCAGGTGGACCAGGTGATCCGCAACGCCCTGGCCTCCCCGGCCTCCGGCGGCGACCTG<br>GGCGAGGCCATCCGCGAGCAGCCGGAGCAGGCCCGCCTGGCCCTGACCCTGGCCGCCGCCGAGTCCG<br>AGCGCTTCGTGCGCCAGGGCACCGGCAACGACGAGGCCGGCGCCGCCAACGCCGACGTGGTGTCCCT<br>GACCTGCCCGGTGGCCGCCGGCGAGTGCGCCGGCCCGGCCGACTCCGGCGACGCCCTGCTGGAGCGC<br>AACTACCCGACCGGCGCCGAGTTCCTGGGCGACGGCGGCGACGTGTCCTTCTCCACCCGCGGCACCC<br>AGACCTGGACCGTGGAGCGCCTGCTGCAGGCCCACCGCCAGCTGGAGGAGCGCGGCTACGTGTTCGT<br>GGGCTACCACGGCACCTTCCTGGAGGCCGCCCAGTCCATCGTGTTCGGCGGCGTGCGCGCCCGCTCC<br>CAGGACCTGGACGCCATCTGGCGCGGCTTCTACATCGCCGGCGACCCGGCCCTGGCCTACGGCTACG<br>CCCAGGACCAGGAGCCGGACGCCCGCGGTCGCATCCGCAACGGCGCCCTGCTGCGCGTGTACGTGCC<br>GCGCTCCTCCCTGCCGGGCTTCTACCGCACCTCCCTGACCCTGGCCGCCCCGGAGGCCGCCGGCGAG<br>GTGGAGCGCCTGATCCGCCACCCGCTGCCGCTGCGCCTGGACGCCATCACCGGCCCGGAGGAGGAGG<br>GCGGTCGCCTGGAGACCATCCTGGGCTGGCCGCTGGCCGAGCGCACCGTGGTGATCCCGTCCGCCAT<br>CCCGACCGACCCGCGCAACGTGGGCGGCGACCTGGACCCGTCCTCCATCCCGGACAAGGAGCAGGCC<br>ATCTCCGCCCTGCCGGACTACGCCTCTCAGCCGGGCAAGCCGCCGCACCACCACCACCACCACAAGG<br>ACGAGCTGTAG |
| 87 | Anti-CD5-PE protein sequence | | MDYKDDDDKGMANIQLVQSGPELKKPGETVKISCKASGYTFTNYGMNWVKQAPGKGLRWMGWINTHT<br>GEPTYADDFKGRFAFSLETSASTAYLQINNLKNEDTATYFCTRRGYDWYFDVWGAGTTVTVFSGGGG<br>SGGGGSGGGSSDIKMTQSPSSMYASLGERVTITCKASQDINSYLSWFHHKPGKSPKTLIYRANRLVD<br>GVPSRFSGSGSGQDYSLTISSLDYEDMGIYYCQQYDESPWTFGGGTKLEMKGGGGSGGGGGSASLIA<br>LTAHQACHLPLETFTASIEPDGWEQLEQCGYPVQRLVALYLAARLSWNQVDQVIRNALASPGSGGDL<br>GEMREQPEQARLALTLAAAESERFVRQGTGNDEAGAANADVVSLTCPVAAGECAGPADSGDALLERN<br>YPTGAEFLGDGGDVSFSTRGTQTWTVERLLQAHRQLEERGYVFVGYHGTFLEAAQSIVFGGVRARSQ<br>DLDAIWRGFYIAGDPALAYGYAQDQEPDARGRIRNGALLRVYVPRSSLPGEYRTSLTLAAPEAAGEV<br>ERLIGHPLPLRLDAITGPEEEGGRLETILGWPLAERTVVIPSAIPTDPRNVGGDLDPSSIPDKEQAI<br>SALPDYASQPGKPPHHHHHHKDEL |
| 88 | Synthetic gene encoding GrB-anti-CD19 | | ATGGGCGTGAAGGTGCTGTTCGCCCTGATCTGCATCGCCGTGGCGctcgccgacaactcgagctaca<br>aggacgacgacgacaagATCATCGGGGGACATGAGGCCAAGCCCCACTCCCGCCCCTACATGGCTTA<br>TCTTATGATCTGGGATCAGAAGTCTCTGAAGAGGTGCGGTGGCTTCCTGATACAAGACGACTTCGTG<br>CTGACAGCTGCTCACTGTTGGGGAAGCTCCATAAATGTCACCTTGGGGGCCCACAATATCAAAGAAC<br>AGGAGCCGACCCAGCAGTTTATCCCTGTGAAAAGACCCATCCCCCATCCAGCCTATAATCCTAAGAA |

-continued

| SEQ ID NO: | NAME | NOTES | SEQUENCE |
|---|---|---|---|
| | | | CTTCTCCAACGACATCATGCTACTGCAGCTGGAGAGAAAGGCCAAGCGGACCAGAGCTGTTCAGCCC CTCAGGCTACCTAGCAACAAGGCCCAGGTGAAGCCAGGGCAGACATGCAGTGTGGCCGGCTGGGGGC AGACGGCCCCCCTGGGAAAACACTCACACACACTACAAGAGGTGAAGATGACAGTGCAGGAAGATCG AAAGTGCGAATCTGACTTACGCCATTATTACGACAGTACCATTGAGTTGTGCGTGGGGGACCCAGAG ATTAAAAAGACTTCCTTTAAGGGGGACTCTGGAGGCCCTCTTGTGTGTAACAAGGTGGCCCAGGGCA TTGTCTCCTATGGACGAAACAATGGCATGCCTCCACGAGCCTGCACCAAAGTCTCAGCTTTGTACAC TGGATAAAGTAAAACCATGAAACGCTACGCCATGGGAGGCGGAGGCTCCGGAGGAGGAGGGTCCGGG GGCGGCGGAAGCATGGCCCAGGTGCAGCTGCAGCAGTCCGGCGCTGAGCTGGTGCGCCCTGGCTCCT CCGTGAAAATCTCCTGCAAGGCTTCCGGCTACGCTTTCTCCTCCTACTGGATGAACTGGGTGAAGCA GCGCCCTGGCCAGGGCCTGGAGTGGATCGGCCAAATCTGGCCGGGCGACGGCGACACCAACTACAAC GGCAAGTTCAAGGGCAAGGCTACCCTGACCGCTGACGAGTCCTCCTCCACCGCTTACATGCAGCTGT CCTCCCTGGCTTCCGAGGACTCCGCTGTGTACTTCTGCGCTCGCCGCGAGACCACCACCGTGGGCCG CTACTACTACGCTATGGACTACTGGCGCCAGGGCACCTCGGTGACCGTGTCCTCCGGCGGCGGCGGC TCCGGCGGCGGCGGCTCCGGCGGCGGGAGCTCCGACATCCTGCTGACCCAGACCCCGGCTTCCCTGG CTGTGTCCCTGGGCCAGCGCGCTACCATCTCCTGCAAGGCTTCCCAGTCCGTGGACTACGACGGCGA GTCCTACCTGAACTGGTACCAGCAGATCCCGGGCCAGCCGCCGAAGCTGCTGATCTACGACGCTTCC AACCTGGTGTCCGGCATCCCGCCGCGCTTCTCCGGCTCCGGCTCCGGCACCGACTTCACCCTGAACA TCCACCCGGTGGAGAAGGTGGACGCTGCTACCTACCACTGCCAGCAGTCCACCGAGGACCCGTGGAC CTTCGGCGGCGGCACCAAGCTGGAGATCAAGCGCGGTGGTGACATGCATCACCATCACCATCACTGA |
| 89 | GrB-anti-CD19 Protein sequence | | MGVKVLFALICIAVALADNSSYKDDDDKIIGGHEAKPHSRPYMAYLMIWDQKSLKRCGGFLIQDDFV LTAAHCWGSSINVTLGAHNIKEQEPTQQFIPVKRPIPHPAYNPKNFSNDIMLLQLERKAKRTRAVQP LRLPSNKAQVKPGQTCSVAGWGQTAPLGKHSHTLQEVKMTVQEDRKCESDLRHYYDSTIELCVGDPE IKKTSFKGDSGGPLVCNKVAAGIVSYGRNNGMPPRACTKVSSFVHWIKKTMKRYAMGGGGSGGGGSG GGGSMAQVQLQQSGAELVRPGSSVKISCKASGYAFSSYWMNWVKQRPGQGLEWIGQIWPGDGDTNYN GKFKGKATLTADESSSTAYMQLSSLASEDSAVYFCARRETTTVGRYYYAMDYWGQGTSVTVSSGGGG SGGGGSGGGSSDILLTQTPASLAVSLGQRATISCKASQSVDYDGDSYLNWYQQIPGQPPKLLIYDAS NLVSGIPPRFSGSGSGTDFTLNIHPVEKVDAATYHCQQSTEDPWTFGGGTKLEIKRGGDMHHHHHH |
| 90 | Synthetic DNA encoding DT-anit-CD5 | | ATGGGTGCCGACGACGTGGTGGACTCCTCCAAGTCCTTCGTGATGGAAAACTTCGCTTCCTACCACG GTACCAAGCCTGGTTACGTGGATTCCATCCAGAAGGGTATCCAGAAGCCTAAGTCCGGTACCCAGGG TAACTACGACGATGATTGGAGGGTTTTTACTCCACCGACAACAAGTACGACGCCGCCGGTTACTCC GTGGATAACGAAAACCCTCTGTCCGGTAAGGCCGGTGGTGTGGTGAAAGTGACCTACCCTGGTCTGA CCAAGGTGCTGGCCCTGAAGGTGGATAACGCCGAAACCATCAAGAAGGAGCTGGGTCTGTCCCTGAC CGAACCTCTGATGGAGCAGGTGGGTACCGAAGAGTTTATCAAGAGATTCGGTGATGGTGCCTCCAGA GTGGTGCTGTCCCTGCCTTTCGCCGAGGGTTCCTCCTCCGTGGAATACATCAACAACTGGGAACAGG CCAAGGCCCTGTCCGTGGAACTGGAGATCAACTTTGAAACCAGAGGTAAGAGAGGTCAGGATGCCAT GTACGAGTACatggcccaggcctgtgccggCAACATCGAGCCTGACACCGGttcctccctgtccTGC ATCAACCTGGACTGGGACGTGATCAGAGACAAGACCAAGACCAAGATCGAGTCCCTGAAGGAGCACG GTCCTATCAAGAACAAGATGTCCGAGTCCCCTGCCAAGACCGTGTCCGAGGAGAAGGCCAAGCAGTA CCTGGAGGAGTTCCACCAGACCGCCCTGGAGCACCCTGAGCTGTCCGAGCTGAAGACCGTGACTGGT ACCAACCCTGTGTTCGCCGGTGCCAACTACGCCGCCTGGGCCGTGAACGTGGCCCAGGTGATCGACT CCGAGACCGCCGACAACCTGGAGAAGACCACCGCCGCCCTGTCCATCCTGCCTGGTATCGGTTCCGT GATGGGTATCGCCGACGGTGCCGTGCACCACAACACCGAGGAGATCGTGGCCCAGTCCATCGCCCTG TCCTCCCTGATGGTGGCCCAGGCCATCCCTCTGGTGGGTGAGCTGGTGGACATCGGTTTCGCCGCCT ACAACTTCGTGGAGTCCATCATCAACCTGTTCCAGGTGGTGCACAACTCCTACAACAGACCTGCCTA CTCCCCTGGTCACAAGACCCAGCCTGCCATGGGAGGCGGAGGCTCCGGAGGAGGAGGGTCCGGGGGC GGCGGAAGCATGGCCCAGGTGCAGCTGCAGCAGTCCGGTGCCGAGCTGGTGAGACCTGGTGCCTCCG TGAAGCTGTCCTGCAAGACCTCCGCCTACACCTTCACCAACTACTGGATCAACTGGGTGAAGCAGAG ACCTGGTCAGGGTCTGGAGTGGATCGGTAACATCTACCCTTCCGACTCCTACACCAACTACAACCAG AAGTTCAAGGACAAGGCCACCCTGACCGTGGACAAGTCCTCCTCCACCGCCTACATCCAGCTGTCCT CCCCTACCTCCGAGGACTCCGCCGTGTACTACTGCACCAGAGGTGGTGCCTACTACAGATCCTTCGA CTACTGGGCCCAGGGTACCACGGTGACCGTGTCCTCCGGTGGCGGTGGCTCCGGGGGCGGTGGTTCC GGTGGTGGGAGCTCCGACATCGTGCTGACCCAGTCCCCTGCCATCCTGTCCGCCTCCCCTGGTGAGA AAGTGACCATGACCTGCAGAGCCACCTCCTCCGTGTCCTACATGCACTGGTACCAGCAGAAGCCTGG TTCCTCCCCTAAGCCTTGGATCTACGCCACCTCCAACCTGGCCTCCGGTGTGCCTGCCAGATTCTCC GGTTCCGGTTCCGGTACCTCCTACTCCCTGACCATCTCCAGAGTGGAGGCCGAGGACGCCGCCACCT ACTACTGCCAGCAGTGGTCCTCCAACCCTCCTACCTTCGGTGCCGGTACCATGCTGGAGCTGAAGAG AGGTGGTCACATGCACCATCACCATCATCACTAA |
| 91 | Protein sequence of DT-anti-CD5 | | MGADDVVDSSKSFVNENFASYHGTKPGYVDSIQKGIQKPKSGTQGNYDDDWKGFYSTDNKYDAAGYS VDNENPLSGKAGGVVKVTYPGLTKVLALKVDNAETIKKELGLSLTEPLMEQVGTEEFIKRFGDGASR VVLSLPFAEGSSSVEYINNWEQAKALSVELEINFETRGKRGQDAMYEYMAQACAGNIEPDTGSSLSC INLDWDVIRDKTKTKIESLKEHGPIKNKMSESPAKTVSEEKAKQYLEEFHQTALEHPELSELKTVTG TNPVFAGANYAAWAVNVAQVIDSETADNLEKTTAALSILEGIGSVMGIADGAVHHNTEEIVAQSIAL SSLNVAQAIPLVGELVDIGFAAYNFVESIINLFQVVHNSYNRPAYSPGHKTQPAMGGGGSGGGGSGG GGSMAQVQLQQSGAELVRPGASVKLSCKTSAYTFTNYWINWVKQRPGQGLEWIGNIYPSDSYTNYNQ KFKDKATLTVDKSSSTAYIQLSSPTSEDSAVYYCTRGGAYYRSFDYWAQGTTVTVSSGGGGSGGGGS GGGSSDIVLTQSPAILSASPGEKVTMTCRATSSVSYMHWYQQKPGSSPKPWIYATSNLASGVPARFS GSGSGTSYSLTISRVEAEDAATYYCQQWSSNPPTFGAGTMLELKRGGRMHHHHHH |
| 92 | pro-aerolysin Protein Sequence | | AEPVYPDQLRLFSLGQGVCGDKYRPVNREEAQSVKSNIVGMNGQWQISGLANGWVIMGPGYNGEIKP GTASNTWCYPTNPVTGEIPTLSALDIPDGDEVDVQWRLVHDSANFIKFTSYLAHYLGYAWVGGNHSQ YVGEDMDVTRDGDGWVIRGNNDGGCDGYRCGDKTAIKVSNFAYNLDPDSFKHGDVTQSDRQLVKTVV GWAVNDSDTPQSGYDVTLRYDTATNWSKTNTYGLSEKVTTKNKFKWPLVGETELSIEIAANQSWASQ NGGSTTTSLSQSVRPTVPARSKIPVKIELYKADISYPYEFKADVSYDLTLSGFLRWGGNAWYTHPDN |

-continued

| SEQ ID NO: | NAME | NOTES | SEQUENCE |
|---|---|---|---|
| | | | RPNWNHTFVIGPYKDKASSIRYQWDKRYIPGEVKWWDWNWTIQQNGLSTMQNNLARVLRPVPAGITG DFSAESQFAGNIEIGAPVPLAADSKVRRARSVDGAGQGLRLEIPLDAQELSGLGFNNVSLSVTPAAN Q |
| 93 | GK-aerolysin$_{GrB}$ Protein Sequence | | GKGGSNSAASGEIPTLSALDIPDGDEVDVQWRLVHDSANFIKPTSYLAHYLGYAWVGGNHSQYVGED MDVTRDGDGWVIRGNNDGGCDGYRCGDKTSIKVSNFAYNLDPDSFKHGDVTQSDRQLVKTVVGWAIN DSDTPQSGYDVTLRYDTATNWSKTNTYGLSEKVTTKNKFKWPLVGETELSIEIAANQSWASQNGGST TTSLSQSVRPTVPAHSKIPVKIELYKADISYPYEFKADVSYDLTLSGFLRWGGNAWYTHPDNRPNWN HTFVIGPYKDKASSIRYQWDKRYIPGEVKWWDWNWTIQQNGLPTMQNNLARVLRPVRAGITGDFSAE SQFAGNIEIGAPVPVAAESKGIEPDSGVEGAGQGLRLEIPLDAQELSGLGFNNVSLSVTPAANQVEH HHHHH |
| 94 | GK-aerolysin$_{GrB}$ DNA Sequence | | GGTAAAGGTGGTTCGAATTCTGCAGCTAGCGGAGAAATACCGACTCTGTCTGCCCTGGATATTCCAG ATGGTGATGAAGTAGATGTGCAATGGCGGCTGGTACATGACAGTGCGAATTTCATCAAACCAACCAG TTATCTGGCCCATTATCTCGGCTATGCCTGGGTAGGGGGGAATCACAGTCAATATGTCGGCGAAGAC ATGGATGTGACCCGTGATGGTGATGGCTGGGTGATCCGTGGCAACAATGACGGTGGCTGCGATGGTT ATCGCTGTGGTGACAAGACCTCCATCAAGGTGAGCAATTTTGCCTACAACCTGGATCCTGACAGTTT CAAGCATGGCGATGTGACCCAGTCCGACCGCCAACTGGTCAAGACGGTGGTGGGGTGGGCTATCAAC GACAGCGACACGCCTCAATCCGGTTATGACGTCACCCTGCGCTACGACACGGCCACCAACTGGTCCA AGACCAACACCTATGGTCTGAGCGAGAAGGTGACCACCAAGAACAAGTTCAAGTGGCCGCTGGTGGG GGAAACCGAGCTCTCCATCGAGATTGCTGCCAACCAGTCCTGGGCCTCCCAGAACGGGGGCTCGACC ACCACCTCTTTGTCCCAGTCCGTGCGCCCGACAGTGCCGGCCCACTCCAAGATCCCGGTGAAGATAG AGCTCTACAAAGCCGACATCTCCTACCCCTACGAGTTCAAGGCCGATGTCAGCTATGACCTGACCCT GAGCGGTTTCCTGCGTTGGGGCGGTAATGCCTGGTATACCCATCCGGACAACCGTCCGAACTGGAAC CACACCTTCGTCATAGGGCCATACAAGGACAAGGCCAGCAGTATCCGCTACCAGTGGGACAAGCGTT ATATCCCGGGTGAAGTGAAGTGGTGGGATTGGAACTGGACCATACAGCAGAACGGTCTGCCTACCAT GCAGAATAACCTGGCCAGGGTGCTGCGCCCGGTGCGGGCCGGGATCACCGGTGATTTCAGTGCCGAG AGCCAGTTTGCCGGCAACATCGAAATCGGCGCTCCCGTGCCGGTCGCTGCCGAATCTAAGGGTATCG AGCCAGATTCTGGTGTTGAAGGTGCCGGTCAGGGTCTGAGACTGGAGATCCCGCTCGATGCACAAGA GCTCTCCGGGCTTGGCTTCAACAATGTCAGCCTCAGCGTGACCCCTGCTGCCAACCAAGTCGAGCAC CACCACCACCACCAC |
| 95 | Anti-CD5 LPETG Protein Sequence | | ANIQLVQSGPELKKPGETVKISCKASGYTFTNYGMNWVKQAPGKGLRWMGWINTHTGEPTYADDFKG RFAFSLETSASTAYLQINNLKNEDTATYFCTRRGYDWYFDVWGAGTTVTVFSGGGGSGGGGSGGGSS DIKMTQSPSSMYASLGERVTITCKASQDINSYLSWFHHKFGKSPKTLIYRANRLVDGVPSRFSGSGS GQDYSLTISSLDYEDMGIYYCQQYDESPWTFGGGTKLEMRLERPHGGGSLPETGGVEHHHHHH |
| 96 | Anti-CD5 LPETG DNA Sequence | | GCCAACATCCAGCTGGTGCAGTCTGGTCCTGAGCTGAAGAAGCCTGGTGAGACTGTCAAAATCTCCT GCAAGGCTTCTGGGTATACCTTCACTAACTATGGTATGAACTGGGTGAAGCAGGCTCCTGGTAAGGG TCTGCGTTGGATGGGCTGGATTAACACCCACACTGGTGAGCCTACTTATGCTGATGACTTCAAGGGA CGTTTTGCCTTCTCTCTGGAAACTTCTGCCAGCACTGCCTATCTCCAGATCAACAACCTCAAAAATG AGGACACTGCTACTTACTTCTGTACACGTCGTGGTTACGACTGGTACTTCGATGTCTGGGGTGCTGG GACCACGGTGACCGTGTTCTCCGGGGGAGGTGGCAGCGGGGGAGGTGGCAGCGGCGGCGGGAGCTCC GACATCAAGATGACCCAGTCTCCTTCTTCCATGTATGCTTCTCTGGGTGAGCGTGTCACTATCACTT GCAAGGCCAGCCAGGACATTAATAGCTATCTGAGCTGGTTCCATCATAAACCTGGGAAATCTCCTAA GACCCTGATCTATCGTGCTAACCGTCTGGTTGATGGGGTCCCTTCTCGTTTCAGCGGCTCTGGTTCT GGGCAAGATTATTCTCTCACCATCAGCAGCCTGGACTATGAAGATATGGGTATTTATTATTGTCAAC AGTATGATGAGTCTCCTTGGACTTTCGGTGGTGGCACCAAGCTGGAGATGCGTCTCGAGCGGCCGCA TGGCGGCGGCTCCCTGCCAGAGACTGGCGGGGTCGAGCACCACCACCACCACCAC |
| 97 | SortaseA conjugated anti-CD5-aerolysin$_{GrB}$ Protein Sequence | | ANIQLVQSGPELKKPGETVKISCKASGYTFTNYGMNWVKQAPGKGLRWMGWINTHTGEPTYADDFKG RFAFSLETSASTAYLQINNLKNEDTATYFCTRRGYDWYFDVWGAGTTVTVESGGGGSGGGGSGGGSS DIKMTQSPSSMYASLGERVTITCKASQDINSYLSWFHHKPGKSPKTLIYRANRLVDGVPSRFSGSGS GQDYSLTISSLDYEDMGIYYCQQYDESPWTFGGGTKLEMRLERPHGGGSLPETGKGGSNSAASGEIP TLSALDIPDGDEVDVQWRLVHDSANFIKPTSYLAHYLGYAWVGGNHSQYVGEDMDVTRDGDGWVIRG NNDGGCDGYRCGDKTSIKVSNFAYNLDPDSFKHGDVTQSDRQLVKTVVGWAINDSDTPQSGYDVTLR YDTATNWSKTNTYGLSEKVTTKNKFKWPLVGETELSIEIAANQSWASQNGGSTTTSLSQSVRPTVPA HSKIPVKIELYKADISYPYEFKADVSYDLTLSGFLRWGGNAWYTHPDNRPNWNHTFVIGPYKDKASS IRYQWDKRYIPGEVKWWDWNWTIQQNGLPTMQNNLARVLRPVRAGITGDFSAESQFAGNIEIGAPVP VAAESKGIEPDSGVEGAGQGLRLEIPLDAQELSGLGFNNVSLSVTPAANQVEHHHHHH |
| 98 | Protein Sequence for anti-CD19-LPETG (underlined is signal sequence) | | MKYLLPTAAAGLLLLAAQPAMAANSAQVQLQQSGAELVRPGSSVKISCKASGYAFSSYWMNWVKQRP GQGLEWIGQIWPGDGDTNYNGKFKGKATLTADESSSTAYMQLSSLASEDSAVYFCARRETTTVGRYY YAMDYWGQGTSVTVSSGGGGSGGGGSGGGGSGSSDILLTQTPASLAVSLGQRATISCKASQSVDYDG DSYLNWYQQIPGQPPKLLIYDASNLVSGIPPRFSGSGSGTDFTLNIHPVEKVDAATYHCQQSTEDPW TFGGGTKLEIKRGGLERPHGGGSLPETGGVEHHHHHH |
| 99 | DNA Sequence for anti-CD19-LPETG (underlined is signal sequence) | (underlined is signal sequence) | ATGAAATACCTGCTGCCGACCGCTGCTGCTGGTCTGCTGCTCCTCGCTGCCCAGCCGGCGATGGCCG CGAATTCTGCCCAGGTGCAGCTGCAGCAGTCCGGCGCTGAGCTGGTGCGCCCTGGCTCCTCCGTGAA AATCTCCTGCAAGGCTTCCGGCTACGCTTTCTCCTCCTACTGGATGAACTGGGTGAAGCAGCGCCCT GGCCAGGGCCTGGAGTGGATCGGCCAAATCTGGCCGGGCGACGGCGACACCAACTACAACGGCAAGT TCAAGGGCAAGGCTACCCTGACCGCTGACGAGTCCTCCTCCACCGCTTACATGCAGCTGTCCTCCCT GGCTTCCGAGGACTCCGCTGTGTACTTCTGCGCTCGCCGCGAGACCACCACCGTGGGCCGCTACTAC TACGCTATGGACTACTGGGGCCAGGGCACCTCGGTGACCGTGTCCTCCGGGGGAGGTGGCAGCGGTG GAGGTGGCAGCGGCGGCGGGGGTTCCGGGAGCTCCGACATCCTGCTGACCCAGACCCCGGCTTCCCT GGCTGTGTCCCTGGGCCAGCGCGCTACCATCTCCTGCAAGGCTTCCCAGTCCGTGGACTACGACGGC |

-continued

| SEQ ID NO: | NAME | NOTES | SEQUENCE |
|---|---|---|---|
| | | | GACTCCTACCTGAACTGGTACCAGCAGATCCCGGGCCAGCCGCCGAAGCTGCTGATCTACGACGCTT CCAACCTGGTGTCCGGCATCCCGCCGCGCTTCTCCGGCTCCGGCTCCGGCACCGACTTCACCCTGAA CATCCACCCGGTGGAGAAGGTGGACGCTGCTACCTACCACTGCCAGCAGTCCACCGAGGACCCGTGG ACCTTCGGCGGCGGCACCAAGCTGCAGATCAAGCGCGGTGGTCTCGAGCGGCCGCATGGCGGCGGCT CCCTGCCAGAGACTGGCGGGGTCGAGCACCACCACCACCACCAC |
| 100 | Protein Sequence for anti-CD19-aerolysin$_{GrB}$ | | ANSAQVQLQQSGELVRPGSSVKISCKSGYAFSSYWMNWVKQRPGQGLEWIGQIWFGDGDTNYNGKFK GKATLTADESSSTAYMQLSSLASEDAVYFCARRETTTVGRYYYAMDYWGQGTSVTVSSGGGGSGGGG SGGGGSGSSDILLTQTPASLAVSLGQRATISCKASQSVDYDGDSYLNWYQQIPGQPPKLLIYDASNL VSGIPPRFSGSGSGTDFTLNIHPVEKVDAATYHCQQSTEDPWTFGGGTKLEIKRGGLERPHGGGSLP ETGKGGSNSAASGEIPTLSALDIPDGDEVDVQWRLVHDSANFIKPTSYLAHYLGYAWVGGNHSQYVG EDMDVTRDGDGWVIRGWNDGGCDGYRCGDKTSIKVSNFAYNLDPDSFKHGDVTQSDRQLVKTVVGWA INDSDTPQSGYDVTLRYDTATNWSKTNTYGLSEKVTTKNKFKWPLVGETELSIEIAANQSWASQNGG STTTSLSQSVRPTVPAHSKIPVKIELYKADISYPYEFKADVSYDLTLSGFLRWGGNAWYTHPDNRPN WNHTFVIGPYKDKASSIRYQWDKRYIPGEVKWWDWNWTIQQNGLPTMQNNLARVLRPVRAGITGDFS AESQFAGNIEIGAPVPVAAESKGIEPDSGVEGAGQGLRLEIPLDAQELSGLGFNNVSLSVTPAANQV EHHHHHH |
| 101 | Protein Sequence for GK-aerolysin$_{TEV}$ | | MKYLLPTAAAGLLLLAAQPAMAGKGGSNSAASGEIPTLSALDIPDGDEVDVQWRLVHDSANFIKPTS YLAHYLGYAWVGGNHSQYVGEDMDVTRDGDGWVIRGNNDGGCDGYRCGDKTSIKVSNFAYNLDPDSF KHGDVTQSDRQLVKTVVGWAINDSDTPQSGYDVTLRYDTATNWSKTNTYGLSEKVTTKNKFKWPLVG ETELSIEIAANQSWASQNGGSTTTSLSQSVRPTVPAHSKIPVKIELYKADISYPYEFKADVSYDLTL SGFLRWGGNAWYTHPDNRPNWNHTFVIGPYKDKASSIRYQWDKRYIPGEVKWWDWNWTIQQNGLPTM QNNLARVLRPVRAGITGDFSAESQFAGNIEIGAPVPVAAESKENLYFQGVEGAGQGLRLEIPLDAQE LSGLGFNNVSLSVTPAANQVEHHHHHH |
| 102 | DNA Sequence for GK-aerolysin$_{TEV}$ | | ATGAAATACCTGCTGCCGACCGCTGCTGCTGGTCTGCTGCTCCTCGCTGCCCAGCCGGCGATGGCCG GTAAAGGTGGTTCGAATTCTGCAGCTAGCGGAGAAATACCGACTCTGTCTGCCCTGGATATTCCAGA TGGTGATGAAGTAGATGTGCAATGGCGGCTGGTACATGACAGTGCGAATTTCATCAAACCAACCAGT TATCTGGCCCATTATCTCGGCTATGCCTGGGTAGGGGGGAATCACAGTCAATATGTCGGCGAAGACA TGGATGTGACCCGTGATGGTGATGGCTGGGTGATCCGTGGCAACAATGACGGTGGCTGCGATGGTTA TCGCTGTGGTGACAAGACCTCCATCAAGGTGAGCAATTTTGCCTACAACCTGGATCCTGACAGTTTC AAGCATGGCGATGTGACCCAGTCCGACCGCCAACTGGTCAAGACGGTGGTGGGGGTGGCTATCAACG ACAGCGACACGCCTCAATCCGGTTATGACGTCACCCTGCGCTACGACACGGCCACCAACTGGTCCAA GACCAACACCTATGGTCTGAGCGAGAAGGTGACCACCAAGTTCAAGTTCAAGTGGCCGCTGGTGGGG GAAACCGAGCTCTCCATCGAGATTGCTGCCAACCAGTCCTGGGCCTCCCAGAACGGGGGCTCGACCA CCACCTCTTTGTCCCAGTCCGTGCGCCCGACAGTGCCGGCCCACTCCAAGATCCCGGTGAAGATAGA GCTCTACAAAGCCGACATCTCCTACCCCTACGAGTTCAAGGCCGATGTCAGCTATGACCTGACCCTG AGCGGTTTCCTGCGTTGGGGCGGTAATGCCTGGTATACCCATCCGGACAACCGTCCGAACTGGAACC ACACCTTCGTCATAGGGCCATACAAGGACAAGGCCAGCAGTATCCGCTACCAGTGGGACAAGCGTTA TATCCCGGGTGAAGTGAAGTGGTGGGATTGGAACTGGACCATACAGCAGAACGGTCTGCCTACCATG CAGAATAACCTGGCCAGGGTGCTGCGCCCGGTGCGGGCCGGGATCACCGGTGATTTCAGTGCCGAGA GCCAGTTTGCCGGCAACATCGAAATCGGCGCTCCCGTGCCGGTCGCTGCCGAATCTAAGGAGAACCT GTACTTCCAAGGTGTTGAAGGTGCCGGTCAGGGTCTGAGACTGGAGATCCCGCTCGATGCACAAGAG CTCTCCGGGCTTGGCTTCAACAATGTCAGCCTCAGCGTGACCCCTGCTGCCAACCAAGTCGAGCACC ACCACCACCACAC |
| 103 | Protein Sequence for GK-aerolysin$_{GrB}$ | | MKYLLPTAAAGLLLLAAQPAMAGKGGSNSAASGEIPTLSALDIPDGPEVDVQWRLVHDSANFIKPTS YLAHYLGYAWVGGNHSQYVGEDMDVTRDGDGWVIRGNNDGGCDGYRCGDKTSIKVSNFAYNLDPDSF KHGDVTQSDRQLVKTVVGWAINDSDTPQSGYDVTLRYDTATNWSKTNTYGLSEKVTTKNKFKWPLVG ETELSIEIAANQSWASQNGGSTTTSLSQSVRPTVPAHSKIPVKIELYKADISYPYEFKADVSYDLTL SGFLRWGGNAWYTHPDNRPNWNHTFVIGPYKDKASSIRYQWDKRYIPGEVKWWDWNWTIQQNGLPTM QNNLARVLRPVRAGITGDFSAESQFAGNIEIGAPVPVAAESKGIEPDSGVEGAGQGLRLEIPLDAQE LSGLGFNNVSLSVTPAANQVEHHHHHH |
| 104 | DNA Sequence for GK-aerolysin$_{GrB}$ | | ATGAAATACCTGCTGCCGACCGCTGCTGCTGGTCTGCTGCTCCTCGCTGCCCAGCCGGCGATGGCCG GTAAAGGTGGTTCGAATTCTGCAGCTAGCGGAGAAATACCGACTCTGTCTGCCCTGGATATTCCAGA TGGTGATGAAGTAGATGTGCAATGGCGGCTGGTACATGACAGTGCGAATTTCATCAAACCAACCAGT TATCTGGCCCATTATCTCGGCTATGCCTGGGTAGGGGGGAATCACAGTCAATATGTCGGCGAAGACA TGGATGTGACCCGTGATGGTGATGGCTGGGTGATCCGTGGCAACAATGACGGTGGCTGCGATGGTTA TCGCTGTGGTGACAAGACCTCCATCAAGGTGACCAATTTTGCCTACAACCTGGATCCTGACAGTTTC AAGCATGGCGATGTGACCCAGTCCGACCGCCAACTGGTCAAGACGGTGGTGGGGTGGGCTATCAACG ACAGCGACACGCCTCAATCCGGTTATGACGTCACCCTGCGCTACGACACGGCCACCAACTGGTCCAA GACCAACACCTATGGTCTGAGCGAGAAGGTGACCACCAAGAACAAGTTCAAGTGGCCGCTGGTGGGG GAAACCGAGCTCTCCATCGAGATTGCTGCCAACCAGTCCTGGGCCTCCCAGAACGGGGGCTCGACCA CCACCTCTTTGTCCCAGTCCGTGCGCCCGACAGTGCCGGCCCACTCCAAGATCCCGGTGAAGATAGA GCTCTACAAAGCCGACATCTCCTACCCCTACGAGTTCAAGGCCGATGTCAGCTATGACCTGACCCTG AGCGGTTTCCTGCGTTGGGGCGGTAATGCCTGGTATACCCATCCGGACAACCGTCCGAACTGGAACC ACACCTTCGTCATAGGGCCATACAAGGACAAGGCCAGCAGTATCCGCTACCAGTGGGACAAGCGTTA TATCCCGGGTGAAGTGAAGTGGTGGGATTGGAACTGGACCATACAGCAGAACGGTCTGCCTACCATG CAGAATAACCTGGCCAGGGTGCTGCGCCCGGTGCGGGCCGGGATCACCGGTGATTTCAGTGCCGAGA GCCAGTTTGCCGGCAACATCGAAATCGGCGCTCCCGTGCCGGTCGCTGCCGAATCTAAGGGTATCGA GCCAGATTCTGGTGTTGAAGGTGCCGGTCAGGGTCTGAGACTGGAGATCCCGCTCGATGCACAAGAG CTCTCCGGGCTTGGCTTCAACAATGTCAGCCTCAGCGTGACCCCTGCTGCCAACCAAGTCGAGCACC ACCACCACCACCAC |

-continued

| SEQ ID NO: | NAME | NOTES | SEQUENCE |
|---|---|---|---|
| 105- | Protein Sequence for anti-CD5-LPETQ | | MANIQLVQSGPELKKPGETVKISCKASGYTFTNYGMNWVKQAPGKGLRWMGWINTHTGEPTYADDFK<br>GRFAFSLETSASTAYLQINNLKNEDTATYFCTRRGYDWYFDVWGAGTTVTVFSCCGGSGGGGSGGGS<br>SDIKMTQSPSSMYASLGERVTITCKASQDINSYLSWFHHKPGKSPKTLIYRANRLVDGVPSRFSGSG<br>SGQDYSLTISSLDYEDMGIYYCQQYDESPWTFGGGTKLEMRLERPHGGGSLPETGGVEHHHHHH |
| 106 | DNA Sequence for anti-CD5-LPETG | | ATGGCCAACATCCAGCTGGTGCAGTCTGGTCCTGAGCTGAAGAAGCCTGGTGAGACTGTCAAAATCT<br>CCTGCAAGGCTTCTGGGTATACCTTCACTAACTATGGTATGAACTGGGTGAAGCAGGCTCCTGGTAA<br>GGGTCTGCGTTGGATGGGCTGGATTAACACCCACACTGGTGAGCCTACTTATGCTGATGACTTCAAG<br>GGACGTTTTGCCTTCTCTCTGGAAACTTCTGCCAGCACTGCCTATCTCCAGATCAACAACCTCAAAA<br>ATGAGGACACTGCTACTTACTTCTGTACACGTCGTGGTTACGACTGGTACTTCGATGTCTGGGGTGC<br>TGGGACCACGGTGACCGTGTTCTCCGGGGGAGGTGGCAGCGGGGGAGGTGGCAGCGGCGGCGGGAGC<br>TCCGACATCAAGATGACCCAGTCTCCTTCTTCCATGTATGCTTCTCTGGGTGAGCGTGTCACTATCA<br>CTTGCAAGGCCAGCCAGGACATTAATAGCTATCTGAGCTGGTTCCATCATAAACCTGGGAAATCTCC<br>TAAGACCCTGATCTATCGTGCTAACCGTCTGGTTGATGGGGTCCCTTCTCGTTTCAGCGGCTCTGGT<br>TCTGGGCAAGATTATTCTCTCACCATCAGCAGCCTGGACTATGAAGATATGGGTATTTATTATTGTC<br>AACAGTATGATGAGTCTCCTTGGACTTTCGGTGGTGGCACCAAGCTGCAGATGCGTCTCGAGCGGCC<br>GCATGGCGGCGGCTCCCTGCCAGAGACTGGCGGGGTCGAGCACCACCACCACCACCAC |
| 107 | Protein Sequence forTrx-DT-CCPE | | 10 20 30 40 50 60<br>MGSDKIIHLT DDSFDTDVLK ADGAILVDFW AHWCGPCKMI APILDEIADE YQGKLTVAKL<br>70 80 90 100 110 120<br>NIDHNPGTAP KYGIRGIPTL LLFKNGEVAA TKVGALSKGQ LKEFLDANLA GSGSCDDDDK<br>130 140 150 160 170 180<br>LGIDPFTEML YFQGGADDVV DSSKSEVMEM FASYHGTKPG YVDSIQKGIQ KPKSGTQGNY<br>190 200 210 220 230 240<br>DDDWKGFYST DNKYDAAGYS VDNENPLSGK AGGVVKVTYP GLTKVLALKV DNAETIKKEL<br>250 260 270 280 290 300<br>GLSLTEPLME QVGTEEFIKR FGDGASRVVL SLPFAEGSSS VEYINNWEQA KALSVELEIN<br>310 320 330 340 350 360<br>FETRGKRGQD AMYEYMAQAC AGNIEPDTGS SLSCINLDWD VIRDKTKTKI ESLKEHGPIK<br>370 380 390 400 410 420<br>NKMSESPAKT VSEEKAKQYL EEFHQTALEH FELSELKTVT GTNPVFAGAN YAAWAVNVAQ<br>430 440 450 460 470 480<br>VIDSETADNL EKTTAALSIL PGIGSVMGIA DGAVHHNTEE IVAQSIALSS LMVAQATPLV<br>490 500 510 520 530 540<br>GELVDIGFAA YNFVESIINL FQVVHNSYNR PAYSPGHKTQ PAMGGGGSGG GGSGGGGSKG<br>550 560 570 580 590 600<br>ELERCVLTVP STDIEKEILD LAAATERLNL TDALNSNPAG NLYDWRSSNS YPWTQKLNLH<br>610 620 630 640 650 660<br>LTITATGQKY RILASKIVDF NIYSNNFNNL VKLEQSLGDG VKDHYVDISL DAGQYVLVMK<br>670 680 690 700<br>ANSSYSGNYP YSILFQKFKL EGKPIPNPLL GLDSTRTGHH HHHH |
| 108 | DNA Sequence for Trx-DT-CCPE | | CC**ATG**GGATCTGATAAAATTATTCATCTGACTGATGATTCTTTTGATACTGATGTACTTAAGGCAGA<br>TGGTGCAATCCTGGTTGATTTCTGGGCACACTGGTGCGGTCCGTGCAAAATGATCGCTCCGATTCTG<br>GATGAAATCGCTGACGAATATCAGGGCAAACTGACCGTTGCAAAACTGAACATCGATCACAACCCGG<br>GCACTGCGCCGAAATATGGCATCCGTGGTATCCCGACTCTGCTGCTGTTCAAAAACGGTGAAGTGGC<br>GGCAACCAAAGTGGGTGCACTGTCTAAAGGTCAGTTGAAAGAGTTCCTCGACGCTAACCTGGCCGGC<br>TCTGGATCCGGTGATGACGATGACAAGCTGGGAATTGATCCCTTCACCGAGAACCTGTACTTCCAGG<br>GCGGTGCCGACGACGTGGTGGACTCCTCCAAGTCCTTCGTGATGGAAAACTTCGCTTCCTACCACGG<br>TACCAAGCCTGGTTACGTGGATTCCATCCAGAAGGGTATCCAGAAGCCTAAGTCCGGTACCCAGGGT<br>AACTACGACGATGATTGGAAGGGTTTTTACTCCACCGACAACAAGTACGACGCCGCCGGTTACTCCG<br>TGGATAACGAAAACCCTCTGTCCGGTAAGGCCGGTGGTGTGGTGAAAGTGACCTACCCTGGTCTGAC<br>CAAGGTGCTGGCCCTGAAGGTGGATAACGCCGAAACCATCAAGAAGGAGCTGGGTCTGTCCCTGACC<br>GAACCTCTGATGGAGCAGGTGGGTACCGAAGAGTTTATCAAGAGATTCGGTGATGGTGCCTCCAGAG<br>TGGTGCTGTCCCTGCCTTTCGCCGAGGGTTCCTCCTCCGTGGAATACATCAACAACTGGGAACAGGC<br>CAAGGCCCTGTCCGTGGAACTGGAGATCAACTTTGAAACCAGAGGTAAGAGAGGTCAGGATGCCATG<br>TACGAGTAcatggcccaggcctgtgccggCAACATCGAGCCTGACACCGgttcctccctgtccTGCA<br>TCAACCTGGACTGGGACGTGATCAGAGACAAGACCAAGACCAAGATCGAGTCCCTGAAGGAGCACGG<br>TCCTATCAAGAACAAGATGTCCGAGTCCCCTGCCAAGACCGTGTCCGAGGAGAAGGCCAAGCAGTAC<br>CTGGAGGAGTTCCACCAGACCGCCCTGGAGCACCCTGAGCTGTCCGAGCTGAAGACCGTGACTGGTA<br>CCAACCCTGTGTTCGCCGGTGCCAACTACGCCGCCTGGGCCGTGAACGTGGCCCAGGTGATCGACTC<br>CGAGACCGCCGACAACCTGGAGAAGACCACCGCCGCCCTGTCCATCCTGCCTGGTATCGGTTCCGTG<br>ATGGGTATCGCCGACGGTGCCGTGCACCACAACACCGAGGAGATCGTGGCCCAGTCCATCGCCCTGT<br>CCTCCCTGATGGTGGCCCAGGCCATCCCTCTGGTGGGTGAGCTGGTGGACATCGGTTTCGCCGCCTA<br>CAACTTCGTGGAGTCCATCATCAACCTGTTCCAGGTGGTGCACAACTCCTACAACAGACCTGCCTAC<br>TCCCCTGGTCACAAGACCCAGCCTGCCATGGGAGGCGGAGGCTCCGGAGGAGGAGGGTCCGGGGGCG<br>GCGGAAGCaagggcgagctcGAAAGATGTGTTTTAACAGTTCCATCTACAGATATAGAAAAAGAAAT<br>CCTTGATTTAGCTGCTGCTACAGAAAGATTAAATTTAACTGATGCATTAAACTCAAATCCAGCTGGT<br>AATTTATATGATTGGCGTTCTTCTAACTCATACCCTTGGACTCAAAAGCTCAATTTACACTTAACAA<br>TTACAGCTACTGGACAAAAATATAGAATCTTAGCTAGCAAAATTGTTGATTTTAATATTTATTCAAA<br>TAATTTTAATAATCTAGTGAAATTAGAACAGTCCTTAGGTGATGGAGTAAAAGATCATTATGTTGAT<br>ATAAGTTTAGATGCTGGACAATATGTTCTTGTAATGAAAGCTAATTCATCATATAGTGGAAATTACC<br>CTTATTCAATATTATTTCAAAAATTTaagcttGAAGGTAAGCCTATCCCTAACCCTCTCCTCGGTCT<br>CGATTCTACGCGTACCGCTCATCATCACCATCACCATTGAgtttaaac |

-continued

| SEQ ID NO: | NAME | NOTES | SEQUENCE |
|---|---|---|---|
| 109 | Protein Sequence for DT-CCPE | | 10 20 30 40 50 60<br>GGADDVVDSS KSFVMENFAS YHGTKPGYVD SIQKGIQKPK SGTQGNYDDD WKGFYSTDNK<br>70 80 90 100 110 120<br>YDAAGYSVDN ENPLSGKAGG VVKVTYPGLT KVLALKVDNA ETIKKELGLS LTEPLMEQVG<br>130 140 150 160 170 180<br>TEEFIKRFGD GASRVVLSLP FAEGSSSVEY INNWEQAKAL SVELEINFET RGKRGQDAMY<br>190 200 210 220 230 240<br>EYMAQACAGN IEPDTGSSLS CINLDWDVIR DKTKTKIESL KEHGPINKM SESPAKTVSE<br>250 260 270 280 290 300<br>EKAKQYLEEE HQTALEHPEL SELKTVTGTN PVFAGANYAA WAVNVAQVID SETADNLEKT<br>310 320 330 340 350 360<br>TAALSILPGI GSVMGIADGA VHHNTEEIVA QSIALSSLMV AQAIFLVGEL VDICFAAYNF<br>370 380 390 400 410 420<br>VESIINLFQV VHNSYNRPAY SPGHKTQPAM GGGGSGGGGS GGGGSKGELE RCVLTVPSTD<br>430 440 450 460 470 480<br>IEKEILDLAA ATERLNLTDA LNSNPAGNLY DWRSSNSYPW TQKLNLHLTI TATGQKYRIL<br>490 500 510 520 530 540<br>ASKIVDFNIY SNNFNNLVKL EQSLGDCVKD HYVDISLDAG QYVLVMKANS SYSGNYPYSI<br>550 560 570<br>LFQKFKLEGK PIPNPLLGLD STRTGHHHHH H |
| 110 | Protein Sequence for Pro-GrB-$(YSA)_2$ (expressed in pEAK15) | | 10 20 30 40 50 60<br>GQRAGCCAVS SFWQRIARGQ QKLAATMGVK VLFALICIAV ALADNSSYKD DDDKIIGGHE<br>70 80 90 100 110 120<br>AKPHSRPYMA YLMIWDQKSL KRCGGFLIQD DFVLTAAHCW GSSINVTLGA HNIKEQEPTQ<br>130 140 150 160 170 180<br>QFIPVKRPIP HPAYNPKNFS NDIMLLQLER KAKRTRAVQP LRLFSNKAQV KPGQTCSVAG<br>190 200 210 220 230 240<br>WGOTAPLGKH SHTLQEVKMT VQEDRKCESD LRHYYDSTIE LCVGDPEIKK TSFKGDSGGP<br>250 260 270 280 290 300<br>LVCNKVAQGI VSYGRNNGNP PRACTKVSSF VHWIKKTMKR YAMGGGGSYS AYPDSVPMMS<br>310 320 330<br>GGGGSYSAYP DSVPMMSGGG GSHHHHHH |
| 111 | DNA Sequence for Pro-GrB-$(YSA)_2$ | | GGGCAACGTGCTGGTTGTTGTGCTGTCTCATCATTTTGGCAAAGAATTgcacgaggtcagcagAagc<br>ttgccgccacc**ATG**GGCGTGAAGGTGCTGTTCGCCCTGATCTGCATCGCCGTGGCGctcgccgacaa<br>ctcgagctacaaggacgacgacgacaagATCATCGGGGGACATGAGGCCAAGCCCCACTCCCGCCCC<br>TACATGGCTTATCTTATGATCTGGGATCAGAAGTCTCTGAAGAGGTGCGGTGGCTTCCTGATACAAG<br>ACGACTTCGTGCTGACAGCTGCTCACTGTTGGGGAAGCTCCATAAATGTCACCTTGGGGGCCCACAA<br>TATCAAAGAACAGGAGCCGACCCAGCAGTTTATCCCTGTGAAAAGACCCATCCCCCATCCAGCCTAT<br>AATCCTAAGAACTTCTCCAACGACATCATGCTACTGCAGCTGGAGAGAAAGGCCAAGCGGACCAGAG<br>CTGTGCAGCCCCTCAGGCTACCTAGCAACAAGGCCCAGGTGAAGCCAGGGCAGACATGCAGTGTGGC<br>CGGCTGGGGGCAGACCGCCCCCCTGGGAAAACACTCACACACACTACAAGAGGTGAAGATCACAGTG<br>CAGGAAGATCGAAAGTGCGAATCTGACTTACGCCATTATTACGACAGTACCATTGAGTTGTGCGTGG<br>GGGACCCAGAGATTAAAAAGACTTCCTTTAAGGGGGACTCTGGAGGCCCTCTTGTGTGTAACAAGGT<br>GGCCCAGGGCATTGTCTCCTATGGACGAAACAATGGCATGCCTCCACGAGCCTGCACCAAAGTCTCA<br>AGCTTTGTACACTGGATAAAGAAAACCATGAAACGCTACGCCATGGGTGGCGGTGGCTCTTACTCCG<br>CTTATCCTGATTCCGTTCCAATGATGTCTGGCGGTGGCGGTTCCTATTCTGCCTACCCAGACTCCGT<br>CCCTATGATGTCTGGTGGCCGTGGCTCCCATCACCATCACCATCACAAGGATTAAAAGCTTGAAGTC<br>CGAGGAATTCGGGACAgcggccgc |
| 112 | Protein Sequence for Activated GrB-$(YSA)_2$ | | 10 20 30 40 50 60<br>IIGGREAKPH SRPYMAYLMI WDQKSLKRCG GFLIQDDFVL TAAHCWGSSI NVTLGAHNIK<br>70 80 90 100 110 120<br>EQEPTQQFIP VKRPIPHPAY NPKNFSNDIM LLQLERKAKR TRAVQPLRLP SNKAQVKPGQ<br>130 140 150 160 170 180<br>TCSVAGWGQT APLGKHSHTL QEVKMTVQED RKCESDLRHY YDSTIELCVG DPEIKKTSFK<br>190 200 210 220 230 240<br>GDSGGPLVCN KVAQGIVSYG RNNGMPPRAC TKVSSFVHWI KKTMKRYAMG GGGSYSAYPD<br>250 260 270<br>SVPMMSGGGG SYSAYPDSVP MMSGGGGSHH HHHH |
| 113 | DNA Sequence for GrB-$(YSA)_2$ | | ATCATCGGGGGACATGAGGCCAAGCCCCACTCCCGCCCCTACATGGCTTATCTTATGATCTGGGATC<br>AGAAGTCTCTGAAGAGGTGCGGTGGCTTCCTGATACAAGACGACTACGTGCTGACAGCTGCTCACTG<br>TTGGGGAAGCTCCATAAATGTCACCTTGGGGGCCCACAATATCAAAGAACAGGAGCCGACCCAGCAG<br>TTTATCCCTGTGAAAAGACCCATCCCCCATCCAGCCTATAATCCTAAGAACTTCTCCAACGACATCA<br>TGCTACTGCAGCTGGAGAGAAAGGCCAAGCGGACCAGAGCTGTGCAGCCCCTCAGGCTACCTAGCAA<br>CAAGGCCCAGGTGAAGCCAGGGCAGACATGCAGTGTGGCCGGCTGGGGGCAGACGGCCCCCCTGGGA<br>AAACACTCACACACACTACAAGAGGTGAAGATGACAGTGCAGGAAGATCGAAAGTGCGAATCTGACT<br>TACGCCATTATTACGACAGTACCATTGAGTTGTGCGTGGGGGACCCAGAGATTAAAAAGACTTCCTT<br>TAAGGGGGACTCTGGAGGCCCTCTTGTGTGTAACAAGGTGGCCCAGGGCATTGTCTCCTATGGACGA<br>AACAATGGCATGCCTCCACGAGCCTGCACCAAAGTCTCAAGCTTTGTACACTGGATAAAGAAAACCA<br>TGAAACGCTACGCCATGGGTGGCGGTGGCTCTTACTCCGCTTATCCTGATTCCGTTCCAATGATGTC<br>TGGCGGTGGCGGTTCCTATTCTGCCTACCCAGACTCCGTCCCTATGATGTCTGGTGGCGGTGGCTCC<br>CATCACCATCACCATCACAAGGATTAAAAGCTT |

-continued

| SEQ ID NO: | NAME | NOTES | SEQUENCE |
|---|---|---|---|
| 114 | Protein Sequence for Trx-DT$^A$-anti-CD19 | Proteins with different underlined sequence, including RVRRS, RVRRSS, RVRRAT were also made. | 10 20 30 40 50 60<br>MGSDKIIHLT DDSFDTDVLK ADGAILVDFW AHWCGPCKMI APILDEIADE YQGKLTVAKL<br>70 80 90 100 110 120<br>NIDRNPGTAP KYGIRGIPIL LLFKNGEVAA TKVGALSKGQ LKEFLDANLA GSGSGDDDDK<br>130 140 150 160 170 180<br>LGIDPFTGAD DVVDSSKSFV MEMFASYHGT KPGYVDSIQK GIQKPKSGTQ GNYDDDWKGF<br>190 200 210 220 230 240<br>YSTDNKYDAA GYSVDNENPL SGKAGGVVKV TYPGLTKVLA LKVDNAETIK KELGLSLTEP<br>250 260 270 280 290 300<br>LMEQVGTEEF IKRFGDGASR VVLSLPFAEG SSSVEYINNW EQAKALSVEL EINFETRGKR<br>310 320 330 340 350 360<br>GQDAMYEYMA QACAGN**RVRR** **AS**VGSSLSCI NLDWDVIRDK TKTKIESLKE HGPIKNKMSE<br>370 380 390 400 410 420<br>SPNKTVSEEK AKQYLEEFHQ TALEHPELSE LKTVTGTNPV FAGANYAAWA VNVAQVIDSE<br>430 440 450 460 470 480<br>TADNLEKTTA ALSILPGIGS VMGIADGAVH HNTEEIVAQS IALSSLMVAQ AIPLVGELVD<br>490 500 510 520 530 540<br>IGFAAYNFVE SIINLFQVVH NSYNRPAYSP GHKTQPKGEL KLANIQLVQS GPELKKPGET<br>550 560 570 580 590 600<br>VKISCKASGY TFTNYGMNWV KQAPGKGLRW MGWINTHTGE PTYADDFKGR FAFSLETSAS<br>610 620 630 640 650 660<br>TAYLQINNLK NEDTATYFCT RRGYDWYFDV WGAGTTVTVF SGGGGSGGGG SGGGSSDIKM<br>670 680 690 700 710 720<br>TQSPSSMYAS LGERVTITCK ASQDINSYLS WFHHKPGKSP KTLIYRANRL VDGVPSRFSG<br>730 740 750 760 770 780<br>SGSGQDYSLT ISSLDYEDMG IYYCQQYDES PWTFGGGTKL ENKEQLLISE EDLGHHHHHH |
| 115 | DNA sequence for Trx-DT$^A$-anti-CD19 | | atgggatctgataaaattattcatctgactgatgattcttttgatactgatgtacttaaggcagatg<br>gtgcaatcctggttgatttctgggcacactggtgcggtccgtgcaaaatgatcgctccgattctgga<br>tgaaatcgctgacgaatatcagggcaaactgaccgttgcaaaactgaacatcgatcacaacccgggc<br>actgcgccgaaatatggcatccgtggtatcccgactctctgctgttcaaaaacggtgaagtggcggc<br>aaccaaagtgggtgcactgtctaaaggtcagttgaaagagttcctcgacgctaacctggccggctct<br>ggatccggtgatgacgatgacaagctgggaattgatcccttcaccggcgccgacgacgtggtggact<br>cctccaagtccttcgtcatggaaaacttcgcttcctaccacgggactaaacctggttatgtagattc<br>cattcaaaaaggtatacaaaagccaaaatctggtacacaaggaaattatgacgatgattggaaaggg<br>ttttatagtaccgacaataaatacgacgctgcgggatactctgtagataatgaaaacccgctctctg<br>gaaaagctggaggcgtggtcaaagtgacgtatccaggactgacgaaggttctcgcactaaaagtgga<br>taatgccgaaactattaagaaagagttaggtttaagtctcactgaaccgttgatggagcaagtcgga<br>acggaagagtttatcaaaaggttcggtgatggtgcttcgcgtgtagtgctcagccttcccttcgctg<br>aggggagttctagcgttgaatatattaataactgggaacaggcgaaagcgttaagcgtagaacttga<br>gattaattttgaaacccgtggaaaacgtggccaagatgcgatgtatgagtatatggctcaagcctgt<br>gccggcaatcgcgtgcgccgcgctagcgtggggagctcattgtcatgcatcaacctggactgggacg<br>tgatccgcgacaagaccaagaccaagatcgagtccctgaaggagcacggcccgatcaagaacaagat<br>gtccgagtccccgaacaagaccgtgtccgaggagaaggctaagcagtacctggaggagttccaccag<br>accgctctggagcacccggagctgtccgagctgaaaaccgtgaccggcaccaacccggtgttcgctg<br>gcgctaactacgctgcttgggctgtgaacgtggctcaggtgatcgactccgagactgctgacaacct<br>ggagacaaccaccgctgctctgtccatcctgccgggcatcggctccgtgatgggcatcgctgacggc<br>gctgtgcaccacaacaccgaggagatcgtggctcagtccatcgctctgtcctccctgatggtggctc<br>aggctatcccgctggtgggcgagctggtggacatcggcttcgctgcttacaacttcgtggagtccat<br>catcaacctgttccaggtggtgcacaactcctacaaccgcccggcttactccccgggccacaagacc<br>cagcccaagggcgagctcaagcttgcccaggtgcagctgcagcagtccggcgctgagctggtgcgcc<br>ctggctcctecgtgaaaatctcctgcaaggcttccggctacgctttctcctcctactggatgaactg<br>ggtgaagcagcgccctggccagggcctggagtggatcggcccaatctggccgggcgacggcgccacc<br>aactacaacggcaagttcaagggcaaggctaccctgaccgctgacgagtcctcctccaccgcttaca<br>tgcagctgtcctccctggcttccgaggactccgctgtgtacttctgcgctcgccgcgagaccaccac<br>cgtgggccgctactactacgctatggactactggggccagggcacctcggtgaccgtgtcctccggc<br>ggcggcggctccggcggcggcggctccggcggcgggagctccgacatcctgctgacccagaccccgg<br>cttccctggctgtgtccctgggccagcgcgctaccatctcctgcaaggcttcccagtccgtggacta<br>cgacggcgactcctacctgaactggtaccagcagatcccgggccagccgccgaagctgctgatctac<br>gacgcttccaacctggtgtccggcatcccgccgcgcttctccggctccggctccggcaccgacttca<br>ccctgaacatccacccggtggagaaggtggacgctgctacctaccactgccagcagtccaccgagga<br>cccgtggaccttcggcggcggcaccaagctggagatcaagcgcggtggtgacatgcatcaccatcac<br>catcactgaagctt |
| 116 | Protein Sequence for TrK-DT (containing native cell binding domain) | | MGSDKIIHLTDDSFDTDVLKADGAILVDFWAHWCGPCKMIAPILDEIADEYQGKLTVAKLNIDHNPG<br>TAPKYGIRGIPTLLLFKNGEVAATKVGALSKGQLKEFLDANLAGSGSGENLYFQLGIDPFTGADDVV<br>DSSKSFVMENFASYHGTKPGYVDSIQKGIQKPKSGTQGNYDDDWKGFYSTDNKYDAAGYSVDNENPL<br>SGKAGGVVKVTYPGLTKVLALKVDNAETIKKELGLSLTEPLMEQVGTEEFIKRFGDGASRVVLSLPF<br>AEGSSSVEYINNWEQAKALSVELEINFETRGKRGQDAMYEYMAQACAGNRVRRASVGSSLSCINLDW<br>DVIRDKTKTKIESLKEHGPIKNKMSESPNKTVSEEKAKQYLEEFHQTALEHPELSELKTVTGTNPVF<br>AGANYAAWAVNVAQVIDSETADNLEKTTAALSILPGIGSVMGIADGAVHHNTEEIVAQSIALSSLMV<br>AQAIPLVGELVDIGFAAYNFVESIINLFQVVHNSYNRPAYSPGHKTQPKGELKLFLHDGYAVSWNTV<br>EDSIIRTGFQGESGHSIKITAENTPLPIAGVLLPTIPGKLDVNKSKTHISVNGRKIRMRCRAIDGDV<br>TFCRPKSPVYVGNGVHANLHVAFNRSSSEKIHSNEISSDSIGVLGYQKTVDHTKVNSKLSLFFEIKS<br>KLEGKPIPNPLLGLDSTRTGHHHHHH |

-continued

| SEQ ID NO: | NAME | NOTES | SEQUENCE |
|---|---|---|---|
| 117 | DNA Sequence for Trx-DT (containing native cell binding domain) | | ATGGCATCTGATAAAATTATTCATCTGACTGATGATTCTTTTGATACTGATGTACTTAAGGCAGATG<br>GTGCAATCCTGGTTGATTTCTGGGCACACTGGTGCGGTCCGTGCAAAATGATCGCTCCGATTCTGGA<br>TGAAATCGCTGACGAATATCAGGGCAAACTGACCGTTGCAAAACTGAACATCGATCACAACCCGGGC<br>ACTGCGCCGAAATATGGCATCCGTGGTATCCCGACTCTGCTGCTGTTCAAAAACGGTGAAGTGGCGG<br>CAACCAAAGTGGGTGCACTGTCTAAAGGTCAGTTGAAAGAGTTCCTCGACGCTAACCTGGCCGGCTC<br>TGGATCCGGT **GAA AAC CTG TAT TTT CAG GGC** CTGGGAATTGATCCCTTCACC<br>GGCGCCGACGACGTGGTGGACTCCTCCAAGTCCTTCGTCATGGAAAACTTCGCTTCCTACCACGGGA<br>CTAAACCTGGTTATGTAGATTCCATTCAAAAAGGTATACAAAAGCCAAAATCTGGTACACAAGGAAA<br>TTATGACGATGATTGGAAAGGGTTTTATAGTACCGACAATAAATACGACGCTGCGGGATACTCTGTA<br>GATAATGAAAACCCGCTCTCTGGAAAAGCTGGAGGCGTGGTCAAAGTGACGTATCCAGGACTGACGA<br>AGGTTCTCGCACTAAAAGTGGATAATGCCGAAACTATTAAGAAAGAGTTAGGTTTAAGTCTCACTGA<br>ACCGTTGATGGAGCAAGTCGGAACGGAAGAGTTTATCAAAAGGTTCGGTGATGGTGCTTCGCGTGTA<br>GTGCTCAGCCTTCCCTTCGCTGAGGGGAGTTCTAGCGTTGAATATATTAATAACTGGGAACAGGCGA<br>AAGCGTTAAGCGTAGAACTTGAGATTAATTTTGAAACCGGTGGAAAACGTGGCCAAGATGCGATGTA<br>TGAGTATatggctcaagcctgtgccggcAAT**cgcgtgcgccgcGCTagcgtgggg**agctcattgtca<br>TGCATCAACCTGGACTGGGACGTGATCCGCGACAAGACCAAGACCAAGATCGAGTCCCTGAAGGAGC<br>ACGGCCCGATCAAGAACAAGATGTCCGAGTCCCCGAACAAGACCGTGTCCGAGGAGAAGGCTAAGCA<br>GTACCTGGAGGAGTTCCACCAGACCGCTCTGGAGCACCCGGAGCTGTCCGAGCTGAAAACCGTGACC<br>GGCACCAACCCGGTGTTCGCTGGCGCTAACTACGCTGCTTGGGCTGTGAACGTGGCTCAGGTGATCG<br>ACTCCGAGACTGCTGACAACCTGGAGAAAACCACCGCTGCTCTGTCCATCCTGCCGGGGATCGGCTC<br>CGTGATGGGCATCGCTGACGGCGCTGTGCACCACAACACCGAGGAGATCGTGCCTCAGTCCATCGCT<br>CTGTCCTCCCTGATGGTGGCTCAGGCTATCCCGCTGGTGGGCGAGCTGGTGGACATCGGCTTCGCTG<br>CTTACAACTTCGTGGAGTCCATCATCAACCTGTTCCAGGTGGTGCACAACTCCTACAACCGCCCGGC<br>TTACTCCCCGGGCCACAAGACCCAGCCC<br>AAGGGCGAGCTCAAGCTTTTTCTTCATGACGGGTATGCTGTCAGTTGGAACACTGTTGAAGATTCGA<br>TAATCCGAACTGGTTTTCAAGGGGAGAGTGGGCACGACATAAAAATTACTGCTGAAAATACCCCGCT<br>TCCAATCGCGGGTGTCCTACTACCGACTATTCCTGGAAAGCTGGACGTTAATAAGTCCAAGACTCAT<br>ATTTCCGTAAATGGTCGGAAAATAAGGATGCGTTGCAGAGCTATAGACGGTGATGTAACTTTTTGTC<br>GCCCTAAATCTCCTGTTTATGTTCGTAATGGTGTGCATGCGAATCTTCACGTGGCATTTCACAGAAG<br>CAGCTCGGAGAAAATTCATTCTAATGAAATTTCGTCGGATTCCATAGGCGTTCTTGGGTACCAGAAA<br>ACAGTAGATCACACCAAGGTTAATTCTAAGCTATCGCTATTTTTTGAAATCAAAAGCAAGCTT |
| 118 | DT-anti-CD2219 protein sequence | | MGADDVVDSS KSFVMENFAS YHGTKPGYVD SIQKGIQKPK SGTQGNYDDD WKGFYSTDNK<br>YDAAGYSVDN ENPLSGKAGG VVKVTYPGLT KVLALKVDNA ETIKKELGLS LTEPLNEQVG<br>TEEFIKRFGD GASRVVLSLP FAEGSSSVEY INNWEQAKAL SVELEINFET RGKRGQDAMY<br>EYNAQACAGN IEPDTGSSLS CINLDWDVIR DKTKTKIESL KEHGPIKNKM SESPAKTVSE<br>EKAKQYLEEF HQTALEHPEL SELKTVTGTN PVFAGANYAA WAVNVAQVID SETADNLEKT<br>TAALSILPGI GSVMGIADGA VHHNTEEIVA QSIALSSLMV AQAIPLVGEL VDIGFAAYNF<br>VESIINLFQV VHNSYNRPAY SPGHKTQPAM EVQLVESGGG LVKPGGSLKL SCAASGFAFS<br>IYDMSWVRQT PEKRLEWVAY ISSGGGTTYY PDTVKGRFTI SRDNAKNTLY LQMSSLKSED<br>TAMYYCARHS GYGTHWGVLF AYWGQGTLVT VSAGGGGSGG GGSGGGSSDI QMTQTTSSLS<br>ASLGDRVTIS CRASQDIARY LNWYQQKPDG TVKLLIYYTS ILHSGVFSRF SGSGSGTDYS<br>LTISNLEQED FATYFCQQGN TLPWTFGGGT KLEIKTGPSG QAGAAASESL FVSNHAYTMA<br>QVQLQQSGAE LVRPGSSVKI SCKASGYAFS SYWMNWVKQR PGQGLEWIGQ IWPGOGDTNY<br>NGKFKGKATL TADESSSTAY MQLSSLASED SAVYFCARRE TTTVGRYYYA MDYWGQGTSV<br>TVSSGGGGSG GGGSGGGSSD ILLTQTPASL AVSLGQRATI SCKASQSVDY DGDSYLNWYQ<br>QIPGQPPKLL IYDASNLVSG IPPRFSGSGS GTDFTLNIHP VEKVDAATYH CQQSTEDPWT<br>FGGGTKLEIK RGGDMHHHHH H |
| 119 | DT-anti-CD2219 DNA sequence | | ATGGGTGCCGACGACGTGGTGGACTCCTCCAAGTCCTTCGTGATGGAAAACTTCGCTTCCTACCACG<br>GTACCAAGCCTGGTTACGTGGATTCCATCCAGAAGGGTATCCAGAAGCCTAAGTCCGGTACCCAGGG<br>TAACTACGACGATGATTGGAAGGGTTTTTACTCCACCGACAACAAGTACGACGCCGCCGGTTACTCC<br>GTGGATAACGAAAACCCTCTGTCCGGTAAGGCCGGTGGTGTGGTGAAAGTGACCTACCCTGGTCTGA<br>CCAAGGTGCTGGCCCTGAAGGTGGATAACGCCGAAACCATCAAGAAGGAGCTGGGTCTGTCCCTGAC<br>CGAACCTCTGATGGAGCAGGTGGGTACCGAAGAGTTTATCAAGAGATTCGGTGATGGTGCCTCCAGA<br>GTGGTGCTGTCCCTGCCTTTCGCCGAGGGTTCCTCCTCCGTGGAATACATCAACAACTGGGAACAGG<br>CCAAGGCCCTGTCCGTGGAACTGGAGATCAACTTTGAAACCAGAGGTAAGAGAGGTCAGGATGCCAT<br>GTACGAGTACatggcccaggcctgtgccggCAACATCGAGCCTGACACCGgttcctccctgtccTGC<br>ATCAACCTGGACTGGGACGTGATCAGAGACAAGACCAAGACCAAGATCGAGTCCCTGAAGGAGCACG<br>GTCCTATCAAGAACAAGATGTCCGAGTCCCCTGCCAAGACCGTGTCCGAGGAGAAGGCCAAGCAGTA<br>CCTGGAGGAGTTCCACCAGACCGCCCTGGAGCACCCTGAGCTGTCCGAGCTGAAGACCGTGACTGGT<br>ACCAACCCTGTGTTCGCCGGTGCCAACTACGCCGCCTGGGCCGTGAACGTGGCCCAGGTGATCGACT<br>CCGAGACCGCCGACAACCTGGAGAAGACCACCGCCGCCCTGTCCATCCTGCCTGGTATCGGTTCCGT<br>GATGGGTATCGCCGACGGTGCCGTCCACCACAACACCGAGGAGATCGTGGCCCAGTCCATCGCCCTG<br>TCCTCCCTGATGGTGGCCCAGGCCATCCCTCTGGTGGGTGAGCTGGTGGACATCGGTTTCGCCGCCT<br>ACAACTTCGTGGAGTCCATCATCAACCTGTTCCAGGTGGTGCACAACTCCTACAACAGACCTGCCTA<br>CTCCCCTGGTCACAAGACCCAGCCTGccATGGAGGTTCAGCTGGTTGAGTCCGGTGGTGGTCTGGTT<br>AAGCCAGGTGGTTCCCTGAAGCTGTCCTGTGCTGCTTCCGGTTTCGCTTTCTCCATCTACGATATGT<br>CCTGGGTTAGACAGACCCCAGAGAAGAGACTGGAGTGGGTTGCTTACATCTCCTCCGGTGGTGGTAC<br>CACCTACTACCCAGACACCGTTAAGGGTAGATTCACCATCTCCAGAGATAACGCTAAGAACACCCTG<br>TACCTGCAGATGTCCTCCCTGAAGTCCGAGGACACCGCTATGTACTACTGTGCTAGACATTCCGGTT<br>ACGGTACCCATTGGGGTGTTCTGTTCGCTTACTGGGGTCAGGGTACCCTGGTTACCGTTTCCGCTGG<br>TGGTGGTGGTTCCGGTGGTGGTGGTTCCGGTGGTGGGAGCTCCGATATCCAGATGACCCAGACCACC<br>TCCTCCCTGTCCGCTTCCCTGGGTGACAGAGTTACCATCTCCTGTAGAGCTTCCCAGGATATCGCTA<br>GATACCTGAACTGGTACCAGCAGAACCCAGACGGTACCGTTAAGCTGCTGATCTACTACACCTCCAT<br>CCTGCATTCCGGTGTTCCATCCAGATTCTCCGGTTCCGGTTCCGGTACCGATTACTCCCTGACCATC |

-continued

| SEQ ID NO: | NAME | NOTES | SEQUENCE |
|---|---|---|---|
| | | | TCCAACCTGGAGCAGGAGGACTTCGCTACCTACTTCTGTCAGCAGGGTAACACCCTGCCTTGGACCT<br>TCGGTGGTGGTACCAAGCTGGAGATCAAGACTGGTCCATCCGGTCAGGCTGGTGCTGCTgctTCCGA<br>GTCCTTGTTCGTTTCCAACCACGCTTACACCATGGCCCAGGTTCAGTTGCAGCAGTCCGGTGCTGAG<br>TTGGTTAGACCAGGTTCCTCTGTTAAGATCTCTTGTAAGGCCTCTGGCTATGCTTTTTCCTCTTACT<br>GGATGAACTGGGTTAAGCAGAGACCAGGTCAGGGCTTGGAATGGATCGGTCAAATTTGGCCAGGTGA<br>TGGTGATACTAACTACAACGGTAAGTTCAAGGGTAAGGCTACTTTGACTGCTGACGAATCCTCCTCT<br>ACTGCCTATATGCAACTGTCCTCTCTGGCTTCTGAAGATTCTGCTGTTTACTTCTGCGCTAGAAGAG<br>AAACCACTACCGTTGGTAGATACTACTATGCTATGGATTACTGGGGTCAAGGTACCTCGGTGACCGT<br>TTCTTCCGGTGGCGGTGGTTCTGGTGGTGGTGGCTCTGGTGGTGGGAGCTCCGATATCTTGTTGACT<br>CAAACCCCAGCTTCTTTGGCTGTGTCTCTGGGTCAAAGAGCTACTATTTCCTGCAAGGCTTCTCAAT<br>CTGTGGATTACGATGGTGACTCCTACTTGAATTGGTATCAGCAGATTCCAGGTCAGCCTCCTAAGCT<br>GTTGATCTACGATGCTTCCAACTTGGTCTCCGGTATCCCACCAAGATTCTCCGGTTCTGGTTCCGGT<br>ACTGACTTCACTTTGAACATCCACCCAGTTGAGAAAGTGGATGCTGCCACTTACCACTGCCAACAAT<br>CTACCGAGGATCCTTGGACTTTCGGTGGTGGTACCAAGTTGGAGATCAAAAGAGGTGGTGACATGCA<br>CCATCACCACCACCATTAA |
| 120 | GrB-anti-CD1919 protein sequence | | IIGGHEAKPR SRPYMAYLMI WDQKSLKRCG GFLIQDDFVL TAAHCWGSSI NVTLGAHNIK<br>EQEETQQFIP VKRPIPHPAY NPKNFSNDIM LLQLERKAKR TRAVQPLRLP SNKAQVKPGQ<br>TCSVAGWGQT APLGKHSHTL QEVKMTVQED RKCESDLRHY YDSTIELCVG DPEIKKTSFK<br>GDSGGPLVCN KVAQGIVSYG RNNGMPPRAC TKVSSFVHWI KKTMKRYPNG GGGSGGGGSG<br>GGGSAQVQLQ QSGAELVRFG SSVKISCKPS GYAFSSYWMN WVKQRPGQGL EWIGQIWPGD<br>GDTNYNGKFK GKATLTADES SSTAYMQLSS LASEOSAVYF CARRETTTVG RYYYAMDYWG<br>QGTSVTVSSG GGGSGGGGSG GGSSDILLTQ TPASLAVSLG QRATISCKAS QSVDYDGDSY<br>LNWYQQIPGQ PPKLLIYDAS NLVSGIPPRF SGSGSGTDFT LNIHPVEKVD AATYHCQQST<br>EDPWTEGGGT KLEIKRGGDM GNSGGGGAQV QLQQSGAELV RPGSSVKISC KASGYAFSSY<br>WMNWVKQRPG QGLEWIGQIW PGDGDTNYNG KFKGKATLTA DESSSTAYMQ LSSLASEDSA<br>VYFCARRETT TVGRYYYAND YWGQGTSVTV SSGGGGSGGG GSGGGSSDIL LTQTPASLAV<br>SLGQRATISC KASQSVDYDG DSYLNWYQQI PGQPPKLLIY DASNLVSGIP PRFSGSGSGT<br>DFTLNIHPVE KVOAATYHCQ QSTEDPWTFG GGTKLEIKRG GDMHHHHHH |
| 121 | GrB-anti-CD1919 DNA sequence | | atcatcgggggacatgaggccaagccccactcccgcccctacatggcttatettatgatctgggatc<br>agaagtctctgaagaggtgcggtggcttcctgatacaagacgacttcgtgctgacagctgctcactg<br>ttggggaagctccataaatgtcaccttgggggcccacaatatcaaagaacaggagccgacccagcag<br>tttatccctgtgaaaagacccatcccccatccagcctataatcctaaggacttctccaacgacatca<br>tgctactgcagctggagagaaaggccaagcggaccagagctgtgcagcccctcaggctacctagcaa<br>caaggcccaggtgaagccagggcagacatgcagtgtggccggctgggggcagacggccccccctggga<br>aaacactcacaCacactacaagaggtgaggattacagtgcaggaagatcgaaagtgcgaatctgact<br>tacgccattattacgacagtaccattgagttgtgcgtgggggacccagagattaaaaagacttcctt<br>taagggggactctggaggccctcttgtgtgtaacaaggtggcccagggcattgtctcctatggacga<br>aacaatggcatgcctccacgagcctgcaccaaagtctcaagctttgtacactggataaagaaaacca<br>tgaaacgctacgccATGGGAGGCGGAGGCTCCGGAGGAGGAGGGTCCGGGGGCGGCGGAAGCGCCCA<br>GGTTCAGTTGCAGCAGTCCGGTGCTGAGTTGGTTAGACCAGGTTCCTCTGTTAAGATCTCTTGTAAG<br>GCCTCTGGCTATGCTTTTTCCTCTTACTGGATGAACTGGGTTAAGCAGAGACCAGGTCAGGGCTTGG<br>AATGGATCGGTCAAATTTGGCCAGGTGATGCTGATACTAACTACAACGGTAAGTTCAAGGGTAAGGC<br>TACTTTGACTGCTGACGAATCCTCCTCTACTGCCTATATGCAACTGTCCTCTCTGGCTTCTGAAGAT<br>TCTGCTGTTTACTTCTGCGCTAGAAGAGAAACCACTACCGTTGGTAGATACTACTATGCTATGGATT<br>ACTGGGGTCAAGGTACCTCGGTGACCGTTTCTTCCGGTGGCGGTGGTTCTGGTGGTGGTGGCTCTGG<br>TGGTGGGAGCTCCGATATCTTGTTGACTCAAACCCCAGCTTCTTTGGCTGTGTCTCTGGGTCAAAGA<br>GCTACTATTTCCTGCAAGGCTTCTCAATCTGTGGATTACGATGGTGACTCCTACTTGAATTGGTATC<br>AGCAGATTCCAGGTCAGCCTCCTAAGCTGTTGATCTACGATGCTTCCAACTTGGTCTCCGGTATCCC<br>ACCAAGATTCTCCGGTTCTGGTTCCGGTACTGACTTCACTTTGAACATCCACCCAGTTGAGAAAGTG<br>GATGCTGCCACTTACCACTGCCAACAATCTACCGAGGATCCTTGGACTTTCGGTGGTGGTACCAAGT<br>TGGAGATCAAAAGAGGTGGTGACATGGggaattctGGAGGCGGAGGCGCCCAGGTTCAGTTGCAGCA<br>GTCCGGTGCTGAGTTGGTTAGACCACGTTCCTCTGTTAAGATCTCTTGTAAGGCCTCTGGCTATGCT<br>TTTTCCTCTTACTGGATGAACTGGGTTAAGCAGAGACCAGGTCAGGGCTTGGAATGGATCGGTCAAA<br>TTTGGCCAGGTGATGGTGATACTAACTACAACGGTAAGTTCAAGGGTAAGGCTACTTTGACTGCTGA<br>CGAATCCTCCTCTACTGCCTATATGCAACTGTCCTCTCTGGCTTCTGAAGATTCTGCTGTTTACTTC<br>TGCGCTAGAAGAGAAACCACTACCGTTGGTAGATACTACTATGCTATGGATTACTGGGGTCAAGGTA<br>CCTCGGTGACCGTTTCTTCCGGTGTCGGTGGTTCTGGTGGTGGTGGCTCTGGTGGTGGGAGCTCCGA<br>TATCTTGTTGACTCAAACCCCAGCTTCTTTGGCTGTGTCTCTGGGTCAAAGAGCTACTATTTCCTGC<br>AAGGCTTCTCAATCTGTGGATTACGATGGTGACTCCTACTTGAATTGGTATCAGCAGATTCCAGGTC<br>AGCCTCCTAAGCTGTTGATCTACGATGCTTCCAACTTGGTCTCCGGTATCCCACCAAGATTCTCCGG<br>TTCTGGTTCCGGTACTGACTTCACTTTGAACATCCACCCAGTTGAGAAAGTGGATGCTGCCACTTAC<br>CACTGCCAACAATCTACCGAGGATCCTTGGACTTTCGGTGGTGGTACCAAGTTGGAGATCAAAAGAG<br>GTGGTGACATGCACCATCACCACCACCATTAAGC |

-continued

| SEQ ID NO: | NAME | NOTES | SEQUENCE |
|---|---|---|---|
| 122 | MBP-GKGgGS-TEV protein sequence | | MFPSHMKTEE GKLVIWINGD KGYNGLAEVG KKFEKDTGIK VTVEHPDKLE EKFPQVAATG<br>DGPDIIFWAH DRFGGYAQSG LLAEITPDKA FQDKLYPFTW DAVRYNGKLI AYPIAVEALS<br>LIYNKDLLPN PPKTWEEIPA LDKELKAKGK SALMFNLQEP YFTWPLIAAD GGYAFKYENG<br>KYDIKDVGVD NAGAKAGLTF IVDLIKNKHM NADTDYSIAE AAFNKGETAM TINGPWAWSN<br>IDTSKVNYGV TVLPTFKGQP SKPFVGVLSA GINAASPNKE LAKEFLENYL LTDEGLEAVN<br>KDKPLGAVAL KSYEEELAKD PRIAATMENA QKGEIMPNIP QMSAFWYAVR TAVINAASGR<br>QTVDEALKDA QTNSSNNSRR ASVAMLRQIL DSQKMEWRSN AMTGGGSKLG DDDDKGKGGG<br>SKGPRDYNPI SSAICHLTNE SDGHTTSLYG IGFGPFIITN KHLFRRNNGT LLVQSLHGVF<br>KVKNTTTLQQ HLIDGRDMML IRMPKDFPPF PQKLKFREPQ REERICLVTT NFQTKSMSSM<br>VSDTSCTFPS SDGIFWKHWI QTKDGHCGSP LVSTRDGFIV GIHSASNFTN TNNYFTSVPK<br>DFMDLLTNQE AQQWVSGWRL NADSVLWGGH KVFMNKPEEP FQPVKEATQL MSHHHHHH |
| 123 | MBP-GKGGGS-TEV DNA sequence | | atgccaccctcccatATGAAAACTGAAGAAGGTAAACTGGTAATCTGGATTAACGGCGATAAAGGCT<br>ATAACGGTCTCGCTGAAGTCGGTAAGAAATTCGAGAAAGATACCGGAATTAAAGTCACCGTTGAGCA<br>TCCGGATAAACTGGAAGAGAAATTCCCACAGGTTGCGGCAACTGGCGATGGCCCTGACATTATCTTC<br>TGGGCACACGACCGCTTTGGTGGCTACGCTCAATCTGGCCTGTTGGCTGAAATCACCCCGGACAAAG<br>CGTTCCAGGACAAGCTGTATCCGTTTACCTGGGATGCCGTACGTTACAACGGCAAGCTGATTGCTTA<br>CCCGATCGCTGTTGAAGCGTTATCGCTGATTTATAACAAAGATCTGCTGCCGAACCCGCCAAAAACC<br>TGGGAAGAGATCCCGGCGCTGGATAAAGAACTGAAAGCGAAAGGTAAGAGCGCGCTGATGTTCAACC<br>TGCAAGAACCGTACTTCACCTGGCCGCTGATTGCTGCTGACGGGGGTTATGCGTTCAAGTATGAAAA<br>CGGCAAGTACGACATTAAAGACGTGGGCGTGGATAACGCTGGCGCGAAAGCGGGTCTGACCTTCCTG<br>GTTGACCTGATTAAAAACAAACACATGAATGCAGACACCGATTACTCCATCGCAGAAGCTGCCTTTA<br>ATAAAGGCGAAACAGCGATGACCATCAACGGCCCGTGGGCATGGTCCAACATCGACACCAGCAAAGT<br>GAATTATGGTGTAACGGTACTGCCGACCTTCAAGGGTCAACCATCCAAACCGTTCGTTGGCGTGCTG<br>AGCGCAGGTATTAACGCCGCCAGTCCGAACAAAGAGCTGGCAAAAGAGTTCCTCGAAAACTATCTGC<br>TGACTGATGAAGGTCTGGAAGCGGTTAATAAAGACAAACCGCTGGGTGCCGTAGCGCTGAAGTCTTA<br>CGAGGAAGAGTTGGCGAAAGATCCACGTATTGCCGCCACTATGGAAAACGCCCAGAAAGGTGAAATC<br>ATGCCGAACATCCCGCAGATGTCCGCTTTCTGGTATGCCGTCCGTACTGCGGTGATCAACGCCGCCA<br>GCGGTCGTCAGACTGTCGATGAAGCCCTGAAAgacgcgcagactaattcgagcaacaactcacggcg<br>ggctagtgtcgccatgctgcgtcaaattctggattctcaaaaaatggaatggcgctctaacgccatg<br>accggtGGCGGGAGCaagcttggggatgacgatgacaagggcaaaGGCGGCGGGAGCAAAGGTCCGC<br>GTGACTACAACCCGATCTCCTCCGCTATCTGCCACCTGACCAACGAATCCGACGGTCACACCACCTC<br>CCTGTACGGTATCGGTTTCGGTCCGTTCATCATCACCAACAAACACCTGTTCCGTCGTAACAACGGG<br>ACCCTGCTGGTTCAGTCCCTGCACGGTGTTTTCAAAGTTAAAAACACCACCACCCTCCAGCAGCACC<br>TGATCGACGGTCGTGACATGATGCTGATCCGTATGCCGAAAGACTTCCCGCCGTTCCCGCAGAAACT<br>GAAATTCCGTGAACCGCAGCGTGAAGAACGTATCTGCCTCGTTACCACCAACTTCCAGACCAAATCC<br>ATGTCCTCTATGGTTTCCGACACCTCCTGCACCTTCCCGTCCTCCGACGGTATCTTCTGGAAACACT<br>GGATTCAGACCAAAGACGGTCACTGCGGTTCCCCGCTGGTTTCCACCCGTGACGGTTTCATCGTTGG<br>TATCCACTCCGCTTCCAACTTCACCAACACCAACAACTACTTCACCTCCGTTCCGAAAGACTTCATG<br>GACCTCCTGACCAACCAGGAAGCTCAGCAGTGGGTTTCCGGTTGGCGTCTGAACGCTGACTCCGTTC<br>TGTGGGGTGGTCACAAAGTTTTTATGAACAAACCGGAAGAACCGTTCCAGCCGGTTAAAGAAGCTAC<br>CCAGCTCATGTCCCACCATCACCACCACCATtaagcggccgcgaattc |
| 124 | GrM-anti-CD19 protein sequence | | IIGGREVIP HSRPYMASLQ RNGSHLCGGV LVHPKWVLTA AHCLAQRMAQ LRLVLGLHTL<br>DSPGLTFHIK AAIQHPRYKP VPALEWDLAL LQLDGKVKPS RTIRPLALPS KRQVVAAGTR<br>CSMAGWGLTH QGGRLSRVLR ELDLQVLDTR MCNNSRFWNG SLSPSMVCLA ADSKDQAPCK<br>GDSGG2LVCG KGRVLAGVLS FSSRVCTDIF KPPVATAVAP YVSWIRKVTG RSAAMAQVQL<br>QQSGAELVRP GSSVKISCKA SGYAFSSYWM NWVKQRPGQG LEWIGQIWPG DGDTNYNGKF<br>KGKATLTADE SSSTAYMQLS SLASEDSAVY FCARRETTTV GRYYYAMDYW GQGTSVTVSS<br>GGGGSGGGGS GGGSSDILLT QTPASLAVSL GQRATISCKA SQSVDYDGDS YLNWYQQIPG<br>QPPKLLIYDA SNLVSGIPPR FSGSGSGTDF TLNIHPVEKV DAATYHCQQS TEDPWTFGGG<br>TKLEIKRGGD MHHHHHH |
| 125 | GrM-anti-CD19 DNA sequence | | ctcgagctacaaggacgacgacgacaagatcatcgggggccgggaggtgatcccccactcgcgcccg<br>tacatggcctcactgcagagaaatggctcccacctgtgcgggggtgtcctggtgcacccaaagtggg<br>tgctgacggctgcccactgcctggcccagcggatggcccagctgaggctggtgctggggctccacac<br>cctggacagccccggtctcaccttccacatcaaggcagccatccagcaccctcgctacaagcccgtc<br>cctgccctggagaacgacctcgcgctgcttcagctggacgggaaagtgaagcccagccggaccatcc<br>ggccgttggccctgcccagtaagcgccaggtggtggcagcagggactcggtgcagcatggccggctg<br>gggggctgacccaccagggcgggcgcctgtcccgggtgctgcgggagctggacctccaagtgctggac<br>acccgcatgtgtaacaacagccgcttctggaacggcagcctctcccccagcatggtctgcctggcgg<br>ccgactccaaggaccaggctccctgcaagggtgactcgggcgggcccctggtgtgtggcaaaggccg<br>ggtgttggccggagtcctgtccttcagctccagggtctgcactgacatcttcaagcctcccgtggcc<br>accgctgtggcgccttacgtgtcctggatcaggaaggtcaccggccgatcggccgccatggccCAGG<br>TGCAGCTGCAGCAGTCCGGCGCTGAGCTGGTGCGCCCTGGCTCCTCCGTGAAAATCTCCTGCAAGGC<br>TTCCGGCTACGCTTTCTCCTCCTACTGGATGAACTGGGTGAAGCAGCGCCCTGGCCAGGGCCTGGAG<br>TGGATCGGCCAAATCTGGCCGGGCGACGGCGACACCAACTACAACGGCAAGTTCAAGGGCTAGGCTA<br>CCCTGACCGCTGACGAGTCCTCCTCCACCGCTTACATGCAGCTGTCCTCCCTGGCTTCCGAGGACTC<br>CGCTGTGTACTTCTGCGCTCGCCGCGAGACCACCACCGTGGGCCGCTACTACTACGCTATGGACTAC<br>TGGGGCCAGGGCACCTCGGTGACCGTGTCCTCCGGCGGCGGCGGCTCCGGCGGCGGCGGCTCCGGCG<br>GCGGGAGCTCCGACATCCTGCTGACCCAGACCCCGGCTTCCCTGGCTGTGTCCCTGGGCCAGCGCGC<br>TACCATCTCCTGCAAGGCTTCCCAGTCCGTGGACTACGACGGCGACTCCTACCTGAACTGGTACCAG<br>CAGATCCCGGGCCAGCCGCCGAAGCTGCTGATCTACGACGCTTCCAACCTGGTGTCCGGCATCCCGC |

-continued

| SEQ ID NO: | NAME | NOTES | SEQUENCE |
|---|---|---|---|
| | | | CGCGCTTCTCCGGCTCCGGCTCCGGCACCGACTTCACCCTGAACATCCACCCGGTGGAGAAGGTGGA<br>CGCTGCTACCTACCACTGCCAGCAGTCCACCGAGGACCCGTGGACCTTCGGCGGCGGCACCAAGCTG<br>GAGATCAAGCGCggtggtgacatgCACCATCACCACCACCATTAAGC |
| 126 | PP2C-anti-CD5 scFv DNA sequence | | ATGGGATCTGATAAAATTATTCATCTGACTGATGATTCTTTTGATACTGATGTACTTAAGGCAGATG<br>GTGCAATCCTGGTTGATTTCTGGGCACACTGGTGCGGTCCGTGCAAAATGATCGCTCCGATTCTGGA<br>TGAAATCGCTGACGAATATCAGGGCAAACTGACCGTTGCAAAACTGAACATCGATCACAACCCGGGC<br>ACTGCGCCGAAATATGGCATCCGTGGTATCCCGACTCTGCTGCTGTTCAAAAACGGTGAAGTGGCGG<br>CAACCAAAGTGGGTGCACTGTCTAAAGGTCAGTTGAAAGAGTTCCTCGACGCTAACCTGGCCGGCTC<br>TGGATCCGGTGATGACGATGACAAGCTGGGAATTGATCCCTTCACCATGGAGCATTTTTAGACAAG<br>CCAAAGATGGAAAAGCATAATGCCCAGGGGCAGGGTAATGGGTTGCGATATGGGCTAAGCAGCATGC<br>AAGGCTGGCGTGTTGAAATGGAGGATGCACATACGGCTGTGATCGGTTTGCCAAGTGGACTTGAATC<br>GTGGTCATTCTTTGCTGTGTATGATGGGCATGCTGGTTCTCAGGTTGCCAAATACTGCTGTGAGCAT<br>TTGTTAGATCACATCACCAATAACCAGGATTTTAAAGGGTCTGCAGGAGCACCTTCTGTGGAAAATG<br>TAAAGAATGGAATCAGAACAGGTTTTCTGGAGATTGATGAACACATGAGAGTTATGTCAGAGAAGAA<br>ACATGGTGCAGATAGAAGTGGGTCAACAGCTGTAGGTGTCTTAATTTCTCCCCAACATATACTTATT<br>TCATTAACTGTGGAGACTCAAGAGGTTACTTTGTAGGAACAGGAAAGTTCATTTCTTCACACAAGAT<br>CACAACCAAGTAATCCGCTGGAGAAAGAACGAATTCAGAATGCAGGTGGCTCTGTAATGATTCAGCG<br>TGTGAATGGCTCTCTGGCTGTATCGAGGGCCCTTGGGGATTTTGATTACAAATGTGTCCATGGAAAA<br>GGTCCTACTGAGCAGCTTGTCTCACCAGAGCCTGAAGTCCATGATATTGAAAGATCTGAAGAAGATG<br>ATCAGTTCATTATCCTTGCATGTGATGGTATCTGGGATGTTATGGGAAATGAAGAGCTCTGTGATTT<br>TGTAAGATCCAGACTTGAAGTCACTGATGACCTTGAGAAAGTTTGCAATGAAGTAGTCGACACCTGT<br>TTGTATAAGGGAAGTCGAGACAACATGAGTGTGATTTTGATCTGTTTTCCAAATGCACCCAAAGTAT<br>CGCCAGAAGCAGTGAAGAAGGAGGCAGAGTTGGACAAGTACCTGGAATGCAGAGTAGAAGAAATCAT<br>AAAGAAGCAGGGGGAAGGCGTCCCCGACTTAGTCCATGTGATGCGCACATTAGCGAGTGAGAACATC<br>CCCAGCCTCCCACCAGGGGGTGAATTGGCAAGCAAGAGGAATGTTATTGAAGCCGTTTACAATAGAC<br>TGAATCCTTACAAAAATGACGACACTGACTCTACATCAACAGATGATATGTGGAAGGGCGAGCTCAA<br>GCTTGCCAACATCCAGCTGGTGCAGTCTGGTCCTGAGCTGAAGAAGCCTGGTGAGACTGTCAAAATC<br>TCCTGCAAGGCTTCTGGGTATACCTTCACTAACTATGGTATGAACTGGGTGAAGCAGGCTCCTGGTA<br>AGGGTCTGCGTTGGATGGGCTGGATIAACACCCACACTGGTGAGCCTACTTATGCTGATGACTTCAA<br>GGGACGTTTTGCCTTCTCTCTGGAAACTTCTGCCAGCACTGCCTATCTCCAGATCAACAACCTCAAA<br>AATGAGGACACTGCTACTTACTTCTGTACACGTCGTGGTTACGACTGGTACTTCGATGTCTGGGGTG<br>CTGGGACCACGGTGACCGTGTTCTCCGGGGGAGGTGGCAGCGGGGGAGGTGGCAGCGGCGGCGGGAG<br>CTCCGACATCAAGATGACCCAGTCTCCTTCTTCCATGTATGCTTCTCTGGGTGAGCGTGTCACTATC<br>ACTTGCAAGGCCAGCCAGGACATTAATAGCTATCTGAGCTGGTTCCATCATAAACCTGGGAAATCTC<br>CTAAGACCCTGATCTATCGTGCTAACCGTCTGGTTGATGGGGTCCCTTCTCGTTTCAGCGGCTCTGG<br>TTCTGGGCAAGATTATTCTCTCACCATCAGCAGCCTGGACTATGAAGATATGGGTATTTATTATTGT<br>CAACAGTATGATGAGTCTCCTTGGACTTTCGGTGGTGGCACCAAGCTGGAGATGAAAGAACAAAAGT<br>TGATCTCCGAAGAGGATTTGGGTCATCATCACCATCACCATTAAGCGGCCGCATAAGCTT |
| 127 | PP2C-anti-CD5 scFv protein sequence | | 10 20 30 40 50 60<br>MGSDKIIHLT DDSFDTDVLK ADGAILVDFW AHWCGPCKMI APILDEIADE YQGKLTVAKL<br>70 80 90 100 110 120<br>NIDHNPGTAP KYGIRGIPTL LLFKNGEVAA TKVGALSKGQ LKEFLDANLA GSGSGDDDDK<br>130 140 150 160 170 180<br>LGIDPFTNDA FLDKPKMEKH NAQGQGNGLR YGLSSMQGWR VEMEDANTAV IGLPSGLESW<br>190 200 210 220 230 240<br>SFFAVYDGRA GSQVAKYCCE HLLDHITNNQ DFKGSAGAPS VENVKNGIRT GFLEIDEHMR<br>250 260 270 280 290 300<br>VMSEKKHGAD RSGSTAVGVL ISPQHTYFIN CGDSRGLLCR NRKVHFFTQD HKPSNPLEKE<br>310 320 330 340 350 360<br>RIQNAGGSVM IQRVNGSLAV SRALGDFDYK CVHGKGPTEQ LVSPEPEVHD IERSEEOQQF<br>370 380 390 400 410 420<br>IILACDGIWD VMGNEELCDF VRSRLEVTDD LEKVCNEVVD TCLYKGSRDN MSVILICFPN<br>430 440 450 460 470 480<br>APKVSPEAVK KEAELDKYLE CRVEEIIKKQ GEGVPDLVHV MRTLASENIP SLPPGGELAS<br>490 500 510 520 530 540<br>KRNVIEAVYN RLNPYKNDDT DSTSTDDMWK GELKLANIQL VQSGPELKKP GETVKISCKA<br>550 560 570 580 590 600<br>SGYTFTNYGM NWVKQAPGKG LRWMGWINTH TGEPTYADDF KGRFAFSLET SASTAYLQIN<br>610 620 630 640 650 660<br>NLKNEDTATY FCTRRGYDWY FDVWGAGTTV TVFSGGGGSG GGGSGGGSSD IKMTQSFSSM<br>670 680 690 700 710 720<br>YASLGERVTI TCKASQDINS YLSWFHHKPG KSPKTLIYRA NRLVDGVPSR FSGSGSGQDY<br>730 740 750 760 770<br>SLTISSLDYE DMGIYYCQQY DESPWTFGGG TKLEMKEQKL ISEEDLGHHN HHH |

OTHER EMBODIMENTS

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, pharmacology, or related fields are intended to be within the scope of the invention.

What is claimed is:

1. A composition comprising;

(i) a protoxin fusion protein comprising a first non-native cell-targeting moiety, a selectively modifiable activation domain and a toxin domain; and a (ii) protoxin activator fusion protein comprising a second non-native cell-targeting moiety and a modification domain;

wherein:

said first cell-targeting moiety of said protoxin fusion protein and said second cell-targeting moiety of said protoxin activator fusion protein each recognize and bind a common target cell;

said modification domain comprises protease or phosphatase enzymatic activity exogenous to said target cell;

said selectively modifiable activation domain comprises a substrate for said modification domain; and modification of said selectively modifiable activation domain by said modification domain results in activation of said toxin domain.

2. The composition of claim 1, wherein said enzymatic activity is protease activity.

3. The composition of claim 1, wherein said modification domain is a phosphatase and said modifiable activation domain comprises phosphorylation of a protease cleavage site.

4. The composition of claim 1, wherein at least one non-native cell-targeting moiety is an artificially diversified binding protein.

5. The composition of claim 1, wherein said protoxin is an activatable toxin.

6. The composition of claim 5, wherein said activatable toxin is selected from the group consisting of an activatable pore forming toxin or an activatable enzymatic toxin.

7. The composition of claim 1, wherein said toxin domain is selected from a group consisting of an AB toxin, a cyotoxic necrotizing factor toxin, a dermonecrotic toxin, and an activatable ADP-ribosylating toxin.

8. The composition of claim 1, wherein said toxin domain is selected from a group consisting of aerolysin, *Vibrio cholerae* exotoxin, *Pseudomonas* exotoxin and diphtheria toxin.

9. The composition of claim 1, wherein said protoxin activator fusion protein further comprises a natively activatable domain wherein said modification domain is inactive prior to activation of said natively activatable domain and, when active, is non-toxic to a target cell.

10. The composition of claim 1, wherein said modification domain is a protease domain.

11. The composition of claim 10, wherein said protease domain is the catalytic domain of a non-human protease.

12. The composition of claim 11, wherein said non-human protease is a viral protease.

13. The composition of claim 1, wherein said non-native cell-targeting moiety recognizes a cancer cell.

14. The composition of claim 1, wherein at least one non-native cell-targeting moiety is an antibody or antibody fragment.

15. The composition of claim 1, wherein both of said cell-targeting moieties is an antibody or antibody fragment.

16. The composition of claim 10, wherein said protease domain is the catalytic domain of an exogenous human protease.

17. A composition comprising:

(i) a protoxin fusion protein comprising a first non-native cell-targeting moiety, a selectively modifiable activation domain and a toxin domain; and a (ii) protoxin activator fusion protein comprising a second non-native cell-targeting moiety and a modification domain;

wherein:

said first cell-targeting moiety of said protoxin fusion protein and said second cell-targeting moiety of said protoxin activator fusion protein each recognize and bind a common target cell;

said modification domain comprises enzymatic activity exogenous to said target cell;

said selectively modifiable activation domain comprises a substrate for said modification domain; and modification of said selectively modifiable activation domain by said modification domain results in proteolytic cleavage and activation of said toxin domain.

* * * * *